(12) United States Patent
Kettle et al.

(10) Patent No.: US 12,410,187 B2
(45) Date of Patent: Sep. 9, 2025

(54) FUSED TRICYCLIC COMPOUNDS USEFUL AS ANTICANCER AGENTS

(71) Applicant: ASTRAZENECA AB, Södertälje (SE)

(72) Inventors: Jason Grant Kettle, Cambridge (GB); Iain Simpson, Cambridge (GB); Christopher Phillips, Cambridge (GB); Scott Boyd, Cambridge (GB); Oliver Ross Steward, Cambridge (GB); Michael Steven Bodnarchuk, Cambridge (GB); Doyle Joseph Cassar, Cambridge (GB); Kurt Gordon Pike, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 1015 days.

(21) Appl. No.: 17/436,137

(22) PCT Filed: Mar. 3, 2020

(86) PCT No.: PCT/EP2020/055551
§ 371 (c)(1),
(2) Date: Sep. 3, 2021

(87) PCT Pub. No.: WO2020/178282
PCT Pub. Date: Sep. 10, 2020

(65) Prior Publication Data
US 2022/0204527 A1 Jun. 30, 2022

Related U.S. Application Data

(60) Provisional application No. 62/951,146, filed on Dec. 20, 2019, provisional application No. 62/813,885, filed on Mar. 5, 2019.

(51) Int. Cl.
*C07D 498/04* (2006.01)
*C07D 498/14* (2006.01)

(52) U.S. Cl.
CPC ......... *C07D 498/04* (2013.01); *C07D 498/14* (2013.01); *C07B 2200/05* (2013.01)

(58) Field of Classification Search
CPC .................................................. C07D 498/04
See application file for complete search history.

(56) References Cited

U.S. PATENT DOCUMENTS

2009/0318412 A1  12/2009  Matsumoto

FOREIGN PATENT DOCUMENTS

| WO | 2013155223 A1 | 10/2013 |
|----|---------------|---------|
| WO | 2014143659 A1 | 9/2014 |
| WO | 2014152588 A1 | 9/2014 |
| WO | 2015054572 A1 | 4/2015 |
| WO | 2016049524 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017201161 A1 | 11/2017 |
| WO | 2018064510 A1 | 4/2018 |
| WO | 2018068017 A1 | 4/2018 |
| WO | 2018119183 A2 | 6/2018 |
| WO | 2018140512 A1 | 8/2018 |
| WO | 2018140513 A1 | 8/2018 |
| WO | 2018140514 A1 | 8/2018 |
| WO | 2018140598 A1 | 8/2018 |
| WO | 2018140599 A1 | 8/2018 |
| WO | 2018140600 A1 | 8/2018 |
| WO | 2018143315 A1 | 8/2018 |
| WO | 2018/206539 A1 | 11/2018 |
| WO | 2018217651 A1 | 11/2018 |
| WO | 2018218069 A1 | 11/2018 |
| WO | 2018218070 A2 | 11/2018 |
| WO | 2018218071 A1 | 11/2018 |
| WO | 2019051291 A1 | 3/2019 |
| WO | 2019099524 A1 | 5/2019 |
| WO | 2019110751 A1 | 6/2019 |
| WO | 2019150305 A1 | 8/2019 |
| WO | 2019155399 A1 | 8/2019 |
| WO | 2019/215203 A1 | 11/2019 |

OTHER PUBLICATIONS

Anonymous, "MRTX849 in Patients With Cancer Having a KRAS G12C Mutation KRYSTAL-1", ClinicalTrials.Gov, 2018, Available at: https://clinicaltrials.gov/ct2/show/NCT0378$249 (retrieved Apr. 6, 2021).

(Continued)

*Primary Examiner* — Brian E McDowell

(57) ABSTRACT

The specification relates to compounds of Formula (A) and pharmaceutically acceptable salts thereof. The specification also relates to processes and intermediates used for their preparation, pharmaceutical compositions containing them and their use in the treatment of cell proliferative disorders.

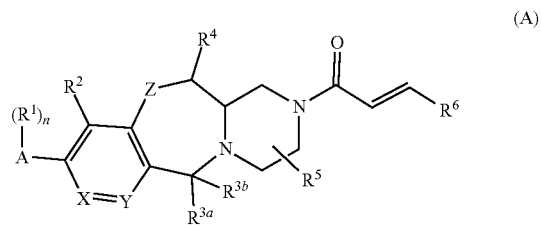

(A)

5 Claims, No Drawings

(56) References Cited

OTHER PUBLICATIONS

Fell et al. "Discovery of Tetrahydropyridopyrimidines as Irreversible Covalent Inhibitors of KRAS-G12C with In Vivo Activity" ACS Medicinal Chemistry Letters, 2018, vol. 9, pp. 1230-1234.

Fell et al, "Identification of the Clinical Development Candidate MRTX849, a Covalent KRASG12C Inhibitor for the Treatment of Cancer" Journal of Medicinal Chemistry, 2020, vol. 63, pp. 6679-6693.

Hansen, et al. "The reactivity-driven biochemical mechanism of covalent $KRAS^{G12C}$ inhibitors." Nature Structural Molecular Biology, 2018, vol. 25, pp. 454-462.

Janes et al. "Targeting KRAS Mutant Cancers with a Covalent G12C-Specific Inhibitor." Cell, 2018, vol. 172, pp. 578-589.

Kettle et al. "Structure-Based Design and Pharmacokinetic Optimization of Covalent Allosteric Inhibitors of the Mutant GTPase $KRAS^{G12C}$" Journal of Medicinal Chemistry, 2020, vol. 63, pp. 4468-4483.

Lanman et al. "Discovery of a Covalent Inhibitor of KRASG12C (AMG 510) for the Treatment of Solid Tumors" Journal of Medicinal Chemistry, 2020, vol. 63, pp. 52-65.

Marx et al, "Structure-based Drug Discovery of MRTX1257: A Selective, Covalent KRAS G12C Inhibitor with Oral Activity in Animal Models of Cancer" 2019, Abstracts of Papers, 257th ACS National Meeting & Exposition, Orlando, FL, United States. Available at: https://www.morressier.com/article/structurebased-drug-discovery-mrtx1257-selective-covalent-kras-g12c-inhibitor-oral-activity-animal-models-cancer/5fc643a32d78d1fec4668986.

Marx et al. "Structure-Based Drug Discovery of MRTX1257, a Selective, Covalent KRAS G12C Inhibitor with Oral Activity in Animal Models of Cancer." Mirati.com, 2018, Available at: https://www.mirati.com/wp-content/uploads/KRAS-Poster-AACR-RAS.pdf.

Ostrem, et al. "K-Ras(G12C) inhibitors allosterically control GTP affinity and effector interactions" Nature, 2013, vol. 503, pp. 548-551.

Patricelli, et al. "Selective Inhibition of Oncogenic KRAS Output with Small Molecules Targeting the Inactive State" Cancer Discovery, 2016, vol. 6, pp. 316-329.

Shin et al. "Discovery of N-(1-Acryloylazetidin-3-y1)-2-(1H-indol-1-yl)acetamides as Covalent Inhibitors of $KRAS^{G12C}$"ACS Medicinal Chemistry Letters, 2019, vol. 10, pp. 1302-1308.

FUSED TRICYCLIC COMPOUNDS USEFUL AS ANTICANCER AGENTS

The specification relates to certain fused tricyclic compounds and pharmaceutically acceptable salts thereof that inhibit G12C mutant RAS proteins and consequently exhibit anti-cancer activity. The specification also relates to use of said fused tricyclic compounds and pharmaceutically acceptable salts thereof in methods of treatment of the human or animal body, for example in prevention or treatment of cancer. The specification also relates to processes and intermediate compounds involved in the preparation of said fused tricyclic compounds and to pharmaceutical compositions containing them.

The KRAS, NRAS and HRAS genes encode a set of closely related small GTPase proteins KRas, NRas and HRas, collectively referred to herein as the Ras proteins or Ras, that share 82-90% overall sequence identity. The Ras proteins are critical components of signalling pathways transmitting signals from cell-surface receptors to regulate cellular proliferation, survival and differentiation. Ras functions as a molecular switch cycling between an inactive GDP-bound state and an active GTP-bound state. The GDP/GTP cycle of Ras is tightly regulated in cells by guanine nucleotide exchange factors (GEFs) such as Sos1 and Sos2, which promote the exchange of GDP for GTP, and GTPase activating proteins (GAPs) such as NF-1 and p120RasGAP which stimulate the intrinsic GTPase activity of Ras hydrolysing GTP to GDP.

The Ras proteins are 188-189 amino acids in length and have a highly conserved N-terminal G-domain containing the p-loop region, which binds nucleotide, and the switch I and switch II regions which are important for regulatory and effector protein interactions. The C-terminal region of the Ras proteins are more divergent and contain elements which regulate the association of Ras with the membrane including the conserved carboxyl terminal CAXX box motif which is necessary for post-translational prenylation modifications. On binding to GTP the switch I and switch II regions of Ras undergo a conformational change which enables its interaction and activation of effector proteins to regulate down-stream signalling pathways. The best characterised effector of Ras is the serine/threonine kinase Raf which regulates the activity of the mitogen-activate protein kinase (MAPK) pathway. The PI3K pathway is another important effector pathway down-stream of Ras with the p110 catalytic subunit of the class I phosphoinositide 3-kinases interacting with Ras. Other effectors of Ras including RalGDS, Tiam1, PLC-ε and Rassf1 have been have also been described (Cox, et al. *Nature Reviews Drug Discovery* 2014, 13:828-851).

RAS mutations are frequently found in cancer and approximately 30% of all human cancers have a mutation in KRAS, NRAS or HRAS genes. Oncogenic Ras is typically, but not exclusively, associated with mutations at glycine 12, glycine 13 or glutamine 61 of Ras. These residues are located at the active site of Ras and mutations impair intrinsic and/or GAP-catalysed GTPase activity favouring the formation of GTP bound Ras and aberrant activation of down-stream effector pathways. KRAS is the most frequently mutated RAS gene in cancer followed by NRAS and then HRAS. There are several tumour types that exhibit a high frequency of activating mutations in KRAS including pancreatic (~90% prevalence), colorectal (~40% prevalence) and non-small cell lung cancer (~30% prevalence). KRAS mutations are also found in other cancer types including multiple myeloma, uterine cancer, bile duct cancer, stomach cancer, bladder cancer, diffuse large B cell lymphoma, rhabdomyosarcoma, cutaneous squamous cell carcinoma, cervical cancer, testicular germ cell cancer and others.

Glycine to cysteine mutations at residue 12 of Ras (the G12C mutation) is generated from a G.C to T.A base transversion at codon 12, a mutation commonly found in RAS genes that accounts for 14% of all KRAS, 2% of all NRAS and 2% of all HRAS mutations across cancer types. The G12C mutation is particularly enriched in KRAS mutant non-small cell lung cancer with approximately half carrying this mutation, which has been associated with the DNA adducts formed by tobacco smoke. The G12C mutation is not exclusively associated with lung cancer and is found in other RAS mutant cancer types including 8% of all KRAS mutant colorectal cancer.

To date there have been no inhibitors of G12C mutant Ras proteins which have been approved for therapeutic use. Hence there is a need for new inhibitors of G12C mutant Ras proteins that possess the required pharmaceutical properties to be suitable for clinical use. The compounds of the specification have been found to possess anti-tumour activity, being useful in inhibiting the uncontrolled cellular proliferation which arises from malignant disease. The compounds of the specification provide an anti-tumour effect by, as a minimum, acting as inhibitors of G12C mutant Ras proteins.

According to a first aspect of the specification there is provided a compound of Formula (A):

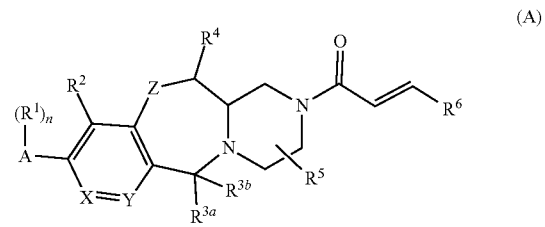

wherein:
A is phenyl or a bicyclic heteroaryl group;
X and Y are connected by a double bond and i) X is $CR^7$ and Y is $CR^8$, ii) X is N and Y is $CR^8$, or iii) X is $CR^7$ and Y is N; or
X and Y together are $C(O)NR^9$; or
X and Y are adjacent ring atoms of an optionally substituted 5- or 6-membered N-heterocycle fused to the aromatic ring substituted with Z, and X and Y are both C or are C and N;
Z is O, NH, or NMe;
$R^1$ is independently selected from F, Cl, Br, OH, $CH_2OH$, OMe, $CH_2OMe$, $C_1$-$C_3$alkyl and $C_1$-$C_3$fluoroalkyl;
n is 0, 1, 2 or 3;
$R^2$ is H, F, Cl, CCH, CCMe, CN, Br, $C_1$-$C_3$alkyl, $C_1$-$C_3$fluoroalkyl, OMe or OEt;
$R^{3a}$ and $R^{3b}$ together are =O or $R^{3a}$ and $R^{3b}$ are H;
$R^4$ is H or Me;
$R^6$ is H or Me;
$R^6$ is H or $CH_2NMe_2$;
$R^7$ and $R^8$ are independently selected from H, F, Cl, CCH, CC($C_1$-$C_3$alkyl), $CCCH_2NMe_2$, $CCCH_2O(C_1$-$C_3$alkyl), CN, Me, $C_1$-$C_6$alkyl, OH, OMe, $O(C_1$-$C_3$alkyl), $O(C_1$-$C_3$deuteroalkyl), $O(C_1$-$C_3$fluoroalkyl), $O(C_3$-$C_6$cycloalkyl), $C_1$-$C_3$fluoroalkyl, $OCH_2CH_2NMe_2$, $OCH_2CH_2OMe$, $CH_2OMe$, $OCH_2CH_2N(CH_2CH_2)_2CH$, $OCH_2CH_2N(CH_2CH_2)_2O$, $OCH_2$ $CH_2$ (2-pyridyl) or an optionally substituted 3-, 4-, 5- or 6-membered carbocycle or heterocycle; or $R^7$ and $R^8$ combine to form an optionally substituted 5- or 6-membered carbocycle or heterocycle;

$R^9$ is selected from H, Me, Et, $C_3H_7$ and $C_1$-$C_3$fluoroalkyl;

or a pharmaceutically acceptable salt thereof.

According to a further aspect of the specification the compound of Formula (A) is a compound of Formula (I):

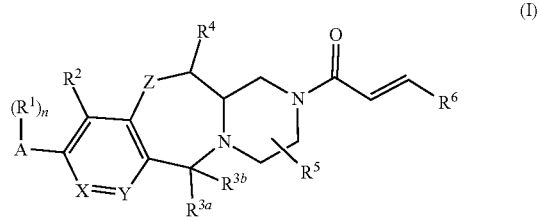

(I)

wherein:

A is phenyl or a bicyclic heteroaryl group;

X and Y are connected by a double bond and i) X is $CR^7$ and Y is $CR^8$, ii) X is N and Y is $CR^8$ or iii) X is $CR^7$ and Y is N; or X and Y together are $C(O)NR^9$; or X and Y are adjacent ring atoms of an optionally substituted 5- or 6-membered N-heterocycle fused to the aromatic ring substituted with Z, and X and Y are both C or are C and N;

Z is O, NH, or NMe;

$R^1$ is independently selected from F, Cl, Br, OH, $CH_2OH$, OMe, $CH_2OMe$, $C_1$-$C_3$alkyl, $C_1$-$C_3$fluoroalkyl;

n is 0, 1, 2 or 3;

$R^2$ is H, F, Cl, CCH, CCMe, CN, Br, $C_1$-$C_3$alkyl, $C_1$-$C_3$fluoroalkyl, OMe or OEt;

$R^{3a}$ and $R^{3b}$ together are =O or $R^{3a}$ and $R^{3b}$ are H;

$R^4$ is H or Me;

$R^5$ is H or Me;

$R^6$ is H or $CH_2NMe_2$;

$R^7$ and $R^8$ are selected from H, F, Cl, CCH, CN, Me, OH, OMe, O($C_1$-$C_3$alkyl), $C_1$-$C_3$fluoroalkyl or an optionally substituted 5- or 6-membered carbocycle or heterocycle; or $R^7$ and $R^8$ combine to form an optionally substituted 5- or 6-membered carbocycle or heterocycle;

$R^9$ is selected from H, Me, Et, $C_3H_7$ and $C_1$-$C_3$fluoroalkyl;

or a pharmaceutically acceptable salt thereof.

In a further aspect there is provided a compound of Formula (A) or Formula (I), or a pharmaceutical acceptable salt thereof, for use as a medicine.

In a further aspect there is provided a pharmaceutical composition comprising a compound of Formula (A) or Formula (I), or a pharmaceutical acceptable salt thereof.

In a further aspect there is provided a method of treating cancer by administering to a patient in need thereof an effective amount of a compound of Formula (A) or Formula (I), or a pharmaceutical acceptable salt thereof.

In a further aspect there is provided a compound of Formula (A) or Formula (I), or a pharmaceutical acceptable salt thereof, for use in the treatment of cancer.

In a further aspect there is provided a compound of Formula (A) or Formula (I), or a pharmaceutical acceptable salt thereof, for use in the manufacture of a medicament, for example a medicament for the treatment of cancer.

In a further aspect there is provided a kit comprising a pharmaceutical composition comprising a compound of Formula (A) or Formula (I), or a pharmaceutical acceptable salt thereof, and instructions for its use in the treatment of cancer.

In a further aspect there is provided a method for the manufacture of a compound of Formula (A) or Formula (I).

The compounds of Formula (A), for example compounds of Formula (I), feature [6,7,6]-tricyclic core in which an aromatic ring containing the groups X and Y is linked to a piperazine by a 1,4-diazepane (Z=N) or 1,4-oxazepane (Z=O) motif. In addition, a group A that is selected from phenyl and bicyclic heteroaryl, is linked through a biaryl bond to the aromatic ring containing the groups X and Y. Subject to the nature of the groups $R^1$, $R^2$ and X rotation around the biaryl bond is restricted and the compounds of Formula (I), as a result, can exist in stable atropisomeric forms. An acrylamide motif is attached to tricyclic core via the non-bridgehead piperazine nitrogen.

It has been found that the compounds of Formula (A), for example compounds of Formula (I), possess potent anti-tumour activity that, it is believed, derives from inhibition of the G12C mutant Ras proteins that are key mediators of proliferation and survival in certain tumour cells. In more detail, it is believed that the compounds of the present specification interact with, and then covalently bind to, G12C mutant Ras through the acrylamide motif attached to the piperazine of Formula (I). In binding to G12C mutant Ras, the compounds of the specification (as described herein) impair or substantially eliminate the ability of the G12C Ras proteins to access their active, pro-proliferative/pro-survival confirmation.

Compounds according to the present specification possess good physicochemical properties that indicate that they will be suited to oral administration to humans to deliver a therapeutic effect. For example, in addition to their ability to inhibit G12C mutant Ras proteins, compounds according to the specification possess good solubility profiles and relatively low molecular weight when compared to known inhibitors of this mutant form of Ras. As described further herein, the stereochemical configurations of the compounds of the specification and, in particular, their atropisomeric form, are key determinants Ras inhibitory activity. Notably, the compounds of the specification express a selective inhibitory effect on G12C mutant Ras proteins relative to wild-type Ras.

In addition to their RasG12C inhibitory properties, certain compounds according to the present specification have been found to possess physicochemical properties that indicate that they will be able to penetrate the blood brain barrier, a particularly advantageous property for the treatment of patients with RasG12C expressing primary tumours that have metastasized to the brain to form brain metastases or that have a propensity to metastasize to the brain. Preclinical studies have confirmed that exemplary compounds of Formula (A), for example compounds of Formula (I), are not substrates for human P-gp or BCRP. Furthermore, in vivo studies revealed that selected compounds of Formula (I) exhibit rat Kpuu values indicative of good distribution to the brain. Good BBB penetrant properties, and hence potential for treatment of tumours that have a propensity to metastasize to the brain, is also demonstrate by efflux ratios measured in Madin-Darby Canine Kidney (MDCK) cells doubly transfected with MDR1 (Pgp) and BCRP (the MDCK_MDR1_BCRP cells). In particular, compounds in which $R^7$ or $R^8$ is ethynyl (i.e. —CCH) or CCMe have proven to have good blood brain barrier (BBB) penetrant properties, for example compounds in which $R^7$ and/or $R^8$ is ethynyl or CCMe and $R^2$ is F or Cl have proven to have good BBB penetrant properties and are highly active RasG12C inhibitors. Certain compounds featuring an $R^8$ group that is CCMe group exhibit reduced clearance as assessed in in vitro assays.

Accordingly, the compounds of the present specification may be of value as anti-tumour agents. In particular, the compounds of the present specification may be of value as selective inhibitors of the proliferation, survival, motility, dissemination and invasiveness of mammalian cancer cells that express G12C mutant Ras. Due to their ability to inhibit G12C mutant Ras, treatment of a subject with a compound according to the present specification may lead to inhibition of tumour growth, trigger tumour regression, and/or inhibit formation of metastases and/or metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of G12C mutant Ras and that are involved in the cell-signalling leading to the proliferation and survival of tumour cells.

Accordingly, there is also provided a method for providing a selective inhibitory effect on G12C mutant Ras, for example in the treatment of tumours expressing RasG12C mutant Ras, which comprises administering an effective amount of a compound of the Formula (I), or a pharmaceutically acceptable salt thereof, as defined herein, to a patient in need thereof.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma.

The present specification also relates to processes for the manufacture of said compounds, to pharmaceutical compositions containing them, to methods of treatment comprising administering the said compounds to patients, for example humans, in need thereof, to use of compounds of formula (I) for the manufacture of medicaments, for example for use in the treatment of a patient suffering from a hyperproliferative disease such as cancer.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

So that the present specification may be more readily understood, certain terms are explicitly defined below. In addition, definitions are set forth as appropriate throughout the detailed description.

Units, prefixes, and symbols are denoted in their Système International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise a compound of Formula (A), for example compounds of Formula (I), or a pharmaceutical acceptable salt thereof, and at least one pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein the term "alkyl" refers to both straight and branched chain saturated hydrocarbon radicals having the specified number of carbon atoms. As used herein the term deuteroalkyl refers to an alkyl groups in which one or more, optionally all, hydrogens are replaced with deuterium atoms. The term cycloalkyl refers to a saturated carbocycle.

The term acetylenyl refers to an ethynyl radical i.e. a —CCH group.

In this specification the prefix $C_x$-$C_y$, as used in terms such as $C_x$-$C_y$ alkyl and the like where x and y are integers, indicates the numerical range of carbon atoms that are present in the group. For example, $C_1$-$C_4$ alkyl includes methyl, ethyl, n-propyl, i-propyl, n-butyl, s-butyl, i-butyl and t-butyl, while examples of $C_1$-$C_3$alkyl groups include methyl, ethyl, n-propyl, and i-propyl. $C_1$-$C_4$ alkoxy groups include methoxy, ethoxy, n-propoxy, i-propoxy, n-butoxy, sec-butoxy and t-butoxy. Examples of $C_1$-$C_3$ alkoxy groups include methoxy, ethoxy, n-propoxy and i-propoxy. Examples of $C_1$-$C_3$ fluoroalkyl groups include fluoromethyl, difluoromethyl, trifluoromethyl, 1,1-difluoroethyl and 2,2,2-trifluoroethyl. Examples of $C_1$-$C_3$ fluoroalkoxy groups include fluoromethoxy, difluoromethoxy, trifluoromethoxy and 2,2,2-trifluoroethoxy. A —O($C_1$-$C_3$deuterioalkyl) group is a partially or fully deuterated O-methyl, O-ethyl or O-n-propyl or O-i-propyl group. A $C_3$-$C_6$cycloalkyl group refers to a cyclopropyl, cyclobutyl, cyclopentyl or cyclohexyl group. A 2-pyridyl group is a pyridine ring attached by a bond meta to the pyridine N-atom, i.e. a group

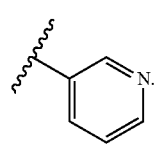

Unless specifically stated, the bonding of an atom or group may be any suitable atom of that group; for example, propyl includes prop-1-yl and prop-2-yl.

Unless otherwise stated, halo is selected from Cl, F, Br and I, generally from Cl, F or Br, or Cl and F.

As noted above the group A may be a phenyl group or a bicyclic heteroaryl group. A bicyclic heteroaryl group in this context is an aromatic group comprising two fused rings and containing 1, 2, 3 or 4 N atoms, or one O atom, or one S atom, or 1 N atom and one S atom, or 1 N atom and one O atom, or 2 N atoms and one S atom, or 2 N atoms and one O atom. Bicyclic heteroaryl groups include those groups where both fused rings are aromatic, or where one fused ring is aromatic and the other fused ring is partially or fully saturated. The said partially or fully saturated fused ring may also comprise a carbonyl group. Examples of suitable bicyclic heteroaryl groups include indolyl, benzofuranyl, benzothienyl, benzoxazolyl, benzimidazolyl, benzotriazolyl, indazolyl, azaindolyl, azaindazolyl, pyrrolo[1,2-b]pyridazinyl, pyrrolo[2,3-b]pyridinyl, quinolinyl, isoquinolinyl, quinazolinyl, cinnolinyl, phthalazinyl, quinoxalinyl and naphthyridinyl.

As noted above the groups X and Y in the compounds of Formula (I) can be adjacent ring atoms of a 5- or 6-membered N-heterocycle fused to the aromatic ring substituted with Z and are both C or are C and N. The term 5- or 6-membered N-heterocycle refers to a saturated or unsaturated, for example aromatic, 5- or 6-membered rings containing at least one nitrogen atom and up to two further heteroatoms selected from O, N and S. The 5-membered N-heterocycle fused to the aromatic ring substituted with Z can be selected from pyrrole, imidazole, pyrazole, 1,2,3-triazole, 1,2,4-triazole, oxazole, isoxazole, oxadiazole, thiazole and isothiazole and partially saturated equivalents thereof.

The 6-membered N-heterocycle fused to the aromatic ring substituted with Z can be selected from pyridine, pyridazine, pyrimidine and pyrazine. The 5- or 6-membered N-heterocycle may be optionally substituted with one or two substituents selected from $C_1$-$C_3$ alkyl, $C_1$-$C_3$ fluoroalkyl, $C_1$-$C_3$ alkoxy, Cl, F, CN, OH, OMe, OEt, $NH_2$, NHMe, $NMe_2$ and $C_1$-$C_3$ alkyl optionally substituted with OH, OMe, $NH_2$, NHMe or $NMe_2$.

As noted above the groups $R^7$ and $R^8$ in the compounds of Formula (I) can be an optionally substituted 5- or 6-membered carbocycle or heterocycle. The term optionally substituted 5- or 6-membered carbocycle or heterocycle refers to a saturated or unsaturated, for example aromatic, ring containing up to three heteroatoms selected from O, N and S. The 5-membered heterocycle may be selected from pyrrole, imidazole, pyrazole, 1,2,3-triazole, 1,2,4-triazole, oxazole, isoxazole, 1,2,3-oxadiazole, thiazole, isothiazole and partially or fully saturated equivalents thereof. The 6-membered heterocycle may be selected from pyridine, pyridazine, pyrimidine and pyrazine. The 5- or 6-membered carbocycle or heterocycle may be optionally substituted with one or two substituents selected from $C_1$-$C_3$ alkyl, $C_1$-$C_3$ fluoroalkyl, $C_1$-$C_3$ alkoxy, Cl, F, CN, OH, OMe, OEt, $NH_2$, NHMe, $NMe_2$ and $C_1$-$C_3$ alkyl optionally substituted with OH, OMe, $NH_2$, NHMe or $NMe_2$.

As noted above, in the instance where the groups $R^7$ and $R^8$ are both present in the compounds of Formula (A), for example in compounds of Formula (I), they can combine to form an optionally substituted 5- or 6-membered carbocycle or heterocycle fused to the aromatic ring substituted with Z. The optionally substituted 5- or 6-membered carbocycle or heterocycle may be saturated or unsaturated. The 5- or 6-membered carbocycle or heterocycle may be optionally substituted with one or two substituents selected from $C_1$-$C_3$ alkyl, $C_1$-$C_3$ fluoroalkyl, $C_1$-$C_3$ alkoxy, Cl, F, CN, OH, OMe, OEt, $NH_2$, NHMe, $NMe_2$ and $C_1$-$C_3$ alkyl optionally substituted with OH, OMe, $NH_2$, NHMe or $NMe_2$. In the case where $R^7$ and $R^8$ combine to form a 5-membered ring, together they may represent a $C_3$, $C_2O$, COC, $C_2N$, CNC, CNO, NCO, CNS or NCS chain. In the case where $R^7$ and $R^8$ combine to form a 6-membered ring, together they may represent a $C_4$, $C_3O$, $COC_2$, $OC_2O$, $C_3N$, $C_2NC$, NCNC, CNNC or NCCN chain. The $R^7$ and $R^8$ chains of atoms are covalently bound and substituted with hydrogen or the optional substituents to satisfy their normal valency.

For the avoidance of doubt, where multiple substituents are independently selected from a given group, the selected substituents may comprise the same substituents or different substituents from within the given group. By way of example only, where ring A is phenyl substituted with $(R^1)_n$, and where n is 2, the two $R^1$ substituents could be the same, for instance both fluoro, or could be different, for instance one fluoro and one hydroxy.

For the further avoidance of doubt, the use of "$\sim\!\!\sim\!\!\sim$" in formulas of this specification denotes the point of attachment between different groups.

Where any embodiment within this specification includes a group which is said to be "optionally substituted", then a further embodiment will include that embodiment wherein the said group is unsubstituted.

According to a first aspect of the specification there is provided a compound of Formula (A):

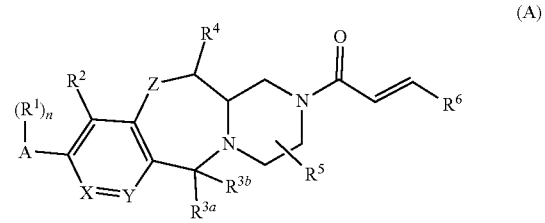

(A)

wherein:

A is phenyl or a bicyclic heteroaryl group;

X and Y are connected by a double bond and i) X is $CR^7$ and Y is $CR^B$, ii) X is N and Y is $CR^B$, or iii) X is $CR^7$ and Y is N; or X and Y together are $C(O)NR^9$; or X and Y are adjacent ring atoms of an optionally substituted 5- or 6-membered N-heterocycle fused to the aromatic ring substituted with Z, and X and Y are both C or are C and N;

Z is O, NH, or NMe;

$R^1$ is independently selected from F, Cl, Br, OH, $CH_2OH$, OMe, $CH_2OMe$, $C_1$-$C_3$alkyl and $C_1$-$C_3$fluoroalkyl;

n is 0, 1, 2 or 3;

$R^2$ is H, F, Cl, CCH, CCMe, CN, Br, $C_1$-$C_3$alkyl, $C_1$-$C_3$fluoroalkyl, OMe or OEt;

$R^{3a}$ and $R^{3b}$ together are =O or $R^{3a}$ and $R^{3b}$ are H;

$R^4$ is H or Me;

$R^6$ is H or Me;

$R^6$ is H or $CH_2NMe_2$;

$R^7$ and $R^8$ are independently selected from H, F, Cl, CCH, $CC(C_1$-$C_3$alkyl), $CCCH_2NMe_2$, $CCCH_2O(C_1$-$C_3$alkyl), CN, Me, $C_1$-$C_6$alkyl, OH, OMe, $O(C_1$-$C_3$alkyl), $O(C_1$-$C_3$deuteroalkyl), $O(C_1$-$C_3$fluoroalkyl), $O(C_3$-$C_6$cycloalkyl), $C_1$-$C_3$fluoroalkyl, $OCH_2CH_2$ NMe$_2$, OCH$_2$CH$_2$OMe, CH$_2$OMe, OCH$_2$CH$_2$N(CH$_2$CH$_2$)$_2$CH, OCH$_2$CH$_2$N(CH$_2$CH$_2$)$_2$O, OCH$_2$CH$_2$(2-pyridyl) or an optionally substituted 3-, 4-, 5- or 6-membered carbocycle or heterocycle; or R$^7$ and R$^8$ combine to form an optionally substituted 5- or 6-membered carbocycle or heterocycle;

R$^9$ is selected from H, Me, Et, C$_3$H$_7$ and C$_1$-C$_3$fluoroalkyl;

or a pharmaceutically acceptable salt thereof.

In embodiments, the compound of Formula (A) is a compound of Formula (Aa) in which R$^6$ is H.

In embodiments, the compound of Formula (A) or (Aa), is a compound of Formula (Ab) in which R$^5$ is H.

In embodiments, the compound of Formula (A), (Aa) or (Ab) is a compound of Formula (Ac) in which R$^4$ is H.

In embodiments, the compound of Formula (A), (Aa), (Ab) or (Ac) is a compound of Formula (Ad) in which A is phenyl.

In embodiments, the compound of Formula (A) is a compound of Formula (Ae)

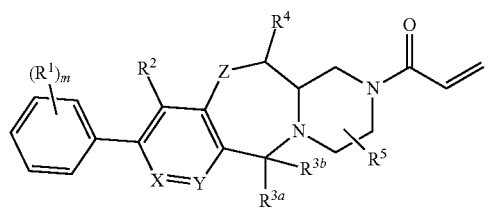

(Ae)

In embodiments, the compound of Formula (Ae) is a compound of Formula (Af) in which R$^5$ is H.

In embodiments, the compound of Formula (Ae) or (Af) is a compound of Formula (Ag) in which R$^{3a}$ and R$^{3b}$ are H.

In embodiments, the compound of Formula (Ae) or (Af) is a compound of Formula (Ah) in which R$^{3a}$ and R$^{3b}$ together are =O.

In embodiments, the compound of Formula (Ae), (Af), (Ag) or (Ah) is a compound of Formula (Ai) in which Z is O.

In embodiments, the compound of Formula (Ae), (Af), (Ag), (Ah) or (Ai) is a compound of Formula (Aj) in which R$^2$ is selected from F or Cl.

In embodiments, the compound of Formula (Ae), (Af), (Ag), (Ah), (Ai) or (Aj) is a compound of Formula (Ak) in which n is 2 or 3 and at least 2 substituents R$^1$ are ortho to the biaryl bond.

In embodiments, the compound of Formula (Ae), (Af), (Ag), (Ah), (Ai), (Aj) or (Ak) is a compound of Formula (Al) in which at least one R$^1$ group is OH.

In embodiments, the compound of Formula (A), (Ae), (Af), (Ag), (Ai), (Aj), (Ak) or (Al) is a compound of Formula (Am)

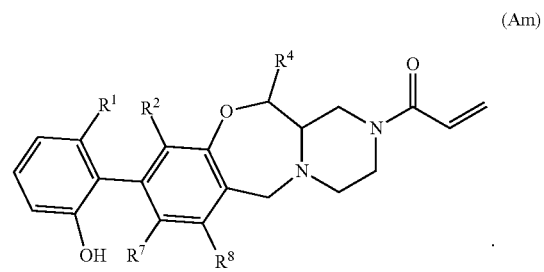

(Am)

In embodiments, the compound of Formula (A), (Ae), (Af), (Ag), (Ah), (Ai), (Aj), (Ak) or (Al) is a compound of Formula (An) or (Ao)

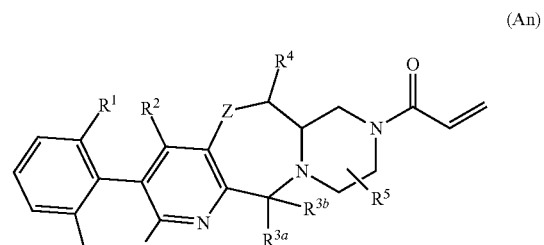

(An)

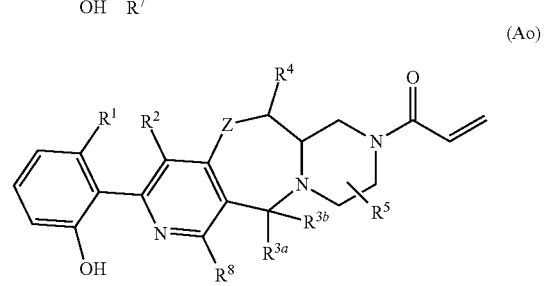

(Ao)

In embodiments, the compound of Formula (A), (Ae), (Af), (Ag), (Ah), (Ai), (Aj), (Ak) or (Al) is a compound of Formula (Ap) in which X and Y are C(O)NR$^9$.

In embodiments, the compound of Formula (A), (Ae), (Af), (Ag), (Ah), (Ai), (Aj), (Ak) or (Al) is a compound of Formula (Aq) in which X and Y are adjacent ring atoms of an optionally substituted pyrrole, imidazole, pyrazole, 1,2,3-triazole, 1,2,4-triazole, oxazole, isoxazole, 1,2,3-oxadiazole, thiazole or isothiazole.

In embodiments, the compound of Formula (Aq) is a compound of Formula (Ar) in which the optional substituent on the 5-membered ring containing X and Y is selected from C$_1$-C$_3$ alkyl, OC$_1$-C$_2$ alkyl, OMe, OH, F and Cl.

In embodiments, the compound of Formula (A), (Aa) to (Ar) has the stereochemistry shown below

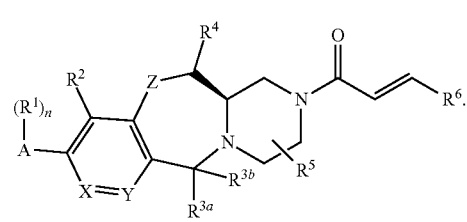

As noted above, the specification provides a compound of the Formula (I):

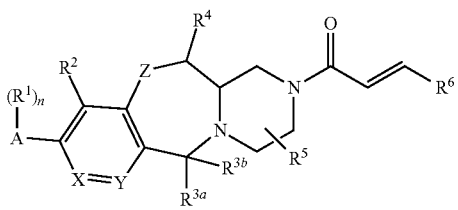

(I)

wherein:
A is phenyl or a bicyclic heteroaryl group;
X and Y are connected by a double bond and i) X is $CR^7$ and Y is $CR^8$, ii) X is N and Y is $CR^8$ or iii) X is $CR^7$ and Y is N; or
X and Y together are $C(O)NR^9$; or
X and Y are adjacent ring atoms of an optionally substituted 5- or 6-membered N-heterocycle fused to the aromatic ring substituted with Z, and X and Y are both C or are C and N;
Z is O, NH, or NMe;
$R^1$ is independently selected from F, Cl, Br, OH, $CH_2OH$, OMe, $CH_2OMe$, $C_1$-$C_3$alkyl, $C_1$-$C_3$fluoroalkyl;
n is 0, 1, 2 or 3;
$R^2$ is H, F, Cl, CCH, CCMe, CN, Br, $C_1$-$C_3$alkyl, $C_1$-$C_3$fluoroalkyl, OMe or OEt;
$R^{3a}$ and $R^{3b}$ together are =O or $R^{3a}$ and $R^{3b}$ are H;
$R^4$ is H or Me;
$R^6$ is H or Me;
$R^6$ is H or $CH_2NMe_2$;
$R^7$ and $R^8$ are selected from H, F, Cl, CCH, CN, Me, OH, OMe, $O(C_1$-$C_3$alkyl), $C_1$-$C_3$fluoroalkyl or an optionally substituted 5- or 6-membered carbocycle or heterocycle; or
$R^7$ and $R^8$ combine to form an optionally substituted 5- or 6-membered carbocycle or heterocycle;
$R^9$ is selected from H, Me, Et, $C_3H_7$ and $C_1$-$C_3$fluoroalkyl;
or a pharmaceutically acceptable salt thereof.

In embodiments, the compound of Formula (I) is a compound of Formula (Ia) in which $R^6$ is H.
In embodiments, the compound of Formula (I) or (Ia), is a compound of Formula (Ib) in which $R^6$ is H.
In embodiments, the compound of Formula (I), (Ia) or (Ib) is a compound of Formula (Ic) in which $R^4$ is H.
In embodiments, the compound of Formula (I), (Ia), (Ib) or (Ic) is a compound of Formula (Id) in which A is phenyl.
In embodiments, the compound of Formula (I) is a compound of Formula (Ie)

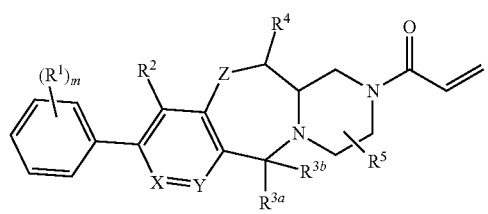

(Ie)

In embodiments, the compound of Formula (Ie) is a compound of Formula (If) in which $R^5$ is H.
In embodiments, the compound of Formula (Ie) or (If) is a compound of Formula (Ig) in which $R^{33}$ and $R^{3b}$ are H.

In embodiments, the compound of Formula (Ie) or (If) is a compound of Formula (Ih) in which $R^{33}$ and $R^{3b}$ together are =O.
In embodiments, the compound of Formula (Ie), (If), (Ig) or (Ih) is a compound of Formula (Ii) in which Z is O.
In embodiments, the compound of Formula (Ie), (If), (Ig), (Ih) or (Ii) is a compound of Formula (Ij) in which $R^2$ is selected from F or Cl.
In embodiments, the compound of Formula (Ie), (If), (Ig), (Ih), (Ii) or (Ij) is a compound of Formula (Ik) in which n is 2 or 3 and at least 2 substituents $R^1$ are ortho to the biaryl bond.
In embodiments, the compound of Formula (Ie), (If), (Ig), (Ih), (Ii), (Ij) or (Ik) is a compound of Formula (Il) in which at least one $R^1$ group is OH.
In embodiments, the compound of Formula (I), (Ie), (If), (Ig), (Ii), (Ij), (Ik) or (Il) is a compound of Formula (Im)

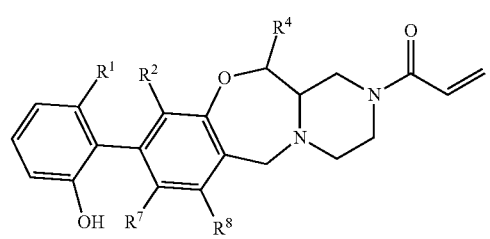

(Im)

In embodiments, the compound of Formula (I), (Ie), (If), (Ig), (Ih), (Ii), (Ij), (Ik) or (Il) is a compound of Formula (In) or (Io)

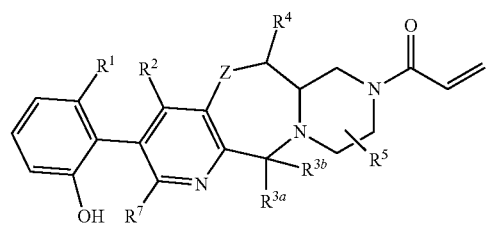

(In)

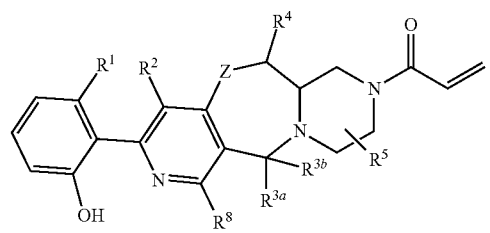

(Io)

In embodiments, the compound of Formula (I), (Ie), (If), (Ig), (Ih), (Ii), (Ij), (Ik) or (Il) is a compound of Formula (Ip) in which X and Y are $C(O)NR^9$.
In embodiments, the compound of Formula (I), (Ie), (If), (Ig), (Ih), (Ii), (Ij), (Ik) or (Il) is a compound of Formula (Iq) in which X and Y are adjacent ring atoms of an optionally substituted pyrrole, imidazole, pyrazole, 1,2,3-triazole, 1,2,4-triazole, oxazole, isoxazole, 1,2,3-oxadiazole, thiazole or isothiazole.
In embodiments, the compound of Formula (Iq) is a compound of Formula (Ir) in which the optional substituent on the 5-membered ring containing X and Y is selected from $C_1$-$C_3$ alkyl, $OC_1$-$C_2$ alkyl, OMe, OH, F and Cl.

In embodiments, the compound of Formula (I), (Ia) to (Ir) has the stereochemistry shown below

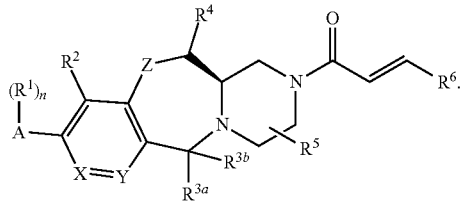

In an embodiment, the compound of Formula (A) is selected from:
(12aS)-2-Acryloyl-10-chloro-9-(5-methyl-1H-indazol-4-yl)-1,2,3,4,12,12a-hexahydro-6H-benzo[f]pyrazino[2,1-c][1,4]oxazepin-6-one;
1-((12aS)-10-Chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one;
1-[(12aR)-10-Chloro-9-(2-fluoro-6-hydroxyphenyl)-7-methoxy-3,4,12,12a-tetrahydro-6H-pyrazino[2,1-c][1,4]benzoxazepin-2(1H)-yl]prop-2-en-1-one;
(12aR)-10-chloro-9-(2-fluoro-6-hydroxyphenyl)-7-hydroxy-2-(prop-2-enoyl)-1,2,3,4,12,12a-hexahydro-6H-pyrazino[2,1-c][1,4]benzoxazepin-6-one;
(12aR)-10-Chloro-9-(5-methyl-1H-indazol-4-yl)-2-(prop-2-enoyl)-1,2,3,4,12,12a-hexahydro-6H-pyrazino[2,1-c][1,4]benzoxazepin-6-one;
1-((12aR)-10-Chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one;
(12aR)-10-Chloro-8-fluoro-9-(2-fluoro-6-hydroxyphenyl)-2-(prop-2-enoyl)-1,2,3,4,12,12a-hexahydro-6H-pyrazino[2,1-c][1,4]benzoxazepin-6-one;
1-[(12aR)-8,10-dichloro-9-(2-fluoro-6-hydroxyphenyl)-7-hydroxy-3,4,12,12a-tetrahydro-6H-pyrazino[2,1-c][1,4]benzoxazepin-2(1H)-yl]prop-2-en-1-one;
1-[(12aR)-10-Chloro-9-(2-fluoro-6-hydroxyphenyl)-7-(1H-imidazol-1-yl)-3,4,12,12a-tetrahydro-6H-pyrazino[2,1-c][1,4]benzoxazepin-2(1H)-yl]prop-2-en-1-one;
(12aR)-10-Chloro-9-(2-fluoro-6-hydroxyphenyl)-2-(prop-2-enoyl)-1,2,3,4,12,12a-hexahydro-6H-pyrazino[2,1-c][1,4]benzoxazepine-7-carbonitrile;
1-[(12aR)-10-Chloro-9-(2-fluoro-6-hydroxyphenyl)-7-(1H-pyrazol-1-yl)-3,4,12,12a-tetrahydro-6H-pyrazino[2,1-c][1,4]benzoxazepin-2(1H)-yl]prop-2-en-1-one;
1-((12aR)-10-Chloro-8-fluoro-9-(5-methyl-1H-benzo[d]imidazol-4-yl)-3,4,12,12a-tetrahydro-6H-benzo[f]pyrazino[2,1-c][1,4]oxazepin-2(1H)-yl)prop-2-en-1-one;
(12aR)-8,10-Dichloro-9-(2-fluoro-6-hydroxyphenyl)-2-(prop-2-enoyl)-1,2,3,4,12,12a-hexahydro-6H-pyrazino[2,1-c][1,4]benzoxazepin-6-one;
(12aR)-10-Chloro-9-(2-fluoro-6-hydroxyphenyl)-2-(prop-2-enoyl)-1,2,3,4,12,12a-hexahydro-6H-pyrazino[2,1-c][1,4]benzoxazepine-8-carbonitrile;
(12aR)-10-Chloro-9-(2-fluoro-6-hydroxyphenyl)-8-methyl-2-(prop-2-enoyl)-1,2,3,4,12,12a-hexahydro-6H-pyrazino[2,1-c][1,4]benzoxazepin-6-one;
1-[(12aR)-8,10-Dichloro-9-(2-fluoro-6-hydroxyphenyl)-3,4,12,12a-tetrahydro-6H-pyrazino[2,1-c][1,4]benzoxazepin-2(1H)-yl]prop-2-en-1-one;
8-[(12aR)-10-Chloro-8-fluoro-2-(prop-2-enoyl)-1,2,3,4,12,12a-hexahydro-6H-pyrazino[2,1-c][1,4]benzoxazepin-9-yl]-7-methylisoquinolin-1(2H)-one;
1-[(12aR)-10-chloro-9-(2-fluoro-6-hydroxyphenyl)-8-methoxy-3,4,12,12a-tetrahydro-6H-pyrazino[2,1-c][1,4]benzoxazepin-2(1H)-yl]prop-2-en-1-one
(12aS)-10-Chloro-9-(5-methyl-1H-indazol-4-yl)-2-(prop-2-enoyl)-1,3,4,11,12,12a-hexahydropyrazino[2,1-c][1,4]benzodiazepin-6(2H)-one;
1-[(12aR)-10-chloro-9-(2-chloro-6-hydroxyphenyl)-8-fluoro-3,4,12,12a-tetrahydro-6H-pyrazino[2,1-c][1,4]benzoxazepin-2(1H)-yl]prop-2-en-1-one;
(12aS)-10-Chloro-11-methyl-9-(5-methyl-1H-indazol-4-yl)-2-(prop-2-enoyl)-1,3,4,11,12,12a-hexahydropyrazino[2,1-c][1,4]benzodiazepin-6(2H)-one;
1-[(12aR)-10-Chloro-9-(2,3-difluoro-6-hydroxyphenyl)-8-fluoro-3,4,12,12a-tetrahydro-6H-pyrazino[2,1-c][1,4]benzoxazepin-2(1H)-yl]prop-2-en-1-one;
(12aR)-10-Chloro-9-(2-hydroxy-6-methylphenyl)-2-(prop-2-enoyl)-1,2,3,4,12,12a-hexahydro-6H-pyrazino[2,1-c][1,4]benzoxazepine-8-carbonitrile;
1-[(12aR)-9-(2-Chloro-6-hydroxyphenyl)-8,10-difluoro-3,4,12,12a-tetrahydro-6H-pyrazino[2,1-c][1,4]benzoxazepin-2(1H)-yl]prop-2-en-1-one;
1-[(12aR)-8,10-Difluoro-9-(2-hydroxy-6-methylphenyl)-3,4,12,12a-tetrahydro-6H-pyrazino[2,1-c][1,4]benzoxazepin-2(1H)-yl]prop-2-en-1-one;
1-[(12aR)-8,10-Difluoro-9-[2-fluoro-6-(hydroxymethyl)phenyl]-3,4,12,12a-tetrahydro-6H-pyrazino[2,1-c][1,4]benzoxazepin-2(1H)-yl]prop-2-en-1-one;
1-[(12aR)-8,10-Difluoro-9-[2-hydroxy-6-(trifluoromethyl)phenyl]-3,4,12,12a-tetrahydro-6H-pyrazino[2,1-c][1,4]benzoxazepin-2(1H)-yl]prop-2-en-1-one;
1-[(12aR)-9-(2-Ethyl-6-hydroxyphenyl)-8,10-difluoro-3,4,12,12a-tetrahydro-6H-pyrazino[2,1-c][1,4]benzoxazepin-2(1H)-yl]prop-2-en-1-one;
1-[(12aR)-9-[2-(Difluoromethyl)-6-hydroxyphenyl]-8,10-difluoro-3,4,12,12a-tetrahydro-6H-pyrazino[2,1-c][1,4]benzoxazepin-2(1H)-yl]prop-2-en-1-one;
(12aR)-9-(2-Chloro-6-hydroxyphenyl)-10-fluoro-2-(prop-2-enoyl)-1,2,3,4,12,12a-hexahydro-6H-pyrazino[2,1-c][1,4]benzoxazepine-8-carbonitrile;
(12aR)-10-Chloro-9-(2-chloro-6-hydroxyphenyl)-2-(prop-2-enoyl)-1,2,3,4,12,12a-hexahydro-6H-pyrazino[2,1-c][1,4]benzoxazepine-8-carbonitrile;
1-[(12aR)-9-(2-Bromo-6-hydroxyphenyl)-8,10-difluoro-3,4,12,12a-tetrahydro-6H-pyrazino[2,1-c][1,4]benzoxazepin-2(1H)-yl]prop-2-en-1-one;
1-[(12aR)-8-Chloro-10-fluoro-9-(2-hydroxy-6-methylphenyl)-3,4,12,12a-tetrahydro-6H-pyrazino[2,1-c][1,4]benzoxazepin-2(1H)-yl]prop-2-en-1-one;
1-[(12aR)-8-Chloro-10-ethynyl-9-(2-hydroxy-6-methylphenyl)-3,4,12,12a-tetrahydro-6H-pyrazino[2,1-c][1,4]benzoxazepin-2(1H)-yl]prop-2-en-1-one;
1-[(12aR)-10-Ethynyl-8-fluoro-9-(2-hydroxy-6-methylphenyl)-3,4,12,12a-tetrahydro-6H-pyrazino[2,1-c][1,4]benzoxazepin-2(1H)-yl]prop-2-en-1-one;
(6aR)-4-Chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one;
1-[(6aR)-1,4-Dichloro-3-(2-fluoro-6-hydroxyphenyl)-6a,7,9,10-tetrahydro-12H-pyrazino[2,1-c]pyrido[3,4-f][1,4]oxazepin-8(6H)-yl]prop-2-en-1-one;
(6aR)-4-Chloro-3-(2-fluoro-6-hydroxyphenyl)-8-(prop-2-enoyl)-2,6,6a,7,8,9,10,12-octahydro-1H-pyrazino[2,1-c]pyrido[3,4-f][1,4]oxazepin-1-one;

1-[(8aR)-6-Chloro-5-(2-fluoro-6-hydroxyphenyl)-8a,9,11,12-tetrahydro-14H-pyrazino[2,1-c][1,2,4]triazolo[4',3':1,2]pyrido[3,4-f][1,4]oxazepin-10(8H)-yl]prop-2-en-1-one;

1-[(7aR)-5-chloro-4-(2-fluoro-6-hydroxyphenyl)-1-methyl-1,7a,8,10,11,13-hexahydropyrazino[2',1':3,4][1,4]oxazepino[7,6-g]indazol-9(7H)-yl]prop-2-en-1-one;

1-[(7aR)-5-Chloro-4-(2-fluoro-6-hydroxyphenyl)-2-methyl-2,7a,8,10,11,13-hexahydropyrazino[2',1':3,4][1,4]oxazepino[7,6-g]indazol-9(7H)-yl]prop-2-en-1-one;

1-[(12aR)-9-(2-chloro-6-hydroxyphenyl)-8-ethynyl-10-fluoro-3,4,12,12a-tetrahydro-6H-pyrazino[2,1-c][1,4]benzoxazepin-2(1H)-yl]prop-2-en-1-one; and 1-[(12aR)-10-Chloro-9-(2-chloro-6-hydroxyphenyl)-8-ethynyl-3,4,12,12a-tetrahydro-6H-pyrazino[2,1-c][1,4]benzoxazepin-2(1H)-yl]prop-2-en-1-one;

1-((12aR)-10-chloro-8-ethynyl-9-(2-fluoro-6-hydroxyphenyl)-3,4,12,12a-tetrahydro-6H-benzo[f]pyrazino[2,1-c][1,4]oxazepin-2(1H)-yl)prop-2-en-1-one;

1-[(7aR)-5-Chloro-4-(2-chloro-6-hydroxyphenyl)-1-methyl-1,7a,8,10,11,13-hexahydroimidazo[4,5-g]pyrazino[2,1-c][1,4]benzoxazepin-9(7H)-yl]prop-2-en-1-one;

1-[(12aR)-8-Chloro-9-(2-chloro-6-hydroxyphenyl)-10-fluoro-3,4,12,12a-tetrahydro-6H-pyrazino[2,1-c][1,4]benzoxazepin-2(1H)-yl]prop-2-en-1-one;

1-[(12aR)-9-(2-Chloro-6-hydroxyphenyl)-10-fluoro-8-(prop-1-yn-1-yl)-3,4,12,12a-tetrahydro-6H-pyrazino[2,1-c][1,4]benzoxazepin-2(1H)-yl]prop-2-en-1-one;

1-[(6aR)-4-Chloro-3-(2-chloro-6-hydroxyphenyl)-2-ethynyl-6a,7,9,10-tetrahydro-12H-pyrazino[2,1-c]pyrido[2,3-f][1,4]oxazepin-8(6H)-yl]prop-2-en-1-one;

1-[(12aR)-9-(2-Chloro-6-hydroxyphenyl)-8-ethynyl-10-methyl-3,4,12,12a-tetrahydro-6H-pyrazino[2,1-c][1,4]benzoxazepin-2(1H)-yl]prop-2-en-1-one;

1-[(12aR)-10-chloro-9-(2-chloro-6-hydroxyphenyl)-7,8-difluoro-3,4,12,12a-tetrahydro-6H-pyrazino[2,1-c][1,4]benzoxazepin-2(1H)-yl]prop-2-en-1-one;

1-[(12aR)-9-(2-chloro-6-hydroxyphenyl)-8-(difluoromethoxy)-10-fluoro-3,4,12,12a-tetrahydro-6H-pyrazino[2,1-c][1,4]benzoxazepin-2(1H)-yl]prop-2-en-1-one;

1-[(12aR)-9-(2-chloro-6-hydroxyphenyl)-8-ethynyl-7,10-difluoro-3,4,12,12a-tetrahydro-6H-pyrazino[2,1-c][1,4]benzoxazepin-2(1H)-yl]prop-2-en-1-one;

1-[(12aR)-10-Chloro-9-(2-chloro-6-hydroxyphenyl)-8-(difluoromethoxy)-3,4,12,12a-tetrahydro-6H-pyrazino[2,1-c][1,4]benzoxazepin-2(1H)-yl]prop-2-en-1-one;

1-[(12aR)-9-(2-chloro-6-hydroxyphenyl)-8-(cyclopropyloxy)-10-fluoro-3,4,12,12a-tetrahydro-6H-pyrazino[2,1-c][1,4]benzoxazepin-2(1H)-yl]prop-2-en-1-one;

1-((12aR)-9-(2-Chloro-6-hydroxyphenyl)-8-(3-(dimethylamino)prop-1-yn-1-yl)-10-fluoro-3,4,12,12a-tetrahydro-6H-benzo[f]pyrazino[2,1-c][1,4]oxazepin-2(1H)-yl)prop-2-en-1-one;

1-[(12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepin-2(1H)-yl]prop-2-en-1-one;

1-[(12aR)-10-chloro-9-(2-chloro-6-hydroxyphenyl)-8-(2-methoxyethoxy)-3,4,12,12a-tetrahydro-6H-pyrazino[2,1-c][1,4]benzoxazepin-2(1H)-yl]prop-2-en-1-one;

1-[(12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepin-2(1H)-yl]prop-2-en-1-one;

1-[(12aR)-10-Chloro-9-(2-chloro-6-hydroxyphenyl)-8-(prop-1-yn-1-yl)-3,4,12,12a-tetrahydro-6H-pyrazino[2,1-c][1,4]benzoxazepin-2(1H)-yl]prop-2-en-1-one;

1-[(6aR)-4-Chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepin-8(6H)-yl]prop-2-en-1-one;

1-[(12aR)-10-Chloro-9-(2-chloro-6-hydroxyphenyl)-8-(methoxymethyl)-3,4,12,12a-tetrahydro-6H-pyrazino[2,1-c][1,4]benzoxazepin-2(1H)-yl]prop-2-en-1-one; and 1-[(12aR)-9-(2-Chloro-6-hydroxyphenyl)-7-[2-(dimethylamino)ethoxy]-10-fluoro-3,4,12,12a-tetrahydro-6H-pyrazino[2,1-c][1,4]benzoxazepin-2(1H)-yl]prop-2-en-1-one;

1-[(6aR)-4-Chloro-3-(2-chloro-6-hydroxyphenyl)-1-(prop-1-yn-1-yl)-6a,7,9,10-tetrahydro-12H-pyrazino[2,1-c]pyrido[3,4-f][1,4]oxazepin-8(6H)-yl]prop-2-en-1-one; and 1-((6aR)-4-Chloro-3-(2-chloro-6-hydroxyphenyl)-1-ethynyl-6a,7,9,10-tetrahydro-12H-pyrazino[2,1-c]pyrido[3,4-f][1,4]oxazepin-8(6H)-yl)prop-2-en-1-one;

or a pharmaceutically acceptable salt thereof.

As will be appreciated by the person of skill in the art, the compounds of the present specification contain a biaryl bond between ring A and the ring containing X and Y.

Statements relating to compounds of Formula (I) herein below, should be read to apply equally to compounds of Formula (A).

The compounds of Formula (A), for example compounds of Formula (I), have one or more chiral centres, for example at the bridgehead carbon between the piperazine to which the acrylamide is attached and the ring comprising Z, and it will be recognised that the compound of Formula (A), for example compounds of Formula (I), may be prepared, isolated and/or supplied with or without the presence, in addition, of one or more of the other possible stereoisomeric forms of the compound of Formula (A) in any relative proportions. The preparation of stereo enriched or stereopure compounds may be carried out by standard techniques of organic chemistry that are well known in the art, for example by synthesis from stereo enriched or stereopure starting materials, use of an appropriate stereo enriched or stereopure catalysts during synthesis, and/or by resolution of a racemic or partially enriched mixture of stereoisomers, for example via chiral chromatography. In preferred embodiments, the compounds of the present specification are in the (R)-configuration when Z is O as shown below.

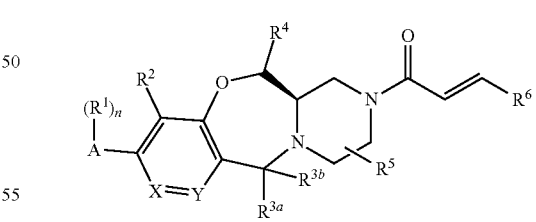

In particular, the compounds of Formula (I) may possess axial chirality, by virtue of restricted rotation around the biaryl bond between A and the ring containing X and Y and as such may exist as mixtures of atropisomers with enantiomeric excess between about 0% and >98% e.e. When a compound is a pure atropisomer, the stereochemistry at each chiral centre may be specified by either aR or aS. Such designations may also be used for mixtures that are enriched in one atropisomer. By way of example only, the following moiety may exhibit atropisomerism and be capable of resolution into the aR and aS atropisomers by chiral chromatography. For illustration, the two atropisomers of a compound of Formula (I) in which the ring A is 2-F, 6-hydroxyphenyl are shown below ($R^3$, $R^4$, $R^5$ and $R^6$ are omitted for clarity).

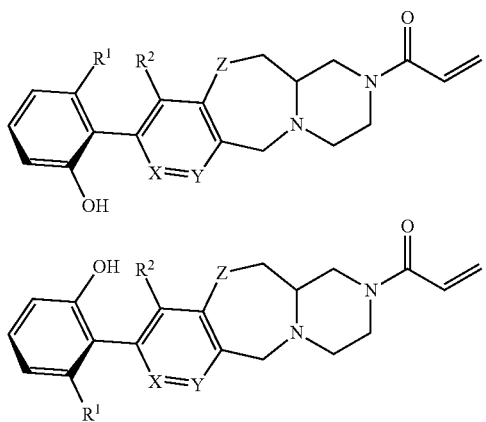

Further description of atropisomerism and axial chirality and rules for assignment of configuration can be found in Eliel, E. L. & Wilen, S. H. 'Stereochemistry of Organic Compounds' John Wiley and Sons, Inc. 1994. In the compounds of the specification the groups $R^1$, $R^2$ and X may be selected to eliminate or substantially reduce the interconversion between the (aR) and (aS) atropisomers.

In more detail, the interaction between the group(s) $A(R^1)_n$ and the substituent $R^2$ and/or X may advantageously restrict the rotation around the bond between the ring A and the ring containing X. The interaction between the substituent $R^2$ and the ring A and/or the substituent(s) $R^1$ thereon may as a result be used to stabilise atropisomers of the compounds according to the present specification. This in turn may advantageously allow isolation of a stable atropisomer that exhibits higher activity as an inhibitor of G12C mutated Ras than the second atropisomer. It will be understood that the more active atropisomers are preferred embodiments.

In embodiments of the compound of Formula (I) wherein the group X is substituted, that substituent may, like $R^2$, be capable of stabilising atropisomers of the compounds according to the specification.

In embodiments of the present specification there is also provided an intermediate (II), or a derivative thereof protected at the piperazine NH (marked with * below for the compound of Formula (IX)) useful for the preparation of a compound of Formula (I) wherein the groups and substituents are as defined for any of compounds of Formula (I) to Formula (Ir) above.

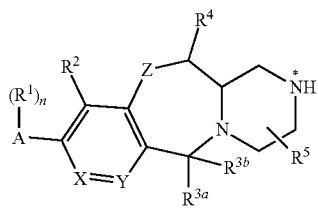

(IX)

In a related embodiment, there is provided a method for synthesising a compound of Formula (I) involving reaction of a compound of Formula (IX) with i) acryloyl chloride, or an equivalent thereof such as acryloyl anhydride, and a base or ii) acrylic acid or an ester thereof and a coupling reagent. In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% d.e.) of 90%.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of 90% and a diastereomeric excess (% de) of >90%.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) may be, for example, an acid addition salt. A suitable pharmaceutically acceptable salt of a compound of the Formula (I) may be, for example, an acid-addition salt of a compound of the Formula (I), for example an acid-addition salt with an inorganic or organic acid. The compounds of the specification may be provided as the free compound, i.e. in the non-salified state.

A further suitable pharmaceutically acceptable salt of a compound of the Formula (I) may be, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

The compound of Formula (I), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses, for example in an oral dose of from 1 mg to 1,000 mg or from 100 mg to 2,000 mg.

The pharmaceutical formulations of the compound of Formula (I) described above may be prepared e.g. for parenteral, subcutaneous, intramuscular or intravenous administration.

The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, PA, (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. An exemplary oral composition would comprise a compound of Formula (I) and at least one pharmaceutically acceptable excipient filled into a two-piece hard shell capsule or a soft elastic gelatin (SEG) capsule.

According to a further embodiment there is provided a compound of the Formula (I), or a pharmaceutically acceptable salt thereof, as defined hereinbefore, for use as a medicament in a warm-blooded animal such as man.

According to a further embodiment, there is provided a compound of the Formula (I), or a pharmaceutically acceptable salt thereof, as defined hereinbefore for use in the production of an anti-proliferative effect in a warm-blooded animal such as man.

According to a further embodiment, there is provided a compound of the Formula (I), or a pharmaceutically acceptable salt thereof, as defined hereinbefore for use in a warm-blooded animal such as man as an anti-invasive agent in the containment and/or treatment of solid tumour disease.

According to a further embodiment, there is provided the use of a compound of the Formula (I), or a pharmaceutically acceptable salt thereof, as defined hereinbefore, for the production of an anti-proliferative effect in a warm-blooded animal such as man.

According to a further embodiment, there is provided the use of a compound of the Formula (I), or a pharmaceutically acceptable salt thereof, as defined hereinbefore, in the manufacture of a medicament for use in the production of an anti-proliferative effect in a warm-blooded animal such as man.

According to a further embodiment, there is provided the use of a compound of the Formula (I), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further embodiment, there is provided a method for producing an anti-proliferative effect in a warm-blooded animal, such as man, in need of such treatment which comprises administering to said animal an effective amount of a compound of the Formula (I), or a pharmaceutically acceptable salt thereof, as defined hereinbefore.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The effective amount will generally be in the range of 0.1 mg to 1,000 mg.

According to a further embodiment, there is provided a method for producing an anti-invasive effect by the containment and/or treatment of solid tumour disease in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore, for use in the prevention or treatment of cancer in a warm-blooded animal such as man.

According to a further embodiment, there is provided the use of a compound of the Formula (I), or a pharmaceutically acceptable salt thereof, as defined hereinbefore in the manufacture of a medicament for use in the prevention or treatment of cancer in a warm-blooded animal such as man.

According to a further embodiment, there is provided a method for the prevention or treatment of cancer in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore for use in the prevention or treatment of solid tumour disease in a warm-blooded animal such as man.

According to a further embodiment, there is provided the use of a compound of the Formula (I), or a pharmaceutically acceptable salt thereof, as defined hereinbefore, in the manufacture of a medicament for use in the prevention or treatment of solid tumour disease in a warm-blooded animal such as man.

According to a further embodiment, there is provided a method for the prevention or treatment of solid tumour disease in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore, for use in the prevention or treatment of tumours which are sensitive to inhibition of G12C mutant Ras.

According to a further embodiment, there is provided the use of a compound of the Formula (I), or a pharmaceutically acceptable salt thereof, as defined hereinbefore, in the manufacture of a medicament for use in the prevention or treatment of those tumours which are sensitive to inhibition of G12C mutant Ras.

According to a further embodiment, there is provided a method for the prevention or treatment of those tumours which are sensitive to inhibition of G12C mutant RAS, which comprises administering to a patient in need thereof an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore for use in providing an inhibitory effect on G12C mutant Ras.

According to a further embodiment, there is provided the use of a compound of the Formula (I), or a pharmaceutically acceptable salt thereof, as defined hereinbefore in the manufacture of a medicament for use in providing an inhibitory effect on G12C mutant Ras.

According to a further embodiment, there is also provided a method for providing an inhibitory effect on G12C mutant RAS which comprises administering an effective amount of a compound of the Formula (I), or a pharmaceutically acceptable salt thereof, as defined hereinbefore, to a patient in need thereof.

According to a further embodiment, there is provided a compound of the Formula (I), or a pharmaceutically acceptable salt thereof, as defined hereinbefore, for use in providing a selective inhibitory effect on G12C mutant Ras.

According to a further embodiment, there is provided the use of a compound of the Formula (I), or a pharmaceutically acceptable salt thereof, as defined hereinbefore, in the manufacture of a medicament for use in providing a selective inhibitory effect on G12C mutant Ras.

According to a further embodiment, there is also provided a method for providing a selective inhibitory effect on G12C mutant Ras which comprises administering an effective amount of a compound of the Formula (I), or a pharmaceutically acceptable salt thereof, to a patient in need thereof.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma.

According to a further embodiment, there is provided a compound of the Formula (I), or a pharmaceutically acceptable salt thereof, as defined hereinbefore, for use in the treatment of disorders mediated by KRas, NRas or HRas G12C mutations.

According to a further embodiment, there is provided a method for treating disorders mediated by KRas, NRas or HRas G12C mutations, which comprises administering an effective amount of a compound of the Formula (I), or a pharmaceutically acceptable salt thereof, as defined hereinbefore.

According to a further embodiment, there is provided the use of a compound of the Formula (I), or a pharmaceutically acceptable salt thereof, as defined hereinbefore, in the manufacture of a medicament for use in the treatment of disorders mediated by KRas, NRas or HRas G12C mutations.

According to a further embodiment, there is provided a compound of the Formula (I), or a pharmaceutically acceptable salt thereof, as defined hereinbefore, for use in the treatment of pancreatic cancer, non-small cell lung cancer or colorectal cancer.

According to a further embodiment, there is provided a compound of the Formula (I), or a pharmaceutically acceptable salt thereof, as defined hereinbefore, for use in the treatment of non-small cell lung cancer.

According to a further embodiment, there is provided a method for treating pancreatic cancer, non-small cell lung cancer or colorectal cancer, which comprises administering an effective amount of a compound of the Formula (I), or a pharmaceutically acceptable salt thereof, as defined hereinbefore to a patient in need thereof.

According to a further embodiment, there is provided a method for treating non-small cell lung cancer, which comprises administering an effective amount of a compound of the Formula (I), or a pharmaceutically acceptable salt thereof, to a patient in need thereof.

According to a further embodiment, there is provided the use of a compound of the Formula (I), or a pharmaceutically acceptable salt thereof, as defined hereinbefore, in the manufacture of a medicament for use in the treatment of pancreatic cancer, non-small cell lung cancer or colorectal cancer.

According to a further aspect of the specification, there is provided the use of a compound of the Formula (I), or a pharmaceutically acceptable salt thereof, as defined hereinbefore, in the manufacture of a medicament for use in the treatment of non-small cell lung cancer.

The anti-cancer treatment defined herein may be applied as a sole therapy or may involve, in addition to the compounds of the specification, conventional surgery or radiotherapy or chemotherapy.

Accordingly, in one embodiment, there is provided a compound of Formula (I), or a pharmaceutically acceptable salt thereof, and an additional anti-tumour substance for the conjoint treatment of cancer.

According to an embodiment of the specification there is provided a combination suitable for use in the treatment of cancer comprising a compound of the Formula (I) or a pharmaceutically acceptable salt thereof and another anti-tumour agent.

In a further embodiment of the specification there is provided a compound of the Formula (I), or a pharmaceutically acceptable salt thereof, in combination with another anti-tumour agent. In a related embodiment there is provided a method of treatment comprising administering a compound of Formula (I) in combination with another anti-tumour agent to a patient in need thereof, for example a patient suffering from a cancer expressing G12C mutant Ras.

Although the compounds of the Formula (I) are primarily of value as therapeutic agents for use in warm-blooded animals (including man), they are also useful whenever it is required to inhibit G12C mutant Ras. Thus, they are useful as pharmacological standards for use in the development of new biological tests and in the search for new pharmacological agents.

Another embodiment is based on identifying a link between the G12C KRas, HRas or NRas mutation status of a patient and potential susceptibility to treatment with a compound of Formula (I). A Ras inhibitor, such as a compound of Formula (I), may then advantageously be used to treat patients with G12C KRas, HRas or NRas mutations who may be resistant to other therapies. This therefore provides opportunities, methods and tools for selecting patients for treatment with a compound of Formula (I), particularly cancer patients. The selection is based on whether the tumour cells to be treated possess wild-type or G12C mutant KRAS, HRAS or NRAS gene. The G12C KRAS, HRAS or NRAS gene status could therefore be used as a biomarker to indicate that selecting treatment with a compound of Formula (I) may be advantageous.

According to one embodiment, there is provided a method for selecting a patient for treatment with a compound of Formula (I), the method comprising providing a tumour cell-containing sample from a patient; determining whether the RAS gene in the patient's tumour cell-containing sample encodes for wild-type (glycine at position 12) or mutant (cysteine at position 12) KRas, HRas or NRas protein; and selecting a patient for treatment with a compound of Formula (I) based thereon.

The method may include or exclude the actual patient sample isolation step. Thus, according to one embodiment there is provided a method for selecting a patient for treatment with a compound of Formula (I), the method comprising determining whether the RAS gene in a tumour cell-containing sample previously isolated from the patient encodes for wild-type (glycine at position 12) or mutant (cysteine at position 12) KRas, HRas or NRas protein; and selecting a patient for treatment with a compound of Formula (I) based thereon.

In embodiments, the patient is selected for treatment with a compound of Formula (I) if the tumour cell DNA has a G12C mutant KRAS gene.

In embodiments, the patient is selected for treatment with a compound of Formula (I) if the tumour cell DNA has a G12C mutant HRAS gene.

In embodiments, the patient is selected for treatment with a compound of Formula (I) if the tumour cell DNA has a G12C mutant NRAS gene.

According to another embodiment, there is provided a compound of Formula (I), or a pharmaceutically acceptable salt thereof, for use in treating cancers with tumour cells identified as harbouring a G12C mutant KRAS gene.

According to another embodiment, there is provided a compound of Formula (I), or a pharmaceutically acceptable salt thereof, for use in treating cancers with tumour cells identified as harbouring a G12C mutant HRAS gene.

According to another aspect of the specification there is provided a compound of Formula (I), or a pharmaceutically acceptable salt thereof, for use in treating cancers with tumour cells identified as harbouring a G12C mutant NRAS gene.

According to another embodiment, there is provided a method of treating cancers with tumour cells identified as harbouring a G12C mutant KRAS, HRAS or NRAS gene comprising administering an effective amount of a compound of Formula (I) or a pharmaceutically acceptable salt thereof.

According to another embodiment, there is provided a pharmaceutical composition comprising a compound of Formula (I) for use in the prevention and treatment of cancer with tumour cells identified as harbouring a G12C mutant KRAS, HRAS or NRAS gene.

It will be appreciated that the following examples are provided so that the nature of the invention may be fully understood. It will also be appreciated that the following examples are not intended to limit the scope of the description in any way.

Biological Assays

The following assays were used to measure the effects of the compounds of the present specification.

KRasG12C Functional Assay

The inactive GDP loaded biotinylated $KRas^{G12C}$ protein was expressed, purified and GDP loaded in house. All enzyme and substrate solutions were prepared in assay buffer containing 20 mM HEPES (pH 7.5), 5 mM $MgCl_2$, 150 mM NaCl, and 0.01% Tween 20. 10 nM GDP loaded biotinylated KRasG12c and 37.5 ng/ml Streptavidin Europium Cryptate (Cisbio) were prepared in assay buffer, 5 µl was dispensed into each well of a 384 polystyrene, Hibase, medium binding white assay plate (Greiner, #784075) containing test and reference samples prepared in DMSO and the samples incubated for 4 hrs. In a separate mix 20 nM GST-Raf Ras binding domain (GST-Raf RBD, purified in house) and 4 µg/ml anti-GST XL665 antibody (Cisbio) was prepared in assay buffer containing 50 mM Potassium Fluoride and 0.05 mg/ml BSA and equilibrated for 4 hours before adding 0.6 µM Guanosine 5'-[γ-thio]triphosphate (GTPγS, Sigma) and 0.08 µM SOS (purified in house). 5 µl of the GST-RAF RBD mix was then dispensed into each well of the assay plate. This addition initiates the nucleotide exchange reaction and transition of inactive GDP loaded $KRas^{G12C}$ to active GTPγS $KRas^{G12C}$. This is detected simultaneously via the specific binding interaction between active GTPγS $KRas^{G12C}$ with GST-Raf RBD which brings the europium and XL665 into close proximity enabling an increased FRET signal to be detected on a Pherastar (BMG) plate reader equipped with the HTRF filter module. Any compound which prevents the activation of KRas via inhibiting the nucleotide exchange process, or inhibits the active KRas:Raf RBD binding interaction, will result in a reduced FRET signal. $IC_{50}$ values were calculated from normalised dose-response response FRET data curve fitted in Genedata screener (Basel, Switzerland).

The data from this KRasG12C Functional Assay is presented in Table A below.

KRasG12C Mass Spectrometry Adducting Assay

The inactive GDP loaded biotinylated $KRas^{G12C}$ protein was expressed, purified and GDP loaded in house. Enzyme solutions were prepared in assay buffer containing 20 mM HEPES (pH 7.5), 5 mM MgCl2, and 150 mM NaCl. 4 µM GDP loaded biotinylated $KRas^{G12C}$ was prepared in assay buffer and 50 µl added into each well of a 96 well polypropylene assay plate (Greiner, #651201) containing 500 nl of 1 mM test compounds (final concentration 10 µM), this was allowed to react for 4 hours before the addition of 50 µl 1% Formic acid to quench the reaction. The plate was sealed before reading on a Xevo G2 QTOF (Waters) and Acquity LC system (Waters). 10 µl of sample was injected onto a Xbridge BEH300; C4; 3.5 um; 2.1×50 mm column (Waters) running a 3 minute gradient. Blank samples were run in between each test sample.

Data was analysed in Mass Lynx software (Waters), the Total ion count (TIC) trace was used and the eluted protein peak data combined. Using the combined spectrum the data was deconvoluted using MaxEnt1 method. The peak area for apo-protein KRas$^{G12C}$ (APO) and KRAS+relative cmpd mass (adduct) were measured, and a percentage adduct was calculated using the following calculation:

Percent adduct=100*(area of adduct peak/(sum of APO+adduct peaks).

The data from this mass spectrometry adducing assay is presented in the column labelled KRasG12C M.S. Binding Mean adduct % in Table A below.

The data shown in Table A were generated for the Examples (the data below may be a result from a single experiment or an average of two or more experiments).

As can be seen from Table A, the compounds of the specification prevent the activation of KRas via inhibiting the nucleotide exchange process, or via inhibiting the active KRas:Raf RBD binding interaction, as seen from the reduced FRET signal in the KRasG12C functional assay. In addition, the compounds of the specification proved to be effective covalently binders to KRasG12C in the KRasG12C Mass Spectrometry adducting assay. It can also be seen that the difference in activity between the various atropisomeric pairs is usually pronounced, for example 10- or 20-fold or more.

TABLE A

| Example | KRasG12C functional assay IC$_{50}$ (μM) | KRasG12C M.S. Binding Mean adduct % |
|---|---|---|
| 1 | 73 | |
| 2 | 4.5 | |
| 3 | 1.41 | 80 |
| 4 | 74 | 0 |
| 5 | 0.157 | 94 |
| 6 | 0.103 | 96 |
| 7 | 82 | |
| 8 | 0.698 | 91 |
| 9 | 26 | |
| 10 | 0.332 | 97 |
| 11 | 0.067 | |
| 12 | 25.2 | |
| 13 | 0.066 | 95 |
| 14 | 8.19 | 13 |
| 15 | 1.28 | |
| 16 | 0.43 | |
| 17 | 0.361 | 88 |
| 18 | 28.7 | 4 |
| 19 | 0.146 | 95 |
| 20 | 0.043 | 96 |
| 21 | 12.9 | 4 |
| 22 | 2.58 | |
| 23 | 0.105 | 93 |
| 24 | 43.8 | 10 |
| 25 | 0.068 | 97 |
| 26 | 1 | |
| 27 | 0.024 | 96 |
| 28 | 17 | 3 |
| 29 | 0.164 | 95 |
| 30 | 90.5 | 4 |
| 31 | 0.279 | 95 |
| 32 | 64.8 | |
| 33 | 0.998 | 90 |
| 34 | 64.9 | |
| 35 | 0.042 | 95 |
| 36 | 98.2 | 2 |
| 37 | 0.273 | 96 |
| 38 | 40.1 | 0 |
| 39 | 0.123 | |
| 40 | 4.62 | |
| 41 | 0.18 | 96 |
| 42 | 2.61 | 12 |
| 43 | 0.033 | 95 |
| 44 | >100 | |
| 45 | 0.066 | 97 |
| 46 | 99.5 | 2 |
| 47 | 1.72 | 51 |
| 48 | 42.7 | 5 |
| 49 | 0.065 | |
| 50 | 99.3 | |
| 51 | 0.542 | 88 |
| 52 | >100 | 1 |
| 53 | 0.66 | 34 |
| 54 | 0.339 | |
| 55 | 0.016 | |
| 56 | 1.7 | 5 |
| 57 | 0.031 | |
| 58 | 11.8 | |
| 59 | 0.032 | |
| 60 | 15.9 | |
| 61 | 0.0277 | 98 |
| 62 | 15.7 | 11 |
| 63 | 0.12 | |
| 64 | 37.1 | |
| 65 | 0.182 | |
| 66 | 21 | |
| 67 | 0.81 | |
| 68 | 0.79 | |
| 69 | 0.618 | |
| 70 | 19 | |
| 71 | 0.539 | |
| 72 | 0.133 | |
| 73 | 23 | |
| 74 | 0.135 | |
| 75 | 50.8 | |
| 76 | 0.0186 | |
| 77 | 0.937 | |
| 78 | 0.0193 | |
| 79 | | |
| 80 | 0.083 | |
| 81 | | |
| 82 | 0.061 | |
| 83 | | |
| 84 | 0.025 | |
| 85 | | |
| 86 | 0.015 | |
| 87 | | |
| 88 | 0.013 | |
| 89 | | |
| 90 | 0.054 | |
| 91 | | |
| 92 | 0.053 | |
| 93 | | |
| 94 | 0.014 | |
| 95 | 0.019 | |
| 96 | | |
| 97 | | |
| 98 | 0.011 | |
| 99 | | |
| 100 | 0.08 | |
| 101 | | |
| 102 | 0.028 | |
| 103 | | |
| 104 | 0.027 | |
| 105 | | |
| 106 | 0.043 | |
| 107 | | |
| 108 | 0.064 | |
| 109 | 0.014 | |
| 110 | | |
| 111 | | |

TABLE A-continued

| Example | KRasG12C functional assay IC$_{50}$ (µM) | KRasG12C M.S. Binding Mean adduct % |
|---|---|---|
| 112 | 0.044 | |
| 113 | | |
| 114 | 0.083 | |
| 115 | 0.055 | |
| 116 | 0.053 | |
| 117 | | |
| 118 | 0.030 | |
| 119 | | |
| 120 | 0.051 | |

Blood Brain Barrier Penetrant Assessment

In order to evaluate blood brain barrier (BBB) penetrant properties the efflux properties of compounds according to the specification was measured in cells transfected with the major efflux pumps expressed in the endothelial cells of the BBB. The assessment of efflux properties was performed using Madin-Darby Canine Kidney (MDCK) cells doubly transfected with MDR1 (Pgp) and BCRP. The transfected cell line, MDCK_MDR1_BCRP, thus expresses the two main efflux pumps that actively serve to exclude transit of compounds across the BBB and the efflux ration from these cell can be measured as described in the literature (Durant et al, *Sci. Adv.* 2018; eeat:1719). A compound that has an efflux ratio of 2 or less as measured by this technique is identified as having the potential for good BBB penetrant properties (Colclough et al, *Drug Disc. Today* 2019; 24(5), 1067-73). Efflux ratios for selected compounds according to the specification are provided in Table B below.

TABLE B

| Example No | Hu MDCK-MDR1-BCRP (0.1 uM) Mean Efflux Ratio |
|---|---|
| 4 | 0.9 |
| 11 | 0.5 |
| 27 | 0.8 |
| 35 | 1.8 |
| 43 | 0.7 |
| 45 | 1.3 |
| 49 | 0.9 |
| 53 | 1.5 |
| 59 | 0.8 |
| 61 | 0.3 |
| 65 | 1.4 |
| 76 | 0.8 |
| 78 | 0.7 |
| 80 | 0.7 |
| 84 | 0.6 |
| 86 | 0.9 |
| 90 | 0.6 |
| 92 | 0.7 |
| 95 | 0.9 |
| 109 | 0.9 |
| 112 | 1.5 |

EXAMPLES

The specification will now be illustrated in the following Examples in which, unless stated otherwise:
 (i) all syntheses were carried out at ambient temperature, i.e. in the range 17 to 25° C. and under an atmosphere of an inert gas such as nitrogen unless otherwise stated;
 (ii) evaporations were carried out by rotary evaporation or utilising Genevac equipment or Biotage v10 evaporator in vacuo and work up procedures were carried out after removal of residual solids by filtration;
 (iii) flash column chromatography was performed on Merck Kieselgel silica (Art. 9385) or on reversed phase silica (Fluka silica gel 90 C18) or on Silicycle cartridges (40-63 µm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 µm silica) or on Interchim puriFlash cartridges (50 µm silica, 4-800 g) either manually or automated using an Isco Combi-Flash Companion system or similar system;
 (iv) preparative reverse phase HPLC was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents;
 (v) yields, where present, are not necessarily the maximum attainable;
 (vi) in general, the structures of end products of the Formula I were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;
 (vii) in general, end products of the Formula I were also characterized by mass spectroscopy following liquid chromatography (LCMS or UPLC); in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the [M+H]+ unless otherwise specified;
 (viii) ion exchange purification was generally performed using an SCX-2 (Biotage) cartridge;
 (ix) where reactions refer to the use of a microwave, one of the following microwave reactors were used: Biotage Initiator, Personal Chemistry Emrys Optimizer, Personal Chemistry Smith Creator or CEM Explorer;

(x) intermediate purity was assessed by thin layer chromatographic, mass spectroscopy, LCMS, UPLC/MS, HPLC and/or NMR analysis;

(xi) the following abbreviations have been used:

Boc—tert-butyloxycarbonyl; DCM—dichloromethane; DIPEA—N,N-diisopropylethylamine; DMA—dimethylacetamide; DMF—dimethylformamide; EtOAc—ethyl acetate; h—hour; HATU—(1-[Bis(dimethylamino)methylene]-1H-1,2,3-triazolo[4,5-b]pyridinium 3-oxid hexafluorophosphate; MeCN—acetonitrile; MeOH—methanol; iPrOH—isopropanol; NMP—N-methyl-2-pyrrolidone; rt—room temperature; RuPhos Pd G3—(2-dicyclohexylphosphino-2',6'-diisopropoxy-1,1'-biphenyl)[2-(2'-amino-1,1'-biphenyl)]palladium(II) methanesulfonate; RuPhos—2-dicyclohexylphosphino-2',6'-diisopropoxybiphenyl; SCX—Strong Cation eXchange; tert-butyl BrettPhos Pd G3—[(2-Di-tert-butylphosphino-3,6-dimethoxy-2',4',6'-triisopropyl-1,1'-biphenyl)-2-(2'-amino-1,1'-biphenyl)]palladium(II) methanesulfonate; TFA—trifluoroacetic acid; THF—tetrahydrofuran; XPhos Pd G3—(2-Dicyclohexylphosphino-2',4',6'-triisopropyl-1,1'-biphenyl)[2-(2'-amino-1,1'-biphenyl)]palladium(II) methanesulfonate.

Tert-butyl (S)-4-(4-bromo-3-chloro-2-fluorobenzoyl)-3-(hydroxymethyl)piperazine-1-carboxylate

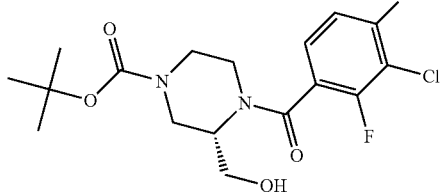

Tert-butyl (S)-3-(hydroxymethyl)piperazine-1-carboxylate (0.875 g, 4.05 mmol) was added to 4-bromo-3-chloro-2-fluorobenzoyl chloride (1 g, 3.68 mmol) and triethylamine (0.538 mL, 3.86 mmol) in THF (36.2 mL) at rt. The reaction was stirred for 1 h. The reaction was diluted with EtOAc (100 mL), washed with water (50 mL) and brine (100 mL), the organic layer was dried (MgSO₄) and evaporated to afford crude product. This was triturated with MeOH to give a solid which was collected by filtration and dried under vacuum to give tert-butyl (S)-4-(4-bromo-3-chloro-2-fluorobenzoyl)-3-(hydroxymethyl)piperazine-1-carboxylate (1.471 g, 89%) as a white solid. 1H NMR (500 MHz, DMSO, 100° C.) 1.43 (9H, s), 2.88 (1H, td), 3.03 (2H, d), 3.37-3.59 (3H, m), 3.79-4.08 (3H, m), 4.54 (1H, t), 7.34 (1H, dd), 7.68 (1H, dd). m/z: ES+ [M-Boc]+ 352.

Tert-butyl (S)-9-bromo-10-chloro-6-oxo-3,4,12,12a-tetrahydro-6H-benzo[f]pyrazino[2,1-c][1,4]oxazepine-2(1H)-carboxylate

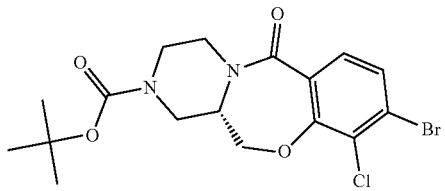 [SMILES: CC(C)(C)OC(=O)N1CCN2C(=O)c3ccc(Br)c(Cl)c3OC[C@@H]2C1]

Sodium hydride (60% in mineral oil) (0.143 g, 3.58 mmol) was added in one portion to tert-butyl (S)-4-(4-bromo-3-chloro-2-fluorobenzoyl)-3-(hydroxymethyl)piperazine-1-carboxylate (1.471 g, 3.26 mmol) in DMF (13.03 mL) at rt. The resulting slurry was stirred at rt overnight. The reaction mixture was diluted with water (100 mL) and EtOAc (100 mL) and washed sequentially with saturated NH₄Cl (20 mL) and brine (3×100 mL). The organic layer was dried (MgSO₄) and evaporated to afford crude product. This was dissolved in DCM (2 mL) and filtered through a small pad of silica, eluting with 50% EtOAc/Heptane, to afford tert-butyl (S)-9-bromo-10-chloro-6-oxo-3,4,12,12a-tetrahydro-6H-benzo[f]pyrazino[2,1-c][1,4]oxazepine-2(1H)-carboxylate (1.25 g, 89%) as a pale yellow oil which solidified on standing. 1H NMR (500 MHz, DMSO, 27° C.) 1.41 (9H, s), 3.47 (2H, s), 3.52 (1H, dd), 3.63 (1H, d), 3.74 (1H, d), 3.85-3.99 (2H, m), 4.34 (2H, s), 7.55 (1H, d), 7.63 (1H, d).

Tert-butyl (12aS)-10-chloro-9-(5-methyl-1H-indazol-4-yl)-6-oxo-3,4,12,12a-tetrahydro-6H-benzo[f]pyrazino[2,1-c][1,4]oxazepine-2(1H)-carboxylate

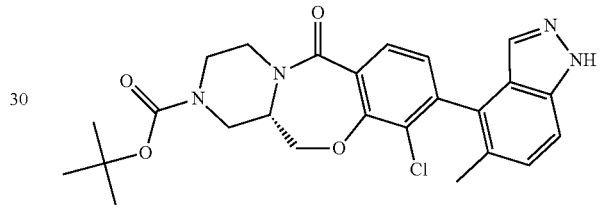

A solution of (5-Methyl-1H-indazol-4-yl)boronic acid (0.306 g, 1.74 mmol), tert-butyl (S)-9-bromo-10-chloro-6-oxo-3,4,12,12a-tetrahydro-6H-benzo[f]pyrazino[2,1-c][1,4]oxazepine-2(1H)-carboxylate (0.5 g, 1.16 mmol) and Pd(PPh₃)₄ (0.134 g, 0.12 mmol) in dioxane (9.84 mL) was degassed and Na₂CO₃ (2M) (1.737 mL, 3.47 mmol) was added. The reaction was stirred at 100° C. for 16 h. The reaction was cooled to rt, diluted with EtOAc (50 mL), washed with brine (2×50 mL), the organic phase dried (MgSO₄) and evaporated to afford crude product. This was purified by flash silica chromatography, elution gradient 0 to 10% MeOH in DCM, to afford tert-butyl (12aS)-10-chloro-9-(5-methyl-1H-indazol-4-yl)-6-oxo-3,4,12,12a-tetrahydro-6H-benzo[f]pyrazino[2,1-c][1,4]oxazepine-2(1H)-carboxylate (0.442 g, 79%) as a pale yellow gum. m/z: ES− [M−H]− 481/483.

(12aS)-10-Chloro-9-(5-methyl-1H-indazol-4-yl)-1,2,3,4,12,12a-hexahydro-6H-benzo[f]pyrazino[2,1-c][1,4]oxazepin-6-one

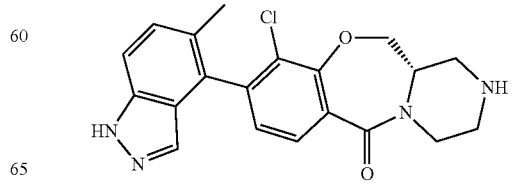

TFA (2.66 mL) was added to a solution of tert-butyl (12aS)-10-chloro-9-(5-methyl-1H-indazol-4-yl)-6-oxo-3,4,12,12a-tetrahydro-6H-benzo[f]pyrazino[2,1-c][1,4]oxazepine-2(1H)-carboxylate (0.642 g, 1.33 mmol) in DCM (2.66 mL). The reaction mixture was stirred at rt for 1 h. The mixture was diluted with MeOH (10 mL) and purified by SCX (7M NH₃/MeOH) to afford (12aS)-10-chloro-9-(5-methyl-1H-indazol-4-yl)-1,2,3,4,12,12a-hexahydro-6H-benzo[f]pyrazino[2,1-c][1,4]oxazepin-6-one (0.479 g, 94%) as a yellow gum. m/z: ES+ [M+H]+ 383.

(12aS)-2-Acryloyl-10-chloro-9-(5-methyl-1H-indazol-4-yl)-1,2,3,4,12,12a-hexahydro-6H-benzo[f]pyrazino[2,1-c][1,4]oxazepin-6-one Rotational Isomer 1, Example 1, and Rotational Isomer 2, Example 2

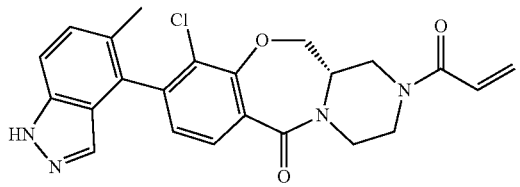 [SMILES: C=CC(=O)N1CCN2C(=O)c3ccc(-c4c(C)ccc5[nH]ncc45)c(Cl)c3OC[C@@H]2C1]

Acryloyl chloride (0.106 mL, 1.31 mmol) was added dropwise to (12aS)-10-chloro-9-(5-methyl-1H-indazol-4-yl)-1,2,3,4,12,12a-hexahydro-6H-benzo[f]pyrazino[2,1-c][1,4]oxazepin-6-one (0.479 g, 1.25 mmol) and DIPEA (0.240 mL, 1.38 mmol) in DMA (2.156 mL) cooled to 0° C. over a period. The resulting solution was stirred at rt for 2 h. The reaction mixture was poured into water and the resulting solid was collected by filtration, washed with water and dried under vacuum to afford crude product. This was purified by preparative HPLC (Waters XSelect CSH C18 ODB column, 5μ silica, 30 mm diameter, 100 mm length), using of water (containing 1% by volume NH₃OH (28-30% in H₂O)) and MeCN as eluents. This gave rotational isomer 1 of (12aS)-2-acryloyl-10-chloro-9-(5-methyl-1H-indazol-4-yl)-1,2,3,4,12,12a-hexahydro-6H-benzo[f]pyrazino[2,1-c][1,4]oxazepin-6-one (0.05 g, 18%) as a colourless gum. 1H NMR (500 MHz, DMSO, 27° C.) 2.16 (3H, s), 3.59 (1H, s), 3.69 (1H, s), 3.75-4.05 (5H, m), 4.32-4.45 (2H, m), 5.66-5.8 (1H, m), 6.11-6.21 (1H, m), 6.67-6.82 (1H, m), 7.21 (1H, d), 7.32 (1H, d), 7.44 (1H, s), 7.51 (1H, d), 7.69-7.79 (1H, m), 13.10 (1H, s). m/z: ES+ [M+H]+ 437/439. This was followed by rotational isomer 2 of (12aS)-2-acryloyl-10-chloro-9-(5-methyl-1H-indazol-4-yl)-1,2,3,4,12,12a-hexahydro-6H-benzo[f]pyrazino[2,1-c][1,4]oxazepin-6-one (0.039 g, 14%) as a colourless gum. 1H NMR (500 MHz, DMSO, 27° C.) 2.12 (3H, s), 3.52-3.74 (1H, m), 3.74-3.88 (3H, m), 3.88-4.04 (2H, m), 4.04-4.21 (1H, m), 4.28-4.43 (2H, m), 5.73 (1H, dd), 6.11-6.24 (1H, m), 6.67-6.82 (1H, m), 7.20 (1H, d), 7.31 (1H, d), 7.46-7.57 (2H, m), 7.71 (1H, dd), 13.09 (1H, s). m/z: ES+ [M+H]+ 437/439.

(12aS)-10-Chloro-9-(5-methyl-1H-indazol-4-yl)-1,2,3,4,12,12a-hexahydro-6H-benzo[f]pyrazino[2,1-c][1,4]oxazepine Rotational Isomer 1 and 2

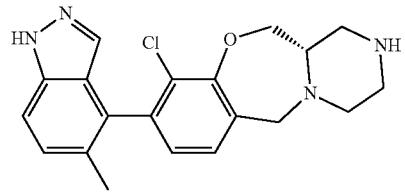 [SMILES: Cc1ccc2[nH]ncc2c1-c1ccc2c(c1Cl)OC[C@@H]1CNCCN1C2]

A solution of borane THF complex (1M) (3.66 mL, 3.66 mmol) was added dropwise to a stirred solution of tert-butyl (12aS)-10-chloro-9-(5-methyl-1H-indazol-4-yl)-6-oxo-3,4,12,12a-tetrahydro-6H-benzo[f]pyrazino[2,1-c][1,4]oxazepine-2(1H)-carboxylate (1:1 mixture of rotational isomers) (0.442 g, 0.92 mmol) in THF (5.49 mL) at rt over a period of 5 min. The resulting solution was stirred at 65° C. for 12 h. The reaction mixture was cooled to rt and MeOH (2 mL) and NaOH (2M, 0.5 mL) were added and the reaction was stirred for 30 min. The reaction was diluted with water (20 mL) and EtOAc (20 mL) and washed with brine (2×20 mL), dried (MgSO₄) and evaporated to dryness. The solid was redissolved in DCM (10 mL), and treated with TFA (5 mL) for 1 h. The mixture was evaporated to dryness, and purified by SCX (7M NH₃/MeOH) to afford a solid. This was purified by preparative HPLC (Waters XSelect CSH C18 column, 5μ silica, 30 mm diameter, 100 mm length), using of water (containing 0.1% NH₃) and MeCN as eluents. This gave rotational isomer 1 of (12aS)-10-chloro-9-(5-methyl-1H-indazol-4-yl)-1,2,3,4,12,12a-hexahydro-6H-benzo[f]pyrazino[2,1-c][1,4]oxazepine (0.156 g, 92%) as a yellow gum. 1H NMR (500 MHz, DMSO, 27° C.) 2.13 (3H, s), 2.27-2.35 (2H, m), 2.6-2.69 (2H, m), 2.72-2.84 (2H, m), 3.17 (2H, s), 3.65 (2H, d), 3.82 (1H, d), 4.27 (1H, dd), 6.97 (1H, d), 7.27-7.29 (1H, m), 7.31 (1H, s), 7.39 (1H, d), 7.47 (1H, dd), 13.05 (1H, s). m/z: ES+ [M+H]+ 369. This was followed by rotational isomer 2 of (12aS)-10-chloro-9-(5-methyl-1H-indazol-4-yl)-1,2,3,4,12,12a-hexahydro-6H-benzo[f]pyrazino[2,1-c][1,4]oxazepine (0.154 g, 91%) as a yellow gum. 1H NMR (500 MHz, DMSO, 27° C.) 2.09 (3H, s), 2.26-2.34 (2H, m), 2.58-2.71 (2H, m), 2.72-2.86 (2H, m), 3.6-3.73 (2H, m), 3.80 (1H, d), 4.08 (2H, s), 4.26 (1H, dd), 6.97 (1H, d), 7.27-7.32 (2H, m), 7.45 (1H, d), 7.47 (1H, dd), 13.06 (1H, s). m/z: ES+ [M+H]+ 369.

1-((12aS)-10-Chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one Rotational Isomer 1, Example 3

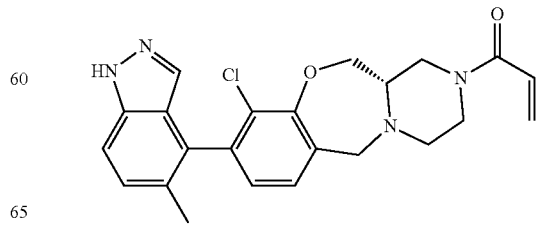

Acryloyl chloride (0.036 mL, 0.44 mmol) was added to rotational isomer 1 of (12aS)-10-chloro-9-(5-methyl-1H-indazol-4-yl)-1,2,3,4,12,12a-hexahydro-6H-benzo[f]pyrazino[2,1-c][1,4]oxazepine (0.156 g, 0.42 mmol) and DIPEA (0.148 mL, 0.85 mmol) in DMA (1.508 mL) at 0° C. The resulting solution was stirred at rt for 1 h. The reaction mixture was poured into water (10 mL) and the resulting precipitate collected by filtration, washing with water and dried under vacuum to afford crude product. This was purified by preparative HPLC (Waters XSelect CSH C18 column, 5μ silica, 30 mm diameter, 100 mm length), using of water (containing 1% NH₃) and MeCN as eluents. This gave rotational isomer 1 of 1-((12aS)-10-chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one (0.025 g, 14%) as a white solid. 1H NMR (500 MHz, MeOD, 27° C.) 2.17 (3H, s), 2.47-2.62 (1H, m), 2.85-3.07 (3H, m), 3.09-3.25 (1H, m), 3.44-3.54 (1H, m), 3.67-3.76 (1H, m), 3.96 (1H, d), 4-4.1 (1H, m), 4.12-4.32 (1H, m), 4.38-4.5 (1H, m), 5.77 (1H, d), 6.23 (1H, d), 6.71-6.87 (1H, m), 7.00 (1H, d), 7.31 (1H, d), 7.34 (1H, d), 7.41 (1H, s), 7.44-7.5 (1H, m). m/z: ES− [M−H]− 421/423.

1-((12aS)-10-chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one Rotational Isomer 2, Example 4

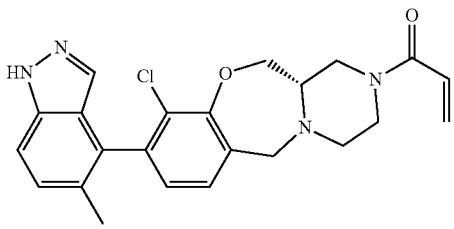 [SMILES: C=CC(=O)N1CCN2Cc3ccc(-c4c(C)ccc5[nH]ncc45)c(Cl)c3OC[C@@H]2C1]

Acryloyl chloride (0.038 g, 0.42 mmol) was added to rotational isomer 2 of (12aS)-10-chloro-9-(5-methyl-1H-indazol-4-yl)-1,2,3,4,12,12a-hexahydro-6H-benzo[f]pyrazino[2,1-c][1,4]oxazepine (0.154 g, 0.42 mmol) and DIPEA (0.054 g, 0.42 mmol) in DMA (1.67 mL) cooled to 0° C. The resulting solution was stirred at rt for 1 h. The reaction was poured into water (10 mL) and the resulting precipitate collected by filtration washing with water and dried under vacuum to afford crude product. The crude product was purified by preparative HPLC (Waters XSelect CSH C18 column, 5μ silica, 30 mm diameter, 100 mm length), using of water (containing 1% NH₃) and MeCN as eluents. This gave rotational isomer 2 of 1-((12aS)-10-chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one (0.038 g, 22%) as a white solid. 1H NMR (500 MHz, CDCl₃, 27° C.) 2.19 (3H, s), 2.57 (1H, t), 2.85-3.06 (3H, m), 3.34 (1H, s), 3.47-3.6 (1H, m), 3.72-3.91 (2H, m), 4.06 (1H, d), 4.18-4.51 (2H, m), 5.75 (1H, d), 6.34 (1H, dd), 6.59 (1H, dd), 7.01 (1H, d), 7.19 (1H, d), 7.32 (1H, d), 7.4-7.47 (1H, m), 7.60 (1H, s), 10.37 (1H, s). m/z: ES+ [M+H]+ 423/425.

Tert-butyl (3R)-4-(4-bromo-2,6-difluorobenzoyl)-3-(hydroxymethyl)piperazine-1-carboxylate

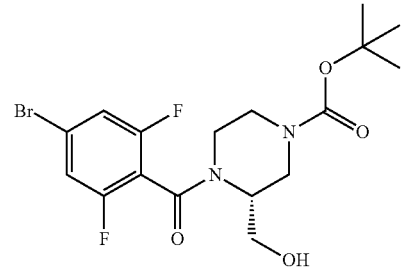 [SMILES: CC(C)(C)OC(=O)N1CCN(C(=O)c2c(F)cc(Br)cc2F)[C@@H](CO)C1]

To 4-bromo-2,6-difluorobenzoic acid (10 g, 42.19 mmol) in DCM (287 mL) was added tert-butyl (3R)-3-(hydroxymethyl)piperazine-1-carboxylate (10.04 g, 46.41 mmol) and triethylamine (23.52 mL, 168.78 mmol). 1-Propanephosphonic anhydride (50% solution in EtOAc) (30 mL, 50.63 mmol) was then added and the reaction mixture was stirred at 25° C. for 3 h. The reaction mixture was diluted with DCM (500 mL) and washed with water (1000 mL), saturated NaHCO₃ solution (500 mL), water (500 mL) and brine (500 mL). The organic phase was dried by passing through a phase separating cartridge and evaporated to dryness to afford tert-butyl (3R)-4-(4-bromo-2,6-difluorobenzoyl)-3-(hydroxymethyl)piperazine-1-carboxylate (15.03 g, 82%). 1H NMR (400 MHz, DMSO, 30° C.) 1.34-1.43 (9H, m), 2.55-3.03 (3H, m), 3.2-3.68 (4H, m), 3.8-4.15 (2H, m), 4.22-4.37 (1H, m), 7.55-7.68 (2H, m). m/z: ES+ [M+H]+= 378.

Tert-butyl (12aR)-9-bromo-7-fluoro-6-oxo-3,4,12,12a-tetrahydro-6H-pyrazino[2,1-c][1,4]benzoxazepine-2(1H)-carboxylate

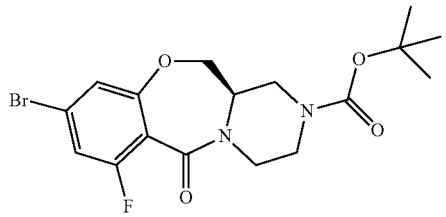 [SMILES: CC(C)(C)OC(=O)N1CCN2C(=O)c3c(F)cc(Br)cc3OC[C@H]2C1]

Sodium hydride (60% in mineral oil) (0.953 g, 23.83 mmol) was added in one portion to tert-butyl (3R)-4-(4-bromo-2,6-difluorobenzoyl)-3-(hydroxymethyl)piperazine-1-carboxylate (9.43 g, 21.67 mmol) in DMF (100 mL) at 0° C. The resulting solution was warmed to 25° C. and stirred for 2 h. The reaction mixture was quenched with ethanol and stirred for 5 min. The resulting solution was diluted with water (50 mL) EtOAc (100 mL) and washed sequentially with saturated NH₄Cl (50 mL), water (50 mL) and brine (50 mL). The organic layer was dried by passing through a phase separating cartridge and the solvent was removed under vacuum to afford tert-butyl (12aR)-9-bromo-7-fluoro-6-oxo-3,4,12,12a-tetrahydro-6H-pyrazino[2,1-c][1,4]benzoxazepine-2(1H)-carboxylate (8.88 g, 99%). 1H NMR (400 MHz, DMSO, 30° C.) 1.41 (9H, d), 3.44-3.54 (1H, m), 3.6-3.71 (3H, m), 3.83-3.96 (2H, m), 4.06-4.29 (3H, m), 7.25 (1H, s), 7.48 (1H, dd). m/z: ES+ [M+H]+=416.

Tert-butyl (12aR)-9-bromo-7-methoxy-6-oxo-3,4,12,12a-tetrahydro-6H-pyrazino[2,1-c][1,4]benzo-xazepine-2(1H)-carboxylate

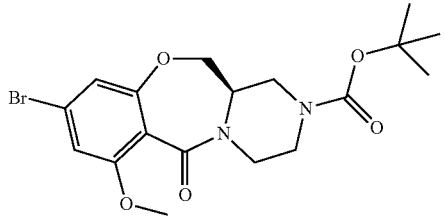 [SMILES: COc1cc(Br)cc2c1C(=O)N1CCN(C(=O)OC(C)(C)C)C[C@@H]1CO2]

Tert-Butyl (12aR)-9-bromo-7-fluoro-6-oxo-3,4,12,12a-tetrahydro-6H-pyrazino[2,1-c][1,4]benzoxazepine-2(1H)-carboxylate (8.65 g, 20.83 mmol) was dissolved in DMF (100 mL) and degassed at 0° C. for 5 min. Sodium methoxide (4.95 g, 91.65 mmol) was added and the reaction mixture was heated at 80° C. for 1 h. Further sodium methoxide (4.95 g, 91.65 mmol) was added and stirred for an additional 2 h. After cooling to 25° C. the solution was diluted with EtOAc (750 mL) and water (750 mL). The organic layer was separated and washed with water (500 mL), brine (500 mL) and dried over a phase separator. The solvent was removed under reduced pressure to afford crude product which was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave tert-butyl (12aR)-9-bromo-7-methoxy-6-oxo-3,4,12,12a-tetrahydro-6H-pyrazino[2,1-c][1,4]benzoxazepine-2(1H)-carboxylate (3.43 g, 39%) as a white solid. 1H NMR (400 MHz, DMSO, 30° C.) 1.41 (9H, s), 3.20 (1H, s), 3.35 (1H, d), 3.45 (1H, s), 3.61-3.75 (2H, m), 3.79 (3H, s), 3.84-3.98 (2H, m), 4.03 (1H, dd), 4.14 (1H, t), 6.93 (1H, d), 7.14 (1H, d). m/z: ES+ [M+H]+=427.

Tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate

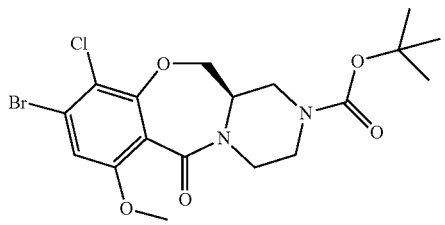 [SMILES: COc1cc(Br)c(Cl)c2c1C(=O)N1CCN(C(=O)OC(C)(C)C)C[C@@H]1CO2]

N-Chlorosuccinimide (1.07 g, 8.03 mmol) and chlorotrimethylsilane (0.102 mL, 0.8 mmol) was added in one portion to a stirred solution of tert-butyl (12aR)-9-bromo-7-methoxy-6-oxo-3,4,12,12a-tetrahydro-6H-pyrazino[2,1-c][1,4]benzoxazepine-2(1H)-carboxylate (3.43 g, 8.03 mmol) in MeCN (80 mL) and the reaction was stirred for 15 min at 25° C. The reaction mixture was diluted with EtOAc (100 mL) and washed with water (100 mL), saturated NaHCO₃ (100 mL), water (100 mL) and brine (100 mL). The organic phase was dried by passing through a phase separating cartridge and the solvent was evaporated under reduced pressure to afford crude product. This was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents, to afford tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate (2.73 g, 74%) as a white foam. 1H NMR (400 MHz, DMSO, 30° C.) 1.41 (9H, s), 3.20 (1H, s), 3.32-3.54 (2H, m), 3.62-3.78 (2H, m), 3.80 (3H, s), 3.85-4.04 (2H, m), 4.10 (1H, dd), 4.22 (1H, t), 7.35 (1H, s). m/z: ES+ [M+H]+=460.

Tert-butyl (12aR)-9-bromo-10-chloro-7-methoxy-3,4,12,12a-tetrahydro-6H-pyrazino[2,1-c][1,4]benzoxazepine-2(1H)-carboxylate

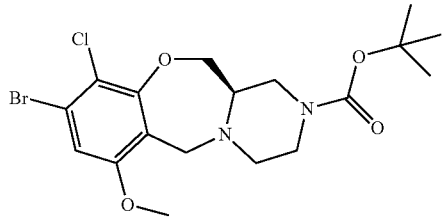 [SMILES: COc1cc(Br)c(Cl)c2c1CN1CCN(C(=O)OC(C)(C)C)C[C@@H]1CO2]

A solution of borane-THF complex (1M) (20.79 mL, 20.79 mmol) was added dropwise to a stirred solution of tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate (1.2 g, 2.6 mmol) in THF (5 mL) at 25° C. The resulting solution was heated at 75° C. for 1 h, cooled to 25° C. and quenched with i-PrOH (20 mL). NaOH (2M, 10 mL) was added and the reaction was stirred for a further 30 min. The reaction was then diluted with water (100 mL) and EtOAc (100 mL) and the organic layer was washed with brine (2×20 mL), dried over a phase separating cartridge and the solvent was removed under reduced pressure to afford tert-butyl (12aR)-9-bromo-10-chloro-7-methoxy-3,4,12,12a-tetrahydro-6H-pyrazino[2,1-c][1,4]benzoxazepine-2(1H)-carboxylate (0.836 g, 72%) as a transparent oil. 1H NMR (400 MHz, DMSO, 30° C.) 1.40 (9H, s), 2.58-2.75 (3H, m), 2.99 (1H, t), 3.34-3.51 (2H, m), 3.6-3.7 (3H, m), 3.81 (3H, s), 3.98 (1H, d), 4.25-4.38 (1H, m), 7.12 (1H, s). m/z: ES+ [M+H]+=446.

Tert-butyl (12aR)-10-chloro-9-(2-fluoro-6-hydroxyphenyl)-7-methoxy-3,4,12,12a-tetrahydro-6H-pyrazino[2,1-c][1,4]benzoxazepine-2(1H)-carboxylate

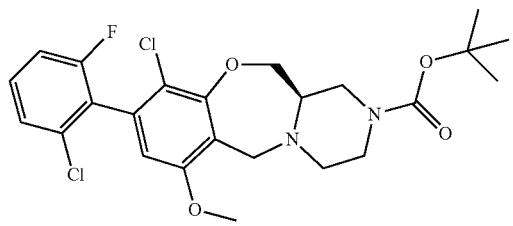 [SMILES: COc1cc(-c2c(F)cccc2Cl)c(Cl)c2c1CN1CCN(C(=O)OC(C)(C)C)C[C@@H]1CO2]

A mixture of tert-butyl (12aR)-9-bromo-10-chloro-7-methoxy-3,4,12,12a-tetrahydro-6H-pyrazino[2,1-c][1,4]benzoxazepine-2(1H)-carboxylate (836 mg, 1.87 mmol), (2-fluoro-6-hydroxyphenyl)boronic acid (291 mg, 1.87 mmol) and potassium carbonate (1.5 g, 11.20 mmol) in 2-methyltetrahydrofuran (14 mL) and water (5 mL) was degassed for 15 min. Ruphos Pd G3 (156 mg, 0.19 mmol) and RuPhos (87 mg, 0.19 mmol) was added at 25° C. and then the reaction was heated at 60° C. for 4 h. After cooling to 25° C. the reaction mixture was diluted with EtOAc (100 mL) and washed with water (2×100 mL) and brine (100 mL). The organic phase was dried over a phase separating cartridge and the solvent was evaporated to dryness to afford crude product. The crude product was purified by preparative HPLC (Waters XSelect CSH C18 ODB column, 5μ silica, 30 mm diameter, 100 mm length), using of water (containing by volume 1% $NH_4OH$ (28-30% in $H_2O$)) and MeCN as eluents. This gave tert-butyl (12aR)-10-chloro-9-(2-fluoro-6-hydroxyphenyl)-7-methoxy-3,4,12,12a-tetrahydro-6H-pyrazino[2,1-c][1,4]benzoxazepine-2(1H)-carboxylate as a cream foam (414 mg). m/z: ES+ [M+H]+=470.

2-[(12aR)-10-Chloro-7-methoxy-1,2,3,4,12,12a-hexahydro-6H-pyrazino[2,1-c][1,4]benzoxazepin-9-yl]-3-fluorophenol

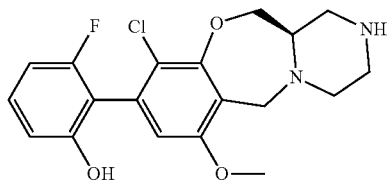 [SMILES: COc1cc(-c2c(O)cccc2F)c(Cl)c2c1CN1CCNC[C@@H]1CO2]

HCl (4M in dioxane) (1.94 mL, 7.77 mmol) was added to tert-butyl (12aR)-10-chloro-9-(2-fluoro-6-hydroxyphenyl)-7-methoxy-3,4,12,12a-tetrahydro-6H-pyrazino[2,1-c][1,4]benzoxazepine-2(1H)-carboxylate (186 mg, 0.39 mmol) in MeOH (2 mL) at 25° C. The resulting solution was stirred at 25° C. for 12 h and purified by SCX (1M $NH_3$/MeOH) to afford 2-[(12aR)-10-chloro-7-methoxy-1,2,3,4,12,12a-hexahydro-6H-pyrazino[2,1-c][1,4]benzoxazepin-9-yl]-3-fluorophenol (139 mg, 94%) as a white solid. 1H NMR (400 MHz, $CD_3CN$, 30° C.) 2.3-2.48 (2H, m), 2.58-2.85 (5H, m), 2.88 (1H, d), 3.46 (1H, dd), 3.59 (1H, ddd), 3.76 (3H, s), 4.07 (1H, d), 4.23 (1H, dd), 6.64-6.81 (3H, m), 7.24 (1H, q). m/z: ES+ [M+H]+=379.

1-[(12aR)-10-Chloro-9-(2-fluoro-6-hydroxyphenyl)-7-methoxy-3,4,12,12a-tetrahydro-6H-pyrazino[2,1-c][1,4]benzoxazepin-2(1H)-yl]prop-2-en-1-one, Example 5

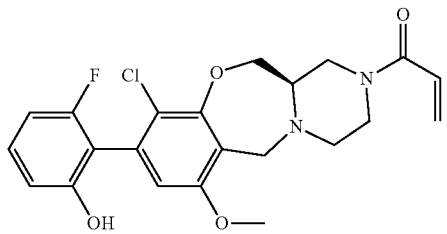 [SMILES: C=CC(=O)N1CCN2Cc3c(OC)cc(-c4c(O)cccc4F)c(Cl)c3OC[C@H]2C1]

To a stirred solution of 2-[(12aR)-10-chloro-7-methoxy-1,2,3,4,12,12a-hexahydro-6H-pyrazino[2,1-c][1,4]benzoxazepin-9-yl]-3-fluorophenol (139 mg, 0.37 mmol) and DIPEA (0.083 mL, 0.48 mmol) in DCM (4 mL) at 0° C. was added acryloyl chloride (0.031 mL, 0.39 mmol) dropwise and the reaction mixture was stirred at 0° C. for 15 min. The reaction mixture was diluted with DCM and quenched with water and the organic layer dried using a phase separating cartridge. The solvent was removed under reduced pressure to afford a crude gum which was dissolved in cold 1M $NH_3$/MeOH (20 mL) and stirred at 25° C. for 1 h. The reaction mixture was concentrated to dryness to afford crude product. The crude product was purified by preparative HPLC (Waters CSH C18 OBD column, 30×100 mm id, 5 micron particle size), using of water (containing 1% by volume of $NH_4OH$ (28-30% in $H_2O$)) and MeCN as eluents. Fractions containing the desired compound were evaporated to dryness and dissolved in MeOH (3 mL) and purified using SFC (Column: Princeton Diol, 30×250 mm, 5 micron; Mobile phase: 20 to 25% MeOH+0.1% $NH_3$/80-75% $scCO_2$ over 8 min; Flow rate: 100 mL/min BPR: 120 bar). The solvent was evaporated to afford 1-[(12aR)-10-chloro-9-(2-fluoro-6-hydroxyphenyl)-7-methoxy-3,4,12,12a-tetrahydro-6H-pyrazino[2,1-c][1,4]benzoxazepin-2(1H)-yl]prop-2-en-1-one (59 mg, 37%). 1H NMR (400 MHz, DMSO, 30° C.) 2.34-2.46 (1H, m), 2.53-2.56 (1H, m), 2.61-2.7 (1H, m), 2.71-2.8 (1H, m), 2.84 (1H, d), 2.89-3.05 (1H, m), 3.55 (1H, dd), 3.68 (1H, dt), 3.76 (3H, s), 3.85-3.99 (1H, m), 4-4.12 (1H, m), 4.31-4.45 (1H, m), 5.70 (1H, s), 6.12 (1H, d), 6.62-6.72 (2H, m), 6.77 (1H, dd), 6.79-6.89 (1H, m), 7.22 (1H, q), 9.82 (1H, s). m/z: ES+ [M+H]+=433.

tert-butyl (3R)-4-(4-bromo-2,6-difluorobenzoyl)-3-(hydroxymethyl)piperazine-1-carboxylate

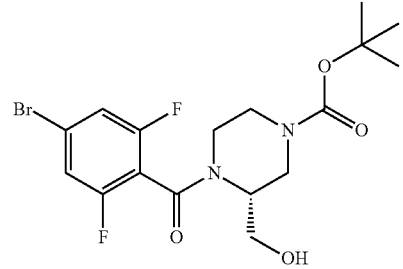 [SMILES: CC(C)(C)OC(=O)N1CCN(C(=O)c2c(F)cc(Br)cc2F)[C@@H](CO)C1]

To 4-bromo-2,6-difluorobenzoic acid (10.00 g, 42.19 mmol) in DCM (287 ml) was added tert-butyl (3R)-3-(hydroxymethyl)piperazine-1-carboxylate (10.04 g, 46.41 mmol) and triethylamine (23.52 ml, 168.78 mmol). T3P® (50% in EtOAc) (30 ml, 50.63 mmol) was then added and the reaction mixture was stirred at 25° C. for 3 h. The reaction mixture was diluted with DCM (500 ml), then washed with water (1 L), saturated $NaHCO_3$ (0.5 L), water (0.5 L) and saturated brine (0.5 L). The organic phase was dried (phase separating cartridge) and evaporated to afford tert-butyl (3R)-4-(4-bromo-2,6-difluorobenzoyl)-3-(hydroxymethyl)piperazine-1-carboxylate (15.03 g, 82%). Material used without further purification. 1H NMR (400 MHz, DMSO, 30° C.) 1.34-1.43 (9H, m), 2.55-3.03 (3H, m), 3.2-3.68 (4H, m), 3.8-4.15 (2H, m), 4.22-4.37 (1H, m), 7.55-7.68 (2H, m). m/z: ES+ [M+H]+=378.

tert-butyl (12aR)-9-bromo-7-fluoro-6-oxo-3,4,12,12a-tetrahydro-6H-pyrazino[2,1-c][1,4]benzoxazepine-2(1H)-carboxylate

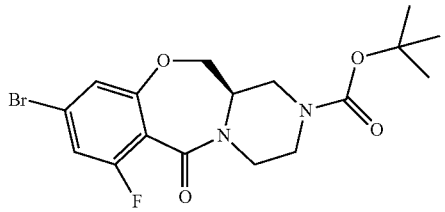 [SMILES: CC(C)(C)OC(=O)N1CCN2C(=O)c3c(F)cc(Br)cc3OC[C@H]2C1]

Sodium hydride (60% in mineral oil) (0.95 g, 23.8 mmol) was added in one portion to tert-butyl (3R)-4-(4-bromo-2,6-difluorobenzoyl)-3-(hydroxymethyl)piperazine-1-carboxylate (9.43 g, 21.7 mmol) in DMF (100 ml) at 0° C. The resulting solution was warmed to rt and stirred for 2 h. The reaction mixture was quenched with EtOH and stirred for 5 min. The resulting solution was diluted with water (50 ml) and EtOAc (100 ml), then washed sequentially with saturated NH$_4$Cl (50 ml), water (50 ml) and saturated brine (50 ml). The organic layer was dried (phase separating cartridge) and evaporated to afford tert-butyl (12aR)-9-bromo-7-fluoro-6-oxo-3,4,12,12a-tetrahydro-6H-pyrazino[2,1-c][1,4]benzoxazepine-2(1H)-carboxylate which was used without further purification. 1H NMR (400 MHz, DMSO, 30° C.) 1.41 (9H, d), 3.44-3.54 (1H, m), 3.6-3.71 (3H, m), 3.83-3.96 (2H, m), 4.06-4.29 (3H, m), 7.25 (1H, s), 7.48 (1H, dd). m/z: ES+ [M+H]+=416.

tert-butyl (12aR)-9-bromo-7-methoxy-6-oxo-3,4,12,12a-tetrahydro-6H-pyrazino[2,1-c][1,4]benzoxazepine-2(1H)-carboxylate

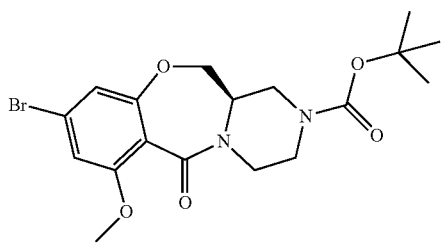 [SMILES: COc1cc(Br)cc2c1C(=O)N1CCN(C(=O)OC(C)(C)C)C[C@@H]1CO2]

tert-Butyl (12aR)-9-bromo-7-fluoro-6-oxo-3,4,12,12a-tetrahydro-6H-pyrazino[2,1-c][1,4]benzoxazepine-2(1H)-carboxylate (8.65 g, 20.83 mmol) was dissolved in DMF (100 ml) and degassed at 0° C. for 5 min. Sodium methoxide (4.95 g, 91.65 mmol) was added and the reaction mixture was heated to 80° C. After 1 h sodium methoxide (4.95 g, 91.65 mmol) was added and stirring was continued for 2 h. After cooling to rt, the solution was diluted with EtOAc (750 ml) and water (750 ml). The organic layer was separated, then washed with water (500 ml) and saturated brine (500 ml) before drying over a phase separator and evaporating. Preparative HPLC (Waters XSelect CSH C18 ODB column, 5µ silica, 30 mm diameter, 100 mm length), using decreasingly polar mixtures of water (containing by volume 1% NH$_4$OH (28-30% in H$_2$O)) and MeCN as eluents, afforded tert-butyl (12aR)-9-bromo-7-methoxy-6-oxo-3,4,12,12a-tetrahydro-6H-pyrazino[2,1-c][1,4]benzoxazepine-2(1H)-carboxylate (3.43 g, 38.5%) as a white solid. 1H NMR (400 MHz, DMSO, 30° C.) 1.41 (9H, s), 3.20 (1H, s), 3.35 (1H, d), 3.45 (1H, s), 3.61-3.75 (2H, m), 3.79 (3H, s), 3.84-3.98 (2H, m), 4.03 (1H, dd), 4.14 (1H, t), 6.93 (1H, d), 7.14 (1H, d). m/z: ES+ [M+H]+=427.

tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate

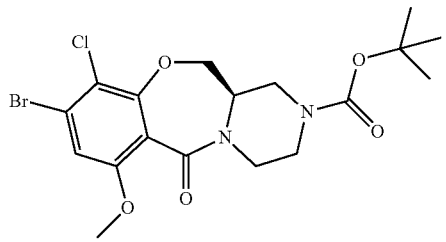 [SMILES: COc1cc(Br)c(Cl)c2c1C(=O)N1CCN(C(=O)OC(C)(C)C)C[C@@H]1CO2]

N-Chlorosuccinimide (1.07 g, 8.03 mmol) and chlorotrimethylsilane (0.102 ml, 0.80 mmol) were added in one portion to a stirred solution of tert-butyl (12aR)-9-bromo-7-methoxy-6-oxo-3,4,12,12a-tetrahydro-6H-pyrazino[2,1-c][1,4]benzoxazepine-2(1H)-carboxylate (3.43 g, 8.03 mmol) in acetonitrile (80 ml). The reaction was stirred for 15 minutes at 25° C. then diluted with EtOAc (100 ml). The separated organic layer was then washed with water (100 ml), saturated NaHCO$_3$ (100 ml), water (100 ml) and saturated brine (100 ml). The organic phase was dried (phase separating cartridge) then evaporated. Preparative HPLC (Waters XSelect CSH C18 ODB column, 5µ silica, 30 mm diameter, 100 mm length), using decreasingly polar mixtures of water (containing by volume 1% NH$_4$OH (28-30% in H$_2$O)) and MeCN as eluents afforded tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate (2.73 g, 73.7%) as a white solid. 1H NMR (400 MHz, DMSO, 30° C.) 1.41 (9H, s), 3.20 (1H, s), 3.32-3.54 (2H, m), 3.62-3.78 (2H, m), 3.80 (3H, s), 3.85-4.04 (2H, m), 4.10 (1H, dd), 4.22 (1H, t), 7.35 (1H, s). m/z: ES+ [M+H]+=460.

tert-butyl (12aR)-10-chloro-9-(2-fluoro-6-hydroxyphenyl)-7-methoxy-6-oxo-3,4,12,12a-tetrahydro-6H-pyrazino[2,1-c][1,4]benzoxazepine-2(1H)-carboxylate

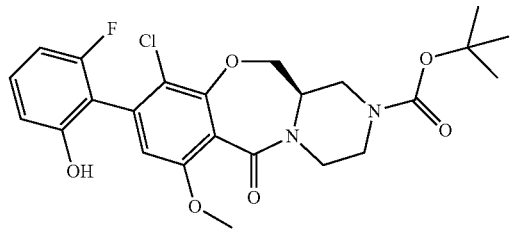 [SMILES: COc1cc(-c2c(O)cccc2F)c(Cl)c2c1C(=O)N1CCN(C(=O)OC(C)(C)C)C[C@@H]1CO2]

A mixture of tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate (1.3 g, 2.82 mmol), (2-fluoro-6-hydroxyphenyl)boronic acid (0.43 g, 2.82 mmol) and potassium carbonate (2.33 g, 16.89 mmol) in methyl-THF (21 ml) and water (7 ml) was degassed for 15 min. RuPhos Pd G3 (0.235 g, 0.28 mmol) and RuPhos (0.131 g, 0.28 mmol) was added at 25° C. and the reaction mixture was heated to 60° C. for 16 h. (2-Fluoro-6-hydroxyphenyl)boronic acid (0.439 g, 2.82 mmol), water (2 ml) and potassium carbonate (1.20 g) was then introduced. After 3 h the reaction was cooled to 25° C., diluted with EtOAc (200 ml), then washed with water (2×100 ml) and saturated brine (100 ml). The organic layer was dried (phase separating cartridge) and evaporated. Preparative HPLC (Waters XSelect CSH C18 ODB column, 5µ silica, 30 mm diameter, 100 mm length), using decreasingly polar mixtures of water (containing by volume 1% NH$_4$OH (28-30% in H$_2$O)) and MeCN as eluents, afforded tert-butyl (12aR)-10-chloro-9-(2-fluoro-6-hydroxyphenyl)-7-methoxy-6-oxo-3,4,12,12a-tetrahydro-6H-pyrazino[2,1-c][1,4]benzoxazepine-2(1H)-carboxylate (0.930 g, 67.0%) as a cream solid. 1H NMR (400 MHz, DMSO, 30° C.) 1.43 (9H, s), 3.41 (1H, d), 3.53 (1H, s), 3.73 (1H, s), 3.76 (3H, s), 3.89-4.03 (2H, m), 4.03-4.16 (3H, m), 4.16-4.3 (1H, m), 6.69-6.84 (2H, m), 6.87-6.93 (1H, m), 7.16-7.36 (1H, m), 9.95 (1H, s). m/z: ES+ [M+H]+=493.

(12aR)-10-Chloro-9-(2-fluoro-6-hydroxyphenyl)-7-hydroxy-1,2,3,4,12,12a-hexahydro-6H-pyrazino[2,1-c][1,4]benzoxazepin-6-one

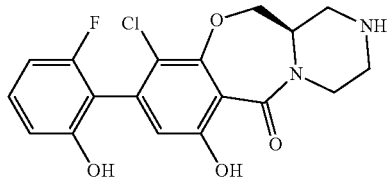 [SMILES: O=C1c2c(O)cc(-c3c(O)cccc3F)c(Cl)c2OC[C@H]2CNCCN12]

To tert-butyl (12aR)-10-chloro-9-(2-fluoro-6-hydroxyphenyl)-7-methoxy-6-oxo-3,4,12,12a-tetrahydro-6H-pyrazino[2,1-c][1,4]benzoxazepine-2(1H)-carboxylate (352 mg, 0.71 mmol) in DCM (3 mL) at 0° C. was added boron tribromide (1M in DCM) (4.28 mL, 4.28 mmol) dropwise and stirred to 25° C. for 2 h. The reaction was quenched with MeOH and purified by SCX (1M NH$_3$/MeOH) to afford (12aR)-10-chloro-9-(2-fluoro-6-hydroxyphenyl)-7-hydroxy-1,2,3,4,12,12a-hexahydro-6H-pyrazino[2,1-c][1,4]benzoxazepin-6-one (243 mg, 90%) as a yellow transparent glass. 1H NMR (400 MHz, DMSO, 30° C.) 2.67-2.76 (1H, m), 2.77-2.9 (2H, m), 2.9-3 (1H, m), 3.35-3.49 (1H, m), 3.72-3.89 (2H, m), 4.05-4.14 (2H, m), 4.59 (1H, t), 6.60 (1H, d), 6.67-6.81 (2H, m), 7.15-7.33 (1H, m), 9.90 (1H, d), 11.01 (1H, s). m/z: ES+ [M+H]+=379.

(12aR)-10-chloro-9-(2-fluoro-6-hydroxyphenyl)-7-hydroxy-2-(prop-2-enoyl)-1,2,3,4,12,12a-hexahydro-6H-pyrazino[2,1-c][1,4]benzoxazepin-6-one, Example 6

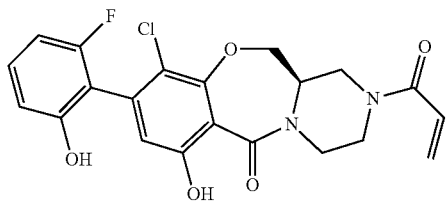 [SMILES: C=CC(=O)N1CCN2C(=O)c3c(O)cc(-c4c(O)cccc4F)c(Cl)c3OC[C@H]2C1]

To a stirred solution of (12aR)-10-chloro-9-(2-fluoro-6-hydroxyphenyl)-7-hydroxy-1,2,3,4,12,12a-hexahydro-6H-pyrazino[2,1-c][1,4]benzoxazepin-6-one (243 mg, 0.64 mmol) and DIPEA (0.145 mL, 0.83 mmol) in DCM (6 mL) at 0° C. was added acryloyl chloride (0.053 mL, 0.67 mmol) dropwise and the reaction mixture was stirred at 0° C. for 15 min. The reaction mixture was diluted with EtOAc (20 mL) and washed with water (20 mL) and brine (20 mL), dried by passing through a phase separating cartridge and evaporated to give a crude gum. The crude product was dissolved in 1M NH$_3$/MeOH (20 mL) and was stirred at 25° C. for 1 h. The reaction mixture was concentrated to dryness to afford crude product. The sample was dissolved in MeOH (2 mL) and DCM (1 mL), filtered and washed in with MeOH (1 mL). The solution was purified using the SFC (Column: Chiralpak IC, 20×250 mm, 5 micron Mobile phase: 30% MeOH=0.1% NH$_3$/70% scCO$_2$ Flow rate: 60 mL/min BPR: 120 bar). The solvent was evaporated to afford (12aR)-10-chloro-9-(2-fluoro-6-hydroxyphenyl)-7-hydroxy-2-(prop-2-enoyl)-1,2,3,4,12,12a-hexahydro-6H-pyrazino[2,1-c][1,4]benzoxazepin-6-one (151 mg, 54%). 1H NMR (400 MHz, DMSO, 30° C.) 3.5-4 (6H, m), 4.07 (1H, s), 4.15-4.38 (2H, m), 5.64-5.81 (1H, m), 6.17 (1H, d), 6.6-6.83 (4H, m), 7.24 (1H, q), 9.98 (1H, s), 10.73 (1H, s). m/z: ES+ [M+H]+=433.

Tert-butyl (3R)-4-(4-bromo-3-chloro-2-fluorobenzoyl)-3-(hydroxymethyl)piperazine-1-carboxylate

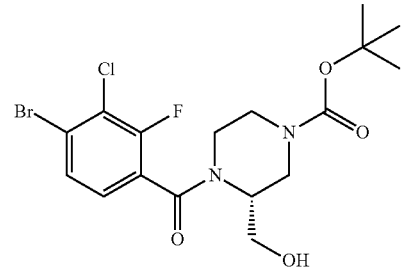 [SMILES: CC(C)(C)OC(=O)N1CCN(C(=O)c2ccc(Br)c(Cl)c2F)[C@@H](CO)C1]

4-Bromo-3-chloro-2-fluorobenzoic acid (5 g, 19.73 mmol), HATU (11.22 g, 29.59 mmol) and DIPEA (10.54 mL, 59.18 mmol) were stirred in THF (200 mL) for 30 min then tert-butyl (3R)-3-(hydroxymethyl)piperazine-1-carboxylate (5.12 g, 23.67 mmol) was added and the mixture was stirred at 25° C. for 3.5 h. The reaction mixture was evaporated to dryness, redissolved in EtOAc (100 mL) and washed with saturated NaHCO$_3$ (50 mL), water (2×50 mL) and brine (50 mL). The organic layer was dried over a phase separating cartridge and the solvent was removed under reduced pressure to afford a yellow oil. The crude product was purified by flash silica chromatography, elution gradient 0 to 5% MeOH in DCM, to afford tert-butyl (3R)-4-(4-bromo-3-chloro-2-fluorobenzoyl)-3-(hydroxymethyl)piperazine-1-carboxylate (11.83 g, >100%) as a white solid that was used without further purification. 1H NMR (400 MHz, DMSO, 30° C.) 1.40 (9H, s), 2.75-3.08 (3H, m), 3.31-3.36 (1H, m), 3.4-3.57 (2H, m), 3.57-3.68 (1H, m), 3.71-3.89 (1H, m), 4.28 (1H, d), 4.8-4.87 (1H, m), 7.35 (1H, t), 7.69-7.75 (1H, m). m/z: ES+ [M+H]+=451.

Tert-butyl (12aR)-9-bromo-10-chloro-6-oxo-3,4,12,12a-tetrahydro-6H-pyrazino[2,1-c][1,4]benzoxazepine-2(1H)-carboxylate

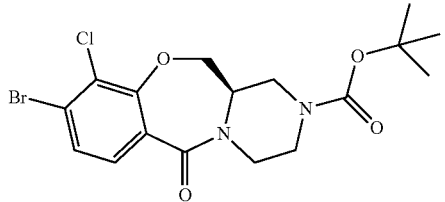 [SMILES: CC(C)(C)OC(=O)N1CCN2C(=O)c3ccc(Br)c(Cl)c3OC[C@H]2C1]

Lithium bis(trimethylsilyl)amide (1M in THF) (26.2 mL, 26.19 mmol) was added to a stirred solution of tert-butyl (3R)-4-(4-bromo-3-chloro-2-fluorobenzoyl)-3-(hydroxymethyl)piperazine-1-carboxylate (11.83 g, 26.19 mmol) in NMP (300 mL) at 25° C. The resulting solution was heated at 120° C. for 18 h. The reaction was cooled to 25° C. and diluted with EtOAc (2000 mL) and washed with water (1000 mL), saturated NaHCO₃ (500 mL), water (500 mL) and brine (500 mL). The organic layer was dried by passing through a phase separating cartridge and the solvent was evaporated to afford crude product. This was purified by flash silica chromatography, elution gradient 0 to 100% EtOAc in heptane to give a colourless oil which was purified by preparative HPLC (Waters XSelect CSH C18 ODB column, 5µ silica, 30 mm diameter, 100 mm length), using of water (containing by volume 1% NH₄OH (28-30% in H₂O)) and MeCN as eluents. This gave tert-butyl (12aR)-9-bromo-10-chloro-6-oxo-3,4,12,12a-tetrahydro-6H-pyrazino[2,1-c][1,4]benzoxazepine-2(1H)-carboxylate (7.25 g, 64%) as a yellow waxy solid. 1H NMR (400 MHz, DMSO, 30° C.) 1.41 (9H, s), 3.43-3.56 (3H, m), 3.61 (1H, d), 3.73 (1H, dd), 3.93 (2H, ddd), 4.34 (2H, d), 7.55 (1H, d), 7.63 (1H, d). m/z: ES+ [M+H]+=433.

Tert-butyl (12aR)-10-chloro-9-(5-methyl-1H-indazol-4-yl)-6-oxo-3,4,12,12a-tetrahydro-6H-pyrazino[2,1-c][1,4]benzoxazepine-2(1H)-carboxylate Rotational Isomer 1 and 2

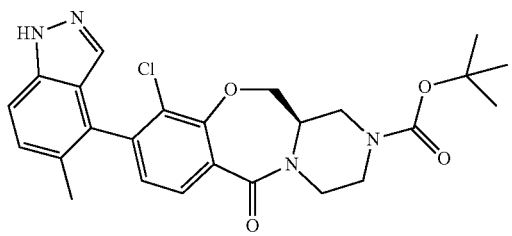 [SMILES: Cc1ccc2[nH]ncc2c1-c1ccc2c(c1Cl)OC[C@H]1CN(C(=O)OC(C)(C)C)CCN1C2=O]

Dichloro[1,1'-bis(di-tert-butylphosphino)ferrocene]palladium(II) (0.302 g, 0.46 mmol) was added to a degassed mixture of tert-butyl (12aR)-9-bromo-10-chloro-6-oxo-3,4,12,12a-tetrahydro-6H-pyrazino[2,1-c][1,4]benzoxazepine-2(1H)-carboxylate (2 g, 4.63 mmol), (5-methyl-1H-indazol-4-yl)boronic acid (1.63 g, 9.27 mmol) and sodium carbonate (2.7 g, 25.48 mmol) in 1,4-dioxane (54 mL) and water (13 mL). The reaction mixture was heated at 85° C. for 6 h and then cooled to 25° C. The reaction mixture was diluted with EtOAc (200 mL) and washed with saturated NaHCO₃ (100 mL), water (2×100 mL), brine (50 mL) and dried over a phase separating cartridge. The solvent was evaporated to afford crude product. This was purified by preparative HPLC (Waters XSelect CSH C18 ODB column, 5µ silica, 30 mm diameter, 100 mm length), using of water (containing by volume 1% NH₄OH (28-30% in H₂O)) and MeCN as eluents. This gave a cream solid that was purified using the SFC (Column: Chiralpak ID, 30×250 mm, 5 micron Mobile phase: 40% MeOH+0.1% NH₃/60% scCO₂ Flow rate: 90 mL/min BPR: 120 bar) to afford rotational isomer 1 of tert-butyl (12aR)-10-chloro-9-(5-methyl-1H-indazol-4-yl)-6-oxo-3,4,12,12a-tetrahydro-6H-pyrazino[2,1-c][1,4]benzoxazepine-2(1H)-carboxylate (198 mg, 8%). 1H NMR (400 MHz, DMSO, 30° C.) 1.43 (9H, s), 2.13 (3H, s), 3.46-3.64 (3H, m), 3.68 (1H, d), 3.79-3.88 (1H, m), 3.88-3.97 (1H, m), 4.06 (1H, q), 4.37 (2H, d), 7.20 (1H, d), 7.32 (1H, d), 7.51 (1H, d), 7.53 (1H, s), 7.71 (1H, d), 13.07 (1H, s). m/z: ES- [M-H]-=481. This was followed by rotational isomer 2 of tert-butyl (12aR)-10-chloro-9-(5-methyl-1H-indazol-4-yl)-6-oxo-3,4,12,12a-tetrahydro-6H-pyrazino[2,1-c][1,4]benzoxazepine-2(1H)-carboxylate (207 mg, 9%). 1H NMR (400 MHz, DMSO, 30° C.) 1.43 (9H, s), 2.16 (3H, s), 3.45-3.64 (3H, m), 3.68 (1H, d), 3.76-3.87 (1H, m), 3.91-4 (1H, m), 4-4.1 (1H, m), 4.37 (2H, d), 7.20 (1H, d), 7.32 (1H, d), 7.43 (1H, s), 7.51 (1H, d), 7.73 (1H, d), 13.08 (1H, s). m/z: ES- [M-H]-=481.

(12aR)-10-Chloro-9-(5-methyl-1H-indazol-4-yl)-1,2,3,4,12,12a-hexahydro-6H-pyrazino[2,1-c][1,4]benzoxazepin-6-one Rotational Isomer 1

HCl (4M in dioxane) (2.05 mL, 8.2 mmol) was added to rotational isomer 1 of tert-butyl (12aR)-10-chloro-9-(5-methyl-1H-indazol-4-yl)-6-oxo-3,4,12,12a-tetrahydro-6H-pyrazino[2,1-c][1,4]benzoxazepine-2(1H)-carboxylate (198 mg, 0.41 mmol) in MeOH (3 mL) at 25° C. and was stirred for 3 h. The reaction mixture was purified by SCX (1M NH₃/MeOH) to afford rotational isomer 1 of (12aR)-10-chloro-9-(5-methyl-1H-indazol-4-yl)-1,2,3,4,12,12a-hexahydro-6H-pyrazino[2,1-c][1,4]benzoxazepin-6-one (155 mg, 99%) as a colourless oil. m/z: ES+ [M+H]+=383.

(12aR)-10-Chloro-9-(5-methyl-1H-indazol-4-yl)-1,2,3,4,12,12a-hexahydro-6H-pyrazino[2,1-c][1,4]benzoxazepin-6-one Rotational Isomer 2

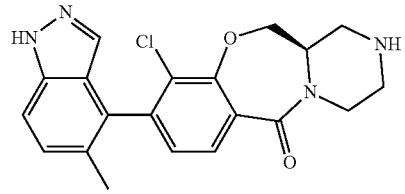 [SMILES: Cc1ccc2[nH]ncc2c1-c1ccc2c(c1Cl)OC[C@H]1CNCCN1C2=O]

HCl (4M in dioxane) (2.15 mL, 8.61 mmol) was added to rotational isomer 2 of tert-butyl (12aR)-10-chloro-9-(5-methyl-1H-indazol-4-yl)-6-oxo-3,4,12,12a-tetrahydro-6H-pyrazino[2,1-c][1,4]benzoxazepine-2(1H)-carboxylate (208 mg, 0.43 mmol) in MeOH (3 mL) at 25° C. and was stirred for 3 h. The reaction mixture was purified by SCX (1M NH₃/MeOH) to afford rotational isomer 2 of (12aR)-10-chloro-9-(5-methyl-1H-indazol-4-yl)-1,2,3,4,12,12a-hexahydro-6H-pyrazino[2,1-c][1,4]benzoxazepin-6-one (164 mg, 99%) as a colourless oil. 1H NMR (400 MHz, DMSO, 30° C.) 2.16 (3H, s), 2.65-2.74 (2H, m), 2.77-2.99 (3H, m), 3.42-3.54 (1H, m), 3.85 (2H, dt), 4.23 (1H, dd), 4.69 (1H, t), 7.18 (1H, d), 7.32 (1H, d), 7.43 (1H, s), 7.50 (1H, d), 7.73 (1H, d), 13.08 (1H, s). m/z: ES+ [M+H]+=383.

(12aR)-10-Chloro-9-(5-methyl-1H-indazol-4-yl)-2-(prop-2-enoyl)-1,2,3,4,12,12a-hexahydro-6H-pyrazino[2,1-c][1,4]benzoxazepin-6-one Rotational Isomer 1, Example 7

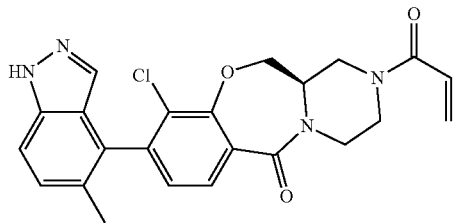 [SMILES: C=CC(=O)N1CCN2C(=O)c3ccc(-c4c(C)ccc5[nH]ncc45)c(Cl)c3OC[C@H]2C1]

To a solution of rotational isomer 1 of (12aR)-10-chloro-9-(5-methyl-1H-indazol-4-yl)-1,2,3,4,12,12a-hexahydro-6H-pyrazino[2,1-c][1,4]benzoxazepin-6-one (155 mg, 0.4 mmol) in DCM (4 mL), i-PrOH (1 mL) and pyridine (0.098 mL, 1.21 mmol) at −78° C. was added acryloyl chloride (0.033 mL, 0.4 mmol) dropwise over 5 min and stirred at −78° C. to rt for 1 h. The solution was quenched with saturated NaHCO₃ (3 mL), diluted with EtOAc (10 mL) and washed with water (10 mL) and brine (5 mL). The organic phase was dried by passing through a phase separating cartridge and the solvent was removed under reduced pressure to afford crude product. This was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave rotational isomer 1 of (12aR)-10-chloro-9-(5-methyl-1H-indazol-4-yl)-2-(prop-2-enoyl)-1,2,3,4,12,12a-hexahydro-6H-pyrazino[2,1-c][1,4]benzoxazepin-6-one (52 mg, 29%) as a white solid. 1H NMR (400 MHz, DMSO, 30° C.) 2.13 (3H, s), 3.64 (1H, d), 3.73-3.89 (3H, m), 3.89-4.08 (2H, m), 4.09-4.2 (1H, m), 4.32-4.45 (2H, m), 5.76 (1H, d), 6.19 (1H, d), 6.68-6.83 (1H, m), 7.21 (1H, d), 7.32 (1H, d), 7.51 (1H, s), 7.52-7.77 (2H, m), 13.07 (1H, s). m/z: ES+ [M+H]+=437.

(12aR)-10-Chloro-9-(5-methyl-1H-indazol-4-yl)-2-(prop-2-enoyl)-1,2,3,4,12,12a-hexahydro-6H-pyrazino[2,1-c][1,4]benzoxazepin-6-one Rotational Isomer 2, Example 8

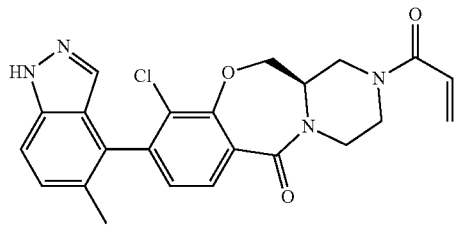 [SMILES: C=CC(=O)N1CCN2C(=O)c3ccc(-c4c(C)ccc5[nH]ncc45)c(Cl)c3OC[C@H]2C1]

To a solution of rotational isomer 2 of (12aR)-10-chloro-9-(5-methyl-1H-indazol-4-yl)-1,2,3,4,12,12a-hexahydro-6H-pyrazino[2,1-c][1,4]benzoxazepin-6-one (164 mg, 0.43 mmol) in DCM (5 mL), i-PrOH (1 mL) and pyridine (0.104 mL, 1.29 mmol) at −78° C. was added acryloyl chloride (0.035 mL, 0.43 mmol) slowly dropwise over 5 min and stirred at −78° C. to rt for 1 h. The solution was quenched with saturated NaHCO₃ (3 mL), diluted with EtOAc (10 mL) and washed with water (10 mL). The product was soluble in the aqueous phase, so water removed under reduced pressure and dissolved in 1M NH₃/MeOH. The crude product was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave rotational isomer 2 of (12aR)-10-chloro-9-(5-methyl-1H-indazol-4-yl)-2-(prop-2-enoyl)-1,2,3,4,12,12a-hexahydro-6H-pyrazino[2,1-c][1,4]benzoxazepin-6-one (53 mg, 28%) as a white solid. 1H NMR (400 MHz, DMSO, 30° C.) 2.16 (3H, s), 3.65 (1H, d), 3.83 (2H, s), 3.86-4.05 (3H, m), 4.05-4.15 (1H, m), 4.40 (2H, t), 5.67-5.8 (1H, m), 6.12-6.23 (1H, m), 6.67-6.83 (1H, m), 7.21 (1H, d), 7.32 (1H, d), 7.44 (1H, s), 7.51 (1H, d), 7.74 (1H, t), 13.09 (1H, s). m/z: ES+ [M+H]+=437.

Tert-butyl (12aR)-9-bromo-10-chloro-3,4,12,12a-tetrahydro-6H-pyrazino[2,1-c][1,4]benzoxazepine-2(1H)-carboxylate

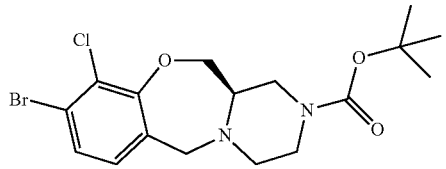 [SMILES: CC(C)(C)OC(=O)N1CCN2Cc3ccc(Br)c(Cl)c3OC[C@H]2C1]

A solution of borane THF complex (1M) (60 mL, 60 mmol) was added dropwise to a stirred solution of tert-butyl (12aR)-9-bromo-10-chloro-6-oxo-3,4,12,12a-tetrahydro-6H-pyrazino[2,1-c][1,4]benzoxazepine-2(1H)-carboxylate (4.9 g, 11.35 mmol) in THF (15 mL) at 25° C. The resulting solution was stirred at 75° C. for 3.5 h and then cooled to 25° C. and quenched with i-PrOH (150 mL). NaOH (2M, 100 mL) was added and the reaction was stirred for 30 min. The reaction was diluted with water (20 mL) and EtOAc (50 mL) and washed with brine (2×20 mL), dried (MgSO₄) and evaporated to afford tert-butyl (12aR)-9-bromo-10-chloro-3,4,12,12a-tetrahydro-6H-pyrazino[2,1-c][1,4]benzoxazepine-2(1H)-carboxylate (3.98 g, 84%) as a colourless oil which solidified on standing. 1H NMR (400 MHz, DMSO, 30° C.) 1.39 (9H, s), 2.30 (1H, ddd), 2.71 (2H, s), 3.07 (1H, ddd), 3.53-3.64 (3H, m), 3.66 (1H, q), 3.70 (1H, s), 3.78 (1H, d), 4.34 (1H, dd), 7.17 (1H, d), 7.41 (1H, d). m/z: ES+ [M+H]+=416.9.

Tert-butyl (12aR)-10-chloro-9-(5-methyl-1H-indazol-4-yl)-3,4,12,12a-tetrahydro-6H-pyrazino[2,1-c][1,4]benzoxazepine-2(1H)-carboxylate Rotational Isomer 1 and 2

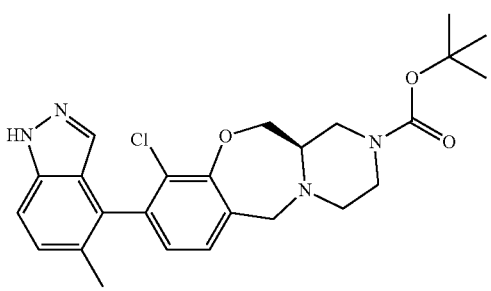 [SMILES: Cc1ccc2[nH]ncc2c1-c1ccc2c(c1Cl)OC[C@H]1CN(C(=O)OC(C)(C)C)CCN1C2]

Dichloro[1,1'-bis(di-tert-butylphosphino)ferrocene]palladium(II) (126 mg, 0.19 mmol) was added to a degassed mixture of tert-butyl (12aR)-9-bromo-10-chloro-3,4,12,12a-tetrahydro-6H-pyrazino[2,1-c][1,4]benzoxazepine-2(1H)-carboxylate (806 mg, 1.93 mmol), (5-methyl-1H-indazol-4-yl)boronic acid (679 mg, 3.86 mmol) and anhydrous sodium carbonate (1125 mg, 10.61 mmol) in 1,4-dioxane (22 mL) and water (5 mL). The reaction mixture was heated at 85° C. for 2 h and then cooled to 25° C. The reaction mixture was diluted with EtOAc (200 mL) and the organic layer was washed with saturated NaHCO₃ (100 mL), water (2×100 mL), brine (50 mL) and dried over a phase separating cartridge. The solvent was evaporated to afford crude product. This was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave a solid that was purified using SFC (Column: Chiralpak IG, 30×250 mm, 5 micron Mobile phase: 40% MeOH+0.1% NH₃/40% scCO₂ Flow rate: 90 mL/min BPR: 120 bar) to afford rotational isomer 1 of tert-butyl (12aR)-10-chloro-9-(5-methyl-1H-indazol-4-yl)-3,4,12,12a-tetrahydro-6H-pyrazino[2,1-c][1,4]benzoxazepine-2(1H)-carboxylate (199 mg, 22%). 1H NMR (400 MHz, DMSO, 100° C.) 1.44 (9H, s), 2.15 (3H, s), 2.78-2.92 (2H, m), 3.12-3.2 (1H, m), 3.62-3.74 (4H, m), 3.77 (2H, d), 3.99 (1H, d), 4.35 (1H, dd), 6.97 (1H, d), 7.29 (2H, d), 7.39 (1H, s), 7.47 (1H, d), 12.74 (1H, s). m/z: ES+ [M+H]+=469. This was followed by rotational isomer 2 of tert-butyl (12aR)-10-chloro-9-(5-methyl-1H-indazol-4-yl)-3,4,12,12a-tetrahydro-6H-pyrazino[2,1-c][1,4]benzoxazepine-2(1H)-carboxylate (224 mg, 25%). 1H NMR (400 MHz, DMSO, 100° C.) 1.44 (9H, s), 2.12 (3H, s), 2.36-2.46 (1H, m), 2.85 (2H, td), 3.11-3.2 (1H, m), 3.64-3.73 (3H, m), 3.71-3.81 (2H, m), 3.96 (1H, d), 4.34 (1H, d), 6.97 (1H, d), 7.29 (2H, dd), 7.4-7.5 (2H, m), 12.74 (1H, s). m/z: ES+ [M+H]+=469.

(12aR)-10-Chloro-9-(5-methyl-1H-indazol-4-yl)-1,2,3,4,12,12a-hexahydro-6H-pyrazino[2,1-c][1,4]benzoxazepine Rotational Isomer 1

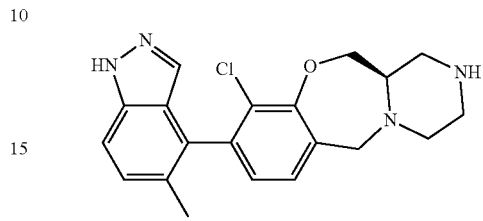

HCl (4M in dioxane) (2.12 mL, 8.49 mmol) was added to rotational isomer 1 of tert-butyl (12aR)-10-chloro-9-(5-methyl-1H-indazol-4-yl)-3,4,12,12a-tetrahydro-6H-pyrazino[2,1-c][1,4]benzoxazepine-2(1H)-carboxylate (199 mg, 0.42 mmol) in MeOH (2 mL) at 25° C. and the resulting solution was stirred for 3 h. The reaction mixture was purified by SCX (1M NH₃/MeOH) to afford rotational isomer 1 of (12aR)-10-chloro-9-(5-methyl-1H-indazol-4-yl)-1,2,3,4,12,12a-hexahydro-6H-pyrazino[2,1-c][1,4]benzoxazepine (157 mg, 100%) as a transparent glass. 1H NMR (400 MHz, DMSO, 30° C.) 2.13 (3H, s), 2.3-2.35 (2H, m), 2.43-2.47 (1H, m), 2.63-2.7 (2H, m), 2.73-2.85 (3H, m), 3.61-3.7 (2H, m), 3.83 (1H, d), 4.27 (1H, dd), 6.97 (1H, d), 7.29 (1H, s), 7.31 (1H, s), 7.39 (1H, s), 7.47 (1H, d), 13.03 (1H, s). m/z: ES+ [M+H]+=369.

(12aR)-10-Chloro-9-(5-methyl-1H-indazol-4-yl)-1,2,3,4,12,12a-hexahydro-6H-pyrazino[2,1-c][1,4]benzoxazepine Rotational Isomer 2

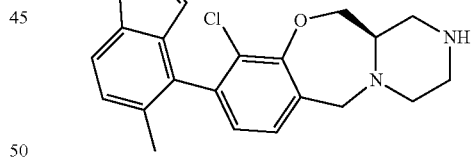

HCl (4M in dioxane) (2.38 mL, 9.55 mmol) was added to rotational isomer 2 of tert-butyl (12aR)-10-chloro-9-(5-methyl-1H-indazol-4-yl)-3,4,12,12a-tetrahydro-6H-pyrazino[2,1-c][1,4]benzoxazepine-2(1H)-carboxylate (224 mg, 0.48 mmol) in MeOH (3 mL) at 25° C. and the resulting solution was stirred for 3 h. The reaction mixture was purified by SCX (1M NH₃/MeOH) to afford rotational isomer 2 of (12aR)-10-chloro-9-(5-methyl-1H-indazol-4-yl)-1,2,3,4,12,12a-hexahydro-6H-pyrazino[2,1-c][1,4]benzoxazepine (180 mg, 100%) as a clear oil. 1H NMR (400 MHz, DMSO, 30° C.) 2.10 (3H, s), 2.29-2.38 (2H, m), 2.43-2.47 (1H, m), 2.59-2.7 (2H, m), 2.77-2.88 (3H, m), 3.63-3.72 (2H, m), 3.81 (1H, d), 4.27 (1H, dd), 6.97 (1H, d), 7.27-7.32 (2H, m), 7.43-7.49 (2H, m), 13.03 (1H, s). m/z: ES+ [M+H]+=369.

1-((12aR)-10-Chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one Rotational Isomer 1, Example 9

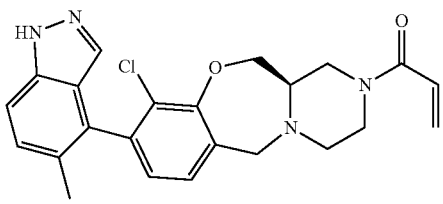 [SMILES: C=CC(=O)N1CCN2Cc3ccc(-c4c(C)ccc5[nH]ncc45)c(Cl)c3OC[C@H]2C1]

To a solution of rotational isomer 1 of (12aR)-10-chloro-9-(5-methyl-1H-indazol-4-yl)-1,2,3,4,12,12a-hexahydro-6H-pyrazino[2,1-c][1,4]benzoxazepine (159 mg, 0.43 mmol) in DCM (5 mL), i-PrOH (1 mL) and pyridine (0.105 mL, 1.29 mmol) at −78° C. was added acryloyl chloride (0.035 mL, 0.43 mmol) dropwise over 5 min and the reaction mixture was warmed to 0° C. and stirred for 10 min. The reaction mixture was evaporated to dryness, dissolved in 1 M $NH_3$/MeOH and purified by preparative HPLC (Waters XSelect CSH C18 ODB column, 5µ silica, 30 mm diameter, 100 mm length), using of water (containing by volume 1% $NH_4OH$ (28-30% in $H_2O$)) and MeCN as eluents. This gave rotational isomer 1 of 1-((12aR)-10-chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one (30 mg, 16%) as a cream solid. 1H NMR (400 MHz, DMSO, 100° C.) 2.15 (3H, s), 2.41-2.48 (2H, m), 2.85-2.92 (2H, m), 3.30 (1H, t), 3.71-3.82 (2H, m), 3.94 (2H, d), 3.99 (1H, d), 4.40 (1H, dd), 5.67 (1H, dd), 6.10 (1H, dd), 6.75 (1H, dd), 6.97 (1H, d), 7.28 (1H, d), 7.30 (1H, d), 7.38 (1H, s), 7.47 (1H, d), 12.75 (1H, s). m/z: ES+ [M+H]+= 423.1.

1-((12aR)-10-Chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one Rotational Isomer 2, Example 10

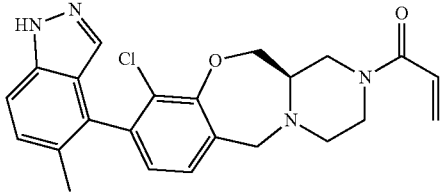 [SMILES: C=CC(=O)N1CCN2Cc3ccc(-c4c(C)ccc5[nH]ncc45)c(Cl)c3OC[C@H]2C1]

To a solution of rotational isomer 2 of (12aR)-10-chloro-9-(5-methyl-1H-indazol-4-yl)-1,2,3,4,12,12a-hexahydro-6H-pyrazino[2,1-c][1,4]benzoxazepine (180 mg, 0.49 mmol) in DCM (5 mL), i-PrOH (1 mL) and pyridine (0.118 mL, 1.46 mmol) at −78° C. was added acryloyl chloride (0.04 mL, 0.49 mmol) dropwise over 5 min and the reaction mixture was warmed to 0° C. and stirred for 10 min. The reaction mixture was evaporated to dryness, dissolved in 1 M $NH_3$/MeOH and purified by preparative HPLC (Waters XSelect CSH C18 ODB column, 5µ silica, 30 mm diameter, 100 mm length), using of water (containing by volume 1% $NH_4OH$ (28-30% in $H_2O$)) and MeCN as eluents. This gave rotational isomer 2 of 1-((12aR)-10-chloro-9-(5-methyl-1H-indazol-4-yl)-3,4,12,12a-tetrahydro-6H-benzo[f]pyrazino[2,1-c][1,4]oxazepin-2(1H)-yl)prop-2-en-1-one (42 mg, 20%) as a cream solid. 1H NMR (400 MHz, DMSO, 30° C.) 2.10 (3H, s), 2.39 (1H, s), 2.72-2.95 (3H, m), 3.08 (1H, d), 3.31-3.43 (1H, m), 3.68-3.8 (2H, m), 3.91 (1H, d), 3.98-4.15 (1H, m), 4.34-4.47 (1H, m), 5.70 (1H, d), 6.14 (1H, d), 6.78-6.9 (1H, m), 6.99 (1H, d), 7.31 (2H, dd), 7.46 (1H, s), 7.48 (1H, s), 13.03 (1H, s). m/z: ES+ [M+H]+=423.

4-Bromo-3-chloro-2,5-difluorobenzoic acid

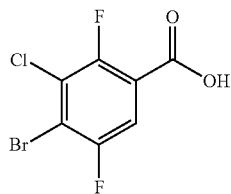 [SMILES: O=C(O)c1cc(F)c(Br)c(Cl)c1F]

4-Bromo-2,5-difluorobenzoic acid (10 g, 42.19 mmol) was added to concentrated sulfuric acid (80 mL) at rt and the resulting suspension heated at 80° C. N-Chlorosuccinimide (11.27 g, 84.39 mmol) was then added and the reaction mixture heated at 80° C. overnight. The reaction was cooled to rt, poured into ice (200 g) and the aqueous phase extracted with EtOAc. The crude product obtained after evaporation was purified by flash C18-flash chromatography, elution gradient 0 to 60% MeOH in water (0.1% formic acid), to afford 4-bromo-3-chloro-2,5-difluorobenzoic acid (4.8 g, 42%) as a white solid. 1H NMR (400 MHz, DMSO, 30° C.) 7.81 (1H, dd), 13.98 (1H, s). m/z: ES− [M+H]−=271.

Tert-butyl (3R)-4-(4-bromo-3-chloro-2,5-difluorobenzoyl)-3-(hydroxymethyl)piperazine-1-carboxylate

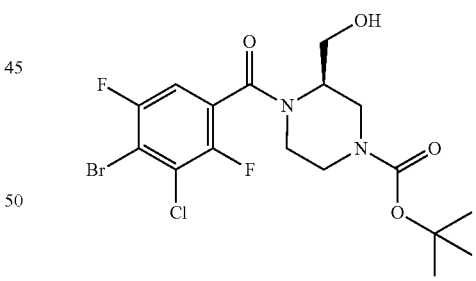

tert-Butyl (3R)-3-(hydroxymethyl)piperazine-1-carboxylate (3.98 g, 18.42 mmol) was added to 4-bromo-3-chloro-2,5-difluorobenzoic acid (5 g, 18.42 mmol), HATU (10.51 g, 27.63 mmol) and DIPEA (6.43 mL, 36.84 mmol) in THF (80 mL) at 25° C. The resulting solution was stirred at rt for 2 h. The solvent was removed under reduced pressure. The crude product obtained was purified by flash silica chromatography, elution gradient 0 to 50% EtOAc in petroleum ether to give tert-butyl (3R)-4-(4-bromo-3-chloro-2,5-difluorobenzoyl)-3-(hydroxymethyl)piperazine-1-carboxylate (5.72 g, 66%) as a white solid. 1H NMR (400 MHz, DMSO, 30° C.) 1.40 (9H, d), 2.74-3.05 (1H, m), 3.15 (1H, t), 3.26-3.37 (2H, m), 3.41-3.63 (2H, m), 3.67-3.90 (1H, m), 3.94-4.14 (1H, m), 4.19-4.33 (1H, m), 4.44-5.00 (1H, m), 7.59 (1H, s). m/z: ES+ [M+H]+=469.

Tert-butyl (12aR)-9-bromo-10-chloro-8-fluoro-6-oxo-3,4,12,12a-tetrahydro-6H-pyrazino[2,1-c][1,4]benzoxazepine-2(1H)-carboxylate

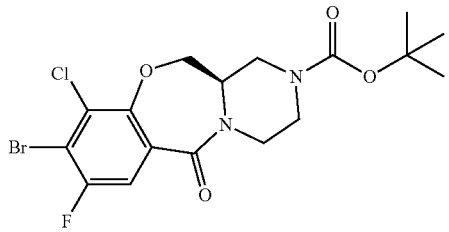 [SMILES: CC(C)(C)OC(=O)N1CCN2C(=O)c3cc(F)c(Br)c(Cl)c3OC[C@H]2C1]

Sodium hydride (0.971 g, 24.27 mmol) was added to tert-butyl (3R)-4-(4-bromo-3-chloro-2,5-difluorobenzoyl)-3-(hydroxymethyl)piperazine-1-carboxylate (5.7 g, 12.14 mmol) in THF (50 mL) at 0° C. The resulting solution was stirred at rt for 16 h. The solvent was removed under reduced pressure and the crude product obtained purified by flash silica chromatography, elution gradient 0 to 40% EtOAc in petroleum ether to give tert-butyl (12aR)-9-bromo-10-chloro-8-fluoro-6-oxo-3,4,12,12a-tetrahydro-6H-pyrazino[2,1-c][1,4]benzoxazepine-2(1H)-carboxylate (2.02 g, 37%) as a white solid. 1H NMR (400 MHz, DMSO, 30° C.) 1.41 (9H, s), 3.13-3.34 (1H, m), 3.44-3.50 (2H, m), 3.58-3.67 (1H, m), 3.72-3.80 (1H, m), 3.85-3.90 (1H, m), 3.92-4.02 (1H, m), 4.32 (2H, d), 7.59 (1H, d). m/z: ES+ [M+H]+=449.

Tert-butyl (12aR)-10-chloro-8-fluoro-9-(2-fluoro-6-methoxyphenyl)-6-oxo-3,4,12,12a-tetrahydro-6H-pyrazino[2,1-c][1,4]benzoxazepine-2(1H)-carboxylate Rotational Isomer 1 and Rotational Isomer

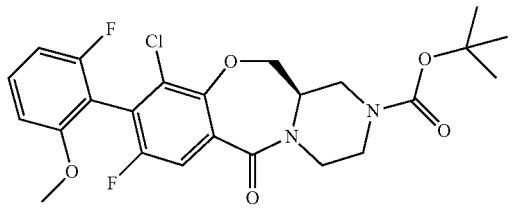 [SMILES: COc1cccc(F)c1-c1c(F)cc2c(c1Cl)OC[C@H]1CN(C(=O)OC(C)(C)C)CCN1C2=O]

A mixture of tert-butyl (12aR)-9-bromo-10-chloro-8-fluoro-6-oxo-3,4,12,12a-tetrahydro-6H-pyrazino[2,1-c][1,4]benzoxazepine-2(1H)-carboxylate (656 mg, 1.46 mmol), (2-fluoro-6-methoxyphenyl)boronic acid (496 mg, 2.92 mmol) and potassium carbonate (1210 mg, 8.75 mmol) in 2-methyltetrahydrofuran (11 mL) and water (4 mL) was degassed for 15 min. RuPhos Pd G3 (122 mg, 0.15 mmol) and RuPhos (68.1 mg, 0.15 mmol) was added at 25° C. and was heated at 60° C. for 2 h. After cooling to 25° C. the solution was diluted with EtOAc (100 mL) and washed with water (2×100 mL) and brine (100 mL). The organic phase was dried over a phase separating cartridge and the solvent was evaporated to dryness to afford crude product. The crude product was purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave a cream foam that was purified using SFC (Column: Chiralpak IG, 30×250 mm, 5 micron Mobile phase: 50% MeOH 0.1% NH₃/50% scCO₂ Flow rate: 100 mL/min BPR: 120 bar) to afford rotational isomer 1 of tert-butyl (12aR)-10-chloro-8-fluoro-9-(2-fluoro-6-methoxyphenyl)-6-oxo-3,4,12,12a-tetrahydro-6H-pyrazino[2,1-c][1,4]benzoxazepine-2(1H)-carboxylate (208 mg, 29%). 1H NMR (400 MHz, DMSO, 30° C.) 1.42 (9H, s), 3.48 (2H, s), 3.54-3.7 (2H, m), 3.75-3.85 (4H, m), 3.85-3.97 (1H, m), 3.97-4.06 (1H, m), 4.32 (2H, d), 6.98 (1H, t), 7.04 (1H, d), 7.47-7.59 (2H, m). m/z: ES+ [M+H]+=439. This was followed by rotational isomer 2 of tert-butyl (12aR)-10-chloro-8-fluoro-9-(2-fluoro-6-methoxyphenyl)-6-oxo-3,4,12,12a-tetrahydro-6H-pyrazino[2,1-c][1,4]benzoxazepine-2(1H)-carboxylate (163 mg, 23%). 1H NMR (400 MHz, DMSO, 30° C.) 1.42 (9H, s), 3.43-3.63 (4H, m), 3.63-3.73 (1H, m), 3.78 (3H, s), 3.89-4.07 (2H, m), 4.35 (2H, d), 6.97 (1H, t), 7.06 (1H, d), 7.49-7.59 (2H, m). m/z: ES- [M-H]- 493.

(12aR)-10-Chloro-8-fluoro-9-(2-fluoro-6-hydroxyphenyl)-1,2,3,4,12,12a-hexahydro-6H-pyrazino[2,1-c][1,4]benzoxazepin-6-one Rotational Isomer 1

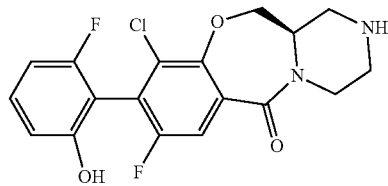 [SMILES: O=C1c2cc(F)c(-c3c(O)cccc3F)c(Cl)c2OC[C@H]2CNCCN12]

To rotational isomer 1 of tert-butyl (12aR)-10-chloro-8-fluoro-9-(2-fluoro-6-methoxyphenyl)-6-oxo-3,4,12,12a-tetrahydro-6H-pyrazino[2,1-c][1,4]benzoxazepine-2(1H)-carboxylate (108 mg, 0.22 mmol) in DCM (3 mL) at 0° C. was added boron tribromide (1M in DCM) (1.309 mL, 1.31 mmol) dropwise and stirred to 25° C. for 4 h. The reaction was quenched with MeOH and purified by SCX (1M NH₃/MeOH) to afford rotational isomer 1 of (12aR)-10-chloro-8-fluoro-9-(2-fluoro-6-hydroxyphenyl)-1,2,3,4,12,12a-hexahydro-6H-pyrazino[2,1-c][1,4]benzoxazepin-6-one (83 mg, 100%) as a white solid. 1H NMR (400 MHz, DMSO, 30° C.) 2.6-2.71 (1H, m), 2.83 (2H, qd), 2.94 (1H, dt), 3.17 (1H, d), 3.38 (1H, ddd), 3.77-3.92 (2H, m), 4.17 (1H, dd), 4.66 (1H, t), 6.73-6.86 (2H, m), 7.32 (1H, td), 7.50 (1H, d), 10.18 (1H, s). m/z: ES+ [M+H]+=380.9.1.

(12aR)-10-Chloro-8-fluoro-9-(2-fluoro-6-hydroxyphenyl)-1,2,3,4,12,12a-hexahydro-6H-pyrazino[2,1-c][1,4]benzoxazepin-6-one Rotational Isomer 2

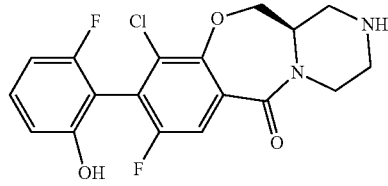 [SMILES: O=C1c2cc(F)c(-c3c(O)cccc3F)c(Cl)c2OC[C@H]2CNCCN12]

To rotational isomer 2 of tert-butyl (12aR)-10-chloro-8-fluoro-9-(2-fluoro-6-methoxyphenyl)-6-oxo-3,4,12,12a-tetrahydro-6H-pyrazino[2,1-c][1,4]benzoxazepine-2(1H)-carboxylate (163 mg, 0.33 mmol) in DCM (5 mL) at 0° C. was added boron tribromide (1M in DCM) (1.309 mL, 1.31 mmol) dropwise and stirred to 25° C. for 4 h. The reaction was quenched with MeOH and purified by SCX (1M NH₃/MeOH) to afford rotational isomer 2 of (12aR)-10-chloro-8-fluoro-9-(2-fluoro-6-hydroxyphenyl)-1,2,3,4,12,12a-hexahydro-6H-pyrazino[2,1-c][1,4]benzoxazepin-6-one (112 mg, 89%) as a white solid. 1H NMR (400 MHz, DMSO, 30° C.) 2.63-2.75 (1H, m), 2.77-2.99 (3H, m), 3.4-3.52 (1H, m), 3.76-3.89 (3H, m), 4.18 (1H, q), 4.66 (1H, t), 6.76 (1H, t), 6.83 (1H, d), 7.32 (1H, q), 7.53 (1H, d), 10.14 (1H, s). m/z: ES+ [M+H]+=381.1.

(12aR)-10-Chloro-8-fluoro-9-(2-fluoro-6-hydroxyphenyl)-2-(prop-2-enoyl)-1,2,3,4,12,12a-hexahydro-6H-pyrazino[2,1-c][1,4]benzoxazepin-6-one Rotational Isomer 1, Example 11

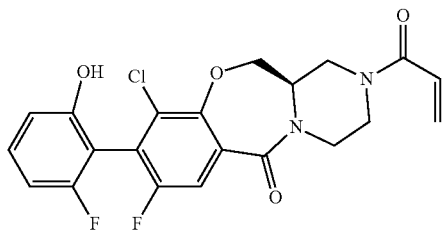 [SMILES: C=CC(=O)N1CCN2C(=O)c3cc(F)c(-c4c(O)cccc4F)c(Cl)c3OC[C@H]2C1]

To a solution of rotational isomer 1 of (12aR)-10-chloro-8-fluoro-9-(2-fluoro-6-hydroxyphenyl)-1,2,3,4,12,12a-hexahydro-6H-pyrazino[2,1-c][1,4]benzoxazepin-6-one (122 mg, 0.32 mmol) in DCM (4 mL), i-PrOH (1 mL) and pyridine (0.078 mL, 0.96 mmol) at −78° C. was added acryloyl chloride (0.026 mL, 0.32 mmol) slowly dropwise over 5 min and the reaction mixture was then stirred for 20 min. The reaction mixture was evaporated to dryness, dissolved in MeCN and purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave rotational isomer 1 of (12aR)-10-chloro-8-fluoro-9-(2-fluoro-6-hydroxyphenyl)-2-(prop-2-enoyl)-1,2,3,4,12,12a-hexahydro-6H-pyrazino[2,1-c][1,4]benzoxazepin-6-one (8 mg, 6%) as a cream solid. 1H NMR (400 MHz, CD₃CN, 30° C.) 3.6-3.85 (3H, m), 3.85-3.98 (2H, m), 4.04 (2H, dq), 4.23-4.42 (2H, m), 5.72 (1H, d), 6.14-6.28 (1H, m), 6.57-6.7 (1H, m), 6.74-6.89 (2H, m), 7.35 (1H, dt), 7.47 (1H, d). m/z: ES+ [M+H]+=435.0.1.

(12aR)-10-Chloro-8-fluoro-9-(2-fluoro-6-hydroxyphenyl)-2-(prop-2-enoyl)-1,2,3,4,12,12a-hexahydro-6H-pyrazino[2,1-c][1,4]benzoxazepin-6-one Rotational Isomer 2, Example 12

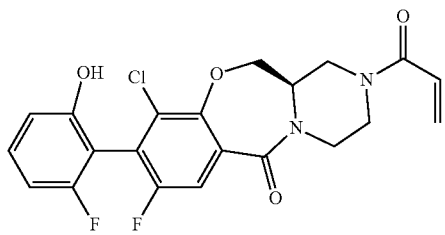 [SMILES: C=CC(=O)N1CCN2C(=O)c3cc(F)c(-c4c(O)cccc4F)c(Cl)c3OC[C@H]2C1]

To a solution of rotational isomer 2 of (12aR)-10-chloro-8-fluoro-9-(2-fluoro-6-hydroxyphenyl)-1,2,3,4,12,12a-hexahydro-6H-pyrazino[2,1-c][1,4]benzoxazepin-6-one (112 mg, 0.29 mmol) in DCM (3 mL), i-PrOH (1 mL) and pyridine (0.071 mL, 0.88 mmol) at −78° C. was added acryloyl chloride (0.024 mL, 0.29 mmol) dropwise and the reaction mixture was stirred for 20 min. The reaction mixture was evaporated to dryness, dissolved in 1 M NH₃/MeOH and purified by preparative HPLC (Waters XSelect CSH C18 ODB column, 5μ silica, 30 mm diameter, 100 mm length), using of water (containing by volume 1% NH₄OH (28-30% in H₂O)) and MeCN as eluents. This gave rotational isomer 2 of (12aR)-10-chloro-8-fluoro-9-(2-fluoro-6-hydroxyphenyl)-2-(prop-2-enoyl)-1,2,3,4,12,12a-hexahydro-6H-pyrazino[2,1-c][1,4]benzoxazepin-6-one (12 mg, 9%) as a cream solid. 1H NMR (400 MHz, DMSO, 100° C.) 3.57-3.82 (4H, m), 3.82-3.97 (2H, m), 3.97-4.14 (2H, m), 4.3-4.46 (2H, m), 5.70 (1H, dd), 6.14 (1H, dd), 6.63-6.76 (2H, m), 6.84 (1H, d), 7.31 (1H, q), 7.51 (1H, d). m/z: ES+ [M+H]+=435.4.

Tert-butyl (12aR)-9-bromo-8,10-dichloro-7-methoxy-6-oxo-3,4,12,12a-tetrahydro-6H-pyrazino[2,1-c][1,4]benzoxazepine-2(1H)-carboxylate

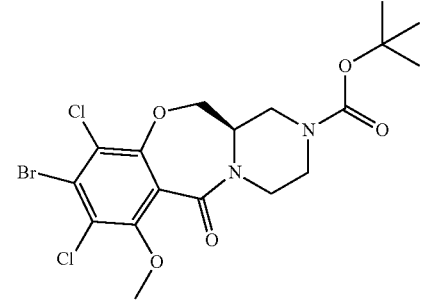 [SMILES: COc1c(Cl)c(Br)c(Cl)c2c1C(=O)N1CCN(C(=O)OC(C)(C)C)C[C@@H]1CO2]

N-Chlorosuccinimide (0.37 g, 2.82 mmol) and chlorotrimethylsilane (0.036 mL, 0.28 mmol) was added in one portion to a stirred solution of tert-butyl (12aR)-9-bromo-10-chloro-7-methoxy-6-oxo-3,4,12,12a-tetrahydro-6H-pyrazino[2,1-c][1,4]benzoxazepine-2(1H)-carboxylate (1.3 g, 2.82 mmol) in MeCN (28 mL) and the reaction was stirred for 15 min at 25° C. The reaction was then diluted with EtOAc (100 mL), water (100 mL) and washed with saturated NaHCO₃ (100 mL), water (100 mL) and brine (100 mL). The organic phase was dried by passing through a phase separating cartridge and the solvent was evaporated under reduced pressure to afford tert-butyl (12aR)-9-bromo-8,10-dichloro-7-methoxy-6-oxo-3,4,12,12a-tetrahydro-6H-pyrazino[2,1-c][1,4]benzoxazepine-2(1H)-carboxylate (1.39 g, 100%) as a cream solid and was used without further purification. 1H NMR (400 MHz, DMSO, 30° C.) 1.41 (9H, s), 3.13-3.28 (1H, m), 3.39 (1H, d), 3.50 (1H, s), 3.67 (1H, d), 3.76 (1H, d), 3.88 (3H, s), 3.93-4 (1H, m), 4.04-4.1 (1H, m), 4.1-4.19 (1H, m), 4.21-4.34 (1H, m). m/z: ES+ [M+H]+=495.

Tert-butyl (12aR)-9-bromo-8,10-dichloro-7-methoxy-3,4,12,12a-tetrahydro-6H-pyrazino[2,1-c][1,4]benzoxazepine-2(1H)-carboxylate

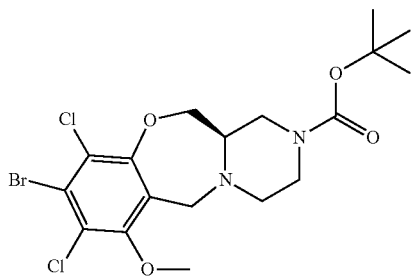 [SMILES: COc1c(Cl)c(Br)c(Cl)c2c1CN1CCN(C(=O)OC(C)(C)C)C[C@@H]1CO2]

A solution of borane THF complex (1M) (24.18 mL, 24.18 mmol) was added dropwise to a stirred solution of tert-butyl (12aR)-9-bromo-8,10-dichloro-7-methoxy-6-oxo-3,4,12,12a-tetrahydro-6H-pyrazino[2,1-c][1,4]benzoxazepine-2(1H)-carboxylate (1.5 g, 3.02 mmol) in THF (6 mL) at 25° C. The resulting solution was stirred at 75° C. for 20 h and was then cooled to 25° C., quenched with water and saturated NH4Cl and stirred for 30 min. The reaction was diluted with water (100 mL) and EtOAc (100 mL) and washed with brine (2×100 mL), dried over a phase separating cartridge and solvent was removed under reduced pressure to afford crude product. This was purified by flash silica chromatography, elution gradient 0 to 50% EtOAc in heptane to give tert-butyl (12aR)-9-bromo-8,10-dichloro-7-methoxy-3,4,12,12a-tetrahydro-6H-pyrazino[2,1-c][1,4]benzoxazepine-2(1H)-carboxylate (0.97 g, 67%) as a white solid. 1H NMR (400 MHz, DMSO, 30° C.) 1.40 (9H, s), 2.34-2.43 (1H, m), 2.69-2.84 (3H, m), 3.03 (1H, t), 3.61-3.75 (4H, m), 3.77 (3H, s), 3.93 (1H, d), 4.39 (1H, dd). m/z: ES+ [M+H]+=480.9.

Tert-butyl (12aR)-8,10-dichloro-9-(2-fluoro-6-hydroxyphenyl)-7-methoxy-3,4,12,12a-tetrahydro-6H-pyrazino[2,1-c][1,4]benzoxazepine-2(1H)-carboxylate

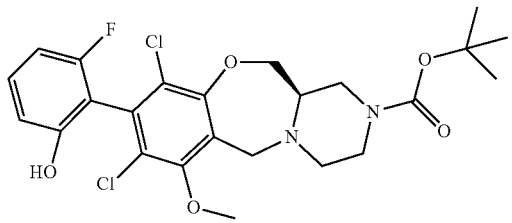 [SMILES: COc1c(Cl)c(-c2c(O)cccc2F)c(Cl)c2c1CN1CCN(C(=O)OC(C)(C)C)C[C@@H]1CO2]

A mixture of (2-fluoro-6-hydroxyphenyl)boronic acid (281 mg, 1.8 mmol), tert-butyl (12aR)-9-bromo-8,10-dichloro-7-methoxy-3,4,12,12a-tetrahydro-6H-pyrazino[2,1-c][1,4]benzoxazepine-2(1H)-carboxylate (870 mg, 1.8 mmol) and potassium carbonate (1496 mg, 10.83 mmol) in 2-methyltetrahydrofuran (13 mL) and water (4 mL) was degassed. RuPhos Pd G3 (151 mg, 0.18 mmol) and RuPhos (84 mg, 0.18 mmol) was added at 25° C. and the reaction mixture was heated at 60° C. for 4 h. After cooling to 25° C. the solution was diluted with EtOAc (100 mL) and washed with water (2×100 mL) and brine (100 mL). The organic phase was dried over a phase separating cartridge and the solvent was evaporated to dryness to afford crude product. The crude product was purified by flash silica chromatography, elution gradient 0 to 100% EtOAc in heptane to give tert-butyl (12aR)-8,10-dichloro-9-(2-fluoro-6-hydroxyphenyl)-7-methoxy-3,4,12,12a-tetrahydro-6H-pyrazino[2,1-c][1,4]benzoxazepine-2(1H)-carboxylate (453 mg, 49%) as a yellow solid. 1H NMR (400 MHz, DMSO, 30° C.) 1.41 (9H, s), 2.39-2.45 (1H, m), 2.63-2.77 (2H, m), 2.82-2.89 (1H, m), 2.95-3.06 (1H, m), 3.65-3.75 (4H, m), 3.77 (3H, s), 3.97 (1H, d), 4.36-4.45 (1H, m), 6.62-6.81 (2H, m), 7.27 (1H, q), 9.89-10.03 (1H, m). m/z: ES+ [M+H]+=512.9.

(12aR)-8,10-Dichloro-9-(2-fluoro-6-hydroxyphenyl)-1,2,3,4,12,12a-hexahydro-6H-pyrazino[2,1-c][1,4]benzoxazepin-7-ol

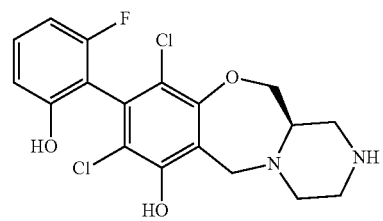 [SMILES: Oc1cccc(F)c1-c1c(Cl)c(O)c2c(c1Cl)OC[C@H]1CNCCN1C2]

To tert-butyl (12aR)-8,10-dichloro-9-(2-fluoro-6-hydroxyphenyl)-7-methoxy-3,4,12,12a-tetrahydro-6H-pyrazino[2,1-c][1,4]benzoxazepine-2(1H)-carboxylate (453 mg, 0.88 mmol) in DCM (3 mL) at 0° C. was added boron tribromide (1M in DCM) (5.29 mL, 5.29 mmol) dropwise and stirred to 25° C. for 2 h. The reaction was quenched with MeOH and purified by SCX (1M NH3/MeOH) to afford (12aR)-8,10-dichloro-9-(2-fluoro-6-hydroxyphenyl)-1,2,3,4,12,12a-hexahydro-6H-pyrazino[2,1-c][1,4]benzoxazepin-7-ol (351 mg, 100%) as a cream solid. 1H NMR (400 MHz, DMSO, 30° C.) 2.35-2.44 (2H, m), 2.55-2.65 (1H, m), 2.69-2.76 (1H, m), 2.76-2.93 (3H, m), 3.49-3.59 (1H, m), 3.59-3.71 (1H, m), 3.98-4.15 (2H, m), 4.21-4.32 (1H, m), 6.57-6.88 (2H, m), 7.24 (1H, q), 9.89 (1H, s). m/z: ES+ [M+H]+=399.

1-[(12aR)-8,10-dichloro-9-(2-fluoro-6-hydroxyphenyl)-7-hydroxy-3,4,12,12a-tetrahydro-6H-pyrazino[2,1-c][1,4]benzoxazepin-2(1H)-yl]prop-2-en-1-one Rotational Isomer 1, Example 13 and Rotational Isomer 2, Example 14

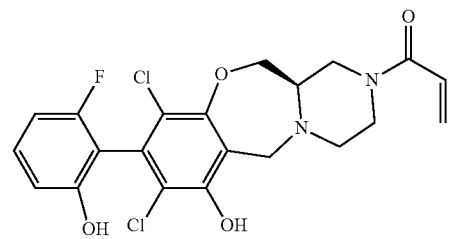 [SMILES: C=CC(=O)N1CCN2Cc3c(O)c(Cl)c(-c4c(O)cccc4F)c(Cl)c3OC[C@H]2C1]

To a stirred solution of (12aR)-8,10-dichloro-9-(2-fluoro-6-hydroxyphenyl)-1,2,3,4,12,12a-hexahydro-6H-pyrazino[2,1-c][1,4]benzoxazepin-7-ol (351 mg, 0.88 mmol) and DIPEA (0.199 mL, 1.14 mmol) in DCM (6 mL) at 0° C. was added acryloyl chloride (0.073 mL, 0.92 mmol) dropwise and the reaction mixture was stirred at 0° C. for 15 min. The reaction mixture was diluted with EtOAc (20 mL), washed with water (2×20 mL), brine (20 mL) and dried by passing through a phase separating cartridge. The solvent was removed to afford a gum which was dissolved in cold 1M $NH_3$/MeOH (20 mL) and was stirred at 25° C. for 1 h. The reaction mixture was concentrated to dryness to afford crude product. This was purified using SFC (Column: YMC Amylose C, 20×250 mm, 5 micron Mobile phase: 40% MeOH=0.1% $NH_3$/60% $scCO_2$ Flow rate: 60 mL/min BPR: 120 bar) to afford rotational isomer 1 of 1-[(12aR)-8,10-dichloro-9-(2-fluoro-6-hydroxyphenyl)-7-hydroxy-3,4,12,12a-tetrahydro-6H-pyrazino[2,1-c][1,4]benzoxazepin-2(1H)-yl]prop-2-en-1-one (105 mg, 26%). 1H NMR (400 MHz, DMSO, 30° C.) 2.35-2.46 (1H, m), 2.64-2.73 (1H, m), 2.73-2.84 (1H, m), 2.89 (1H, d), 2.93-3.09 (1H, m), 3.57-3.74 (2H, m), 3.83-4.01 (1H, m), 4.01-4.22 (2H, m), 4.38 (1H, t), 5.70 (1H, d), 6.13 (1H, d), 6.66-6.87 (3H, m), 7.24 (1H, q), 9.48 (1H, s), 9.87 (1H, s). m/z: ES+ [M+H]+=453. This was followed by rotational isomer 2 of 1-[(12aR)-8,10-dichloro-9-(2-fluoro-6-hydroxyphenyl)-7-hydroxy-3,4,12,12a-tetrahydro-6H-pyrazino[2,1-c][1,4]benzoxazepin-2(1H)-yl]prop-2-en-1-one (60 mg, 15%). 1H NMR (400 MHz, DMSO, 30° C.) 2.37-2.45 (1H, m), 2.70 (1H, s), 2.77-2.95 (2H, m), 2.95-3.08 (1H, m), 3.61 (1H, d), 3.64-3.71 (1H, m), 3.90 (1H, t), 4.04 (1H, d), 4.14 (1H, d), 4.35 (1H, t), 5.70 (1H, s), 6.12 (1H, d), 6.71 (1H, t), 6.76 (1H, d), 6.79-6.88 (1H, m), 7.24 (1H, q), 9.58 (1H, s), 9.89 (1H, s). m/z: ES+ [M+H]+=453.

Tert-butyl (3R)-4-(4-bromo-2,6-difluorobenzoyl)-3-(hydroxymethyl)piperazine-1-carboxylate

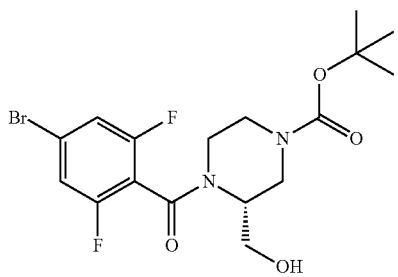 [SMILES: CC(C)(C)OC(=O)N1CCN(C(=O)c2c(F)cc(Br)cc2F)[C@@H](CO)C1]

To 4-bromo-2,6-difluorobenzoic acid (10 g, 42.19 mmol) in DCM (200 ml) was added tert-butyl (3R)-3-(hydroxymethyl)piperazine-1-carboxylate (10.95 g, 50.63 mmol) and triethylamine (23.52 ml, 168.78 mmol). 2,4,6-Tripropyl-1,3,5,2,4,6-trioxatriphosphinane 2,4,6-trioxide (29.8 ml of a 50% solution in EtOAc, 50.63 mmol) was added and the reaction mixture was stirred at rt. After 3 h, further portions of tert-butyl (3R)-3-(hydroxymethyl)piperazine-1-carboxylate (2.5 g) and 2,4,6-tripropyl-1,3,5,2,4,6-trioxatriphosphinane 2,4,6-trioxide (10 ml of a 50% solution in EtOAc) were added and the mixture was stirred at rt. After a further 2 h the reaction mixture was washed with aqueous saturated sodium hydrogen carbonate (200 mL) and then brine (200 mL). The organic portion was passed through a hydrophobic frit and concentrated under reduced pressure to give a pale brown oil. This was purified by flash silica chromatography, using an elution gradient of 0 to 100% EtOAc in heptane to give tert-butyl (3R)-4-(4-bromo-2,6-difluorobenzoyl)-3-(hydroxymethyl)piperazine-1-carboxylate (8.32 g, 45%) as a white foam. 1H NMR (400 MHz, DMSO, 30° C.) 1.41 (9H, 2×s), 2.69-3.24 (3H, m), 3.31-3.62 (3H, m), 3.72-4.19 (2H, m), 4.26-4.58 (1H, m), 4.78-4.98 (1H, m), 7.53-7.69 (2H, m). m/z: ES+ [M-Boc]334.9.

Tert-butyl (12aR)-9-bromo-7-fluoro-6-oxo-3,4,12,12a-tetrahydro-6H-pyrazino[2,1-c][1,4]benzoxazepine-2(1H)-carboxylate

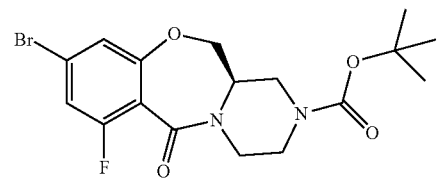 [SMILES: CC(C)(C)OC(=O)N1CCN2C(=O)c3c(F)cc(Br)cc3OC[C@H]2C1]

Sodium hydride (0.84 g of a 60% dispersion in mineral oil, 21.03 mmol) was added to tert-butyl (3R)-4-(4-bromo-2,6-difluorobenzoyl)-3-(hydroxymethyl)piperazine-1-carboxylate (8.32 g, 19.11 mmol) in DMF (100 ml) at 0° C. The resulting solution was stirred at 0° C. for 5 min before being warmed to rt. After 2 h a further portion of sodium hydride (200 mg) was added and the mixture was stirred at rt. After 4 h the reaction mixture was cooled in an ice-bath and aqueous saturated ammonium chloride solution (100 mL) was added dropwise. Water (100 mL) was added and the mixture was extracted with EtOAc (3×200 mL). The combined organics were washed with brine (200 mL), dried ($MgSO_4$) and concentrated under reduced pressure to give a pale yellow oil. This was purified by flash silica chromatography, elution gradient 0 to 80% EtOAc in heptane to give tert-butyl (12aR)-9-bromo-7-fluoro-6-oxo-3,4,12,12a-tetrahydro-6H-pyrazino[2,1-c][1,4]benzoxazepine-2(1H)-carboxylate (6.46 g, 81%) as a white foam. 1H NMR (400 MHz, DMSO, 30° C.) 1.42 (9H, s), 3.3-3.38 (1H, m), 3.42-3.53 (1H, m), 3.59-3.71 (3H, m), 3.83-3.96 (1H, m), 4.01-4.13 (1H, m), 4.13-4.29 (2H, m), 7.21-7.29 (1H, m), 7.49 (1H, dd). 19F NMR (376 MHz, DMSO, 30° C.)–111.16. m/z: ES+ [M+H]+ 415.0.

(12aR)-9-Bromo-10-chloro-7-fluoro-1,2,3,4,12,12a-hexahydro-6H-pyrazino[2,1-c][1,4]benzoxazepin-6-one

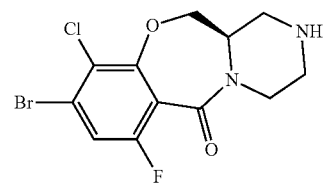 [SMILES: O=C1c2c(F)cc(Br)c(Cl)c2OC[C@H]2CNCCN12]

Tert-butyl (12aR)-9-bromo-7-fluoro-6-oxo-3,4,12,12a-tetrahydro-6H-pyrazino[2,1-c][1,4]benzoxazepine-2(1H)-carboxylate (6.46 g, 15.56 mmol) was dissolved in concentrated sulfuric acid (78 ml) and the mixture was stirred at rt for 5 min. The mixture was heated at 60° C. and N-chlorosuccinimide (4.15 g, 31.11 mmol) was added in one portion and reaction mixture was stirred at 60° C. After 30 min a further portion of N-chlorosuccinimide (2 g) was added. After a further 45 min the reaction mixture was cooled to rt and poured onto crushed ice (200 g). The aqueous was basified to ~pH 10 using aqueous 2 M sodium hydroxide solution. The aqueous layer was extracted with EtOAc (3×200 mL) and the combined organics were dried (MgSO₄) and concentrated under reduced pressure to give (12aR)-9-bromo-10-chloro-7-fluoro-1,2,3,4,12,12a-hexahydro-6H-pyrazino[2,1-c][1,4]benzoxazepin-6-one (6.33 g, >100%) as a brown foam that was used without further purification. 1H NMR (400 MHz, DMSO, 30° C.): 2.78-2.85 (2H, m), 2.95-3.09 (2H, m), 3.18 (1H, d), 3.87-3.98 (1H, m), 4.01-4.13 (3H, m), 4.75 (1H, dd), 7.73 (1H, d). 19F NMR (376 MHz, DMSO, 30° C.): −114.39 (J=9.1). m/z: ES+ [M+H]+ 348.8.

Tert-butyl (12aR)-9-bromo-10-chloro-7-fluoro-6-oxo-3,4,12,12a-tetrahydro-6H-pyrazino[2,1-c][1,4]benzoxazepine-2(1H)-carboxylate

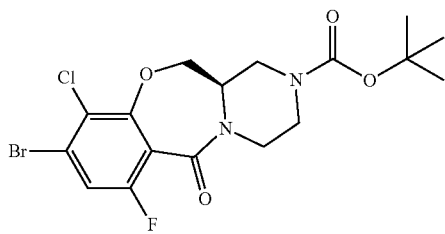 [SMILES: CC(C)(C)OC(=O)N1CCN2C(=O)c3c(F)cc(Br)c(Cl)c3OC[C@H]2C1]

(12aR)-9-Bromo-10-chloro-7-fluoro-1,2,3,4,12,12a-hexahydro-6H-pyrazino[2,1-c][1,4]benzoxazepin-6-one (6.33 g, 14.49 mmol) was dissolved in DCM (150 ml) and triethylamine (6.06 ml, 43.46 mmol) and di-tert-butyl dicarbonate (4.74 g, 21.73 mmol) were added sequentially. The resulting solution was stirred at rt. After 60 min, the reaction mixture was washed with water (100 mL). The organic portion was passed through a hydrophobic frit and concentrated under reduced pressure to give a dark brown residue. The crude product was purified by flash silica chromatography, elution gradient 0 to 60% EtOAc in heptane, to afford tert-butyl (12aR)-9-bromo-10-chloro-7-fluoro-6-oxo-3,4,12,12a-tetrahydro-6H-pyrazino[2,1-c][1,4]benzoxazepine-2(1H)-carboxylate (5.81 g, 89%) as a pale brown foam. 1H NMR (400 MHz, DMSO, 30° C.): 1.42 (9H, s), 3.42-3.53 (1H, m), 3.59-3.73 (4H, m), 3.85-3.99 (1H, m), 4.05-4.16 (1H, m), 4.24 (1H, dd), 4.28-4.41 (1H, m), 7.75 (1H, d). 19F NMR (376 MHz, DMSO, 30° C.): −114.46-−112.02. m/z: ES+ [M-tBu]+ 394.8.

Tert-butyl (12aR)-9-bromo-10-chloro-7-fluoro-3,4,12,12a-tetrahydro-6H-pyrazino[2,1-c][1,4]benzoxazepine-2(1H)-carboxylate

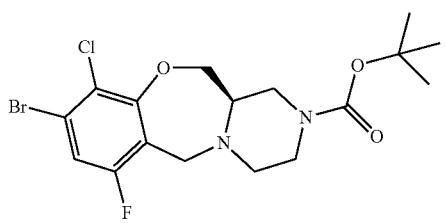 [SMILES: CC(C)(C)OC(=O)N1CCN2Cc3c(F)cc(Br)c(Cl)c3OC[C@H]2C1]

Tert-butyl (12aR)-9-bromo-10-chloro-7-fluoro-6-oxo-3,4,12,12a-tetrahydro-6H-pyrazino[2,1-c][1,4]benzoxazepine-2(1H)-carboxylate (5.81 g, 12.92 mmol) was dissolved in THF (50 mL) and borane-THF complex (129 mL of a 1M solution, 129.20 mmol) was added at rt. The resultant solution was heated at 75° C. After 2 h the reaction mixture was cooled in an ice-bath and quenched by dropwise addition of aqueous saturated ammonium chloride solution (200 mL). The resultant mixture was stirred until effervescence halted and then was extracted with EtOAc (2×200 mL). The combined organics were washed with brine (150 mL), dried (MgSO₄) and concentrated to give a pale yellow residue. This was purified by flash silica chromatography, elution gradient 0 to 100% EtOAc in heptane to give tert-butyl (12aR)-9-bromo-10-chloro-7-fluoro-3,4,12,12a-tetrahydro-6H-pyrazino[2,1-c][1,4]benzoxazepine-2(1H)-carboxylate (5.34 g, 95%) as a colourless residue. 1H NMR (400 MHz, DMSO, 30° C.): 1.40 (9H, s), 2.32-2.41 (1H, m), 2.68-2.83 (3H, m), 3-3.11 (1H, m), 3.55-3.73 (3H, m), 3.80 (1H, dd), 3.90 (1H, d), 4.41 (1H, dd), 7.50 (1H, d). 19F NMR (376 MHz, DMSO, 30° C.): −116.50 (J=8.8). m/z: ES+ [M+H]+ 434.9.

Tert-butyl (12aR)-9-bromo-10-chloro-7-(1H-imidazol-1-yl)-3,4,12,12a-tetrahydro-6H-pyrazino[2,1-c][1,4]benzoxazepine-2(1H)-carboxylate

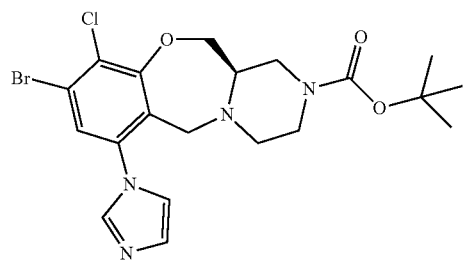 [SMILES: CC(C)(C)OC(=O)N1CCN2Cc3c(-n4ccnc4)cc(Br)c(Cl)c3OC[C@H]2C1]

Tert-butyl (12aR)-9-bromo-10-chloro-7-fluoro-3,4,12,12a-tetrahydro-6H-pyrazino[2,1-c][1,4]benzoxazepine-2(1H)-carboxylate (500 mg, 1.15 mmol) was dissolved in DMF (10 mL) and potassium phosphate (1.22 g, 5.74 mmol) and 1H-imidazole (117 mg, 1.72 mmol) were added consecutively. The mixture was sealed and heated at 120° C. in a microwave reactor for 1 h. The mixture was diluted with water (20 mL) and extracted with EtOAc (2×30 mL). The combined organics were washed with brine (20 mL), dried (MgSO₄) and concentrated under reduced pressure to give a pale yellow residue. The crude product was purified by flash silica chromatography, elution gradient 0 to 100% EtOAc in heptane to give tert-butyl (12aR)-9-bromo-10-chloro-7-(1H-imidazol-1-yl)-3,4,12,12a-tetrahydro-6H-pyrazino[2,1-c][1,4]benzoxazepine-2(1H)-carboxylate (162 mg, 29%) as a colourless dry film. 1H NMR (400 MHz, CDCl₃, 30° C.) 1.46 (9H, s), 2.31 (1H, td), 2.6-2.81 (3H, m), 3-3.1 (1H, m), 3.22 (1H, d), 3.58 (1H, d), 3.63-3.88 (3H, m), 4.40 (1H, dd), 7.08 (1H, t), 7.21-7.23 (1H, m), 7.35 (1H, s), 7.6-7.63 (1H, m). m/z: ES+ [M+H]+ 482.9.

Tert-butyl (12aR)-10-chloro-9-(2-fluoro-6-methoxyphenyl)-7-(1H-imidazol-1-yl)-3,4,12,12a-tetrahydro-6H-pyrazino[2,1-c][1,4]benzoxazepine-2(1H)-carboxylate

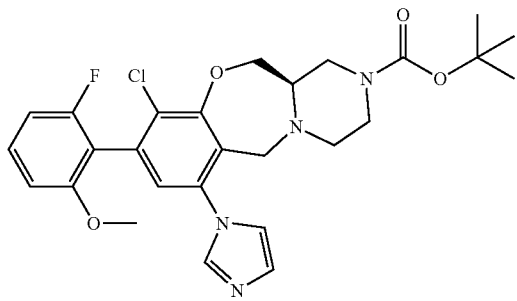 [SMILES: COc1cccc(F)c1-c1cc(-n2ccnc2)c2c(c1Cl)OC[C@H]1CN(C(=O)OC(C)(C)C)CCN1C2]

A solution of tert-butyl (12aR)-9-bromo-10-chloro-7-(1H-imidazol-1-yl)-3,4,12,12a-tetrahydro-6H-pyrazino[2,1-c][1,4]benzoxazepine-2(1H)-carboxylate (160 mg, 0.33 mmol) and (2-fluoro-6-methoxyphenyl)boronic acid (112 mg, 0.66 mmol) in 2M aqueous sodium carbonate (0.50 mL, 0.99 mmol) and 2-methyltetrahydrofuran (2.5 mL) was degassed. RuPhos G3 (28 mg, 0.03 mmol) and RuPhos (15 mg, 0.03 mmol) were added and the mixture was heated at 60° C. After 3 h a further portion of (2-fluoro-6-methoxyphenyl)boronic acid (112 mg, 0.66 mmol) was added and the mixture was left to stir at 60° C. After a further 5 h the reaction mixture was cooled to rt. The organic portion was collected and the aqueous was washed with EtOAc (10 mL). The combined organics were dried (MgSO₄) and concentrated to give a brown residue. The crude product was purified by flash silica chromatography, elution gradient 0 to 10% MeOH in DCM to give tert-butyl (12aR)-10-chloro-9-(2-fluoro-6-methoxyphenyl)-7-(1H-imidazol-1-yl)-3,4,12,12a-tetrahydro-6H-pyrazino[2,1-c][1,4]benzoxazepine-2(1H)-carboxylate (170 mg, 97%) as a pale yellow foam. 1H NMR (400 MHz, DMSO, 30° C.): 1.36-1.45 (9H, m), 2.2-2.32 (2H, m), 2.92-3.04 (1H, m), 3.15 (1H, dd), 3.57-3.9 (8H, m), 4.34-4.58 (2H, m), 6.93 (1H, td), 7.00 (1H, dd), 7.07-7.16 (2H, m), 7.36-7.43 (1H, m), 7.43-7.51 (1H, m), 7.78-7.87 (1H, m). 19F NMR (376 MHz, DMSO, 30° C.): −114.02−−113.92, −113.86−−113.69. m/z: ES+ [M+H]+ 529.0.

2-[(12aR)-10-Chloro-7-(1H-imidazol-1-yl)-1,2,3,4,12,12a-hexahydro-6H-pyrazino[2,1-c][1,4]benzoxazepin-9-yl]-3-fluorophenol

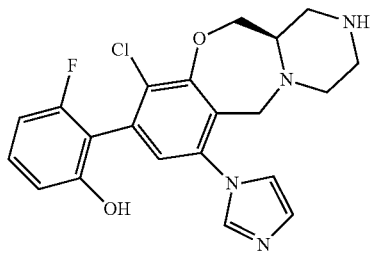 [SMILES: Oc1cccc(F)c1-c1cc(-n2ccnc2)c2c(c1Cl)OC[C@H]1CNCCN1C2]

Tert-butyl (12aR)-10-chloro-9-(2-fluoro-6-methoxyphenyl)-7-(1H-imidazol-1-yl)-3,4,12,12a-tetrahydro-6H-pyrazino[2,1-c][1,4]benzoxazepine-2(1H)-carboxylate (170 mg, 0.32 mmol) was dissolved in DCM (2 mL) and the mixture was cooled to 0° C. and then boron tribromide (3.78 mL of a 1M solution in DCM, 3.78 mmol) was added dropwise. The suspension was brought to rt and stirred. After 15 min the reaction mixture was cooled in an ice-bath and MeOH (20 mL) was added dropwise and the volatiles were removed under reduced pressure. The resultant residue was purified by SCX (1M NH₃/MeOH) to give 2-[(12aR)-10-chloro-7-(1H-imidazol-1-yl)-1,2,3,4,12,12a-hexahydro-6H-pyrazino[2,1-c][1,4]benzoxazepin-9-yl]-3-fluorophenol (123 mg, 92%) as a pale yellow residue. m/z: ES+ [M+H]+ 415.0.

1-[(12aR)-10-Chloro-9-(2-fluoro-6-hydroxyphenyl)-7-(1H-imidazol-1-yl)-3,4,12,12a-tetrahydro-6H-pyrazino[2,1-c][1,4]benzoxazepin-2(1H)-yl]prop-2-en-1-one, Example 15

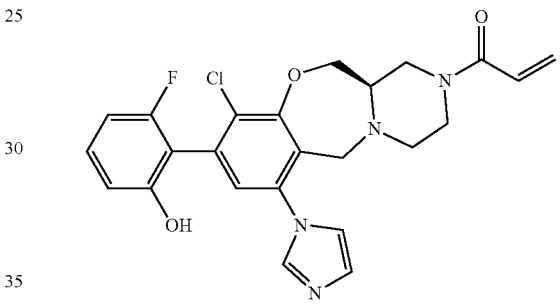

To a solution of 2-[(12aR)-10-chloro-7-(1H-imidazol-1-yl)-1,2,3,4,12,12a-hexahydro-6H-pyrazino[2,1-c][1,4]benzoxazepin-9-yl]-3-fluorophenol (123 mg, 0.30 mmol) and triethylamine (54 µL, 0.39 mmol) in DCM (2 ml) at 0° C. was added acryloyl chloride (26.5 µL, 0.33 mmol). The resultant mixture was stirred at 0° C. After 10 min the mixture was quenched by addition of water (10 mL) and extracted with DCM (2×10 mL) and then 2-methyltetrahydrofuran (2×10 mL). The combined organic extracts were dried (MgSO₄) and concentrated to give a pale yellow residue. This was dissolved in 7N ammonia in MeOH and stirred at rt for 5 min. The mixture was concentrated under reduced pressure to give a pale yellow residue. This was purified by flash silica chromatography, elution gradient 0 to 10% MeOH in DCM to give 1-[(12aR)-10-chloro-9-(2-fluoro-6-hydroxyphenyl)-7-(1H-imidazol-1-yl)-3,4,12,12a-tetrahydro-6H-pyrazino[2,1-c][1,4]benzoxazepin-2(1H)-yl]prop-2-en-1-one (6.3 mg, 5%) as a white residue. 1H NMR (400 MHz, CDCl₃, 30° C.): 2.25-2.49 (1H, m), 2.47-2.87 (3H, m), 2.91-3.13 (1H, m), 3.14-3.44 (2H, m), 3.51-3.95 (3H, m), 4.22-4.53 (2H, m), 5.7-5.78 (1H, m), 6.26-6.39 (1H, m), 6.54 (1H, ddd), 6.67-6.76 (1H, m), 6.84 (1H, dd), 7.07-7.16 (2H, m), 7.19-7.25 (1H, m), 7.63-7.69 (1H, m), 8.56 (1H, s). 19F NMR (376 MHz, CDCl₃, 30° C.): −113.58−−113, −112.98−−112.7. m/z: ES+ [M+H]+ 469.0.

5-Bromo-2-(bromomethyl)-1-fluoro-3-nitrobenzene

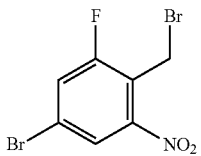

To a solution of 5-bromo-1-fluoro-2-methyl-3-nitrobenzene (5 g, 21.37 mmol) in MeCN (200 ml) was added N-bromosuccinimide (4.94 g, 27.77 mmol) and benzoic peroxyanhydride (0.26 g, 1.07 mmol) and the solution was stirred at reflux. After 6 h, a further portion of N-bromosuccinimide (2 g, 0.6 eq) was added and the mixture was stirred at reflux overnight. The solvent was removed in vacuo and the crude product was dissolved in DCM (20 mL), filtered and was purified by flash silica chromatography, elution gradient 0 to 20% EtOAc in heptane, to give 5-bromo-2-(bromomethyl)-1-fluoro-3-nitrobenzene (5.88 g, 88%) as a pale yellow oil. 1H NMR (400 MHz, CDCl$_3$, 30° C.): 4.76 (2H, d), 7.58 (1H, dd), 8.01 (1H, t). 19F NMR (376 MHz, CDCl$_3$, 30° C.): −109.66 (J=8.6, 1.6).

Tert-butyl (3R)-4-[(4-bromo-2-fluoro-6-nitrophenyl)methyl]-3-(hydroxymethyl)piperazine-1-carboxylate

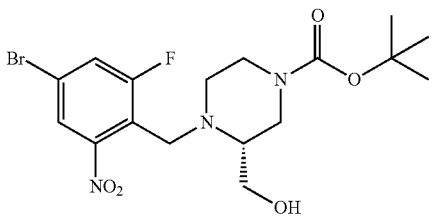 [SMILES: CC(C)(C)OC(=O)N1CCN(Cc2c(F)cc(Br)cc2[N+](=O)[O-])[C@@H](CO)C1]

To a solution of 5-bromo-2-(bromomethyl)-1-fluoro-3-nitrobenzene (5.88 g, 18.79 mmol) and tert-butyl (3R)-3-(hydroxymethyl)piperazine-1-carboxylate (4.47 g, 20.67 mmol) in MeCN (150 ml) was added potassium carbonate (7.79 g, 56.37 mmol) and the mixture was stirred at rt overnight. The reaction mixture was filtered and concentrated under reduced pressure. The crude product was purified by flash silica chromatography, elution gradient 0 to 40% EtOAc in heptane to give a pale yellow oil which solidified on standing. The solid was dissolved in DCM (100 mL) and washed with aqueous 1 M citric acid solution (100 mL). The organic portion was dried (MgSO$_4$) and concentrated to give tert-butyl (3R)-4-[(4-bromo-2-fluoro-6-nitrophenyl)methyl]-3-(hydroxymethyl)piperazine-1-carboxylate (8.2 g, 97%) as a pale yellow oil which solidified on standing. 1H NMR (400 MHz, DMSO, 30° C.): 1.38 (9H, s), 2.02-2.15 (1H, m), 2.33-2.39 (1H, m), 2.4-2.47 (1H, m), 2.96-3.11 (2H, m), 3.11-3.45 (3H, m), 3.53-3.76 (2H, m), 4.11 (1H, d), 4.46-4.75 (1H, m), 7.87-8.04 (2H, m). 19F NMR (376 MHz, DMSO, 30° C.): −112.06. m/z: ES+ [M+H]+ 448.0.

Tert-butyl (12aR)-7-amino-9-bromo-3,4,12,12a-tetrahydro-6H-pyrazino[2,1-c][1,4]benzoxazepine-2(1H)-carboxylate

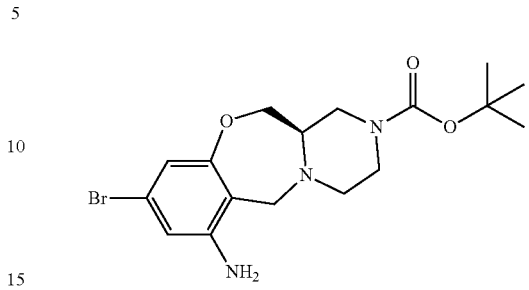

Sodium hydride (4 g of a 6% dispersion in mineral oil, 15.95 mmol) was added to tert-butyl (3R)-4-[(4-bromo-2-fluoro-6-nitrophenyl)methyl]-3-(hydroxymethyl)piperazine-1-carboxylate (6.5 g, 14.50 mmol) in THF (100 mL) at −78° C. The resulting solution was stirred at −78° C. for 5 min and then slowly brought to rt and stirred overnight. The reaction mixture was quenched by slow addition of aqueous saturated ammonium chloride solution (100 mL) and extracted with EtOAc (2×100 mL). The combined organics were dried (MgSO$_4$) and concentrated under reduced pressure to give a brown residue. This was purified by flash silica chromatography, elution gradient 0 to 40% methyl tert-butyl ether in heptane, to give a 2:1 mixture of tert-butyl (12aR)-9-bromo-7-nitro-3,4,12,12a-tetrahydro-6H-pyrazino[2,1-c][1,4]benzoxazepine-2(1H)-carboxylate and tert-butyl (12aR)-9-bromo-7-fluoro-3,4,12,12a-tetrahydro-6H-pyrazino[2,1-c][1,4]benzoxazepine-2(1H)-carboxylate as a brown dry film (3.11 g, 7.26 mmol). This mixture was dissolved in acetic acid (50 ml) and iron (1.014 g, 18.15 mmol) was added in one portion. The resultant mixture was stirred at 70° C. After 1 h, the reaction mixture was cooled to rt and concentrated under reduced pressure. The residue was diluted with water (20 mL) and aqueous saturated sodium hydrogen carbonate solution (100 mL) added. The resultant mixture was stirred for 10 min until effervescence has stopped. The aqueous layer was extracted with EtOAc (2×150 mL). The combined organics were dried (MgSO$_4$) and concentrated under reduced pressure to give a brown residue. The crude product was purified by flash silica chromatography, elution gradient 0 to 100% EtOAc in DCM to give tert-butyl (12aR)-7-amino-9-bromo-3,4,12,12a-tetrahydro-6H-pyrazino[2,1-c][1,4]benzoxazepine-2(1H)-carboxylate (0.97 g, 17%) as a dark yellow gum. The gum was dissolved in 1:1 DCM/heptane (10 mL) and concentrated under reduced pressure to give the title compound as a pale brown solid. 1H NMR (400 MHz, CDCl$_3$, 30° C.): 1.46 (9H, s), 2.46 (1H, ddd), 2.68 (1H, tt), 2.78-2.9 (2H, m), 3.18 (1H, ddd), 3.60 (2H, d), 3.62-3.73 (4H, m), 3.74-3.82 (1H, m), 4.15 (1H, dd), 6.59 (1H, d), 6.63 (1H, d). m/z: ES+ [M+H]+ 398.0.

Tert-butyl (12aR)-7-amino-9-bromo-10-chloro-3,4, 12,12a-tetrahydro-6H-pyrazino[2,1-c][1,4]benzoxazepine-2(1H)-carboxylate

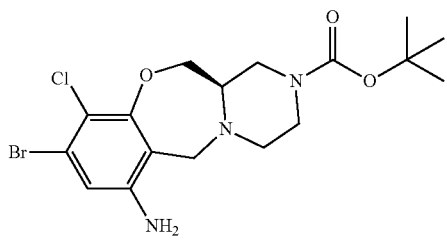 [SMILES: CC(C)(C)OC(=O)N1CCN2Cc3c(N)cc(Br)c(Cl)c3OC[C@H]2C1]

Tert-butyl (12aR)-7-amino-9-bromo-3,4,12,12a-tetrahydro-6H-pyrazino[2,1-c][1,4]benzoxazepine-2(1H)-carboxylate (800 mg, 2.01 mmol) was dissolved in MeCN (20 mL) and cooled to −10° C. N-Chlorosuccinimide (268 mg, 2.01 mmol) and a drop of chlorotrimethylsilane were added consecutively and the resultant mixture was stirred at −10° C. After 1 h, the mixture was slowly brought to rt and stirred. After a further 1 h, the reaction mixture was quenched by addition of aqueous saturated sodium hydrogen carbonate (20 mL) and the mixture was extracted with EtOAc (2×30 mL). The combined organics were dried (MgSO$_4$) and concentrated under reduced pressure to give a brown foam. This was purified by flash silica chromatography, elution gradient 0 to 80% EtOAc in heptane to give tert-butyl (12aR)-7-amino-9-bromo-10-chloro-3,4,12,12a-tetrahydro-6H-pyrazino[2,1-c][1,4]benzoxazepine-2(1H)-carboxylate (301 mg, 35%) as a pale brown solid. 1H NMR (400 MHz, DMSO, 30° C.): 1.40 (9H, s), 2.24-2.35 (1H, m), 2.56-2.73 (2H, m), 2.83-2.9 (1H, m), 3.03 (1H, t), 3.41 (1H, d), 3.48-3.66 (3H, m), 3.70 (1H, d), 4.25 (1H, dd), 5.51 (2H, s), 6.76 (1H, s). m/z: ES+ [M+H]+ 431.9.

Tert-butyl (12aR)-9-bromo-10-chloro-7-iodo-3,4,12, 12a-tetrahydro-6H-pyrazino[2,1-c][1,4]benzoxazepine-2(1H)-carboxylate

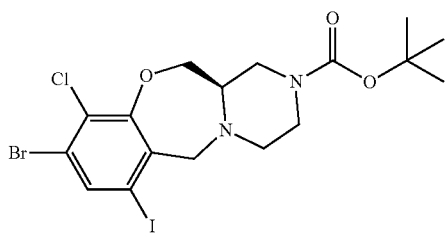 [SMILES: CC(C)(C)OC(=O)N1CCN2Cc3c(I)cc(Br)c(Cl)c3OC[C@H]2C1]

To a solution of tert-butyl (12aR)-7-amino-9-bromo-10-chloro-3,4,12,12a-tetrahydro-6H-pyrazino[2,1-c][1,4]benzoxazepine-2(1H)-carboxylate (300 mg, 0.69 mmol) in MeCN (5 mL) was added copper(I) iodide (158 mg, 0.83 mmol). Tert-butyl nitrite (0.116 mL, 1.39 mmol) was added dropwise and the mixture was stirred at 50° C. After 2 h, the reaction mixture was allowed to cool to rt and stirred overnight. The reaction mixture was diluted with aqueous saturated ammonium chloride (10 mL) and the mixture was extracted with EtOAc (2×20 mL). The combined organics were dried (MgSO$_4$) and concentrated under reduced pressure to give a brown residue. The crude product was purified by flash silica chromatography, elution gradient 0 to 40% EtOAc in heptane to give tert-butyl (12aR)-9-bromo-10-chloro-7-iodo-3,4,12,12a-tetrahydro-6H-pyrazino[2,1-c][1,4]benzoxazepine-2(1H)-carboxylate (107 mg, 28%) as a pale yellow dry film. 1H NMR (400 MHz, CDCl$_3$, 30° C.): 1.45 (9H, s), 2.49-2.58 (1H, m), 2.74-2.87 (1H, m), 2.87-3.06 (2H, m), 3.25-3.37 (1H, m), 3.57-3.69 (2H, m), 3.7-3.79 (1H, m), 3.91-4.09 (2H, m), 4.32 (1H, dd), 7.86 (1H, s). m/z: ES+ [M+H]+ 542.7.

Tert-butyl (12aR)-9-bromo-10-chloro-7-cyano-3,4, 12,12a-tetrahydro-6H-pyrazino[2,1-c][1,4]benzoxazepine-2(1H)-carboxylate

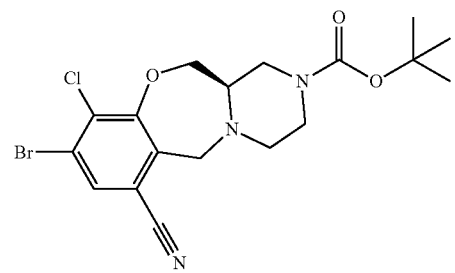 [SMILES: CC(C)(C)OC(=O)N1CCN2Cc3c(C#N)cc(Br)c(Cl)c3OC[C@H]2C1]

Tert-butyl (12aR)-9-bromo-10-chloro-7-iodo-3,4,12,12a-tetrahydro-6H-pyrazino[2,1-c][1,4]benzoxazepine-2(1H)-carboxylate (100 mg, 0.18 mmol) was dissolved in DMF (2 mL). Zinc cyanide (25.9 mg, 0.22 mmol) and tetrakis(triphenylphosphine)palladium(0) (42.5 mg, 0.04 mmol) were added consecutively and the resultant solution was heated at 100° C. After 1 h, the reaction mixture was cooled to rt and diluted with aqueous saturated sodium hydrogen carbonate solution (10 mL). The solution was extracted with EtOAc (2×20 mL) and the combined organics were washed with brine (10 mL), dried (MgSO$_4$) and concentrated under reduced pressure to give a brown residue. This was purified by flash silica chromatography, elution gradient 0 to 30% EtOAc in heptane, to afford tert-butyl (12aR)-9-bromo-10-chloro-7-cyano-3,4,12,12a-tetrahydro-6H-pyrazino[2,1-c][1,4]benzoxazepine-2(1H)-carboxylate (63 mg, 77%) as a colourless dry film. 1H NMR (400 MHz, CDCl$_3$, 30° C.): 1.46 (9H, s), 2.47-2.61 (1H, m), 2.75-2.89 (1H, m), 2.9-3.02 (2H, m), 3.19-3.35 (1H, m), 3.6-3.82 (3H, m), 3.93 (1H, d), 4.08 (1H, d), 4.29-4.38 (1H, m), 7.63 (1H, s). m/z: ES+ [M-tBu]+ 385.9.

Tert-butyl (12aR)-10-chloro-7-cyano-9-(2-fluoro-6-hydroxyphenyl)-3,4,12,12a-tetrahydro-6H-pyrazino[2,1-c][1,4]benzoxazepine-2(1H)-carboxylate

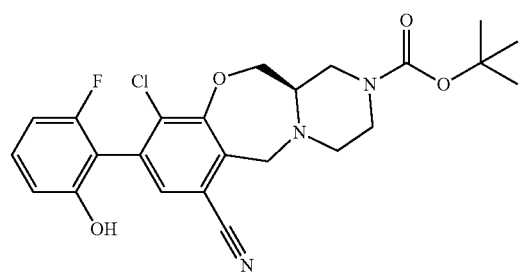 [SMILES: CC(C)(C)OC(=O)N1CCN2Cc3c(C#N)cc(-c4c(O)cccc4F)c(Cl)c3OC[C@H]2C1]

A solution of tert-butyl (12aR)-9-bromo-10-chloro-7-cyano-3,4,12,12a-tetrahydro-6H-pyrazino[2,1-c][1,4]benzoxazepine-2(1H)-carboxylate (63 mg, 0.14 mmol) and (2-fluoro-6-hydroxyphenyl)boronic acid (44.4 mg, 0.28 mmol) in 2M aqueous sodium carbonate (0.213 mL, 0.43 mmol) and 2-methyltetrahydrofuran (1 mL) was degassed with nitrogen for 5 min. RuPhos G3 (12 mg, 0.01 mmol) and RuPhos (7 mg, 0.01 mmol) were added and the mixture was heated at 60° C. After 1 h, the mixture was cooled to rt and diluted with water (10 mL). The mixture was filtered through a short pad of CELITE™ and extracted with EtOAc (2×10 mL). The combined organics were washed with brine (10 mL), dried (MgSO$_4$) and concentrated under reduced pressure to give a brown residue. This was purified by flash silica chromatography, elution gradient 0 to 50% EtOAc in heptane to give tert-butyl (12aR)-10-chloro-7-cyano-9-(2-fluoro-6-hydroxyphenyl)-3,4,12,12a-tetrahydro-6H-pyrazino[2,1-c][1,4]benzoxazepine-2(1H)-carboxylate (54 mg, 80%) as a white solid. 1H NMR (400 MHz, CDCl$_3$, 30° C.) 1.47 (9H, s), 2.47-2.68 (1H, m), 2.8-3.01 (3H, m), 3.16-3.34 (1H, m), 3.66-3.91 (3H, m), 3.96-4.18 (2H, m), 4.31-4.42 (1H, m), 5.33 (1H, s), 6.71-6.81 (3H, m), 7.38 (1H, d). 19F NMR (376 MHz, CDCl$_3$, 30° C.): −112.90. m/z: ES+ [M+H]+ 474.1.

(12aR)-10-Chloro-9-(2-fluoro-6-hydroxyphenyl)-1,2,3,4,12,12a-hexahydro-6H-pyrazino[2,1-c][1,4]benzoxazepine-7-carbonitrile

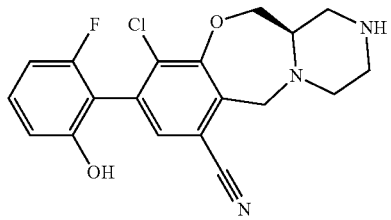 [SMILES: N#Cc1cc(-c2c(O)cccc2F)c(Cl)c2c1CN1CCNC[C@@H]1CO2]

Tert-butyl (12aR)-10-chloro-7-cyano-9-(2-fluoro-6-hydroxyphenyl)-3,4,12,12a-tetrahydro-6H-pyrazino[2,1-c][1,4]benzoxazepine-2(1H)-carboxylate (54 mg, 80%) (54 mg, 0.11 mmol) was dissolved in DCM (1 mL) and TFA (0.5 mL) was added. The solution was stirred at rt. After 1 h, the mixture was diluted with DCM (10 mL) and saturated sodium hydrogen carbonate (10 mL) was added. The resultant mixture was stirred for 5 min. The organic portion was collected and the aqueous was washed with DCM (10 mL). The combined organics were passed through a hydrophobic frit and concentrated under reduced pressure to give (12aR)-10-chloro-9-(2-fluoro-6-hydroxyphenyl)-1,2,3,4,12,12a-hexahydro-6H-pyrazino[2,1-c][1,4]benzoxazepine-7-carbonitrile (33 mg, 77%) as a colourless solid. m/z: ES+ [M+H]+ 374.0.

(12aR)-10-Chloro-9-(2-fluoro-6-hydroxyphenyl)-2-(prop-2-enoyl)-1,2,3,4,12,12a-hexahydro-6H-pyrazino[2,1-c][1,4]benzoxazepine-7-carbonitrile, Example 16

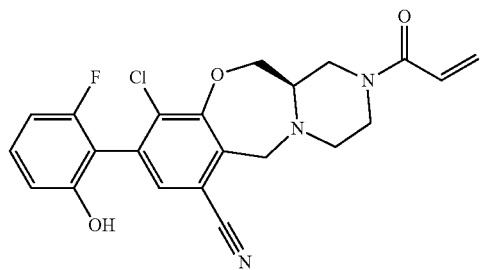 [SMILES: C=CC(=O)N1CCN2Cc3c(C#N)cc(-c4c(O)cccc4F)c(Cl)c3OC[C@H]2C1]

To a solution of (12aR)-10-chloro-9-(2-fluoro-6-hydroxyphenyl)-1,2,3,4,12,12a-hexahydro-6H-pyrazino[2,1-c][1,4]benzoxazepine-7-carbonitrile (33 mg, 0.09 mmol) and triethylamine (16 µL, 0.11 mmol) in DCM (1 ml) at 0° C. was added acryloyl chloride (7.89 µL, 0.10 mmol). The resultant mixture was stirred at 0° C. After 5 min, the reaction mixture was quenched by addition of a few drops of MeOH. The mixture was concentrated under reduced pressure and the resultant solid was dissolved in MeOH (1 mL) and 7N ammonia in MeOH (0.5 mL) was added. The solution was stirred at rt for 5 min and then concentrated under reduced pressure. The residue was suspended in DCM (5 mL) and the mixture was filtered. The filtrate was concentrated under reduced pressure to give a pale yellow residue. This was purified by preparative HPLC (Waters CSH C18 OBD column, 30×100 mm id, 5 micron particle size), eluting with 30-60% MeCN in water (containing 0.1% formic acid), to give (12aR)-10-chloro-9-(2-fluoro-6-hydroxyphenyl)-2-(prop-2-enoyl)-1,2,3,4,12,12a-hexahydro-6H-pyrazino[2,1-c][1,4]benzoxazepine-7-carbonitrile (9.9 mg, 26%) as a white solid. 1H NMR (400 MHz, CDCl$_3$, 30° C.): 2.48-2.63 (1H, m), 2.81-3.1 (3H, m), 3.33-3.5 (1H, m), 3.61-3.87 (2H, m), 3.93-4.16 (3H, m), 4.25-4.38 (1H, m), 5.65-5.73 (1H, m), 6.18-6.31 (1H, m), 6.41-6.55 (1H, m), 6.61-6.77 (2H, m), 7.15-7.24 (1H, m), 7.32 (1H, 2×s). 19F NMR (376 MHz, CDCl$_3$, 30° C.): −113.47--112.63. m/z: ES+ [M+H]+ 428.0.

Tert-butyl (12aR)-9-bromo-10-chloro-7-(1H-pyrazol-1-yl)-3,4,12,12a-tetrahydro-6H-pyrazino[2,1-c][1,4]benzoxazepine-2(1H)-carboxylate

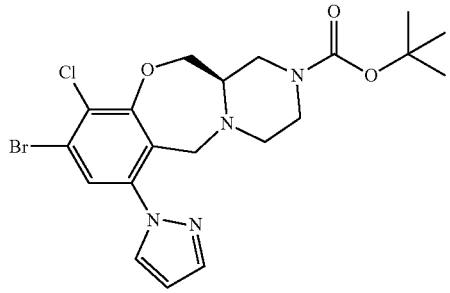 [SMILES: CC(C)(C)OC(=O)N1CCN2Cc3c(-n4cccn4)cc(Br)c(Cl)c3OC[C@H]2C1]

Tert-butyl (12aR)-9-bromo-10-chloro-7-fluoro-3,4,12,12a-tetrahydro-6H-pyrazino[2,1-c][1,4]benzoxazepine-2(1H)-carboxylate (580 mg, 1.33 mmol), 1H-pyrazole (109 mg, 1.60 mmol) and potassium phosphate (1.41 g, 6.66 mmol) were suspended in DMF (10 mL) and sealed into a microwave tube. The reaction mixture was heated at 120° C. in a microwave reactor for 1 h. A further portion of 1H-pyrazole (100 mg) was added to the microwave tube and resealed. The reaction was heated at 120° C. in the microwave reactor for 1.25 h. The mixture was diluted with water (30 mL) and extracted with EtOAc (2×30 mL). The combined organics were dried (MgSO$_4$) and concentrated under reduced pressure to give a pale yellow residue (1.1 g). The crude product was purified by flash silica chromatography, elution gradient 0 to 100% EtOAc in heptane, to afford tert-butyl (12aR)-9-bromo-10-chloro-7-(1H-pyrazol-1-yl)-3,4,12,12a-tetrahydro-6H-pyrazino[2,1-c][1,4]benzoxazepine-2(1H)-carboxylate (337 mg, 52%) as a colourless gum. 1H NMR (400 MHz, CDCl$_3$, 30° C.): 1.42 (9H, s), 2.35 (1H, ddd), 2.58-2.71 (1H, m), 2.71-2.85 (2H, m), 3.11 (1H, t), 3.46 (1H, d), 3.62 (1H, d), 3.65-3.86 (3H, m), 4.36 (1H, dd), 6.41-6.45 (1H, m), 7.40 (1H, s), 7.60 (1H, dd), 7.69 (1H, dd). m/z: ES+ [M+H]+ 482.9.

Tert-butyl (12aR)-10-chloro-9-(2-fluoro-6-hydroxyphenyl)-7-(1H-pyrazol-1-yl)-3,4,12,12a-tetrahydro-6H-pyrazino[2,1-c][1,4]benzoxazepine-2(1H)-carboxylate

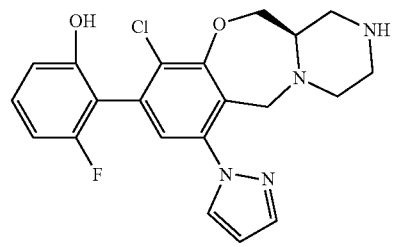

A solution of tert-butyl (12aR)-9-bromo-10-chloro-7-(1H-pyrazol-1-yl)-3,4,12,12a-tetrahydro-6H-pyrazino[2,1-c][1,4]benzoxazepine-2(1H)-carboxylate (337 mg, 0.70 mmol) and (2-fluoro-6-hydroxyphenyl)boronic acid (217 mg, 1.39 mmol) in 2M aqueous sodium carbonate (1.05 mL, 2.09 mmol) and 2-methyltetrahydrofuran (6 mL) was degassed with nitrogen for 5 min. RuPhos G3 (58.3 mg, 0.07 mmol) and RuPhos (32.5 mg, 0.07 mmol) were added and the mixture was heated at 60° C. for 3 h. A further portion of (2-fluoro-6-hydroxyphenyl)boronic acid (100 mg) was added and the reaction stirred at temperature for 1 h. A further portion of (2-fluoro-6-hydroxyphenyl)boronic acid (100 mg) was added and the mixture stirred at 60° C. for a further 1 h. The reaction mixture was diluted with water (20 mL) and 2-methyltetrahydrofuran (20 mL). The organic layer was collected, and the aqueous layer extracted with a further portion of 2-methyltetrahydrofuran (20 mL). The combined organic extracts were washed with brine (20 mL), dried (MgSO$_4$) and concentrated under pressure to give an orange residue. This was purified by flash silica chromatography, elution gradient 0 to 60% EtOAc in heptane to give tert-butyl (12aR)-10-chloro-9-(2-fluoro-6-hydroxyphenyl)-7-(1H-pyrazol-1-yl)-3,4,12,12a-tetrahydro-6H-pyrazino[2,1-c][1,4]benzoxazepine-2(1H)-carboxylate (224 mg, 62%) as a pale yellow solid. 1H NMR (400 MHz, DMSO, 30° C.): 1.40 (9H, s), 2.26-2.37 (1H, m), 2.54-2.63 (1H, m), 2.64-2.87 (2H, m), 2.91-3.1 (1H, m), 3.34-3.51 (1H, m), 3.57-3.77 (2H, m), 3.77-3.92 (2H, m), 4.34-4.57 (1H, m), 6.49-6.59 (1H, m), 6.73 (1H, td), 6.80 (1H, dd), 7.09 (1H, s), 7.16-7.33 (1H, m), 7.67-7.82 (1H, m), 7.9-8.1 (1H, m), 9.9-10.1 (1H, m). 19F NMR (376 MHz, DMSO, 30° C.): −115.79-−112.35. m/z: ES+ [M+H]+ 515.0.

2-[(12aR)-10-Chloro-7-(1H-pyrazol-1-yl)-1,2,3,4,12,12a-hexahydro-6H-pyrazino[2,1-c][1,4]benzoxazepin-9-yl]-3-fluorophenol

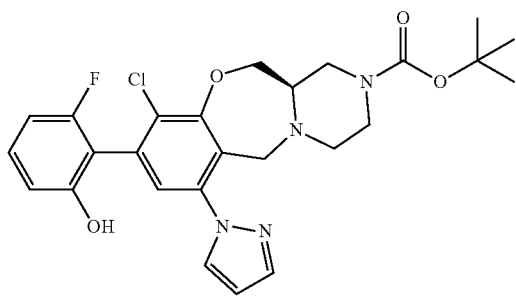 [SMILES: CC(C)(C)OC(=O)N1CCN2Cc3c(-n4cccn4)cc(-c4c(O)cccc4F)c(Cl)c3OC[C@H]2C1]

6 M HCl in i-PrOH (0.725 mL, 4.35 mmol) was added to tert-butyl (12aR)-10-chloro-9-(2-fluoro-6-hydroxyphenyl)-7-(1H-pyrazol-1-yl)-3,4,12,12a-tetrahydro-6H-pyrazino[2,1-c][1,4]benzoxazepine-2(1H)-carboxylate (224 mg, 0.430 mmol) in MeOH (5 mL) at rt. The resulting solution was stirred for 0.5 h. A further portion of 6 M HCl in i-PrOH (1 mL) was added and the reaction mixture stirred for 1 h. A further portion of 6 M HCl acid in i-PrOH (1 mL) was added and the reaction mixture stirred for 0.5 h. The reaction mixture was concentrated under reduced pressure to give a yellow powder. This was purified by SCX (1M NH$_3$/MeOH) to afford 2-[(12aR)-10-chloro-7-(1H-pyrazol-1-yl)-1,2,3,4,12,12a-hexahydro-6H-pyrazino[2,1-c][1,4]benzoxazepin-9-yl]-3-fluorophenol (141 mg, 78%) as a colourless dry film. 1H NMR (400 MHz, CDCl$_3$, 30° C.): 2.23-2.49 (2H, m), 2.58-2.96 (6H, m), 3.26-3.39 (1H, m), 3.45-3.78 (2H, m), 4.25 (1H, dd), 5.19 (1H, s), 6.38 (1H, dt), 6.57 (2H, dt), 7.02-7.17 (2H, m), 7.54-7.74 (2H, m). 19F NMR (376 MHz, CDCl$_3$, 30° C.): −113.33 (J=7.7), −112.91 (J=7.6). m/z: ES+ [M+H]+ 415.0.

1-[(12aR)-10-Chloro-9-(2-fluoro-6-hydroxyphenyl)-7-(1H-pyrazol-1-yl)-3,4,12,12a-tetrahydro-6H-pyrazino[2,1-c][1,4]benzoxazepin-2(1H)-yl]prop-2-en-1-one, Example 17

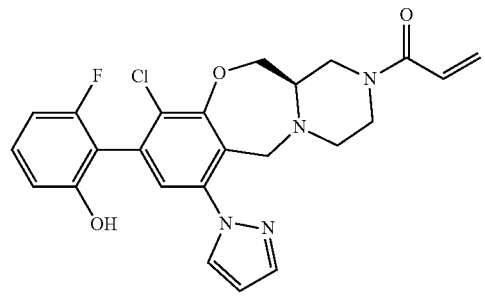 [SMILES: C=CC(=O)N1CCN2Cc3c(-n4cccn4)cc(-c4c(O)cccc4F)c(Cl)c3OC[C@H]2C1]

To a solution of 2-[(12aR)-10-chloro-7-(1H-pyrazol-1-yl)-1,2,3,4,12,12a-hexahydro-6H-pyrazino[2,1-c][1,4]benzoxazepin-9-yl]-3-fluorophenol (141 mg, 0.340 mmol) and triethylamine (262 µL, 1.88 mmol) in DCM (3 mL) at 0° C. was added acryloyl chloride (30.4 µL, 0.370 mmol). The resultant mixture was stirred at 0° C. for 0.5 h. A further portion of acryloyl chloride (30.4 µL, 0.37 mmol) was added and the mixture stirred for 0.1 h. The mixture was quenched by addition of water (10 mL) and extracted with DCM (2×10 mL). The combined organics were passed through a hydrophobic frit and concentrated under reduced pressure to give a pale yellow foam. This was dissolved in 7 M NH$_3$/MeOH (3 mL) and stirred for 5 min. The resulting solution was concentrated under reduced pressure to give a pale yellow residue (201 mg). This was purified by preparative HPLC (Waters CSH C18 OBD column, 30×100 mm id, 5 micron particle size),using 25-50% MeCN in water (containing 0.1% formic acid) to afford 65 mg of product. This was re-purified by preparative HPLC (Waters CSH C18 OBD column, 30×100 mm id, 5 micron particle size), using of water (containing 0.1% NH$_3$) and MeCN as eluents. This gave 1-[(12aR)-10-chloro-9-(2-fluoro-6-hydroxyphenyl)-7-(1H-pyrazol-1-yl)-3,4,12,12a-tetrahydro-6H-pyrazino[2,1-c][1,4]benzoxazepin-2(1H)-yl]prop-2-en-1-one (36 mg, 23%) as a yellow powder. 1H NMR (400 MHz, DMSO, 30° C.): 2.24-2.41 (2H, m), 2.69-3.14 (3H, m), 3.35-3.51 (1H, m), 3.75-4.02 (3H, m), 4.03-4.21 (1H, m), 4.42-4.6 (1H, m), 5.61-5.78 (1H, m), 6.12 (1H, d), 6.5-6.57 (1H, m), 6.61-6.9 (3H, m), 7.07 (1H, d), 7.23 (1H, q), 7.77 (1H, d), 7.97-8.04 (1H, m), 10.01 (1H, br s). 19F NMR (376 MHz, DMSO, 30° C.): −114.42−−113.57. m/z: ES+ [M+H]+ 469.0.

4-Bromo-5-methyl-1H-benzimidazole

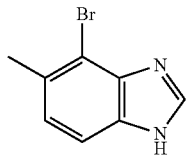

3-Bromo-4-methylbenzene-1,2-diamine (2.0 g, 9.95 mmol) was dissolved in formic acid (20 mL, 530.15 mmol) and the resulting mixture stirred at 100° C. for 75 min. The reaction was cooled to rt and the solvent removed under reduced pressure. The residue was purified by SCX (7M NH$_3$/MeOH) to afford 4-bromo-5-methyl-1H-benzimidazole (2.1 g, 100%) as a brown solid. 1H NMR (400 MHz, CDCl$_3$, 30° C.) 2.54 (3H, s), 7.19 (1H, d), 7.57 (1H, s), 8.03 (1H, s), 9.25 (1H, s). m/z: ES+ [M+H]+=211.

4-Bromo-5-methyl-1-(oxan-2-yl)-1H-benzimidazole

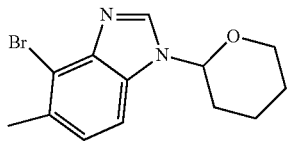 [SMILES: Cc1ccc2c(ncn2C2CCCCO2)c1Br]

A mixture of 4-bromo-5-methyl-1H-benzimidazole (2.1 g, 9.94 mmol), 3,4-dihydro-2H-pyran (4.54 mL, 49.68 mmol) and 4-methylbenzenesulfonic acid hydrate (0.283 g, 1.49 mmol) in THF (80 mL) was stirred at 65° C. for 23 h. The reaction mixture was cooled to rt and concentrated under reduced pressure. The resultant residue was dissolved in EtOAc (150 mL) and washed sequentially with aqueous saturated sodium hydrogen carbonate (75 mL) and brine (50 mL). The organic layer was passed through a hydrophobic frit and concentrated under reduced pressure to afford the crude product. This was purified by flash silica chromatography, elution gradient 0 to 80% EtOAc in heptane, to give 4-bromo-5-methyl-1-(oxan-2-yl)-1H-benzimidazole (2.2 g, 75%) as an orange solid. 1H NMR (400 MHz, CDCl$_3$, 30° C.) 1.63-1.85 (3H, m), 2.04-2.21 (3H, m), 2.54 (3H, s), 3.74 (1H, td), 4.10 (1H, d), 5.46 (1H, dd), 7.17 (1H, d), 7.36 (1H, d), 8.06 (1H, s). m/z: ES+ [M+H]+=297.

[5-Methyl-1-(oxan-2-yl)-1H-benzimidazol-4-yl]boronic acid

Dichlorobis(tricyclohexylphosphine)palladium(II) (525 mg, 0.71 mmol), bis(pinacolato)diboron (1.81 g, 7.11 mmol), 4-bromo-5-methyl-1-(oxan-2-yl)-1H-benzimidazole (2.1 g, 7.11 mmol) and potassium acetate (1.75 g, 17.79 mmol) were dissolved in DMA (20 mL). The resulting solution was stirred at 155° C. for 105 min. The reaction mixture was cooled to rt and diluted with water (80 mL). The aqueous was extracted with EtOAc (80 mL×3) and the combined organic extracts washed with water (80 mL) and brine (80 mL). The organic portion was passed through a hydrophobic frit and concentrated under reduced pressure to afford a crude product as a brown solid, that was purified by preparative HPLC (RediSepRF C18 GOLD, 150 gram HP C18), eluting with of water (containing 0.1% by volume of formic acid) and MeCN, to afford [5-methyl-1-(oxan-2-yl)-1H-benzimidazol-4-yl]boronic acid (1.87 g, >100%) as an orange solid which was used without further purification. 1H NMR (400 MHz, DMSO, 30° C.) 1.75 (2H, d), 2.13-2.25 (2H, m), 2.60 (3H, s), 2.63-2.69 (2H, m), 3.75 (2H, td), 5.68 (1H, dd), 7.13 (1H, d), 7.61 (1H, d), 8.46 (1H, s), 8.95 (2H, s). m/z: ES+ [M+H]+=261.

Tert-butyl (12aR)-10-chloro-8-fluoro-9-[5-methyl-1-(oxan-2-yl)-1H-benzimidazol-4-yl]-3,4,12,12a-tetrahydro-6H-pyrazino[2,1-c][1,4]benzoxazepine-2(1H)-carboxylate

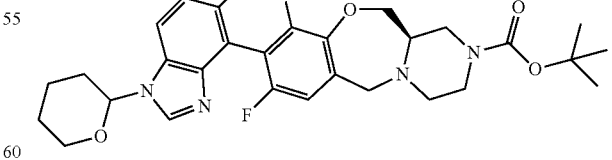

Tert-butyl (12aR)-9-bromo-10-chloro-8-fluoro-3,4,12,12a-tetrahydro-6H-pyrazino[2,1-c][1,4]benzoxazepine-2(1H)-carboxylate (653 mg, 1.50 mmol) was added to [5-methyl-1-(oxan-2-yl)-1H-benzimidazol-4-yl]boronic acid (780 mg, 3 mmol), RuPhos (70 mg, 0.15 mmol), RuPhos-Pd-G3 (125 mg, 0.15 mmol) and potassium carbonate (518 mg, 3.75 mmol) in 1,4-dioxane (10 mL) and water (2.5 mL) (4:1 ratio) at 25° C. The resulting solution was stirred at 100° C. for 1 h. The crude reaction mixture obtained was purified by C18-flash chromatography, elution gradient 0 to 70% MeCN in water (0.1% formic acid) to give tert-butyl (12aR)-10-chloro-8-fluoro-9-[5-methyl-1-(oxan-2-yl)-1H-benzimidazol-4-yl]-3,4,12,12a-tetrahydro-6H-pyrazino[2,1-c][1,4]benzoxazepine-2(1H)-carboxylate (845 mg, 99%) as a brown solid. 1H NMR (400 MHz, DMSO, 30° C.) 1.40 (9H, s), 1.52-1.82 (4H, m), 1.95-2.07 (2H, m), 2.13 (3H, d), 2.21 (1H, d), 2.35-2.39 (1H, m), 2.74-2.82 (3H, m), 3.06-3.14 (1H, m), 3.17 (2H, s), 3.75 (2H, d), 3.85-4.05 (2H, m), 4.34 (1H, d), 5.66 (1H, d), 7.26 (1H, d), 7.63 (1H, d), 8.16 (1H, s), 8.24 (1H, d). m/z: ES+ [M+H]+=571.

(12aR)-10-Chloro-8-fluoro-9-(5-methyl-1H-benzimidazol-4-yl)-1,2,3,4,12,12a-hexahydro-6H-pyrazino[2,1-c][1,4]benzoxazepine

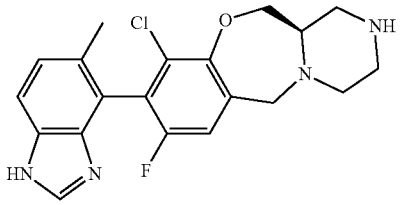 [SMILES: Cc1ccc2[nH]cnc2c1-c1c(F)cc2c(c1Cl)OC[C@H]1CNCCN1C2]

Tert-butyl (12aR)-10-chloro-8-fluoro-9-[5-methyl-1-(oxan-2-yl)-1H-benzimidazol-4-yl]-3,4,12,12a-tetrahydro-6H-pyrazino[2,1-c][1,4]benzoxazepine-2(1H)-carboxylate (785 mg, 1.37 mmol) was added to p-toluenesulfonic acid (1183 mg, 6.87 mmol) in MeOH (15 mL) and water (3 mL) at 25° C. The resulting solution was stirred at 80° C. for 1 h. The crude product was purified by C18-flash chromatography, elution gradient 0 to 30% MeOH in water (0.1% NH₄OH) to give (12aR)-10-Chloro-8-fluoro-9-(5-methyl-1H-benzimidazol-4-yl)-1,2,3,4,12,12a-hexahydro-6H-pyrazino[2,1-c][1,4]benzoxazepine (310 mg, 58%) as a yellow solid. 1H NMR (400 MHz, DMSO, 30° C.) 2.12 (3H, d), 2.22-2.43 (3H, m), 2.60-2.89 (5H, m), 3.52-3.77 (2H, m), 3.78-3.89 (1H, m), 4.16-4.30 (1H, m), 7.08-7.20 (1H, m), 7.25-7.36 (1H, m), 7.54 (1H, d), 8.07 (1H, d), 12.21 (1H, s). m/z: ES+ [M+H]+=387.

1-((12aR)-10-Chloro-8-fluoro-9-(5-methyl-1H-benzo[d]imidazol-4-yl)-3,4,12,12a-tetrahydro-6H-benzo[f]pyrazino[2,1-c][1,4]oxazepin-2(1H)-yl)prop-2-en-1-one Rotational Isomer 1, Example 18 and Rotational Isomer 2, Example 19

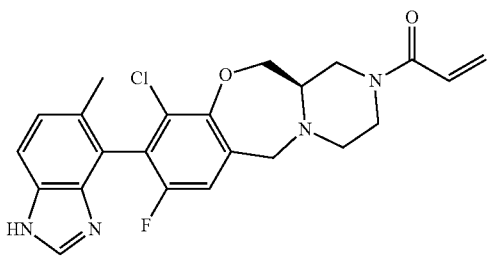 [SMILES: C=CC(=O)N1CCN2Cc3cc(F)c(-c4c(C)ccc5[nH]cnc45)c(Cl)c3OC[C@H]2C1]

Acryloyl chloride (45.6 mg, 0.50 mmol) was added to (12aR)-10-chloro-8-fluoro-9-(5-methyl-1H-benzimidazol-4-yl)-1,2,3,4,12,12a-hexahydro-6H-pyrazino[2,1-c][1,4]benzoxazepine (150 mg, 0.39 mmol) and DIPEA (0.203 mL, 1.16 mmol) in DMF (2 mL) at 0° C. The resulting solution was stirred at 0° C. for 30 min. The crude reaction mixture was purified by C18-flash chromatography, elution gradient 0 to 50% MeCN in water (0.1% NH₄HCO₃) to give crude product as a white solid. The crude product was purified by preparative HPLC (Column: XBridge Prep OBD C18 Column 30×150 mm 5 μm), eluting with water (10 mmol/L NH₄HCO₃) and MeCN. This gave rotational isomer 1 of 1-((12aR)-10-chloro-8-fluoro-9-(5-methyl-1H-benzo[d]imidazol-4-yl)-3,4,12,12a-tetrahydro-6H-benzo[f]pyrazino[2,1-c][1,4]oxazepin-2(1H)-yl)prop-2-en-1-one (19.5 mg, 27%) as a white solid. 1H NMR (400 MHz, DMSO, 30° C.) 2.14 (3H, s), 2.36-2.46 (1H, m), 2.77-2.90 (2H, m), 3.05-3.17 (1H, m), 3.35-3.44 (1H, m), 3.59-3.71 (1H, m), 3.74-4.07 (4H, m), 4.32-4.45 (1H, m), 5.66-5.74 (1H, m), 6.08-6.18 (1H, m), 6.76-6.89 (1H, m), 7.12-7.21 (1H, m), 7.23-7.38 (1H, m), 7.45-7.63 (1H, m), 8.05 (1H, d), 12.29 (1H, d). m/z: ES+ [M+H]+=441. This was followed by rotational isomer 2 of 1-((12aR)-10-chloro-8-fluoro-9-(5-methyl-1H-benzo[d]imidazol-4-yl)-3,4,12,12a-tetrahydro-6H-benzo[f]pyrazino[2,1-c][1,4]oxazepin-2(1H)-yl)prop-2-en-1-one (14 mg, 20%) as a white solid. 1H NMR (400 MHz, DMSO, 30° C.) 2.10 (3H, s), 2.37-2.46 (1H, m), 2.80-2.90 (2H, m), 3.15-3.21 (1H, m), 3.36-3.47 (1H, m), 3.58-4.02 (5H, m), 4.32-4.45 (1H, m), 5.67-5.75 (1H, m), 6.09-6.19 (1H, m), 6.77-6.90 (1H, m) 7.11-7.20 (1H, m), 7.23-7.36 (1H, m), 7.45-7.63 (1H, m), 8.08 (1H, d), 12.31 (1H, d). m/z: ES+ [M+H]+=441.

(12aR)-9-Bromo-8,10-dichloro-1,2,3,4,12,12a-hexahydro-6H-pyrazino[2,1-c][1,4]benzoxazepin-6-one

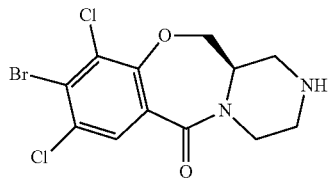 [SMILES: O=C1c2cc(Cl)c(Br)c(Cl)c2OC[C@H]2CNCCN12]

N-Chlorosuccinimide (1.856 g, 13.90 mmol) was added to tert-butyl (12aR)-9-bromo-10-chloro-6-oxo-3,4,12,12a-tetrahydro-6H-pyrazino[2,1-c][1,4]benzoxazepine-2(1H)-carboxylate (2 g, 4.63 mmol) in concentrated sulfuric acid (30 mL). The resulting mixture was stirred at 100° C. for 20 h. The reaction mixture was basified with 2M NaOH, extracted with DCM (200 mL×3) and the organic layer dried (Na₂SO₄) and evaporated to afford crude product. This was purified by C18-flash chromatography, elution gradient 5 to 60% MeOH in water to give (12aR)-9-bromo-8,10-dichloro-1,2,3,4,12,12a-hexahydro-6H-pyrazino[2,1-c][1,4]benzoxazepin-6-one (0.5 g, 30%) as a yellow solid. 1H NMR (400 MHz, DMSO, 30° C.) 2.05-2.36 (4H, m), 2.87-3.23 (3H, m), 3.38-3.76 (1H, m), 3.78-3.98 (1H, m), 7.16 (1H, s). m/z: ES+ [M+H]+=365.

(12aR)-8,10-Dichloro-9-(2-fluoro-6-hydroxyphenyl)-1,2,3,4,12,12a-hexahydro-6H-pyrazino[2,1-c][1,4]benzoxazepin-6-one

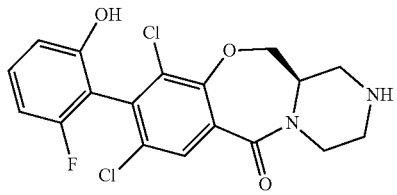 [SMILES: O=C1c2cc(Cl)c(-c3c(O)cccc3F)c(Cl)c2OC[C@H]2CNCCN12]

RuPhos-Pd-G3 (91 mg, 0.11 mmol) and RuPhos (51 mg, 0.11 mmol) were added to (12aR)-9-bromo-8,10-dichloro-1,2,3,4,12,12a-hexahydro-6H-pyrazino[2,1-c][1,4]benzoxazepin-6-one (400 mg, 1.09 mmol), (2-fluoro-6-hydroxyphenyl)boronic acid (204 mg, 1.31 mmol) and sodium carbonate (290 mg, 2.73 mmol) in 1,4-dioxane (8 mL) and water (2 mL) (4:1 ratio) at rt. The resulting mixture was stirred at 100° C. for 1 h. The reaction mixture was purified by C18-flash chromatography, elution gradient 0 to 60% MeCN in water (0.1% NH$_4$OH) to give (12aR)-8,10-dichloro-9-(2-fluoro-6-hydroxyphenyl)-1,2,3,4,12,12a-hexahydro-6H-pyrazino[2,1-c][1,4]benzoxazepin-6-one (50 mg, 12%) as a yellow solid. 1H NMR (400 MHz, DMSO, 30° C.) 2.96-3 (4H, m), 3.72-3.76 (3H, m), 3.93-3.98 (1H, m), 4.29 (1H, d), 4.66-4.76 (1H, m), 6.71-6.86 (2H, m), 7.25-7.36 (1H, m), 7.88 (1H, d), 10.14 (1H, s). m/z: ES+ [M+H]+= 397.

(12aR)-8,10-Dichloro-9-(2-fluoro-6-hydroxyphenyl)-2-(prop-2-enoyl)-1,2,3,4,12,12a-hexahydro-6H-pyrazino[2,1-c][1,4]benzoxazepin-6-one Rotational Isomer 1, Example 20 and Rotational Isomer 2, Example 21

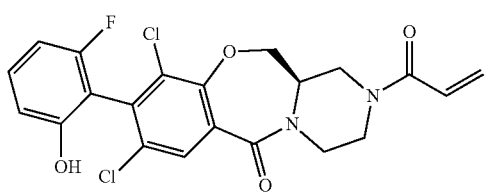 [SMILES: C=CC(=O)N1CCN2C(=O)c3cc(Cl)c(-c4c(O)cccc4F)c(Cl)c3OC[C@H]2C1]

Acryloyl chloride (10 mg, 0.11 mmol) was added to (12aR)-8,10-dichloro-9-(2-fluoro-6-hydroxyphenyl)-1,2,3,4,12,12a-hexahydro-6H-pyrazino[2,1-c][1,4]benzoxazepin-6-one (50 mg, 0.13 mmol) and DIPEA (0.066 mL, 0.38 mmol) in DMF (2 mL) at 0° C. The resulting solution was stirred at 0° C. for 30 min. The reaction mixture was purified by C18-flash chromatography, elution gradient 0 to 50% MeCN in water (0.1% NH$_4$HCO$_3$) to give crude product as a solid. This was purified by preparative HPLC (Column: XBridge Prep OBD C18 Column 30×150 mm 5 μm) eluting with water (10 mmol/L NH4HCO$_3$) and MeCN. This gave rotational isomer 1 of (12aR)-8,10-dichloro-9-(2-fluoro-6-hydroxyphenyl)-2-(prop-2-enoyl)-1,2,3,4,12,12a-hexahydro-6H-pyrazino[2,1-c][1,4]benzoxazepin-6-one (24 mg, 42%) as a yellow solid. 1H NMR (400 MHz, DMSO, 30° C.) 3.35-4.17 (7H, m), 4.27-4.70 (2H, m), 5.59-5.96 (1H, m), 6.03-6.39 (1H, m), 6.49-7 (3H, m), 7.15-7.39 (1H, m), 7.77 (1H, d), 10.10 (1H, s). m/z: ES+ [M+H]+=451. This was followed by rotational isomer 2 of (12aR)-8,10-dichloro-9-(2-fluoro-6-hydroxyphenyl)-2-(prop-2-enoyl)-1,2,3,4,12,12a-hexahydro-6H-pyrazino[2,1-c][1,4]benzoxazepin-6-one (13 mg, 23%) as a yellow solid. 1H NMR (400 MHz, DMSO, 30° C.) 3.35-4.21 (7H, m), 4.21-4.56 (2H, m), 5.47-5.85 (1H, m), 6.05-6.41 (1H, m), 6.58-7.14 (3H, m), 7.14-7.58 (1H, m), 7.80 (1H, d), 10.19 (1H, s). m/z: ES+ [M+H]+=451.

(12aR)-9-Bromo-10-chloro-1,2,3,4,12,12a-hexahydro-6H-pyrazino[2,1-c][1,4]benzoxazepine-8-carbonitrile

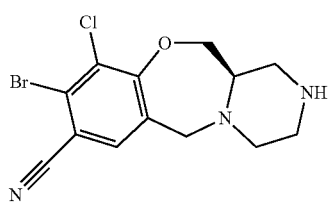 [SMILES: N#Cc1cc2c(c(Cl)c1Br)OC[C@H]1CNCCN1C2]

Tetrakis(triphenylphosphine)palladium(0) (208 mg, 0.18 mmol) was added to dicyanozinc (127 mg, 1.08 mmol), and (12aR)-9-bromo-10-chloro-8-iodo-1,2,3,4,12,12a-hexahydro-6H-pyrazino[2,1-c][1,4]benzoxazepine (400 mg, 0.9 mmol) in DMF (5 mL). The resulting mixture was stirred at 100° C. for 5 h and purified by C18-flash chromatography, elution gradient 5 to 80% MeOH in water to give (12aR)-9-bromo-10-chloro-1,2,3,4,12,12a-hexahydro-6H-pyrazino[2,1-c][1,4]benzoxazepine-8-carbonitrile (200 mg, 65%) as a yellow solid. 1H NMR (400 MHz, DMSO, 30° C.) 2.30-2.35 (2H, m), 2.61-2.65 (2H, m), 2.72-2.76 (3H, m), 3.75-3.80 (2H, m), 4.03 (1H, q), 4.30-4.38 (1H, m), 7.73 (1H, s). m/z: ES+ [M+H]+=342.

(12aR)-10-Chloro-9-(2-fluoro-6-hydroxyphenyl)-1,2,3,4,12,12a-hexahydro-6H-pyrazino[2,1-c][1,4]benzoxazepine-8-carbonitrile

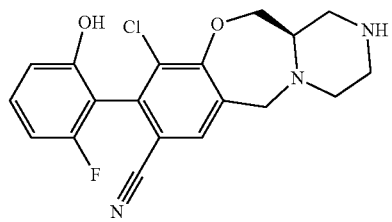 [SMILES: N#Cc1cc2c(c(Cl)c1-c1c(O)cccc1F)OC[C@H]1CNCCN1C2]

RuPhos-Pd-G3 (48.8 mg, 0.06 mmol) and RuPhos (27 mg, 0.06 mmol) were added to (12aR)-9-bromo-10-chloro-1,2,3,4,12,12a-hexahydro-6H-pyrazino[2,1-c][1,4]benzoxazepine-8-carbonitrile (200 mg, 0.58 mmol), (2-fluoro-6-hydroxyphenyl)boronic acid (109 mg, 0.70 mmol) and sodium carbonate (155 mg, 1.46 mmol) in 1,4-dioxane (5 mL) and water (1 mL) (5:1 ratio) at rt. The resulting mixture was stirred at 100° C. for 1 h and was purified by C18-flash chromatography, elution gradient 0 to 60% MeCN in water (0.1% NH$_4$OH) to give (12aR)-10-chloro-9-(2-fluoro-6-hydroxyphenyl)-1,2,3,4,12,12a-hexahydro-6H-pyrazino[2,1-c][1,4]benzoxazepine-8-carbonitrile (110 mg, 50%) as a yellow solid. 1H NMR (400 MHz, DMSO, 30° C.) 2.20-2.42

(1H, m), 2.59-2.83 (4H, m), 3.48-3.96 (5H, m), 4.27-4.42 (1H, m), 6.83 (1H, s), 7.12-7.23 (2H, m), 7.33-7.44 (1H, m). m/z: ES+ [M+H]+=374.

(12aR)-10-Chloro-9-(2-fluoro-6-hydroxyphenyl)-2-(prop-2-enoyl)-1,2,3,4,12,12a-hexahydro-6H-pyrazino[2,1-c][1,4]benzoxazepine-8-carbonitrile Rotational Isomer 1, Example 22 and Rotational Isomer 2, Example 23

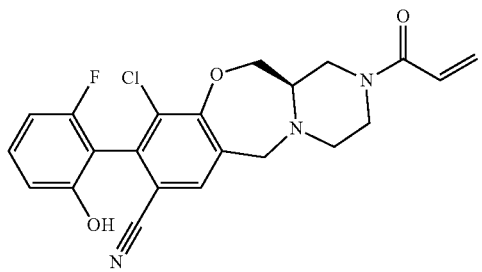 [SMILES: C=CC(=O)N1CCN2Cc3cc(C#N)c(-c4c(O)cccc4F)c(Cl)c3OC[C@H]2C1]

Acryloyl chloride (19.37 mg, 0.21 mmol) was added to (12aR)-10-chloro-9-(2-fluoro-6-hydroxyphenyl)-1,2,3,4,12,12a-hexahydro-6H-pyrazino[2,1-c][1,4]benzoxazepine-8-carbonitrile (80 mg, 0.21 mmol) and DIPEA (0.112 mL, 0.64 mmol) in DMF (2 mL) at 0° C. The resulting solution was stirred at 0° C. for 30 min. The reaction mixture was purified by C18-flash chromatography, elution gradient 0 to 50% MeCN in water (0.1% NH$_4$HCO$_3$), to afford crude product. This was purified by preparative HPLC (Column: Kinetex EVO C18 Column 30*150, 5 μm), eluting with water (10 mmol/L NH$_4$HCO$_3$) and MeCN, to give rotational isomer 1 of (12aR)-10-chloro-9-(2-fluoro-6-hydroxyphenyl)-1,2,3,4,12,12a-hexahydro-6H-pyrazino[2,1-c][1,4]benzoxazepine-8-carbonitrile (15 mg, 16%) as a yellow solid. 1H NMR (400 MHz, DMSO, 30° C.) 2.41-2.51 (1H, m), 2.62-2.80 (3H, m), 2.94-3.15 (1H, m), 3.65-4.15 (5H, m), 4.38-4.91 (1H, m), 5.41-5.88 (1H, m), 6.09 (1H, d), 6.62-6.91 (3H, m), 7.35 (1H, d), 7.84 (1H, s), 10.31 (1H, s). m/z: ES+ [M+H]+=428. This was followed by rotational isomer 2 of (12aR)-10-chloro-9-(2-fluoro-6-hydroxyphenyl)-1,2,3,4,12,12a-hexahydro-6H-pyrazino[2,1-c][1,4]benzoxazepine-8-carbonitrile (10 mg, 11%) as a yellow solid. 1H NMR (400 MHz, DMSO, 30° C.) 2.41-2.51 (1H, m), 2.73-2.77 (1H, m), 2.85-2.89 (2H, m), 2.99-3.03 (1H, m), 3.79-3.94 (4H, m), 3.95-4.03 (1H, m), 4.51-4.59 (1H, m), 5.70-5.81 (1H, m), 6.13 (1H, d), 6.72-6.77 (3H, m), 7.28-7.34 (1H, m), 7.82 (1H, s). m/z: ES+ [M+H]+=428.

Tert-butyl (3R)-4-(4-bromo-2-fluoro-5-methylbenzoyl)-3-(hydroxymethyl)piperazine-1-carboxylate

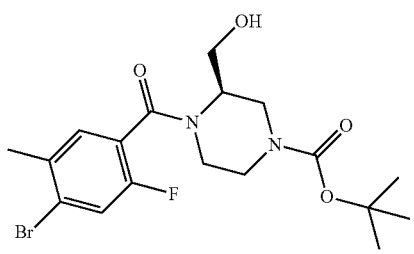 [SMILES: Cc1cc(C(=O)N2CCN(C(=O)OC(C)(C)C)C[C@@H]2CO)c(F)cc1Br]

DIPEA (8.99 mL, 51.49 mmol) was added to 4-bromo-2-fluoro-5-methylbenzoic acid (4 g, 17.16 mmol), HATU (9.79 g, 25.75 mmol) and tert-butyl (3R)-3-(hydroxymethyl)piperazine-1-carboxylate (3.90 g, 18.02 mmol) in DMF (30 mL). The resulting mixture was stirred at 25° C. for 2 h. The reaction mixture was diluted with EtOAc (150 mL) and washed with brine (100 mL×3). The organic layer was dried (Na$_2$SO$_4$) and evaporated to afford crude product. This was purified by flash silica chromatography, elution gradient 20 to 50% EtOAc in petroleum ether, to give tert-butyl (3R)-4-(4-bromo-2-fluoro-5-methylbenzoyl)-3-(hydroxymethyl)piperazine-1-carboxylate (6 g, 81%) as a yellow solid. 1H NMR (400 MHz, DMSO, 30° C.) 1.25 (9H, s), 2.78-3.04 (2H, m), 3.16-3.62 (5H, m), 3.77-4.22 (2H, m), 4.20-4.75 (2H, m), 4.82-5.23 (1H, m), 7.39 (1H, d), 7.50-7.81 (1H, m). m/z: ES+ [M+H]+=431.

Tert-butyl (12aR)-9-bromo-8-methyl-6-oxo-3,4,12,12a-tetrahydro-6H-pyrazino[2,1-c][1,4]benzoxazepine-2(1H)-carboxylate

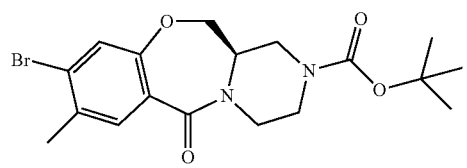 [SMILES: Cc1cc2c(cc1Br)OC[C@H]1CN(C(=O)OC(C)(C)C)CCN1C2=O]

1M Lithium bis(trimethylsilyl)amide in THF (13.91 mL, 13.91 mmol) was added to tert-butyl (3R)-4-(4-bromo-2-fluoro-5-methylbenzoyl)-3-(hydroxymethyl)piperazine-1-carboxylate (5 g, 11.59 mmol) in DMF (200 mL). The resulting mixture was stirred at 100° C. for 5 h. The solvent was removed under reduced pressure. The crude oil obtained was triturated with water to afford tert-butyl (12aR)-9-bromo-8-methyl-6-oxo-3,4,12,12a-tetrahydro-6H-pyrazino[2,1-c][1,4]benzoxazepine-2(1H)-carboxylate (3.5 g, 73%) as a yellow solid. 1H NMR (300 MHz, DMSO, 30° C.) 1.25 (9H, s), 2.80-3.04 (2H, m), 3.04-3.65 (6H, m), 3.65-4.20 (2H, m), 4.17-4.63 (1H, m), 4.63-5.07 (1H, m), 7.14-7.50 (1H, m), 7.62-7.83 (1H, m). m/z: ES+ [M+H]+=411.

(12aR)-9-Bromo-10-chloro-8-methyl-1,2,3,4,12,12a-hexahydro-6H-pyrazino[2,1-c][1,4]benzoxazepin-6-one

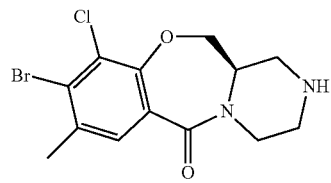 [SMILES: Cc1cc2c(c(Cl)c1Br)OC[C@H]1CNCCN1C2=O]

N-Chlorosuccinimide (0.649 g, 4.86 mmol) was added to tert-butyl (12aR)-9-bromo-8-methyl-6-oxo-3,4,12,12a-tetrahydro-6H-pyrazino[2,1-c][1,4]benzoxazepine-2(1H)-carboxylate (1 g, 2.43 mmol), in concentrated sulfuric acid (10 mL). The resulting mixture was stirred at 100° C. for 20 h. The reaction mixture was adjusted to pH 8 with 2 M NaOH. The aqueous layer was extracted with DCM (200 mL×3). The solvent was removed under reduced pressure. The crude product obtained was purified by C18-flash chromatography, elution gradient 20 to 80% MeOH in water, to give (12aR)-9-bromo-10-chloro-8-methyl-1,2,3,4,12,12a-hexahydro-6H-pyrazino[2,1-c][1,4]benzoxazepin-6-one (0.35 g, 42%) as a yellow solid. 1H NMR (400 MHz, CD$_3$OD, 30° C.) 2.45 (3H, s), 2.77-3.15 (4H, m), 3.47-3.75 (1H, m), 3.77-4.07 (2H, m), 4-4.37 (1H, m), 4.66 (1H, t), 7.60 (1H, s). m/z: ES+ [M+H]+=345.

(12aR)-10-Chloro-9-(2-fluoro-6-hydroxyphenyl)-8-methyl-1,2,3,4,12,12a-hexahydro-6H-pyrazino[2,1-c][1,4]benzoxazepin-6-one

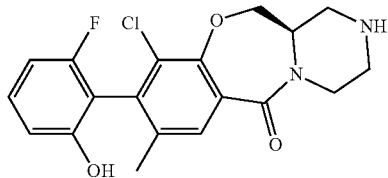 [SMILES: Cc1cc2c(c(Cl)c1-c1c(O)cccc1F)OC[C@H]1CNCCN1C2=O]

RuPhos-Pd-G3 (145 mg, 0.17 mmol) was added to (2-fluoro-6-hydroxyphenyl)boronic acid (338 mg, 2.17 mmol), RuPhos (81 mg, 0.17 mmol), (12aR)-9-bromo-10-chloro-8-methyl-1,2,3,4,12,12a-hexahydro-6H-pyrazino[2,1-c][1,4]benzoxazepin-6-one (300 mg, 0.87 mmol) and K$_2$CO$_3$ (360 mg, 2.6 mmol) in 1,4-dioxane (5 mL) and water (1 mL) (5:1 ratio) at 25° C. The resulting solution was stirred at 80° C. for 1 h. The reaction mixture was purified by C18-flash chromatography, elution gradient 5 to 80% MeOH in water to give (12aR)-10-chloro-9-(2-fluoro-6-hydroxyphenyl)-8-methyl-1,2,3,4,12,12a-hexahydro-6H-pyrazino[2,1-c][1,4]benzoxazepin-6-one (130 mg, 40%) as a yellow solid. 1H NMR (300 MHz, CD$_3$OD, 30° C.) 2.12 (3H, s), 3.17-3.25 (3H, m), 3.87-4.21 (4H, m), 4.21-4.38 (1H, m), 4.62-4.77 (1H, m), 6.68-6.80 (2H, m), 7.18-7.36 (1H, m), 7.72 (1H, d). m/z: ES+ [M+H]+=377.

(12aR)-10-Chloro-9-(2-fluoro-6-hydroxyphenyl)-8-methyl-2-(prop-2-enoyl)-1,2,3,4,12,12a-hexahydro-6H-pyrazino[2,1-c][1,4]benzoxazepin-6-one Rotational Isomer 1, Example 24 and Rotational Isomer 2, Example 25

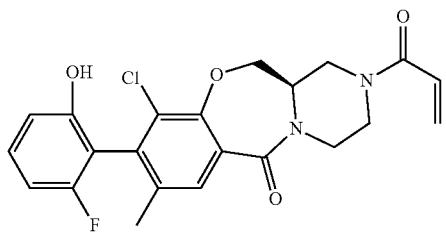 [SMILES: C=CC(=O)N1CCN2C(=O)c3cc(C)c(-c4c(O)cccc4F)c(Cl)c3OC[C@H]2C1]

Acryloyl chloride (25.9 mg, 0.29 mmol) was added to DIPEA (0.167 mL, 0.96 mmol) and (12aR)-10-chloro-9-(2-fluoro-6-hydroxyphenyl)-8-methyl-1,2,3,4,12,12a-hexahydro-6H-pyrazino[2,1-c][1,4]benzoxazepin-6-one (120 mg, 0.32 mmol) in DMF (3 mL). The resulting mixture was stirred at 25° C. for 4 h and purified by C18-flash chromatography, elution gradient 5 to 80% MeCN in water (0.1% NH$_4$OH), to give crude product. This was purified by preparative chiral-HPLC (Column: CHIRALPAK IG, 20*250 mm, 5 μm; Mobile Phase A:Hex:DCM=3:1-HPLC, Mobile Phase B: IPA-HPLC; Flow rate: 20 mL/min; Gradient: 50 B to 50 B in 10 min). This gave rotational isomer 1 of (12aR)-10-chloro-9-(2-fluoro-6-hydroxyphenyl)-8-methyl-2-(prop-2-enoyl)-1,2,3,4,12,12a-hexahydro-6H-pyrazino[2,1-c][1,4]benzoxazepin-6-one (18 mg, 36%) as a white solid. 1H NMR (400 MHz, DMSO, 30° C.) 2.01 (3H, s), 3.65-3.83 (1H, m), 3.90-4.04 (6H, m), 4.15-4.31 (2H, m), 5.72 (1H, d), 6.10-6.22 (1H, m), 6.66-6.89 (3H, m), 7.28 (1H, t), 7.53 (1H, d), 9.98 (1H, s). m/z: ES+ [M+H]+=431. This was followed by rotational isomer 2 of (12aR)-10-chloro-9-(2-fluoro-6-hydroxyphenyl)-8-methyl-2-(prop-2-enoyl)-1,2,3,4,12,12a-hexahydro-6H-pyrazino[2,1-c][1,4]benzoxazepin-6-one (18 mg, 36%) as a white solid. 1H NMR (400 MHz, DMSO, 30° C.) 2.03 (3H, s), 3.71-3.88 (1H, m), 3.90-4.04 (6H, m), 4.25-4.35 (2H, m), 5.72 (1H, d), 6.10-6.22 (1H, m), 6.66-6.84 (3H, m), 7.28 (1H, t), 7.53 (1H, d), 9.98 (1H, s). m/z: ES+ [M+H]+=431.

(12aR)-9-Bromo-8,10-dichloro-1,2,3,4,12,12a-hexahydro-6H-pyrazino[2,1-c][1,4]benzoxazepine

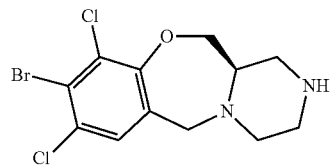 [SMILES: Clc1cc2c(c(Cl)c1Br)OC[C@H]1CNCCN1C2]

N-Chlorosuccinimide (162 mg, 1.21 mmol) was added to tert-butyl (12aR)-9-bromo-10-chloro-3,4,12,12a-tetrahydro-6H-pyrazino[2,1-c][1,4]benzoxazepine-2(1H)-carboxylate in concentrated sulfuric acid (5 mL) at rt. The resulting mixture was stirred at 80° C. for 20 h, then quenched with 2M NaOH, extracted with DCM (100 mL×3) and the organic layer was dried (Na$_2$SO$_4$) and evaporated to afford crude product. This was purified by C18-flash chromatography, elution gradient 30 to 90% MeOH in water, to give (12aR)-9-bromo-8,10-dichloro-1,2,3,4,12,12a-hexahydro-6H-pyrazino[2,1-c][1,4]benzoxazepine (300 mg, 77%) as a yellow solid. 1H NMR (300 MHz, DMSO, 30° C.) 2.34-2.51 (2H, m), 2.68-2.81 (5H, m), 3.33-3.95 (3H, m), 4.28-4.30 (1H, m), 7.59 (1H, s). m/z: ES+ [M+H]+=351.

2-[(12aR)-8,10-Dichloro-1,2,3,4,12,12a-hexahydro-6H-pyrazino[2,1-c][1,4]benzoxazepin-9-yl]-3-fluorophenol, Rotational Isomer 1 and Rotational Isomer 2

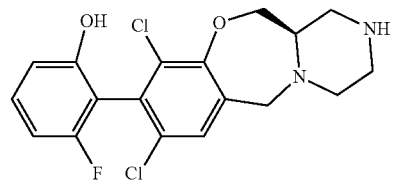 [SMILES: Oc1cccc(F)c1-c1c(Cl)cc2c(c1Cl)OC[C@H]1CNCCN1C2]

RuPhos-Pd-G3 (23.76 mg, 0.03 mmol) and RuPhos (13 mg, 0.03 mmol) were added to (12aR)-9-bromo-8,10-dichloro-1,2,3,4,12,12a-hexahydro-6H-pyrazino[2,1-c][1,4]benzoxazepine (100 mg, 0.28 mmol), 2-fluoro-6-hydroxyphenyl)boronic acid (53 mg, 0.34 mmol) and sodium carbonate (75 mg, 0.71 mmol) in 1,4-dioxane (5 mL) and water (1 mL) (5:1 ratio) at rt. The resulting mixture was stirred at 80° C. for 1 h and purified by C18-flash chromatography, elution gradient 0 to 60% MeCN in water (0.1% NH₄OH) to give rotational isomer 1 of 2-[(12aR)-8,10-dichloro-1,2,3,4,12,12a-hexahydro-6H-pyrazino[2,1-c][1,4]benzoxazepin-9-yl]-3-fluorophenol (25 mg, 23%) as a yellow solid. 1H NMR (400 MHz, DMSO, 30° C.) 1.32-2.27 (5H, m), 2.69-2.93 (3H, m), 2.95-3.16 (2H, m), 3.33-3.69 (1H, m), 5.66-6.08 (2H, m), 6.27-6.47 (1H, m), 6.58 (1H, s). m/z: ES+ [M+H]+=383. This was followed by rotational isomer 2 of 2-[(12aR)-8,10-dichloro-1,2,3,4,12,12a-hexahydro-6H-pyrazino[2,1-c][1,4]benzoxazepin-9-yl]-3-fluorophenol (35 mg, 32%) as a yellow solid. m/z: ES+ [M+H]+= 383.

1-[(12aR)-8,10-Dichloro-9-(2-fluoro-6-hydroxyphenyl)-3,4,12,12a-tetrahydro-6H-pyrazino[2,1-c][1,4]benzoxazepin-2(1H)-yl]prop-2-en-1-one Rotational Isomer 1, Example 26

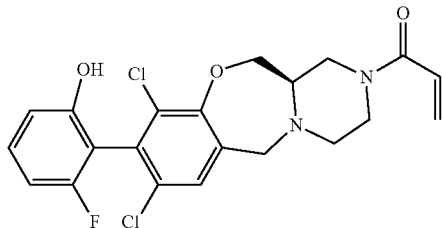 [SMILES: C=CC(=O)N1CCN2Cc3cc(Cl)c(-c4c(O)cccc4F)c(Cl)c3OC[C@H]2C1]

Acryloyl chloride (5.9 mg, 0.07 mmol) was added to DIPEA (0.034 mL, 0.2 mmol) and rotational isomer 1 of 2-[(12aR)-8,10-dichloro-1,2,3,4,12,12a-hexahydro-6H-pyrazino[2,1-c][1,4]benzoxazepin-9-yl]-3-fluorophenol (25 mg, 0.07 mmol) in DMF (2 mL). The resulting mixture was stirred at 25° C. for 4 h. The reaction mixture was purified by C18-flash chromatography, elution gradient 5 to 70% MeCN in water to give rotational isomer 1 of 1-[(12aR)-8,10-dichloro-9-(2-fluoro-6-hydroxyphenyl)-3,4,12,12a-tetrahydro-6H-pyrazino[2,1-c][1,4]benzoxazepin-2(1H)-yl]prop-2-en-1-one (8 mg, 28%) as a yellow solid. 1H NMR (300 MHz, CD₃OD, 30° C.) 2.49-2.59 (1H, m), 2.93-3.13 (3H, m), 3.50-3.60 (1H, m), 3.69-3.79 (2H, m), 3.89-4.13 (3H, m), 4.33-4.47 (1H, m), 5.78 (1H, d), 6.24 (1H, d), 6.60-6.89 (3H, m), 7.25 (1H, t), 7.38 (1H, s). m/z: ES+ [M+H]+=437.

1-[(12aR)-8,10-Dichloro-9-(2-fluoro-6-hydroxyphenyl)-3,4,12,12a-tetrahydro-6H-pyrazino[2,1-c][1,4]benzoxazepin-2(1H)-yl]prop-2-en-1-one Rotational Isomer 2, Example 27

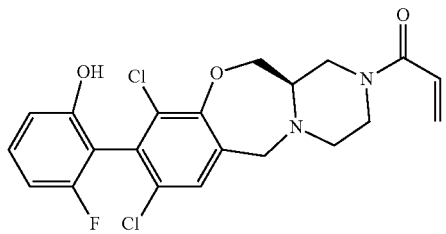 [SMILES: C=CC(=O)N1CCN2Cc3cc(Cl)c(-c4c(O)cccc4F)c(Cl)c3OC[C@H]2C1]

Acryloyl chloride (7.08 mg, 0.08 mmol) was added to DIPEA (0.041 mL, 0.23 mmol) and rotational isomer 2 of 2-[(12aR)-8,10-dichloro-1,2,3,4,12,12a-hexahydro-6H-pyrazino[2,1-c][1,4]benzoxazepin-9-yl]-3-fluorophenol (30 mg, 0.08 mmol) in DMF (2 mL). The resulting mixture was stirred at 25° C. for 4 h The reaction mixture was purified by C18-flash chromatography, elution gradient 5 to 70% MeCN in water to give rotational isomer 2 of 1-[(12aR)-8,10-dichloro-9-(2-fluoro-6-hydroxyphenyl)-3,4,12,12a-tetrahydro-6H-pyrazino[2,1-c][1,4]benzoxazepin-2(1H)-yl]prop-2-en-1-one (8 mg, 28%) as a yellow solid. 1H NMR (300 MHz, CD₃OD, 30° C.) 2.52-2.58 (1H, m), 3.16-3.22 (2H, m), 3.11-3.21 (1H, m), 3.46-3.55 (1H, m), 3.69-3.80 (2H, m), 3.86-4.06 (3H, m), 4.34-4.40 (1H, m), 5.77 (1H, d), 6.22 (1H, d), 6.58-6.79 (3H, m), 7.23 (1H, t), 7.37 (1H, s). m/z: ES+ [M+H]+=437.

8-Bromo-7-methylisoquinoline

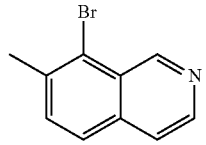

2,2-Diethoxyethan-1-amine (2.68 g, 20.10 mmol) was added dropwise to 2-bromo-3-methylbenzaldehyde (4 g, 20.1 mmol) in toluene (12 mL) at 25° C. The resulting suspension was stirred at 100° C. for 16 h. After cooling to rt the solvent was removed under reduced pressure. The residue obtained was dissolved in DCM (16 mL) and aluminium trichloride (8.84 g, 66.32 mmol) added portionwise to the solution at rt. The resulting suspension was stirred at rt for 3 h. The reaction mixture was poured into ice (100 mL), extracted with DCM (50 mL×3) and the organic layer was dried (Na₂SO₄) and evaporated. The crude product was purified by flash silica chromatography, elution gradient 0 to 20% EtOAc in petroleum ether to give 8-bromo-7-methylisoquinoline (1.56 g, 35%) as a yellow solid. m/z: ES+ [M+H]+=222.

8-Bromo-7-methyl-2-oxo-2λ⁵-isoquinoline

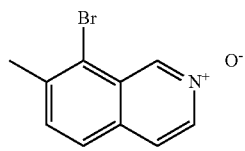

3-Chloroperbenzoic acid (3.25 g, 16 mmol) was added to 8-bromo-7-methylisoquinoline (3.23 g, 14.54 mmol) in DCM (70 mL) at rt. The resulting suspension was stirred at 25° C. for 6 h. The reaction mixture was diluted with DCM (200 mL) and washed with saturated NaHCO₃ (100 mL×3). The organic layer was dried (MgSO₄) and evaporated to afford 8-bromo-7-methyl-2-oxo-2λ⁵-isoquinoline (3.75 g, >100%) as a pale yellow solid. 1H NMR (400 MHz, CDCl₃, 30° C.) 2.64 (3H, s), 7.46-7.56 (1H, m), 7.68 (2H, t), 8.21 (1H, d), 9.30 (1H, s). m/z ES+ [M+H]+=238.

8-Bromo-1-methoxy-7-methylisoquinoline

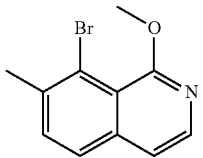

Methyl chloroformate (2.245 mL, 28.98 mmol) was added dropwise to 8-bromo-7-methyl-2-oxo-2λ5-isoquinoline (4.6 g, 19.32 mmol) and triethylamine (5.06 mL, 36.32 mmol) in MeOH (110 mL) at 25° C. The resulting solution was stirred at 25° C. for 5 h. Additional triethylamine (5.06 mL, 36.32 mmol) and methyl chloroformate (2.245 mL, 28.98 mmol) were then added and reaction mixture stirred at 25° C. for 16 h. Additional methyl chloroformate (2.245 mL, 28.98 mmol) was then added and reaction mixture stirred at 25° C. for a further 6 h. The reaction mixture was evaporated to dryness, diluted with EtOAc (300 mL) and washed with brine (50 mL×3). The organic layer was dried (Na$_2$SO$_4$) and evaporated. The crude product obtained was purified by flash silica chromatography, elution gradient 0 to 8% EtOAc in petroleum ether, to give 8-bromo-1-methoxy-7-methylisoquinoline (2.58 g, 53%) as a white solid. 1H NMR (400 MHz, CDCl$_3$, 30° C.) 2.61 (3H, s), 4.12 (3H, s), 7.18 (1H, d), 7.48 (1H, d), 7.57 (1H, d), 7.96 (1H, d). m/z ES+ [M+H]+=252.

Tert-butyl (3R)-4-(4-bromo-2,5-difluorobenzoyl)-3-(hydroxymethyl)piperazine-1-carboxylate

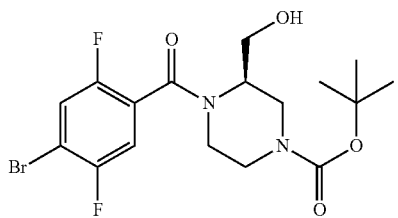 [SMILES: CC(C)(C)OC(=O)N1CCN(C(=O)c2cc(F)c(Br)cc2F)[C@@H](CO)C1]

DIPEA (2.95 mL, 16.88 mmol) was added to 4-bromo-2,5-difluorobenzoic acid (2 g, 8.44 mmol), tert-butyl (R)-3-(hydroxymethyl)piperazine-1-carboxylate (2.01 g, 9.28 mmol) and HATU (4.81 g, 12.66 mmol) in DMF (20 mL). The resulting mixture was stirred at rt for 4 h. The reaction mixture was diluted with EtOAc (150 mL), washed with water (100 mL) and brine (100 mL×2). The organic layer was dried (Na$_2$SO$_4$) and evaporated to afford crude product. The crude product was purified by flash silica chromatography, elution gradient 10 to 40% EtOAc in petroleum ether to give tert-butyl (3R)-4-(4-bromo-2,5-difluorobenzoyl)-3-(hydroxymethyl)piperazine-1-carboxylate (3.2 g, 87%) as a white foam. 1H NMR (400 MHz, CDCl$_3$, 30° C.) 1.49 (9H, d), 2.84-3.24 (3H, m), 3.27-3.41 (1H, m), 3.51-3.72 (1H, m), 3.72-3.87 (1H, m), 3.91-4.35 (2H, m), 4.42-4.89 (1H, m), 7.13-7.25 (1H, m), 7.33-7.41 (1H, m). m/z ES+ [M-$^t$Bu]+=379.

Tert-butyl (12aR)-9-bromo-8-fluoro-6-oxo-3,4,12,12a-tetrahydro-6H-pyrazino[2,1-c][1,4]benzoxazepine-2(1H)-carboxylate

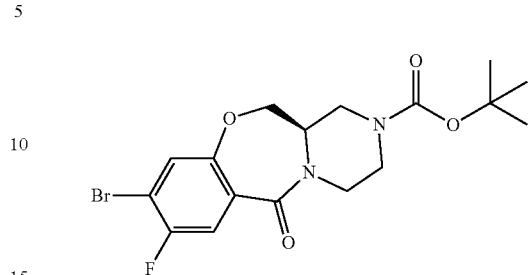

Sodium hydride (0.423 g, 10.57 mmol) was added slowly to tert-butyl (3R)-4-(4-bromo-2,5-difluorobenzoyl)-3-(hydroxymethyl)piperazine-1-carboxylate (2.3 g, 5.28 mmol) in DMF (30 mL) at 0° C.

The resulting solution was stirred at rt for 2 h. The reaction mixture was quenched with ice (100 mL), extracted with EtOAc (100 mL×2), the organic layer was dried (Na$_2$SO$_4$) and evaporated to afford crude product. The crude product was purified by flash silica chromatography, elution gradient 20 to 30% EtOAc in petroleum ether to give tert-butyl (12aR)-9-bromo-8-fluoro-6-oxo-3,4,12,12a-tetrahydro-6H-pyrazino[2,1-c][1,4]benzoxazepine-2(1H)-carboxylate (1.67 g, 76%) as a white foam. 1H NMR (400 MHz, CDCl$_3$, 30° C.) 1.50 (9H, s), 3.45-3.61 (2H, m), 3.64-3.81 (2H, m), 3.84-3.99 (1H, m), 4.08-4.25 (3H, m), 4.26-4.38 (1H, m), 7.29 (1H, d), 7.67 (1H, d). m/z ES+ [M-$^t$Bu]+=359.

Tert-butyl (12aR)-9-bromo-8-fluoro-3,4,12,12a-tetrahydro-6H-pyrazino[2,1-c][1,4]benzoxazepine-2(1H)-carboxylate

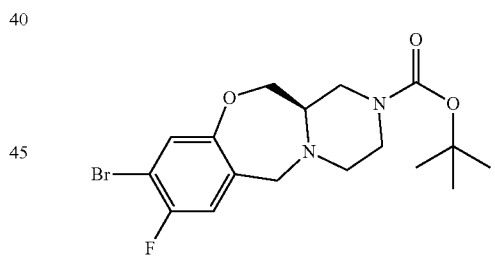

A solution of tert-butyl (12aR)-9-bromo-8-fluoro-6-oxo-3,4,12,12a-tetrahydro-6H-pyrazino[2,1-c][1,4]benzoxazepine-2(1H)-carboxylate (1.67 g, 4.02 mmol) and 1M borane-THF complex solution in THF (40 mL, 40 mmol) was stirred at reflux for 2 h. The solvent was removed under reduced pressure.

The residue was dissolved in MeOH (20 mL) and the resulting solution stirred at reflux for 1 h. The reaction mixture was purified by C18-flash chromatography, elution gradient 5 to 30% MeCN in water (0.1% formic acid) to give tert-butyl (12aR)-9-bromo-8-fluoro-3,4,12,12a-tetrahydro-6H-pyrazino[2,1-c][1,4]benzoxazepine-2(1H)-carboxylate (1.06 g, 66%) as a white dry film. 1H NMR (300 MHz, CDCl$_3$, 30° C.) 1.48 (9H, s), 2.35-2.55 (1H, m), 2.62-3.09 (3H, m), 3.23-3.40 (1H, m), 3.43-3.60 (1H, m), 3.62-3.81 (3H, m), 3.95 (1H, d), 4.14-4.25 (1H, m), 6.97 (1H, d), 7.24 (1H, d). m/z ES+ [M+H]+=401.

[(12aR)-2-(Tert-butoxycarbonyl)-8-fluoro-1,2,3,4,12,12a-hexahydro-6H-pyrazino[2,1-c][1,4]benzoxazepin-9-yl]boronic acid.1TFA

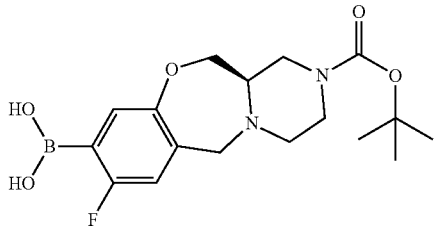 [SMILES: CC(C)(C)OC(=O)N1CCN2Cc3cc(F)c(B(O)O)cc3OC[C@H]2C1]

Tert-butyl (12aR)-9-bromo-8-fluoro-3,4,12,12a-tetrahydro-6H-pyrazino[2,1-c][1,4]benzoxazepine-2(1H)-carboxylate (1.06 g, 2.64 mmol), bis(pinacolato)diboron (1.01 g, 3.96 mmol), [1,1'-bis(diphenylphosphino)ferrocene]dichloropalladium(II)) (0.193 g, 0.26 mmol) and potassium acetate (0.518 g, 5.28 mmol) in 1,4-dioxane (10 mL) was stirred at 100° C. for 4 h. The solvent was removed under reduced pressure. The crude product obtained was purified by C18 flash chromatography, elution gradient 10 to 40% MeCN in water (0.05% TFA) to give [(12aR)-2-(tert-butoxycarbonyl)-8-fluoro-1,2,3,4,12,12a-hexahydro-6H-pyrazino[2,1-c][1,4]benzoxazepin-9-yl]boronic acid. 1TFA (1.06 g, 84%) as a white foam. 1H NMR (300 MHz, CD$_3$OD, 30° C.) 1.51 (9H, s), 2.76-3.20 (2H, m), 3.36-3.44 (1H, m), 3.54-3.75 (1H, m), 3.75-3.93 (2H, m), 4.10-4.27 (2H, m), 4.38 (1H, d), 4.48-4.74 (2H, m), 7.16-7.25 (2H, m). m/z ES+ [M+H]+=367.

Tert-butyl (12aR)-8-fluoro-9-(1-methoxy-7-methylisoquinolin-8-yl)-3,4,12,12a-tetrahydro-6H-pyrazino[2,1-c][1,4]benzoxazepine-2(1H)-carboxylate.1TFA

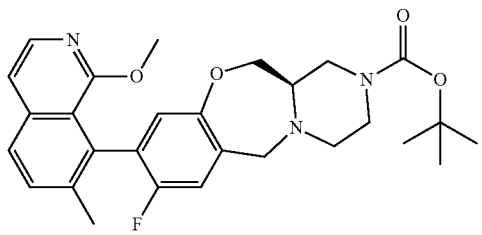 [SMILES: COc1nccc2ccc(C)c(-c3cc4c(cc3F)CN3CCN(C(=O)OC(C)(C)C)C[C@@H]3CO4)c12]

8-Bromo-1-methoxy-7-methylisoquinoline (350 mg, 1.39 mmol), [(12aR)-2-(tert-butoxycarbonyl)-8-fluoro-1,2,3,4,12,12a-hexahydro-6H-pyrazino[2,1-c][1,4]benzoxazepin-9-yl]boronic acid. 1TFA (1000 mg, 2.08 mmol), RuPhos (64.8 mg, 0.14 mmol), RuPhos-Pd-G3 (116 mg, 0.14 mmol) and potassium carbonate (767 mg, 5.55 mmol) in 1,4-dioxane (12 mL) and water (3 mL) (4:1 ratio) was stirred at 100° C. for 1 h. The solvent was removed under reduced pressure. The crude product obtained was purified by C18-flash chromatography, elution gradient 5 to 40% MeCN in water (0.05% TFA) to afford tert-butyl (12aR)-8-fluoro-9-(1-methoxy-7-methylisoquinolin-8-yl)-3,4,12,12a-tetrahydro-6H-pyrazino[2,1-c][1,4]benzoxazepine-2(1H)-carboxylate. 1TFA (637 mg, 76%) as a white foam. 1H NMR (400 MHz, CDCl$_3$, 30° C.) 1.45-1.53 (9H, m), 2.20 (3H, d), 2.41-2.59 (1H, m), 2.73-3.54 (4H, m), 3.56-3.95 (7H, m), 3.95-4.30 (2H, m), 6.77-6.86 (1H, m), 6.93-7.02 (1H, m), 7.23 (1H, t), 7.58 (1H, d), 7.70 (1H, dd), 7.94 (1H, t). m/z ES+ [M+H]+= 494.

(12aR)-10-Chloro-9-(4-chloro-1-methoxy-7-methylisoquinolin-8-yl)-8-fluoro-1,2,3,4,12,12a-hexahydro-6H-pyrazino[2,1-c][1,4]benzoxazepine

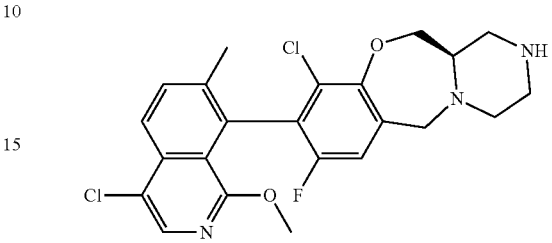

N-Chlorosuccinimide (330 mg, 2.47 mmol) was added to tert-butyl (12aR)-8-fluoro-9-(1-methoxy-7-methylisoquinolin-8-yl)-3,4,12,12a-tetrahydro-6H-pyrazino[2,1-c][1,4]benzoxazepine-2(1H)-carboxylate. 1TFA (500 mg, 0.82 mmol) in concentrated sulfuric acid (8 mL). The resulting mixture was stirred at 100° C. overnight. Additional N-chlorosuccinimide (330 mg, 2.47 mmol) was added and the reaction mixture heated for a further 16 h. The reaction mixture was poured into ice water and basified with 2M NaOH, extracted with DCM (200 mL×4), the organic layer was dried (Na$_2$SO$_4$) and evaporated. The residue obtained was purified by C18-flash chromatography, elution gradient 5 to 30% MeCN in water (0.05% TFA). Pure fractions were evaporated to dryness and purified by SCX (7M NH$_3$/MeOH) to afford (12aR)-10-chloro-9-(4-chloro-1-methoxy-7-methylisoquinolin-8-yl)-8-fluoro-1,2,3,4,12,12a-hexahydro-6H-pyrazino[2,1-c][1,4]benzoxazepine (223 mg, 59%) as a yellow solid. 1H NMR (400 MHz, CD$_3$OD, 30° C.) 2.19 (3H, d), 2.88-2.96 (1H, m), 3.09-3.28 (4H, m), 3.61 (3H, s), 3.70-3.75 (4H, m), 4.12-4.20 (2H, m), 7.16 (1H, d), 7.88 (1H, s), 8.02 (1H, d), 8.20 (1H, d). m/z ES+ [M+H]+= 462.

Tert-butyl (12aR)-10-chloro-9-(4-chloro-1-methoxy-7-methylisoquinolin-8-yl)-8-fluoro-3,4,12,12a-tetrahydro-6H-pyrazino[2,1-c][1,4]benzoxazepine-2(1H)-carboxylate

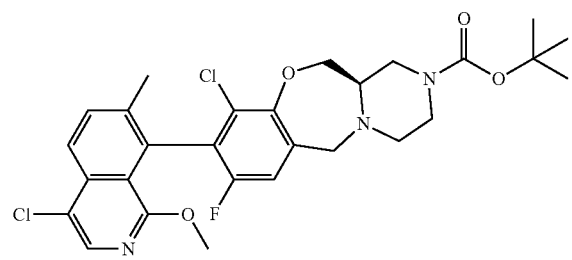 [SMILES: COc1ncc(Cl)c2ccc(C)c(-c3c(F)cc4c(c3Cl)OC[C@H]3CN(C(=O)OC(C)(C)C)CCN3C4)c12]

Di-tert-butyl dicarbonate (0.181 mL, 0.78 mmol) was added to (12aR)-10-chloro-9-(4-chloro-1-methoxy-7-methylisoquinolin-8-yl)-8-fluoro-1,2,3,4,12,12a-hexahydro-6H-pyrazino[2,1-c][1,4]benzoxazepine (240 mg, 0.52 mmol) and triethylamine (0.145 mL, 1.04 mmol) in DCM (10 mL) at 0° C. The resulting solution was stirred at rt for 2 h. The solvent was removed under reduced pressure. The residue obtained was purified by flash silica chromatography, elution gradient 20 to 40% EtOAc in petroleum ether to give tert-butyl (12aR)-10-chloro-9-(4-chloro-1-methoxy-7-methylisoquinolin-8-yl)-8-fluoro-3,4,12,12a-tetrahydro-6H-pyrazino[2,1-c][1,4]benzoxazepine-2(1H)-carboxylate (120 mg, 41%) as a pale yellow solid. 1H NMR (400 MHz, CD$_3$OD, 30° C.) 1.48 (9H, d), 2.22 (3H, d), 2.50-2.55 (2H, m), 2.88-2.97 (4H, m), 3.65 (3H, dd), 3.73-3.82 (3H, m), 4.08 (1H, d), 4.36 (1H, d), 7.14 (1H, dd), 7.88 (1H, d), 8.01 (1H, d), 8.19 (1H, d). m/z ES+ [M+H]+=562.

Tert-butyl (12aR)-10-chloro-8-fluoro-9-(1-methoxy-7-methylisoquinolin-8-yl)-3,4,12,12a-tetrahydro-6H-pyrazino[2,1-c][1,4]benzoxazepine-2(1H)-carboxylate

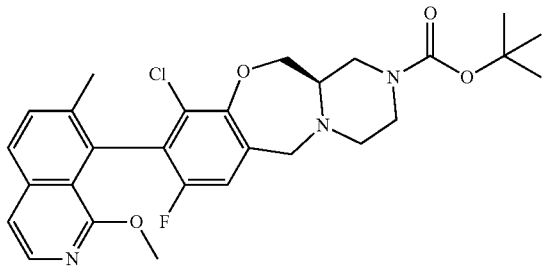 [SMILES: COc1nccc2ccc(C)c(-c3c(F)cc4c(c3Cl)OC[C@H]3CN(C(=O)OC(C)(C)C)CCN3C4)c12]

Tert-butyl (12aR)-10-chloro-9-(4-chloro-1-methoxy-7-methylisoquinolin-8-yl)-8-fluoro-3,4,12,12a-tetrahydro-6H-pyrazino[2,1-c][1,4]benzoxazepine-2(1H)-carboxylate (110 mg, 0.2 mmol) and 10% palladium on charcoal (25 mg, 0.01 mmol) in MeOH (10 mL) was stirred under an atmosphere of hydrogen at rt for 2 days. The reaction mixture was filtered through a CELITE™ pad and the solvent removed under reduced pressure to afford tert-butyl (12aR)-10-chloro-8-fluoro-9-(1-methoxy-7-methylisoquinolin-8-yl)-3,4,12,12a-tetrahydro-6H-pyrazino[2,1-c][1,4]benzoxazepine-2(1H)-carboxylate (103 mg, 100%) as a white solid. 1H NMR (400 MHz, CD$_3$OD, 30° C.) 1.51 (9H, d), 2.11-2.25 (3H, m), 2.88-3 (1H, m), 3.33-3.53 (4H, m), 3.58-3.73 (3H, m), 3.77-4.32 (4H, m), 4.52-4.73 (2H, m), 6.94 (1H, s), 7.37 (1H, dd), 7.72 (1H, dd), 7.87 (1H, dd), 7.92 (1H, dd). m/z ES+ [M+H]+=528.

8-[(12aR)-10-Chloro-8-fluoro-1,2,3,4,12,12a-hexahydro-6H-pyrazino[2,1-c][1,4]benzoxazepin-9-yl]-7-methylisoquinolin-1(2H)-one

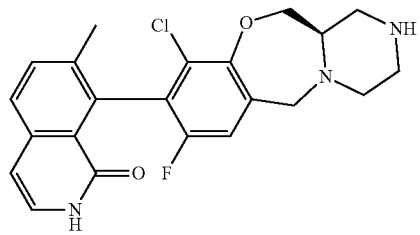 [SMILES: Cc1ccc2cc[nH]c(=O)c2c1-c1c(F)cc2c(c1Cl)OC[C@H]1CNCCN1C2]

Tert-butyl (12aR)-10-chloro-8-fluoro-9-(1-methoxy-7-methylisoquinolin-8-yl)-3,4,12,12a-tetrahydro-6H-pyrazino[2,1-c][1,4]benzoxazepine-2(1H)-carboxylate (100 mg, 0.19 mmol), lithium chloride (40.1 mg, 0.95 mmol) and p-toluenesulfonic acid (180 mg, 0.95 mmol) were dissolved in DMF (5 mL) and sealed into a microwave tube. The reaction was heated at 120° C. for 30 min in the microwave reactor and cooled to rt. The reaction mixture was purified by C18-flash chromatography, elution gradient 5 to 30% MeCN in water (0.05% TFA). The isolated product was purified using an SCX column (7M NH$_3$/MeOH) to afford 8-[(12aR)-10-chloro-8-fluoro-1,2,3,4,12,12a-hexahydro-6H-pyrazino[2,1-c][1,4]benzoxazepin-9-yl]-7-methylisoquinolin-1(2H)-one (50 mg, 64%) as a yellow film. 1H NMR (400 MHz, CD$_3$OD, 30° C.) 2.10 (3H, d), 2.75-3.03 (2H, m), 3.09-3.29 (3H, m), 3.38-3.52 (1H, m), 3.69-3.95 (3H, m), 4.11 (1H, dd), 4.30-4.46 (1H, m), 6.68 (1H, dd), 7.07 (1H, dd), 7.11 (1H, dd), 7.65-7.72 (2H, m). m/z ES+ [M+H]+=414.

8-[(12aR)-10-Chloro-8-fluoro-2-(prop-2-enoyl)-1,2,3,4,12,12a-hexahydro-6H-pyrazino[2,1-c][1,4]benzoxazepin-9-yl]-7-methylisoquinolin-1(2H)-one Rotational Isomer 1, Example 28 and Rotational Isomer 2, Example 29

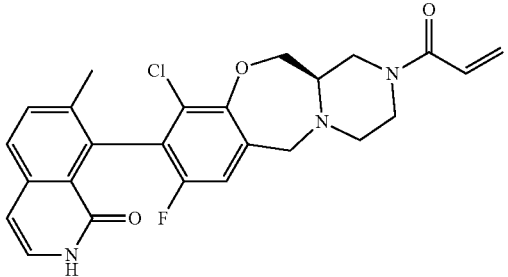 [SMILES: C=CC(=O)N1CCN2Cc3cc(F)c(-c4c(C)ccc5cc[nH]c(=O)c45)c(Cl)c3OC[C@H]2C1]

A solution of acryloyl chloride (10.93 mg, 0.12 mmol) in DMF (1 mL) was added dropwise to a stirred solution of 8-[(12aR)-10-chloro-8-fluoro-1,2,3,4,12,12a-hexahydro-6H-pyrazino[2,1-c][1,4]benzoxazepin-9-yl]-7-methylisoquinolin-1(2H)-one (50 mg, 0.12 mmol) in DMF (5 mL) at −10° C. The resulting solution was stirred at −10° C. for 30 min. The reaction mixture was purified by preparative HPLC (Column: Xselect CSH OBD Column 30*150 mm 5 μm), eluting with water (0.1% formic acid) and MeCN, to give rotational isomer 1 of 8-[(12aR)-10-chloro-8-fluoro-2-(prop-2-enoyl)-1,2,3,4,12,12a-hexahydro-6H-pyrazino[2,1-c][1,4]benzoxazepin-9-yl]-7-methylisoquinolin-1(2H)-one (18 mg, 32%) as a white solid. 1H NMR (400 MHz, CD$_3$CN, 30° C.) 2.11 (3H, s), 2.40-2.54 (1H, m), 2.81-3.53 (4H, m), 3.62-3.75 (2H, m), 3.74-3.87 (1H, m), 3.90-4.15 (2H, m), 4.32 (1H, dd), 5.69 (1H, dd), 6.18 (1H, dd), 6.54 (1H, d), 6.72 (1H, dd), 7.02 (2H, d), 7.57-7.79 (2H, m), 9.07 (1H, s). m/z ES+ [M+H]+=468. This was followed by rotational isomer 2 of 8-[(12aR)-10-chloro-8-fluoro-2-(prop-2-enoyl)-1,2,3,4,12,12a-hexahydro-6H-pyrazino[2,1-c][1,4]benzoxazepin-9-yl]-7-methylisoquinolin-1(2H)-one (13 mg, 23%) as a white solid. 1H NMR (400 MHz, CD$_3$CN, 30° C.) 2.08 (3H, s), 2.39-3.51 (5H, m), 3.53-3.91 (3H, m), 3.93-4.21 (2H, m), 4.34 (1H, dd), 5.70 (1H, dd), 6.19 (1H, dd), 6.54 (1H, d), 6.72 (1H, dd), 6.94-7.12 (2H, m), 7.56-7.74 (2H, m), 9.07 (1H, s). m/z ES+ [M+H]+=468.

4-Amino-3-chloro-2-fluoro-5-methoxybenzoic acid

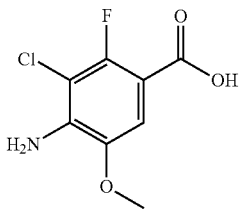

4-Amino-2-fluoro-5-methoxybenzoic acid (2.5 g, 13.5 mmol) was added to N-chlorosuccinimide (1.803 g, 13.5 mmol) in MeCN (50 mL) at 25° C. The resulting mixture was stirred at 80° C. for 12 h. The solvent was removed under reduced pressure. The crude product obtained was purified by C18-flash chromatography, elution gradient 5 to 100% MeOH in water, to give 4-amino-3-chloro-2-fluoro-5-methoxybenzoic acid (1.241 g, 42%) as a black solid. 1H NMR (300 MHz, CD$_3$OD, 30° C.) 3.90 (3H, s), 7.26 (1H, d). m/z: ES+ [M+H]+=220.

4-Bromo-3-chloro-2-fluoro-5-methoxybenzoic acid

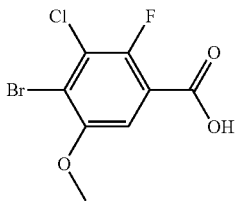

4-Amino-3-chloro-2-fluoro-5-methoxybenzoic acid (1.241 g, 5.65 mmol) was added to tert-butyl nitrite (1.166 g, 11.30 mmol) in MeCN (45 mL) cooled to 0° C. Copper(II) bromide (2.52 g, 11.30 mmol) was then added at 0° C. over a period of 10 min. The resulting mixture was stirred at 25° C. for 2 h. The reaction mixture was purified by C18-flash chromatography, elution gradient 70 to 72% MeOH in water (0.1% formic acid) to give 4-bromo-3-chloro-2-fluoro-5-methoxybenzoic acid (1 g, 62%) as a yellow solid. m/z: ES−[M−H]−=281.

Tert-butyl (3R)-4-(4-bromo-3-chloro-2-fluoro-5-methoxybenzoyl)-3-(hydroxymethyl)piperazine-1-carboxylate

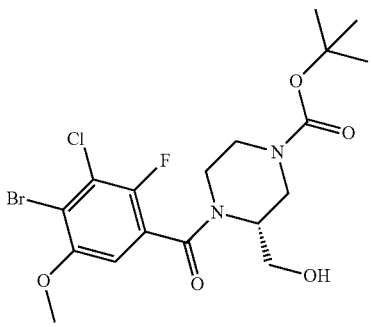 [SMILES: COc1cc(C(=O)N2CCN(C(=O)OC(C)(C)C)C[C@@H]2CO)c(F)c(Cl)c1Br]

4-Bromo-3-chloro-2-fluoro-5-methoxybenzoic acid (1 g, 3.53 mmol) was added to tert-butyl (3R)-3-(hydroxymethyl) piperazine-1-carboxylate (1.144 g, 5.29 mmol), DIPEA (1.848 ml, 10.58 mmol) and HATU (2.012 g, 5.29 mmol) in DMF (20 ml) at 25° C. over a period of 3 h. The resulting mixture was stirred at 25° C. for 3 h. The reaction mixture was diluted with EtOAc (200 mL) and washed with brine (50 mL×3). The organic layer was dried (Na$_2$SO$_4$) and evaporated to afford crude product. This was purified by C18-flash chromatography, elution gradient 15 to 60% MeOH in water, to give tert-butyl (3R)-4-(4-bromo-3-chloro-2-fluoro-5-methoxybenzoyl)-3-(hydroxymethyl)piperazine-1-carboxylate (0.8 g, 47%) as a yellow solid. 1H NMR (300 MHz, DMSO, 30° C.) 1.40 (9H, s), 2.65-3.11 (3H, m), 3.40-3.64 (2H, m), 3.88 (3H, s), 3.93-4.15 (1H, m), 4.15-4.41 (1H, m), 4.39-4.68 (1H, m), 4.69-5.28 (1H, m), 7.15 (1H, d). m/z: ES+ [M-$^t$Bu]+=425.

Tert-butyl (12aR)-9-bromo-10-chloro-8-methoxy-6-oxo-3,4,12,12a-tetrahydro-6H-pyrazino[2,1-c][1,4]benzoxazepine-2(1H)-carboxylate

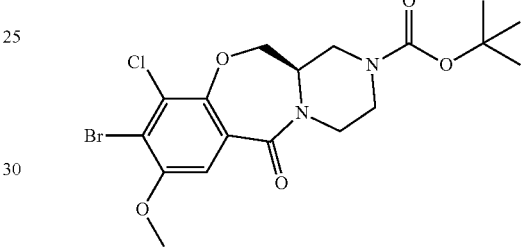

1M Lithium bis(trimethylsilyl)amide in THF (1.495 mL, 1.49 mmol) was added to tert-butyl (3R)-4-(4-bromo-3-chloro-2-fluoro-5-methoxybenzoyl)-3-(hydroxymethyl)piperazine-1-carboxylate (600 mg, 1.25 mmol) in DMF (15 mL). The resulting mixture was stirred at 100° C. for 4 h. The crude product was purified by C18-flash chromatography, elution gradient 5 to 80% MeOH in water to give tert-butyl (12aR)-9-bromo-10-chloro-8-methoxy-6-oxo-3,4,12,12a-tetrahydro-6H-pyrazino[2,1-c][1,4]benzoxazepine-2(1H)-carboxylate (400 mg, 70%) as a yellow solid. 1H NMR (400 MHz, CDCl$_3$, 30° C.) 1.49 (9H, s), 3.45-3.83 (4H, m), 3.86-3.90 (2H, m), 3.94 (3H, s), 4.04-4.08 (1H, m), 4.21-4.29 (1H, m), 4.30-4.35 (1H, m), 7.23 (1H, s). m/z: ES+ [M+H]+=461.

Tert-butyl (12aR)-10-chloro-9-(2-fluoro-6-hydroxyphenyl)-8-methoxy-6-oxo-3,4,12,12a-tetrahydro-6H-pyrazino[2,1-c][1,4]benzoxazepine-2(1H)-carboxylate

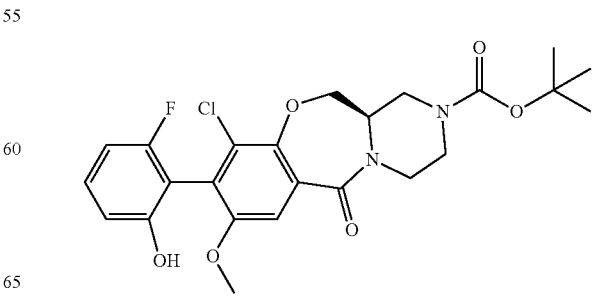

RuPhos-Pd-G3 (72.5 mg, 0.09 mmol) was added to 2-fluoro-6-hydroxyphenyl)boronic acid (203 mg, 1.3 mmol), RuPhos (40 mg, 0.09 mmol), tert-butyl (12aR)-9-bromo-10-chloro-8-methoxy-6-oxo-3,4,12,12a-tetrahydro-6H-pyrazino[2,1-c][1,4]benzoxazepine-2(1H)-carboxylate (400 mg, 0.87 mmol) and $K_2CO_3$ (359 mg, 2.60 mmol) in 1,4-dioxane (10 mL) and water (2.5 mL) (4:1 ratio) at 25° C. The resulting solution was stirred at 80° C. for 1 h. The reaction mixture was purified by C18-flash chromatography, elution gradient 40 to 80% MeOH in water to give tert-butyl (12aR)-10-chloro-9-(2-fluoro-6-hydroxyphenyl)-8-methoxy-6-oxo-3,4,12,12a-tetrahydro-6H-pyrazino[2,1-c][1,4]benzoxazepine-2(1H)-carboxylate (280 mg, 66%) as a yellow solid. 1H NMR (300 MHz, $CD_3OD$, 30° C.) 1.51 (9H, s), 3.69-3.90 (7H, m), 3.89-4.19 (3H, m), 4.22-4.51 (2H, m), 6.36-6.79 (2H, m), 7.12-7.28 (2H, m). m/z: ES+ [M+H]+=493.

Tert-butyl (12aR)-10-chloro-9-(2-fluoro-6-hydroxyphenyl)-8-methoxy-3,4,12,12a-tetrahydro-6H-pyrazino[2,1-c][1,4]benzoxazepine-2(1H)-carboxylate

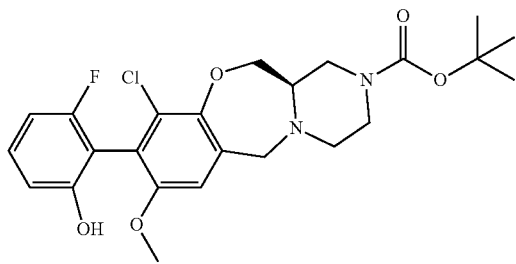 [SMILES: COc1cc2c(c(Cl)c1-c1c(O)cccc1F)OC[C@H]1CN(C(=O)OC(C)(C)C)CCN1C2]

Tert-butyl (12aR)-10-chloro-9-(2-fluoro-6-hydroxyphenyl)-8-methoxy-6-oxo-3,4,12,12a-tetrahydro-6H-pyrazino[2,1-c][1,4]benzoxazepine-2(1H)-carboxylate (260 mg, 0.53 mmol) in 1M borane-THF complex solution in THF (10 mL, 10.0 mmol) was stirred at 25° C. for 5 h. The reaction mixture was quenched with 2M HCl and the solvent was removed under reduced pressure. The crude product obtained was purified by C18-flash chromatography, elution gradient 10 to 80% MeOH in water, to give tert-butyl (12aR)-10-chloro-9-(2-fluoro-6-hydroxyphenyl)-8-methoxy-3,4,12,12a-tetrahydro-6H-pyrazino[2,1-c][1,4]benzoxazepine-2(1H)-carboxylate (220 mg, 87%) as a yellow solid. 1H NMR (400 MHz, $CDCl_3$, 30° C.) 1.48 (9H, s), 2.34-2.75 (2H, m), 2.80-2.92 (1H, m), 3.18-3.42 (2H, m), 3.57-3.95 (7H, m), 4-4.17 (1H, m), 4.24-4.51 (1H, m), 6.60-6.89 (3H, m), 7.30 (1H, s). m/z: ES+ [M+H]+=479.

2-[(12aR)-10-Chloro-8-methoxy-1,2,3,4,12,12a-hexahydro-6H-pyrazino[2,1-c][1,4]benzoxazepin-9-yl]-3-fluorophenol

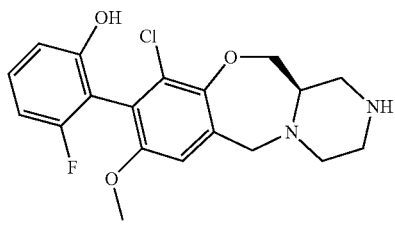 [SMILES: COc1cc2c(c(Cl)c1-c1c(O)cccc1F)OC[C@H]1CNCCN1C2]

Tert-butyl (12aR)-10-chloro-9-(2-fluoro-6-hydroxyphenyl)-8-methoxy-3,4,12,12a-tetrahydro-6H-pyrazino[2,1-c][1,4]benzoxazepine-2(1H)-carboxylate (210 mg, 0.44 mmol) in TFA (9 mL) and DCM (1 mL) was stirred at 25° C. for 1 h. The solvent was removed under reduced pressure. The crude product obtained was purified by SCX (7M $NH_3$/MeOH) to afford 2-[(12aR)-10-chloro-8-methoxy-1,2,3,4,12,12a-hexahydro-6H-pyrazino[2,1-c][1,4]benzoxazepin-9-yl]-3-fluorophenol (140 mg, 84%) as a solid. 1H NMR (400 MHz, $CDCl_3$, 30° C.) 2.41-2.68 (3H, m), 2.70-3.28 (6H, m), 3.59-3.71 (1H, m), 3.76 (3H, s), 3.88-4.10 (1H, m), 4.10-4.39 (1H, m), 6.48-6.99 (3H, m), 7.28-7.30 (1H, m). m/z: ES+ [M+H]+=379.

1-[(12aR)-10-chloro-9-(2-fluoro-6-hydroxyphenyl)-8-methoxy-3,4,12,12a-tetrahydro-6H-pyrazino[2,1-c][1,4]benzoxazepin-2(1H)-yl]prop-2-en-1-one Rotational Isomer 1, Example 30 and Rotational Isomer 2, Example 31

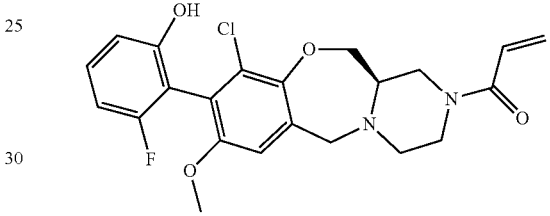

Acryloyl chloride (25.8 mg, 0.29 mmol) was added to triethylamine (0.044 mL, 0.32 mmol) and 2-[(12aR)-10-chloro-8-methoxy-1,2,3,4,12,12a-hexahydro-6H-pyrazino[2,1-c][1,4]benzoxazepin-9-yl]-3-fluorophenol (120 mg, 0.32 mmol) in DMF (5 mL). The resulting mixture was stirred at 25° C. for 4 h. The reaction mixture was purified by preparative chiral-HPLC (Column: XBridge Prep OBD C18 Column 30×150 mm 5 μm) eluting with Water (10 mmol/L $NH_4HCO_3$) and MeCN, to give rotational isomer 1 of 1-[(12aR)-10-chloro-9-(2-fluoro-6-hydroxyphenyl)-8-methoxy-3,4,12,12a-tetrahydro-6H-pyrazino[2,1-c][1,4]benzoxazepin-2(1H)-yl]prop-2-en-1-one (40 mg, 29%) as a white solid. 1H NMR (300 MHz, DMSO, 30° C.) 2.35-2.41 (1H, m), 2.70-3.41 (4H, m), 3.44-3.57 (1H, m), 3.65 (3H, s), 3.70-3.76 (1H, m), 3.87-4.15 (3H, m), 4.23-4.39 (1H, m), 5.68 (1H, d), 6.12 (1H, d), 6.59-6.75 (2H, m), 6.75-6.88 (1H, m), 6.99 (1H, s), 7.11-7.25 (1H, m), 9.71 (1H, s). m/z: ES+ [M+H]+=433. This was followed by rotational isomer 2 of 1-[(12aR)-10-chloro-9-(2-fluoro-6-hydroxyphenyl)-8-methoxy-3,4,12,12a-tetrahydro-6H-pyrazino[2,1-c][1,4]benzoxazepin-2(1H)-yl]prop-2-en-1-one (33 mg, 24%) as a white solid. 1H NMR (300 MHz, DMSO, 30° C.) 2.35-2.41 (1H, m), 2.69-3.35 (4H, m), 3.44-3.57 (1H, m), 3.64 (3H, s), 3.66-3.75 (1H, m), 3.81-3.92 (2H, m), 3.95-4.18 (1H, m), 4.22-4.38 (1H, m), 5.68 (1H, d), 6.11 (1H, d), 6.57-6.67 (1H, m), 6.67-6.74 (1H, m), 6.74-6.87 (1H, m), 6.97 (1H, s), 7.10-7.24 (1H, m), 9.67 (1H, s). m/z: ES+ [M+H]+=433.

Tert-butyl (3aR)-1-oxotetrahydro-1H-1λ⁴-[1,2,3]oxathiazolo[3,4-a]pyrazine-5(3H)-carboxylate

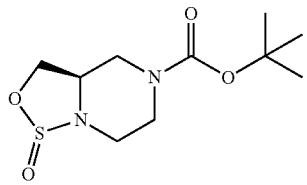

Thionyl chloride (4.70 ml, 64.73 mmol) was added to a solution of 1H-imidazole (14.64 g, 215 mmol) in DCM (100 mL) at 0° C. and the reaction mixture stirred for 1 h. The reaction mixture was cooled to −78° C. and a solution of tert-butyl (3R)-3-(hydroxymethyl)piperazine-1-carboxylate (5 g, 23.12 mmol) in DCM (100 mL) was added dropwise with stirring. On addition, the resultant yellow mixture was brought to rt and stirred overnight. The reaction mixture was cooled in an ice-bath and quenched by dropwise addition of aqueous saturated ammonium chloride solution (200 mL). The organic portion was collected and the aqueous was washed with DCM (200 mL). The combined organics were passed through a hydrophobic frit and concentrated under reduced pressure to afford tert-butyl (3aR)-1-oxotetrahydro-1H-1λ⁴-[1,2,3]oxathiazolo[3,4-a]pyrazine-5(3H)-carboxylate (6.4 g, >100%) as a yellow oil which solidified on standing and was used without further purification. 1H NMR (400 MHz, CDCl₃, 30° C.) 1.47 (9H, d), 2.05-2.75 (1H, m), 2.82 (1H, td), 2.88-3.14 (1H, m), 3.20 (1H, td), 3.32 (1H, d), 3.55-3.67 (1H, m), 3.88 (1H, dd), 3.95-4.44 (1H, m), 4.46-4.52 (1H, m), 4.52-4.6 (1H, m), 4.77 (1H, dd). m/z: ES+ [M-Boc]=163.

Tert-butyl (3aR)-1,1-dioxotetrahydro-1H-1λ⁶-[1,2,3]oxathiazolo[3,4-a]pyrazine-5(3H)-carboxylate

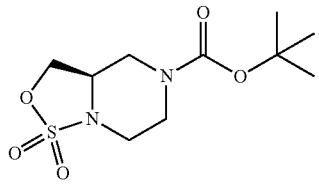 [SMILES: CC(C)(C)OC(=O)N1CCN2[C@@H](COS2(=O)=O)C1]

A solution of tert-butyl (3aR)-1-oxotetrahydro-1H-1λ⁴-[1,2,3]oxathiazolo[3,4-a]pyrazine-5(3H)-carboxylate (6.4 g, 24.4 mmol) in MeCN (90 mL) and EtOAc (18 mL) was added dropwise to a suspension of sodium periodate (6.78 g, 31.72 mmol) and ruthenium(III) chloride hydrate (0.011 g, 0.05 mmol) in water (30 mL) at 0° C. and stirred at 0° C. for 5 min then the reaction mixture was brought to rt and stirred overnight. The reaction mixture was diluted with aqueous saturated ammonium chloride solution (200 mL) and extracted with DCM (200 mL×2). The combined organics were dried (MgSO₄) and concentrated under reduced pressure to afford tert-butyl (3aR)-1,1-dioxotetrahydro-1H-1λ⁶-[1,2,3]oxathiazolo[3,4-a]pyrazine-5(3H)-carboxylate (6.02 g, 89%) as a pale yellow solid. 1H NMR (400 MHz, CDCl₃, 30° C.) 1.50 (9H, s), 2.99 (2H, td), 3.08-3.24 (1H, m), 3.41-3.52 (1H, m), 3.61-3.74 (1H, m), 4.01-4.18 (1H, m), 4.18-4.31 (2H, m), 4.65 (1H, dd).

Methyl 2-amino-4-bromo-3-chlorobenzoate

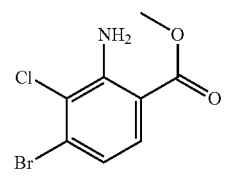

N-Chlorosuccinimide (12.19 g, 91.28 mmol) was added to methyl 2-amino-4-bromobenzoate (20 g, 86.93 mmol) in DMF (400 mL). The resulting mixture was stirred at 100° C. for 4 h. The reaction mixture was diluted with EtOAc (500 mL), washed with water (500 mL×3), brine (350 mL). The organic layer was dried (Na₂SO₄) and evaporated to afford crude product. This was purified by flash silica chromatography, elution gradient 0 to 5% EtOAc in petroleum ether, to give methyl 2-amino-4-bromo-3-chlorobenzoate (4.5 g, 20%) as a white solid. 1H NMR (400 MHz, CDCl₃, 30° C.) 3.91 (3H, s), 6.50 (2H, s), 6.93 (1H, d), 7.69 (1H, d). m/z: ES+ [M+H]+=264.

4-Bromo-2-({[(2S)-4-(tert-butoxycarbonyl)-1-sulfopiperazin-2-yl]methyl}amino)-3-chlorobenzoic acid

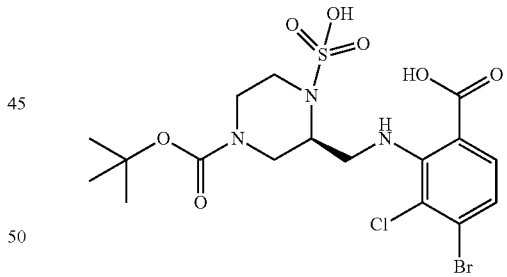

Sodium hydride (0.544 g, 13.61 mmol) was added to tert-butyl (3aR)-1,1-dioxotetrahydro-1H-1λ⁶-[1,2,3]oxathiazolo[3,4-a]pyrazine-5(3H)-carboxylate (2.84 g, 10.21 mmol) and methyl 2-amino-4-bromo-3-chlorobenzoate (1.8 g, 6.81 mmol) in DMF (30 mL) at 0° C. The resulting mixture was stirred at 0° C. for 2 h. The reaction mixture was diluted with ice water and the resulting crude reaction mixture was purified by C18-flash chromatography, elution gradient 0 to 50% MeCN in water (0.1% TFA), to give 4-bromo-2-({[(2S)-4-(tert-butoxycarbonyl)-1-sulfopiperazin-2-yl]methyl}amino)-3-chlorobenzoic acid (1.7 g, 47%) as a yellow solid. m/z: ES+ [M+H]+=528.

4-Bromo-3-chloro-2-({[(2R)-piperazin-2-yl]methyl}amino)benzoic acid

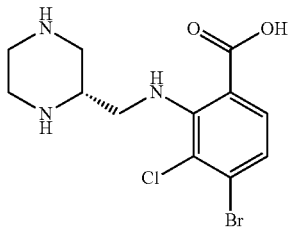 [SMILES: O=C(O)c1ccc(Br)c(Cl)c1NC[C@H]1CNCCN1]

36% HCl (2 mL, 23.70 mmol) was added portionwise to 4-bromo-2-({[(2S)-4-(tert-butoxycarbonyl)-1-sulfopiperazin-2-yl]methyl}amino)-3-chlorobenzoic acid (1.65 g, 3.12 mmol) in THF (10 mL). The resulting mixture was stirred at 80° C. overnight. The solvent was removed under reduced pressure. The crude product was purified by SCX (7M NH$_3$/MeOH) to afford (4-bromo-3-chloro-2-({[(2R)-piperazin-2-yl]methyl}amino)benzoic acid (1 g, 92%) as a yellow solid. 1H NMR (400 MHz, DMSO, 30° C.) 2.60-2.71 (1H, m), 2.74-2.95 (2H, m), 2.97-3.16 (3H, m), 3.19-3.32 (2H, m), 3.35-3.47 (1H, m), 7.14 (1H, d), 7.71 (1H, d). m/z: ES+ [M+H]+=348.

(12aR)-9-Bromo-10-chloro-1,3,4,11,12,12a-hexahydropyrazino[2,1-c][1,4]benzodiazepin-6(2H)-one

DIPEA (0.451 mL, 2.58 mmol) was added 4-bromo-3-chloro-2-({[(2R)-piperazin-2-yl]methyl}amino)benzoic acid (300 mg, 0.86 mmol) and HATU (491 mg, 1.29 mmol) in DMF (6 mL). The resulting mixture was stirred at rt for 1 h. The reaction mixture was purified by C18-flash chromatography, elution gradient 0 to 45% MeCN in water to give (12aR)-9-bromo-10-chloro-1,3,4,11,12,12a-hexahydropyrazino[2,1-c][1,4]benzodiazepin-6(2H)-one (235 mg, 83%) as a yellow solid. 1H NMR (400 MHz, DMSO, 30° C.) 2.96-3.21 (2H, m), 3.22-3.50 (4H, m), 3.52-3.65 (1H, m), 3.86-4.01 (1H, m), 4.24-4.39 (1H, m), 6.67 (1H, t), 7.14 (1H, d), 7.92 (1H, d). m/z: ES+ [M+H]+=330.

(12aR)-10-Chloro-9-(5-methyl-1H-indazol-4-yl)-1,3,4,11,12,12a-hexahydropyrazino[2,1-c][1,4]benzodiazepin-6(2H)-one

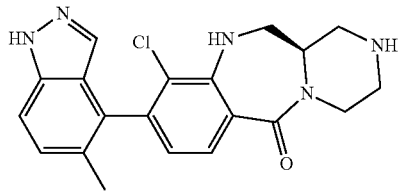 [SMILES: Cc1ccc2[nH]ncc2c1-c1ccc2c(c1Cl)NC[C@H]1CNCCN1C2=O]

Tetrakis(triphenylphosphine)palladium(0) (73.4 mg, 0.06 mmol) was added to (12aR)-9-bromo-10-chloro-1,3,4,11,12,12a-hexahydropyrazino[2,1-c][1,4]benzodiazepin-6(2H)-one (210 mg, 0.64 mmol), (5-methyl-1H-indazol-4-yl) boronic acid (224 mg, 1.27 mmol) and sodium carbonate (202 mg, 1.91 mmol) in 1,4-dioxane (5 mL) and water (1 mL) (5:1 ratio). The resulting mixture was stirred at 100° C. for 3 h. The solvent was removed under reduced pressure. The crude product obtained was purified by C18-flash chromatography, elution gradient 0 to 30% MeCN in water (0.1% NH$_4$HCO$_3$) to give (12aR)-10-chloro-9-(5-methyl-1H-indazol-4-yl)-1,3,4,11,12,12a-hexahydropyrazino[2,1-c][1,4]benzodiazepin-6(2H)-one (100 mg, 41%) as a yellow solid. 1H NMR (400 MHz, DMSO, 30° C.) 2.12 (3H, d), 2.59-2.93 (4H, m), 3.42-3.69 (4H, m), 3.69-3.82 (1H, m), 6.04-6.14 (1H, m), 6.68 (1H, d), 7.30 (1H, dd), 7.39-7.51 (2H, m), 7.78-7.87 (1H, m), 13.07 (1H, s). m/z: ES+ [M+H]+=382.

(12aS)-10-Chloro-9-(5-methyl-1H-indazol-4-yl)-2-(prop-2-enoyl)-1,3,4,11,12,12a-hexahydropyrazino[2,1-c][1,4]benzodiazepin-6(2H)-one Rotational Isomer 1, Example 32 and Rotational Isomer 2, Example 33

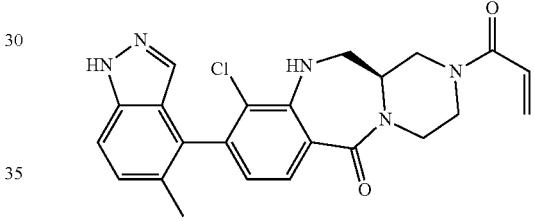

Acryloyl chloride (0.02 mL, 0.25 mmol) was added to (12aR)-10-chloro-9-(5-methyl-1H-indazol-4-yl)-1,3,4,11,12,12a-hexahydropyrazino[2,1-c][1,4]benzodiazepin-6(2H)-one (95 mg, 0.25 mmol) and DIPEA (0.087 mL, 0.50 mmol) in DMF (4 mL) at 0° C. The resulting mixture was stirred at 0° C. for 1 h. The reaction mixture was purified by C18-flash chromatography, elution gradient 0 to 50% MeCN in water (0.1% NH$_4$HCO$_3$) to give crude product as a white solid. This was purified by preparative chiral-HPLC (Column: CHIRALPAK IE, 2*25 cm, 5 μm; Mobile Phase A:Hexane:DCM=3:1 (10 mM NH$_3$-MeOH), Mobile Phase B: EtOH). This gave rotational isomer 1 of (12aS)-10-chloro-9-(5-methyl-1H-indazol-4-yl)-2-(prop-2-enoyl)-1,3,4,11,12,12a-hexahydropyrazino[2,1-c][1,4]benzodiazepin-6(2H)-one (9 mg, 18%) as a white solid. 1H NMR (400 MHz, DMSO, 30° C.) 2.11 (3H, s), 3.40-3.52 (1H, m), 3.54-3.75 (4H, m), 3.76-4.13 (4H, m), 5.66-5.79 (1H, m), 6.07-6.30 (2H, m), 6.66 (1H, d), 6.68-6.93 (1H, m), 7.30 (1H, d), 7.38-7.53 (2H, m), 7.82 (1H, t), 13.08 (1H, s). m/z: ES+ [M+H]+=436. This was followed by rotational isomer 2 of (12aS)-10-chloro-9-(5-methyl-1H-indazol-4-yl)-2-(prop-2-enoyl)-1,3,4,11,12,12a-hexahydropyrazino[2,1-c][1,4]benzodiazepin-6(2H)-one (6 mg, 12%) as a white solid. 1H NMR (400 MHz, DMSO, 30° C.) 2.13 (3H, s), 3.39-3.53 (1H, m), 3.55-4.14 (8H, m), 5.67-5.80 (1H, m), 6.07-6.34 (2H, m), 6.66 (1H, d), 6.69-6.92 (1H, m), 7.30 (1H, d), 7.36-7.54 (2H, m), 7.76-7.93 (1H, m), 13.08 (1H, s). m/z: ES+ [M+H]+=436.

Tert-butyl (12aR)-10-chloro-9-(2-chloro-6-hydroxyphenyl)-8-fluoro-3,4,12,12a-tetrahydro-6H-pyrazino[2,1-c][1,4]benzoxazepine-2(1H)-carboxylate

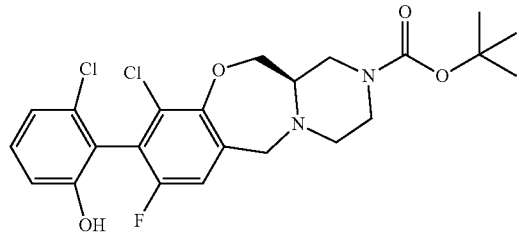 [SMILES: CC(C)(C)OC(=O)N1CCN2Cc3cc(F)c(-c4c(O)cccc4Cl)c(Cl)c3OC[C@H]2C1]

RuPhos-Pd-G3 (48 mg, 0.06 mmol) was added to tert-butyl (12aR)-9-bromo-10-chloro-8-fluoro-3,4,12,12a-tetrahydro-6H-pyrazino[2,1-c][1,4]benzoxazepine-2(1H)-carboxylate (250 mg, 0.57 mmol), (2-chloro-6-hydroxyphenyl)boronic acid (495 mg, 2.87 mmol), sodium carbonate (304 mg, 2.87 mmol) and RuPhos (26.8 mg, 0.06 mmol) in 1,4-dioxane (12 mL) and water (3 mL) (4:1 ratio) at 25° C. The resulting mixture was stirred at 120° C. for 3 h. The solvent was removed by distillation under vacuum and the crude product obtained purified by C18-flash chromatography, elution gradient 50 to 90% MeOH in water (0.1% Formic acid), to give tert-butyl (12aR)-10-chloro-9-(2-chloro-6-hydroxyphenyl)-8-fluoro-3,4,12,12a-tetrahydro-6H-pyrazino[2,1-c][1,4]benzoxazepine-2(1H)-carboxylate (167 mg, 60%) as a white solid. 1H NMR (300 MHz, DMSO, 30° C.) 1.45 (9H, s), 2.59-2.96 (5H, m), 2.96-3.21 (3H, m), 3.77-3.96 (2H, m), 4.18-4.43 (2H, m), 6.87-6.96 (1H, m), 6.95-7.05 (1H, m), 7.22-7.28 (2H, m). m/z: ES+ [M+H]+=483.

3-Chloro-2-[(12aR)-10-chloro-8-fluoro-1,2,3,4,12,12a-hexahydro-6H-pyrazino[2,1-c][1,4]benzoxazepin-9-yl]phenol

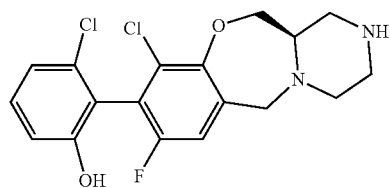 [SMILES: Oc1cccc(Cl)c1-c1c(F)cc2c(c1Cl)OC[C@H]1CNCCN1C2]

TFA (1 mL, 0.33 mmol) was added to tert-butyl (12aR)-10-chloro-9-(2-chloro-6-hydroxyphenyl)-8-fluoro-3,4,12,12a-tetrahydro-6H-pyrazino[2,1-c][1,4]benzoxazepine-2(1H)-carboxylate (160 mg, 0.33 mmol) in DCM (10 mL) at 25° C. The resulting mixture was stirred at 25° C. for 30 min. The solvent was removed under vacuum and the crude product obtained purified by SCX (7M NH3/MeOH) to afford 3-chloro-2-[(12aR)-10-chloro-8-fluoro-1,2,3,4,12,12a-hexahydro-6H-pyrazino[2,1-c][1,4]benzoxazepin-9-yl]phenol (74 mg, 58%) as a white solid. m/z: ES+ [M+H]+=383.

1-[(12aR)-10-chloro-9-(2-chloro-6-hydroxyphenyl)-8-fluoro-3,4,12,12a-tetrahydro-6H-pyrazino[2,1-c][1,4]benzoxazepin-2(1H)-yl]prop-2-en-1-one Rotational Isomer 1, Example 34 and Rotational Isomer 2, Example 35

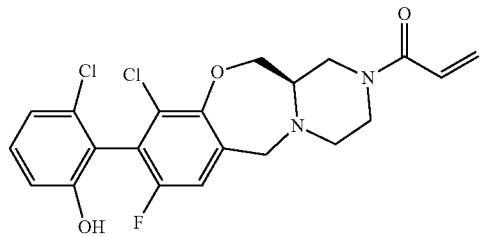 [SMILES: C=CC(=O)N1CCN2Cc3cc(F)c(-c4c(O)cccc4Cl)c(Cl)c3OC[C@H]2C1]

DIPEA (0.101 mL, 0.58 mmol) was added dropwise to 3-chloro-2-[(12aR)-10-chloro-8-fluoro-1,2,3,4,12,12a-hexahydro-6H-pyrazino[2,1-c][1,4]benzoxazepin-9-yl]phenol (74 mg, 0.19 mmol) in DMF (3 mL) at 25° C. Acryloyl chloride (17 mg, 0.19 mmol) was then added at 0° C. and the reaction mixture stirred at 25° C. for 30 min. The reaction mixture was purified by preparative HPLC (column: Xselect CSH OBD Column 30*150 mm 5 μm), eluting with water (0.1% formic acid) and MeCN, to afford rotational isomer 1 of 1-[(12aR)-10-chloro-9-(2-chloro-6-hydroxyphenyl)-8-fluoro-3,4,12,12a-tetrahydro-6H-pyrazino[2,1-c][1,4]benzoxazepin-2(1H)-yl]prop-2-en-1-one (19 mg, 22%) as a white solid. 1H NMR (300 MHz, DMSO, 30° C.) 2.68-3.05 (2H, m), 3.05-3.19 (3H, m), 3.57-3.78 (2H, m), 3.82-4.30 (2H, m), 4.29-4.61 (2H, m), 5.78 (1H, m), 6.16 (1H, m), 6.67-6.86 (1H, m), 6.92 (1H, m), 7.02 (1H, m), 7.19-7.57 (2H, m), 10.11 (1H, m). m/z: ES+ [M+H]+=437. This was followed by rotational isomer 2 of 1-[(12aR)-10-chloro-9-(2-chloro-6-hydroxyphenyl)-8-fluoro-3,4,12,12a-tetrahydro-6H-pyrazino[2,1-c][1,4]benzoxazepin-2(1H)-yl]prop-2-en-1-one (11 mg, 13%) as a white solid. 1H NMR (300 MHz, DMSO, 30° C.) 2.29-2.45 (1H, m), 2.65-2.99 (3H, m), 3.03-3.18 (1H, m), 3.56-3.65 (1H, m), 3.68-3.79 (1H, m), 3.80-4 (3H, m), 4.29-4.44 (1H, m), 5.57-5.75 (1H, m), 6.02-6.25 (1H, m), 6.70-6.88 (1H, m), 6.88-7.05 (2H, m), 7.15-7.35 (2H, m), 10.01-10.28 (1H, m). m/z: ES+ [M+H]+=437.

4-Bromo-2-({[(2S)-4-(tert-butoxycarbonyl)piperazin-2-yl]methyl}amino)-3-chlorobenzoic acid

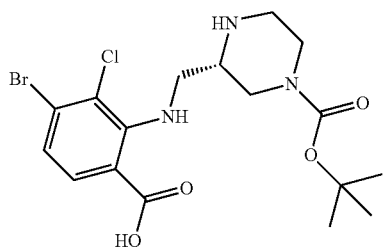 [SMILES: CC(C)(C)OC(=O)N1CCN[C@@H](CNc2c(C(=O)O)ccc(Br)c2Cl)C1]

Di-tert-butyl dicarbonate (0.599 mL, 2.58 mmol) was added to 4-bromo-2-({[(2S)-4-(tert-butoxycarbonyl)-1-sulfopiperazin-2-yl]methyl}amino)-3-chlorobenzoic acid (450 mg, 1.29 mmol) in DCM (10 mL) at 0° C. The resulting mixture was stirred at 0° C. for 3 h. The solvent was removed under reduced pressure. The crude product obtained was purified by C18-flash chromatography, elution gradient 0 to 50% MeCN in water, to give 4-bromo-2-({[(2S)-4-(tert-butoxycarbonyl)piperazin-2-yl]methyl}amino)-3-chlorobenzoic acid (360 mg, 62%) as a white solid. 1H NMR (400 MHz, DMSO, 30° C.) 1.39 (9H, s), 2.73-3.55 (7H, m), 3.78-4.09 (2H, m), 7.21 (1H, d), 7.62 (1H, d). m/z: ES+ [M+H]+=448.

Tert-butyl (12aS)-9-bromo-10-chloro-6-oxo-3,4,6,11,12,12a-hexahydropyrazino[2,1-c][1,4]benzodiazepine-2(1H)-carboxylate

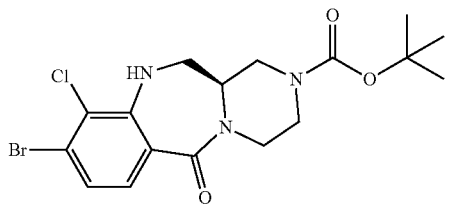 [SMILES: CC(C)(C)OC(=O)N1CCN2C(=O)c3ccc(Br)c(Cl)c3NC[C@H]2C1]

DIPEA (0.397 mL, 2.27 mmol) was added to 4-bromo-2-({[(2S)-4-(tert-butoxycarbonyl)piperazin-2-yl]methyl}amino)-3-chlorobenzoic acid (340 mg, 0.76 mmol) and HATU (432 mg, 1.14 mmol) in DMF (8 mL). The resulting mixture was stirred at rt for 2 h. The reaction mixture was purified by C18-flash chromatography, elution gradient 0 to 50% MeCN in water (0.1% formic acid), to give tert-butyl (12aS)-9-bromo-10-chloro-6-oxo-3,4,6,11,12,12a-hexahydropyrazino[2,1-c][1,4]benzodiazepine-2(1H)-carboxylate (320 mg, 98%) as a white solid. 1H NMR (400 MHz, DMSO, 30° C.) 1.41 (9H, s), 3.26-3.37 (2H, m), 3.40-3.58 (3H, m), 3.63-3.94 (4H, m), 6.30-6.41 (1H, m), 7.06 (1H, d), 7.63 (1H, d). m/z: ES+ [M+H]+=430.

Tert-butyl (12aS)-9-bromo-10-chloro-11-methyl-6-oxo-3,4,6,11,12,12a-hexahydropyrazino[2,1-c][1,4]benzodiazepine-2(1H)-carboxylate

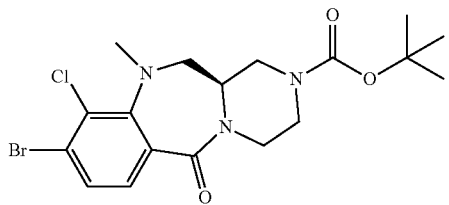 [SMILES: CN1C[C@H]2CN(C(=O)OC(C)(C)C)CCN2C(=O)c2ccc(Br)c(Cl)c21]

Iodomethane (0.087 mL, 1.39 mmol) was added to tert-butyl (12aS)-9-bromo-10-chloro-6-oxo-3,4,6,11,12,12a-hexahydropyrazino[2,1-c][1,4]benzodiazepine-2(1H)-carboxylate (300 mg, 0.7 mmol) and sodium hydride (84 mg, 2.09 mmol) in DMF (6 mL) at 0° C. The resulting mixture was stirred at rt for 2 h. The reaction mixture was diluted with water and purified by C18-flash chromatography, elution gradient 0 to 70% MeCN in water (0.1% formic acid) to give tert-butyl (12aS)-9-bromo-10-chloro-11-methyl-6-oxo-3,4,6,11,12,12a-hexahydropyrazino[2,1-c][1,4]benzodiazepine-2(1H)-carboxylate (260 mg, 84%) as a yellow solid. 1H NMR (400 MHz, DMSO, 30° C.) 11.41 (9H, s), 2.92 (3H, s), 3.09-3.33 (3H, m), 3.40-3.89 (6H, m), 7.35 (1H, d), 7.57 (1H, d). m/z: ES+ [M+H]+=444.

Tert-butyl (12aS)-10-chloro-11-methyl-9-(5-methyl-1H-indazol-4-yl)-6-oxo-3,4,6,11,12,12a-hexahydropyrazino[2,1-c][1,4]benzodiazepine-2(1H)-carboxylate

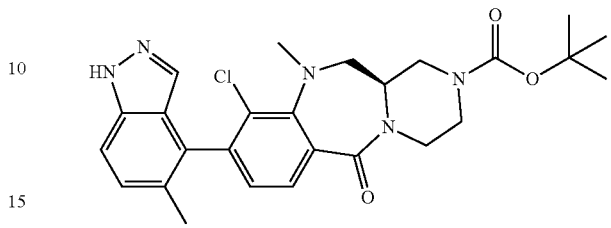

Tetrakis(triphenylphosphine)palladium(0) (62.4 mg, 0.05 mmol) was added to tert-butyl (12aS)-9-bromo-10-chloro-11-methyl-6-oxo-3,4,6,11,12,12a-hexahydropyrazino[2,1-c][1,4]benzodiazepine-2(1H)-carboxylate (240 mg, 0.54 mmol), (5-methyl-1H-indazol-4-yl)boronic acid (142 mg, 0.81 mmol) and sodium carbonate (172 mg, 1.62 mmol) in 1,4-dioxane (5 mL) and water (1 mL) (5:1 ratio). The resulting mixture was stirred at 100° C. for 4 h. The solvent was removed under reduced pressure. The crude product obtained was purified by C18-flash chromatography, elution gradient 0 to 50% MeCN in water (0.1% formic acid), to give tert-butyl (12aS)-10-chloro-11-methyl-9-(5-methyl-1H-indazol-4-yl)-6-oxo-3,4,6,11,12,12a-hexahydropyrazino[2,1-c][1,4]benzodiazepine-2(1H)-carboxylate (180 mg, 67%) as a white solid. 1H NMR (400 MHz, DMSO, 30° C.) 1.43 (9H, s), 2.15 (3H, d), 2.98 (3H, d), 3.18-3.27 (1H, m), 3.32-3.49 (2H, m), 3.48-3.80 (4H, m), 3.82-3.97 (2H, m), 7.13 (1H, dd), 7.31 (1H, dd), 7.45-7.57 (3H, m), 13.07 (1H, s). m/z: ES+ [M+H]+=496.

(12aR)-10-Chloro-11-methyl-9-(5-methyl-1H-indazol-4-yl)-1,3,4,11,12,12a-hexahydropyrazino[2,1-c][1,4]benzodiazepin-6(2H)-one

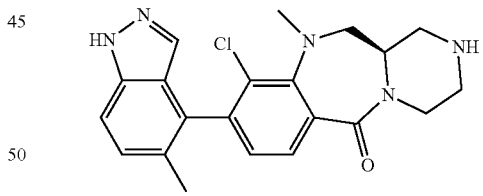

TFA (1 mL, 12.98 mmol) was added dropwise to tert-butyl (12aS)-10-chloro-11-methyl-9-(5-methyl-1H-indazol-4-yl)-6-oxo-3,4,6,11,12,12a-hexahydropyrazino[2,1-c][1,4]benzodiazepine-2(1H)-carboxylate (170 mg, 0.34 mmol) in DCM (5 mL). The resulting mixture was stirred at rt for 1 h. The solvent was removed under reduced pressure. The crude product was purified by SCX (7M NH$_3$/MeOH) to afford (12aR)-10-chloro-11-methyl-9-(5-methyl-1H-indazol-4-yl)-1,3,4,11,12,12a-hexahydropyrazino[2,1-c][1,4]benzodiazepin-6(2H)-one (125 mg, 92%) as a yellow solid. 1H NMR (400 MHz, DMSO, 30° C.) 2.14 (3H, d), 2.54-2.87 (3H, m), 2.93-3.01 (4H, m), 3.04-3.25 (2H, m), 3.51-3.81 (2H, m), 3.92-4.21 (1H, m), 7.11 (1H, dd), 7.30 (1H, dd), 7.45-7.56 (3H, m), 13.08 (1H, s). m/z: ES+ [M+H]+=396.

(12aS)-10-Chloro-11-methyl-9-(5-methyl-1H-indazol-4-yl)-2-(prop-2-enoyl)-1,3,4,11,12,12a-hexahydropyrazino[2,1-c][1,4]benzodiazepin-6(2H)-one Rotational Isomer 1, Example 36 and Rotational Isomer 2, Example 37

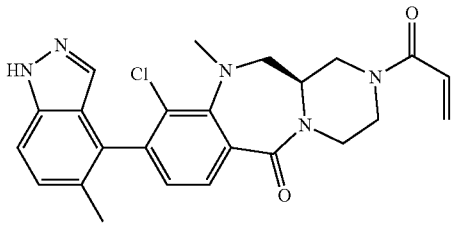

Acryloyl chloride (0.026 mL, 0.32 mmol) was added dropwise to (12aR)-10-chloro-11-methyl-9-(5-methyl-1H-indazol-4-yl)-1,3,4,11,12,12a-hexahydrobenzo[e]pyrazino[1,2-a][1,4]diazepin-6(2H)-one (120 mg, 0.3 mmol) and DIPEA (0.106 mL, 0.61 mmol) in DMF (4 mL) at 0° C. The resulting mixture was stirred at 0° C. for 1 h. The reaction mixture was purified by C18-flash chromatography, elution gradient 0 to 50% MeCN in water (0.1% NH$_4$HCO$_3$) to give crude product as a white solid. This was purified by preparative chiral-HPLC (Column: Chiralpak IA, 2*25 cm, 5 µm; Mobile Phase A:Hexane:DCM=3:1 (10 mM NH$_3$-MeOH), Mobile Phase B: EtOH) to give rotational isomer 1 of (12aS)-10-chloro-11-methyl-9-(5-methyl-1H-indazol-4-yl)-2-(prop-2-enoyl)-1,3,4,11,12,12a-hexahydropyrazino[2,1-c][1,4]benzodiazepin-6(2H)-one (54 mg, 42%) as a white solid. 1H NMR (400 MHz, DMSO, 30° C.) 2.14 (3H, s), 2.97 (3H, s), 3.16-3.32 (1H, m), 3.36-4.13 (8H, m), 5.64-5.82 (1H, m), 6.09-6.28 (1H, m), 6.69-6.85 (1H, m), 7.13 (1H, d), 7.30 (1H, d), 7.42-7.62 (3H, m), 13.09 (1H, s). m/z: ES+ [M+H]+=450. This was followed by rotational isomer 2 of (12aS)-10-chloro-11-methyl-9-(5-methyl-1H-indazol-4-yl)-2-(prop-2-enoyl)-1,3,4,11,12,12a-hexahydropyrazino[2,1-c][1,4]benzodiazepin-6(2H)-one (45 mg, 35%) as a white solid. 1H NMR (400 MHz, DMSO, 30° C.) 2.16 (3H, s), 2.98 (3H, s), 3.13-3.32 (1H, m), 3.35-4.09 (8H, m), 5.66-5.80 (1H, m), 6.12-6.23 (1H, m), 6.70-6.85 (1H, m), 7.14 (1H, d), 7.31 (1H, d), 7.43-7.61 (3H, m), 13.07 (1H, s). m/z: ES+ [M+H]+=450.

4-Bromo-3-chloro-2,5-difluorobenzoic acid

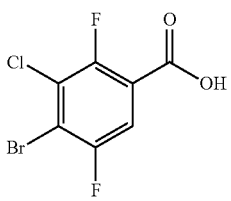

4-Bromo-2,5-difluorobenzoic acid (10 g, 42.2 mmol) was added to concentrated sulphuric acid (80 mL) at room temperature and the resulting suspension heated to 80° C. N-Chlorosuccinimide (11.27 g, 84.4 mmol) was then added and the reaction mixture heated at 80° C. overnight. The reaction mixture was cooled to rt, poured into ice (200 g) and the aqueous phase extracted with EtOAc. The crude product obtained after evaporation of the organic layer was purified by flash C18-flash chromatography, elution gradient 0 to 60% MeOH in water (0.1% formic acid). Pure fractions were evaporated to dryness to afford 4-bromo-3-chloro-2,5-difluorobenzoic acid (4.80 g, 41.9%) as a white solid. 1H NMR (400 MHz, DMSO, 30° C.) 7.81 (1H, dd), 13.98 (1H, s). m/z: ES– [M+H]–=271.

Tert-butyl (3R)-4-(4-bromo-3-chloro-2,5-difluorobenzoyl)-3-(hydroxymethyl)piperazine-1-carboxylate

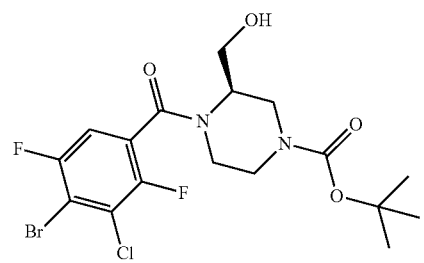 [SMILES: CC(C)(C)OC(=O)N1CCN(C(=O)c2cc(F)c(Br)c(Cl)c2F)[C@@H](CO)C1]

Tert-butyl (3R)-3-(hydroxymethyl)piperazine-1-carboxylate (3.98 g, 18.42 mmol) was added to 4-bromo-3-chloro-2,5-difluorobenzoic acid (5 g, 18.42 mmol), HATU (10.51 g, 27.63 mmol) and DIPEA (6.43 mL, 36.84 mmol) in THF (80 mL) at 25° C. The resulting solution was stirred at rt for 2 h. The solvent was removed under reduced pressure. Flash silica chromatography, elution gradient 0 to 50% EtOAc in petroleum ether, afforded tert-butyl (3R)-4-(4-bromo-3-chloro-2,5-difluorobenzoyl)-3-(hydroxymethyl)piperazine-1-carboxylate (5.72 g, 66.1%) as a white solid. 1H NMR (400 MHz, DMSO, 30° C.) 1.40 (9H, d), 2.74-3.05 (1H, m), 3.15 (1H, t), 3.26-3.37 (2H, m), 3.41-3.63 (2H, m), 3.67-3.90 (1H, m), 3.94-4.14 (1H, m), 4.19-4.33 (1H, m), 4.44-5.00 (1H, m), 7.59 (1H, s). m/z: ES+ [M+H]+=469.

Tert-butyl (12aR)-9-bromo-10-chloro-8-fluoro-6-oxo-3,4,12,12a-tetrahydro-6H-pyrazino[2,1-c][1,4]benzoxazepine-2(1H)-carboxylate

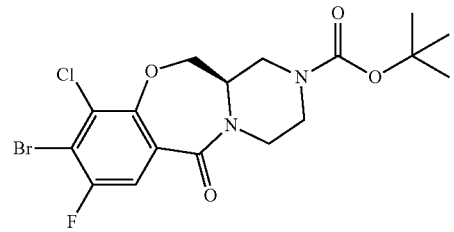 [SMILES: CC(C)(C)OC(=O)N1CCN2C(=O)c3cc(F)c(Br)c(Cl)c3OC[C@H]2C1]

Sodium hydride (0.971 g, 24.3 mmol) was added to tert-butyl (3R)-4-(4-bromo-3-chloro-2,5-difluorobenzoyl)-3-(hydroxymethyl)piperazine-1-carboxylate (5.7 g, 12.14 mmol) in THF (50 mL) at 0° C. under nitrogen. The resulting solution was stirred at rt for 16 h then evaporated. Flash silica chromatography, elution gradient 0 to 40% EtOAc in petroleum ether, afforded tert-butyl (12aR)-9-bromo-10-chloro-8-fluoro-6-oxo-3,4,12,12a-tetrahydro-6H-pyrazino[2,1-c][1,4]benzoxazepine-2(1H)-carboxylate (2.020 g, 37.0%) as a white solid. 1H NMR (400 MHz, DMSO, 30° C.) 1.41 (9H, s), 3.13-3.34 (1H, m), 3.44-3.50 (2H, m), 3.58-3.67 (1H, m), 3.72-3.80 (1H, m), 3.85-3.90 (1H, m), 3.92-4.02 (1H, m), 4.32 (2H, d), 7.59 (1H, d). m/z: ES+ [M+H]+=449.

Tert-butyl (12aR)-9-bromo-10-chloro-8-fluoro-3,4, 12,12a-tetrahydro-6H-pyrazino[2,1-c][1,4]benzoxazepine-2(1H)-carboxylate

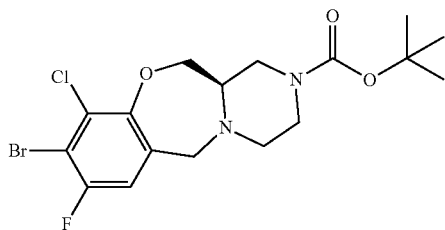 [SMILES: CC(C)(C)OC(=O)N1CCN2Cc3cc(F)c(Br)c(Cl)c3OC[C@H]2C1]

Tert-butyl (12aR)-9-bromo-10-chloro-8-fluoro-6-oxo-3, 4,12,12a-tetrahydro-6H-pyrazino[2,1-c][1,4]benzoxazepine-2(1H)-carboxylate (900 mg, 2.00 mmol) was added to 1M Borane-THF complex solution in THF (4 ml, 4.00 mmol) at 25° C. under nitrogen. The resulting solution was stirred at 60° C. for 16 hours. MeOH (8 ml) was then added and the resulting solution stirred at room temperature for 1 hour. The solvent was removed under reduced pressure and the crude product obtained was purified by flash silica chromatography, elution gradient 0 to 30% EtOAc in petroleum ether. Pure fractions were evaporated to dryness to afford tert-butyl (12aR)-9-bromo-10-chloro-8-fluoro-3,4,12, 12a-tetrahydro-6H-pyrazino[2,1-c][1,4]benzoxazepine-2 (1H)-carboxylate (678 mg, 78%) as a white solid. 1H NMR (400 MHz, DMSO, 30° C.) 1.38 (9H, s), 2.27-2.37 (1H, m), 2.64-2.71 (1H, m), 2.73-2.94 (2H, m), 3.07-3.17 (1H, m), 3.48-3.65 (3H, m), 3.70 (1H, d), 3.81 (1H, d), 4.32 (1H, dd), 7.37 (1H, d). m/z: ES+ [M+H]+=435.

Tert-butyl (12aR)-10-chloro-9-(2,3-difluoro-6-methoxyphenyl)-8-fluoro-3,4,12,12a-tetrahydro-6H-pyrazino[2,1-c][1,4]benzoxazepine-2(1H)-carboxylate

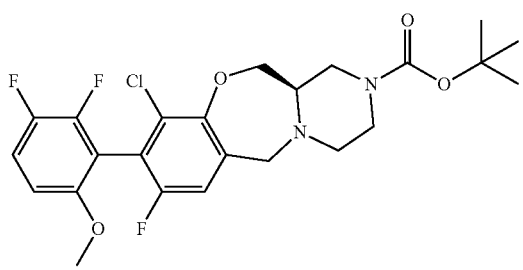 [SMILES: COc1ccc(F)c(F)c1-c1c(F)cc2c(c1Cl)OC[C@H]1CN(C(=O)OC(C)(C)C)CCN1C2]

RuPhos-Pd-G3 (101 mg, 0.12 mmol) was added to tert-butyl (12aR)-9-bromo-10-chloro-8-fluoro-3,4,12,12a-tetrahydro-6H-pyrazino[2,1-c][1,4]benzoxazepine-2(1H)-carboxylate (350 mg, 0.8 mmol), (2,3-difluoro-6-methoxyphenyl)boronic acid (906 mg, 4.82 mmol), RuPhos (56.2 mg, 0.12 mmol) and sodium carbonate (426 mg, 4.02 mmol) in 1,4-dioxane (12 mL) and water (3 mL) (4:1 ratio) at 25° C. The resulting mixture was stirred at 120° C. for 10 h. The solvent was evaporated and the crude product obtained purified by C18-flash chromatography, elution gradient 80 to 90% MeOH in water (0.1% Formic acid) to give tert-butyl (12aR)-10-chloro-9-(2,3-difluoro-6-methoxyphenyl)-8-fluoro-3,4,12,12a-tetrahydro-6H-pyrazino[2,1-c][1, 4]benzoxazepine-2(1H)-carboxylate (100 mg, 25%) as a white solid. 1H NMR (300 MHz, DMSO, 30° C.) 1.42 (9H, s), 1.54-1.71 (2H, m), 1.73-1.77 (1H, m), 2.73 (1H, s), 3.71-3.77 (3H, m), 3.81-4.23 (3H, m), 4.36-4.52 (3H, m), 4.53-4.76 (1H, m), 6.98-7.07 (1H, m), 7.42-7.51 (1H, m), 7.53-7.66 (1H, m). m/z: ES+ [M+H]+=499.

2-[(12aR)-10-Chloro-8-fluoro-1,2,3,4,12,12a-hexahydro-6H-pyrazino[2,1-c][1,4]benzoxazepin-9-yl]-3, 4-difluorophenol.2HBr

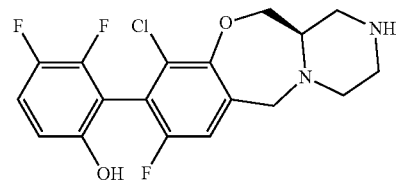 [SMILES: Oc1ccc(F)c(F)c1-c1c(F)cc2c(c1Cl)OC[C@H]1CNCCN1C2]

1 M Boron tribromide in DCM (3 mL, 3 mmol) was added to tert-butyl (12aR)-10-chloro-9-(2,3-difluoro-6-methoxyphenyl)-8-fluoro-3,4,12,12a-tetrahydro-6H-pyrazino[2,1-c] [1,4]benzoxazepine-2(1H)-carboxylate (95 mg, 0.19 mmol) in DCM (3 mL) at 25° C. The resulting solution was stirred at 25° C. for 30 min. MeOH (1 mL) was added and the solvent then removed under vacuum. The crude product obtained was purified by C18-flash chromatography, elution gradient 50 to 90% MeOH in water (0.1% Formic acid) to give 2-[(12aR)-10-chloro-8-fluoro-1,2,3,4,12,12a-hexahydro-6H-pyrazino[2,1-c][1,4]benzoxazepin-9-yl]-3,4-difluorophenol. 2HBr (92 mg, 88%) as a yellow solid. 1H NMR (300 MHz, DMSO, 30° C.) 2.16-2.38 (4H, m), 2.70-2.82 (2H, m), 3.54-3.71 (4H, m), 3.75-3.85 (1H, m), 4.18-4.28 (1H, m), 6.68-6.80 (1H, m), 7.23-7.30 (1H, m), 7.30-7.43 (1H, m). m/z: ES+ [M+H]+=385.

1-[(12aR)-10-Chloro-9-(2,3-difluoro-6-hydroxyphenyl)-8-fluoro-3,4,12,12a-tetrahydro-6H-pyrazino[2, 1-c][1,4]benzoxazepin-2(1H)-yl]prop-2-en-1-one Rotational Isomer 1, Example 38 and Rotational Isomer 2, Example 39

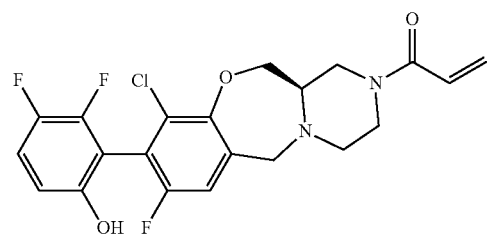 [SMILES: C=CC(=O)N1CCN2Cc3cc(F)c(-c4c(O)ccc(F)c4F)c(Cl)c3OC[C@H]2C1]

DIPEA (0.081 mL, 0.47 mmol) was added dropwise to 2-[(12aR)-10-chloro-8-fluoro-1,2,3,4,12,12a-hexahydro-6H-pyrazino[2,1-c][1,4]benzoxazepin-9-yl]-3,4-difluorophenol.2HBr (85 mg, 0.16 mmol) in DMF (2 mL) at 25° C. Acryloyl chloride (0.018 mL, 0.22 mmol) was added at 0° C. and the resulting mixture stirred at 0° C. for 30 min. Water (0.5 mL) was added and the resulting solution purified by preparative HPCL (column: XBridge Prep OBD C18 Column 30×150 mm 5 μm), eluting with water (10 mmol/L NH₄HCO₃) and MeCN, to give rotational isomer 1 of 1-[(12aR)-10-chloro-9-(2,3-difluoro-6-hydroxyphenyl)-8-fluoro-3,4,12,12a-tetrahydro-6H-pyrazino[2,1-c][1,4]benzoxazepin-2(1H)-yl]prop-2-en-1-one (20 mg, 29%) as a white solid. 1H NMR (300 MHz, DMSO, 30° C.) 2.38-2.44 (1H, m), 2.62-3.23 (4H, m), 3.57-3.70 (1H, m), 3.70-4.10 (4H, m), 4.31-4.46 (1H, m), 5.65-5.74 (1H, m), 6.07-6.19 (1H, m), 6.70-6.89 (2H, m), 7.26-7.43 (2H, m), 10.13-10.19 (1H, m). m/z: ES+ [M+H]+=439. This was followed by rotational isomer 2 of 1-[(12aR)-10-chloro-9-(2,3-difluoro-6-hydroxyphenyl)-8-fluoro-3,4,12,12a-tetrahydro-6H-pyrazino[2,1-c][1,4]benzoxazepin-2(1H)-yl]prop-2-en-1-one (5.7 mg, 8%) as a white solid. 1H NMR (300 MHz, DMSO, 30° C.) 2.34-2.49 (1H, m), 2.78-2.84 (3H, m), 3.09-3.15 (1H, m), 3.57-3.70 (1H, m), 3.67-4.14 (4H, m), 4.32-4.47 (1H, m), 5.68-5.74 (1H, m), 6.08-6.19 (1H, m), 6.67-6.92 (2H, m), 7.24-7.38 (2H, m). m/z: ES+ [M+H]+=439.

(12aR)-9-Bromo-10-chloro-8-iodo-1,2,3,4,12,12a-hexahydro-6H-pyrazino[2,1-c][1,4]benzoxazepine

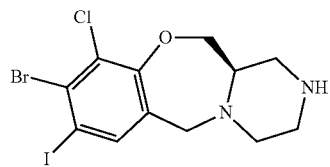

N-Iodosuccinimide (7.54 g, 33.51 mmol) was added to tert-butyl (12aR)-9-bromo-10-chloro-3,4,12,12a-tetrahydro-6H-pyrazino[2,1-c][1,4]benzoxazepine-2(1H)-carboxylate (7 g, 16.76 mmol) in concentrated sulfuric acid (60 mL). The resulting mixture was stirred at 25° C. for 20 h. The reaction mixture was quenched with 2M NaOH, extracted with DCM (200 mL×4). The organic layer was dried (Na₂SO₄) and evaporated to afford (12aR)-9-bromo-10-chloro-8-iodo-1,2,3,4,12,12a-hexahydro-6H-pyrazino[2,1-c][1,4]benzoxazepine (4 g, 54%) as a yellow solid. 1H NMR (300 MHz, DMSO, 30° C.) 2.18-2.43 (3H, m), 2.56-2.73 (3H, m), 2.73-2.96 (2H, m), 3.59-3.63 (2H, m), 4.24 (2H, d), 7.84 (1H, s). m/z: ES+ [M+H]+=443.

(12aR)-9-Bromo-10-chloro-1,2,3,4,12,12a-hexahydro-6H-pyrazino[2,1-c][1,4]benzoxazepine-8-carbonitrile

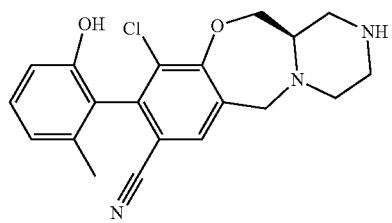

Tetrakis(triphenylphosphine)palladium(0) (2.084 g, 1.8 mmol) was added to dicyanozinc (1.271 g, 10.82 mmol), and (12aR)-9-bromo-10-chloro-8-iodo-1,2,3,4,12,12a-hexahydro-6H-pyrazino[2,1-c][1,4]benzoxazepine (4 g, 9.02 mmol) in DMF (40 mL). The resulting mixture was stirred at 100° C. for 5 h. The crude product was purified by C18-flash chromatography, elution gradient 5 to 80% MeOH in water (0.1% formic acid) to give (12aR)-9-bromo-10-chloro-1,2,3,4,12,12a-hexahydro-6H-pyrazino[2,1-c][1,4]benzoxazepine-8-carbonitrile (1.8 g, 51%) as a yellow solid. 1H NMR (300 MHz, DMSO, 30° C.) 2.27-2.46 (2H, m), 2.67-2.82 (3H, m), 2.74-2.99 (2H, m), 3.61-3.91 (3H, m), 4.41 (1H, dd), 7.87 (1H, s). m/z: ES+ [M+H]+=342.

(12aR)-10-Chloro-9-(2-methoxy-6-methyl phenyl)-1,2,3,4,12,12a-hexahydro-6H-pyrazino[2,1-c][1,4]benzoxazepine-8-carbonitrile.1TFA

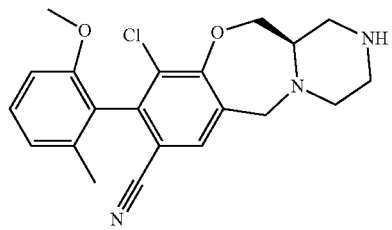 [SMILES: COc1cccc(C)c1-c1c(C#N)cc2c(c1Cl)OC[C@H]1CNCCN1C2]

RuPhos-Pd-G3 (0.387 g, 0.46 mmol) and RuPhos (0.216 g, 0.46 mmol) were added to (12aR)-9-bromo-10-chloro-1,2,3,4,12,12a-hexahydro-6H-pyrazino[2,1-c][1,4]benzoxazepine-8-carbonitrile (1.8 g, 4.63 mmol), (2-methoxy-6-methylphenyl)boronic acid (1.076 g, 6.48 mmol) and sodium carbonate (1.227 g, 11.58 mmol) in 1,4-dioxane (30 mL) and water (6 mL) (5:1 ratio) at rt. The resulting mixture was stirred at 80° C. for 2.5 h. The reaction mixture was concentrated and diluted with EtOAc (150 mL) and washed with water (50 mL×2). The organic layer was dried (Na₂SO₄) and evaporated to afford crude product. The crude product was purified by C18-flash chromatography, elution gradient 20 to 60% MeOH in water (0.1% TFA) to give (12aR)-10-chloro-9-(2-methoxy-6-methylphenyl)-1,2,3,4,12,12a-hexahydro-6H-pyrazino[2,1-c][1,4]benzoxazepine-8-carbonitrile.1TFA (1.55 g, 67%) as a yellow oil. 1H NMR (400 MHz, DMSO, 30° C.) 1.87-2.04 (3H, m), 2.60-3.12 (6H, m), 3.20-3.46 (2H, m), 3.69 (3H, s), 3.78-3.93 (1H, m), 3.98-4.28 (2H, m), 4.48-4.68 (1H, m), 6.82-6.96 (1H, m), 6.94-7.06 (1H, m), 7.26-7.41 (1H, m), 7.74-7.92 (1H, m). m/z: ES+ [M+H]+=384.

(12aR)-10-Chloro-9-(2-hydroxy-6-methylphenyl)-1,2,3,4,12,12a-hexahydro-6H-pyrazino[2,1-c][1,4]benzoxazepine-8-carbonitrile Rotational Isomer 1 and 2

1M Boron tribromide in DCM (15.60 mL, 15.60 mmol) was added to (12aR)-10-chloro-9-(2-methoxy-6-methylphenyl)-1,2,3,4,12,12a-hexahydro-6H-pyrazino[2,1-c][1,4]benzoxazepine-8-carbonitrile.1TFA (1.55 g, 3.12 mmol) in DCM (20 mL) at rt. The resulting mixture was stirred at 25° C. for 4 h. The reaction mixture was quenched with MeOH (20 ml) and evaporated to afford a yellow oil. This was purified by C18-flash chromatography, elution gradient 20 to 50% MeOH in water (0.1% NH₄OH) to give crude product as a yellow solid. This was purified by preparative chiral-HPLC (Column: CHIRALPAK IC, 2*25 cm, 5 μm), eluting with hexane (8 mmol/L NH₃·MeOH) and EtOH, to give rotational isomer 1 of (12aR)-10-chloro-9-(2-hydroxy-6-methylphenyl)-1,2,3,4,12,12a-hexahydro-6H-pyrazino[2,1-c][1,4]benzoxazepine-8-carbonitrile (210 mg, 35%) as a white solid. 1H NMR (400 MHz, DMSO, 30° C.) 1.90 (3H, s), 2.17-2.46 (2H, m), 2.61-3.01 (6H, m), 3.69-3.95 (3H, m), 4.40 (1H, d), 6.67-6.89 (2H, m), 7.01-7.28 (1H, m), 7.80 (1H, s), 8.25 (1H, s). m/z: ES+ [M+H]+=370. This was followed by rotational isomer 2 of (12aR)-10-chloro-9-(2-hydroxy-6-methylphenyl)-1,2,3,4,12,12a-hexahydro-6H-pyrazino[2,1-c][1,4]benzoxazepine-8-carbonitrile (240 mg, 40%) as a white solid. m/z: ES+ [M+H]+=370.

(12aR)-10-Chloro-9-(2-hydroxy-6-methylphenyl)-2-(prop-2-enoyl)-1,2,3,4,12,12a-hexahydro-6H-pyrazino[2,1-c][1,4]benzoxazepine-8-carbonitrile Rotational Isomer 1, Example 40

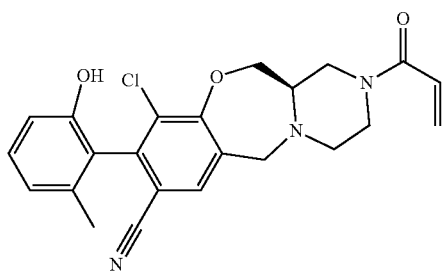 [SMILES: C=CC(=O)N1CCN2Cc3cc(C#N)c(-c4c(C)cccc4O)c(Cl)c3OC[C@H]2C1]

Acryloyl chloride (55.8 mg, 0.62 mmol) was added to rotational isomer 1 of (12aR)-10-chloro-9-(2-hydroxy-6-methylphenyl)-1,2,3,4,12,12a-hexahydro-6H-pyrazino[2,1-c][1,4]benzoxazepine-8-carbonitrile (240 mg, 0.65 mmol) and DIPEA (0.340 mL, 1.95 mmol) in DMF (5 mL). The resulting mixture was stirred at 25° C. for 4 h. The reaction mixture was purified by C18-flash chromatography, elution gradient 25 to 40% MeCN in water (0.1% formic acid) to give rotational isomer 1 of (12aR)-10-chloro-9-(2-hydroxy-6-methylphenyl)-2-(prop-2-enoyl)-1,2,3,4,12,12a-hexahydro-6H-pyrazino[2,1-c][1,4]benzoxazepine-8-carbonitrile (150 mg, 55%) as a white solid. 1H NMR (400 MHz, DMSO, 30° C.) 1.93 (3H, s), 2.45-2.51 (1H, m), 2.73-2.78 (1H, m), 2.84-2.89 (2H, m), 3.05-3.13 (1H, m), 3.83-3.88 (4H, m), 4.06-4.10 (1H, m), 4.48-4.52 (1H, m), 5.71 (1H, d), 6.13 (1H, d), 6.75-6.82 (3H, m), 7.12-7.20 (1H, m), 7.81 (1H, s), 9.50 (1H, s). m/z: ES+ [M+H]+=424.

(12aR)-10-Chloro-9-(2-hydroxy-6-methylphenyl)-2-(prop-2-enoyl)-1,2,3,4,12,12a-hexahydro-6H-pyrazino[2,1-c][1,4]benzoxazepine-8-carbonitrile Rotational Isomer 2, Example 41

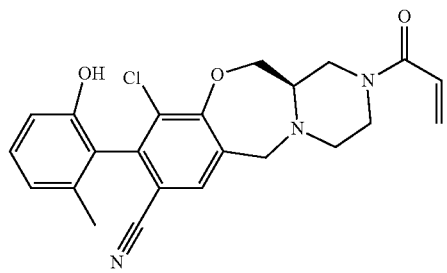 [SMILES: C=CC(=O)N1CCN2Cc3cc(C#N)c(-c4c(C)cccc4O)c(Cl)c3OC[C@H]2C1]

Acryloyl chloride (48.8 mg, 0.54 mmol) was added to rotational isomer 2 of (12aR)-10-chloro-9-(2-hydroxy-6-methylphenyl)-1,2,3,4,12,12a-hexahydro-6H-pyrazino[2,1-c][1,4]benzoxazepine-8-carbonitrile (210 mg, 0.57 mmol) and DIPEA (0.298 mL, 1.70 mmol) in DMF (5 mL). The resulting mixture was stirred at 25° C. for 4 h. The reaction mixture was purified by C18-flash chromatography, elution gradient 25 to 40% MeCN in water (0.1% formic acid) to give rotational isomer 2 of (12aR)-10-chloro-9-(2-hydroxy-6-methylphenyl)-2-(prop-2-enoyl)-1,2,3,4,12,12a-hexahydro-6H-pyrazino[2,1-c][1,4]benzoxazepine-8-carbonitrile (121 mg, 50%) as a white solid. 1H NMR (400 MHz, DMSO, 30° C.) 1.90 (3H, s), 2.41-2.45 (1H, m), 2.73-2.77 (1H, m), 2.83-2.90 (2H, m), 3-3.25 (1H, m), 3.79-4.01 (4H, m), 4.05-4.13 (1H, m), 4.52 (1H, t), 5.71 (1H, d), 6.13 (1H, d), 6.76-6.87 (3H, m), 7.12-7.20 (1H, m), 7.81 (1H, s), 9.50 (1H, s). m/z: ES+ [M+H]+=424.

Methyl 4-amino-2,3,5-trifluorobenzoate

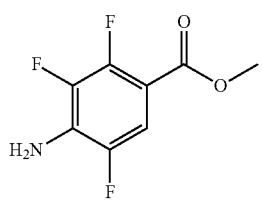

DIPEA (17.05 mL, 97.61 mmol) and methyl 4-amino-2,3,5,6-tetrafluorobenzoate (6.6 g, 29.58 mmol) were added to a solution of tris(2-phenylpyridine)iridium(III) (300 mL, 0.15 mmol) in MeCN (300 mL). The reaction was heated to 45° C. and illuminated with blue LED light for 7 days. The solvent was removed under reduced pressure. The crude product obtained was purified by flash silica chromatography, elution gradient 0 to 8% EtOAc in petroleum ether to give methyl 4-amino-2,3,5-trifluorobenzoate (5.54 g, 91%) as a pale yellow solid. 1H NMR (400 MHz, CDCl₃, 30° C.) 3.91 (3H, s), 4.29 (2H, s), 7.45 (1H, ddd). m/z: ES+ [M+H]+=206.

4-Amino-2,3,5-trifluorobenzoic acid

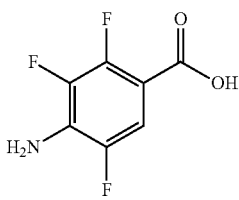 [SMILES: Nc1c(F)cc(C(=O)O)c(F)c1F]

2M sodium-hydroxide (40.2 mL, 80.43 mmol) was added to methyl 4-amino-2,3,5-trifluorobenzoate (5.5 g, 26.81 mmol) in THF (25 mL) and MeOH (25 mL) (1:1 ratio). The resulting solution was stirred at rt for 2 h. The reaction mixture pH was adjusted to pH 5 with 2M HCl. The aqueous layer was extracted with EtOAc (100 mL×3). The solvent was removed under reduced pressure to afford 4-amino-2,3,5-trifluorobenzoic acid (5 g, 98%) as a yellow solid. 1H NMR (400 MHz, DMSO, 30° C.) 6.44 (2H, s), 7.26-7.36 (1H, m), 12.91 (1H, s).

4-Bromo-2,3,5-trifluorobenzoic acid

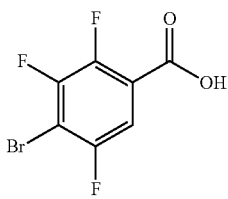

Tert-butyl nitrite (1.295 g, 12.56 mmol) was added to 4-amino-2,3,5-trifluorobenzoic acid (1.6 g, 8.37 mmol) and copper(II) bromide (2.80 g, 12.56 mmol) in MeCN (32 mL) at 0° C. The resulting mixture was stirred at rt for 1 h. The reaction mixture was diluted with EtOAc (150 mL) and washed with 2M HCl (100 mL×2). The organic layer was dried (Na$_2$SO$_4$) and evaporated to afford 4-bromo-2,3,5-trifluorobenzoic acid (2.05 g, 96%) as a yellow solid. 1H NMR (400 MHz, DMSO, 30° C.) 7.63-7.69 (1H, m), 14.03 (1H, s). m/z: ES− [M+H]−=253.

Tert-butyl (3R)-4-(4-bromo-2,3,5-trifluorobenzoyl)-3-(hydroxymethyl)piperazine-1-carboxylate

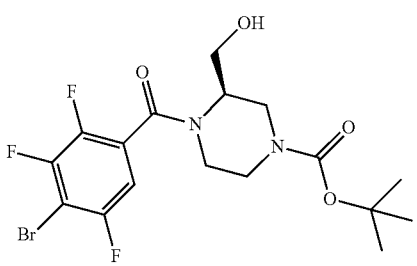 [SMILES: CC(C)(C)OC(=O)N1CCN(C(=O)c2cc(F)c(Br)c(F)c2F)[C@@H](CO)C1]

DIPEA (2.74 mL, 15.69 mmol) was added to 4-bromo-2,3,5-trifluorobenzoic acid (2 g, 7.84 mmol), tert-butyl (3R)-3-(hydroxymethyl)piperazine-1-carboxylate (1.696 g, 7.84 mmol) and HATU (4.47 g, 11.77 mmol) in DMF (40 mL) at 0° C. The resulting solution was stirred at rt for 2 h. The reaction mixture was diluted with EtOAc (150 mL) and washed with water (150 mL) and brine (100 mL×3). The organic layer was dried (Na$_2$SO$_4$) and evaporated to afford crude product. This was purified by C18-flash chromatography, elution gradient 0 to 30% EtOAc in petroleum ether to give tert-butyl (3R)-4-(4-bromo-2,3,5-trifluorobenzoyl)-3-(hydroxymethyl)piperazine-1-carboxylate (2.47 g, 70%) as a white solid. 1H NMR (400 MHz, DMSO, 30° C.) 1.40 (9H, d), 2.72-3.22 (3H, m), 3.30-3.63 (2H, m), 3.68-3.90 (1H, m), 3.91-4.14 (1H, m), 4.20-4.30 (1H, m), 4.43-4.54 (1H, m), 4.83-4.89 (1H, m), 7.32-7.50 (1H, m). m/z: ES+ [M+H]+=453.

Tert-butyl (12aR)-9-bromo-8,10-difluoro-6-oxo-3,4,12,12a-tetrahydro-6H-pyrazino[2,1-c][1,4]benzoxazepine-2(1H)-carboxylate

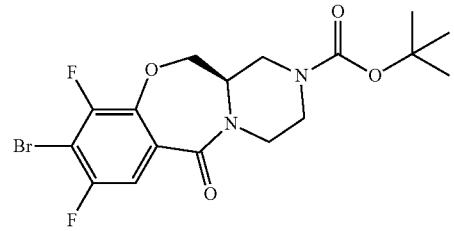 [SMILES: CC(C)(C)OC(=O)N1CCN2C(=O)c3cc(F)c(Br)c(F)c3OC[C@H]2C1]

Sodium hydride (0.635 g, 15.89 mmol) was added to tert-butyl (3R)-4-(4-bromo-2,3,5-trifluorobenzoyl)-3-(hydroxymethyl)piperazine-1-carboxylate (2.4 g, 5.3 mmol) in DMF (48 mL) at 0° C. The resulting mixture was stirred at 0° C. for 1 h. The reaction mixture was diluted with water and EtOAc (150 mL). The organic layer was washed with water (150 mL×2) and brine (150 mL×2) then dried (Na$_2$SO$_4$) and evaporated to afford crude product. The crude product was purified by flash silica chromatography, elution gradient 0 to 30% EtOAc in petroleum ether to give tert-butyl (12aR)-9-bromo-8,10-difluoro-6-oxo-3,4,12,12a-tetrahydro-6H-pyrazino[2,1-c][1,4]benzoxazepine-2(1H)-carboxylate (1.85 g, 81%) as a white solid. 1H NMR (400 MHz, DMSO, 30° C.) 1.41 (9H, s), 3.39-3.56 (3H, m), 3.57-3.70 (1H, m), 3.70-3.81 (1H, m), 3.85-3.94 (1H, m), 3.95-4.08 (1H, m), 4.28-4.38 (2H, m), 7.48 (1H, dd). m/z: ES+ [M+H]+=433.

Tert-butyl (12aR)-9-bromo-8,10-difluoro-3,4,12,12a-tetrahydro-6H-pyrazino[2,1-c][1,4]benzoxazepine-2(1H)-carboxylate

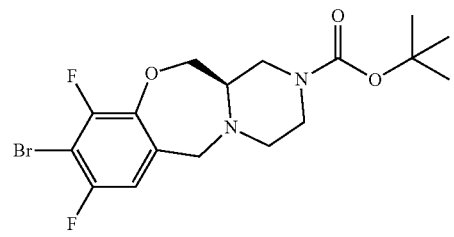 [SMILES: CC(C)(C)OC(=O)N1CCN2Cc3cc(F)c(Br)c(F)c3OC[C@H]2C1]

1M Borane-THF complex solution in THF (18 mL, 18 mmol) was added to tert-butyl (12aR)-9-bromo-8,10-difluoro-6-oxo-3,4,12,12a-tetrahydro-6H-pyrazino[2,1-c][1,4]

benzoxazepine-2(1H)-carboxylate (1.8 g, 4.15 mmol) in THF (18 mL). The resulting mixture was stirred at 60° C. for 1 h. The reaction mixture was diluted with 2M HCl and EtOAc (100 mL). The organic layer was washed sequentially with water (100 mL×2) and brine (100 mL×2) then dried (Na₂SO₄) and evaporated to afford tert-butyl (12aR)-9-bromo-8,10-difluoro-3,4,12,12a-tetrahydro-6H-pyrazino[2,1-c][1,4]benzoxazepine-2(1H)-carboxylate (1.5 g, 86%) as a white solid. 1H NMR (400 MHz, DMSO, 30° C.) 1.39 (9H, s), 2.26-2.38 (1H, m), 2.63-3 (3H, m), 3.07-3.19 (1H, m), 3.44-3.59 (2H, m), 3.61-3.90 (3H, m), 4.30 (1H, d), 7.23 (1H, dd). m/z: ES+ [M+H]+=419.

Tert-butyl (12aR)-9-(2-chloro-6-hydroxyphenyl)-8,10-difluoro-3,4,12,12a-tetrahydro-6H-pyrazino[2,1-c][1,4]benzoxazepine-2(1H)-carboxylate

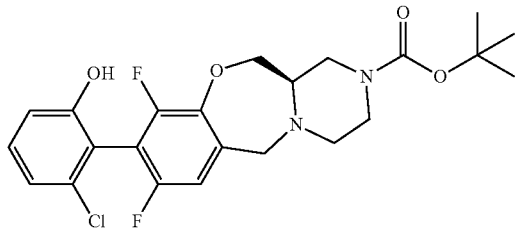 [SMILES: CC(C)(C)OC(=O)N1CCN2Cc3cc(F)c(-c4c(O)cccc4Cl)c(F)c3OC[C@H]2C1]

Tert-butyl (12aR)-9-bromo-8,10-difluoro-3,4,12,12a-tetrahydro-6H-pyrazino[2,1-c][1,4]benzoxazepine-2(1H)-carboxylate (1300 mg, 3.1 mmol), (2-chloro-6-hydroxyphenyl)boronic acid (1603 mg, 9.3 mmol), RuPhos (145 mg, 0.31 mmol), RuPhos-Pd-G3 (259 mg, 0.31 mmol) and K₂CO₃ (1286 mg, 9.3 mmol) in 1,4-dioxane (25.0 mL) and water (5 mL) (5:1 ratio) was stirred at 100° C. for 1 h. The reaction mixture was concentrated and diluted with EtOAc (150 mL) then washed sequentially with water (100 mL×2) and brine (100 mL). The organic layer was dried (Na₂SO₄) and evaporated to afford crude product. This was purified by C18-flash chromatography, elution gradient 0 to 40% MeCN in water (0.1% formic acid) to give tert-butyl (12aR)-9-(2-chloro-6-hydroxyphenyl)-8,10-difluoro-3,4,12,12a-tetrahydro-6H-pyrazino[2,1-c][1,4]benzoxazepine-2(1H)-carboxylate (1300 mg, 90%) as a yellow solid. 1H NMR (400 MHz, DMSO, 30° C.) 1.40 (9H, s), 2.30-2.40 (1H, m), 2.65-2.92 (3H, m), 3.02-3.17 (1H, m), 3.54-3.76 (4H, m), 3.84-3.95 (1H, m), 4.26-4.36 (1H, m), 6.90-6.95 (1H, m), 7-7.04 (1H, m), 7.08 (1H, dd), 7.28 (1H, t), 10.14 (1H, s). m/z: ES+ [M+H]+=467.

3-Chloro-2-[(12aR)-8,10-difluoro-1,2,3,4,12,12a-hexahydro-6H-pyrazino[2,1-c][1,4]benzoxazepin-9-yl]phenol Rotational Isomer 1 and 2

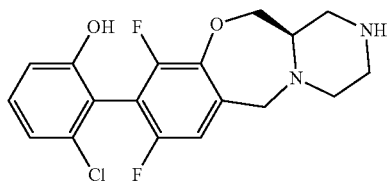 [SMILES: Oc1cccc(Cl)c1-c1c(F)cc2c(c1F)OC[C@H]1CNCCN1C2]

TFA (5 mL, 64.90 mmol) was added to tert-butyl (12aR)-9-(2-chloro-6-hydroxyphenyl)-8,10-difluoro-3,4,12,12a-tetrahydro-6H-pyrazino[2,1-c][1,4]benzoxazepine-2(1H)-carboxylate (1250 mg, 2.68 mmol) in DCM (25 mL). The resulting mixture was stirred at rt for 2 h. The solvent was removed under reduced pressure. The residue obtained was purified by C18-flash chromatography, elution gradient 0 to 35% MeCN in water (0.1% TFA) to give a TFA salt, and further purified by SCX (7M NH₃/MeOH) to afford a yellow solid. This was purified by C18-flash chromatography, elution gradient 0 to 40% MeCN in water (0.1% TFA). The first eluted rotational isomer was purified by SCX (7M NH₃/MeOH) to afford rotational isomer 1 of 3-chloro-2-[(12aR)-8,10-difluoro-1,2,3,4,12,12a-hexahydro-6H-pyrazino[2,1-c][1,4]benzoxazepin-9-yl]phenol (360 mg, 38%) as a yellow solid. 1H NMR (400 MHz, DMSO, 30° C.) 2.58-2.73 (1H, m), 2.78-2.88 (1H, m), 2.92-3.07 (3H, m), 3.15-3.37 (2H, m), 3.73-3.85 (2H, m), 3.98 (1H, d), 4.36 (1H, dd), 6.91-6.96 (1H, m), 7.01-7.04 (1H, m), 7.09 (1H, dd), 7.29 (1H, t), 10.20 (1H, s). m/z: ES+ [M+H]+=367. The second eluted rotational isomer was purified by SCX (7M NH₃/MeOH) to afford rotational isomer 2 of 3-chloro-2-[(12aR)-8,10-difluoro-1,2,3,4,12,12a-hexahydro-6H-pyrazino[2,1-c][1,4]benzoxazepin-9-yl]phenol (320 mg, 34%) as a yellow solid. 1H NMR (400 MHz, DMSO, 30° C.) 2.63-2.73 (1H, m), 2.74-2.87 (1H, m), 2.95-3.07 (3H, m), 3.19-3.34 (2H, m), 3.71-3.84 (2H, m), 3.99 (1H, d), 4.37 (1H, dd), 6.94 (1H, dd), 7.02 (1H, dd), 7.09 (1H, dd), 7.29 (1H, t), 10.19 (1H, s). m/z: ES+ [M+H]+=367.

1-[(12aR)-9-(2-Chloro-6-hydroxyphenyl)-8,10-difluoro-3,4,12,12a-tetrahydro-6H-pyrazino[2,1-c][1,4]benzoxazepin-2(1H)-yl]prop-2-en-1-one Rotational Isomer 1, Example 42

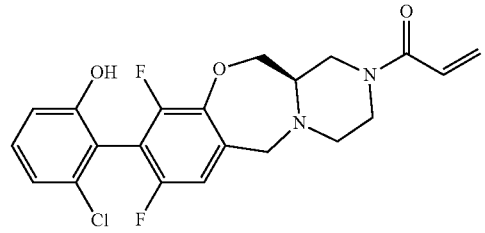 [SMILES: C=CC(=O)N1CCN2Cc3cc(F)c(-c4c(O)cccc4Cl)c(F)c3OC[C@H]2C1]

Acryloyl chloride (0.079 mL, 0.97 mmol) was added dropwise to rotational isomer 1 of 3-chloro-2-[(12aR)-8,10-difluoro-1,2,3,4,12,12a-hexahydro-6H-pyrazino[2,1-c][1,4]benzoxazepin-9-yl]phenol (340 mg, 0.93 mmol) and DIPEA (0.486 mL, 2.78 mmol) in DMF (8 mL) at 0° C. The resulting mixture was stirred at 0° C. for 1 h. The reaction mixture was purified by C18-flash chromatography, elution gradient 0 to 42% MeCN in water (0.1% formic acid) to give rotational isomer 1 of 1-[(12aR)-9-(2-chloro-6-hydroxyphenyl)-8,10-difluoro-3,4,12,12a-tetrahydro-6H-pyrazino[2,1-c][1,4]benzoxazepin-2(1H)-yl]prop-2-en-1-one (220 mg, 56%) as a white solid. 1H NMR (400 MHz, DMSO, 30° C.) 2.31-2.46 (1H, m), 2.70-2.93 (3H, m), 3-3.20 (1H, m), 3.59-3.78 (2H, m), 3.80-4.08 (3H, m), 4.29-4.45 (1H, m), 5.65-5.73 (1H, m), 6.12 (1H, d), 6.76-6.88 (1H, m), 6.92 (1H, dd), 7.02 (1H, dd), 7.08 (1H, dd), 7.28 (1H, t), 10.14 (1H, s). m/z: ES+ [M+H]+=421.

1-[(12aR)-9-(2-Chloro-6-hydroxyphenyl)-8,10-difluoro-3,4,12,12a-tetrahydro-6H-pyrazino[2,1-c][1,4]benzoxazepin-2(1H)-yl]prop-2-en-1-one Rotational Isomer 2, Example 43

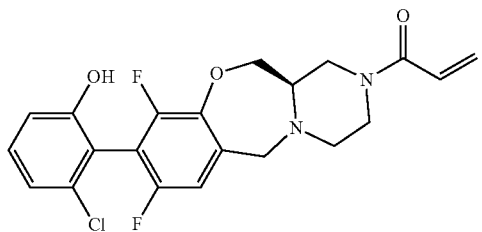 [SMILES: C=CC(=O)N1CCN2Cc3cc(F)c(-c4c(O)cccc4Cl)c(F)c3OC[C@H]2C1]

Acryloyl chloride (0.070 mL, 0.86 mmol) was added dropwise to rotational isomer 2 of 3-chloro-2-[(12aR)-8,10-difluoro-1,2,3,4,12,12a-hexahydro-6H-pyrazino[2,1-c][1,4]benzoxazepin-9-yl]phenol (300 mg, 0.82 mmol) and DIPEA (0.429 mL, 2.45 mmol) in DMF (8 mL) at 0° C. The resulting mixture was stirred at 0° C. for 1 h. The reaction mixture was purified by C18-flash chromatography, elution gradient 0 to 42% MeCN in water (0.1% formic acid) to give the rotational isomer 2 of 1-[(12aR)-9-(2-chloro-6-hydroxyphenyl)-8,10-difluoro-3,4,12,12a-tetrahydro-6H-pyrazino[2,1-c][1,4]benzoxazepin-2(1H)-yl]prop-2-en-1-one (210 mg, 61%) as a white solid. 1H NMR (400 MHz, DMSO, 30° C.) 2.29-2.46 (1H, m), 2.67-2.97 (3H, m), 3.02-3.19 (1H, m), 3.59-3.78 (2H, m), 3.79-4.07 (3H, m), 4.29-4.42 (1H, m), 5.64-5.74 (1H, m), 6.13 (1H, d), 6.74-6.87 (1H, m), 6.93 (1H, dd), 7.02 (1H, dd), 7.08 (1H, dd), 7.28 (1H, t), 10.14 (1H, s). m/z: ES+ [M+H]+=421.

Tert-butyl (12aR)-8,10-difluoro-9-(2-methoxy-6-methylphenyl)-3,4,12,12a-tetrahydro-6H-pyrazino[2,1-c][1,4]benzoxazepine-2(1H)-carboxylate

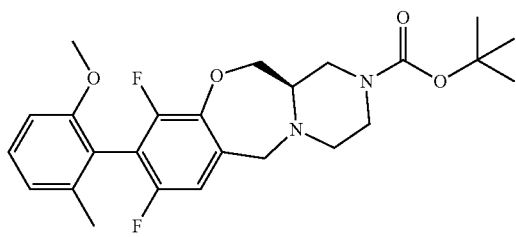 [SMILES: COc1cccc(C)c1-c1c(F)cc2c(c1F)OC[C@H]1CN(C(=O)OC(C)(C)C)CCN1C2]

Tert-butyl (12aR)-9-bromo-8,10-difluoro-3,4,12,12a-tetrahydro-6H-pyrazino[2,1-c][1,4]benzoxazepine-2(1H)-carboxylate (140 mg, 0.33 mmol), (2-methoxy-6-methylphenyl)boronic acid (83 mg, 0.5 mmol), RuPhos (15.58 mg, 0.03 mmol), RuPhos-Pd-G3 (27.9 mg, 0.03 mmol) and K2CO3 (138 mg, 1 mmol) in 1,4-dioxane (12.0 mL) and water (3.0 mL) (4:1 ratio) was stirred at 100° C. for 1 h. The reaction mixture was diluted with EtOAc (100 mL) and washed with water (50 mL). The organic layer was dried (Na2SO4) and evaporated to afford crude product. This was purified by flash silica chromatography, elution gradient 40 to 60% EtOAc in petroleum ether, to give tert-butyl (12aR)-8,10-difluoro-9-(2-methoxy-6-methylphenyl)-3,4,12,12a-tetrahydro-6H-pyrazino[2,1-c][1,4]benzoxazepine-2(1H)-carboxylate (165 mg, >100%) as a white solid that was used without further purification. 1H NMR (400 MHz, CDCl3, 30° C.) 1.49 (9H, s), 2.12 (3H, d), 2.45-2.54 (1H, m), 2.75-3.18 (5H, m), 3.23-3.42 (1H, m), 3.75-3.91 (5H, m), 4.02-4.10 (1H, m), 4.21-4.39 (1H, m), 6.75-6.87 (2H, m), 6.93 (1H, dd), 7.31 (1H, t). m/z: ES+ [M+H]+=461.

2-[(12aR)-8,10-Difluoro-1,2,3,4,12,12a-hexahydro-6H-pyrazino[2,1-c][1,4]benzoxazepin-9-yl]-3-methylphenol

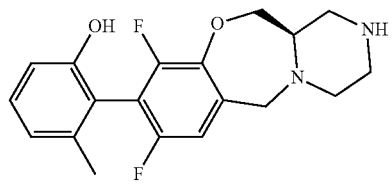 [SMILES: Cc1cccc(O)c1-c1c(F)cc2c(c1F)OC[C@H]1CNCCN1C2]

1M Boron tribromide in DCM (4 mL, 4 mmol) was added to tert-butyl (12aR)-8,10-difluoro-9-(2-methoxy-6-methylphenyl)-3,4,12,12a-tetrahydro-6H-pyrazino[2,1-c][1,4]benzoxazepine-2(1H)-carboxylate (150 mg, 0.33 mmol) in DCM (4 mL). The resulting mixture was stirred at rt for 1 h. The reaction mixture was quenched with MeOH and the solvent removed under reduced pressure. The crude product obtained was purified by C18-flash chromatography, elution gradient 5 to 35% MeCN in water (0.05% TFA) to give a TFA salt which was purified by SCX (7M NH3/MeOH) to afford 2-[(12aR)-8,10-difluoro-1,2,3,4,12,12a-hexahydro-6H-pyrazino[2,1-c][1,4]benzoxazepin-9-yl]-3-methylphenol (119 mg, >100%) as a pale yellow solid that was used without further purification. 1H NMR (300 MHz, CD3OD, 30° C.) 2.04 (3H, d), 2.72-2.85 (1H, m), 2.85-2.96 (1H, m), 3.04-3.16 (2H, m), 3.20 (1H, dd), 3.42 (1H, d), 3.73-3.86 (3H, m), 4.07 (1H, d), 4.36-4.46 (1H, m), 6.74 (1H, d), 6.80 (1H, d), 6.93 (1H, d), 7.14 (1H, t). m/z: ES+ [M+H]+=347.

1-[(12aR)-8,10-Difluoro-9-(2-hydroxy-6-methylphenyl)-3,4,12,12a-tetrahydro-6H-pyrazino[2,1-c][1,4]benzoxazepin-2(1H)-yl]prop-2-en-1-one Rotational Isomer 1, Example 44 and Rotational Isomer 2, Example 45

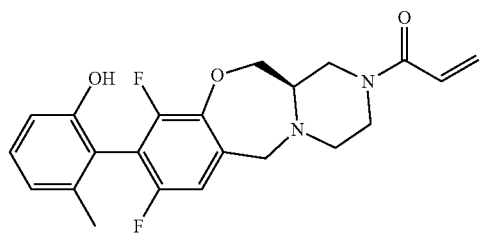 [SMILES: C=CC(=O)N1CCN2Cc3cc(F)c(-c4c(C)cccc4O)c(F)c3OC[C@H]2C1]

A solution of acryloyl chloride (31.1 mg, 0.34 mmol) in DMF (2.5 mL) was added dropwise to a stirred solution of 2-[(12aR)-8,10-difluoro-1,2,3,4,12,12a-hexahydro-6H-pyrazino[2,1-c][1,4]benzoxazepin-9-yl]-3-methylphenol (119 mg, 0.34 mmol) and triethylamine (0.096 mL, 0.69 mmol) in DMF (5 mL) at −10° C. The resulting solution was stirred at −10° C. for 30 min. The reaction mixture was purified by C18-flash chromatography directly, elution gradient 0 to 37% MeCN in water (0.1% formic acid) to give crude product. The crude product was separated by preparative HPLC (Column: Xselect CSH OBD Column 30*150 mm 5 µm), eluting with water and MeCN, to give rotational isomer 1 of 1-[(12aR)-8,10-difluoro-9-(2-hydroxy-6-methylphenyl)-3,4,12,12a-tetrahydro-6H-pyrazino[2,1-c][1,4]benzoxazepin-2(1H)-yl]prop-2-en-1-one (41 mg, 30%) as a white solid. 1H NMR (300 MHz, CD₃OD, 30° C.) 2.06 (3H, s), 2.45-2.66 (1H, m), 2.83-3.62 (4H, m), 3.65-3.84 (2H, m), 3.88-4.31 (3H, m), 4.28-4.46 (1H, m), 5.79 (1H, d), 6.25 (1H, d), 6.74-6.88 (3H, m), 6.94 (1H, d), 7.14 (1H, t). m/z: ES+ [M+H]+=402. This was followed by rotational isomer 2 of 1-[(12aR)-8,10-difluoro-9-(2-hydroxy-6-methylphenyl)-3,4,12,12a-tetrahydro-6H-pyrazino[2,1-c][1,4]benzoxazepin-2(1H)-yl]prop-2-en-1-one (36 mg, 25%) as a white solid. 1H NMR (300 MHz, CD₃OD, 30° C.) 2.06 (3H, s), 2.44-2.64 (1H, m), 2.87-3.10 (2H, m), 3.10-3.30 (1H, m), 3.51-3.65 (1H, m), 3.68-3.96 (3H, m), 3.95-4.20 (2H, m), 4.26-4.42 (1H, m), 5.78 (1H, d), 6.24 (1H, d), 6.74-6.88 (3H, m), 6.94 (1H, d), 7.14 (1H, t). m/z: ES+ [M+H]+=402.

Tert-butyl (12aR)-8,10-difluoro-9-[2-fluoro-6-(hydroxymethyl)phenyl]-3,4,12,12a-tetrahydro-6H-pyrazino[2,1-c][1,4]benzoxazepine-2(1H)-carboxylate

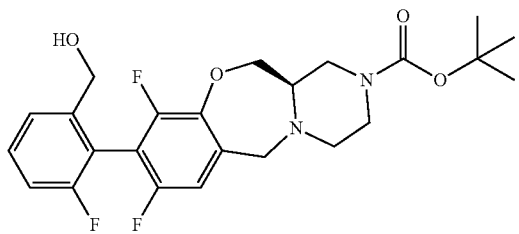 [SMILES: CC(C)(C)OC(=O)N1CCN2Cc3cc(F)c(-c4c(F)cccc4CO)c(F)c3OC[C@H]2C1]

Tert-butyl (12aR)-9-bromo-8,10-difluoro-3,4,12,12a-tetrahydro-6H-pyrazino[2,1-c][1,4]benzoxazepine-2(1H)-carboxylate (140 mg, 0.33 mmol), [2-fluoro-6-(hydroxymethyl)phenyl]boronic acid (85 mg, 0.5 mmol), RuPhos (15.58 mg, 0.03 mmol), RuPhos-Pd-G3 (27.9 mg, 0.03 mmol) and K₂CO₃ (138 mg, 1 mmol) in) in 1,4-dioxane (12 mL) and water (3 mL) (4:1 ratio) was stirred at 100° C. for 1 h. The reaction mixture was diluted with EtOAc (100 mL) and washed with water (50 mL). The organic layer was dried (Na₂SO₄) and evaporated to afford crude product. This was purified by flash silica chromatography, elution gradient 40 to 60% EtOAc in petroleum ether, to give tert-butyl (12aR)-8,10-difluoro-9-[2-fluoro-6-(hydroxymethyl)phenyl]-3,4,12,12a-tetrahydro-6H-pyrazino[2,1-c][1,4]benzoxazepine-2(1H)-carboxylate (174 mg, >100%) as a white solid that was used without further purification. m/z: ES+ [M+H]+=465.

{2-[(12aR)-8,10-Difluoro-1,2,3,4,12,12a-hexahydro-6H-pyrazino[2,1-c][1,4]benzoxazepin-9-yl]-3-fluorophenyl}methanol.2TFA

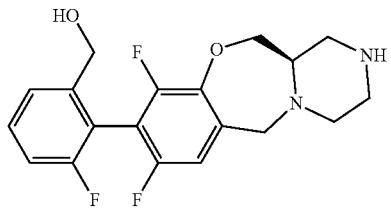 [SMILES: OCc1cccc(F)c1-c1c(F)cc2c(c1F)OC[C@H]1CNCCN1C2]

TFA (2 mL, 25.96 mmol) was added to tert-butyl (12aR)-8,10-difluoro-9-[2-fluoro-6-(hydroxymethyl)phenyl]-3,4,12,12a-tetrahydro-6H-pyrazino[2,1-c][1,4]benzoxazepine-2(1H)-carboxylate (174 mg, 0.37 mmol) in DCM (10 mL). The resulting solution was stirred at rt overnight. The solvent was removed under reduced pressure. The residue was dissolved in MeOH (10 mL) and K₂CO₃ (155 mg, 1.12 mmol) added. The resulting mixture was stirred at 60° C. for 1 h. The solvent was removed under reduced pressure. The crude product obtained was purified by C18-flash chromatography, elution gradient 5 to 33% MeCN in water (0.05% TFA) to give {2-[(12aR)-8,10-difluoro-1,2,3,4,12,12a-hexahydro-6H-pyrazino[2,1-c][1,4]benzoxazepin-9-yl]-3-fluorophenyl}methanol. 2TFA (119 mg, 54%) as a yellow solid. 1H NMR (300 MHz, DMSO, 30° C.) 2.61-2.89 (2H, m), 2.90-3.09 (3H, m), 3.20-3.35 (2H, m), 3.75-3.90 (3H, m), 3.99 (1H, d), 4.22-4.28 (2H, m), 4.39 (1H, d), 7.13-7.32 (2H, m), 7.42-7.62 (2H, m). m/z: ES+ [M+H]+=365.

1-[(12aR)-8,10-Difluoro-9-[2-fluoro-6-(hydroxymethyl)phenyl]-3,4,12,12a-tetrahydro-6H-pyrazino[2,1-c][1,4]benzoxazepin-2(1H)-yl]prop-2-en-1-one Rotational Isomer 1, Example 46 and Rotational Isomer 2, Example 47

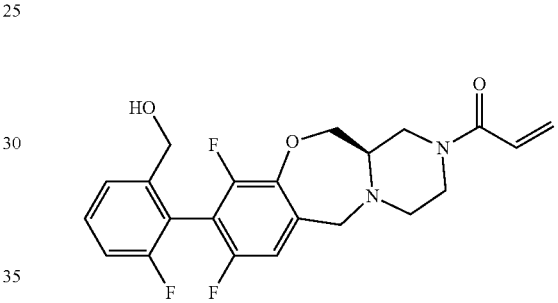

A solution of acryloyl chloride (18 mg, 0.2 mmol) in DMF (2.5 mL) was added dropwise to a stirred solution of {2-[(12aR)-8,10-difluoro-1,2,3,4,12,12a-hexahydro-6H-pyrazino[2,1-c][1,4]benzoxazepin-9-yl]-3-fluorophenyl}methanol.2TFA (119 mg, 0.20 mmol) and triethylamine (0.112 mL, 0.8 mmol) in DMF (5 mL) at −10° C. The resulting solution was stirred at −10° C. for 30 min. The reaction mixture was purified by C18-flash chromatography, elution gradient 0 to 37% MeCN in water (0.1% formic acid) to give a mixture of 2 rotational isomers. This mixture was separated by preparative HPLC (Column: SunFire C18 OBD Prep Column, 100 Å, 5 µm, 19 mm×250 mm), eluting with water (0.1% formic acid) and MeCN, to give rotational isomer 1 of 1-[(12aR)-8,10-difluoro-9-[2-fluoro-6-(hydroxymethyl)phenyl]-3,4,12,12a-tetrahydro-6H-pyrazino[2,1-c][1,4]benzoxazepin-2(1H)-yl]prop-2-en-1-one (22 mg, 26%) as a white solid. 1H NMR (300 MHz, CD₃OD, 30° C.) 2.48-2.64 (1H, m), 2.89-3.05 (2H, m), 3.07-3.31 (1H, m), 3.49-3.62 (1H, m), 3.71-3.83 (2H, m), 3.87-4 (1H, m), 3.99-4.24 (2H, m), 4.32-4.45 (3H, m), 5.78 (1H, d), 6.25 (1H, d), 6.75-6.86 (1H, m), 7.03 (1H, d), 7.12-7.18 (1H, m), 7.43-7.57 (2H, m). m/z: ES+ [M+H]+= 419. This was followed by rotational isomer 2 of 1-[(12aR)-8,10-difluoro-9-[2-fluoro-6-(hydroxymethyl)phenyl]-3,4,12,12a-tetrahydro-6H-pyrazino[2,1-c][1,4]benzoxazepin-2(1H)-yl]prop-2-en-1-one (25 mg, 30%) as a white solid. 1H NMR (300 MHz, CD₃OD, 30° C.) 1.64-1.84 (1H, m), 2.02-2.23 (2H, m), 2.23-2.46 (1H, m), 2.62-2.83 (1H, m), 2.86-3.05 (2H, m), 3.05-3.18 (2H, m), 3.17-3.43 (2H, m), 3.46-3.70 (3H, m), 4.89-5.05 (1H, m), 5.44 (1H, d), 5.90-6.07 (1H, m), 6.12-6.27 (1H, m), 6.25-6.39 (1H, m), 6.58-6.78 (2H, m). m/z: ES+ [M+H]+=419.

2-[2-Methoxy-6-(trifluoromethyl)phenyl]-4,4,5,5-tetramethyl-1,3,2-dioxaborolane

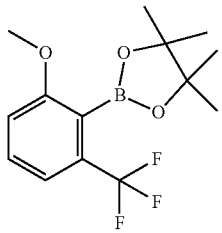 [SMILES: COc1cccc(C(F)(F)F)c1B1OC(C)(C)C(C)(C)O1]

2.5M n-Butyllithium in hexanes (2.447 mL, 6.12 mmol) was added to 2-bromo-1-methoxy-3-(trifluoromethyl)benzene (1.3 g, 5.10 mmol) in THF (20 mL) at −78° C. The resulting mixture was stirred at −78° C. for 1 h, 4,4,5,5-tetramethyl-2-[(propan-2-yl)oxy]-1,3,2-dioxaborolane (1.768 mL, 8.67 mmol) was added and the reaction mixture stirred at rt for 16 h. The reaction mixture was diluted with EtOAc (20 mL) and washed with brine (20 mL×3). The organic layer was dried (Na₂SO₄) and evaporated to afford crude product. The crude product was purified by flash silica chromatography, elution gradient 0 to 10% EtOAc in petroleum ether to give 2-[2-methoxy-6-(trifluoromethyl)phenyl]-4,4,5,5-tetramethyl-1,3,2-dioxaborolane (0.89 g, 58%) as a white solid. 1H NMR (400 MHz, DMSO, 30° C.) 1.29 (12H, s), 3.79 (3H, s), 7.21-7.29 (2H, m), 7.54-7.60 (1H, m).

Tert-butyl (12aR)-8,10-difluoro-9-[2-methoxy-6-(trifluoromethyl)phenyl]-3,4,12,12a-tetrahydro-6H-pyrazino[2,1-c][1,4]benzoxazepine-2(1H)-carboxylate

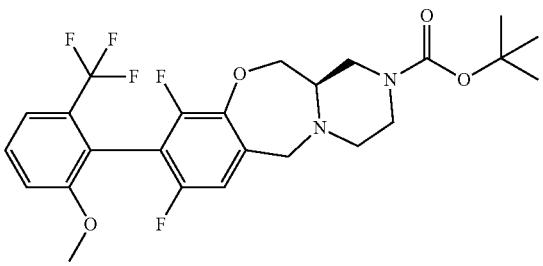 [SMILES: COc1cccc(C(F)(F)F)c1-c1c(F)cc2c(c1F)OC[C@H]1CN(C(=O)OC(C)(C)C)CCN1C2]

RuPhos-Pd-G3 (40 mg, 0.05 mmol) and RuPhos (22 mg, 0.05 mmol) were added to tert-butyl (12aR)-9-bromo-8,10-difluoro-3,4,12,12a-tetrahydro-6H-pyrazino[2,1-c][1,4]benzoxazepine-2(1H)-carboxylate (200 mg, 0.48 mmol), 2-[2-methoxy-6-(trifluoromethyl)phenyl]-4,4,5,5-tetramethyl-1,3,2-dioxaborolane (576 mg, 1.91 mmol) and K₂CO₃ (198 mg, 1.43 mmol) in 1,4-dioxane (5 mL) and water (1 mL) (5:1 ratio). The resulting mixture was stirred at 100° C. for 1 h then the solvent was removed under reduced pressure. The crude product obtained was purified by C18-flash chromatography, elution gradient 0 to 50% MeCN in water (0.1% TFA) to give tert-butyl (12aR)-8,10-difluoro-9-[2-methoxy-6-(trifluoromethyl)phenyl]-3,4,12,12a-tetrahydro-6H-pyrazino[2,1-c][1,4]benzoxazepine-2(1H)-carboxylate (140 mg, 57%) as a yellow solid. 1H NMR (400 MHz, DMSO, 30° C.) 1.43 (9H, s), 2.61-2.88 (2H, m), 2.92-3.36 (5H, m), 3.77 (3H, s), 3.91-4.13 (1H, m), 4.32-4.72 (3H, m), 7.10 (1H, d), 7.27-7.33 (1H, m), 7.67-7.76 (2H, m). m/z: ES+ [M+H]+=515.

2-[(12aR)-8,10-Difluoro-1,2,3,4,12,12a-hexahydro-6H-pyrazino[2,1-c][1,4]benzoxazepin-9-yl]-3-(trifluoromethyl)phenol

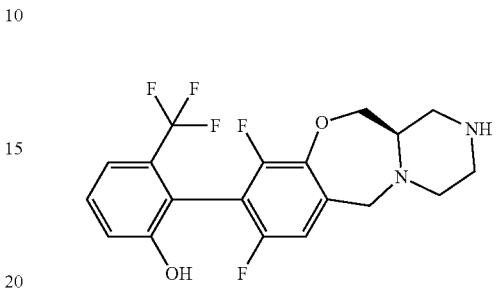

3M Boron tribromide in DCM (4 mL, 12 mmol) was added dropwise to tert-butyl (12aR)-8,10-difluoro-9-[2-methoxy-6-(trifluoromethyl)phenyl]-3,4,12,12a-tetrahydro-6H-pyrazino[2,1-c][1,4]benzoxazepine-2(1H)-carboxylate (130 mg, 0.25 mmol). The resulting mixture was stirred at rt for 1 h. The reaction mixture was diluted with MeOH and the solvent then removed under reduced pressure. The crude product obtained was purified by C18-flash chromatography, elution gradient 0 to 35% MeCN in water (0.1% NH₄HCO₃) to give 2-[(12aR)-8,10-difluoro-1,2,3,4,12,12a-hexahydro-6H-pyrazino[2,1-c][1,4]benzoxazepin-9-yl]-3-(trifluoromethyl)phenol (45 mg, 45%) as a white solid. 1H NMR (400 MHz, DMSO, 30° C.) 2.30-2.47 (1H, m), 2.53-2.62 (1H, m), 2.64-2.88 (3H, m), 2.89-3.06 (2H, m), 3.59-3.76 (2H, m), 3.81-3.95 (1H, m), 4.20-4.31 (1H, m), 7.01-7.13 (1H, m), 7.20-7.36 (2H, m), 7.45-7.54 (1H, m), 10.25-10.35 (1H, m). m/z: ES+ [M+H]+=401.

1-[(12aR)-8,10-Difluoro-9-[2-hydroxy-6-(trifluoromethyl)phenyl]-3,4,12,12a-tetrahydro-6H-pyrazino[2,1-c][1,4]benzoxazepin-2(1H)-yl]prop-2-en-1-one Rotational Isomer 1 Example 48 and Rotational-Isomer 2, Example 49

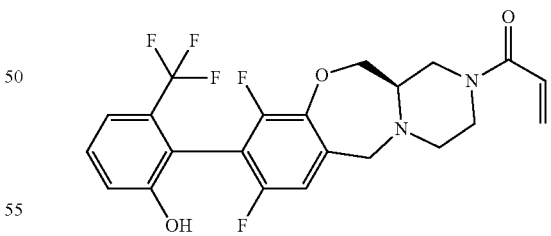

Acryloyl chloride (9.04 mg, 0.1 mmol) was added dropwise to afford 2-[(12aR)-8,10-difluoro-1,2,3,4,12,12a-hexahydro-6H-pyrazino[2,1-c][1,4]benzoxazepin-9-yl]-3-(trifluoromethyl)phenol (40 mg, 0.1 mmol) and DIPEA (0.052 mL, 0.3 mmol) in DMF (3 mL) at 0° C. and the reaction mixture stirred at 0° C. for 1 h. The reaction mixture was purified by preparative HPCL (Column: Xselect CSH OBD Column 30*150 mm 5 μm), eluting with water (0.1% formic acid) and MeCN, to give rotational isomer 1 of 1-[(12aR)-8,10-difluoro-9-[2-hydroxy-6-(trifluoromethyl)phenyl]-3,4, 12,12a-tetrahydro-6H-pyrazino[2,1-c][1,4]benzoxazepin-2 (1H)-yl]prop-2-en-1-one (13 mg, 27%) as a white solid. 1H NMR (400 MHz, DMSO, 30° C.) 2.29-2.46 (1H, m), 2.64-2.92 (3H, m), 2.97-3.17 (1H, m), 3.43-3.78 (2H, m), 3.79-3.94 (2H, m), 3.95-4.09 (1H, m), 4.28-4.45 (1H, m), 5.65-5.76 (1H, m), 6.06-6.19 (1H, m), 6.75-6.90 (1H, m), 7.07 (1H, d), 7.21-7.34 (2H, m), 7.43-7.55 (1H, m), 10.03-10.92 (1H, m). m/z: ES+ [M+H]+=455. This was followed by rotational isomer 2 of 1-[(12aR)-8,10-difluoro-9-[2-hydroxy-6-(trifluoromethyl)phenyl]-3,4,12,12a-tetrahydro-6H-pyrazino[2,1-c][1,4]benzoxazepin-2(1H)-yl]prop-2-en-1-one (6 mg, 13%) as a white solid. 1H NMR (400 MHz, DMSO, 30° C.) 2.29-2.44 (1H, m), 2.63-2.96 (3H, m), 3-3.19 (1H, m), 3.55-3.78 (2H, m), 3.79-4.14 (3H, m), 4.25-4.45 (1H, m), 5.56-5.78 (1H, m), 6.01-6.21 (1H, m), 6.72-6.91 (1H, m), 7.07 (1H, d), 7.17-7.38 (2H, m), 7.43-7.55 (1H, m), 10.23-10.69 (1H, m). m/z: ES+ [M+H]+=455.

2-Bromo-1-ethenyl-3-methoxybenzene

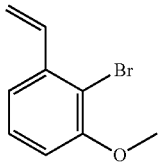

Tetrakis(triphenylphosphine)palladium(0) (1.108 g, 0.96 mmol) was added to 2-bromo-1-iodo-3-methoxybenzene (3 g, 9.59 mmol), 2-ethenyl-4,4,5,5-tetramethyl-1,3,2-dioxaborolane (1.772 g, 11.50 mmol) and $K_2CO_3$ (3.97 g, 28.76 mmol) in 1,4-dioxane (40 mL) and water (10 mL) (4:1 ratio). The resulting mixture was stirred at 100° C. for 4 h. The solvent was removed under reduced pressure. The crude product obtained was purified by flash silica chromatography, elution gradient 2 to 5% petroleum ether in EtOAc to give 2-bromo-1-ethenyl-3-methoxybenzene (1.5 g, 73%) as a yellow solid. 1H NMR (300 MHz, DMSO, 30° C.) 3.85 (3H, s), 5.42 (1H, dd), 5.82 (1H, dd), 6.83-7.19 (2H, m), 7.21-7.32 (1H, m), 7.28-7.41 (1H, m).

2-(2-Ethenyl-6-methoxyphenyl)-4,4,5,5-tetramethyl-1,3,2-dioxaborolane

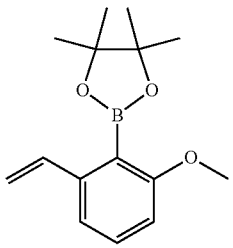 [SMILES: C=Cc1cccc(OC)c1B1OC(C)(C)C(C)(C)O1]

2-Bromo-1-ethenyl-3-methoxybenzene (500 mg, 2.35 mmol), bis(pinacolato)diboron (11.92 mg, 4.69 mmol), dichlorobis(tricyclohexylphosphine)palladium (II) (1732 mg, 2.35 mmol) and potassium acetate (806 mg, 8.21 mmol) in DMA (15 mL) were stirred at 120° C. for 2 h. The crude reaction mixture was purified by C18-flash chromatography, elution gradient 2 to 60% MeOH in water, to give 2-(2-ethenyl-6-methoxyphenyl)-4,4,5,5-tetramethyl-1,3,2-dioxaborolane (170 mg, 28%) as a yellow solid. 1H NMR (400 MHz, DMSO, 30° C.) 1.31 (12H, s), 3.72 (3H, s), 5.27 (1H, dd), 5.76 (1H, dd), 6.59-6.71 (1H, m), 6.85 (1H, d), 7.18 (1H, d), 7.32 (1H, t).

Tert-butyl (12aR)-9-(2-ethenyl-6-methoxyphenyl)-8,10-difluoro-3,4,12,12a-tetrahydro-6H-pyrazino[2,1-c][1,4]benzoxazepine-2(1H)-carboxylate

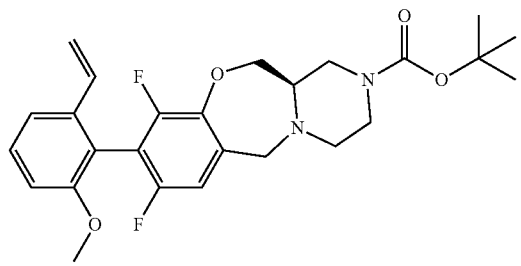 [SMILES: C=Cc1cccc(OC)c1-c1c(F)cc2c(c1F)OC[C@H]1CN(C(=O)OC(C)(C)C)CCN1C2]

RuPhos-Pd-G3 (30 mg, 0.04 mmol) was added to tert-butyl (12aR)-9-bromo-8,10-difluoro-3,4,12,12a-tetrahydro-6H-pyrazino[2,1-c][1,4]benzoxazepine-2(1H)-carboxylate (150 mg, 0.36 mmol), 2-(2-ethenyl-6-methoxyphenyl)-4,4,5,5-tetramethyl-1,3,2-dioxaborolane (140 mg, 0.54 mmol) and RuPhos (16.70 mg, 0.04 mmol) and $K_2CO_3$ (99 mg, 0.72 mmol) in) in 1,4-dioxane (8 mL) and water (2 mL) (4:1 ratio). The resulting mixture was stirred at 100° C. for 5 h. The crude reaction mixture was purified by C18-flash chromatography, elution gradient 10 to 50% MeOH in water, to give tert-butyl (12aR)-9-(2-ethenyl-6-methoxyphenyl)-8,10-difluoro-3,4,12,12a-tetrahydro-6H-pyrazino[2,1-c][1,4] benzoxazepine-2(1H)-carboxylate (110 mg, 65%) as a yellow solid. 1H NMR (400 MHz, DMSO, 30° C.) 1.25 (9H, s), 2.25-2.45 (1H, m), 2.57-3.27 (4H, m), 3.25 (3H, s), 3.43-3.85 (5H, m), 4.21-4.35 (1H, m), 5.21-5.28 (1H, m), 5.60-5.88 (1H, m), 6.32-6.39 (1H, m), 6.05-7.16 (1H, m), 7.35-7.59 (2H, m), 8.21 (1H, s). m/z: ES+ [M+H]+=473.

Tert-butyl (12aR)-9-(2-ethyl-6-methoxyphenyl)-8,10-difluoro-3,4,12,12a-tetrahydro-6H-pyrazino[2,1-c][1,4]benzoxazepine-2(1H)-carboxylate

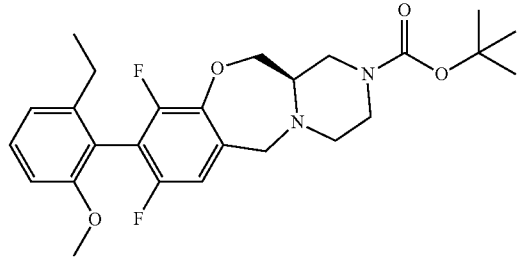 [SMILES: CCc1cccc(OC)c1-c1c(F)cc2c(c1F)OC[C@H]1CN(C(=O)OC(C)(C)C)CCN1C2]

10% Palladium on carbon (25 mg, 0.02 mmol) was added to tert-butyl (12aR)-9-(2-ethenyl-6-methoxyphenyl)-8,10-difluoro-3,4,12,12a-tetrahydro-6H-pyrazino[2,1-c][1,4]benzoxazepine-2(1H)-carboxylate (110 mg, 0.23 mmol) in MeOH (5 mL) and the reaction mixture was stirred at 25° C. for 4 h under an atmosphere of hydrogen. The mixture was filtered through a CELITE™ pad. The filtrate was removed under reduced pressure to afford tert-butyl (12aR)-9-(2- ethyl-6-methoxyphenyl)-8,10-difluoro-3,4,12,12a-tetrahydro-6H-pyrazino[2,1-c][1,4]benzoxazepine-2(1H)-carboxylate (80 mg, 72%) as a yellow solid. 1H NMR (300 MHz, DMSO, 30° C.) 0.84-1.03 (3H, m), 1.38 (9H, s), 2.19-2.37 (3H, m), 2.61-2.92 (3H, m), 2.92-3.25 (1H, m), 3.52-3.71 (6H, m), 3.72-3.79 (1H, m), 3.79-3.99 (1H, m), 4.15-4.40 (1H, m), 6.85-7 (2H, m), 7.05 (1H, d), 7.35 (1H, t). m/z: ES+ [M+H]+=475.

2-[(12aR)-8,10-Difluoro-1,2,3,4,12,12a-hexahydro-6H-pyrazino[2,1-c][1,4]benzoxazepin-9-yl]-3-ethylphenol

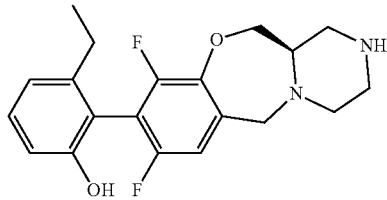 [SMILES: CCc1cccc(O)c1-c1c(F)cc2c(c1F)OC[C@H]1CNCCN1C2]

1M Boron tribromide in DCM (0.316 mL, 0.32 mmol) was added to tert-butyl (12aR)-9-(2-ethyl-6-methoxyphenyl)-8,10-difluoro-3,4,12,12a-tetrahydro-6H-pyrazino[2,1-c][1,4]benzoxazepine-2(1H)-carboxylate (75 mg, 0.16 mmol) in DCM (1 mL). The resulting mixture was stirred at 25° C. for 5 h. The reaction mixture was quenched with MeOH (2 mL) and the crude reaction mixture obtained was purified by C18-flash chromatography, elution gradient 40 to 80% MeOH in water (0.1% NH4OH), to give 2-[(12aR)-8,10-difluoro-1,2,3,4,12,12a-hexahydro-6H-pyrazino[2,1-c][1,4]benzoxazepin-9-yl]-3-ethylphenol (40 mg, 70%) as a yellow solid. m/z: ES+ [M+H]+=361.

1-[(12aR)-9-(2-Ethyl-6-hydroxyphenyl)-8,10-difluoro-3,4,12,12a-tetrahydro-6H-pyrazino[2,1-c][1,4]benzoxazepin-2(1H)-yl]prop-2-en-1-one Rotational Isomer 1, Example 50 and Rotational Isomer 2, Example 51

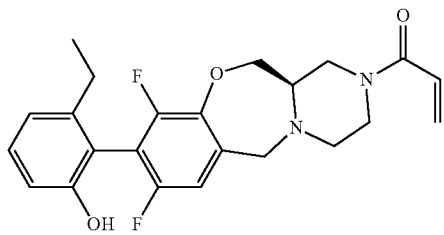 [SMILES: C=CC(=O)N1CCN2Cc3cc(F)c(-c4c(O)cccc4CC)c(F)c3OC[C@H]2C1]

Acryloyl chloride (8.79 mg, 0.1 mmol) was added to 2-[(12aR)-8,10-difluoro-1,2,3,4,12,12a-hexahydro-6H-pyrazino[2,1-c][1,4]benzoxazepin-9-yl]-3-ethylphenol (35 mg, 0.1 mmol) and DIPEA (0.051 mL, 0.29 mmol) in DMF (1 mL). The resulting mixture was stirred at 25° C. for 5 h. The crude reaction mixture was purified by preparative HPLC (Column: XBridge Prep OBD C18 Column 30×150 mm 5 μm), eluting with water (10 mmol/L formic acid) and MeCN, to give rotational isomer 1 of 1-[(12aR)-9-(2-ethyl-6-hydroxyphenyl)-8,10-difluoro-3,4,12,12a-tetrahydro-6H-pyrazino[2,1-c][1,4]benzoxazepin-2(1H)-yl]prop-2-en-1-one (9 mg, 22%) as a yellow solid. 1H NMR (300 MHz, DMSO, 30° C.) 0.96 (3H, t), 2.03-2.34 (3H, m), 2.56-2.87 (3H, m), 2.92-3.26 (1H, m), 3.54-3.78 (2H, m), 3.78-3.94 (2H, m), 2.94-4.15 (1H, m), 4.31-4.48 (1H, m), 5.70 (1H, d), 6.13 (1H, d), 6.57-6.91 (3H, m), 7.06 (1H, d), 7.18 (1H, t), 9.55 (1H, s). m/z: ES+ [M+H]+=415. This was followed by rotational isomer 2 of 1-[(12aR)-9-(2-ethyl-6-hydroxyphenyl)-8,10-difluoro-3,4,12,12a-tetrahydro-6H-pyrazino[2,1-c][1,4]benzoxazepin-2(1H)-yl]prop-2-en-1-one (12 mg, 30%) as a yellow solid. 1H NMR (300 MHz, DMSO, 30° C.) 0.93 (3H, t), 2.05-2.34 (2H, m), 2.32-2.46 (1H, m), 2.58-2.87 (3H, m), 2.92-3.13 (1H, m), 3.45-3.83 (2H, m), 3.78-4.19 (3H, m), 4.05-4.46 (1H, m), 5.70 (1H, d), 6.13 (1H, d), 6.57-6.88 (3H, m), 7.06 (1H, d), 7.18 (1H, t), 9.45 (1H, s). m/z: ES+ [M+H]+=415.

2-Bromo-3-[(4-methoxyphenyl)methoxy]benzaldehyde

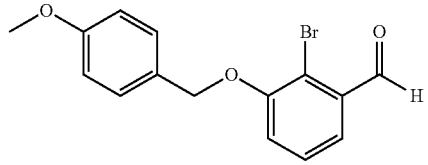 [SMILES: COc1ccc(COc2cccc(C=O)c2Br)cc1]

1-(Chloromethyl)-4-methoxybenzene (4.28 g, 27.36 mmol) was added to 2-bromo-3-hydroxybenzaldehyde (5 g, 24.87 mmol), K2CO3 (6.88 g, 49.75 mmol) and potassium iodide (0.826 g, 4.97 mmol) in DMF (50 mL) at rt. The resulting mixture was stirred at rt overnight. The reaction mixture was diluted with EtOAc (150 mL), washed sequentially with water (100 mL) and brine (100 mL×2).

The organic layer was dried (Na2SO4) and evaporated to afford crude product. This was purified by flash silica chromatography, elution gradient 0 to 100% EtOAc in petroleum ether to give 2-bromo-3-[(4-methoxyphenyl)methoxy]benzaldehyde (5 g, 63%) as a white solid. 1H NMR (400 MHz, DMSO, 30° C.) 3.76 (3H, s), 5.20 (2H, s), 6.91-7.04 (2H, m), 7.36-7.62 (5H, m), 10.28 (1H, s).

2-Bromo-1-(2,2-difluoroethyl)-3-[(4-methoxyphenyl)methoxy]benzene

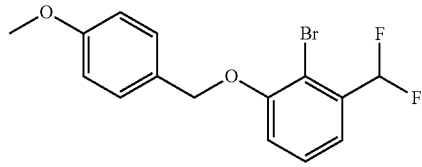 [SMILES: COc1ccc(COc2cccc(C(F)F)c2Br)cc1]

(Diethylamino)sulfur trifluoride (2.057 mL, 15.57 mmol) was added to 2-bromo-3-[(4-methoxyphenyl)methoxy]benzaldehyde (2 g, 6.23 mmol) in THF (30 mL) at −78° C. The resulting mixture was stirred at rt overnight. The reaction mixture was quenched with saturated NaHCO3 (100 mL), diluted with EtOAc (200 mL), washed sequentially with saturated NaHCO3 (200 mL) and brine (200 mL×2). The organic layer was dried (Na2SO4) and evaporated to afford crude product. This was purified by C18-flash chromatography, elution gradient 0 to 100% EtOAc/petroleum ether, to give 2-bromo-1-(2,2-difluoroethyl)-3-[(4-methoxyphenyl)methoxy]benzene (1.4 g, 66%) as a white solid. 1H NMR (400 MHz, DMSO, 30° C.) 3.76 (3H, s), 5.18 (2H, s), 6.94-7.02 (2H, m), 7.13-7.28 (2H, m), 7.36-7.53 (4H, m).

2-{2-(Difluoromethyl)-6-[(4-methoxyphenyl)methoxy]phenyl}-4,4,5,5-tetramethyl-1,3,2-dioxaborolane

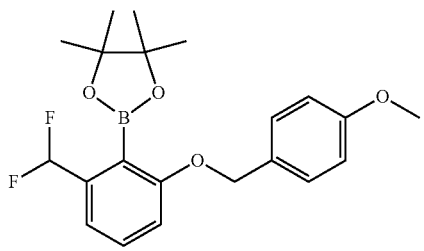 [SMILES: COc1ccc(COc2cccc(C(F)F)c2B2OC(C)(C)C(C)(C)O2)cc1]

Dichlorobis(tricyclohexylphosphine)palladium (II) (43 mg, 0.06 mmol) was added to 2-bromo-1-(2,2-difluoroethyl)-3-[(4-methoxyphenyl)methoxy]benzene (200 mg, 0.58 mmol), bis(pinacolato)diboron (296 mg, 1.17 mmol) and potassium acetate (200 mg, 2.04 mmol) in DMA (5 mL). The resulting mixture was stirred at 120° C. for 5 h. The crude reaction mixture was purified by C18-flash chromatography, elution gradient 5 to 80% MeOH in water to give 2-{2-(difluoromethyl)-6-[(4-methoxyphenyl)methoxy]phenyl}-4,4,5,5-tetramethyl-1,3,2-dioxaborolane (80 mg, 35%) as a yellow solid. 1H NMR (400 MHz, DMSO, 30° C.) 1.19 (12H, d), 3.75 (3H, s), 5.03 (2H, s), 6.80-6.99 (3H, m), 7.04-7.30 (2H, m), 7.28-7.57 (3H, m).

Tert-butyl (12aR)-9-{2-(difluoromethyl)-6-[(4-methoxyphenyl)methoxy]phenyl}-8,10-difluoro-3,4,12,12a-tetrahydro-6H-pyrazino[2,1-c][1,4]benzoxazepine-2(1H)-carboxylate

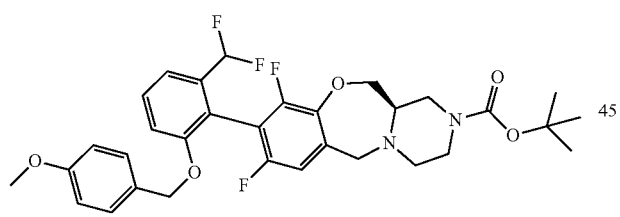

Tert-butyl (12aR)-9-bromo-8,10-difluoro-3,4,12,12a-tetrahydro-6H-pyrazino[2,1-c][1,4]benzoxazepine-2(1H)-carboxylate (60 mg, 0.14 mmol), 2-{2-(difluoromethyl)-6-[(4-methoxyphenyl)methoxy]phenyl}-4,4,5,5-tetramethyl-1,3,2-dioxaborolane (73 mg, 0.19 mmol), K₂CO₃ (39.6 mg, 0.29 mmol), RuPhos (7 mg, 0.01 mmol) and RuPhos-Pd-G3 (12 mg, 0.01 mmol) were suspended in 1,4-dioxane (4 mL) and water (1 mL) (4:1 ratio) and sealed into a microwave tube. The reaction was heated at 100° C. for 45 min in the microwave reactor and cooled to rt. The solvent was removed under reduced pressure and the crude product obtained was purified by flash silica chromatography, elution gradient 30 to 70% EtOAc in petroleum ether, to give tert-butyl (12aR)-9-{2-(difluoromethyl)-6-[(4-methoxyphenyl)methoxy]phenyl}-8,10-difluoro-3,4,12,12a-tetrahydro-6H-pyrazino[2,1-c][1,4]benzoxazepine-2(1H)-carboxylate (50 mg, 58%) as a yellow solid. 1H NMR (400 MHz, DMSO, 30° C.) 1.41 (9H, s), 2.29-2.44 (1H, m), 2.62-2.91 (3H, m), 3.03-3.28 (1H, m), 3.43-3.66 (1H, m), 3.65-3.80 (5H, m), 3.81-3.96 (1H, m), 4-4.15 (1H, m), 4.34-4.35 (1H, m), 4.86-5.19 (2H, m), 6.77 (2H, d), 6.88 (2H, d), 6.98 (1H, d), 7.18-7.34 (4H, m). m/z: ES+ [M+H]+=603.

1-[(12aR)-9-[2-(difluoromethyl)-6-hydroxyphenyl]-8,10-difluoro-3,4,12,12a-tetrahydro-6H-pyrazino[2,1-c][1,4]benzoxazepin-2(1H)-yl]-2,2,2-trifluoroethan-1-one

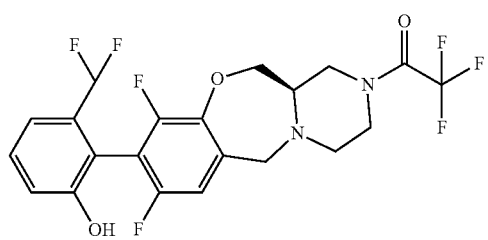 [SMILES: O=C(N1CCN2Cc3cc(F)c(-c4c(O)cccc4C(F)F)c(F)c3OC[C@H]2C1)C(F)(F)F]

Tert-butyl (12aR)-9-{2-(difluoromethyl)-6-[(4-methoxyphenyl)methoxy]phenyl}-8,10-difluoro-3,4,12,12a-tetrahydro-6H-pyrazino[2,1-c][1,4]benzoxazepine-2(1H)-carboxylate (50 mg, 0.08 mmol) in TFA (1 mL) was stirred at 50° C. for 4 h. The solvent was removed under reduced pressure and the crude product obtained was purified by C18-flash chromatography, elution gradient 2 to 70% MeOH in water, to give 1-[(12aR)-9-(2-(difluoromethyl)-6-hydroxyphenyl]-8,10-difluoro-3,4,12,12a-tetrahydro-6H-pyrazino[2,1-c][1,4]benzoxazepin-2(1H)-yl]-2,2,2-trifluoroethan-1-one (30 mg, 76%) as a yellow solid. m/z: ES+ [M+H]+=679.

2-[(12aR)-8,10-Difluoro-1,2,3,4,12,12a-hexahydro-6H-pyrazino[2,1-c][1,4]benzoxazepin-9-yl]-3-(difluoromethyl)phenol

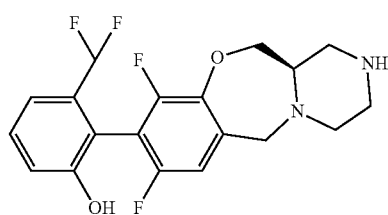 [SMILES: Oc1cccc(C(F)F)c1-c1c(F)cc2c(c1F)OC[C@H]1CNCCN1C2]

Sodium hydroxide (7.52 mg, 0.19 mmol) was added to 1-[(12aR)-9-[2-(difluoromethyl)-6-hydroxyphenyl]-8,10-difluoro-3,4,12,12a-tetrahydro-6H-pyrazino[2,1-c][1,4]benzoxazepin-2(1H)-yl]-2,2,2-trifluoroethan-1-one (30 mg, 0.06 mmol) in MeOH (0.5 mL) and water (0.1 mL) (5:1 ratio). The resulting mixture was stirred at 60° C. for 24 h. The crude reaction mixture was purified by C18-flash chromatography, elution gradient 10 to 50% MeCN in water (0.1% NH₄OH), to give 2-[(12aR)-8,10-difluoro-1,2,3,4,12,12a-hexahydro-6H-pyrazino[2,1-c][1,4]benzoxazepin-9-yl]-3-(difluoromethyl)phenol (13 mg, 54%) as a yellow solid. m/z: ES+ [M+H]+=383.

1-[(12aR)-9-[2-(Difluoromethyl)-6-hydroxyphenyl]-8,10-difluoro-3,4,12,12a-tetrahydro-6H-pyrazino[2,1-c][1,4]benzoxazepin-2(1H)-yl]prop-2-en-1-one Rotational Isomer 1, Example 52 and Rotational Isomer 2, Example 53

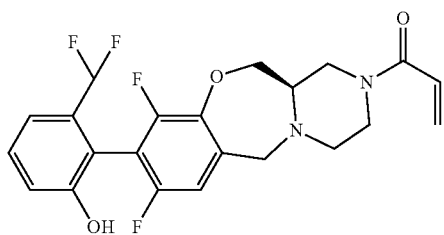 [SMILES: C=CC(=O)N1CCN2Cc3cc(F)c(-c4c(O)cccc4C(F)F)c(F)c3OC[C@H]2C1]

Acryloyl chloride (2.367 mg, 0.03 mmol) was added to 2-[(12aR)-8,10-difluoro-1,2,3,4,12,12a-hexahydro-6H-pyrazino[2,1-c][1,4]benzoxazepin-9-yl]-3-(difluoromethyl)phenol (10 mg, 0.03 mmol) and DIPEA (0.014 mL, 0.08 mmol) in DMF (0.5 mL). The resulting mixture was stirred at 25° C. for 4 h. The crude reaction mixture was purified by preparative HPCL (Column: XBridge Prep OBD C18 Column 30×150 mm 5 μm), eluting with water (10 mmolL/L NH₄HCO₃) and MeCN, to give rotational isomer 1 of 1-[(12aR)-9-[2-(difluoromethyl)-6-hydroxyphenyl]-8,10-difluoro-3,4,12,12a-tetrahydro-6H-pyrazino[2,1-c][1,4]benzoxazepin-2(1H)-yl]prop-2-en-1-one (2.8 mg, 25%) as a yellow solid. 1H NMR (400 MHz, DMSO, 30° C.) 2.36-2.41 (1H, m), 2.81-2.94 (2H, m), 3.10-3.18 (1H, m), 3.28-3.33 (1H, m), 3.71-3.78 (2H, m), 3.81-3.93 (3H, m), 4.27-4.39 (1H, m), 5.70 (1H, d), 6.13 (1H, d), 6.50-6.78 (1H, m), 6.79-6.92 (1H, m), 7.04-7.19 (3H, m), 7.38-7.47 (1H, m), 10.02 (1H, s). m/z: ES+ [M+H]+=437. This was followed by rotational isomer 2 of 1-[(12aR)-9-[2-(difluoromethyl)-6-hydroxyphenyl]-8,10-difluoro-3,4,12,12a-tetrahydro-6H-pyrazino[2,1-c][1,4]benzoxazepin-2(1H)-yl]prop-2-en-1-one (2.8 mg, 25%) as a yellow solid 1H NMR (400 MHz, DMSO, 30° C.) 2.30-2.48 (1H, m), 2.73-2.80 (1H, m), 2.86-2.90 (1H, m), 3.01-3.18 (1H, m), 3.38-3.57 (1H, m), 3.57-3.71 (1H, m), 3.71-3.86 (1H, m), 3.86-3.95 (2H, m), 3.95-4.19 (1H, m), 4.34-4.51 (1H, m), 5.73 (1H, d), 6.10 (1H, d), 6.29-6.79 (1H, m), 6.77-6.96 (1H, m), 6.99-7.28 (3H, m), 7.42-7.51 (1H, m), 10.02 (1H, s). m/z: ES+ [M+H]+=437.

Tert-butyl (3R)-4-(4-bromo-2,3-difluorobenzoyl)-3-(hydroxymethyl)piperazine-1-carboxylate

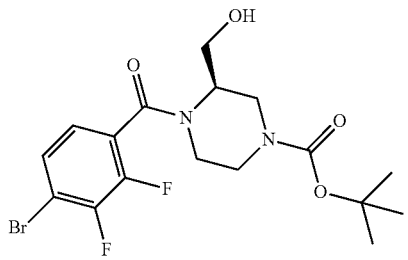 [SMILES: CC(C)(C)OC(=O)N1CCN(C(=O)c2ccc(Br)c(F)c2F)[C@@H](CO)C1]

DIPEA (15.48 mL, 88.61 mmol) was added to 4-bromo-2,3-difluorobenzoic acid (7 g, 29.54 mmol), HATU (16.85 g, 44.30 mmol) and tert-butyl (3R)-3-(hydroxymethyl)piperazine-1-carboxylate (7.03 g, 32.49 mmol) in DMF (80 mL). The resulting mixture was stirred at 25° C. for 2 h. The reaction mixture was diluted with EtOAc (150 mL) and washed with brine (100 mL×3). The organic layer was dried (Na₂SO₄) and evaporated to afford crude product. This was purified by flash silica chromatography, elution gradient 20 to 50% EtOAc in petroleum ether, to give tert-butyl (3R)-4-(4-bromo-2,3-difluorobenzoyl)-3-(hydroxymethyl)piperazine-1-carboxylate (10 g, 78%) as a yellow solid. 1H NMR (300 MHz, DMSO, 30° C.) 1.39 (9H, s), 2.75-3.23 (3H, m), 3.38-3.59 (2H, m), 3.62-3.93 (1H, m), 3.88-4.10 (1H, m), 4.15-4.63 (1H, m), 4.72-5.33 (1H, m), 6.91-7.41 (1H, m), 7.49-7.92 (1H, m). m/z: ES+ [M-tBu]+=379.

Tert-butyl (12aR)-9-bromo-10-fluoro-6-oxo-3,4,12,12a-tetrahydro-6H-pyrazino[2,1-c][1,4]benzoxazepine-2(1H)-carboxylate

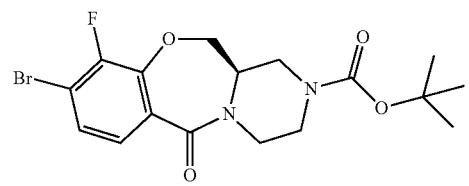 [SMILES: CC(C)(C)OC(=O)N1CCN2C(=O)c3ccc(Br)c(F)c3OC[C@H]2C1]

Sodium hydride (1.47 g, 36.76 mmol) was added to tert-butyl (3R)-4-(4-bromo-2,3-difluorobenzoyl)-3-(hydroxymethyl)piperazine-1-carboxylate (8 g, 18.38 mmol) in THF (50 mL). The resulting mixture was stirred at 25° C. for 5 h. The reaction mixture was quenched with water (100 mL) and extracted with EtOAc (100 mL×3). The organic layer was dried (Na₂SO₄) and evaporated to afford crude product. This was purified by flash silica chromatography, elution gradient 10 to 20% MeOH in DCM to give tert-butyl (12aR)-9-bromo-10-fluoro-6-oxo-3,4,12,12a-tetrahydro-6H-pyrazino[2,1-c][1,4]benzoxazepine-2(1H)-carboxylate (6 g, 79%) as a white solid. 1H NMR (300 MHz, DMSO, 30° C.) 1.39 (9H, s), 3.43-3.56 (2H, m), 3.57-3.84 (2H, m), 3.82-4.13 (3H, m), 4.22-4.45 (2H, m), 7.29-7.67 (2H, m). m/z: ES+ [M+H]+=415.

Tert-butyl (12aR)-9-bromo-10-fluoro-3,4,12,12a-tetrahydro-6H-pyrazino[2,1-c][1,4]benzoxazepine-2(1H)-carboxylate

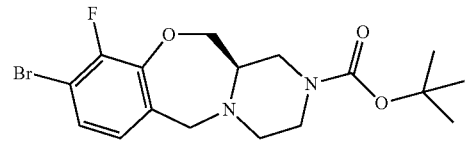 [SMILES: CC(C)(C)OC(=O)N1CCN2Cc3ccc(Br)c(F)c3OC[C@H]2C1]

1M Borane-THF complex solution in THF (40 ml, 40 mmol) was added to tert-butyl (12aR)-9-bromo-10-fluoro-6-oxo-3,4,12,12a-tetrahydro-6H-pyrazino[2,1-c][1,4]benzoxazepine-2(1H)-carboxylate (6 g, 14.45 mmol). The resulting mixture was stirred at 60° C. for 4 h. The reaction mixture was quenched with MeOH and the solvent removed under reduced pressure. The crude product was purified by C18-flash chromatography, elution gradient 40 to 60% MeOH in water (0.1% formic acid) to give tert-butyl (12aR)-9-bromo-10-fluoro-3,4,12,12a-tetrahydro-6H-pyrazino[2,1- c][1,4]benzoxazepine-2(1H)-carboxylate (3 g, 52%) as a yellow solid. 1H NMR (400 MHz, DMSO, 30° C.) 1.40 (9H, s), 2.19-2.43 (1H, m), 2.61-2.82 (2H, m), 2.97-3.12 (1H, m), 3.51-3.66 (2H, m), 3.66-3.76 (2H, m), 3.75-3.90 (1H, m), 4.11 (1H, d), 4.33 (1H, d), 7.04 (1H, d), 7.31 (1H, d). m/z: ES+ [M+H]+=401.

(12aR)-9-Bromo-10-fluoro-8-iodo-1,2,3,4,12,12a-hexahydro-6H-pyrazino[2,1-c][1,4]benzoxazepine

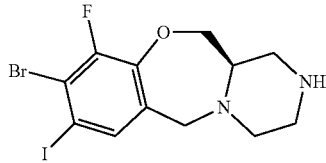 [SMILES: Fc1c(Br)c(I)cc2c1OC[C@H]1CNCCN1C2]

N-Iodosuccinimide (1.682 g, 7.48 mmol) was added to tert-butyl (12aR)-9-bromo-10-fluoro-3,4,12,12a-tetrahydro-6H-pyrazino[2,1-c][1,4]benzoxazepine-2(1H)-carboxylate (1.5 g, 3.74 mmol) in concentrated sulfuric acid. The resulting mixture was stirred at 25° C. for 20 h. The reaction mixture was quenched with 2M NaOH (100 mL) and extracted with DCM (100 mL×3). The organic layer was dried (Na$_2$SO$_4$) and evaporated to afford crude product as a yellow oil. The crude product was purified by C18-flash chromatography, elution gradient 40 to 80% MeOH in water, to afford (12aR)-9-bromo-10-fluoro-8-iodo-1,2,3,4,12,12a-hexahydro-6H-pyrazino[2,1-c][1,4]benzoxazepine (0.8 g, 50%) as a yellow solid. 1H NMR (300 MHz, DMSO, 30° C.) 2.17-2.46 (2H, m), 2.61-2.80 (3H, m), 2.78-3 (2H, m), 3.54-3.98 (3H, m), 4.25 (1H, d), 7.70 (1H, s). m/z: ES+ [M+H]+=427.

(12aR)-9-Bromo-10-fluoro-1,2,3,4,12,12a-hexahydro-6H-pyrazino[2,1-c][1,4]benzoxazepine-8-carbonitrile

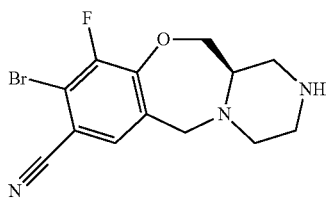

Tetrakis(triphenylphosphine)palladium(0) (271 mg, 0.23 mmol) was added to dicyanozinc (206 mg, 1.76 mmol) and (12aR)-9-bromo-10-fluoro-8-iodo-1,2,3,4,12,12a-hexahydro-6H-pyrazino[2,1-c][1,4]benzoxazepine (500 mg, 1.17 mmol) in DMF (15 mL). The resulting mixture was stirred at 100° C. for 5 h. The crude reaction mixture was purified by C18-flash chromatography, elution gradient 20 to 60% MeOH in water (0.1% NH$_4$OH) to give (12aR)-9-bromo-10-fluoro-1,2,3,4,12,12a-hexahydro-6H-pyrazino[2,1-c][1,4]benzoxazepine-8-carbonitrile (300 mg, 79%) as a yellow solid. 1H NMR (300 MHz, DMSO, 30° C.) 2.17-2.42 (2H, m), 2.54-2.84 (5H, m), 3.73 (2H, d), 3.80-3.97 (1H, m), 4.23-4.45 (1H, m), 7.74 (1H, s). m/z: ES+ [M+H]+=326.

(12aR)-9-(2-Chloro-6-hydroxyphenyl)-10-fluoro-1,2,3,4,12,12a-hexahydro-6H-pyrazino[2,1-c][1,4]benzoxazepine-8-carbonitrile Rotational Isomer 1 and Rotational Isomer 2

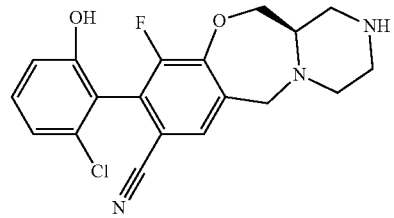 [SMILES: N#Cc1cc2c(c(F)c1-c1c(O)cccc1Cl)OC[C@H]1CNCCN1C2]

RuPhos-Pd-G3 (77 mg, 0.09 mmol) and RuPhos (42.9 mg, 0.09 mmol) were added to (12aR)-9-bromo-10-fluoro-1,2,3,4,12,12a-hexahydro-6H-pyrazino[2,1-c][1,4]benzoxazepine-8-carbonitrile (300 mg, 0.92 mmol), (2-chloro-6-hydroxyphenyl)boronic acid (793 mg, 4.6 mmol) and potassium phosphate (586 mg, 2.76 mmol) in 1,4-dioxane (10 mL) and water (2 mL) (5:1 ratio) at rt. The resulting mixture was stirred at 115° C. for 40 min in a microwave. The crude reaction mixture was purified by C18-flash chromatography, elution gradient 40 to 70% MeOH in water (0.1% NH$_4$OH) to give rotational isomer 1 of (12aR)-9-(2-chloro-6-hydroxyphenyl)-10-fluoro-1,2,3,4,12,12a-hexahydro-6H-pyrazino[2,1-c][1,4]benzoxazepine-8-carbonitrile (65 mg, 19%) as a yellow solid. 1H NMR (300 MHz, DMSO, 30° C.) 2.19-2.45 (2H, m), 2.53-2.88 (5H, m), 3.55-3.99 (3H, m), 4.37 (1H, d), 6.96 (1H, d), 7.06 (1H, d), 7.33 (1H, t), 7.69 (1H, d). m/z: ES+ [M+H]+=374. This was followed by rotational isomer 2 of (12aR)-9-(2-chloro-6-hydroxyphenyl)-10-fluoro-1,2,3,4,12,12a-hexahydro-6H-pyrazino[2,1-c][1,4]benzoxazepine-8-carbonitrile (65 mg, 19%) as a yellow solid. 1H NMR (300 MHz, DMSO, 30° C.) 2.12-2.45 (2H, m), 2.54-2.81 (5H, m), 3.60-4.01 (3H, m), 4.37 (1H, d), 6.97 (1H, d), 7.06 (1H, d), 7.33 (1H, t), 7.69 (1H, d). m/z: ES+ [M+H]+=374.

(12aR)-9-(2-Chloro-6-hydroxyphenyl)-10-fluoro-2-(prop-2-enoyl)-1,2,3,4,12,12a-hexahydro-6H-pyrazino[2,1-c][1,4]benzoxazepine-8-carbonitrile Rotational Isomer 1, Example 54

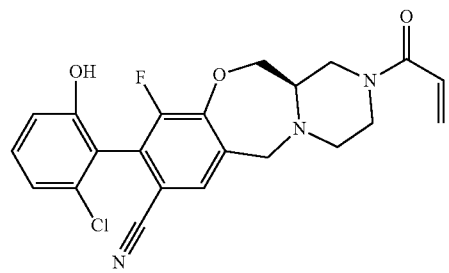 [SMILES: C=CC(=O)N1CCN2Cc3cc(C#N)c(-c4c(O)cccc4Cl)c(F)c3OC[C@H]2C1]

Acryloyl chloride (16 mg, 0.17 mmol) was added to rotational isomer 1 of (12aR)-9-(2-chloro-6-hydroxyphenyl)-10-fluoro-1,2,3,4,12,12a-hexahydro-6H-pyrazino[2,1-c][1,4]benzoxazepine-8-carbonitrile (65 mg, 0.17 mmol) and DIPEA (0.091 mL, 0.52 mmol) in DMF (2 mL). The resulting mixture was stirred at 25° C. for 4 h. The crude reaction mixture was purified by preparative HPLC (Column: XBridge Shield RP18 OBD 30*150 mm, 5 μm), eluting with water (10 mmol/L NH₄HCO₃) and MeCN, to give rotational isomer 1 of (12aR)-9-(2-chloro-6-hydroxyphenyl)-10-fluoro-2-(prop-2-enoyl)-1,2,3,4,12,12a-hexahydro-6H-pyrazino[2,1-c][1,4]benzoxazepine-8-carbonitrile (27.mg, 36%) as a white solid. 1H NMR (300 MHz, DMSO, 30° C.) 2.38-2.44 (1H, m), 2.68-2.74 (1H, m), 2.82-3.02 (3H, m), 3.77-4.03 (4H, m), 4.06-4.16 (1H, m), 4.44-4.50 (1H, m), 5.69 (1H, d), 6.11 (1H, d), 6.91-7 (1H, m), 7.02 (1H, d), 7.05 (1H, d), 7.32 (1H, t), 7.68 (1H, s), 10.31 (1H, s). m/z: ES+ [M+H]+=428.

(12aR)-9-(2-chloro-6-hydroxyphenyl)-10-fluoro-2-(prop-2-enoyl)-1,2,3,4,12,12a-hexahydro-6H-pyrazino[2,1-c][1,4]benzoxazepine-8-carbonitrile Rotational Isomer 2, Example 55

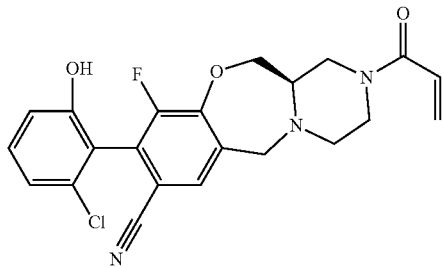 [SMILES: C=CC(=O)N1CCN2Cc3cc(C#N)c(-c4c(O)cccc4Cl)c(F)c3OC[C@H]2C1]

Acryloyl chloride (15.74 mg, 0.17 mmol) was added to rotational isomer 2 of (12aR)-9-(2-chloro-6-hydroxyphenyl)-10-fluoro-1,2,3,4,12,12a-hexahydro-6H-pyrazino[2,1-c][1,4]benzoxazepine-8-carbonitrile (65 mg, 0.17 mmol) and DIPEA (0.091 mL, 0.52 mmol) in DMF (2 mL). The resulting mixture was stirred at 25° C. for 4 h. The crude reaction mixture was purified by preparative HPCL (Column: XBridge BEH C18 OBD, 5 μm, 19 mm 250 mm), eluting with water (10 mmol/L NH₄HCO₃) and MeCN, to give rotational isomer 2 of (12aR)-9-(2-chloro-6-hydroxyphenyl)-10-fluoro-2-(prop-2-enoyl)-1,2,3,4,12,12a-hexahydro-6H-pyrazino[2,1-c][1,4]benzoxazepine-8-carbonitrile (30 mg, 40%) as a white solid. 1H NMR (300 MHz, DMSO, 30° C.) 2.32-2.42 (1H, m), 2.64-2.77 (1H, m), 2.80-3.14 (3H, m), 3.72-4.21 (5H, m), 4.33-4.92 (1H, m), 5.68 (1H, d), 6.11 (1H, d), 6.60-6.91 (1H, m), 6.95 (1H, d), 7.04 (1H, d), 7.31 (1H, t), 7.68 (1H, s), 10.31 (1H, s). m/z: ES+ [M+H]+=428.

(12aR)-10-Chloro-9-(2-chloro-6-hydroxyphenyl)-1,2,3,4,12,12a-hexahydro-6H-pyrazino[2,1-c][1,4]benzoxazepine-8-carbonitrile

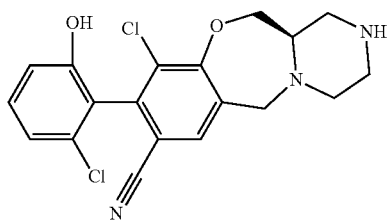 [SMILES: N#Cc1cc2c(c(Cl)c1-c1c(O)cccc1Cl)OC[C@H]1CNCCN1C2]

RuPhos-Pd-G3 (36.6 mg, 0.04 mmol) and RuPhos (20.43 mg, 0.04 mmol) were added to (12aR)-9-bromo-10-chloro-1,2,3,4,12,12a-hexahydro-6H-pyrazino[2,1-c][1,4]benzoxazepine-8-carbonitrile (150 mg, 0.44 mmol), (2-chloro-6-hydroxyphenyl)boronic acid (377 mg, 2.19 mmol) and potassium phosphate (279 mg, 1.31 mmol) in 1,4-dioxane (5 mL) and water (1 mL) (5:1 ratio) at rt. The resulting mixture was stirred at 115° C. for 40 min in a microwave reactor. The reaction mixture was purified by C18-flash chromatography, elution gradient 40 to 70% MeOH in water (0.1% NH₄OH), to give (12aR)-10-chloro-9-(2-chloro-6-hydroxyphenyl)-1,2,3,4,12,12a-hexahydro-6H-pyrazino[2,1-c][1,4]benzoxazepine-8-carbonitrile (70 mg, 41%) as a yellow solid. 1H NMR (400 MHz, DMSO, 30° C.) 2.20-2.42 (2H, m), 2.60-2.81 (4H, m), 3.56-3.89 (4H, m), 4.38 (1H, d), 6.78-6.88 (2H, m), 7.39 (1H, d), 7.74 (1H, s), 11.31 (1H, s). m/z: ES+ [M+H]+=390.

(12aR)-10-Chloro-9-(2-chloro-6-hydroxyphenyl)-2-(prop-2-enoyl)-1,2,3,4,12,12a-hexahydro-6H-pyrazino[2,1-c][1,4]benzoxazepine-8-carbonitrile Rotational Isomer 1, Example 56 and Rotational Isomer 2, Example 57

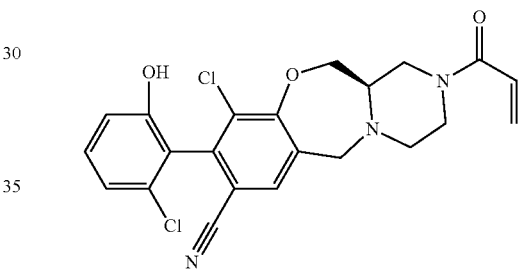

Acryloyl chloride (16 mg, 0.18 mmol) was added to (12aR)-10-chloro-9-(2-chloro-6-hydroxyphenyl)-1,2,3,4,12,12a-hexahydro-6H-pyrazino[2,1-c][1,4]benzoxazepine-8-carbonitrile (70 mg, 0.18 mmol) and DIPEA (0.094 mL, 0.54 mmol) in DMF (5 mL). The resulting mixture was stirred at 25° C. for 4 h. The reaction mixture was purified by preparative HPLC (Column: SunFire C18 OBD 100 Å, 5 μm, 19 mm×250 mm), eluting with water (0.1% formic acid) and MeCN, to give rotational isomer 1 of (12aR)-10-chloro-9-(2-chloro-6-hydroxyphenyl)-2-(prop-2-enoyl)-1,2,3,4,12,12a-hexahydro-6H-pyrazino[2,1-c][1,4]benzoxazepine-8-carbonitrile (17 mg, 21%) as a white solid. 1H NMR (300 MHz, DMSO, 30° C.) 2.35-2.45 (1H, m), 2.60-3.14 (4H, m), 3.67-4.18 (5H, m), 4.35-4.88 (1H, m), 5.72 (1H, d), 6.15 (1H, d), 6.35-7.16 (3H, m), 7.12-7.50 (1H, m), 7.81 (1H, s). m/z: ES+ [M+H]+=444. This was followed by rotational isomer 2 of (12aR)-10-chloro-9-(2-chloro-6-hydroxyphenyl)-2-(prop-2-enoyl)-1,2,3,4,12,12a-hexahydro-6H-pyrazino[2,1-c][1,4]benzoxazepine-8-carbonitrile (17 mg, 21%) as a white solid. 1H NMR (300 MHz, DMSO, 30° C.) 2.61-3.22 (5H, m), 3.65-4.35 (5H, m), 4.28-4.73 (1H, m), 5.71 (1H, d), 6.11 (1H, d), 6.56-7.12 (3H, m), 7.24 (1H, t), 7.80 (1H, s). m/z: ES+ [M+H]+=444.

131

3-Methoxy-2-(4,4,5,5-tetramethyl-1,3,2-dioxaborolan-2-yl)aniline

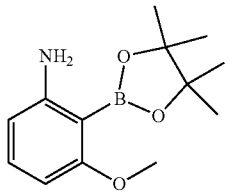 [SMILES: COc1cccc(N)c1B1OC(C)(C)C(C)(C)O1]

Dichlorobis(tricyclohexylphosphine)palladium (II) (0.365 g, 0.49 mmol) was added to 2-bromo-3-methoxyaniline (1 g, 4.95 mmol), bis(pinacolato)diboron (2.51 g, 9.9 mmol) and potassium acetate (1.457 g, 14.85 mmol) in DMA (25 mL) at 25° C. The resulting solution was stirred at 155° C. for 30 min.

The reaction mixture was diluted with EtOAc (150 mL) and washed with brine (100 mL×3). The organic layer was dried (Na$_2$SO$_4$) and evaporated to afford crude product. This was purified by flash silica chromatography, elution gradient 10 to 30% THF in petroleum ether, to give 3-methoxy-2-(4,4,5,5-tetramethyl-1,3,2-dioxaborolan-2-yl)aniline (0.576 g, 47%) as a white solid. 1H NMR (400 MHz, CDCl$_3$, 30° C.) 1.38 (12H, s), 3.80 (3H, s), 6.27 (1H, d), 6.34 (1H, dd), 7.16 (1H, t). m/z: ES+ [M-82]+=168.

Tert-butyl (12aR)-9-(2-amino-6-methoxyphenyl)-8,10-difluoro-3,4,12,12a-tetrahydro-6H-pyrazino[2,1-c][1,4]benzoxazepine-2(1H)-carboxylate

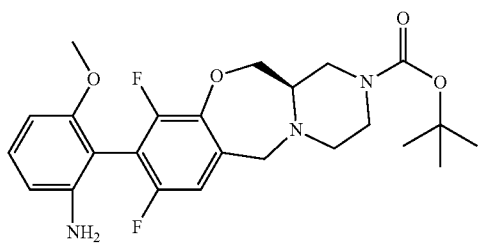 [SMILES: COc1cccc(N)c1-c1c(F)cc2c(c1F)OC[C@H]1CN(C(=O)OC(C)(C)C)CCN1C2]

Tert-butyl (12aR)-9-bromo-8,10-difluoro-3,4,12,12a-tetrahydro-6H-pyrazino[2,1-c][1,4]benzoxazepine-2(1H)-carboxylate (260 mg, 0.62 mmol), 3-methoxy-2-(4,4,5,5-tetramethyl-1,3,2-dioxaborolan-2-yl)aniline (463 mg, 1.86 mmol), RuPhos (28.9 mg, 0.06 mmol), RuPhos-Pd-G3 (51.9 mg, 0.06 mmol) and K$_2$CO$_3$ (257 mg, 1.86 mmol) in 1,4-dioxane (12.0 mL) and water (3.0 mL) (4:1 ratio) was stirred at 100° C. for 1 h. The reaction mixture was diluted with EtOAc (100 mL) and washed with water (50 mL). The organic layer was dried (Na$_2$SO$_4$) and evaporated to afford crude product. This was purified by flash silica chromatography, elution gradient 40 to 60% EtOAc in petroleum ether, to give tert-butyl (12aR)-9-(2-amino-6-methoxyphenyl)-8,10-difluoro-3,4,12,12a-tetrahydro-6H-pyrazino[2,1-c][1,4]benzoxazepine-2(1H)-carboxylate (238 mg, 83%) as a yellow foam. 1H NMR (400 MHz, CDCl$_3$, 30° C.) 1.49 (9H, s), 2.72 (3H, d), 3.48-3.67 (2H, m), 3.74 (3H, d), 3.76-4.20 (5H, m), 4.20-4.50 (1H, m), 6.40-6.50 (1H, m), 6.75-6.90 (1H, m), 7.21 (1H, t). m/z: ES+ [M+H]+=462.

132

Tert-butyl (12aR)-9-(2-bromo-6-methoxyphenyl)-8,10-difluoro-3,4,12,12a-tetrahydro-6H-pyrazino[2,1-c][1,4]benzoxazepine-2(1H)-carboxylate

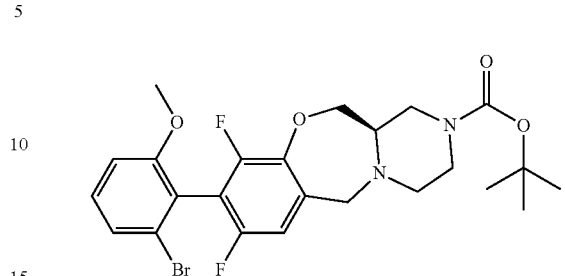

A solution of tert-butyl nitrite (160 mg, 1.55 mmol) in dibromomethane (0.5 mL) was added dropwise to a stirred solution of tert-butyl (12aR)-9-(2-amino-6-methoxyphenyl)-8,10-difluoro-3,4,12,12a-tetrahydro-6H-pyrazino[2,1-c][1,4]benzoxazepine-2(1H)-carboxylate (238 mg, 0.52 mmol) in dibromomethane (2 mL) at −20° C., followed by the addition of bromotrimethylsilane (0.2 mL, 1.55 mmol) in dibromomethane (0.5 mL). The resulting solution was stirred at −40° C. for 1 h. The reaction mixture was quenched with saturated NaHCO$_3$ (100 mL), extracted with DCM (3×100 mL), the organic layer was dried (Na$_2$SO$_4$) and evaporated to afford crude product. This was purified by flash silica chromatography, elution gradient 10 to 20% THF in petroleum ether to give tert-butyl (12aR)-9-(2-bromo-6-methoxyphenyl)-8,10-difluoro-3,4,12,12a-tetrahydro-6H-pyrazino[2,1-c][1,4]benzoxazepine-2(1H)-carboxylate (134 mg, 50%) as a red oil. m/z: ES+ [M+H]+=525.

3-Bromo-2-[(12aR)-8,10-difluoro-1,2,3,4,12,12a-hexahydro-6H-pyrazino[2,1-c][1,4]benzoxazepin-9-yl]phenol

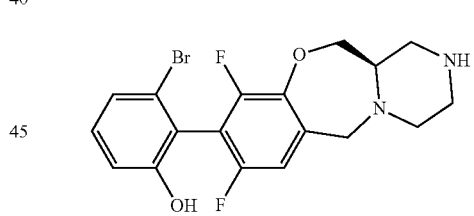

1M Boron tribromide in DCM (4 mL, 4 mmol) was added to tert-butyl (12aR)-9-(2-bromo-6-methoxyphenyl)-8,10-difluoro-3,4,12,12a-tetrahydro-6H-pyrazino[2,1-c][1,4]benzoxazepine-2(1H)-carboxylate (130 mg, 0.25 mmol) in DCM (4 mL). The resulting mixture was stirred at rt for 1 h. The reaction mixture was quenched with MeOH. The solvent was removed under reduced pressure. The crude product was purified by C18-flash chromatography, elution gradient 5 to 35% MeCN in water (0.05% TFA) to give a TFA salt which was purified by SCX (7M NH$_3$/MeOH) to afford 3-bromo-2-[(12aR)-8,10-difluoro-1,2,3,4,12,12a-hexahydro-6H-pyrazino[2,1-c][1,4]benzoxazepin-9-yl]phenol (75 mg, 74%) as a pale yellow solid. 1H NMR (400 MHz, CD$_3$OD, 30° C.) 2.70-2.97 (2H, m), 3.05-3.25 (3H, m), 3.38-3.52 (2H, m), 3.62-3.85 (2H, m), 4-4.13 (1H, m), 4.37 (1H, dd), 6.84-6.98 (2H, m), 7.07-7.20 (2H, m). m/z: ES+ [M+H]+=411.

1-[(12aR)-9-(2-Bromo-6-hydroxyphenyl)-8,10-difluoro-3,4,12,12a-tetrahydro-6H-pyrazino[2,1-c][1,4]benzoxazepin-2(1H)-yl]prop-2-en-1-one Rotational Isomer 1, Example 58 and Rotational Isomer 2, Example 59

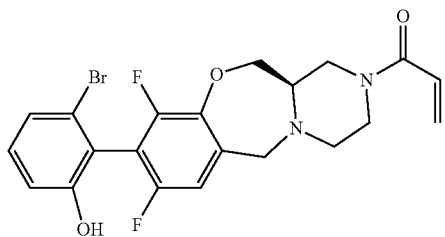 [SMILES: C=CC(=O)N1CCN2Cc3cc(F)c(-c4c(O)cccc4Br)c(F)c3OC[C@H]2C1]

Acryloyl chloride (9.02 µl, 0.11 mmol) was added dropwise to 3-bromo-2-[(12aR)-8,10-difluoro-1,2,3,4,12,12a-hexahydro-6H-pyrazino[2,1-c][1,4]benzoxazepin-9-yl]phenol (65 mg, 0.11 mmol) and DIPEA (0.039 mL, 0.22 mmol) in THF (4 mL) at 0° C. The resulting mixture was stirred at 0° C. for 1 h. The solvent was removed under reduced pressure. The crude product obtained was purified by preparative HPLC (Column: SunFire C18 OBD Prep Column, 100 Å, 5 µm, 19 mm×250 mm) eluting with water (0.1% TFA) and MeCN, to give rotational isomer 1 of 1-[(12aR)-9-(2-bromo-6-hydroxyphenyl)-8,10-difluoro-3,4,12,12a-tetrahydro-6H-pyrazino[2,1-c][1,4]benzoxazepin-2(1H)-yl]prop-2-en-1-one (6 mg, 6%) as a white solid. 1H NMR (400 MHz, DMSO, 30° C.) 2.61-3.23 (3H, m), 3.50-4.62 (8H, m), 5.65-5.79 (1H, m), 6.06-6.21 (1H, m), 6.76-6.92 (1H, m), 6.94-6.98 (1H, m), 7.03-7.29 (3H, m), 10.15 (1H, s). m/z: ES+ [M+H]+=465. This was followed by rotational isomer 2 of 1-[(12aR)-9-(2-bromo-6-hydroxyphenyl)-8,10-difluoro-3,4,12,12a-tetrahydro-6H-pyrazino[2,1-c][1,4]benzoxazepin-2(1H)-yl]prop-2-en-1-one (9 mg, 15%) as a white solid. 1H NMR (400 MHz, DMSO, 30° C.) 2.56-4.51 (11H, m), 5.62-5.83 (1H, m), 6.08-6.21 (1H, m), 6.72-6.89 (1H, m), 6.92-7.02 (1H, m), 7.03-7.25 (3H, m), 10.12 (1H, s). m/z: ES+ [M+H]+=465.

(12aR)-9-Bromo-8-chloro-10-fluoro-1,2,3,4,12,12a-hexahydro-6H-pyrazino[2,1-c][1,4]benzoxazepine

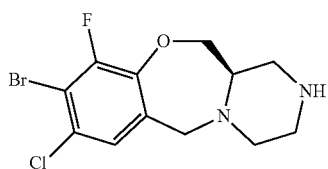 [SMILES: Fc1c(Br)c(Cl)cc2c1OC[C@H]1CNCCN1C2]

N-Chlorosuccinimide (0.666 g, 4.98 mmol) was added to tert-butyl (12aR)-9-bromo-10-fluoro-3,4,12,12a-tetrahydro-6H-pyrazino[2,1-c][1,4]benzoxazepine-2(1H)-carboxylate (1 g, 2.49 mmol) in concentrated sulfuric acid (15 mL). The resulting mixture was stirred at 25° C. for 16 h. The reaction mixture was poured into ice water (100 ml) and neutralised with 2M NaOH then extracted with DCM (100 mL×3). The organic layer was dried (Na₂SO₄) and evaporated to afford a yellow oil. The crude product obtained was purified by C18-flash chromatography, elution gradient 40 to 80% MeOH in water to give (12aR)-9-bromo-8-chloro-10-fluoro-1,2,3,4,12,12a-hexahydro-6H-pyrazino[2,1-c][1,4]benzoxazepine (0.6 g, 72%) as a yellow solid. 1H NMR (400 MHz, DMSO, 30° C.) 2.28-2.45 (2H, m), 2.62-2.75 (3H, m), 2.79-2.88 (2H, m), 3.67-3.71 (1H, m), 3.71-3.81 (2H, m), 4.20-4.31 (1H, m), 7.44 (1H, d). m/z: ES+ [M+H]+=335.

(12aR)-10-Chloro-8-fluoro-9-(2-methoxy-6-methylphenyl)-1,2,3,4,12,12a-hexahydro-6H-pyrazino[2,1-c][1,4]benzoxazepine

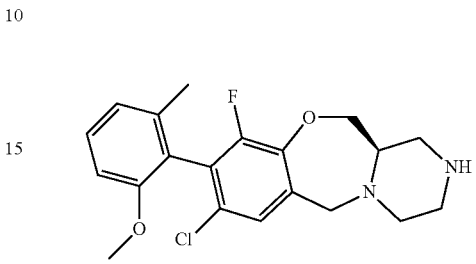

RuPhos-Pd-G3 (74.8 mg, 0.09 mmol) and RuPhos (41.7 mg, 0.09 mmol) were added (12aR)-9-bromo-8-chloro-10-fluoro-1,2,3,4,12,12a-hexahydro-6H-pyrazino[2,1-c][1,4]benzoxazepine (300 mg, 0.89 mmol), (2-methoxy-6-methylphenyl)boronic acid (297 mg, 1.79 mmol) and potassium phosphate, (311 mg, 1.79 mmol) in 1,4-dioxane (8 mL) and water (2 mL) (4:1 ratio) at 20° C. The resulting mixture was stirred at 100° C. for 40 min. The solvent was removed under reduced pressure and the crude product obtained purified by C18-flash chromatography, elution gradient 0 to 100% MeOH in water (0.1% formic acid) to give (12aR)-10-chloro-8-fluoro-9-(2-methoxy-6-methylphenyl)-1,2,3,4,12,12a-hexahydro-6H-pyrazino[2,1-c][1,4]benzoxazepine (280 mg, 74%) as a brown solid. 1H NMR (400 MHz, DMSO, 30° C.) 1.90-2.01 (3H, m), 2.05-2.10 (1H, m), 2.22 (1H, s), 2.62-2.96 (3H, m), 3.26-3.58 (2H, m), 3.56-3.76 (5H, m), 3.75-3.96 (1H, m), 4.19-4.41 (1H, m), 6.62-6.80 (1H, m), 6.87-7 (1H, m), 7.27-7.41 (1H, m), 7.98 (1H, s). m/z: ES+ [M+H]+=377.

2-[(12aR)-10-Chloro-8-fluoro-1,2,3,4,12,12a-hexahydro-6H-pyrazino[2,1-c][1,4]benzoxazepin-9-yl]-3-methylphenol

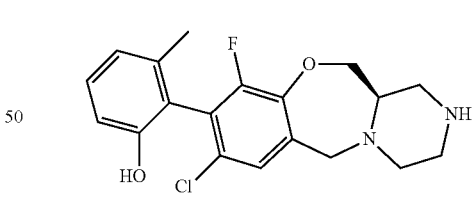

1M boron tribromide in DCM (5.11 mL, 5.11 mmol) was added to (12aR)-10-chloro-8-fluoro-9-(2-methoxy-6-methylphenyl)-1,2,3,4,12,12a-hexahydro-6H-pyrazino[2,1-c][1,4]benzoxazepine and formic acid (270 mg, 0.64 mmol) in DCM (3 mL) at 0° C. The resulting mixture was stirred at rt for 4 h. The reaction mixture was quenched with MeOH (25 mL) and the solvent was removed under reduced pressure. The crude product obtained was purified by C18-flash chromatography, elution gradient 0 to 100% MeCN in water (0.1% NH₄OH) to give 2-[(12aR)-10-chloro-8-fluoro-1,2,3,4,12,12a-hexahydro-6H-pyrazino[2,1-c][1,4]benzoxazepin-9-yl]-3-methylphenol (148 mg, 64%) as a brown solid. 1H NMR (400 MHz, DMSO, 30° C.) 1.93 (3H, d), 2.25-2.37

(3H, m), 2.59-2.68 (2H, m), 2.68-2.82 (3H, m), 3.61-3.74 (2H, m), 4.04-4.12 (1H, m), 4.18-4.27 (1H, m), 6.72-6.79 (2H, m), 7.07-7.16 (1H, m), 7.26-7.31 (1H, m), 9.36 (1H, s). m/z: ES+ [M+H]+=363.

1-[(12aR)-8-Chloro-10-fluoro-9-(2-hydroxy-6-methylphenyl)-3,4,12,12a-tetrahydro-6H-pyrazino[2,1-c] [1,4]benzoxazepin-2(1H)-yl]prop-2-en-1-one Rotational Isomer 1, Example 60 and Rotational Isomer 2, Example 61

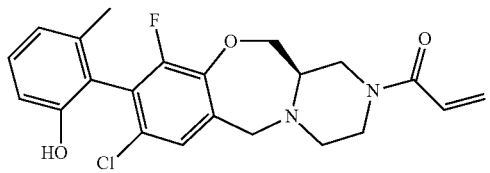 [SMILES: C=CC(=O)N1CCN2Cc3cc(Cl)c(-c4c(C)cccc4O)c(F)c3OC[C@H]2C1]

Acryloyl chloride (35 mg, 0.39 mmol) and DIPEA (0.135 mL, 0.77 mmol) were added to 2-[(12aR)-10-chloro-8-fluoro-1,2,3,4,12,12a-hexahydro-6H-pyrazino[2,1-c][1,4] benzoxazepin-9-yl]-3-methylphenol (140 mg, 0.39 mmol) in DMF (3 mL) at −20° C. The resulting mixture was stirred at −20° C. for 1 h. The mixture was filtered through a filter membrane. The filtrate was purified by preparative HPLC (Column: Sunfire prep C18 column 30*150, 5 μm), eluting with water (0.1% formic acid) and MeCN), to give rotational isomer 1 of 1-[(12aR)-8-chloro-10-fluoro-9-(2-hydroxy-6-methylphenyl)-3,4,12,12a-tetrahydro-6H-pyrazino[2,1-c][1, 4]benzoxazepin-2(1H)-yl]prop-2-en-1-one (40 mg, 25%) as a white solid. 1H NMR (400 MHz, DMSO, 30° C.) 1.95 (3H, s), 2.38-2.43 (1H, m), 2.63-3.07 (3H, m), 3-3.19 (1H, m), 3.64-4.21 (5H, m), 4.33-4.42 (1H, m), 5.70 (1H, d), 6.13 (1H, d), 6.72-6.90 (3H, m), 7.12 (1H, t), 7.31 (1H, s), 9.37 (1H, s). m/z: ES+ [M+H]+=417. This was followed by rotational isomer 2 of 1-[(12aR)-8-chloro-10-fluoro-9-(2-hydroxy-6-methylphenyl)-3,4,12,12a-tetrahydro-6H-pyrazino[2,1-c][1,4]benzoxazepin-2(1H)-yl]prop-2-en-1-one (24 mg, 15%) as a white solid. 1H NMR (400 MHz, DMSO, 30° C.) 1.91 (3H, s), 2.38-2.43 (1H, m), 2.73-2.77 (1H, m), 2.84-2.89 (2H, m), 3.07-3.12 (1H, m), 3.67-3.81 (2H, m), 3.81-4.10 (3H, m), 4.36-4.41 (1H, m), 5.70 (1H, d), 6.13 (1H, d), 6.72-6.90 (3H, m), 7.12 (1H, t), 7.31 (1H, s), 9.35 (1H, s). m/z: ES+ [M+H]+=417.

Tert-butyl (3R)-4-(4-bromo-5-chloro-2-fluorobenzoyl)-3-(hydroxymethyl)piperazine-1-carboxylate

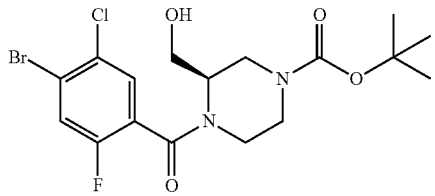 [SMILES: CC(C)(C)OC(=O)N1CCN(C(=O)c2cc(Cl)c(Br)cc2F)[C@@H](CO)C1]

DIPEA (6.89 mL, 39.46 mmol) was added to 4-bromo-5-chloro-2-fluorobenzoic acid (5 g, 19.73 mmol), tert-butyl (3R)-3-(hydroxymethyl)piperazine-1-carboxylate (4.27 g, 19.73 mmol) and HATU (15.00 g, 39.46 mmol) in DMF (100 mL) at 0° C. The resulting mixture was stirred at rt for 2 h. The reaction mixture was diluted with EtOAc (250 mL), washed with water (200 mL×2) and brine (200 mL×2). The organic layer was dried (Na2SO4) and evaporated to afford crude product. This was purified by flash silica chromatography, elution gradient 0 to 25% EtOAc in petroleum ether to give tert-butyl (3R)-4-(4-bromo-5-chloro-2-fluorobenzoyl)-3-(hydroxymethyl)piperazine-1-carboxylate (6 g, 67%) as a yellow solid. 1H NMR (300 MHz, DMSO, 30° C.) 1.40 (9H, d), 2.75-3.28 (2H, m), 3.39-3.60 (4H, m), 3.68-4.15 (2H, m), 4.18-4.59 (1H, m), 4.92 (1H, s), 7.62-7.79 (1H, m), 7.87-7.97 (1H, m). m/z: ES+ [M+H]+=451.

Tert-butyl (12aR)-9-bromo-8-chloro-6-oxo-3,4,12, 12a-tetrahydro-6H-pyrazino[2,1-c][1,4]benzoxazepine-2(1H)-carboxylate

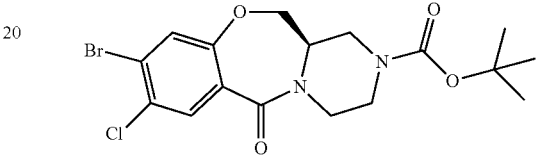

Sodium hydride (1.54 g, 38.52 mmol) was added to tert-butyl (3R)-4-(4-bromo-5-chloro-2-fluorobenzoyl)-3-(hydroxymethyl)piperazine-1-carboxylate (5.8 g, 12.84 mmol) in DMF (120 mL) at 0° C. The resulting mixture was stirred at rt for 2 h. The reaction mixture was quenched with water, diluted with EtOAc (200 mL) and washed with water (200 mL×2) and brine (200 mL×2). The organic layer was dried (Na2SO4) and evaporated to afford crude product. This was purified by flash silica chromatography, elution gradient 0 to 25% EtOAc in petroleum ether to give tert-butyl (12aR)-9-bromo-8-chloro-6-oxo-3,4,12,12a-tetrahydro-6H-pyrazino[2,1-c][1,4]benzoxazepine-2(1H)-carboxylate (5.4 g, 97%) as a white solid. 1H NMR (300 MHz, DMSO, 30° C.) 1.42 (9H, s), 3.25-3.81 (5H, m), 3.88-4.05 (2H, m), 4.24-4.35 (2H, m), 7.55 (1H, s), 7.89 (1H, s). m/z: ES+ [M+H]+=431.

Tert-butyl (12aR)-9-bromo-8-chloro-3,4,12,12a-tetrahydro-6H-pyrazino[2,1-c][1,4]benzoxazepine-2 (1H)-carboxylate

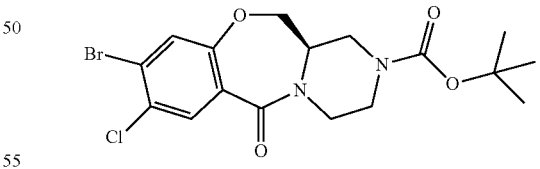

1M Borane-THF complex solution in THF (50 mL, 50 mmol) was added to afford tert-butyl (12aR)-9-bromo-8-chloro-6-oxo-3,4,12,12a-tetrahydro-6H-pyrazino[2,1-c][1, 4]benzoxazepine-2(1H)-carboxylate (5.2 g, 12.05 mmol) in THF (50 mL). The resulting mixture was stirred at 60° C. for 2 h. The reaction mixture was diluted with 2M HCl and EtOAc (200 mL) then washed sequentially with water (200 mL×2) and brine (200 mL). The organic layer was dried (Na2SO4) and evaporated to afford crude product. This was purified by flash silica chromatography, elution gradient 0 to 30% EtOAc in petroleum ether to give tert-butyl (12aR)-9- bromo-8-chloro-3,4,12,12a-tetrahydro-6H-pyrazino[2,1-c][1,4]benzoxazepine-2(1H)-carboxylate (4 g, 79%) as a white solid. 1H NMR (300 MHz, DMSO, 30° C.) 1.40 (9H, s), 2.22-2.39 (1H, m), 2.59-2.94 (3H, m), 2.99-3.16 (1H, m), 3.49-3.81 (5H, m), 4.15-4.29 (1H, m), 7.37 (1H, s), 7.55 (1H, s). m/z: ES+ [M+H]+=417.

(12aR)-9-Bromo-8-chloro-10-iodo-1,2,3,4,12,12a-hexahydro-6H-pyrazino[2,1-c][1,4]benzoxazepine

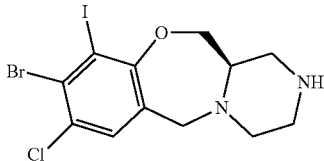 [SMILES: Clc1cc2c(c(I)c1Br)OC[C@H]1CNCCN1C2]

N-Iodosuccinimide (1.616 g, 7.18 mmol) was added to tert-butyl (12aR)-9-bromo-8-chloro-3,4,12,12a-tetrahydro-6H-pyrazino[2,1-c][1,4]benzoxazepine-2(1H)-carboxylate (1.5 g, 3.59 mmol) in concentrated sulfuric acid (15 mL). The resulting mixture was stirred at rt for 2 h. The reaction mixture was poured into ice water (100 mL), neutralised with 2M NaOH and extracted with DCM (150 mL×2) The organic layer was dried (Na$_2$SO$_4$) and evaporated to afford (12aR)-9-bromo-8-chloro-10-iodo-1,2,3,4,12,12a-hexahydro-6H-pyrazino[2,1-c][1,4]benzoxazepine (1.5 g, 94%) as a yellow solid. 1H NMR (300 MHz, DMSO, 30° C.) 2.54-2.66 (1H, m), 2.71-2.91 (4H, m), 2.96-3.19 (2H, m), 3.49-3.83 (3H, m), 4.16-4.39 (1H, m), 7.62 (1H, s). m/z: ES+ [M+H]+=443.

Tert-butyl (12aR)-9-bromo-8-chloro-10-iodo-3,4,12,12a-tetrahydro-6H-pyrazino[2,1-c][1,4]benzoxazepine-2(1H)-carboxylate

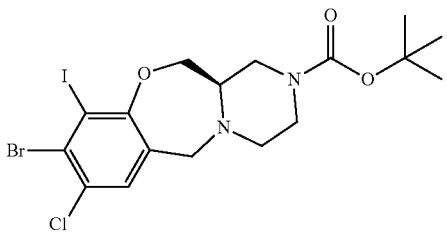 [SMILES: CC(C)(C)OC(=O)N1CCN2Cc3cc(Cl)c(Br)c(I)c3OC[C@H]2C1]

Di-tert-butyl dicarbonate (1.183 mL, 5.10 mmol) was added to (12aR)-9-bromo-8-chloro-10-iodo-1,2,3,4,12,12a-hexahydro-6H-pyrazino[2,1-c][1,4]benzoxazepine (1.13 g, 2.55 mmol) and triethylamine (1.065 mL, 7.64 mmol) in DCM (20 mL). The resulting mixture was stirred at 0° C. for 2 h. The solvent was removed under reduced pressure. The crude product obtained was purified by flash silica chromatography, elution gradient 0 to 50% THF in petroleum ether to give tert-butyl (12aR)-9-bromo-8-chloro-10-iodo-3,4,12,12a-tetrahydro-6H-pyrazino[2,1-c][1,4]benzoxazepine-2(1H)-carboxylate (0.75 g, 54%) as a brown solid. 1H NMR (300 MHz, DMSO, 30° C.) 1.39 (9H, s), 2.26-2.35 (1H, m), 2.62-2.66 (1H, m), 2.75-2.80 (1H, m), 3.08-3.17 (1H, m), 3.45-3.62 (4H, m), 3.66-3.74 (1H, m), 3.74-3.82 (1H, m), 4.19-4.33 (1H, m), 7.63 (1H, s). m/z: ES+ [M+H]+=543.

Tert-butyl (12aR)-9-bromo-8-chloro-10-[(trimethylsilyl)ethynyl]-3,4,12,12a-tetrahydro-6H-pyrazino[2,1-c][1,4]benzoxazepine-2(1H)-carboxylate

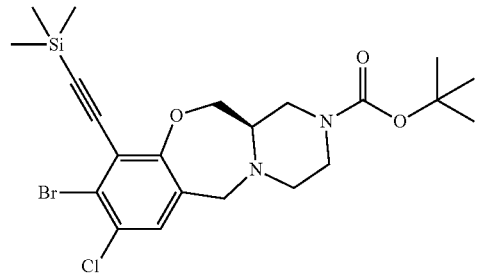 [SMILES: CC(C)(C)OC(=O)N1CCN2Cc3cc(Cl)c(Br)c(C#C[Si](C)(C)C)c3OC[C@H]2C1]

Tetrakis(triphenylphosphine)palladium(0) (149 mg, 0.13 mmol) was added to tert-butyl (12aR)-9-bromo-8-chloro-10-iodo-3,4,12,12a-tetrahydro-6H-pyrazino[2,1-c][1,4]benzoxazepine-2(1H)-carboxylate (700 mg, 1.29 mmol), ethynyltrimethylsilane (632 mg, 6.44 mmol), copper (1) iodide (245 mg, 1.29 mmol) and triethylamine (0.718 mL, 5.15 mmol) in toluene (10 mL). The resulting mixture was stirred at 100° C. overnight. The solvent was removed under reduced pressure. The crude product obtained was purified by flash silica chromatography, elution gradient 0 to 80% THF in petroleum ether to give tert-butyl (12aR)-9-bromo-8-chloro-10-[(trimethylsilyl)ethynyl]-3,4,12,12a-tetrahydro-6H-pyrazino[2,1-c][1,4]benzoxazepine-2(1H)-carboxylate (560 mg, 85%) as a brown solid. 1H NMR (400 MHz, DMSO, 30° C.) 0.25 (9H, s), 1.39 (9H, s), 2.25-2.35 (1H, m), 2.64-2.71 (1H, m), 2.71-2.75 (2H, m), 2.84-2.88 (1H, m), 3.05-3.16 (2H, m), 3.59-3.68 (1H, m), 3.68-3.74 (1H, m), 3.70-3.81 (1H, m), 4.26-4.35 (1H, m), 7.58 (1H, s). m/z: ES+ [M+H]+=513.

Tert-butyl (12aR)-8-chloro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate

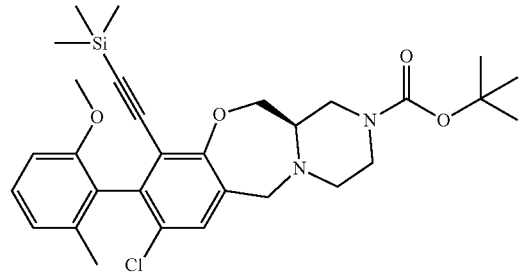 [SMILES: COc1cccc(C)c1-c1c(Cl)cc2c(c1C#C[Si](C)(C)C)OC[C@H]1CN(C(=O)OC(C)(C)C)CCN1C2]

RuPhos-Pd-G3 (81 mg, 0.10 mmol) was added to tert-butyl (12aR)-9-bromo-8-chloro-10-[(trimethylsilyl)ethynyl]-3,4,12,12a-tetrahydro-6H-pyrazino[2,1-c][1,4]benzoxazepine-2(1H)-carboxylate (500 mg, 0.97 mmol), RuPhos (45.4 mg, 0.1 mmol), (2-methoxy-6-methylphenyl)boronic acid (323 mg, 1.95 mmol) and K$_2$CO$_3$ (269 mg, 1.95 mmol) in 1,4-dioxane (8 mL) and water (2 mL) (4:1 ratio). The resulting mixture was stirred at 100° C. for 40 min. The solvent was removed under reduced pressure. The crude product obtained was purified by flash silica chromatography, elution gradient 0 to 100% THF in petroleum ether to give tert-butyl (12aR)-8-chloro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate (500 mg, 93%) as a brown solid. 1H NMR (400 MHz, DMSO, 30° C.) −0.09 (9H, s), 1.40 (9H, d), 1.86-2.01 (3H, m), 2.26-2.42 (1H, m), 2.56-2.70 (2H, m), 2.70-2.88 (2H, m), 2.90-3.17 (2H, m), 3.56-3.67 (3H, m), 3.63-3.73 (2H, m), 3.76-3.84 (1H, m), 4.28-4.37 (1H, m), 6.83-6.95 (2H, m), 7.22-7.32 (1H, m), 7.38-7.47 (1H, m). m/z: ES+ [M+H]+= 555.

(12aR)-8-Chloro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl

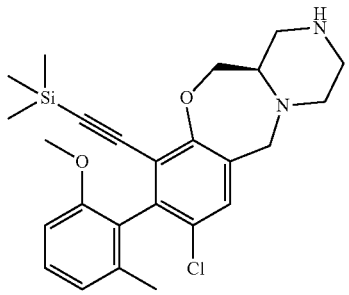 [SMILES: COc1cccc(C)c1-c1c(Cl)cc2c(c1C#C[Si](C)(C)C)OC[C@H]1CNCCN1C2]

Tert-butyl (12aR)-8-chloro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate (500 mg, 0.9 mmol) was added to 4M HCl in 1,4-dioxane (5 mL). The resulting mixture was stirred at 20° C. for 40 min. The solvent was removed under reduced pressure to afford (12aR)-8-chloro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl (440 mg, 99%) as a brown solid. 1H NMR (400 MHz, DMSO, 30° C.) −0.08 (9H, d), 1.87-1.96 (3H, m), 3.05-3.09 (2H, m), 3.26-3.31 (3H, m), 3.59-3.71 (4H, m), 3.81 (2H, s), 3.96-4.04 (2H, m), 4.30-4.35 (1H, m), 4.52-4.60 (1H, m), 6.87-6.97 (2H, m), 7.24-7.33 (1H, m), 7.58-7.63 (1H, m). m/z: ES+ [M+H]+=455.

2-[(12aR)-8-Chloro-10-ethynyl-1,2,3,4,12,12a-hexahydro-6H-pyrazino[2,1-c][1,4]benzoxazepin-9-yl]-3-methylphenol

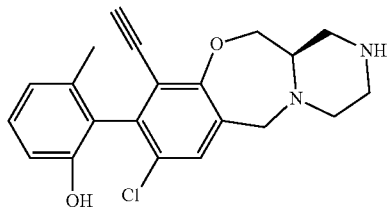 [SMILES: C#Cc1c2c(cc(Cl)c1-c1c(C)cccc1O)CN1CCNC[C@@H]1CO2]

1M Boron tribromide in DCM (7.16 mL, 7.16 mmol) was added to (12aR)-8-chloro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl (440 mg, 0.9 mmol) in DCM (5 mL). The resulting mixture was stirred at 20° C. for 2 h. The reaction mixture was quenched with MeOH (25 mL) and the solvent was removed under reduced pressure. The crude product obtained was purified by C18-flash chromatography, elution gradient 0 to 100% MeCN in water (0.1% NH4OH) to give 2-[(12aR)-8-chloro-10-ethynyl-1,2,3,4,12,12a-hexahydro-6H-pyrazino[2,1-c][1,4]benzoxazepin-9-yl]-3-methylphenol (200 mg, 61%) as a yellow solid. 1H NMR (400 MHz, DMSO, 30° C.) 1.83-1.93 (3H, m), 2.29-2.41 (4H, m), 2.61-2.65 (1H, m), 2.65-2.75 (1H, m), 2.75-2.79 (1H, m), 2.79-2.91 (1H, m), 3.57-3.69 (1H, m), 3.68-3.79 (1H, m), 3.96 (1H, s), 4.21-4.30 (1H, m), 6.65-6.75 (2H, m), 7.02-7.10 (1H, m), 7.42-7.47 (1H, m), 9.16 (1H, d). m/z: ES+ [M+H]+=369.

1-[(12aR)-8-Chloro-10-ethynyl-9-(2-hydroxy-6-methylphenyl)-3,4,12,12a-tetrahydro-6H-pyrazino[2,1-c][1,4]benzoxazepin-2(1H)-yl]prop-2-en-1-one Rotational Isomer 1, Example 62 and Rotational Isomer 2, Example 63

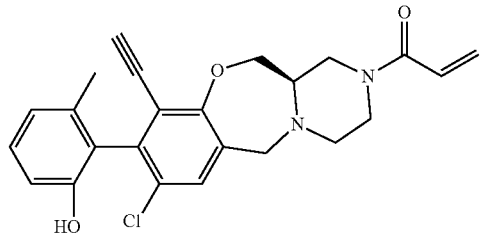 [SMILES: C#Cc1c2c(cc(Cl)c1-c1c(C)cccc1O)CN1CCN(C(=O)C=C)C[C@@H]1CO2]

Acryloyl chloride (46.6 mg, 0.51 mmol) and DIPEA (0.176 mL, 1.01 mmol) were added 2-[(12aR)-8-chloro-10-ethynyl-1,2,3,4,12,12a-hexahydro-6H-pyrazino[2,1-c][1,4]benzoxazepin-9-yl]-3-methylphenol (186 mg, 0.5 mmol) in DMF (3 mL) at −20° C. The resulting mixture was stirred at −20° C. for 1 h. The mixture was filtered at rt and the filtrate purified by preparative HPLC (Column: Xselect CSH OBD Column 30*150 mm 5 μm), eluting with water (0.1% formic acid) and MeCN, to give rotational isomer 1 of 1-[(12aR)-8-chloro-10-ethynyl-9-(2-hydroxy-6-methylphenyl)-3,4,12,12a-tetrahydro-6H-pyrazino[2,1-c][1,4]benzoxazepin-2(1H)-yl]prop-2-en-1-one (14 mg, 6%) as a white solid. 1H NMR (400 MHz, DMSO, 30° C.) 1.90 (3H, s), 2.35-2.42 (1H, m), 2.68-2.73 (1H, m), 2.80-2.88 (2H, m), 3.02-3.12 (1H, m), 3.57-3.78 (2H, m), 3.78-3.94 (2H, m), 3.94-4.13 (2H, m), 4.29-4.42 (1H, m), 5.66-5.74 (1H, m), 6.08-6.18 (1H, m), 6.67-6.74 (1H, m), 6.76-6.89 (1H, m), 7.06 (1H, t), 7.46 (1H, s), 9.14 (1H, s). m/z: ES+ [M+H]+=423. This was followed by rotational isomer 2 of 1-[(12aR)-8-chloro-10-ethynyl-9-(2-hydroxy-6-methylphenyl)-3,4,12,12a-tetrahydro-6H-pyrazino[2,1-c][1,4]benzoxazepin-2(1H)-yl]prop-2-en-1-one (27 mg, 13%) as a white solid. 1H NMR (400 MHz, DMSO, 30° C.) 1.90 (3H, s), 2.35-2.42 (1H, m), 2.68-2.73 (1H, m), 2.80-2.88 (2H, m), 3.02-3.12 (1H, m), 3.57-3.78 (2H, m), 3.78-3.94 (2H, m), 3.94-4.13 (2H, m), 4.29-4.42 (1H, m), 5.66-5.74 (1H, m), 6.08-6.18 (1H, m), 6.67-6.91 (3H, m), 7.06 (1H, t), 7.46 (1H, s), 9.14 (1H, s). m/z: ES+ [M+H]+=423.

(12aR)-9-Bromo-8-fluoro-10-iodo-1,2,3,4,12,12a-hexahydro-6H-pyrazino[2,1-c][1,4]benzoxazepine

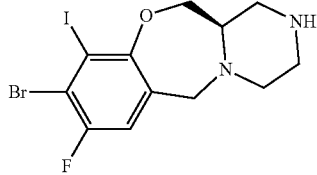

N-Iodosuccinimide (3.36 g, 14.95 mmol) was added to tert-butyl (12aR)-9-bromo-8-fluoro-3,4,12,12a-tetrahydro-6H-pyrazino[2,1-c][1,4]benzoxazepine-2(1H)-carboxylate (1.5 g, 3.74 mmol) in concentrated sulfuric acid (15 mL). The resulting mixture was stirred at rt for 2 h. The reaction mixture was poured into ice water (100 mL). The aqueous solution was neutralised with 2M NaOH and extracted with DCM (150 mL×2). The organic layer was dried (Na$_2$SO$_4$) and evaporated to afford (12aR)-9-bromo-8-fluoro-10-iodo-1,2,3,4,12,12a-hexahydro-6H-pyrazino[2,1-c][1,4]benzoxazepine (1.5 g, 94%) as a yellow solid. 1H NMR (400 MHz, DMSO, 30° C.) 2.65-2.78 (1H, m), 2.84-3.06 (3H, m), 3.11-3.29 (3H, m), 3.53-3.63 (1H, m), 3.65-3.86 (2H, m), 4.20-4.41 (1H, m), 7.43 (1H, d). m/z: ES+ [M+H]+=427.

Tert-butyl (12aR)-9-bromo-8-fluoro-10-iodo-3,4,12,12a-tetrahydro-6H-pyrazino[2,1-c][1,4]benzoxazepine-2(1H)-carboxylate

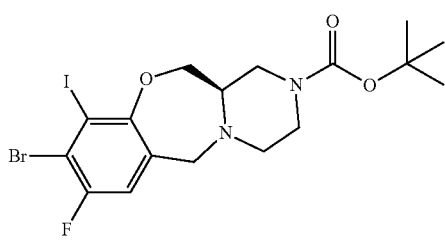

Di-tert-butyl dicarbonate (0.87 mL, 3.75 mmol) was added to (12aR)-9-bromo-8-fluoro-10-iodo-1,2,3,4,12,12a-hexahydro-6H-pyrazino[2,1-c][1,4]benzoxazepine (800 mg, 1.87 mmol) and triethylamine (0.783 mL, 5.62 mmol) in DCM (20 mL) at 0° C. The resulting mixture was stirred at 0° C. for 2 h. The solvent was removed under reduced pressure. The crude product was purified by flash silica chromatography, elution gradient 0 to 60% THF in petroleum ether, to give tert-butyl (12aR)-9-bromo-8-fluoro-10-iodo-3,4,12,12a-tetrahydro-6H-pyrazino[2,1-c][1,4]benzoxazepine-2(1H)-carboxylate (780 mg, 79%) as a pale yellow solid. 1H NMR (400 MHz, DMSO, 30° C.) 1.39 (9H, s), 2.25-2.35 (1H, m), 2.60-2.68 (1H, m), 2.75-2.82 (2H, m), 3.08-3.19 (1H, m), 3.45-3.61 (3H, m), 3.63-3.74 (1H, m), 3.76-3.84 (1H, m), 4.23-4.36 (1H, m), 7.41 (1H, d). m/z: ES+ [M+H]+=527.

Tert-butyl (12aR)-9-bromo-8-fluoro-10-[(trimethylsilyl)ethynyl]-3,4,12,12a-tetrahydro-6H-pyrazino[2,1-c][1,4]benzoxazepine-2(1H)-carboxylate

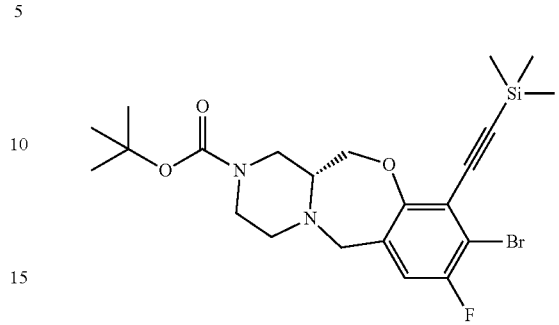

Tetrakis(triphenylphosphine)palladium(0) (123 mg, 0.11 mmol) and copper(I) iodide (202 mg, 1.06 mmol) were added to tert-butyl (12aR)-9-bromo-8-fluoro-10-iodo-3,4,12,12a-tetrahydro-6H-pyrazino[2,1-c][1,4]benzoxazepine-2(1H)-carboxylate (560 mg, 1.06 mmol), ethynyltrimethylsilane (417 mg, 4.25 mmol) and triethylamine (0.592 mL, 4.25 mmol) in toluene (15 mL). The resulting mixture was stirred at 80° C. overnight. The solvent was removed under reduced pressure. The crude product obtained was purified by flash silica chromatography, elution gradient 0 to 60% THF in petroleum ether to give tert-butyl (12aR)-9-bromo-8-fluoro-10-[(trimethylsilyl)ethynyl]-3,4,12,12a-tetrahydro-6H-pyrazino[2,1-c][1,4]benzoxazepine-2(1H)-carboxylate (400 mg, 76%) as a brown solid. 1H NMR (400 MHz, DMSO, 30° C.) 0.26 (9H, s), 1.39 (9H, s), 2.28-2.36 (1H, m), 2.65-2.73 (3H, m), 3.05-3.18 (1H, m), 3.48-3.73 (5H, m), 4.23-4.35 (1H, m), 7.26-7.49 (1H, m). m/z: ES+ [M+H]+=497.

Tert-butyl (12aR)-8-fluoro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate

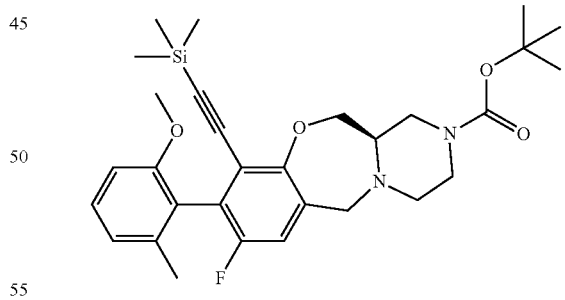

RuPhos-Pd-G3 (67.2 mg, 0.08 mmol) was added to tert-butyl (12aR)-9-bromo-8-fluoro-10-[(trimethylsilyl)ethynyl]-3,4,12,12a-tetrahydro-6H-pyrazino[2,1-c][1,4]benzoxazepine-2(1H)-carboxylate (400 mg, 0.8 mmol), (2-methoxy-6-methylphenyl)boronic acid (267 mg, 1.61 mmol), K$_2$CO$_3$ (222 mg, 1.61 mmol) and RuPhos (37.5 mg, 0.08 mmol) in 1,4-dioxane (10 mL) and water (2 mL) (5:1 ratio). The resulting mixture was stirred at 100° C. for 40 min. The solvent was removed under reduced pressure. The crude product obtained was purified by flash silica chromatography, elution gradient 0 to 60% THF in petroleum ether to give tert-butyl (12aR)-8-fluoro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate (400 mg, 92%) as a brown solid. 1H NMR (400 MHz, DMSO, 30° C.) –0.07 (9H, s), 1.40 (9H, d), 1.91-2.04 (3H, m), 2.27-3.35 (1H, m), 2.61-2.85 (3H, m), 2.98-3.08 (1H, m), 3.55-3.64 (3H, m), 3.63-3.66 (4H, m), 3.72-3.84 (1H, m), 4.25-4.35 (1H, m), 6.77-7.04 (2H, m), 7.14-7.32 (2H, m). m/z: ES+ [M+H]+=539.

(12aR)-8-Fluoro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl

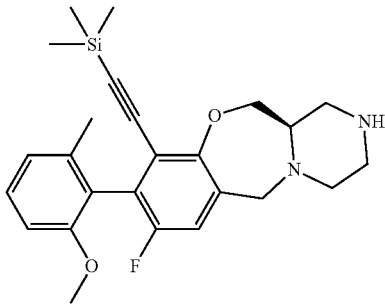 [SMILES: COc1cccc(C)c1-c1c(F)cc2c(c1C#C[Si](C)(C)C)OC[C@H]1CNCCN1C2]

Tert-butyl (12aR)-8-fluoro-9-(2-methoxy-6-methylphenyl)-10-[(trimethylsilyl)ethynyl]-3,4,12,12a-tetrahydro-6H-pyrazino[2,1-c][1,4]benzoxazepine-2(1H)-carboxylate (400 mg, 0.74 mmol) was added to 4M HCl in 1,4-dioxane (5 mL). The resulting mixture was stirred at 20° C. for 1 h. The solvent was removed under reduced pressure to afford (12aR)-8-fluoro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl (350 mg, 99%) as a brown solid. 1H NMR (400 MHz, DMSO, 30° C.) –0.05 (9H, s), 1.87-2.05 (5H, m), 3.03-3.07 (2H, m), 3.25-3.29 (3H, m), 3.58-3.75 (5H, m), 3.94-3.99 (1H, m), 4.49-4.57 (1H, m), 6.87-6.97 (3H, m), 7.34-7.40 (1H, m). m/z: ES+ [M+H]+=439.

2-{(12aR)-8-Fluoro-10-[(trimethylsilyl)ethynyl]-1,2,3,4,12,12a-hexahydro-6H-pyrazino[2,1-c][1,4]benzoxazepin-9-yl}-3-methylphenol

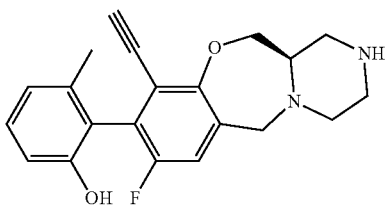 [SMILES: C#Cc1c2c(cc(F)c1-c1c(C)cccc1O)CN1CCNC[C@@H]1CO2]

1M Boron tribromide in DCM (4.72 mL, 4.72 mmol) was added to afford (12aR)-8-fluoro-9-(2-methoxy-6-methylphenyl)-10-[(trimethylsilyl)ethynyl]-1,2,3,4,12,12a-hexahydro-6H-pyrazino[2,1-c][1,4]benzoxazepine.1HCl (350 mg, 0.59 mmol) in DCM (4 mL). The resulting mixture was stirred at 20° C. for 4 h. The reaction mixture was quenched with MeOH (25 mL) and the solvent removed under reduced pressure. The crude product obtained was purified by C18-flash chromatography, elution gradient 0 to 100% MeCN in water (0.1% NH4OH) to give 2-{(12aR)-8-fluoro-10-[(trimethylsilyl)ethynyl]-1,2,3,4,12,12a-hexahydro-6H-pyrazino[2,1-c][1,4]benzoxazepin-9-yl}-3-methylphenol (125 mg, 60%) as a brown solid. 1H NMR (400 MHz, DMSO, 30° C.) 1.94 (3H, d), 2.24-2.36 (4H, m), 2.57-2.68 (1H, m), 2.72-2.85 (3H, m), 3.52-3.61 (1H, m), 3.65-3.77 (1H, m), 3.98 (1H, d), 4.16-4.25 (1H, m), 6.65-6.75 (2H, m), 7.03-7.11 (1H, m), 7.19 (1H, d), 9.21 (1H, d). m/z: ES+ [M+H]+=353.

1-[(12aR)-10-Ethynyl-8-fluoro-9-(2-hydroxy-6-methylphenyl)-3,4,12,12a-tetrahydro-6H-pyrazino[2,1-c][1,4]benzoxazepin-2(1H)-yl]prop-2-en-1-one Rotational Isomer 1, Example 64 and Rotational Isomer 2, Example 65

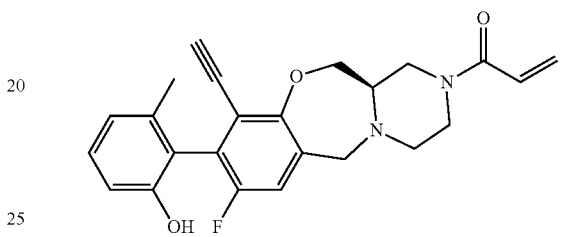

Acryloyl chloride (31 mg, 0.34 mmol) and DIPEA (0.116 mL, 0.66 mmol) were added to 2-{(12aR)-8-fluoro-10-[(trimethylsilyl)ethynyl]-1,2,3,4,12,12a-hexahydro-6H-pyrazino[2,1-c][1,4]benzoxazepin-9-yl}-3-methylphenol (117 mg, 0.33 mmol) in DMF (1.5 mL) at –20° C. The resulting mixture was stirred at –20° C. for 1 h. The mixture was filtered and the filtrate purified by preparative HPLC (Column: Sunfire prep C18 column 30*150, 5 μm), eluting with water (0.1% formic acid) and MeCN, to give rotational isomer 1 of 1-[(12aR)-10-ethynyl-8-fluoro-9-(2-hydroxy-6-methylphenyl)-3,4,12,12a-tetrahydro-6H-pyrazino[2,1-c][1,4]benzoxazepin-2(1H)-yl]prop-2-en-1-one (29 mg, 21%) as a white solid. 1H NMR (400 MHz, DMSO, 30° C.) 1.96 (3H, s), 2.35-2.40 (1H, m), 2.69-2.75 (1H, m), 2.79-2.86 (2H, m), 3.04-3.12 (1H, m), 3.54-3.64 (1H, m), 3.64-3.72 (1H, m), 3.77-3.91 (2H, m), 3.89-4.10 (2H, m), 4.27-4.40 (1H, m), 5.65-5.72 (1H, m), 6.08-6.17 (1H, m), 6.68-6.75 (2H, m), 6.76-6.87 (1H, m), 7.07 (1H, t), 7.21 (1H, d), 9.23 (1H, s). m/z: ES+ [M+H]+=407. This was followed by rotational isomer 2 of 1-[(12aR)-10-ethynyl-8-fluoro-9-(2-hydroxy-6-methylphenyl)-3,4,12,12a-tetrahydro-6H-pyrazino[2,1-c][1,4]benzoxazepin-2(1H)-yl]prop-2-en-1-one (34 mg, 26%) as a white solid. 1H NMR (400 MHz, DMSO, 30° C.) 1.96 (3H, s), 2.35-2.40 (1H, m), 2.69-2.75 (1H, m), 2.79-2.86 (2H, m), 3.04-3.12 (1H, m), 3.51-3.72 (2H, m), 3.77-3.91 (2H, m), 3.89-4.10 (2H, m), 4.27-4.40 (1H, m), 5.65-5.72 (1H, m), 6.08-6.17 (1H, m), 6.68-6.90 (3H, m), 7.07 (1H, t), 7.21 (1H, d), 9.23 (1H, s). m/z: ES+ [M+H]+=407.

Methyl 2-chloro-4-fluoropyridine-3-carboxylate

A mixture of 2-chloro-4-fluoropyridine-3-carboxylic acid (10 g, 56.97 mmol) and potassium carbonate (11.81 g, 85.45 mmol) in DMF (100 mL) was treated with iodomethane (4.26 mL, 68.36 mmol) and stirred at rt for 2 h. The mixture was partitioned between EtOAc and water then organics were washed with water then brine then dried and evaporated to afford a dark brown oil. The crude product was purified by flash silica chromatography, elution gradient 0 to 30% EtOAc in heptane to give methyl 2-chloro-4-fluoropyridine-3-carboxylate (7.9 g, 73%) as a colourless oil. 1H NMR (400 MHz, CDCl$_3$) 4.00 (3H, s), 7.09 (1H, dd), 8.44 (1H, dd).

Methyl 2,5-dichloro-4-fluoropyridine-3-carboxylate

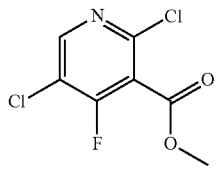

Methyl 2-chloro-4-fluoropyridine-3-carboxylate (7.9 g, 41.67 mmol) was dissolved in THF (100 mL) and the mixture was cooled t −45° C. and lithium magnesium 2,2,6,6-tetramethylpiperidin-1-ide dichloride (1M solution, 45.8 mL, 45.84 mmol) was added dropwise. The mixture was stirred for 20 min at −45° C. then a solution of perchloroethane (12.33 g, 52.09 mmol) in THF (10 mL) was added dropwise and the mixture was stirred at −45° C. for 1.5 h. The mixture was quenched by addition of saturated ammonium chloride then partitioned between EtOAc and water. The organics were washed with brine then dried and evaporated. The crude product was purified by flash silica chromatography, elution gradient 0 to 50% EtOAc in heptane to give methyl 2,5-dichloro-4-fluoropyridine-3-carboxylate (6.33 g, 68%) as a colourless oil. 1H NMR (400 MHz, CDCl$_3$) 4.01 (3H, s), 8.46 (1H, d).

2,5-Dichloro-4-fluoropyridine-3-carbaldehyde

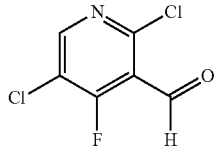 [SMILES: O=Cc1c(Cl)ncc(Cl)c1F]

Methyl 2,5-dichloro-4-fluoropyridine-3-carboxylate (6.1 g, 27.23 mmol) was dissolved in DCM (100 mL) and the mixture was cooled to −78° C. Diisobutylaluminum hydride (1M in toluene, 28.6 mL, 28.59 mmol) was added dropwise over ~20 min keeping temperature <−70° C., then the mixture was stirred at −78° C. for 1 h. The mixture was quenched by dropwise addition of 1M HCl (40 mL) then mixture was allowed to warm to rt and stirred for 20 min. The mixture was diluted with DCM (300 mL) and water (300 mL) then organics were separated. The aqueous layer was extracted with DCM (150 mL) then combined organics were dried and evaporated to afford 2,5-dichloro-4-fluoropyridine-3-carbaldehyde (5.1 g, 97%) as a colourless oil. 1H NMR (400 MHz, CDCl3, 30° C.) 8.57 (1H, d), 10.37 (1H, d).

Tert-butyl (3R)-4-[(2,5-dichloro-4-fluoropyridin-3-yl)methyl]-3-(hydroxymethyl)piperazine-1-carboxylate

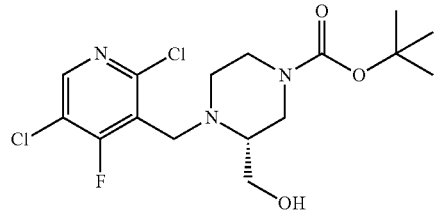 [SMILES: CC(C)(C)OC(=O)N1CCN(Cc2c(Cl)ncc(Cl)c2F)[C@@H](CO)C1]

2,5-Dichloro-4-fluoropyridine-3-carbaldehyde (5.1 g, 26.29 mmol) was dissolved in DCM (112 mL) and acetic acid (0.158 g, 2.63 mmol) was added followed by tert-butyl (R)-3-(hydroxymethyl)piperazine-1-carboxylate (6.82 g, 31.55 mmol) and the mixture was stirred for 1 h. Sodium triacetoxyhydroborate (8.36 g, 39.44 mmol) was added and the mixture was stirred at rt overnight. More sodium triacetoxyhydroborate (2.79 g, 13.1 mmol) was added and the mixture was stirred for 4 h. Saturated sodium bicarbonate solution (100 mL) was added portionwise and the mixture was stirred until effervescence ceased. The mixture was diluted with DCM (200 mL) then organics were separated, dried and evaporated then purified by flash silica chromatography, elution gradient 0 to 50% EtOAc in heptane to give tert-butyl (3R)-4-[(2,5-dichloro-4-fluoropyridin-3-yl)methyl]-3-(hydroxymethyl)piperazine-1-carboxylate (5.7 g, 55%) as a colourless oil. 1H NMR (400 MHz, CDCl$_3$) 1.46 (9H, s), 2.38 (2H, s), 2.59-2.84 (2H, m), 3.29 (1H, s), 3.38-3.64 (3H, m), 3.64-3.75 (2H, m), 3.85 (1H, ddd), 4.03-4.19 (1H, m), 8.36 (1H, d). m/z: ES+ [M+H]+ 394.

Tert-butyl (6aR)-1,4-dichloro-6a,7,9,10-tetrahydro-12H-pyrazino[2,1-c]pyrido[3,4-f][1,4]oxazepine-8(6H)-carboxylate

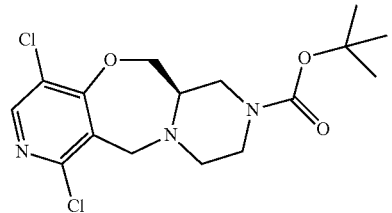 [SMILES: CC(C)(C)OC(=O)N1CCN2Cc3c(Cl)ncc(Cl)c3OC[C@H]2C1]

Tert-butyl (3R)-4-[(2,5-dichloro-4-fluoropyridin-3-yl)methyl]-3-(hydroxymethyl)piperazine-1-carboxylate (5.7 g, 14.46 mmol) was dissolved in THF (250 mL) and the mixture was cooled to 20° C. and 2-(tert-butylimino)-N,N-diethyl-1,3-dimethyl-1,3,2$\lambda^5$-diazaphosphinan-2-amine (4.59 mL, 15.9 mmol) was added in one portion. The mixture was stirred at 20° C. for 2 h. The mixture was evaporated then partitioned between EtOAc and water. The organics were washed with saturated sodium bicarbonate solution then brine then dried and evaporated to afford tert-butyl (6aR)-1,4-dichloro-6a,7,9,10-tetrahydro-12H-pyrazino[2,1-c]pyrido[3,4-f][1,4]oxazepine-8(6H)-carboxylate (5.5 g, >100%) as a colourless oil that was used without further purification. 1H NMR (400 MHz, CDCl$_3$) 1.47 (9H, s), 2.59 (1H, td), 2.69-2.79 (1H, m), 2.79-2.92 (1H, m), 2.93-3.09 (1H, m), 3.09-3.23 (1H, m), 3.87 (3H, dd), 4.03 (1H, dd), 4.08-4.18 (1H, m), 4.38 (1H, dd), 8.20 (1H, d). m/z: ES+ [M+H]+ 375.

Tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate

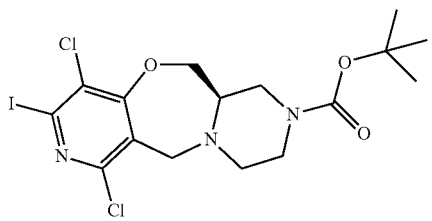 [SMILES: CC(C)(C)OC(=O)N1CCN2Cc3c(Cl)nc(I)c(Cl)c3OC[C@H]2C1]

Tert-butyl (6aR)-1,4-dichloro-6a,7,9,10-tetrahydro-12H-pyrazino[2,1-c]pyrido[3,4-f][1,4]oxazepine-8(6H)-carboxylate (5 g, 13.36 mmol) in dry THF (50 mL) was cooled to −45° C. and lithium magnesium 2,2,6,6-tetramethylpiperidin-1-ide dichloride (20.04 mL, 20.04 mmol) was added dropwise. The mixture was stirred at −45° C. for 20 min then iodine (5.09 g, 20.04 mmol) was added in one portion. The mixture was stirred at −45° C. for 15 min then mixture was allowed to warm to 0° C. then quenched by dropwise addition of saturated ammonium chloride solution (5 mL). The mixture was diluted with water (100 mL) then extracted into EtOAc (100 mL). The organics were washed with sodium thiosulfate solution then brine then dried and evaporated to afford a brown oil. The crude product was purified by flash silica chromatography, elution gradient 0 to 40% EtOAc in heptane, to give tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate (4.7 g, 70%) as a yellow oil. 1H NMR (400 MHz, CDCl3) 1.46 (9H, d), 2.48-2.7 (1H, m), 2.7-2.9 (2H, m), 3.01 (1H, s), 3.15 (1H, t), 3.73-3.9 (3H, m), 3.95-4.17 (2H, m), 4.38 (1H, dt). m/z: ES+ [M+H]+ 500.

Tert-butyl (6aR)-1,4-dichloro-3-(2-fluoro-6-methoxyphenyl)-6a,7,9,10-tetrahydro-12H-pyrazino[2,1-c]pyrido[3,4-f][1,4]oxazepine-8(6H)-carboxylate

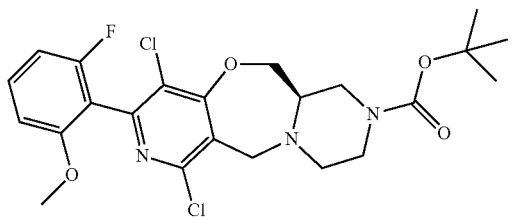 [SMILES: COc1cccc(F)c1-c1nc(Cl)c2c(c1Cl)OC[C@H]1CN(C(=O)OC(C)(C)C)CCN1C2]

Tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate (2.5 g, 5 mmol), (2-fluoro-6-methoxyphenyl)boronic acid (1.104 g, 6.5 mmol), RuPhos (0.233 g, 0.5 mmol), RuPhos Pd G3 (0.418 g, 0.5 mmol) and 2M aqueous sodium carbonate (5 mL, 10 mmol) were stirred in dioxane (30 mL) and the mixture was degassed by bubbling nitrogen. The mixture was heated to 50° C. for 3 h, then partitioned between EtOAc and water, then the organics were washed with brine then dried and evaporated to afford a brown oil. This was purified by flash silica chromatography, elution gradient 0 to 60% EtOAc in heptane to give tert-butyl (6aR)-1,4-dichloro-3-(2-fluoro-6-methoxyphenyl)-6a,7,9,10-tetrahydro-12H-pyrazino[2,1-c]pyrido[3,4-f][1,4]oxazepine-8(6H)-carboxylate (1.83 g, 74%) as a yellow oil. 1H NMR (400 MHz, CDCl3) 1.48 (9H, d), 2.62 (1H, tdd), 2.75 (1H, ddd), 2.83-3.07 (2H, m), 3.06-3.25 (1H, m), 3.77 (3H, s), 3.8-4.04 (3H, m), 4-4.27 (2H, m), 4.43 (1H, dd), 6.72-6.82 (2H, m), 7.34 (1H, dd). m/z: ES+ [M+H]+ 498.

Tert-butyl (6aR)-4-chloro-3-(2-fluoro-6-methoxyphenyl)-1-oxo-2,6a,7,9,10,12-hexahydro-1H-pyrazino[2,1-c]pyrido[3,4-f][1,4]oxazepine-8(6H)-carboxylate

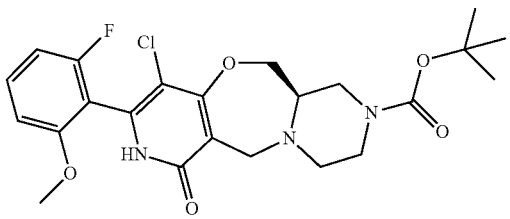 [SMILES: COc1cccc(F)c1-c1[nH]c(=O)c2c(c1Cl)OC[C@H]1CN(C(=O)OC(C)(C)C)CCN1C2]

Tert-butyl (6aR)-1,4-dichloro-3-(2-fluoro-6-methoxyphenyl)-6a,7,9,10-tetrahydro-12H-pyrazino[2,1-c]pyrido[3,4-f][1,4]oxazepine-8(6H)-carboxylate (1 g, 2.01 mmol) was dissolved in dioxane (10 mL)/water (2 mL) and caesium carbonate (1.961 g, 6.02 mmol) was added followed by tert-butyl Brettphos Pd G3 (0.171 g, 0.20 mmol) and the mixture was degassed. The mixture was stirred at rt overnight. The mixture was partitioned between EtOAc and water then the organics were dried and evaporated to afford a brown oil. The crude product was purified by flash silica chromatography, elution gradient 0 to 10% MeOH in DCM, to give tert-butyl (6aR)-4-chloro-3-(2-fluoro-6-methoxyphenyl)-1-oxo-2,6a,7,9,10,12-hexahydro-1H-pyrazino[2,1-c]pyrido[3,4-f][1,4]oxazepine-8(6H)-carboxylate (0.22 g, 23%) as a brown solid. 1H NMR (400 MHz, CDCl3) 1.47 (9H, s), 2.58 (2H, dd), 2.8-3.21 (3H, m), 3.59 (1H, d), 3.81 (3H, d), 3.95 (2H, s), 4.08 (2H, dd), 4.44 (1H, dd), 6.71-6.85 (2H, m), 7.35-7.47 (1H, m), 9.24 (1H, s). m/z: ES+ [M+H]+ 480.

Tert-butyl (6aR)-4-chloro-3-(2-fluoro-6-methoxyphenyl)-2-methyl-1-oxo-2,6a,7,9,10,12-hexahydro-1H-pyrazino[2,1-c]pyrido[3,4-f][1,4]oxazepine-8(6H)-carboxylate

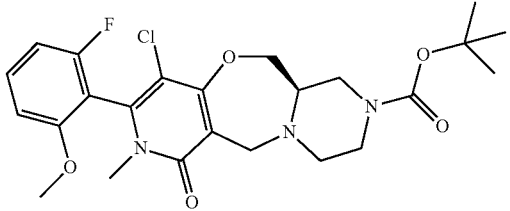 [SMILES: COc1cccc(F)c1-c1c(Cl)c2c(c(=O)n1C)CN1CCN(C(=O)OC(C)(C)C)C[C@@H]1CO2]

Tert-butyl (6aR)-4-chloro-3-(2-fluoro-6-methoxyphenyl)-1-oxo-2,6a,7,9,10,12-hexahydro-1H-pyrazino[2,1-c]

pyrido[3,4-f][1,4]oxazepine-8(6H)-carboxylate (0.22 g, 0.46 mmol) was dissolved in THF (4 mL) and sodium hydride (0.028 g, 0.69 mmol) was added. The mixture was stirred for 10 min then iodomethane (0.057 mL, 0.92 mmol) was added and the mixture was stirred at rt overnight. The mixture was quenched by addition of water then partitioned between water and EtOAc. The aqueous was extracted with EtOAc (×2) then combined organic extracts were dried and evaporated to afford a brown oil. This was purified by flash silica chromatography, elution gradient 0 to 8% MeOH in DCM to give tert-butyl (6aR)-4-chloro-3-(2-fluoro-6-methoxyphenyl)-2-methyl-1-oxo-2,6a,7,9,10,12-hexahydro-1H-pyrazino[2,1-c]pyrido[3,4-f][1,4]oxazepine-8(6H)-carboxylate (0.15 g, 66%) as a yellow oil. 1H NMR (400 MHz, CDCl$_3$) 1.47 (9H, s), 2.59 (2H, dd), 2.86-3.17 (3H, m), 3.26 (3H, d), 3.66 (1H, dd), 3.81 (3H, d), 3.84-4.01 (2H, m), 4.06 (1H, ddd), 4.15-4.28 (1H, m), 4.42 (1H, dd), 6.73-6.89 (2H, m), 7.38-7.52 (1H, m). m/z: ES+ [M+H]+ 494.

(6aR)-4-Chloro-3-(2-fluoro-6-hydroxyphenyl)-2-methyl-2,6,6a,7,8,9,10,12-octahydro-1H-pyrazino[2,1-c]pyrido[3,4-f][1,4]oxazepin-1-one Rotational Isomer 1 and Rotational Isomer 2

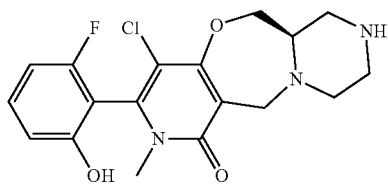 [SMILES: Cn1c(-c2c(O)cccc2F)c(Cl)c2c(c1=O)CN1CCNC[C@@H]1CO2]

Tert-Butyl (6aR)-4-chloro-3-(2-fluoro-6-methoxyphenyl)-2-methyl-1-oxo-2,6a,7,9,10,12-hexahydro-1H-pyrazino[2,1-c]pyrido[3,4-f][1,4]oxazepine-8(6H)-carboxylate (0.15 g, 0.3 mmol) was dissolved in DCM (3 mL) and boron tribromide (3.04 mL, 3.04 mmol) was added. The mixture was stirred at rt for 2 h, then heated at reflux overnight. The mixture was cooled in an ice bath then quenched by dropwise addition of methanol then mixture was purified by SCX (1M NH$_3$/MeOH) to afford a light brown oil. This was purified by preparative LCMS (Waters XSelect CSH C18 ODB column, 5µ silica, 30 mm diameter, 100 mm length), using of water (containing 0.1% formic acid) and MeCN as eluents. This gave rotational isomer 1 of (6aR)-4-chloro-3-(2-fluoro-6-hydroxyphenyl)-2-methyl-2,6,6a,7,8,9,10,12-octahydro-1H-pyrazino[2,1-c]pyrido[3,4-f][1,4]oxazepin-1-one (0.035 g, 27%) as a white solid. m/z: ES+ [M+H]+ 380. This was followed by rotational isomer 2 of (6aR)-4-chloro-3-(2-fluoro-6-hydroxyphenyl)-2-methyl-2,6,6a,7,8,9,10,12-octahydro-1H-pyrazino[2,1-c]pyrido[3,4-f][1,4]oxazepin-1-one (0.032 g, 25%) as a white solid. 1H NMR (400 MHz, CDCl$_3$) 2.75-2.92 (2H, m), 3-3.32 (6H, m), 3.35 (3H, s), 3.85-4.13 (2H, m), 4.23 (1H, d), 4.58 (1H, dd), 6.70 (1H, t), 6.94 (1H, d), 7.34 (1H, td). m/z: ES+ [M+H]+ 380.

(6aR)-4-Chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one Rotational Isomer 1, Example 66

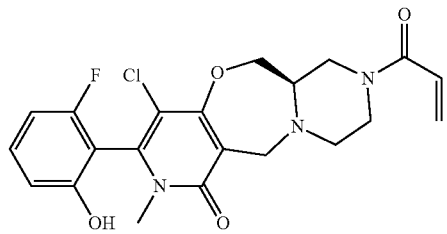 [SMILES: C=CC(=O)N1CCN2Cc3c(c(Cl)c(-c4c(O)cccc4F)n(C)c3=O)OC[C@H]2C1]

Rotational isomer 1 of (6aR)-4-Chloro-3-(2-fluoro-6-hydroxyphenyl)-2-methyl-2,6,6a,7,8,9,10,12-octahydro-1H-pyrazino[2,1-c]pyrido[3,4-f][1,4]oxazepin-1-one (0.035 g, 0.07 mmol) was dissolved in DCM (1 mL)/i-PrOH (1 mL) and triethylamine (0.02 mL, 0.15 mmol) was added followed by acryloyl chloride (6.59 µl, 0.08 mmol) and the mixture was stirred for 20 min at rt. A further portion of acryloyl chloride (6.59 µl, 0.08 mmol) was added and the mixture was stirred for 20 min. 1M NH$_3$/MeOH (2 mL) was added then the mixture was stirred for 10 min then evaporated to afford a colourless oil. The crude product was purified by preparative LCMS (Waters XSelect CSH C18 ODB column, 5µ silica, 30 mm diameter, 100 mm length), using of water (containing 1% NH$_3$) and MeCN as eluents. This gave rotational isomer 1 of (6aR)-4-chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one (7 mg, 22%) as a colourless dry film. 1H NMR (400 MHz, CDCl$_3$) 2.45-2.67 (2H, m), 2.96 (2H, dd), 3.33 (3H, s), 3.35-3.5 (1H, m), 3.64 (1H, d), 3.91 (1H, d), 4.02-4.2 (2H, m), 4.37 (2H, dd), 5.77 (1H, d), 6.35 (1H, d), 6.57 (1H, dd), 6.74 (1H, t), 6.91 (1H, d), 7.29-7.39 (1H, m), 8.27 (1H, s). m/z: ES+ [M+H]+ 434.

(6aR)-4-Chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one Rotational Isomer 2, Example 67

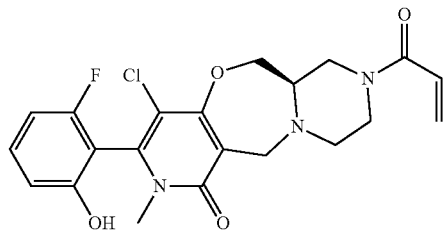 [SMILES: C=CC(=O)N1CCN2Cc3c(c(Cl)c(-c4c(O)cccc4F)n(C)c3=O)OC[C@H]2C1]

Rotational isomer 2 of (6aR)-4-Chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one (0.035 g, 0.09 mmol) was dissolved in DCM (1 mL)/i-PrOH (1 mL) and triethylamine (0.025 mL, 0.18 mmol) was added followed by acryloyl chloride (8.19 µl, 0.10 mmol) and the mixture was stirred for 20 min at rt. A further portion of acryloyl chloride (8.19 µl, 0.10 mmol) was added and the mixture was stirred for 20 min. 1M NH$_3$/

MeOH (2 mL) was added then the mixture was stirred for 10 min then evaporated to afford a colourless oil. This was purified by preparative LCMS (Waters XSelect CSH C18 ODB column, 5μ silica, 30 mm diameter, 100 mm length), using of water (containing 0.1% AcOH) and MeCN as eluents. This gave (6aR)-4-chloro-3-(2-fluoro-6-hydroxyphenyl)-2-methyl-8-(prop-2-enoyl)-2,6,6a,7,8,9,10,12-octahydro-1H-pyrazino[2,1-c]pyrido[3,4-f][1,4]oxazepin-1-one (0.015 g, 38%) as a colourless solid. 1H NMR (400 MHz, CDCl₃) 2.49-2.76 (2H, m), 2.87-3.02 (2H, m), 3.32 (4H, s), 3.59-3.96 (2H, m), 4.07 (1H, d), 4.16 (1H, d), 4.42 (2H, d), 5.73 (1H, d), 6.29 (1H, d), 6.54 (1H, dd), 6.73 (1H, t), 6.88 (1H, d), 7.32 (1H, td). m/z: ES+ [M+H]+ 434.

2-[(6aR)-1,4-Dichloro-6,6a,7,8,9,10-hexahydro-12H-pyrazino[2,1-c]pyrido[3,4-f][1,4]oxazepin-3-yl]-3-fluorophenol

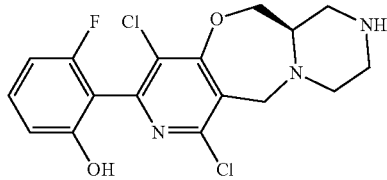 [SMILES: Oc1cccc(F)c1-c1nc(Cl)c2c(c1Cl)OC[C@H]1CNCCN1C2]

Tert-butyl (6aR)-1,4-dichloro-3-(2-fluoro-6-methoxyphenyl)-6a,7,9,10-tetrahydro-12H-pyrazino[2,1-c]pyrido[3,4-f][1,4]oxazepine-8(6H)-carboxylate (0.1 g, 0.2 mmol) was dissolved in DCM (2 mL) and boron tribromide (2.007 mL, 2.01 mmol) was added. The mixture was stirred at rt overnight. The mixture was cooled in an ice bath then quenched by dropwise addition of methanol and purified by SCX (1M NH₃/MeOH) to afford 2-[(6aR)-1,4-dichloro-6,6a,7,8,9,10-hexahydro-12H-pyrazino[2,1-c]pyrido[3,4-f][1,4]oxazepin-3-yl]-3-fluorophenol (0.045 g, 58.4%) as a colourless oil. m/z: ES+ [M+H]+ 384.

1-[(6aR)-1,4-Dichloro-3-(2-fluoro-6-hydroxyphenyl)-6a,7,9,10-tetrahydro-12H-pyrazino[2,1-c]pyrido[3,4-f][1,4]oxazepin-8(6H)-yl]prop-2-en-1-one, Example 68

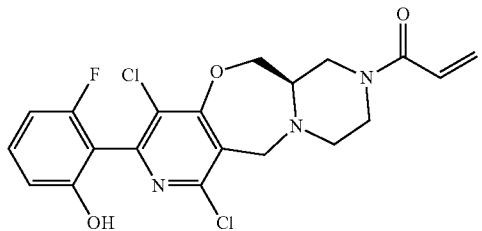 [SMILES: C=CC(=O)N1CCN2Cc3c(Cl)nc(-c4c(O)cccc4F)c(Cl)c3OC[C@H]2C1]

2-[(6aR)-1,4-Dichloro-6,6a,7,8,9,10-hexahydro-12H-pyrazino[2,1-c]pyrido[3,4-f][1,4]oxazepin-3-yl]-3-fluorophenol (0.042 g, 0.11 mmol) was dissolved in DCM (1 mL)/i-PrOH (1 mL) and triethylamine (0.022 g, 0.22 mmol) was added followed by acryloyl chloride (0.012 g, 0.13 mmol) and the mixture was stirred at rt for 1 h. The mixture was evaporated then purified by preparative HPLC (Waters XSelect CSH C18 ODB column, 5μ silica, 30 mm diameter, 100 mm length), using of water (containing 1% NH₃) and MeCN as eluents. This gave 1-[(6aR)-1,4-dichloro-3-(2-fluoro-6-hydroxyphenyl)-6a,7,9,10-tetrahydro-12H-pyrazino[2,1-c]pyrido[3,4-f][1,4]oxazepin-8(6H)-yl]prop-2-en-1-one (0.018 g, 38%) as a white solid. 1H NMR (400 MHz, DMSO) 2.56 (1H, s), 2.62-2.74 (1H, m), 2.78-3.05 (2H, m), 3.17 (1H, s), 3.89-4.21 (3H, m), 4.29 (2H, s), 4.66 (1H, s), 5.71 (1H, s), 6.14 (1H, d), 6.67-6.91 (3H, m), 7.24-7.35 (1H, m). m/z: ES+ [M+H]+ 438.

(6aR)-4-Chloro-3-(2-fluoro-6-hydroxyphenyl)-2,6,6a,7,8,9,10,12-octahydro-1H-pyrazino[2,1-c]pyrido[3,4-f][1,4]oxazepin-1-one

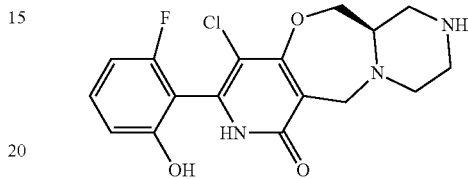

Tert-butyl (6aR)-4-chloro-3-(2-fluoro-6-methoxyphenyl)-1-oxo-2,6a,7,9,10,12-hexahydro-1H-pyrazino[2,1-c]pyrido[3,4-f][1,4]oxazepine-8(6H)-carboxylate (0.1 g, 0.21 mmol) was dissolved in DCM (2 mL) and boron tribromide (2.08 mL, 2.08 mmol) was added. The mixture was stirred at rt for 4 h, quenched with MeOH and purified by SCX (1M NH₃/MeOH) to afford (6aR)-4-chloro-3-(2-fluoro-6-hydroxyphenyl)-2,6,6a,7,8,9,10,12-octahydro-1H-pyrazino[2,1-c]pyrido[3,4-f][1,4]oxazepin-1-one (0.075 g, 98%) as a colourless oil. m/z: ES+ [M+H]+ 366.

(6aR)-4-Chloro-3-(2-fluoro-6-hydroxyphenyl)-8-(prop-2-enoyl)-2,6,6a,7,8,9,10,12-octahydro-1H-pyrazino[2,1-c]pyrido[3,4-f][1,4]oxazepin-1-one, Example 69

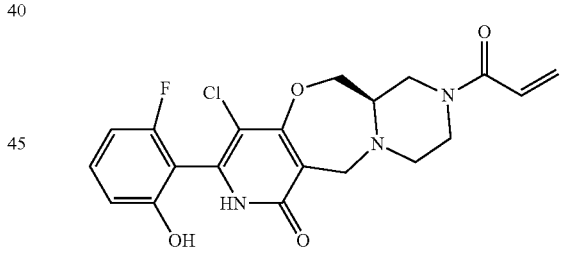

(6aR)-4-Chloro-3-(2-fluoro-6-hydroxyphenyl)-2,6,6a,7,8,9,10,12-octahydro-1H-pyrazino[2,1-c]pyrido[3,4-f][1,4]oxazepin-1-one (0.080 g, 0.22 mmol) was dissolved in DCM (1 mL)/i-PrOH (1 mL) and triethylamine (0.044 g, 0.44 mmol) was added followed by acryloyl chloride (0.024 g, 0.26 mmol) and the mixture was stirred at rt for 1 h. The mixture was evaporated then purified by preparative HPLC (Waters XSelect CSH C18 ODB column, 5μ silica, 30 mm diameter, 100 mm length), using of water (containing 1% NH₃) and MeCN as eluents. This gave (6aR)-4-chloro-3-(2-fluoro-6-hydroxyphenyl)-8-(prop-2-enoyl)-2,6,6a,7,8,9,10,12-octahydro-1H-pyrazino[2,1-c]pyrido[3,4-f][1,4]oxazepin-1-one (0.02 g, 22%) as a white solid. 1H NMR (400 MHz, CDCl₃) 2.55 (2H, d), 2.89 (2H, s), 3.35 (1H, s), 3.49 (1H, d), 3.99 (3H, s), 4.39 (2H, s), 5.72 (1H, d), 6.28 (1H, d), 6.44-6.58 (1H, m), 6.63 (1H, t), 6.79 (1H, d), 7.21 (1H, d). m/z: ES+ [M+H]+ 420.

Tert-Butyl (6aR)-4-chloro-1-[2-(diphenylmethylidene)hydrazinyl]-3-(2-fluoro-6-methoxyphenyl)-6a,7,9,10-tetrahydro-12H-pyrazino[2,1-c]pyrido[3,4-f][1,4]oxazepine-8(6H)-carboxylate

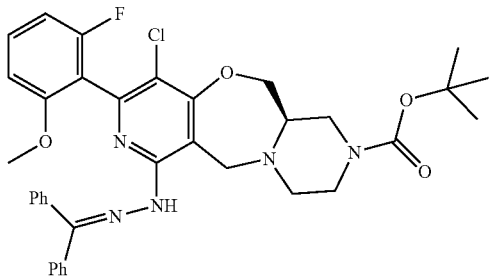 [SMILES: COc1cccc(F)c1-c1nc(NN=C(c2ccccc2)c2ccccc2)c2c(c1Cl)OC[C@H]1CN(C(=O)OC(C)(C)C)CCN1C2]

Tert-butyl (6aR)-1,4-dichloro-3-(2-fluoro-6-methoxyphenyl)-6a,7,9,10-tetrahydro-12H-pyrazino[2,1-c]pyrido[3,4-f][1,4]oxazepine-8(6H)-carboxylate (0.55 g, 1.1 mmol), potassium 2-methylpropan-2-olate (0.186 g, 1.66 mmol) and Xphos Pd G3 (0.093 g, 0.11 mmol) were dissolved in toluene (10 mL) and the mixture was degassed. (Diphenylmethylene)hydrazine (0.26 g, 1.32 mmol) was added and the mixture was stirred at rt for 20 min. The mixture was partitioned between EtOAc and water then the organics were washed with brine, dried and evaporated to afford a dark brown solid. The crude product was purified by flash silica chromatography, elution gradient 0 to 60% EtOAc in heptane to give tert-butyl (6aR)-4-chloro-1-[2-(diphenylmethylidene)hydrazinyl]-3-(2-fluoro-6-methoxyphenyl)-6a,7,9,10-tetrahydro-12H-pyrazino[2,1-c]pyrido[3,4-f][1,4]oxazepine-8(6H)-carboxylate (0.36 g, 50%) as a tan solid. 1H NMR (400 MHz, CDCl$_3$, 30° C.) 1.49 (9H, s), 2.44-2.6 (1H, m), 2.68 (1H, s), 2.92 (2H, d), 3.11 (1H, s), 3.74 (3H, d), 3.83-4.18 (4H, m), 4.36 (1H, dd), 4.55 (1H, dd), 6.67-6.78 (2H, m), 7.31 (6H, ddq), 7.4-7.48 (1H, m), 7.47-7.57 (4H, m), 7.96 (1H, s). m/z: ES+ [M+H]+ 658.

Tert-Butyl (6aR)-4-chloro-3-(2-fluoro-6-methoxyphenyl)-1-hydrazinyl-6a,7,9,10-tetrahydro-12H-pyrazino[2,1-c]pyrido[3,4-f][1,4]oxazepine-8(6H)-carboxylate

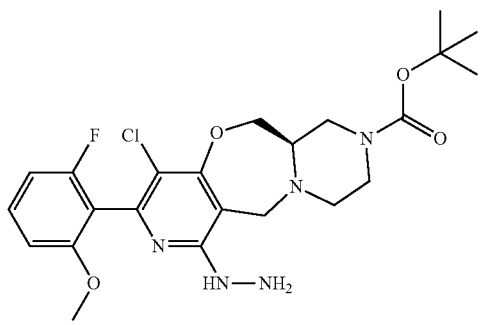 [SMILES: COc1cccc(F)c1-c1nc(NN)c2c(c1Cl)OC[C@H]1CN(C(=O)OC(C)(C)C)CCN1C2]

tert-Butyl (6aR)-4-chloro-1-[2-(diphenylmethylidene)hydrazinyl]-3-(2-fluoro-6-methoxyphenyl)-6a,7,9,10-tetrahydro-12H-pyrazino[2,1-c]pyrido[3,4-f][1,4]oxazepine-8(6H)-carboxylate (0.3 g, 0.46 mmol) was dissolved in MeOH (5 mL) and 2M HCl (5 ml, 10 mmol) was added and the mixture was stirred at rt for 4 h. The mixture was purified by SCX (1M NH$_3$/MeOH) to afford tert-butyl (6aR)-4-chloro-3-(2-fluoro-6-methoxyphenyl)-1-hydrazinyl-6a,7,9,10-tetrahydro-12H-pyrazino[2,1-c]pyrido[3,4-f][1,4]oxazepine-8(6H)-carboxylate (0.22 g, 98%) as a colourless oil. m/z: ES+ [M+H]+ 494.

2-[(8aR)-6-Chloro-8,8a,9,10,11,12-hexahydro-14H-pyrazino[2,1-c][1,2,4]triazolo[4',3':1,2]pyrido[3,4-f][1,4]oxazepin-5-yl]-3-fluorophenol Rotational Isomer 1 and Rotational Isomer 2

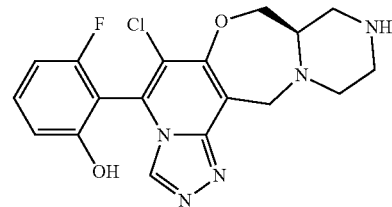 [SMILES: Oc1cccc(F)c1-c1c(Cl)c2c(c3nncn13)CN1CCNC[C@@H]1CO2]

tert-Butyl (6aR)-4-chloro-3-(2-fluoro-6-methoxyphenyl)-1-hydrazinyl-6a,7,9,10-tetrahydro-12H-pyrazino[2,1-c]pyrido[3,4-f][1,4]oxazepine-8(6H)-carboxylate (0.22 g, 0.45 mmol) was dissolved in trimethoxymethane (3 ml, 27.42 mmol) and the mixture was heated at 60° C. for 3 h. The mixture was evaporated to afford a brown oil. This was dissolved in DCM (5 mL) and boron tribromide (4.45 ml, 4.45 mmol) was added and the mixture, which was then heated at 40° C. for 3 h then cooled to rt and stirred overnight. The mixture was quenched with MeOH (10 ml) and purified by SCX (1M NH$_3$/MeOH) to afford a brown oil. This was purified by preparative LCMS (Waters XSelect CSH C18 ODB column, 5p silica, 30 mm diameter, 100 mm length), using of water (containing 0.1% formic acid) and MeCN as eluents, to give rotational isomer 1 of the title compound with impurities. This was purified by SCX (1M NH$_3$/MeOH) to afford rotational isomer 1 of 2-[(8aR)-6-chloro-8,8a,9,10,11,12-hexahydro-14H-pyrazino[2,1-c][1,2,4]triazolo[4',3':1,2]pyrido[3,4-f][1,4]oxazepin-5-yl]-3-fluorophenol (0.039 g, 22%) as a colourless film. 1H NMR (400 MHz, MeOD, 30° C.) 2.47-2.75 (3H, m), 2.81-3.12 (4H, m), 3.74-4.15 (2H, m), 4.41-4.5 (1H, m), 4.54 (1H, dd), 6.57-6.88 (2H, m), 7.46 (1H, d), 8.44-8.6 (1H, m). m/z: ES+ [M+H]+ 390. Further elution of the preparative LCMS gave rotational isomer 2 of 2-[(8aR)-6-chloro-8,8a,9,10,11,12-hexahydro-14H-pyrazino[2,1-c][1,2,4]triazolo[4',3':1,2]pyrido[3,4-f][1,4]oxazepin-5-yl]-3-fluorophenol (0.032 g, 18%). 1H NMR (400 MHz, MeOD, 30° C.) 2.57-2.72 (2H, m), 2.78-3.15 (5H, m), 3.9-4.11 (2H, m), 4.39-4.62 (2H, m), 6.7-6.92 (2H, m), 7.47 (1H, td), 8.53 (1H, s). m/z: ES+ [M+H]+ 390.

1-[(8aR)-6-Chloro-5-(2-fluoro-6-hydroxyphenyl)-8a, 9,11,12-tetrahydro-14H-pyrazino[2,1-c][1,2,4]triazolo[4',3':1,2]pyrido[3,4-f][1,4]oxazepin-10(8H)-yl]prop-2-en-1-one Rotational Isomer 1, Example 70

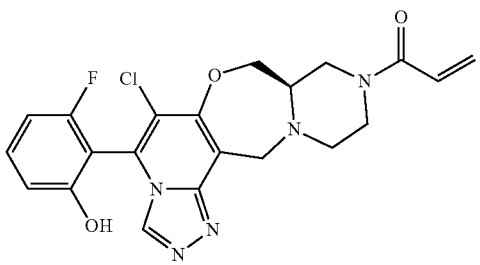 [SMILES: C=CC(=O)N1CCN2Cc3c(c(Cl)c(-c4c(O)cccc4F)n4cnnc34)OC[C@H]2C1]

Rotational isomer 1 of 2-[(8aR)-6-Chloro-8,8a,9,10,11,12-hexahydro-14H-pyrazino[2,1-c][1,2,4]triazolo[4',3':1,2]pyrido[3,4-f][1,4]oxazepin-5-yl]-3-fluorophenol (0.039 g, 0.1 mmol) was dissolved in DCM (0.5 mL)/i-PrOH (0.5 mL) and triethylamine (0.027 mL, 0.2 mmol) was added followed by acryloyl chloride (9.7 µL, 0.12 mmol) and the mixture was stirred at rt for 20 min. 1M $NH_3$ in MeOH (5 ml) was added and the mixture was stirred for 30 min. The mixture was evaporated then purified by preparative HPLC (Waters XSelect CSH C18 ODB column, 5µ silica, 30 mm diameter, 100 mm length), using of water (containing 0.1% $NH_3$) and MeCN as eluents. This gave 1-[(8aR)-6-Chloro-5-(2-fluoro-6-hydroxyphenyl)-8a,9,11,12-tetrahydro-14H-pyrazino[2,1-c][1,2,4]triazolo[4',3':1,2]pyrido[3,4-f][1,4]oxazepin-10(8H)-yl]prop-2-en-1-one (0.012 g, 27%) as a white solid. 1H NMR (400 MHz, DMSO, 30° C.) 2.54-2.63 (1H, m), 2.77 (1H, s), 2.82-3.2 (3H, m), 3.87-4.33 (4H, m), 4.41 (1H, s), 4.62 (1H, s), 5.72 (1H, s), 6.14 (1H, d), 6.77 (3H, d), 7.41 (1H, d), 8.59 (1H, s). m/z: ES+ [M+H]+ 444.

1-[(8aR)-6-Chloro-5-(2-fluoro-6-hydroxyphenyl)-8a, 9,11,12-tetrahydro-14H-pyrazino[2,1-c][1,2,4]triazolo[4',3':1,2]pyrido[3,4-f][1,4]oxazepin-10(8H)-yl]prop-2-en-1-one Rotational Isomer 2, Example 71

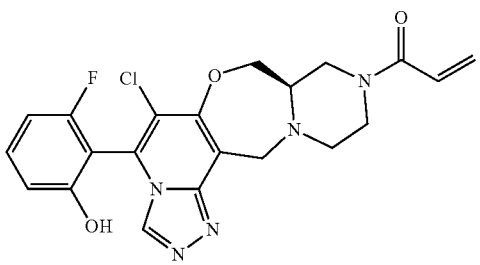 [SMILES: C=CC(=O)N1CCN2Cc3c(c(Cl)c(-c4c(O)cccc4F)n4cnnc34)OC[C@H]2C1]

Rotational isomer 2 of 2-[(8aR)-6-Chloro-8,8a,9,10,11,12-hexahydro-14H-pyrazino[2,1-c][1,2,4]triazolo[4',3':1,2]pyrido[3,4-f][1,4]oxazepin-5-yl]-3-fluorophenol (0.028 g, 0.07 mmol) was dissolved in DCM (0.5 mL)/i-PrOH (0.5 mL) and triethylamine (0.015 g, 0.14 mmol) was added followed by acryloyl chloride (7.8 mg, 0.09 mmol) and the mixture was stirred at rt for 20 min. 1M $NH_3$ in MeOH (5 ml) was added and the mixture was stirred for 30 min. Mixture was evaporated then purified by preparative HPLC (Waters XSelect CSH C18 ODB column, 5µ silica, 30 mm diameter, 100 mm length), using of water (containing 0.1% $NH_3$) and MeCN as eluents. This gave 1-[(8aR)-6-Chloro-5-(2-fluoro-6-hydroxyphenyl)-8a,9,11,12-tetrahydro-14H-pyrazino[2,1-c][1,2,4]triazolo[4',3':1,2]pyrido[3,4-f][1,4]oxazepin-10(8H)-yl]prop-2-en-1-one (0.013 g, 41%) as a white solid. 1H NMR (400 MHz, DMSO, 30° C.) 2.55 (1H, d), 2.77 (1H, s), 2.83-3.22 (3H, m), 3.91-4.21 (3H, m), 4.26 (1H, s), 4.40 (1H, s), 4.64 (1H, s), 5.72 (1H, s), 6.14 (1H, d), 6.85 (3H, d), 7.45 (1H, q), 8.62 (1H, s). m/z: ES+ [M+H]+ 444.

(2E)-N-(3-Bromo-5-fluoro-2-methylphenyl)-2-(hydroxyimino)acetamide

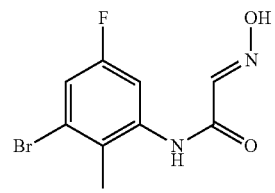

Sodium sulfate (5.57 g, 39.21 mmol), hydroxylamine hydrochloride (1.19 g, 17.15 mmol) and 2,2,2-trichloroethane-1,1-diol (1.21 g, 7.35 mmol) were dissolved in water (25 mL). A solution of 3-bromo-5-fluoro-2-methylaniline (1.0 g, 4.90 mmol) in water (2 mL), EtOH (3.5 mL) and conc. HCl (0.85 mL) was added and heated overnight at 60° C. The reaction was cooled to 25° C. forming a precipitate. The precipitate was collected by filtration and washed with excess water, then dried under vacuum to afford (2E)-N-(3-bromo-5-fluoro-2-methylphenyl)-2-(hydroxyimino)acetamide (1.08 g, 80%) as a light brown solid. 1H NMR (400 MHz, DMSO, 30° C.) 2.23 (3H, s), 7.34-7.53 (2H, m), 7.68 (1H, s), 9.79 (1H, s), 12.28 (1H, s). m/z: ES+ [M+H]+= 274.8.

6-Bromo-4-fluoro-7-methyl-1H-indole-2,3-dione

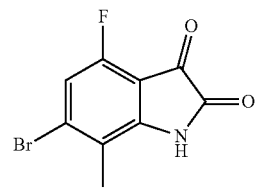

(2E)-N-(3-Bromo-5-fluoro-2-methylphenyl)-2-(hydroxyimino)acetamide (36.9 g, 107.32 mmol) was added portionwise to sulfuric acid (270 mL) at 60° C. The reaction mixture was then heated at 60° C. for 1 h. The reaction mixture was cooled to 25° C. and slowly added to ice water. The resulting precipitate was collected by filtration, washing with water and dried under vacuum to afford 6-bromo-4-fluoro-7-methyl-1H-indole-2,3-dione (25 g, 90%) as a dark red solid. 1H NMR (400 MHz, DMSO, 30° C.) 2.21 (3H, s), 7.30 (1H, d), 11.43 (1H, s). m/z: ES+ [M+H]+=257.9.

2-Amino-4-bromo-6-fluoro-3-methylbenzoic acid

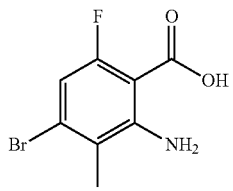

Hydrogen peroxide (30% in H₂O) (45 mL, 440.81 mmol) was added dropwise to 6-bromo-4-fluoro-7-methyl-1H-indole-2,3-dione (25 g, 88.16 mmol) in sodium hydroxide (2M in H₂O) (397 mL, 793.46 mmol) at 25° C. and the reaction was stirred for 3 h. Excess hydrogen peroxide was quenched by slow addition into an aqueous solution of sodium sulfite and the mixture neutralised to pH7. The brown precipitate was collected by filtration and discarded. The remaining solution was slowly acidified to pH4 with conc. HCl. The resulting solution was extracted with DCM (300 mL) and dried using a phase separating cartridge. The solvent was removed under reduced pressure to afford 2-amino-4-bromo-6-fluoro-3-methylbenzoic acid (21.71 g, 99%) as a cream solid. 1H NMR (400 MHz, DMSO, 30° C.) 2.17 (3H, s), 6.66 (1H, d). m/z: ES+ [M+H]+=247.8.

2-Amino-4-bromo-5-chloro-6-fluoro-3-methylbenzoic acid

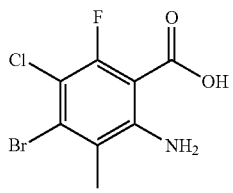

N-Chlorosuccinimide (13.1 g, 98.10 mmol) was added to 2-amino-4-bromo-6-fluoro-3-methylbenzoic acid (22.12 g, 89.18 mmol) in DMF (250 mL) at 25° C. The resulting solution was stirred to 70° C. for 2 h. The reaction mixture was cooled to 25° C. and diluted with water (500 mL). The resulting solid was extracted with EtOAc (1000 mL) and the layers were separated. The organic layer was washed with water (4×500 mL), brine (200 mL) and dried by passing through a phase separation cartridge. The solvent was removed under reduced pressure to afford 2-amino-4-bromo-5-chloro-6-fluoro-3-methylbenzoic acid (25 g, 99%) as a brown solid. m/z: ES− [M+H]+=281.

Methyl 2-amino-4-bromo-5-chloro-6-fluoro-3-methylbenzoate

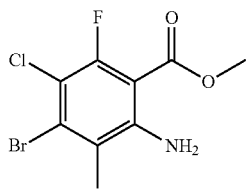

2-Amino-4-bromo-5-chloro-6-fluoro-3-methylbenzoic acid (21.62 g, 76.53 mmol) was dissolved in MeOH (214 mL) before sulfuric acid (40.8 mL, 765.33 mmol) was added slowly and the solution heated at 80° C. for 16 h and then cooled to rt. MeOH was removed under reduced pressure and the residue was diluted with excess ice and DCM (500 mL). The organic layer was dried over a phase separating cartridge and concentrated under reduced pressure to afford a red oil. This was purified by flash silica chromatography, elution gradient 0 to 50% EtOAc in heptane, to afford methyl 2-amino-4-bromo-5-chloro-6-fluoro-3-methylbenzoate (11.58 g, 51%) as a red oil which solidified on standing. 1H NMR (400 MHz, CDCl₃, 30° C.) 2.33 (3H, s), 3.92 (3H, s), 5.91 (2H, s). m/z: ES− [M−H]−=293.8.

Methyl 4-bromo-5-chloro-6-fluoro-1H-indazole-7-carboxylate

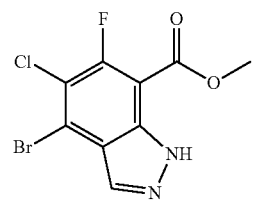 [SMILES: COC(=O)c1c(F)c(Cl)c(Br)c2cn[nH]c12]

To a stirred solution of methyl 2-amino-4-bromo-5-chloro-6-fluoro-3-methylbenzoate (5.08 g, 17.13 mmol) in chloroform (120 mL) was added potassium acetate (1.84 g, 18.85 mmol) at 25° C. The mixture was cooled to 0° C. and acetic anhydride (3.23 mL, 34.26 mmol) was added and stirred to 25° C. for 20 min. 18-Crown-6 (0.81 g, 3.08 mmol) and isopentyl nitrite (5.06 mL, 37.69 mmol) was added and the reaction was heated at 65° C. for 2 h and then returned to 25° C. Water (100 mL) was added and the organic layer was dried using a phase separating cartridge. The solvent was removed under reduced pressure to afford a red solid which was diluted with MeOH (200 mL) and conc. HCl (29.4 mL, 342.64 mmol). The suspension was stirred for 1 h at 25° C. The solvent was evaporated, and the residue was diluted with water (200 mL) and extracted with DCM (400 mL). The organic layer was washed with saturated NaHCO₃ (250 mL) and the organics dried by using a phase separating cartridge. The solid on the phase separating cartridge was dried under vacuum to afford methyl 4-bromo-5-chloro-6-fluoro-1H-indazole-7-carboxylate as a white solid (1.28 g). The solvent filtrate was concentrated under reduced pressure and the resulting solid was filtered under vacuum to afford additional methyl 4-bromo-5-chloro-6-fluoro-1H-indazole-7-carboxylate (2.43 g) as a white solid. The filtrate was loaded on to silica and purified by flash silica chromatography, elution gradient 0 to 50% EtOAc in heptane, to afford further methyl 4-bromo-5-chloro-6-fluoro-1H-indazole-7-carboxylate (0.46 g) as a white solid, to give an overall yield of 79%. 1H NMR (400 MHz, DMSO, 30° C.) 3.98 (3H, s), 8.25 (1H, d), 13.75 (1H, s). m/z: ES− [M−H]−=304.7.

159

Methyl 4-bromo-5-chloro-6-fluoro-1-methyl-1H-indazole-7-carboxylate

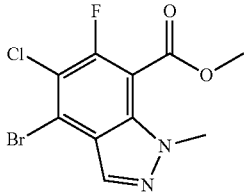 [SMILES: COC(=O)c1c(F)c(Cl)c(Br)c2cnn(C)c12]

To methyl 4-bromo-5-chloro-6-fluoro-1H-indazole-7-carboxylate (4.16 g, 13.53 mmol) in DMF (27 mL) was added caesium carbonate (5.28 g, 16.23 mmol) and iodomethane (1.01 mL, 16.23 mmol). The reaction was stirred at 25° C. for 3 h. The reaction was diluted with EtOAc (500 mL) and washed with water (2×250 mL) and brine (100 mL). The organic layer was dried over a phase separating cartridge and the solvent was removed under reduced pressure to afford crude product. This was purified by flash silica chromatography, elution gradient 0 to 100% EtOAc in heptane to give methyl 4-bromo-5-chloro-6-fluoro-1-methyl-1H-indazole-7-carboxylate (2.69 g, 62%) as a white solid. 1H NMR (400 MHz, CDCl$_3$, 30° C.) 4.03 (3H, s), 4.05 (3H, s), 8.00 (1H, s). m/z: ES+ [M+H]+=320.7.

4-Bromo-5-chloro-6-fluoro-1-methyl-1H-indazole-7-carboxylic acid

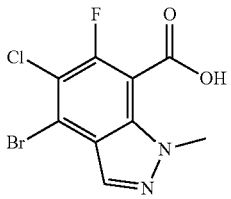 [SMILES: Cn1ncc2c(Br)c(Cl)c(F)c(C(=O)O)c21]

Sodium hydroxide (2M) (7.42 mL, 14.84 mmol) was added to methyl 4-bromo-5-chloro-6-fluoro-1-methyl-1H-indazole-7-carboxylate (1.59 g, 4.95 mmol) in THF (15 mL) at 70° C. for 5 h. The reaction was cooled to 25° C. and the solvent was removed under reduced pressure. The solution was acidified to pH4 using conc. HCl and the resulting solid was filtered under vacuum and washed with excess water.

The solid was dried for 16 h in a vacuum oven to afford 4-bromo-5-chloro-6-fluoro-1-methyl-1H-indazole-7-carboxylic acid (1.5 g, 99%) as a white solid. 1H NMR (400 MHz, DMSO, 30° C.) 4.04 (3H, s), 8.19 (1H, s), 14.58 (1H, s). m/z: ES+ [M+H]+=306.7.

160

Tert-butyl (3R)-4-(4-bromo-5-chloro-6-fluoro-1-methyl-1H-indazole-7-carbonyl)-3-(hydroxymethyl)piperazine-1-carboxylate

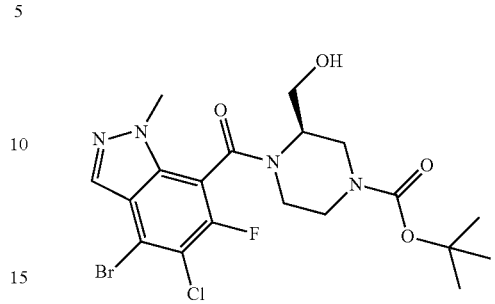

4-Bromo-5-chloro-6-fluoro-1-methyl-1H-indazole-7-carboxylic acid (1.59 g, 5.17 mmol), HATU (2.35 g, 6.20 mmol) and DIPEA (2.76 mL, 15.51 mmol) were stirred in DMF (25 mL) for 30 min then tert-butyl (3R)-3-(hydroxymethyl)piperazine-1-carboxylate (1.23 g, 5.69 mmol) was added and the mixture was stirred at 25° C. for 2 h. The reaction was diluted with EtOAc (300 mL) and washed with water (2×200 mL) and brine (100 mL). The organic layer was dried over a phase separating cartridge and the solvent was removed under reduced pressure to afford crude product as an orange oil. The crude product was purified by flash silica chromatography, elution gradient 0 to 100% EtOAc in heptane, to afford tert-butyl (3R)-4-(4-bromo-5-chloro-6-fluoro-1-methyl-1H-indazole-7-carbonyl)-3-(hydroxymethyl) piperazine-1-carboxylate (2.12 g, 81%) as an orange dry foam. m/z: ES+ [M-tBu]+=450.6.

Tert-butyl (7aR)-4-bromo-5-chloro-1-methyl-13-oxo-1,7a,8,10,11,13-hexahydropyrazino[2',1':3,4][1,4]oxazepino[7,6-g]indazole-9(7H)-carboxylate

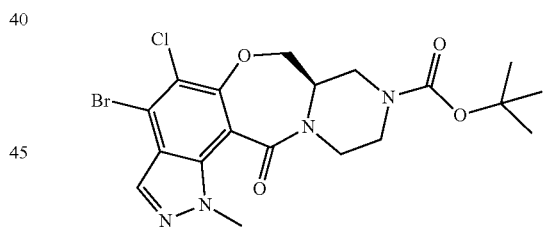

Sodium hydride (60% in mineral oil) (0.184 g, 4.61 mmol) was added in one portion to tert-butyl (3R)-4-(4-bromo-5-chloro-6-fluoro-1-methyl-1H-indazole-7-carbonyl)-3-(hydroxymethyl)piperazine-1-carboxylate (2.12 g, 4.19 mmol) in DMF (35 mL) at 0° C. The resulting solution was warmed to 25° C. and stirred for 2 h. The reaction mixture was diluted with water (300 mL) and extracted with EtOAc (500 mL). The organic layer was separated and washed with water (2×400 mL) and brine (50 mL). The organic layer was dried by passing through a phase separating cartridge and the solvent was removed under vacuum to afford crude product. This was purified by flash silica chromatography, elution gradient 0 to 10% MeOH in DCM to give tert-butyl (7aR)-4-bromo-5-chloro-1-methyl-13-oxo-1,7a,8,10,11,13-hexahydropyrazino[2',1':3,4][1,4]oxazepino[7,6-g]indazole-9(7H)-carboxylate (1.5 g, 74%) as a yellow solid. 1H NMR (400 MHz, DMSO, 100° C.) 1.46 (9H, s), 3.32-3.4 (1H, m), 3.44-3.53 (1H, m), 3.66-3.76

(1H, m), 4.01 (3H, s), 4.05-4.14 (2H, m), 4.14-4.25 (2H, m), 4.26-4.34 (1H, m), 4.38 (1H, dd), 8.05 (1H, s). m/z: ES+ [M+H]+=486.06.

Tert-butyl (7aR)-4-bromo-5-chloro-1-methyl-1,7a,8,10,11,13-hexahydropyrazino[2',1':3,4][1,4]oxazepino[7,6-g]indazole-9(7H)-carboxylate

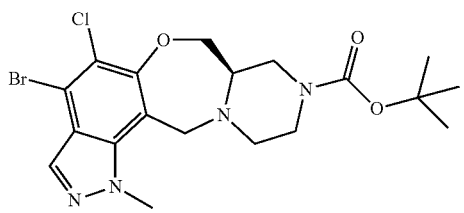 [SMILES: Cn1ncc2c(Br)c(Cl)c3c(c21)CN1CCN(C(=O)OC(C)(C)C)C[C@@H]1CO3]

A solution of borane-THF complex (1M) (23.06 mL, 23.06 mmol) was added dropwise to a stirred solution of tert-butyl (7aR)-4-bromo-5-chloro-1-methyl-13-oxo-1,7a,8,10,11,13-hexahydropyrazino [2',1':3,4][1,4]oxazepino[7,6-g]indazole-9(7H)-carboxylate (1.4 g, 2.88 mmol) in THF (5 mL) at 25° C. The resulting solution was stirred at 75° C. for 16 h. The reaction mixture was cooled to 25° C. and quenched with i-PrOH and NaOH (2M) and stirred for 20 min. The reaction was diluted with water (100 mL) and EtOAc (200 mL), layers separated, and the organic layer washed with brine (50 mL). The organics were dried over a phase separating cartridge and evaporated to afford a colourless oil which was purified by flash silica chromatography, elution gradient 0 to 100% EtOAc in heptane, to afford tert-butyl (7aR)-4-bromo-5-chloro-1-methyl-1,7a,8,10,11,13-hexahydropyrazino[2',1':3,4][1,4]oxazepino[7,6-g]indazole-9(7H)-carboxylate (0.73 g, 54%) as a white solid. 1H NMR (400 MHz, DMSO, 30° C.) 1.40 (9H, s), 2.44 (1H, td), 2.75 (2H, s), 2.85-2.95 (1H, m), 3.03 (1H, s), 3.65-3.75 (3H, m), 4.00 (1H, d), 4.22 (3H, s), 4.35-4.44 (2H, m), 7.94 (1H, s). m/z: ES+ [M+H]+=472.7.

Tert-butyl (7aR)-5-chloro-4-(2-fluoro-6-hydroxyphenyl)-1-methyl-1,7a,8,10,11,13-hexahydropyrazino[2',1':3,4][1,4]oxazepino[7,6-g]indazole-9(7H)-carboxylate

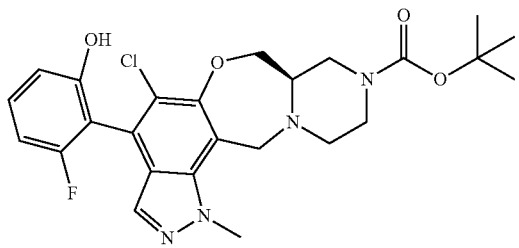 [SMILES: Cn1ncc2c(-c3c(O)cccc3F)c(Cl)c3c(c21)CN1CCN(C(=O)OC(C)(C)C)C[C@@H]1CO3]

A mixture of tert-butyl (7aR)-4-bromo-5-chloro-1-methyl-1,7a,8,10,11,13-hexahydropyrazino [2',1':3,4][1,4]oxazepino[7,6-g]indazole-9(7H)-carboxylate (630 mg, 1.34 mmol), (2-fluoro-6-hydroxyphenyl)boronic acid (250 mg, 1.60 mmol) and potassium carbonate (1107 mg, 8.01 mmol) in methyltetrahydrofuran (10 mL) and water (3.33 mL) was degassed for 5 min. Ruphos Pd G3 (112 mg, 0.13 mmol) and RuPhos (62.3 mg, 0.13 mmol) was added at 25° C. and the reaction was heated at 60° C. for 1 h. The reaction was cooled to 25° C. and diluted with EtOAc (200 mL), washed with water (2×50 mL), brine (50 mL) and dried over a phase separating cartridge. The solvent was removed under reduced pressure to afford a brown oil. This was purified by flash silica chromatography, elution gradient 0 to 10% MeOH in DCM to give tert-butyl (7aR)-5-chloro-4-(2-fluoro-6-hydroxyphenyl)-1-methyl-1,7a,8,10,11,13-hexahydropyrazino[2',1':3,4][1,4]oxazepino[7,6-g]indazole-9(7H)-carboxylate (575 mg, 86%) as a yellow solid. m/z: ES+ [M+H]+=502.8.

2-[(7aR)-5-Chloro-1-methyl-1,7,7a,8,9,10,11,13-octahydropyrazino[2',1':3,4][1,4] oxazepino [7,6-g] indazol-4-yl]-3-fluorophenol

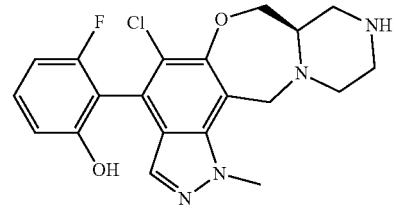 [SMILES: Cn1ncc2c(-c3c(O)cccc3F)c(Cl)c3c(c21)CN1CCNC[C@@H]1CO3]

To tert-butyl (7aR)-5-chloro-4-(2-fluoro-6-hydroxyphenyl)-1-methyl-1,7a,8,10,11,13-hexahydropyrazino[2',1':3,4][1,4]oxazepino[7,6-g]indazole-9(7H)-carboxylate (575 mg, 1.14 mmol) in MeOH (5 mL) was added HCl (6N in i-PrOH) (7.62 mL, 45.73 mmol) and the solution was stirred at 25° C. for 3 h. The reaction mixture was then purified by SCX (1M NH₃/MeOH) to afford 2-[(7aR)-5-chloro-1-methyl-1,7,7a,8,9,10,11,13-octahydropyrazino[2',1':3,4][1,4]oxazepino[7,6-g]indazol-4-yl]-3-fluorophenol (386 mg, 84%) as a pale yellow solid. 1H NMR (400 MHz, DMSO, 30° C.) 2.23-2.31 (1H, m), 2.52-2.63 (2H, m), 2.68 (1H, d), 2.76 (2H, d), 3.51-3.63 (1H, m), 3.63-3.82 (1H, m), 3.87 (1H, dd), 4.08 (3H, s), 4.18-4.26 (2H, m), 6.64 (1H, td), 6.71 (1H, dd), 7.18 (1H, td), 7.29 (1H, s), 9.77 (1H, s). m/z: ES+ [M+H]+=402.8.

1-[(7aR)-5-chloro-4-(2-fluoro-6-hydroxyphenyl)-1-methyl-1,7a,8,10,11,13-hexahydropyrazino[2',1':3,4][1,4]oxazepino[7,6-g]indazol-9(7H)-yl]prop-2-en-1-one Rotational isomer 1, Example 72 and Rotational Isomer 2, Example 73

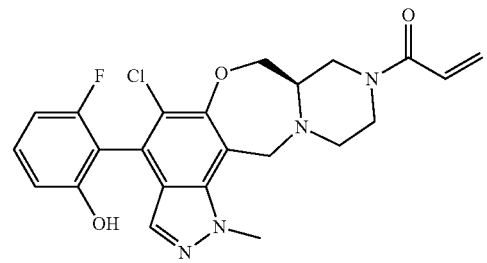 [SMILES: C=CC(=O)N1CCN2Cc3c(c(Cl)c(-c4c(O)cccc4F)c4cnn(C)c34)OC[C@H]2C1]

To a solution of 2-[(7aR)-5-chloro-1-methyl-1,7,7a,8,9,10,11,13-octahydropyrazino[2',1':3,4][1,4]oxazepino[7,6-g]indazol-4-yl]-3-fluorophenol (386 mg, 0.96 mmol) and DIPEA (0.217 mL, 1.25 mmol) in DCM (18 mL) at 0° C.

was added acryloyl chloride (0.084 mL, 1.05 mmol) and the solution was stirred at 0° C. for 2 h. The reaction mixture was quenched with MeOH (5 mL) and the solvent was removed under reduced pressure to afford a yellow oil. The oil was dissolved in MeOH (5 mL) and 7N NH₃/MeOH (1 mL) was added. The resulting solution was stirred at 25° C. for 1 h. The solvent was removed under reduced pressure to afford a yellow film. The sample was dissolved in MeOH (2 mL) and DCM (2 mL) filtered then washed with MeOH (1 mL). The solution was purified by SFC (Column: Chiralpak IC, 20×250 mm, 5 micron) eluting with 40% MeOH+0.1% NH₃/60% scCO₂, to afford rotational isomer 1 of 1-[(7aR)-5-chloro-4-(2-fluoro-6-hydroxyphenyl)-1-methyl-1,7a,8,10,11,13-hexahydropyrazino[2',1':3,4][1,4]oxazepino[7,6-g]indazol-9(7H)-yl]prop-2-en-1-one (107 mg, 24%). 1H NMR (500 MHz, DMSO, 27° C.) 2.71-2.83 (2H, m), 2.94-3.09 (2H, m), 3.7-3.77 (1H, m), 3.97 (1H, t), 4.07-4.17 (2H, m), 4.22 (3H, s), 4.38-4.52 (2H, m), 5.71 (1H, t), 6.08-6.21 (1H, m), 6.76 (1H, t), 6.8-6.89 (2H, m), 7.27-7.34 (1H, m), 7.42 (1H, s), 9.89 (1H, s). m/z: ES+ [M+H]+=457.0. This was followed by rotational isomer 2 of 1-[(7aR)-5-chloro-4-(2-fluoro-6-hydroxyphenyl)-1-methyl-1,7a,8,10,11,13-hexahydropyrazino[2',1':3,4][1,4] oxazepino[7,6-g]indazol-9(7H)-yl]prop-2-en-1-one (80 mg, 18%). 1H NMR (400 MHz, DMSO, 30° C.) 2.73-2.84 (2H, m), 2.96-3.09 (2H, m), 3.65-3.82 (1H, m), 3.91-4.02 (1H, m), 4.06-4.14 (1H, m), 4.23 (3H, s), 4.39-4.53 (2H, m), 5.67-5.76 (1H, m), 6.14 (1H, d), 6.73-6.8 (1H, m), 6.82-6.91 (2H, m), 7.26-7.37 (1H, m), 7.43 (1H, s), 9.90 (1H, s). m/z: ES+ [M+H]+=456.9.

Methyl 4-bromo-5-chloro-6-fluoro-2-methyl-2H-indazole-7-carboxylate

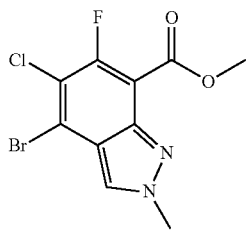 [SMILES: COC(=O)c1c(F)c(Cl)c(Br)c2cn(C)nc12]

To methyl 4-bromo-5-chloro-6-fluoro-1H-indazole-7-carboxylate (4.16 g, 13.5 mmol) in DMF (27 mL) was added caesium carbonate (5.28 g, 16.2 mmol) and iodomethane (1.01 mL, 16.2 mmol). The reaction was stirred at 25° C. for 3 h then diluted with EtOAc (500 mL), washed with water (2×250 mL) and brine (100 mL). The organic layer was dried (phase separating cartridge) and evaporated to afford a cream solid. Flash silica chromatography, elution gradient 0 to 100% EtOAc in heptane gave methyl 4-bromo-5-chloro-6-fluoro-2-methyl-2H-indazole-7-carboxylate (1.03 g, 24%) as a white solid. 1H NMR (400 MHz, CDCl₃, 30° C.) 4.04 (3H, s), 4.26 (3H, s), 7.99 (1H, s). m/z: ES+ [M+H]+=320.7.

4-Bromo-5-chloro-6-fluoro-2-methyl-2H-indazole-7-carboxylic acid

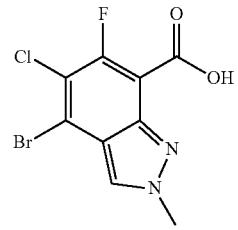 [SMILES: Cn1cc2c(Br)c(Cl)c(F)c(C(=O)O)c2n1]

Sodium hydroxide (2M) (3.5 mL, 7 mmol) was added to methyl 4-bromo-5-chloro-6-fluoro-2-methyl-2H-indazole-7-carboxylate (1.03 g, 3.2 mmol) in THF (10 mL) and stirred at 70° C. for 4 h. The reaction was cooled to rt, filtered under vacuum and dried in a vacuum oven for 16 h to afford 4-bromo-5-chloro-6-fluoro-2-methyl-2H-indazole-7-carboxylic acid (0.813 g, 77%) as a white solid (isolated as sodium salt). 1H NMR (400 MHz, DMSO, 30° C.) 4.14 (3H, s), 8.37 (1H, s). m/z: ES+ [M+H]+=306.7.

Tert-butyl (3R)-4-(4-bromo-5-chloro-6-fluoro-2-methyl-2H-indazole-7-carbonyl)-3-(hydroxymethyl) piperazine-1-carboxylate

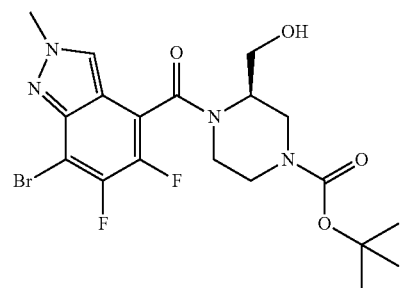 [SMILES: Cn1cc2c(C(=O)N3CCN(C(=O)OC(C)(C)C)C[C@@H]3CO)c(F)c(F)c(Br)c2n1]

4-Bromo-5-chloro-6-fluoro-2-methyl-2H-indazole-7-carboxylic acid (sodium salt) (813 mg, 2.64 mmol), HATU (1203 mg, 3.17 mmol) and DIPEA (1.41 mL, 7.93 mmol) were stirred in DMF (15 mL) for 0.5 h. tert-Butyl (3R)-3-(hydroxymethyl)piperazine-1-carboxylate (629 mg, 2.91 mmol) was then added and the mixture stirred at 25° C. for 2 h and then diluted with EtOAc (150 mL). The reaction mixture was then washed with water (2×100 mL), brine (50 mL), then dried and evaporated. Flash silica chromatography, (elution gradient 0 to 100% EtOAc in heptane) gave tert-butyl (3R)-4-(4-bromo-5-chloro-6-fluoro-2-methyl-2H-indazole-7-carbonyl)-3-(hydroxymethyl)piperazine-1-carboxylate (779 mg, 58%) as a red oil that solidified on standing. 1H NMR (400 MHz, DMSO, 100° C.) 1.44 (9H, s), 3.07-3.17 (1H, m), 3.36-3.55 (2H, m), 3.58-3.69 (1H, m), 3.67-3.81 (1H, m), 3.82-3.95 (1H, m), 3.98-4.1 (1H, m), 4.20 (3H, s), 4.37-4.48 (1H, m), 4.62 (1H, m), 8.50 (1H, s). m/z: ES+ [M+H]+=504.7.

Tert-butyl (7aR)-4-bromo-5-chloro-2-methyl-13-oxo-2,7a,8,10,11,13-hexahydropyrazino[2',1':3,4][1,4]oxazepino[7,6-g]indazole-9(7H)-carboxylate

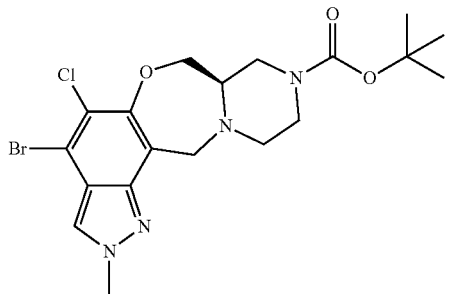 [SMILES: Cn1cc2c(Br)c(Cl)c3c(c2n1)CN1CCN(C(=O)OC(C)(C)C)C[C@@H]1CO3]

Sodium hydride (60% in mineral oil) (67.8 mg, 1.69 mmol) was added in one portion to tert-butyl (3R)-4-(4-bromo-5-chloro-6-fluoro-2-methyl-2H-indazole-7-carbonyl)-3-(hydroxymethyl)piperazine-1-carboxylate (779 mg, 1.54 mmol) in DMF (15 mL) at 0° C. The resulting solution was warmed to 25° C. and then stirred for 3 hours before diluting with water (300 mL) and extracting with EtOAc (500 mL).

The organic layer was separated, washed with water (2×400 mL) then brine (50 mL) dried and evaporated. Flash silica chromatography, elution gradient 0 to 10% MeOH in DCM, gave tert-butyl (7aR)-4-bromo-5-chloro-2-methyl-13-oxo-2,7a,8,10,11,13-hexahydropyrazino[2',1':3,4][1,4]oxazepino[7,6-g]indazole-9(7H)-carboxylate (690 mg, 92%) as a yellow solid. 1H NMR (400 MHz, DMSO, 30° C.) 1.42 (9H, s), 3.49 (1H, d), 3.58-3.62 (1H, m), 3.62-3.7 (2H, m), 3.75 (1H, s), 3.9-4.06 (2H, m), 4.17 (3H, s), 4.22-4.35 (2H, m), 8.47-8.56 (1H, m). m/z: ES+ [M+H]+=484.7.

Tert-butyl (7aR)-4-bromo-5-chloro-2-methyl-2,7a,8,10,11,13-hexahydropyrazino[2',1':3,4][1,4]oxazepino[7,6-g]indazole-9(7H)-carboxylate

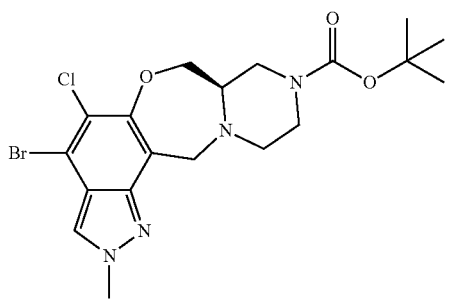 [SMILES: Cn1cc2c(Br)c(Cl)c3c(c2n1)CN1CCN(C(=O)OC(C)(C)C)C[C@@H]1CO3]

A solution of borane-THF complex (1M) (11.36 mL, 11.36 mmol) was added dropwise to a stirred solution of tert-butyl (7aR)-4-bromo-5-chloro-2-methyl-13-oxo-2,7a,8,10,11,13-hexahydropyrazino [2',1':3,4][1,4]oxazepino[7,6-g]indazole-9(7H)-carboxylate (690 mg, 1.42 mmol) in THF (10 mL) at 25° C. under nitrogen. The resulting solution was heated to 75° C. for 16 h, then cooled to 25° C., quenched with i-PrOH (5 mL) and NaOH (2M, 10 mL) and stirred for 20 min. The reaction mixture was diluted with water (100 mL) and EtOAc (200 mL), washed with brine (50 mL), dried and evaporated. Flash silica chromatography, elution gradient 0 to 100% EtOAc in heptane, gave tert-butyl (7aR)-4-bromo-5-chloro-2-methyl-2,7a,8,10,11,13-hexahydropyrazino[2',1':3,4][1,4]oxazepino[7,6-g]indazole-9(7H)-carboxylate (370 mg, 55%) as a white solid. 1H NMR (400 MHz, DMSO, 30° C.) 1.40 (9H, s), 2.31-2.43 (1H, m), 2.63-2.75 (2H, m), 2.76-2.9 (1H, m), 3.02 (1H, t), 3.62-3.76 (3H, m), 3.79 (1H, d), 4.15 (3H, s), 4.29 (1H, d), 4.36 (1H, d), 8.38 (1H, s). m/z: ES+ [M+H]+=470.8.

Tert-butyl (7aR)-5-chloro-4-(2-fluoro-6-hydroxyphenyl)-2-methyl-2,7a,8,10,11,13-hexahydropyrazino[2',1':3,4][1,4]oxazepino[7,6-g]indazole-9(7H)-carboxylate

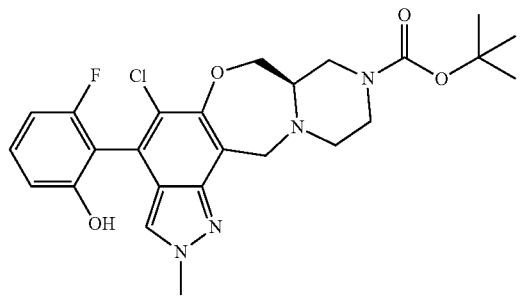 [SMILES: Cn1cc2c(-c3c(O)cccc3F)c(Cl)c3c(c2n1)CN1CCN(C(=O)OC(C)(C)C)C[C@@H]1CO3]

A stirred solution of tert-butyl (7aR)-4-bromo-5-chloro-2-methyl-2,7a,8,10,11,13-hexahydropyrazino[2',1':3,4][1,4]oxazepino[7,6-g]indazole-9(7H)-carboxylate (302 mg, 0.64 mmol), (2-fluoro-6-hydroxyphenyl)boronic acid (200 mg, 1.28 mmol) and potassium carbonate (531 mg, 3.84 mmol) in 1,4-dioxane (10 mL) and water (2 mL) was degassed for 10 minutes. RuPhos Pd G3 (53.5 mg, 0.06 mmol) and RuPhos (29.9 mg, 0.06 mmol) were added and the mixture was heated at 90° C. After stirring for 3 h, additional (2-fluoro-6-hydroxyphenyl)boronic acid (200 mg, 1.28 mmol) and RuPhos Pd G3 (53.5 mg, 0.06 mmol) were added. After a further 2 h stirring, the reaction solvent was evaporated and the brown oil was diluted with EtOAc (50 mL). The organics were washed with water (50 mL) and brine (50 mL), then dried and evaporated. Flash silica chromatography, elution gradient 0 to 10% MeOH in DCM gave tert-butyl (7aR)-5-chloro-4-(2-fluoro-6-hydroxyphenyl)-2-methyl-2,7a,8,10,11,13-hexahydropyrazino[2',1':3,4][1,4]oxazepino[7,6-g]indazole-9(7H)-carboxylate (215 mg, 67%) as a yellow dry film. m/z: ES+ [M+H]+=503.4.

2-[(7aR)-5-Chloro-2-methyl-2,7,7a,8,9,10,11,13-octahydropyrazino[2',1':3,4][1,4]oxazepino[7,6-g]indazol-4-yl]-3-fluorophenol

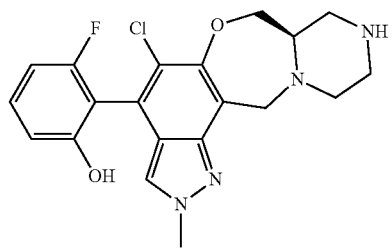 [SMILES: Cn1cc2c(-c3c(O)cccc3F)c(Cl)c3c(c2n1)CN1CCNC[C@@H]1CO3]

A solution of tert-butyl (7aR)-5-chloro-4-(2-fluoro-6-hydroxyphenyl)-2-methyl-2,7a,8,10,11,13-hexahydropyrazino[2',1':3,4][1,4]oxazepino[7,6-g]indazole-9(7H)-carboxylate (215 mg, 0.43 mmol) and HCl (6M in i-PrOH) (2.85 mL, 17.10 mmol) in MeOH (4 mL) was stirred at 25° C. for 3 h. The reaction mixture was then purified by ion exchange chromatography, using an SCX column, the desired product was eluted from the column using 1M NH₃/MeOH to afford 2-[(7aR)-5-chloro-2-methyl-2,7,7a,8,9,10,11,13-octahydropyrazino[2',1':3,4][1,4]oxazepino[7,6-g]indazol-4-yl]-3-fluorophenol (172 mg, 100%) as a pale yellow solid. m/z: ES+ [M+H]+=403.2.

1-[(7aR)-5-Chloro-4-(2-fluoro-6-hydroxyphenyl)-2-methyl-2,7a,8,10,11,13-hexahydropyrazino [2',1':3,4][1,4]oxazepino[7,6-g]indazol-9(7H)-yl]prop-2-en-1-one Rotational Isomer 1, Example 74 and Rotational Isomer 2, Example 75

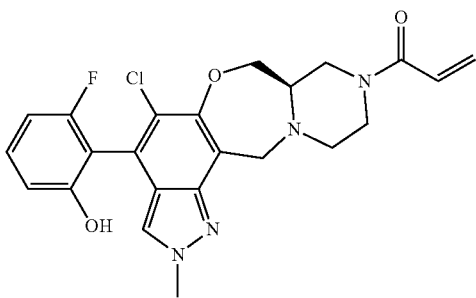 [SMILES: C=CC(=O)N1CCN2Cc3c(c(Cl)c(-c4c(O)cccc4F)c4cn(C)nc34)OC[C@H]2C1]

To a solution of 2-[(7aR)-5-chloro-2-methyl-2,7,7a,8,9,10,11,13-octahydropyrazino[2',1':3,4][1,4]oxazepino[7,6-g]indazol-4-yl]-3-fluorophenol (185 mg, 0.46 mmol) and DIPEA (0.104 mL, 0.60 mmol) in DCM (18 mL) under nitrogen at 0° C. was added acryloyl chloride (0.040 mL, 0.51 mmol). After stirring at 0° C. for 2 h the reaction was quenched with MeOH (5 mL) and the solvent removed under reduced pressure. The resultant oil was dissolved in MeOH (5 mL) and 7N NH₃/MeOH (1 mL) was added then stirred at 25° C. for 1 h after which time the solvent evaporated. The sample was then dissolved in MeOH (3 mL), filtered and the residue washed with MeOH (0.5 mL). The solution was purified using the SFC (Column: Chiralpak IC, 20×250 mm, 5 micron Mobile phase: 35% MeOH+0.1% NH₃/65% scCO₂ Flow rate: 60 mL/min BPR: 120 bar Column temperature: 40° C. UV max 216 nm) to afford rotational isomer 1 of 1-[(7aR)-5-chloro-4-(2-fluoro-6-hydroxyphenyl)-2-methyl-2,7a,8,10,11,13-hexahydropyrazino [2',1':3,4][1,4]oxazepino[7,6-g]indazol-9(7H)-yl]prop-2-en-1-one (61 mg, 29%). 1H NMR (400 MHz, DMSO, 30° C.) 2.37-2.47 (1H, m), 2.68-2.88 (2H, m), 2.88-3.12 (2H, m), 3.78 (1H, dd), 3.83-4.02 (2H, m), 4.09 (4H, s), 4.3-4.57 (2H, m), 5.62-5.82 (1H, m), 6.04-6.22 (1H, m), 6.7-6.79 (1H, m), 6.79-6.89 (2H, m), 7.21-7.42 (1H, m), 7.91 (1H, s), 9.83 (1H, s). m/z: ES+ [M+H]+=457. This was followed by rotational isomer 2 of 1-[(7aR)-5-chloro-4-(2-fluoro-6-hydroxyphenyl)-2-methyl-2,7a,8,10,11,13-hexahydropyrazino [2',1':3,4][1,4]oxazepino[7,6-g]indazol-9(7H)-yl]prop-2-en-1-one (25 mg, 12%). 1H NMR (400 MHz, DMSO, 30° C.) 2.36-2.48 (1H, m), 2.68-2.83 (2H, m), 2.88-3.14 (2H, m), 3.7-3.82 (1H, m), 3.82-4.02 (2H, m), 4.02-4.29 (4H, m), 4.3-4.63 (2H, m), 5.61-5.81 (1H, m), 6.02-6.23 (1H, m), 6.62-6.99 (3H, m), 7.16-7.4 (1H, m), 7.92 (1H, s), 9.83 (1H, s). m/z: ES+ [M+H]+=457.

Tert-butyl (3R)-4-[(4-bromo-2,3-difluorophenyl)methyl]-3-(hydroxymethyl)piperazine-1-carboxylate

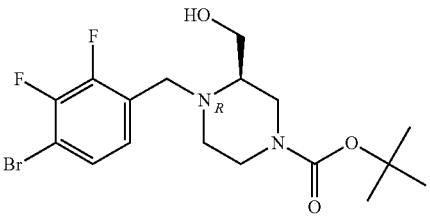

4-Bromo-2,3-difluorobenzaldehyde (28 g, 126.70 mmol) was dissolved in dry DCM (300 ml) and tert-butyl (3R)-3-(hydroxymethyl)piperazine-1-carboxylate (41.1 g, 190.04 mmol) added followed by glacial acetic acid (0.725 ml, 12.67 mmol) and the reaction mixture stirred at room temperature for two hours under nitrogen. Sodium triacetoxyhydroborate (53.7 g, 253.39 mmol) and DCM (300 ml) were then added and the reaction mixture stirred at room temperature overnight. The reaction mixture was quenched by careful addition of aqueous saturated sodium hydrogen carbonate solution and the aqueous layer extracted with DCM. The organic layer obtained was washed with saturated brine and dried by passing through a phase separator cartridge then evaporated to a pale yellow oil The crude product obtained was purified by flash silica chromatography, elution gradient 0 to 60% EtOAc in heptane to afford tert-butyl (3R)-4-[(4-bromo-2,3-difluorophenyl)methyl]-3-(hydroxymethyl)piperazine-1-carboxylate (51.8 g, 97%) as a yellow gum. 1H NMR (400 MHz, DMSO, 30° C.) 1.40 (9H, s), 2.14 (1H, ddd), 2.3-2.45 (1H, m), 2.56-2.63 (1H, m), 3.02 (2H, ddd), 3.31-3.4 (1H, m), 3.48 (2H, d), 3.69 (2H, dt), 3.94-4.09 (1H, m), 4.65 (1H, t), 7.18-7.34 (1H, m), 7.51 (1H, ddd). m/z: ES+ [M+H]+=421.

Tert-butyl (12aR)-9-bromo-10-fluoro-3,4,12,12a-tetrahydro-6H-pyrazino[2,1-c][1,4]benzoxazepine-2(1H)-carboxylate

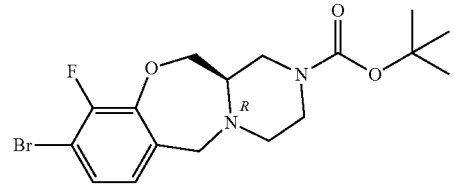

Sodium hydride (2.70 g, 67.55 mmol) was added portionwise over thirty minutes to tert-butyl (3R)-4-[(4-bromo-2,3-difluorophenyl)methyl]-3-(hydroxymethyl)piperazine-1-carboxylate (25.87 g, 61.41 mmol) in DMF (300 ml) at 0° C. under nitrogen (effervescence observed). The resulting mixture was stirred at 0° C. for thirty minutes then at 10° C. for thirty minutes. The reaction mixture was then cooled to 0° C. and quenched with aqueous saturated ammonium chloride solution. The reaction mixture was diluted with water and extracted with ethyl acetate. The combined organic layer was washed with saturated brine and dried by passing through a phase separator cartridge. Evaporation afforded a yellow oil tert-butyl (12aR)-9-bromo-10-fluoro-3,4,12,12a-tetrahydro-6H-pyrazino[2,1-c][1,4]benzoxazepine-2(1H)-carboxylate (29.5 g, >100%). m/z: ES+ [M+H]+ 401. The reaction was repeated and several crude batches combined for a single purification below.

Tert-butyl (12aR)-9-bromo-10-fluoro-3,4,12,12a-tetrahydro-6H-pyrazino[2,1-c][1,4]benzoxazepine-2(1H)-carboxylate

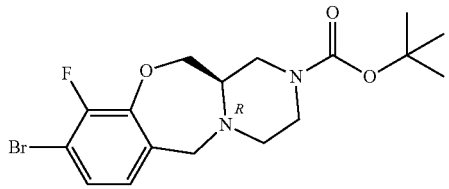

Tert-butyl (12aR)-9-bromo-10-fluoro-3,4,12,12a-tetrahydro-6H-pyrazino[2,1-c][1,4]benzoxazepine-2(1H)-carboxylate (64.3 g, 160.24 mmol) was dissolved in DCM and purified by flash silica chromatography, elution gradient 0 to 100% EtOAc in heptane. Pure fractions were evaporated to dryness to afford tert-butyl (12aR)-9-bromo-10-fluoro-3,4,12,12a-tetrahydro-6H-pyrazino[2,1-c][1,4]benzoxazepine-2(1H)-carboxylate (48.1 g, 74.8%) as a yellow foam. 1H NMR (400 MHz, DMSO, 30° C.) 1.40 (9H, s), 2.31 (1H, ddd), 2.74 (2H, td), 2.80 (1H, d), 3.09 (1H, ddd), 3.58 (2H, d), 3.66-3.75 (2H, m), 3.81 (1H, d), 4.33 (1H, dd), 7.03 (1H, dd), 7.31 (1H, dd). m/z: ES+ [M+H]+=401.

(12aR)-9-Bromo-10-fluoro-8-iodo-1,2,3,4,12,12a-hexahydro-6H-pyrazino[2,1-c][1,4]benzoxazepine

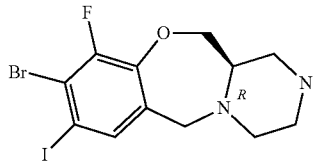

Concentrated sulphuric acid (60.2 ml) was added dropwise to tert-butyl (12aR)-9-bromo-10-fluoro-3,4,12,12a-tetrahydro-6H-pyrazino[2,1-c][1,4]benzoxazepine-2(1H)-carboxylate (14.5 g, 36.13 mmol) dropwise at 0° C. The resulting mixture was stirred at 0° C. for fifteen minutes until a solution formed. N-Iodosuccinimide (16.26 g, 72.27 mmol) was added in one portion and the reaction mixture stirred at 0° C. for thirty minutes then room temperature for three hours. The reaction mixture was slowly poured onto ice and the pH adjusted to pH 10 with NaOH (50% w/w aqueous solution) and extracted with DCM. The organic extracts were combined, washed with saturated brine then dried by passing through a phase extractor cartridge and evaporated to afford (12aR)-9-bromo-10-fluoro-8-iodo-1,2,3,4,12,12a-hexahydro-6H-pyrazino[2,1-c][1,4]benzoxazepine (17.1 g, >100%) as a brown foam. 1H NMR (400 MHz, DMSO, 30° C.) 2.36 (2H, ddd), 2.61-2.97 (5H, m), 3.71 (3H, dtd), 4.12-4.34 (1H, m), 7.71 (1H, d). One exchangeable proton not seen. m/z: ES+ [M+H]+=427.

Tert-butyl (12aR)-9-bromo-10-fluoro-8-iodo-3,4,12,12a-tetrahydro-6H-pyrazino[2,1-c][1,4]benzoxazepine-2(1H)-carboxylate

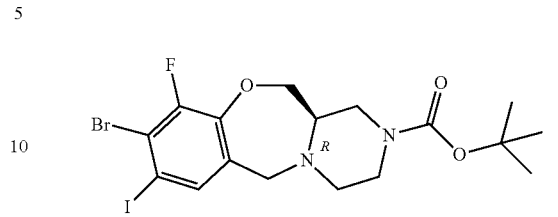

Di-tert-butyl dicarbonate (13.11 g, 60.06 mmol) was added to a stirred solution of (12aR)-9-bromo-10-fluoro-8-iodo-1,2,3,4,12,12a-hexahydro-6H-pyrazino[2,1-c][1,4]benzoxazepine and triethylamine (16.74 mL, 120.12 mmol) in DCM (200 mL) at room temperature. The resulting solution was stirred at room temperature for seventeen hours. The reaction mixture was diluted with DCM (150 mL) and washed with water (150 mL) then saturated brine (150 mL). The organic layer was dried by passing through a phase separator cartridge and evaporated to afford crude product. The crude product was purified by flash silica chromatography, elution gradient 0 to 60% EtOAc in heptane. Pure fractions were evaporated to dryness to afford tert-butyl (12aR)-9-bromo-10-fluoro-8-iodo-3,4,12,12a-tetrahydro-6H-pyrazino[2,1-c][1,4]benzoxazepine-2(1H)-carboxylate (9.53 g, 45%) as a pale yellow foam. 1H NMR (400 MHz, DMSO, 30° C.) 1.40 (9H, s), 2.23-2.38 (1H, m), 2.63-2.8 (2H, m), 2.88 (1H, s), 3.12 (1H, ddd), 3.55 (2H, t), 3.67-3.82 (3H, m), 4.32 (1H, dd), 7.71 (1H, d). m/z: ES+ [M+H]+=527.

Tert-butyl (12aR)-9-bromo-10-fluoro-8-[(trimethylsilyl)ethynyl]-3,4,12,12a-tetrahydro-6H-pyrazino[2,1-c][1,4]benzoxazepine-2(1H)-carboxylate

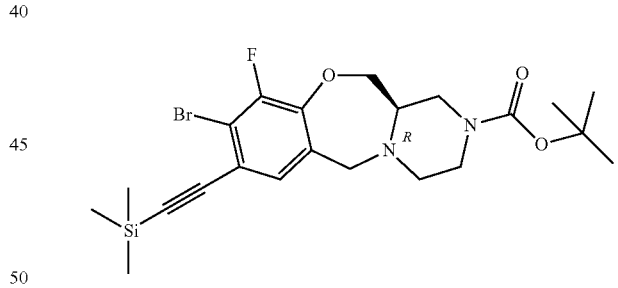

Tert-butyl (12aR)-9-bromo-10-fluoro-8-iodo-3,4,12,12a-tetrahydro-6H-pyrazino[2,1-c][1,4]benzoxazepine-2(1H)-carboxylate (9.33 g, 17.70 mmol), tetrakis(triphenylphosphine) palladium(0) (4.09 g, 3.54 mmol) and copper(I) iodide (3.37 g, 17.70 mmol) were suspended in toluene (160 ml). Ethynyltrimethylsilane (12.24 ml, 88.49 mmol) and triethylamine (4.93 ml, 35.40 mmol) were added consecutively and the reaction mixture heated at 100° C. for thirty minutes. The reaction mixture was cooled to room temperature and evaporated. The residue obtained was dissolved in DCM and filtered through a layer of celite. Evaporation afforded an oil which was dissolved in diethyl ether and filtered. The filtrate was evaporated to a brown oil. The crude product obtained was dissolved in heptane and purified by flash silica chromatography, elution gradient 0 to 40% EtOAc in heptane. Pure fractions were evaporated to dryness to afford tert-butyl (12aR)-9-bromo-10-fluoro-8-[(trimethylsilyl)ethynyl]-3,4,12,12a-tetrahydro-6H-pyrazino[2,1-c][1,4]benzoxazepine-2(1H)-carboxylate (6.76 g, 77%) as a pale yellow foam. 1H NMR (400 MHz, DMSO, 30° C.) 0.25 (9H, s), 1.40 (9H, s), 2.34 (1H, ddd), 2.65-2.85 (2H, m), 2.91 (1H, s), 3.13 (1H, ddd), 3.55 (2H, t), 3.72-3.94 (3H, m), 4.35 (1H, dd), 7.35 (1H, d). m/z: ES+ [M+H]+=497.

Tert-butyl (12aR)-9-(2-chloro-6-hydroxyphenyl)-10-fluoro-8-[(trimethylsilyl)ethynyl]-3,4,12,12a-tetrahydro-6H-pyrazino[2,1-c][1,4]benzoxazepine-2(1H)-carboxylate

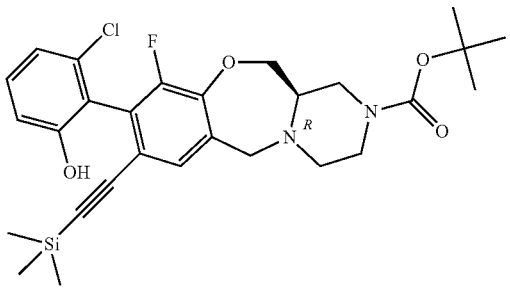

A solution of tert-butyl (12aR)-9-bromo-10-fluoro-8-[(trimethylsilyl)ethynyl]-3,4,12,12a-tetrahydro-6H-pyrazino[2,1-c][1,4]benzoxazepine-2(1H)-carboxylate (6.5 g, 13.07 mmol), (2-chloro-6-hydroxyphenyl)boronic acid (3.38 g, 19.60 mmol) and aqueous 2M sodium carbonate (19.60 ml, 39.20 mmol) in 1,4-dioxane (111 ml) was degassed with nitrogen for 5 minutes. RuPhos-Pd-G3 (1.093 g, 1.31 mmol) and 2-Dicyclohexylphosphino-2',6'-diisopropoxybiphenyl (0.610 g, 1.31 mmol) were then added and reaction mixture heated at 90° C. for thirty minutes. The reaction mixture was cooled to room temperature diluted with EtOAc (150 mL) and water (150 mL). The combined organics were dried over magnesium sulphate, filtered and concentrated under reduced pressure to give a brown residue. The residue obtained was purified by flash silica chromatography, elution gradient 0 to 50% EtOAc in heptane. Pure fractions were evaporated to dryness to afford crude product as a pale yellow dry film. The crude product was purified and atropisomers separated by chiral SFC, using a Chiralpak IC column, 20×250 mm, 5 micron mobile phase: 25% MeOH+0.1% NH₃/75% scCO2 Flow rate: 60 ml/min BPR: 120 bar Column temperature: 40° C. UV max 220 nm. Pure first eluting atropisomer fractions were collected and concentrated under reduced pressure to afford rotational isomer 1 of tert-butyl (12aR)-9-(2-chloro-6-hydroxyphenyl)-10-fluoro-8-[(trimethylsilyl)ethynyl]-3,4,12,12a-tetrahydro-6H-pyrazino[2,1-c][1,4]benzoxazepine-2(1H)-carboxylate (2.55 g, 33%) as a pale yellow solid. 1H NMR (400 MHz, DMSO, 30° C.) -0.00 (9H, s), 1.43 (9H, s), 2.33-2.45 (1H, m), 2.68-2.77 (1H, m), 2.77-2.84 (1H, m), 2.89 (1H, s), 3.11 (1H, t), 3.59-3.71 (2H, m), 3.72-3.83 (2H, m), 3.93 (1H, d), 4.39 (1H, dd), 6.92 (1H, dd), 7.00 (1H, dd), 7.23-7.33 (2H, m), 9.84 (1H, s). m/z: ES+ [M+H]+=545. >99% ee. This was followed by pure second eluting atropisomer fractions was collected and concentrated under reduced pressure to afford rotational isomer 2 of tert-butyl (12aR)-9-(2-chloro-6-hydroxyphenyl)-10-fluoro-8-[(trimethylsilyl)ethynyl]-3,4,12,12a-tetrahydro-6H-pyrazino[2,1-c][1,4]benzoxazepine-2(1H)-carboxylate (3.15 g, 41%) as a pale yellow solid. 1H NMR (400 MHz, DMSO, 30° C.) -0.00 (9H, s), 1.43 (9H, s), 2.32-2.44 (1H, m), 2.68-2.76 (1H, m), 2.76-2.83 (1H, m), 2.88 (1H, s), 3.11 (1H, t), 3.66 (2H, d), 3.72-3.81 (2H, m), 3.91 (1H, d), 4.38 (1H, dd), 6.91 (1H, dd), 7.00 (1H, dd), 7.22-7.3 (2H, m), 9.86 (1H, s).m/z: ES+ [M+H]+=545. >98.1% ee.

3-Chloro-2-[(12aR)-8-ethynyl-10-fluoro-1,2,3,4,12,12a-hexahydro-6H-pyrazino[2,1-c][1,4]benzoxazepin-9-yl]phenol

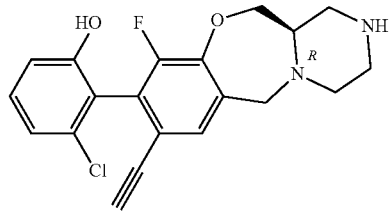

Tert-butyl (12aR)-9-(2-chloro-6-hydroxyphenyl)-10-fluoro-8-[(trimethylsilyl)ethynyl]-3,4,12,12a-tetrahydro-6H-pyrazino[2,1-c][1,4]benzoxazepine-2(1H)-carboxylate (2.55 g, 4.68 mmol) was dissolved in DCM (20 mL) and TFA (10.74 mL, 140.34 mmol) added and the resulting solution was stirred at room temperature for one hour. The crude reaction mixture was purified by ion exchange chromatography, using an SCX column. The desired product was eluted from the column using 1M NH₃/MeOH and pure fractions were evaporated to dryness to afford a yellow foam, which was triturated with diethyl ether to afford 3-chloro-2-[(12aR)-8-ethynyl-10-fluoro-1,2,3,4,12,12a-hexahydro-6H-pyrazino[2,1-c][1,4]benzoxazepin-9-yl]phenol (1.61 g, 92%) as a white solid. 1H NMR (400 MHz, DMSO, 30° C.) 2.29-2.42 (2H, m), 2.6-2.72 (2H, m), 2.74-2.87 (3H, m), 3.36 (1H, d), 3.62-3.86 (3H, m), 3.89 (1H, s), 4.29 (1H, dd), 6.93 (1H, dd), 7.00 (1H, dd), 7.2-7.32 (2H, m), 9.94 (1H, s).m/z: ES+ [M+H]+=373.

1-[(12aR)-9-(2-chloro-6-hydroxyphenyl)-8-ethynyl-10-fluoro-3,4,12,12a-tetrahydro-6H-pyrazino[2,1-c][1,4]benzoxazepin-2(1H)-yl]prop-2-en-1-one, Example 76

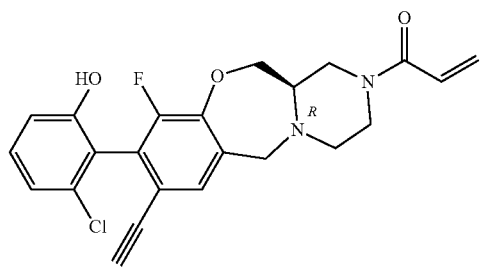

To a suspension of 3-chloro-2-[(12aR)-8-ethynyl-10-fluoro-1,2,3,4,12,12a-hexahydro-6H-pyrazino[2,1-c][1,4]benzoxazepin-9-yl]phenol (1.515 g, 4.06 mmol) and DIPEA (0.920 mL, 5.28 mmol) in DCM (30 mL) under nitrogen at 0° C. was added acryloyl chloride (0.355 mL, 4.47 mmol) dropwise and reaction mixture stirred at 0° C. for thirty minutes. The reaction mixture was then evaporated at 40° C. to afford a yellow oil which was dissolved in cold 7N NH₃/MeOH (50 mL) and stirred to room temperature over thirty minutes. The reaction mixture was evaporated at 40° C. to afford a yellow residue which was dissolved in DCM and extracted with water. The resulting organic layer was dried by passing through a phase separator cartridge. Evaporation afforded crude product which was dissolved in DCM and purified by flash silica chromatography, elution gradient 0 to 1% MeOH in EtOAc. Pure fractions were evaporated to dryness to afford a white foam which was dried at 55° C. for one day under high vacuum then dissolved in acetonitrile (10 ml) and water (10 ml) and freeze dried over the weekend to afford 1-[(12aR)-9-(2-chloro-6-hydroxyphenyl)-8-ethynyl-10-fluoro-3,4,12,12a-tetrahydro-6H-pyrazino[2,1-c][1,4]benzoxazepin-2(1H)-yl]prop-2-en-1-one (1.03 g, 59%) as a white solid. 1H NMR (400 MHz, DMSO, 30° C.) 2.43 (1H, s), 2.73 (1H, s), 2.87 (1H, d), 3.09 (1H, d), 3.35 (1H, s), 3.72-3.82 (2H, m), 3.85-3.96 (3H, m), 3.98-4.1 (1H, m), 4.40 (1H, d), 5.70 (1H, d), 6.13 (1H, d), 6.75-6.87 (1H, m), 6.90 (1H, dd), 6.98 (1H, dd), 7.24 (1H, t), 7.27-7.31 (1H, m), 9.88 (1H, s). m/z: ES+ [M+H]+=427.

3-Chloro-2-((12aR)-8-ethynyl-10-fluoro-1,2,3,4,12,12a-hexahydro-6H-benzo[f]pyrazino[2,1-c][1,4]oxazepin-9-yl)phenol

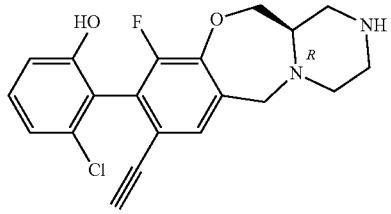

Tert-butyl (12aR)-9-(2-chloro-6-hydroxyphenyl)-10-fluoro-8-[(trimethylsilyl)ethynyl]-3,4,12,12a-tetrahydro-6H-pyrazino[2,1-c][1,4]benzoxazepine-2(1H)-carboxylate (200 mg, 0.37 mmol) was dissolved in DCM (3 mL) and TFA (0.562 mL, 7.34 mmol) was added. The resulting solution was stirred at room temperature for two hours and a further portion of TFA (0.562 mL, 7.34 mmol) added and the reaction mixture then stirred for thirty minutes. The crude reaction mixture was purified by ion exchange chromatography, using an SCX column. The desired product was eluted from the column using 1M NH₃/MeOH and pure fractions evaporated to dryness to afford 3-chloro-2-((12aR)-8-ethynyl-10-fluoro-1,2,3,4,12,12a-hexahydro-6H-benzo[f]pyrazino[2,1-c][1,4]oxazepin-9-yl)phenol (177 mg, >100%) as a yellow foam. 1H NMR (400 MHz, DMSO, 30° C.) 2.83 (3H, dd), 2.98 (2H, t), 3.41 (2H, dt), 3.71-3.82 (2H, m), 3.87 (2H, d), 4.13 (1H, s), 4.34 (1H, d), 6.92 (1H, dd), 7.01 (1H, dd), 7.21-7.32 (2H, m), 9.97 (1H, s). m/z: ES+ [M+H]+=373.

1-[(12aR)-9-(2-chloro-6-hydroxyphenyl)-8-ethynyl-10-fluoro-3,4,12,12a-tetrahydro-6H-pyrazino[2,1-c][1,4]benzoxazepin-2(1H)-yl]prop-2-en-1-one, Example 77

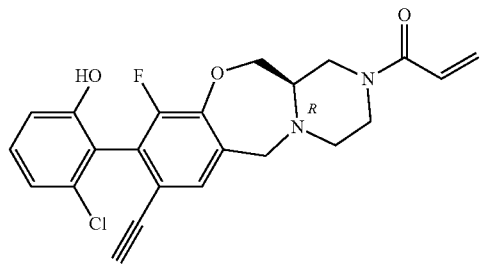

To a suspension of 3-chloro-2-((12aR)-8-ethynyl-10-fluoro-1,2,3,4,12,12a-hexahydro-6H-benzo[f]pyrazino[2,1-c][1,4]oxazepin-9-yl)phenol (0.170 g, 0.46 mmol) and DIPEA (0.103 mL, 0.59 mmol) in DCM (3 mL) under nitrogen at 0° C. was added acryloyl chloride (0.040 mL, 0.50 mmol) dropwise and the reaction mixture stirred at 0° C. for fifteen minutes. The reaction mixture was evaporated at 40° C. to afford a yellow oil which was dissolved in cold 1N NH₃/MeOH (10 mL) and stirred to room temperature over thirty minutes. The reaction mixture was evaporated at 40° C. to afford a yellow solid which was dissolved in DCM and extracted with water. The resulting organic layer was dried by passing through a phase separator cartridge. Evaporation afforded crude product as a yellow foam. The crude product was purified by preparative HPLC (Waters CSH C18 OBD column, 30×100 mm id, 5 micron particle size), using decreasingly polar mixtures of water (containing 0.3% NH₃ aq) and MeCN as eluents. Shallow gradient: 20 to 40% MeCN. Fractions containing the desired compound were evaporated to dryness to afford 1-[(12aR)-9-(2-chloro-6-hydroxyphenyl)-8-ethynyl-10-fluoro-3,4,12,12a-tetrahydro-6H-pyrazino[2,1-c][1,4]benzoxazepin-2(1H)-yl]prop-2-en-1-one (81 mg, 42%) as a white solid. 1H NMR (400 MHz, DMSO, 30° C.) 2.42 (1H, s), 2.66-2.78 (1H, m), 2.87 (2H, dd), 3.09 (1H, d), 3.72-3.79 (2H, m), 3.86-3.93 (3H, m), 4.05 (1H, d), 4.39 (1H, d), 5.70 (1H, d), 6.13 (1H, d), 6.83 (1H, s), 6.89 (1H, d), 6.97 (1H, d), 7.22 (1H, t), 7.27-7.31 (1H, m), 9.95 (1H, s). m/z: ES+ [M+H]+=427.

4-Bromo-3-chloro-2-fluorobenzaldehyde

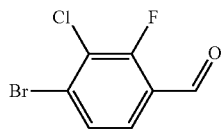

A mechanically-stirred solution of diisopropylamine (6.96 mL, 49.66 mmol) in THF (35 mL) was cooled to −20° C. and a solution of 1.6 M n-butyllithium in hexane (31.0 mL, 49.66 mmol) was added dropwise. On addition the solution was stirred at 0° C. for 20 minutes. The mixture was cooled to −78° C. and a solution of 1-bromo-2-chloro-3-fluorobenzene (10 g, 47.75 mmol) in THF (10 mL) was added dropwise over 20 minutes. The resultant yellow suspension was stirred at −78° C. for one hour. DMF (5.55 mL, 71.62 mmol) was added dropwise over 5 minutes and then the mixture allowed to warm to −20° C. At −20° C. the clear yellow solution was quenched with saturated aqueous ammonium chloride (100 mL) and extracted with diethyl ether (2×100 mL). The combined organic layers were dried over magnesium sulphate, filtered and the solvent removed under reduced pressure to afford a pale yellow solid. The residue was purified by flash silica chromatography, elution gradient 0 to 5% ethyl acetate in heptane to afford 4-bromo-3-chloro-2-fluorobenzaldehyde (6.83 g, 60%) as a white solid. 1H NMR (400 MHz, CDCl$_3$, 30° C.): 7.51 (1H, ddd), 7.59 (1H, dd), 10.24 (1H, d). m/z: ES− [M−H]− 235.

Tert-butyl (3R)-4-[(4-bromo-3-chloro-2-fluorophenyl)methyl]-3-(hydroxymethyl)piperazine-1-carboxylate

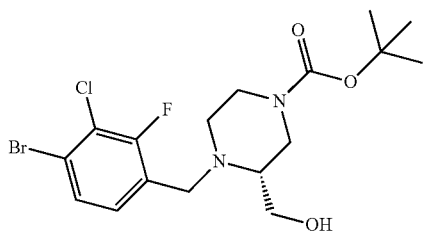 [SMILES: CC(C)(C)OC(=O)N1CCN(Cc2ccc(Br)c(Cl)c2F)[C@@H](CO)C1]

4-Bromo-3-chloro-2-fluorobenzaldehyde (1 g, 4.21 mmol) was dissolved in DCM (20 mL) and tert-butyl (3R)-3-(hydroxymethyl)piperazine-1-carboxylate (1.37 g, 6.32 mmol) was added followed by acetic acid (0.024 mL, 0.42 mmol) and the mixture was stirred at room temperature for one hour. Sodium triacetoxyborohydride (1.79 g, 8.42 mmol) was added and the solution was stirred at room temperature for 17 hours. A further portion of sodium triacetoxyborohydride (0.9 g) was added and the solution was stirred for 3 hours. The mixture was quenched by careful addition of the reaction mixture to aqueous saturated sodium hydrogen carbonate solution (100 mL) and then the aqueous layer extracted with DCM (2×100 mL). The combined organic layers were passed through a phase separator cartridge and dried under reduced pressure to give the crude product as a pale yellow oil. The residue was purified by flash silica chromatography, elution gradient 0 to 60% ethyl acetate in heptane to afford tert-butyl (3R)-4-[(4-bromo-3-chloro-2-fluorophenyl)methyl]-3-(hydroxymethyl)piperazine-1-carboxylate (1.56 g, 85%) as a colourless gum. 1H NMR (400 MHz, DMSO, 30° C.): 1.39 (9H, s), 2.14 (1H, ddd), 2.33-2.44 (1H, m), 2.55-2.65 (1H, m), 2.81-3.17 (2H, m), 3.36 (1H, dt), 3.46 (2H, d), 3.68 (2H, dt), 4.02 (1H, d), 4.65 (1H, t), 7.33-7.51 (1H, m), 7.61 (1H, dd). m/z: ES+ [M+H]+ 437.

Tert-butyl (12aR)-9-bromo-10-chloro-3,4,12,12a-tetrahydro-6H-pyrazino[2,1-c][1,4]benzoxazepine-2(1H)-carboxylate

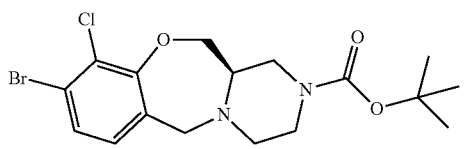 [SMILES: CC(C)(C)OC(=O)N1CCN2Cc3ccc(Br)c(Cl)c3OC[C@H]2C1]

Sodium hydride (50.5 mg of a 60% dispersion in mineral oil, 1.26 mmol) was added in one portion to tert-butyl (3R)-4-[(4-bromo-3-chloro-2-fluorophenyl)methyl]-3-(hydroxymethyl)piperazine-1-carboxylate (502 mg, 1.15 mmol) in DMF (10 mL) at room temperature under nitrogen. The resulting mixture was stirred at room temperature for 30 minutes then cooled and quenched with aqueous saturated ammonium chloride solution (20 mL). The reaction mixture was diluted with water and extracted with ethyl acetate (2×50 mL) and the combined organic layer was washed with water (3×100 mL). The organic layer was dried over magnesium sulphate, filtered and evaporated to afford a white foam. The residue was purified by flash silica chromatography, elution gradient 0 to 50% ethyl acetate in heptane to afford tert-butyl (12aR)-9-bromo-10-chloro-3,4,12,12a-tetrahydro-6H-pyrazino[2,1-c][1,4]benzoxazepine-2(1H)-carboxylate (381 mg, 80%) as a colourless gum. 1H NMR (400 MHz, CDCl$_3$, 30° C.): 1.46 (9H, s), 2.42 (1H, ddd), 2.77 (1H, ddd), 2.81-3.03 (2H, m), 3.26 (1H, ddd), 3.55 (1H, d), 3.6-3.76 (3H, m), 3.93 (1H, d), 4.24-4.38 (1H, m), 6.94 (1H, d), 7.29 (1H, d). m/z: ES+ [M+H]+ 417.

(12aR)-9-Bromo-10-chloro-8-iodo-1,2,3,4,12,12a-hexahydro-6H-pyrazino[2,1-c][1,4]benzoxazepine

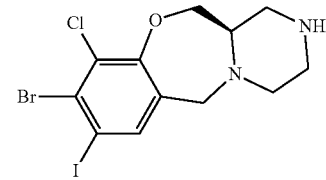 [SMILES: Clc1c(Br)c(I)cc2c1OC[C@H]1CNCCN1C2]

N-Iodosuccinimide (5.39 g, 23.94 mmol) was added portionwise to a solution of tert-butyl (12aR)-9-bromo-10-chloro-3,4,12,12a-tetrahydro-6H-pyrazino[2,1-c][1,4]benzoxazepine-2(1H)-carboxylate (5 g, 11.97 mmol) in concentrated sulphuric acid (40 mL) at room temperature. The resulting mixture was stirred at room temperature for 2 hours then cooled in an ice-bath and treated with ice cold aqueous 25% sodium hydroxide solution (200 mL) to pH 10. The reaction mixture was diluted with water (500 mL) and extracted with ethyl acetate (3×500 mL) and the combined organic layers were washed with water (2×500 mL). The organic layer was dried over magnesium sulphate, filtered and evaporated to afford (12aR)-9-bromo-10-chloro-8-iodo-1,2,3,4,12,12a-hexahydro-6H-pyrazino[2,1-c][1,4]benzoxazepine as a brown foam. 1H NMR (400 MHz, CDCl3, 30° C.): 2.54-2.68 (2H, m), 2.89-3.19 (5H, m), 3.44 (1H, d), 3.71 (1H, dd), 3.88 (1H, d), 4.22-4.39 (1H, m), 7.62 (1H, s). m/z: ES+ [M+H]+ 443.

Tert-butyl (12aR)-9-bromo-10-chloro-8-iodo-3,4,12,12a-tetrahydro-6H-pyrazino[2,1-c][1,4]benzoxazepine-2(1H)-carboxylate

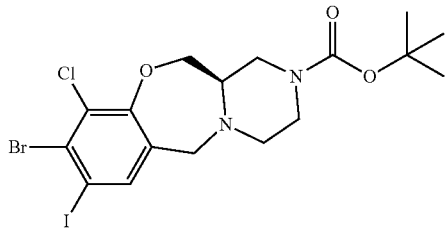 [SMILES: CC(C)(C)OC(=O)N1CCN2Cc3cc(I)c(Br)c(Cl)c3OC[C@H]2C1]

Di-tert-butyl dicarbonate (11.76 g, 53.88 mmol) was added portionwise to a solution of (12aR)-9-bromo-10-chloro-8-iodo-1,2,3,4,12,12a-hexahydro-6H-pyrazino[2,1-c][1,4]benzoxazepine (15.93 g, 35.92 mmol) in DCM (300 mL) and triethylamine (15.02 mL, 107.75 mmol) at room temperature. The solution was stirred at room temperature for 30 minutes and then evaporated to dryness to afford a brown solid. The residue was purified by flash silica chromatography, elution gradient 0 to 30% ethyl acetate in heptane to afford tert-butyl (12aR)-9-bromo-10-chloro-8-iodo-3,4,12,12a-tetrahydro-6H-pyrazino[2,1-c][1,4]benzoxazepine-2(1H)-carboxylate (12.34 g, 63%) as a pale brown solid. 1H NMR (400 MHz, CDCl3, 30° C.): 1.45 (9H, s), 2.33-2.52 (1H, m), 2.68-2.82 (1H, m), 2.83-3.07 (2H, m), 3.18-3.38 (1H, m), 3.50 (1H, d), 3.55-3.77 (3H, m), 3.91 (1H, d), 4.29 (1H, dd), 7.62 (1H, s). m/z: ES+ [M+H]+ 543.

Tert-butyl (12aR)-9-bromo-10-chloro-8-[(trimethylsilyl)ethynyl]-3,4,12,12a-tetrahydro-6H-pyrazino[2,1-c][1,4]benzoxazepine-2(1H)-carboxylate

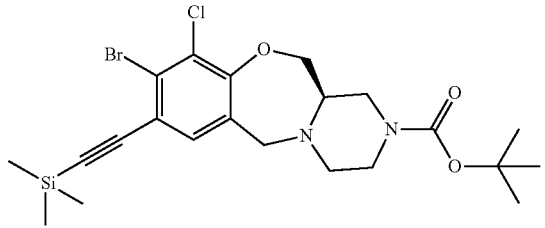 [SMILES: CC(C)(C)OC(=O)N1CCN2Cc3cc(C#C[Si](C)(C)C)c(Br)c(Cl)c3OC[C@H]2C1]

Tert-butyl (12aR)-9-bromo-10-chloro-8-iodo-3,4,12,12a-tetrahydro-6H-pyrazino[2,1-c][1,4]benzoxazepine-2(1H)-carboxylate (7 g, 12.88 mmol), tetrakis(triphenylphosphine)palladium(0) (2.98 g, 2.58 mmol) and copper(I) iodide (2.45 g, 12.88 mmol) were suspended in toluene (116 mL). Ethynyltrimethylsilane (8.91 mL, 64.38 mmol) and triethylamine (3.59 mL, 25.75 mmol) were added consecutively and the mixture was heated at 100° C. After 30 minutes the reaction mixture was cooled to room temperature and filtered through a short pad of celite (washing through with EtOAc, 100 mL). The filtrate was concentrated to give a crude brown residue. Diethylether (50 mL) was added causing a precipitate to form. The solids were filtered off and washed with diethylether (100 mL). The filtrate was concentrated under reduced pressure to give a brown residue. The crude product was purified by flash silica chromatography, elution gradient 0 to 40% ethyl acetate in heptane. Fractions were evaporated to dryness to afford tert-butyl (12aR)-9-bromo-10-chloro-8-[(trimethylsilyl)ethynyl]-3,4,12,12a-tetrahydro-6H-pyrazino[2,1-c][1,4]benzoxazepine-2(1H)-carboxylate (6.18 g, 93%) as a pale brown foam. 1H NMR (400 MHz, DMSO, 30° C.): 0.25 (9H, s), 1.40 (9H, s), 2.3-2.37 (1H, m), 2.68-2.79 (2H, m), 2.88 (1H, s), 3.06-3.18 (1H, m), 3.56 (2H, t), 3.67-3.86 (3H, m), 4.37 (1H, dd), 7.50 (1H, s). m/z: ES+ [M+H]+ 513.2.

Tert-butyl (12aR)-10-chloro-9-(2-chloro-6-methoxyphenyl)-8-[(trimethylsilyl)ethynyl]-3,4,12,12a-tetrahydro-6H-pyrazino[2,1-c][1,4]benzoxazepine-2(1H)-carboxylate

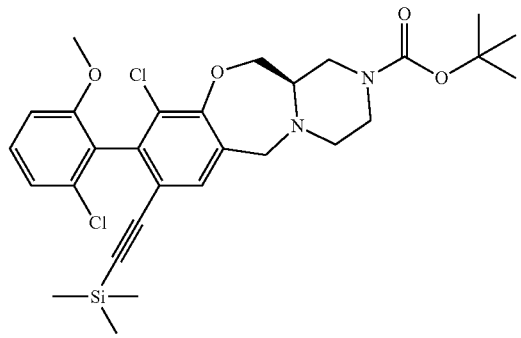 [SMILES: COc1cccc(Cl)c1-c1c(C#C[Si](C)(C)C)cc2c(c1Cl)OC[C@H]1CN(C(=O)OC(C)(C)C)CCN1C2]

A solution of tert-butyl (12aR)-9-bromo-10-chloro-8-[(trimethylsilyl)ethynyl]-3,4,12,12a-tetrahydro-6H-pyrazino[2,1-c][1,4]benzoxazepine-2(1H)-carboxylate (6.18 g, 12.02 mmol), (2-chloro-6-methoxyphenyl)boronic acid (4.48 g, 24.05 mmol) and aqueous 2M sodium carbonate (18.04 mL, 36.07 mmol) in 1,4-dioxane (102 mL) was degassed with nitrogen for 5 minutes. RuPhos Pd G3 (1.01 g, 1.20 mmol) and dicyclohexyl(2',6'-diisopropoxy-[1,1'-biphenyl]-2-yl)phosphane (0.56 g, 1.20 mmol) were added and the mixture was heated at 90° C. After 2 hours, a minor amount of starting material remained so a further portion of boronic acid was added (2.2 g). After 7 hours, the reaction mixture was cooled to room temperature and diluted with EtOAc (100 mL) and water (100 mL). The organic portion was collected and the aqueous was washed with EtOAc (100 mL). The combined organics were dried over magnesium sulphate, filtered and concentrated under reduced pressure to give a brown film. The crude product was purified by flash silica chromatography, elution gradient 0 to 40% ethyl acetate in heptane. Pure fractions were evaporated to dryness to afford tert-butyl (12aR)-10-chloro-9-(2-chloro-6-methoxyphenyl)-8-[(trimethylsilyl)ethynyl]-3,4,12,12a-tetrahydro-6H-pyrazino[2,1-c][1,4]benzoxazepine-2(1H)-carboxylate (3.40 g) as a pale brown foam (as a mixture of atropisomers). The atropisomers were separated using supercritical fluid chromatography (SFC) (Column: Phenomenex C4, 30×250 mm, 5 micron; Mobile phase A: 30% methanol (+0.1% NH3)/Mobile Phase B: 70% scCO2; flow rate: 90 mL/min; BPR: 120 bar; Column temperature: 40° C.). Fractions containing the desired products were evaporated to dryness to afford atropisomer 1 of tert-butyl (12aR)-10-chloro-9-(2-chloro-6-methoxyphenyl)-8-[(trimethylsilyl)ethynyl]-3,4,12,12a-tetrahydro-6H-pyrazino[2,1-c][1,4]benzoxazepine-2(1H)-carboxylate (1.3 g, 2.26 mmol, 19%) as a pale brown foam. 1H NMR (400 MHz, CDCl3, 30° C.): −0.03 (9H, s), 1.47 (9H, s), 2.47 (1H, ddd), 2.77-3.03 (3H, m), 3.2-3.33 (1H, m), 3.58 (1H, d), 3.67-3.88 (6H, m), 4.00 (1H, d), 4.28-4.39 (1H, m), 6.87 (1H, dd), 7.09 (1H, dd), 7.27-7.32 (2H, m). m/z: ES+ [M+H]+ 575.3. This was followed by atropisomer 2 of tert-butyl (12aR)-10-chloro-9-(2-chloro-6-methoxyphenyl)-8-[(trimethylsilyl)ethynyl]-3,4,12,12a-tetrahydro-6H-pyrazino[2,1-c][1,4]benzoxazepine-2(1H)-carboxylate (1.62 g, 2.82 mmol, 24%) as a pale brown foam. 1H NMR (400 MHz, CDCl$_3$, 30° C.): −0.03 (9H, s), 1.46 (9H, s), 2.45 (1H, ddd), 2.74-3 (3H, m), 3.27 (1H, ddd), 3.58 (1H, d), 3.64-3.84 (6H, m), 3.99 (1H, d), 4.26-4.38 (1H, m), 6.87 (1H, dd), 7.09 (1H, dd), 7.27-7.32 (2H, m). m/z: ES+ [M+H]+ 575.2.

1-[(12aR)-10-Chloro-9-(2-chloro-6-hydroxyphenyl)-8-ethynyl-3,4,12,12a-tetrahydro-6H-pyrazino[2,1-c][1,4]benzoxazepin-2(1H)-yl]prop-2-en-1-one, Example 78

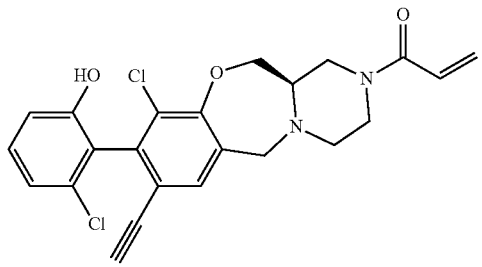 [SMILES: C#Cc1cc2c(c(Cl)c1-c1c(O)cccc1Cl)OC[C@H]1CN(C(=O)C=C)CCN1C2]

A solution of atropisomer 1 of tert-butyl (12aR)-10-chloro-9-(2-chloro-6-methoxyphenyl)-8-[(trimethylsilyl)ethynyl]-3,4,12,12a-tetrahydro-6H-pyrazino[2,1-c][1,4]benzoxazepine-2(1H)-carboxylate (1.20 g, 2.08 mmol) in DCM (20 mL) was cooled at 0° C. and tribromoborane (20.85 mL of a 1M solution in DCM, 20.85 mmol) was added dropwise with stirring. On addition the mixture was brought to room temperature and stirred. After 4 hours, the mixture was cooled in an ice-bath and the mixture was diluted with DCM (20 mL). The mixture was quenched by dropwise addition of aqueous saturated sodium hydrogen carbonate solution (added until aqueous portion remained at pH 8). The organic portion was collected and the aqueous was washed with ethyl acetate (2×50 mL). The combined organics were dried over magnesium sulphate, filtered and concentrated under reduced pressure to give 3-chloro-2-[(12aR)-10-chloro-8-ethynyl-1,2,3,4,12,12a-hexahydro-6H-pyrazino[2,1-c][1,4]benzoxazepin-9-yl]phenol as a pale brown solid (812 mg) which was suspended in DCM (20 mL) and triethylamine (0.569 mL, 4.17 mmol) was added. Acryloyl chloride (0.202 mL, 2.5 mmol) was added and the mixture was stirred at room temperature. After 10 minutes the reaction mixture was quenched by addition of aqueous saturated sodium hydrogen carbonate solution (10 mL). The organic portion was collected and the aqueous was washed with DCM (20 mL). The combined organics were passed through a phase separator cartridge and concentrated under reduced pressure. The crude residue was dissolved in methanol (5 mL) and 7N ammonia in methanol (5 mL) and stirred at room temperature. After 5 minutes the reaction mixture was concentrated under reduced pressure to give a pale yellow foam. The crude product was purified by flash silica chromatography, elution gradient 0 to 90% MeOH/EtOAc (1:9) in heptane. Pure fractions were evaporated to dryness to afford 1-[(12aR)-10-chloro-9-(2-chloro-6-hydroxyphenyl)-8-ethynyl-3,4,12,12a-tetrahydro-6H-pyrazino[2,1-c][1,4]benzoxazepin-2(1H)-yl]prop-2-en-1-one (193 mg) as a pale yellow solid. The product was further purified again using supercritical fluid chromatography (SFC) (Column: Princeton Diol, 30×250 mm, 5 micron; Mobile phase A: methanol (+0.1% NH3)/Mobile Phase B: scCO2; gradient: 24-40% over 10 minutes; flow rate: 90 mL/min; BPR: 120 bar; Column temperature: 40° C.). Fractions containing the desired product were evaporated to dryness to afford 1-[(12aR)-10-chloro-9-(2-chloro-6-hydroxyphenyl)-8-ethynyl-3,4,12,12a-tetrahydro-6H-pyrazino[2,1-c][1,4]benzoxazepin-2(1H)-yl]prop-2-en-1-one (127 mg, 14%) as a white solid. 1H NMR (400 MHz, DMSO, 30° C.): 2.37-2.44 (1H, m), 2.71-2.81 (1H, m), 2.81-2.94 (2H, m), 3.02-3.14 (1H, m), 3.67-3.81 (2H, m), 3.85-3.94 (3H, m), 3.97-4.11 (1H, m), 4.31-4.56 (1H, m), 5.62-5.81 (1H, m), 6.13 (1H, d), 6.75-6.86 (1H, m), 6.89 (1H, dd), 6.96 (1H, dd), 7.22 (1H, t), 7.44 (1H, s), 9.76 (1H, s). m/z: ES+ [M+H]+ 443.2.

Tert-butyl (12aR)-10-chloro-9-(2-fluoro-6-hydroxyphenyl)-8-[(trimethylsilyl)ethynyl]-3,4,12,12a-tetrahydro-6H-pyrazino[2,1-c][1,4]benzoxazepine-2(1H)-carboxylate

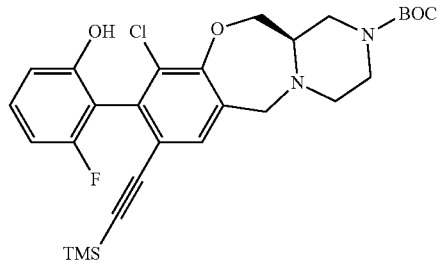 [SMILES: CC(C)(C)OC(=O)N1CCN2Cc3cc(C#C[Si](C)(C)C)c(-c4c(O)cccc4F)c(Cl)c3OC[C@H]2C1]

2-Dicyclohexylphosphino-2',6'-diisopropoxybiphenyl (45.4 mg, 0.1 mmol) and RuPhos-Pd-G3 (81 mg, 0.1 mmol) were added to tert-butyl (12aR)-9-bromo-10-chloro-8-[(trimethylsilyl)ethynyl]-3,4,12,12a-tetrahydro-6H-pyrazino[2,1-c][1,4]benzoxazepine-2(1H)-carboxylate (500 mg, 0.97 mmol), (2-fluoro-6-hydroxyphenyl)boronic acid (303 mg, 1.95 mmol) and K$_2$CO$_3$ (269 mg, 1.95 mmol) in 1,4-dioxane (8 mL) and H$_2$O (2 mL) (4:1 ratio) at 20° C. under nitrogen. The resulting mixture was stirred at 100° C. for 1 hour. The solvent was removed under reduced pressure. The crude product obtained was purified by flash silica chromatography, elution gradient 0 to 50% THF in petroleum ether. Pure fractions were evaporated to dryness to afford tert-butyl (12aR)-10-chloro-9-(2-fluoro-6-hydroxyphenyl)-8-[(trimethylsilyl)ethynyl]-3,4,12,12a-tetrahydro-6H-pyrazino[2,1-c][1,4]benzoxazepine-2(1H)-carboxylate (400 mg, 75%) as a yellow solid. 1H NMR (400 MHz, DMSO, 30° C.) 0.01 (9H, s), 1.39 (9H, s), 2.25-2.45 (1H, m), 2.62-2.93 (3H, m), 2.98-3.21 (1H, m), 3.45-3.78 (4H, m), 3.78-3.94 (1H, m), 4.24-4.44 (1H, m), 6.59-6.80 (2H, m), 7.10-7.29 (1H, m), 7.33-7.46 (1H, m), 9.64-9.84 (1H, m). m/z: ES+ [M+H]+=545.

2-[(12aR)-10-Chloro-8-ethynyl-1,2,3,4,12,12a-hexahydro-6H-pyrazino[2,1-c][1,4]benzoxazepin-9-yl]-3-fluorophenol

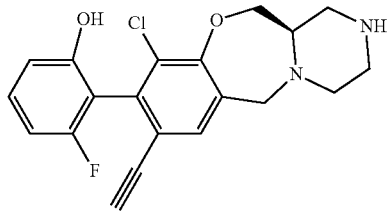 [SMILES: C#Cc1cc2c(c(Cl)c1-c1c(O)cccc1F)OC[C@H]1CNCCN1C2]

TFA (1 mL, 12.98 mmol) was added to tert-butyl (12aR)-10-chloro-9-(2-fluoro-6-hydroxyphenyl)-8-[(trimethylsilyl)ethynyl]-3,4,12,12a-tetrahydro-6H-pyrazino[2,1-c][1,4]benzoxazepine-2(1H)-carboxylate (356 mg, 0.65 mmol) in DCM (4 mL) at 20° C. The resulting mixture was stirred at 20° C. for 1 hour. The solvent was removed under reduced pressure. The crude product obtained was purified by ion exchange chromatography, using an SCX column. The desired product was eluted from the column using 7M NH$_3$/MeOH and pure fractions were evaporated to dryness to afford 2-[(12aR)-10-chloro-8-ethynyl-1,2,3,4,12,12a-hexahydro-6H-pyrazino[2,1-c][1,4]benzoxazepin-9-yl]-3-fluorophenol (140 mg, 58%) as a brown solid. 1H NMR (400 MHz, DMSO, 30° C.) 2.13-2.26 (1H, m), 2.66-2.91 (2H, m), 2.93-3.07 (2H, m), 3.19-3.42 (2H, m), 3.54-3.74 (1H, m), 3.74-4.10 (3H, m), 4.38-4.48 (1H, m), 6.54-6.94 (2H, m), 7.15-7.32 (1H, m), 7.32-7.57 (1H, m), 9.78-10.04 (1H, m) one exchangeable proton not seen. m/z: ES+ [M+H]+=373.

1-((12aR)-10-chloro-8-ethynyl-9-(2-fluoro-6-hydroxyphenyl)-3,4,12,12a-tetrahydro-6H-benzo[f]pyrazino[2,1-c][1,4]oxazepin-2(1H)-yl)prop-2-en-1-one Rotational Isomer 1, Example 79 and Rotational Isomer 2, Example 80

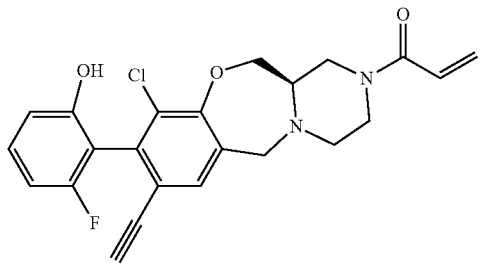 [SMILES: C#Cc1cc2c(c(Cl)c1-c1c(O)cccc1F)OC[C@H]1CN(C(=O)C=C)CCN1C2]

Acryloyl chloride (34 mg, 0.38 mmol) and DIPEA (0.328 mL, 1.88 mmol) were added to 2-[(12aR)-10-chloro-8-ethynyl-1,2,3,4,12,12a-hexahydro-6H-pyrazino[2,1-c][1,4]benzoxazepin-9-yl]-3-fluorophenol (140 mg, 0.38 mmol) in DMF (3 mL) at −20° C. under nitrogen. The reaction mixture was stirred at −20° C. for 1 hour then quenched with water and purified directly by flash C18-flash chromatography, elution gradient 0 to 100% MeCN in water (0.1% formic acid) to afford after evaporation crude product as a white solid. The crude product was purified by preparative HPLC Column: XSelect CSH Prep C18 OBD Column, 5 um, 19*150 mm; Mobile Phase A:Water (0.1% formic acid), Mobile Phase B:MeCN; Flow rate:25 mL/min; Gradient:50 B to 55 B in 7 min; 254; 220 nm. Fractions containing the desired compounds were evaporated to dryness to afford firstly rotational isomer 1 of 1-((12aR)-10-chloro-8-ethynyl-9-(2-fluoro-6-hydroxyphenyl)-3,4,12,12a-tetrahydro-6H-benzo[f]pyrazino[2,1-c][1,4]oxazepin-2(1H)-yl)prop-2-en-1-one (13 mg, 8%) as a white solid. 1H NMR (400 MHz, DMSO, 30° C.) 2.27-2.45 (1H, m), 2.63-2.77 (1H, m), 2.77-2.94 (2H, m), 2.97-3.16 (1H, m), 3.62-3.81 (2H, m), 3.82-3.99 (3H, m), 3.99-4.15 (1H, m), 4.42 (1H, t), 5.63-5.78 (1H, m), 6.09-6.26 (1H, m), 6.77-6.94 (2H, m), 6.94-7.04 (1H, m), 7.21 (1H, t), 7.43 (1H, s), 9.82 (1H, s). m/z: ES+ [M+H]+=427. This was followed by rotational isomer 2 of 1-((12aR)-10-chloro-8-ethynyl-9-(2-fluoro-6-hydroxyphenyl)-3,4,12,12a-tetrahydro-6H-benzo[f]pyrazino[2,1-c][1,4]oxazepin-2(1H)-yl)prop-2-en-1-one (16 mg, 10%) as a white solid. 1H NMR (400 MHz, DMSO, 30° C.) 2.31-2.44 (1H, m), 2.68-2.81 (1H, m), 2.80-2.98 (2H, m), 3.00-3.19 (1H, m), 3.68-3.81 (2H, m), 3.81-3.95 (3H, m), 3.95-4.13 (1H, m), 4.42 (1H, t), 5.64-5.74 (1H, m), 6.13 (1H, d), 6.76-6.92 (2H, m), 6.95 (1H, dd), 7.21 (1H, t), 7.43 (1H, s), 9.79 (1H, s). m/z: ES+ [M+H]+=427.

Ethyl 2-amino-5-chloro-6-fluoro-3-nitrobenzoate

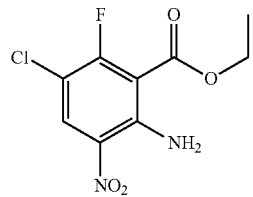 [SMILES: CCOC(=O)c1c(N)c([N+](=O)[O-])cc(Cl)c1F]

1-Chloropyrrolidine-2,5-dione (10.53 g, 78.9 mmol) was added to ethyl 2-amino-6-fluoro-3-nitrobenzoate (15 g, 65.74 mmol) in DMF (200 mL). The resulting mixture was stirred at 60° C. overnight. The reaction mixture was diluted with EtOAc (500 mL), washed sequentially with water (400 mL) and saturated brine (300 mL). The organic layer was dried over anhydrous sodium sulphate, filtered and evaporated to afford crude product. The crude product was purified by flash C18-flash chromatography, elution gradient 0 to 25% EtOAc in petroleum ether. Pure fractions were evaporated to dryness to afford ethyl 2-amino-5-chloro-6-fluoro-3-nitrobenzoate (16 g, 93%) as a yellow solid. 1H NMR (400 MHz, DMSO, 30° C.) 1.32 (3H, t), 4.39 (2H, q), 8.04 (2H, s), 8.44 (1H, d). m/z: ES+ [M+H]+=263.

Ethyl 2,3-diamino-5-chloro-6-fluorobenzoate

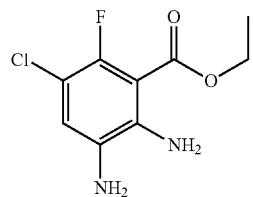

Iron (21.26 g, 380.78 mmol) was added to ethyl 2-amino-5-chloro-6-fluoro-3-nitrobenzoate (20 g, 76.16 mmol) and saturated ammonium chloride (50 mL, 76.16 mmol) in MeOH (200 mL). The resulting mixture was stirred at 80° C.

for 2 hours. The reaction mixture was filtered through celite. The solvent was removed under reduced pressure. The crude product obtained was purified by flash C18-flash chromatography, elution gradient 0 to 25% EtOAc in petroleum ether. Pure fractions were evaporated to dryness to afford ethyl 2,3-diamino-5-chloro-6-fluorobenzoate (14.4 g, 81%) as a yellow solid. 1H NMR (400 MHz, DMSO, 30° C.) 1.27 (3H, t), 4.28 (2H, q), 4.88 (2H, s), 6.04 (2H, s), 6.69 (1H, d). m/z: ES+ [M+H]+=233.

Ethyl 6-chloro-5-fluoro-1H-benzimidazole-4-carboxylate

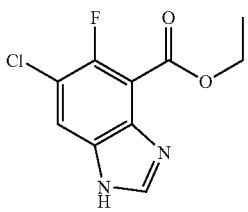 [SMILES: CCOC(=O)c1c(F)c(Cl)cc2[nH]cnc12]

Ethyl 2,3-diamino-5-chloro-6-fluorobenzoate (14 g, 60.2 mmol) was added to triethoxymethane (210 mL). The resulting mixture was stirred at 120° C. overnight. The reaction mixture was cooled to room temperature and the precipitate formed collected by filtration, washed with petroleum ether (200 mL) and dried under vacuum to afford ethyl 6-chloro-5-fluoro-1H-benzimidazole-4-carboxylate (10 g, 69%) as a white solid, 1H NMR (400 MHz, DMSO, 30° C.) 11.36 (3H, t), 4.43 (2H, q), 8.16 (1H, d), 8.35 (1H, d), 12.69 (1H, s). m/z: ES+ [M+H]+=243.

Methyl 5-chloro-6-fluoro-1-methyl-1H-benzimidazole-7-carboxylate

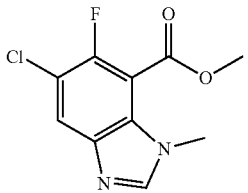 [SMILES: COC(=O)c1c(F)c(Cl)cc2ncn(C)c12]

Iodomethane (2.111 mL, 33.75 mmol) was added to ethyl 6-chloro-5-fluoro-1H-benzimidazole-4-carboxylate (7.8 g, 32.15 mmol) and K$_2$CO$_3$ (8.9 g, 64.3 mmol) in DMF (50 mL). The resulting mixture was stirred at 60° C. for 2 hours. The reaction mixture was diluted with EtOAc (300 mL) and washed sequentially with water (80 mL×3) and saturated brine (50 mL×3). The organic layer was dried over anhydrous sodium sulphate, filtered and evaporated to afford crude product. The crude product was purified by flash C18-flash chromatography, elution gradient 0 to 90% MeOH in water (0.1% formic acid). Pure fractions were evaporated to dryness to afford methyl 5-chloro-6-fluoro-1-methyl-1H-benzimidazole-7-carboxylate benzo[d]imidazole-7-carboxylate (1.6 g, 21%) as a white solid. 1H NMR (400 MHz, DMSO, 30° C.) 3.31 (3H, s), 3.98 (3H, s), 8.09 (1H, d), 8.35 (1H, s). m/z: ES+ [M+H]+=243.

4-Bromo-5-chloro-6-fluoro-1-methyl-1H-benzimidazole-7-carboxylic acid

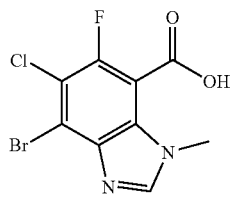

1-Bromopyrrolidine-2,5-dione (3.5 g, 19.68 mmol) was added to methyl 5-chloro-6-fluoro-1-methyl-1H-benzimidazole-7-carboxylate (1.5 g, 6.56 mmol) in concentrated sulphuric acid (20 mL). The resulting mixture was stirred at 100° C. overnight. The reaction mixture was poured into ice water and neutralised with 4M NaOH and purified directly by flash C18-flash chromatography, elution gradient 10 to 50% MeCN in water (0.05% formic acid). Pure fractions were evaporated to dryness to afford 4-bromo-5-chloro-6-fluoro-1-methyl-1H-benzimidazole-7-carboxylic acid (0.45 g, 22%) as a yellow solid. 1H NMR (400 MHz, DMSO, 30° C.) 3.86 (3H, s), 8.44 (1H, s), 14.51 (1H, s). m/z: ES+ [M+H]+=307.

Tert-butyl (3R)-4-(4-bromo-5-chloro-6-fluoro-1-methyl-1H-benzimidazole-7-carbonyl)-3-(hydroxymethyl)piperazine-1-carboxylate

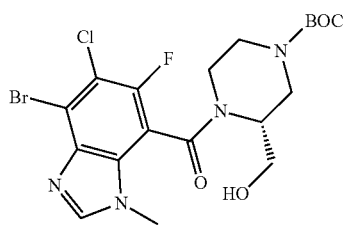 [SMILES: Cn1cnc2c(Br)c(Cl)c(F)c(C(=O)N3CCN(C(=O)OC(C)(C)C)C[C@@H]3CO)c21]

DIPEA (0.477 mL, 2.73 mmol) was added to 4-bromo-5-chloro-6-fluoro-1-methyl-1H-benzimidazole-7-carboxylic acid (420 mg, 1.37 mmol), tert-butyl (3R)-3-(hydroxymethyl)piperazine-1-carboxylate (443 mg, 2.05 mmol) and HATU (779 mg, 2.05 mmol) in DMF (10 mL) at 20° C. under nitrogen. The resulting mixture was stirred at 20° C. for 1 hour. The reaction mixture was diluted with EtOAc (150 mL) and washed with saturated brine (50 mL×3). The organic layer was dried over anhydrous sodium sulphate, filtered and evaporated to afford crude product. The crude product was purified by flash silica chromatography, elution gradient 5 to 20% MeOH in DCM. Pure fractions were evaporated to dryness to afford tert-butyl (3R)-4-(4-bromo-5-chloro-6-fluoro-1-methyl-1H-benzimidazole-7-carbonyl)-3-(hydroxymethyl)piperazine-1-carboxylate (420 mg, 61%) as a yellow solid. 1H NMR (400 MHz, DMSO, 30° C.) 1.40 (9H, s), 2.92-3.26 (4H, m), 3.64-3.93 (5H, m), 4.00-5.42 (4H, m), 8.28-8.47 (1H, m). m/z: ES+ [M+H]+=505.

Tert-butyl (7aR)-4-bromo-5-chloro-1-methyl-13-oxo-1,7a,8,10,11,13-hexahydroimidazo[4,5-g]pyrazino[2,1-c][1,4]benzoxazepine-9(7H)-carboxylate

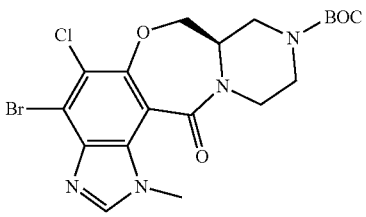 [SMILES: Cn1cnc2c(Br)c(Cl)c3c(c21)C(=O)N1CCN(C(=O)OC(C)(C)C)C[C@@H]1CO3]

Sodium hydride (79 mg, 1.98 mmol) was added to tert-butyl (3R)-4-(4-bromo-5-chloro-6-fluoro-1-methyl-1H-benzimidazole-7-carbonyl)-3-(hydroxymethyl)piperazine-1-carboxylate (400 mg, 0.79 mmol) in DMF (10 mL) at 0° C. under nitrogen. The resulting mixture was stirred at 25° C. for 1 hour. The reaction mixture was quenched with saturated NH$_4$Cl (50 mL) and extracted with EtOAc (3×75 mL). The organic layer was dried over anhydrous sodium sulphate, filtered and evaporated to afford crude. The crude product was purified by flash silica chromatography, elution gradient 5 to 20% MeOH in DCM. Pure fractions were evaporated to dryness to afford tert-butyl (7aR)-4-bromo-5-chloro-1-methyl-13-oxo-1,7a,8,10,11,13-hexahydroimidazo[4,5-g]pyrazino[2,1-c][1,4]benzoxazepine-9(7H)-carboxylate (350 mg, 91%) as a yellow solid. 1H NMR (400 MHz, DMSO, 30° C.) 1.41 (9H, d), 3.15-3.50 (3H, m), 3.78 (5H, s), 3.90-4.48 (4H, m), 8.37 (1H, s). m/z: ES+ [M+H]+=485.

Tert-butyl (7aR)-5-chloro-4-(2-chloro-6-hydroxyphenyl)-1-methyl-13-oxo-1,7a,8,10,11,13-hexahydroimidazo[4,5-g]pyrazino[2,1-c][1,4]benzoxazepine-9(7H)-carboxylate

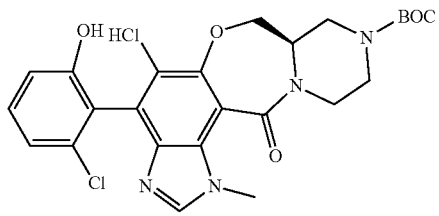 [SMILES: Cn1cnc2c(-c3c(O)cccc3Cl)c(Cl)c3c(c21)C(=O)N1CCN(C(=O)OC(C)(C)C)C[C@@H]1CO3]

K$_2$CO$_3$ (256 mg, 1.85 mmol) was added to 2-Dicyclohexylphosphino-2',6'-diisopropoxybiphenyl (28.8 mg, 0.06 mmol), RuPhos-Pd-G3 (51.7 mg, 0.06 mmol), (2-chloro-6-hydroxyphenyl)boronic acid (319 mg, 1.85 mmol) and tert-butyl (7aR)-4-bromo-5-chloro-1-methyl-13-oxo-1,7a,8,10,11,13-hexahydroimidazo[4,5-g]pyrazino[2,1-c][1,4]benzoxazepine-9(7H)-carboxylate (300 mg, 0.62 mmol) in 1,4-dioxane (5 mL) and water (1 mL)(5:1 ratio) under nitrogen. The resulting mixture was stirred at 100° C. for 1 hour. Then purified directly by flash C18-flash chromatography, elution gradient 5 to 50% MeCN in water (0.1% formic acid). Pure fractions were evaporated to dryness to afford tert-butyl (7aR)-5-chloro-4-(2-chloro-6-hydroxyphenyl)-1-methyl-13-oxo-1,7a,8,10,11,13-hexahydroimidazo[4,5-g]pyrazino[2,1-c][1,4]benzoxazepine-9(7H)-carboxylate (220 mg, 67%) as a yellow solid. 1H NMR (400 MHz, DMSO, 30° C.) 1.43 (9H, s), 3.37-3.57 (2H, m), 3.58-3.94 (5H, m), 3.93-4.41 (5H, m), 6.83-7.09 (2H, m), 7.20-7.31 (1H, m), 8.15 (1H, s), 9.85 (1H, s). m/z: ES+ [M+H]+=533.

Tert-butyl (7aR)-5-chloro-4-(2-chloro-6-hydroxyphenyl)-1-methyl-1,7a,8,10,11,13-hexahydroimidazo[4,5-g]pyrazino[2,1-c][1,4]benzoxazepine-9(7H)-carboxylate

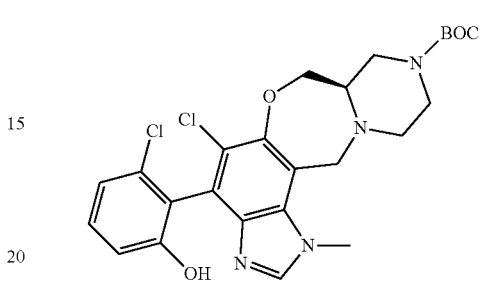

1M Borane-THF complex solution in THF (4124 µl, 4.12 mmol) was added to tert-butyl (7aR)-5-chloro-4-(2-chloro-6-hydroxyphenyl)-1-methyl-13-oxo-1,7a,8,10,11,13-hexahydroimidazo[4,5-g]pyrazino[2,1-c][1,4]benzoxazepine-9(7H)-carboxylate (220 mg, 0.41 mmol) at room temperature. The resulting mixture was stirred at 60° C. for 4 hours. The reaction mixture was quenched with MeOH (20 mL) and the solvent removed under reduced pressure. The crude product obtained was purified by flash silica chromatography, elution gradient 5 to 20% MeOH in DCM. Pure fractions were evaporated to dryness to afford tert-butyl (7aR)-5-chloro-4-(2-chloro-6-hydroxyphenyl)-1-methyl-1,7a,8,10,11,13-hexahydroimidazo[4,5-g]pyrazino[2,1-c][1,4]benzoxazepine-9(7H)-carboxylate (120 mg, 56%) as a yellow solid. m/z: ES+ [M+H]+=519.

3-Chloro-2-[(7aR)-5-chloro-1-methyl-1,7,7a,8,9,10,11,13-octahydroimidazo[4,5-g]pyrazino[2,1-c][1,4]benzoxazepin-4-yl]phenol

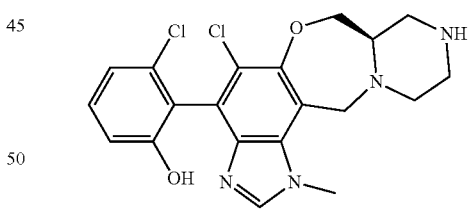

TFA (0.5 mL, 6.49 mmol) was added to tert-butyl (7aR)-5-chloro-4-(2-chloro-6-hydroxyphenyl)-1-methyl-1,7a,8,10,11,13-hexahydroimidazo[4,5-g]pyrazino[2,1-c][1,4]benzoxazepine-9(7H)-carboxylate (120 mg, 0.22 mmol) in DCM (5 mL). The resulting mixture was stirred at 25° C. for 4 hours. The solvent was removed under reduced pressure. The crude product obtained was purified by ion exchange chromatography, using an SCX column. The desired product was eluted from the column using 7M NH$_3$/MeOH and pure fractions were evaporated to dryness to 3-chloro-2-((7aR)-5-chloro-1-methyl-1,7,7a,8,9,10,11,13-octahydroimidazo[4',5':5,6]benzo[1,2-f]pyrazino[2,1-c][1,4]oxazepin-4-yl)phenol (80 mg, 85%) as a yellow solid. m/z: ES+ [M+H]+=419.

1-[(7aR)-5-Chloro-4-(2-chloro-6-hydroxyphenyl)-1-methyl-1,7a,8,10,11,13-hexahydroimidazo[4,5-g]pyrazino[2,1-c][1,4]benzoxazepin-9(7H)-yl]prop-2-en-1-one Rotational Isomer 1, Example 81 and Rotational Isomer 2, Example 82

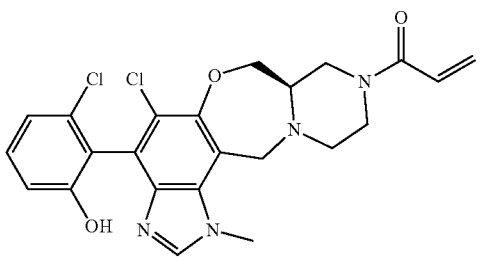 [SMILES: C=CC(=O)N1CCN2Cc3c(c(Cl)c(-c4c(O)cccc4Cl)c4ncn(C)c34)OC[C@H]2C1]

Acryloyl chloride (19.43 mg, 0.21 mmol) was added to 3-chloro-2-[(7aR)-5-chloro-1-methyl-1,7,7a,8,9,10,11,13-octahydroimidazo[4,5-g]pyrazino[2,1-c][1,4]benzoxazepin-4-yl]phenol and DIPEA (0.112 mL, 0.64 mmol) in DMF (2 mL). The resulting mixture was stirred at 0° C. for 4 hours then purified directly and each atropisomer separated by preparative HPLC Column: XBridge Shield RP18 OBD Column, 30*150 mm, 5 um; Mobile Phase A:Water (0.05% NH3H2O), Mobile Phase B:MeCN; Flow rate:60 mL/min; Gradient:24 B to 38 B in 7 min; 254/220 nm. Fractions containing the desired compounds were evaporated to dryness to afford firstly rotational isomer 1 of 1-[(7aR)-5-chloro-4-(2-chloro-6-hydroxyphenyl)-1-methyl-1,7a,8,10,11,13-hexahydroimidazo[4,5-g]pyrazino[2,1-c][1,4]benzoxazepin-9(7H)-yl]prop-2-en-1-one (25 mg, 25%) as a white solid. 1H NMR (400 MHz, DMSO, 30° C.) 2.19-2.45 (1H, m), 2.61-2.88 (2H, m), 2.88-3.10 (2H, m), 3.49-3.70 (1H, m), 3.75-4.35 (5H, m), 4.32-4.90 (3H, m), 5.26-5.96 (1H, m), 6.06-6.51 (1H, m), 6.63-7.04 (3H, m), 7.43 (1H, t), 7.98 (1H, s), 9.60 (1H, s). m/z: ES+ [M+H]+=473. This was followed by rotational isomer 2 of 1-[(7aR)-5-chloro-4-(2-chloro-6-hydroxyphenyl)-1-methyl-1,7a,8,10,11,13-hexahydroimidazo[4,5-g]pyrazino[2,1-c][1,4]benzoxazepin-9(7H)-yl]prop-2-en-1-one (15 mg, 15%) as a white solid 1H NMR (400 MHz, DMSO, 30° C.) 2.49-2.51 (1H, m), 2.71-2.89 (2H, m), 2.89-3.14 (2H, m), 3.50-3.76 (1H, m), 3.79-4.17 (6H, m), 4.17-4.83 (2H, m), 5.59-5.84 (1H, m), 6.15 (1H, d), 6.85-6.91 (2H, m), 6.93-7.08 (1H, m), 7.24 (1H, t), 8.01 (1H, s), 9.57 (1H, s). m/z: ES+ [M+H]+=473.

4-Bromo-5-chloro-2,3-difluorobenzoic acid

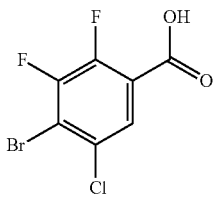

1-Chloropyrrolidine-2,5-dione (5.63 g, 42.19 mmol) was added to 4-bromo-2,3-difluorobenzoic acid (5 g, 21.1 mmol) in concentrated sulphuric acid (30 mL). The resulting mixture was stirred at 80° C. for 1 hour. The reaction mixture was poured into water and extracted with EtOAc (2×100 mL). The organic layer was dried over anhydrous sodium sulphate, filtered and solvent removed under reduced pressure. The crude product obtained was purified by flash C18-flash chromatography, elution gradient 0 to 50% MeOH in water (0.1% formic acid). Pure fractions were evaporated to dryness to afford 4-bromo-5-chloro-2,3-difluorobenzoic acid (5 g, 87%) as a yellow solid. 1H NMR (400 MHz, DMSO, 30° C.) 7.09-7.17 (1H, m), 11.52-11.83 (1H, m). m/z: ES+ [M+H]+=271.

Tert-butyl (3R)-4-(4-bromo-5-chloro-2,3-difluorobenzoyl)-3-(hydroxymethyl)piperazine-1-carboxylate

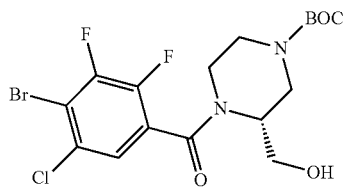 [SMILES: CC(C)(C)OC(=O)N1CCN(C(=O)c2cc(Cl)c(Br)c(F)c2F)[C@@H](CO)C1]

DIPEA (7.14 g, 55.26 mmol) was added to 4-bromo-5-chloro-2,3-difluorobenzoic acid (5 g, 18.42 mmol), HATU (14 g, 36.84 mmol) and tert-butyl (3R)-3-(hydroxymethyl)piperazine-1-carboxylate (3.98 g, 18.42 mmol) in DMF (100 mL) at 0° C. The resulting mixture was stirred at 0° C. for 1 hour. The reaction mixture was diluted with EtOAc (150 mL), washed sequentially with water (150 mL×3) and saturated brine (150 mL). The organic layer was dried over anhydrous sodium sulphate, filtered and evaporated. The crude product obtained was purified by flash silica chromatography, elution gradient 0 to 50% THF in petroleum ether. Pure fractions were evaporated to dryness to afford tert-butyl (3R)-4-(4-bromo-5-chloro-2,3-difluorobenzoyl)-3-(hydroxymethyl)piperazine-1-carboxylate (2.3 g, 27%) as a yellow solid. 1H NMR (400 MHz, DMSO, 30° C.) 1.37-1.43 (9H, m), 2.73-3.22 (3H, m), 3.28-3.31 (2H, m), 3.39-3.89 (2H, m), 3.90-4.12 (1H, m), 4.20-4.33 (1H, m), 7.49-7.74 (1H, m) one exchangeable proton not seen. m/z: ES+ [M+H]+=469.

Tert-butyl (12aR)-9-bromo-8-chloro-10-fluoro-6-oxo-3,4,12,12a-tetrahydro-6H-pyrazino[2,1-c][1,4]benzoxazepine-2(1H)-carboxylate

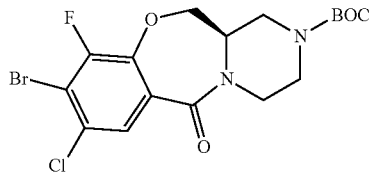 [SMILES: CC(C)(C)OC(=O)N1CCN2C(=O)c3cc(Cl)c(Br)c(F)c3OC[C@H]2C1]

Sodium hydride (0.358 g, 8.94 mmol) was added to tert-butyl (3R)-4-(4-bromo-5-chloro-2,3-difluorobenzoyl)-3-(hydroxymethyl)piperazine-1-carboxylate (2.1 g, 4.47 mmol) in DMF (50 mL) at 0° C. under nitrogen. The resulting mixture was stirred at room temperature for 1 hour. The reaction mixture was quenched with ice water, extracted with EtOAc (100 mL), washed sequentially with water (100 mL) and saturated brine (100 mL×2). The organic layer was dried over anhydrous sodium sulphate, filtered and evaporated. The crude product obtained was purified by flash silica chromatography, elution gradient 0 to 50% EtOAc in petroleum ether. Pure fractions were evaporated to dryness to tert-butyl (12aR)-9-bromo-8-chloro-10-fluoro-6-oxo-3,4,12,12a-tetrahydro-6H-pyrazino[2,1-c][1,4]benzoxazepine-2(1H)-carboxylate (2 g, 99%) as a yellow solid. m/z: ES+ [M+H]+=469.

Tert-butyl (12aR)-9-bromo-8-chloro-10-fluoro-3,4,12,12a-tetrahydro-6H-pyrazino[2,1-c][1,4]benzoxazepine-2(1H)-carboxylate

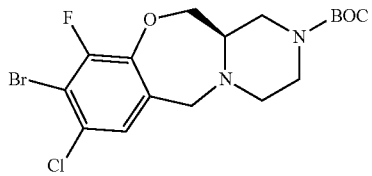 [SMILES: CC(C)(C)OC(=O)N1CCN2Cc3cc(Cl)c(Br)c(F)c3OC[C@H]2C1]

1M Borane-THF complex solution in THF (10 mL, 10 mmol) was added to tert-butyl (12aR)-9-bromo-8-chloro-10-fluoro-6-oxo-3,4,12,12a-tetrahydro-6H-pyrazino[2,1-c][1,4]benzoxazepine-2(1H)-carboxylate (1 g, 2.22 mmol) in THF (10 mL) at room temperature. The resulting mixture was stirred at 60° C. for 45 minutes. The reaction mixture was quenched with saturated NH₄Cl. The reaction mixture was diluted with EtOAc (50 mL), washed sequentially with water (50 mL) and saturated brine (50 mL×2). The organic layer was dried over anhydrous sodium sulphate, filtered and evaporated to afford crude product. The crude product was purified by flash silica chromatography, elution gradient 0 to 40% THF in petroleum ether. Pure fractions were evaporated to dryness to afford tert-butyl (12aR)-9-bromo-8-chloro-10-fluoro-3,4,12,12a-tetrahydro-6H-pyrazino[2,1-c][1,4]benzoxazepine-2(1H)-carboxylate (0.9 g, 93%) as a yellow solid. 1H NMR (400 MHz, DMSO, 30° C.) 1.39 (9H, s), 2.16-2.39 (2H, m), 2.61-2.83 (2H, m), 3.09-3.19 (1H, m), 3.48-3.64 (1H, m), 3.61-3.96 (4H, m), 4.27-4.39 (1H, m), 7.42-7.46 (1H, m). m/z: ES+ [M+H]+=435.

Tert-butyl (12aR)-8-chloro-9-(2-chloro-6-hydroxyphenyl)-10-fluoro-3,4,12,12a-tetrahydro-6H-pyrazino[2,1-c][1,4]benzoxazepine-2(1H)-carboxylate

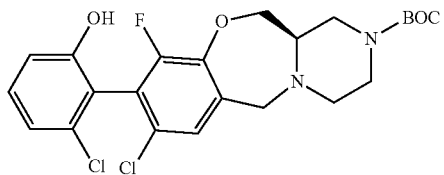 [SMILES: CC(C)(C)OC(=O)N1CCN2Cc3cc(Cl)c(-c4c(O)cccc4Cl)c(F)c3OC[C@H]2C1]

K₂CO₃ (0.793 g, 5.74 mmol) and (2-chloro-6-hydroxyphenyl)boronic acid (1.187 g, 6.89 mmol) were added to tert-butyl (12aR)-9-bromo-8-chloro-10-fluoro-3,4,12,12a-tetrahydro-6H-pyrazino[2,1-c][1,4]benzoxazepine-2(1H)-carboxylate (1.00 g, 2.30 mmol), 2-dicyclohexylphosphino-2',6'-diisopropoxybiphenyl (0.107 g, 0.23 mmol) and RuPhos-Pd-G3 (0.192 g, 0.23 mmol) in 1,4-dioxane (15 mL) and water (3 mL) (5:1 ratio) under nitrogen. The resulting mixture was stirred at 100° C. for 1 hour.

The reaction mixture cooled to room temperature was purified by flash C18-flash chromatography, elution gradient 0 to 60% MeOH in water (0.1% formic acid). Pure fractions were evaporated to dryness to afford tert-butyl (12aR)-8-chloro-9-(2-chloro-6-hydroxyphenyl)-10-fluoro-3,4,12,12a-tetrahydro-6H-pyrazino[2,1-c][1,4]benzoxazepine-2(1H)-carboxylate (0.5 g, 45%) as a yellow solid. 1H NMR (400 MHz, DMSO, 30° C.) 1.40 (9H, s), 2.29-2.43 (1H, m), 2.67-2.74 (2H, m), 2.74-2.86 (1H, m), 3.01-3.14 (1H, m), 3.60-3.68 (2H, m), 3.69-3.84 (1H, m), 3.87-3.94 (1H, m), 4.25-4.41 (2H, m), 6.88-6.96 (1H, m), 6.98-7.04 (1H, m), 7.24-7.28 (1H, m), 7.28-7.33 (1H, m), 9.87-10.25 (1H, m). m/z: ES+ [M+H]+=483.

3-Chloro-2-[(12aR)-8-chloro-10-fluoro-1,2,3,4,12,12a-hexahydro-6H-pyrazino[2,1-c][1,4]benzoxazepin-9-yl]phenol

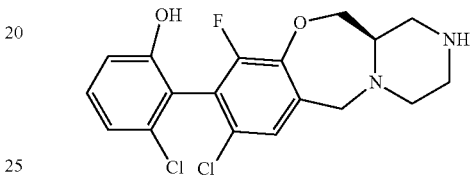

TFA (1 mL, 12.98 mmol) was added to tert-butyl (12aR)-8-chloro-9-(2-chloro-6-hydroxyphenyl)-10-fluoro-3,4,12,12a-tetrahydro-6H-pyrazino[2,1-c][1,4]benzoxazepine-2(1H)-carboxylate (500 mg, 1.03 mmol) in DCM (5 mL). The resulting mixture was stirred at room temperature for 1 hour. The solvent was removed under reduced pressure. The residue obtained was purified by ion exchange chromatography, using an SCX column. The desired product was eluted from the column using 7M NH₃/MeOH and pure fractions were evaporated to dryness to afford 3-chloro-2-[(12aR)-8-chloro-10-fluoro-1,2,3,4,12,12a-hexahydro-6H-pyrazino[2,1-c][1,4]benzoxazepin-9-yl]phenol (350 mg, 88%) as a yellow solid. 1H NMR (400 MHz, DMSO, 30° C.) 2.27-2.36 (3H, m), 2.67-2.87 (4H, m), 3.55-3.82 (4H, m), 4.14-4.32 (1H, m), 6.89-6.94 (1H, m), 6.97-7.05 (1H, m), 7.23-7.32 (2H, m) one exchangeable proton not seen. m/z: ES+ [M+H]+=383.

1-[(12aR)-8-Chloro-9-(2-chloro-6-hydroxyphenyl)-10-fluoro-3,4,12,12a-tetrahydro-6H-pyrazino[2,1-c][1,4]benzoxazepin-2(1H)-yl]prop-2-en-1-one Rotational Isomer 1, Example 83 and Rotational Isomer 2, Example 84

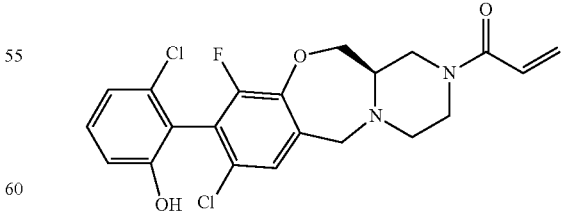

Acryloyl chloride (0.074 mL, 0.91 mmol) was added to 3-chloro-2-[(12aR)-8-chloro-10-fluoro-1,2,3,4,12,12a-hexahydro-6H-pyrazino[2,1-c][1,4]benzoxazepin-9-yl]phenol (350 mg, 0.91 mmol) and DIPEA (0.479 mL, 2.74 mmol) in DMF (6 mL) at 0° C. The resulting mixture was stirred at 0° C. for 1 hour. The reaction mixture was quenched with water (0.5 mL) and purified directly by flash C18-flash chromatography, elution gradient 0 to 60% MeOH in water (0.1% formic acid). Product containing fractions were evaporated to dryness to afford crude product as a white solid. The crude product was purified and each atropisomer separated by preparative HPLC Column: XBridge Prep OBD C18 Column, 19*250 mm, 5 um; Mobile Phase A:Water (10 mmol/L $NH_4HCO_3$+0.1% $NH_3·H_2O$), Mobile Phase B:MeCN; Flow rate:25 mL/min; Gradient:47 B to 60 B in 7 min; 254; 220 nm. Fractions containing the desired compounds were evaporated to dryness to afford firstly rotational isomer 1 of 1-[(12aR)-8-chloro-9-(2-chloro-6-hydroxyphenyl)-10-fluoro-3,4,12,12a-tetrahydro-6H-pyrazino[2,1-c][1,4]benzoxazepin-2(1H)-yl]prop-2-en-1-one (42 mg, 20%) as a white solid. 1H NMR (400 MHz, DMSO, 30° C.) 2.32-2.44 (1H, m), 2.64-2.94 (3H, m), 3.01-3.18 (1H, m), 3.67-3.81 (2H, m), 3.81-3.96 (2H, m), 3.97-4.10 (1H, m), 4.30-4.52 (1H, m), 5.66-5.75 (1H, m), 6.05-6.20 (1H, m), 6.75-6.88 (1H, m), 6.89-6.97 (1H, m), 6.99-7.07 (1H, m), 7.21-7.37 (2H, m), 10.07 (1H, s). m/z: ES+ [M+H]+= 437. This was followed by rotational isomer 2 of 1-[(12aR)-8-chloro-9-(2-chloro-6-hydroxyphenyl)-10-fluoro-3,4,12,12a-tetrahydro-6H-pyrazino[2,1-c][1,4]benzoxazepin-2(1H)-yl]prop-2-en-1-one (37 mg, 17%) as a white solid. 1H NMR (400 MHz, DMSO, 30° C.) 2.33-2.46 (1H, m), 2.65-2.80 (1H, m), 2.81-2.98 (2H, m), 3.03-3.18 (1H, m), 3.66-3.79 (2H, m), 3.81-4.11 (3H, m), 4.31-4.47 (1H, m), 5.64-5.77 (1H, m), 6.08-6.18 (1H, m), 6.73-6.91 (1H, m), 6.87-7.05 (2H, m), 7.22-7.36 (2H, m), 10.05 (1H, s). m/z: ES+ [M+H]+=437.

Tert-butyl (12aR)-9-bromo-10-fluoro-8-(prop-1-yn-1-yl)-3,4,12,12a-tetrahydro-6H-pyrazino[2,1-c][1,4]benzoxazepine-2(1H)-carboxylate

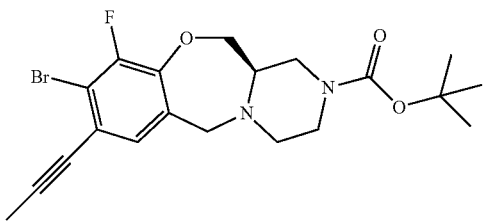 [SMILES: CC#Cc1cc2c(c(F)c1Br)OC[C@H]1CN(C(=O)OC(C)(C)C)CCN1C2]

Tert-butyl (12aR)-9-bromo-10-fluoro-8-iodo-3,4,12,12a-tetrahydro-6H-pyrazino[2,1-c][1,4]benzoxazepine-2(1H)-carboxylate (2 g, 3.79 mmol), tetrakis(triphenylphosphine)palladium(0) (0.219 g, 0.19 mmol) and copper(I) iodide (0.217 g, 1.14 mmol) were suspended in toluene (31.4 mL) and triethylamine (1.745 mL, 12.52 mmol) was added. 1-(Trimethylsilyl)propyne (0.618 mL, 4.17 mmol) and 1M tetrabutylammonium fluoride in THF (4.17 mL, 4.17 mmol) were then added consecutively and the resulting solution was stirred at room temperature for 3 hours. Additional 1-(trimethylsilyl)propyne (0.618 mL, 4.17 mmol) and 1M tetrabutylammonium fluoride solution in THF (4.17 mL, 4.17 mmol) were added and the reaction mixture stirred at room temperature overnight. The mixture was diluted with diethyl ether, filtered through a short pad of celite and the filtrate concentrated under reduced pressure. The crude product obtained was purified by flash silica chromatography, elution gradient 0 to 50% EtOAc in heptane. Pure fractions were evaporated to dryness to afford tert-butyl (12aR)-9-bromo-10-fluoro-8-(prop-1-yn-1-yl)-3,4,12,12a-tetrahydro-6H-pyrazino[2,1-c][1,4]benzoxazepine-2(1H)-carboxylate (1.47 g, 88%) as a brown foam. 1H NMR (400 MHz, DMSO, 30° C.) 1.40 (9H, s), 2.10 (3H, s), 2.33 (1H, ddd), 2.63-2.78 (2H, m), 2.89 (1H, s), 3.12 (1H, ddd), 3.56 (2H, t), 3.63-3.85 (3H, m), 4.33 (1H, dd), 7.27 (1H, d). m/z: ES+ [M+H]+=439.

Tert-butyl (12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepine-2(1H)-carboxylate

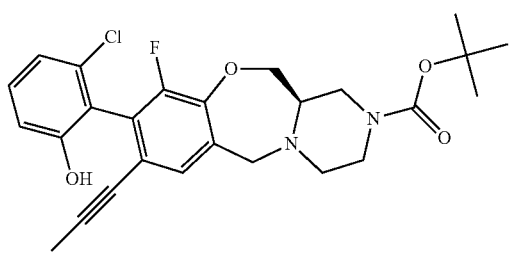 [SMILES: CC#Cc1cc2c(c(F)c1-c1c(O)cccc1Cl)OC[C@H]1CN(C(=O)OC(C)(C)C)CCN1C2]

A solution of tert-butyl (12aR)-9-bromo-10-fluoro-8-(prop-1-yn-1-yl)-3,4,12,12a-tetrahydro-6H-pyrazino[2,1-c][1,4]benzoxazepine-2(1H)-carboxylate (1.47 g, 3.35 mmol), (2-chloro-6-hydroxyphenyl)boronic acid (0.865 g, 5.02 mmol) and aqueous 2M sodium carbonate (5.02 mL, 10.04 mmol) in 1,4-dioxane (28.4 mL) was degassed with nitrogen for 5 minutes. RuPhos-Pd-G3 (0.280 g, 0.33 mmol) and 2-dicyclohexylphosphino-2',6'-diisopropoxybiphenyl (0.156 g, 0.33 mmol) were added and the mixture was heated at 90° C. for 1 hour. The reaction mixture was evaporated, water and DCM added and the organic layer washed with saturated brine. The organic layer was dried by passing through a phase transfer cartridge. Evaporation afforded a crude product as a gum. The crude product was purified by flash silica chromatography, elution gradient 0 to 10% EtOAc in heptane. Pure fractions were evaporated to dryness to afford a yellow foam tert-butyl (12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepine-2(1H)-carboxylate (1.43 g, 88%). m/z: ES+ [M+H]+=487.

3-Chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol Rotational Isomer 1 and 2

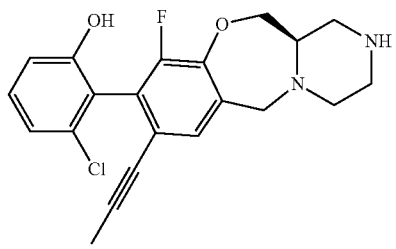 [SMILES: CC#Cc1cc2c(c(F)c1-c1c(O)cccc1Cl)OC[C@H]1CNCCN1C2]

Tert-butyl (12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepine-2(1H)-carboxylate (1.43 g, 2.94 mmol) was dissolved in DCM (20 mL) and TFA (6.74 mL, 88.10 mmol) added. The resulting solution was stirred at room temperature for 1 hour. The crude reaction mixture was purified by ion exchange chromatography, using an SCX column. The desired product was eluted from the column using 1M NH₃/MeOH and pure fractions were evaporated to dryness to afford crude product 3-chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol (1.014 g, 89%) as yellow foam. m/z: ES+ [M+H]+=387. This was purified by preparative HPLC (Waters CSH C18 OBD column, 30×100 mm id, 5 micron particle size), using decreasingly polar mixtures of water (containing 1% by volume of NH₄OH (28-30% in H₂O)) and MeCN as eluents. Shallow gradient: 20 to 40% MeCN. Detection UV @ 254 nm. Acetonitrile was removed by evaporation and the resulting aqueous suspension was extracted with DCM and dried by passing through a phase separator cartridge. Evaporation afforded firstly rotational isomer 1 of 3-chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol (0.272 g, 27%) as a yellow foam. 1H NMR (400 MHz, DMSO, 30° C.) 1.79 (3H, s), 2.05 (1H, d), 2.23-2.38 (2H, m), 2.57-2.69 (2H, m), 2.69-2.82 (3H, m), 3.59-3.8 (3H, m), 4.24 (1H, dd), 6.88 (1H, dd), 6.98 (1H, dd), 7.15-7.18 (1H, m), 7.22 (1H, t), 9.81 (1H, s). m/z: ES+ [M+H]+=387. This was followed by rotational isomer 2 of 3-chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol (0.271 g, 27%). 1H NMR (400 MHz, DMSO, 30° C.) 1.79 (3H, s), 2.13 (1H, s), 2.26-2.38 (2H, m), 2.57-2.68 (2H, m), 2.76 (3H, ddd), 3.61 (1H, d), 3.66-3.8 (2H, m), 4.24 (1H, dd), 6.89 (1H, dd), 6.97 (1H, dd), 7.16-7.18 (1H, m), 7.22 (1H, t), 9.82 (1H, s). m/z: ES+ [M+H]+=387.

1-[(12aR)-9-(2-Chloro-6-hydroxyphenyl)-10-fluoro-8-(prop-1-yn-1-yl)-3,4,12,12a-tetrahydro-6H-pyrazino[2,1-c][1,4]benzoxazepin-2(1H)-yl]prop-2-en-1-one Rotational Isomer 1, Example 85

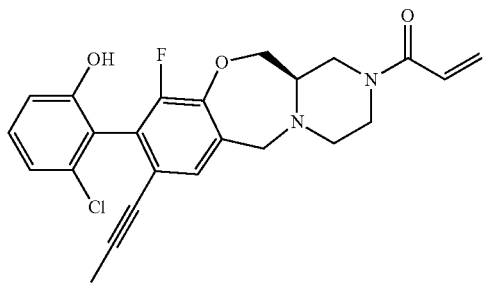 [SMILES: C=CC(=O)N1CCN2Cc3cc(C#CC)c(-c4c(O)cccc4Cl)c(F)c3OC[C@H]2C1]

To a suspension of 3-chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol (0.272 g, 0.70 mmol) and DIPEA (0.159 mL, 0.91 mmol) in DCM (2 mL) under nitrogen at 0° C. was added acryloyl chloride (0.061 mL, 0.77 mmol) dropwise and reaction mixture stirred at 0° C. for 30 minutes. The reaction mixture was evaporated (40° C. water bath) to afford a yellow oil. The oil was dissolved in cold 7N NH₃/MeOH (10 mL). The resulting solution was stirred to room temperature over 30 minutes. Evaporation at 40° C. afforded crude product as a yellow gum. The crude product was purified by preparative HPLC (Waters CSH C18 OBD column, 30×100 mm id, 5 micron particle size), using decreasingly polar mixtures of water (containing 1% by volume of NH₄OH (28-30% in H2O)) and MeCN as eluents. Shallow gradient: 20 to 45% MeCN. Detection UV @254 nm. Fractions containing the desired compound were evaporated to dryness to afford rotational isomer 1 of 1-[(12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepin-2(1H)-yl]prop-2-en-1-one (0.188 g, 61%) as a white solid. 1H NMR (400 MHz, DMSO, 30° C.) 1.79 (3H, s), 2.41 (1H, s), 2.62-2.78 (1H, m), 2.79-2.91 (2H, m), 3.10 (1H, s), 3.64-3.79 (2H, m), 3.87 (2H, d), 4.03 (1H, d), 4.37 (1H, d), 5.70 (1H, d), 6.13 (1H, d), 6.93 (3H, ddd), 7.21 (2H, dd), 9.82 (1H, s). m/z: ES+ [M+H]+=441.

1-[(12aR)-9-(2-Chloro-6-hydroxyphenyl)-10-fluoro-8-(prop-1-yn-1-yl)-3,4,12,12a-tetrahydro-6H-pyrazino[2,1-c][1,4]benzoxazepin-2(1H)-yl]prop-2-en-1-one Rotational Isomer 2, Example 86

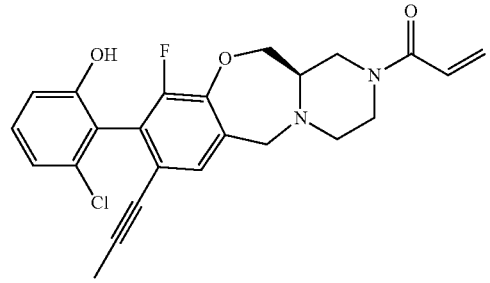 [SMILES: C=CC(=O)N1CCN2Cc3cc(C#CC)c(-c4c(O)cccc4Cl)c(F)c3OC[C@H]2C1]

To a suspension of 3-chloro-2-[(12aR)-10-fluoro-8-(prop-1-yn-1-yl)-1,2,3,4,12,12a-hexahydro-6H-pyrazino[2,1-c][1,4]benzoxazepin-9-yl]phenol (0.271 g, 0.70 mmol) and DIPEA (0.159 mL, 0.91 mmol) in DCM (2 mL) under nitrogen at 0° C. was added acryloyl chloride (0.061 mL, 0.77 mmol) dropwise and reaction mixture stirred at 0° C. for 30 minutes. The reaction mixture was evaporated (40° C. water bath) to afford a yellow oil. The oil was dissolved in cold 7N NH₃/MeOH (10 mL). The resulting solution was stirred to room temperature over 30 minutes. Evaporation at 40° C. afforded crude product as a yellow gum. The crude product was purified by preparative HPLC (Waters CSH C18 OBD column, 30×100 mm id, 5 micron particle size), using decreasingly polar mixtures of water (containing 1% by volume of NH₄OH (28-30% in H₂O)) and MeCN as eluents. Shallow gradient: 20 to 45% MeCN. Detection UV @254 nm. Fractions containing the desired compound were evaporated to dryness to afford rotational isomer 2 of 1-[(12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepin-2(1H)-yl]prop-2-en-1-one (0.154 g, 50%) as a white solid. 1H NMR (400 MHz, DMSO, 30° C.) 1.79 (3H, s), 2.42 (1H, s), 2.63-2.77 (1H, m), 2.87 (2H, t), 3.09 (1H, s), 3.73 (2H, dd), 3.89 (2H, d), 4.01 (1H, d), 4.37 (1H, d), 5.70 (1H, d), 6.13 (1H, d), 6.74-7.01 (3H, m), 7.12-7.26 (2H, m), 9.86 (1H, s). m/z: ES+ [M+H]+=441.

Tert-butyl (3R)-4-(5-bromo-3-fluoropyridine-2-carbonyl)-3-(hydroxymethyl)piperazine-1-carboxylate

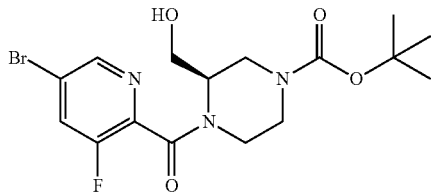 [SMILES: CC(C)(C)OC(=O)N1CCN(C(=O)c2ncc(Br)cc2F)[C@@H](CO)C1]

HATU (20.73 g, 54.55 mmol) was added to a solution of 5-bromo-3-fluoropyridine-2-carboxylic acid (10 g, 45.46 mmol), tert-butyl (3R)-3-(hydroxymethyl)piperazine-1-carboxylate (10.81 g, 50 mmol) and DIPEA (18.06 mL, 104.55 mmol) in THF (200 mL) at room temperature. The reaction mixture was stirred overnight, diluted with EtOAc (150 mL) and water (150 mL) then extracted with EtOAc (100 mL). The combined organics were washed with water (150 mL) and brine (150 mL). The organic layer was then dried over anhydrous MgSO$_4$, filtered and reduced under pressure to afford crude product as a brown oil. The crude product was then purified by flash silica chromatography, elution gradient 0 to 100% EtOAc in heptane. Pure fractions were evaporated to dryness to afford tert-butyl (3R)-4-(5-bromo-3-fluoropyridine-2-carbonyl)-3-(hydroxymethyl)piperazine-1-carboxylate (20.8 g, >100%) as a pale yellow gum. 1H NMR (400 MHz, DMSO, 30° C.) 1.41 (9H, d), 2.74-3.27 (4H, m), 3.32-3.81 (3H, m), 3.91 (1H, d), 4.22-4.55 (1H, m), 4.66-5.03 (1H, m), 8.31-8.41 (1H, m), 8.59-8.67 (1H, m). m/z: ES+ [M-tBu]+ 364.

Tert-butyl (6aR)-3-bromo-12-oxo-6a,7,9,10-tetrahydro-12H-pyrazino[2,1-c]pyrido[2,3-f][1,4]oxazepine-8(6H)-carboxylate

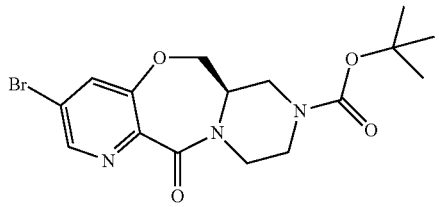 [SMILES: CC(C)(C)OC(=O)N1CCN2C(=O)c3ncc(Br)cc3OC[C@H]2C1]

Tert-butyl (3R)-4-(5-bromo-3-fluoropyridine-2-carbonyl)-3-(hydroxymethyl)piperazine-1-carboxylate (0.1 g, 0.24 mmol) was dissolved in acetonitrile (2 mL) under nitrogen and caesium carbonate (0.078 g, 0.24 mmol) added in one portion. The reaction mixture was stirred at room temperature for 1 hour then heated at 80° C. overnight. The reaction mixture was diluted with MeCN (10 mL), filtered and reduced under pressure to afford tert-butyl (6aR)-3-bromo-12-oxo-6a,7,9,10-tetrahydro-12H-pyrazino[2,1-c]pyrido[2,3-f][1,4]oxazepine-8(6H)-carboxylate (0.103 g, >100%) as a brown gum. 1H NMR (400 MHz, DMSO, 30° C.) 1.41 (9H, s), 3.43 (1H, s), 3.54-3.59 (3H, m), 3.72-3.83 (1H, m), 3.83-3.93 (1H, m), 3.98-4.04 (1H, m), 4.21-4.35 (2H, m), 7.94 (1H, d), 8.61 (1H, d). m/z: ES+ [M+H]+=398.

Tert-butyl (6aR)-3-bromo-6a,7,9,10-tetrahydro-12H-pyrazino[2,1-c]pyrido[2,3-f][1,4]oxazepine-8(6H)-carboxylate

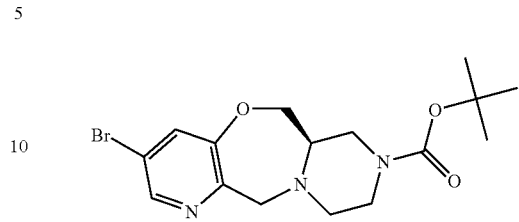

Tert-butyl (6aR)-3-bromo-12-oxo-6a,7,9,10-tetrahydro-12H-pyrazino[2,1-c]pyrido[2,3-f][1,4]oxazepine-8(6H)-carboxylate (8.7 g, 21.85 mmol) was dissolved in THF (200 mL) and 1M Borane-THF complex solution in THF (65.5 mL, 65.54 mmol) was added at room temperature and the mixture was stirred at 75° C. for 10 minutes. The mixture was cooled in an ice-bath and aqueous saturated ammonium chloride solution (150 mL) was added dropwise until effervescence stopped. The mixture was extracted with EtOAc (2×200 mL) and the combined organics washed with brine (200 mL). The organic layer was dried over anhydrous MgSO$_4$, filtered and concentrated under pressure to afford crude product as a yellow foam. The crude product was dissolved in DCM and filtered. The yellow filtrate was then purified by flash silica chromatography, elution gradient 0 to 60% EtOAc in heptane. Pure fractions were evaporated to dryness to afford tert-butyl (6aR)-3-bromo-6a,7,9,10-tetrahydro-12H-pyrazino[2,1-c]pyrido[2,3-f][1,4]oxazepine-8(6H)-carboxylate (4.35 g, 52%) as a colourless gum. 1H NMR (400 MHz, DMSO, 30° C.) 1.40 (9H, s), 2.3-2.41 (1H, m), 2.62-2.71 (1H, m), 2.74-2.92 (2H, m), 3.04 (1H, t), 3.59-3.71 (2H, m), 3.72-3.83 (2H, m), 4.00 (1H, d), 4.31 (1H, dd), 7.68 (1H, d), 8.30 (1H, d). m/z: ES+ [M+H]+=384.

Tert-butyl (6aR)-3-bromo-4-chloro-6a,7,9,10-tetrahydro-12H-pyrazino[2,1-c]pyrido[2,3-f][1,4]oxazepine-8(6H)-carboxylate

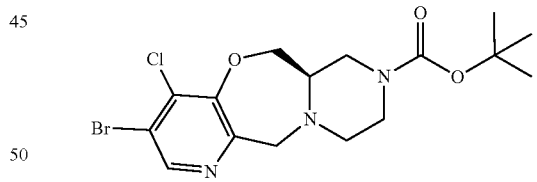

A solution of tert-butyl (6aR)-3-bromo-6a,7,9,10-tetrahydro-12H-pyrazino[2,1-c]pyrido[2,3-f][1,4]oxazepine-8(6H)-carboxylate (7.94 g, 20.65 mmol) in THF (200 mL) was cooled to −50° C. under nitrogen and 1M 2,2,6,6-Tetramethylpiperidinylmagnesium chloride lithium chloride complex solution in THF/toluene (31 mL, 30.98 mmol) was added dropwise. The solution was allowed to stir for 0.5 hours at −40° C. Additional 1M 2,2,6,6-Tetramethylpiperidinylmagnesium chloride lithium chloride complex solution in THF/toluene (10 mL, 10 mmol) was added and the solution allowed to stir for 0.5 hours at −40° C. Perchloroethane (7.33 g, 30.98 mmol) was added and the reaction mixture stirred at −40° C. for 0.5 hours. The reaction mixture was quenched at 0° C. by addition of aqueous saturated ammonium chloride solution (10 mL), diluted with water (20 mL)

and extracted with EtOAc (2×20 mL). The combined organics were washed with brine (20 mL), dried over anhydrous MgSO₄, filtered and concentrated under pressure to afford crude product. The crude product was purified by flash silica chromatography, elution gradient 0 to 50% EtOAc in heptane. Pure fractions were evaporated to dryness to afford tert-butyl (6aR)-3-bromo-4-chloro-6a,7,9,10-tetrahydro-12H-pyrazino[2,1-c]pyrido[2,3-f][1,4]oxazepine-8(6H)-carboxylate (6.8 g, 79%) as white dry solid. 1H NMR (400 MHz, DMSO, 30° C.) 1.41 (9H, s), 2.35-2.44 (1H, m), 2.72-2.83 (2H, m), 2.87 (1H, s), 3.02-3.13 (1H, m), 3.63 (2H, dd), 3.79 (1H, d), 3.88 (1H, dd), 4.08 (1H, d), 4.43 (1H, dd), 8.45 (1H, s). m/z: ES+ [M+H]+=418.

Tert-butyl (6aR)-3-bromo-4-chloro-2-iodo-6a,7,9, 10-tetrahydro-12H-pyrazino[2,1-c]pyrido[2,3-f][1,4] oxazepine-8(6H)-carboxylate

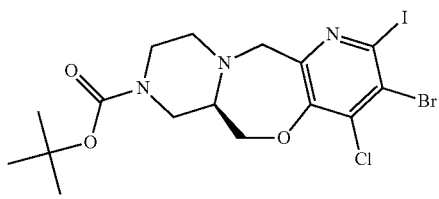 [SMILES: CC(C)(C)OC(=O)N1CCN2Cc3nc(I)c(Br)c(Cl)c3OC[C@H]2C1]

A solution of tert-butyl (6aR)-3-bromo-4-chloro-6a,7,9, 10-tetrahydro-12H-pyrazino[2,1-c]pyrido[2,3-f][1,4] oxazepine-8(6H)-carboxylate (0.562 g, 1.34 mmol)) in THF (50 mL) was cooled to −50° C. under nitrogen and a 1M 2,2,6,6-tetramethylpiperidinylmagnesium chloride lithium chloride complex solution in THF/toluene (4.03 mL, 4.03 mmol) was added dropwise. The solution was allowed to stir for 0.5 hours at −40° C. Then diiodine (0.511 g, 2.01 mmol) was added and the reaction mixture allowed to stir at −40° C. to room temperature for 2 hours. Additional 1M 2,2,6, 6-tetramethylpiperidinylmagnesium chloride lithium chloride complex solution in THF/toluene (4.03 mL, 4.03 mmol) was added at −20° C. and reaction mixture stirred to room temperature for 1 hour. The reaction mixture was quenched at 0° C. by addition of aqueous saturated ammonium chloride solution and extracted with EtOAc, washed with saturated brine and evaporated. The yellow residue obtained was dissolved in DCM and dried by passing through a phase separator cartridge. Evaporation afforded crude product as a yellow gum. The crude product was purified by flash silica chromatography, elution gradient 0 to 50% EtOAc in heptane. Pure fractions were evaporated to dryness to afford tert-butyl (6aR)-3-bromo-4-chloro-2-iodo-6a,7,9,10-tetrahydro-12H-pyrazino[2,1-c]pyrido[2,3-f][1,4]oxazepine-8 (6H)-carboxylate (0.66 g, 90%) as a yellow gum. 1H NMR (400 MHz, CDCl₃, 30° C.) 1.46 (9H, s), 2.51 (1H, ddd), 2.72-2.92 (2H, m), 2.99 (1H, s), 3.15-3.31 (1H, m), 3.65-3.75 (2H, m), 3.78-3.87 (1H, m), 3.90 (1H, d), 4.02 (1H, d), 4.32 (1H, dt). m/z: ES+ [M+H]+=544.

Tert-butyl (6aR)-3-bromo-4-chloro-2-[(trimethylsilyl)ethynyl]-6a,7,9,10-tetrahydro-12H-pyrazino[2,1-c]pyrido[2,3-f][1,4]oxazepine-8(6H)-carboxylate

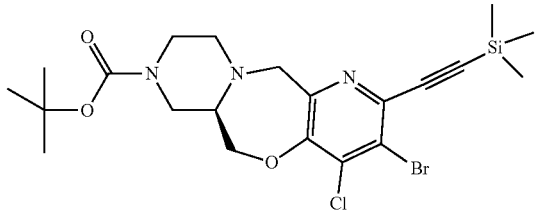 [SMILES: CC(C)(C)OC(=O)N1CCN2Cc3nc(C#C[Si](C)(C)C)c(Br)c(Cl)c3OC[C@H]2C1]

Tert-butyl (6aR)-3-bromo-4-chloro-2-iodo-6a,7,9,10-tetrahydro-12H-pyrazino[2,1-c]pyrido[2,3-f][1,4]oxazepine-8 (6H)-carboxylate (0.645 g, 1.18 mmol), tetrakis(triphenylphosphine)palladium(0) (0.274 g, 0.24 mmol) and copper(I) iodide (0.226 g, 1.18 mmol) were suspended in toluene (11 mL) at room temperature under nitrogen. Ethynyltrimethylsilane (0.819 mL, 5.92 mmol) and triethylamine (0.33 mL, 2.37 mmol) were added. The resulting mixture was heated at 100° C. for 10 minutes. The reaction mixture was cooled to room temperature, filtered through a layer of celite and washed with diethyl ether. Evaporation afforded crude product as an oil. The crude product was dissolved in DCM and purified by flash silica chromatography, elution gradient 0 to 50% EtOAc in heptane to afford tert-butyl (6aR)-3-bromo-4-chloro-2-[(trimethylsilyl)ethynyl]-6a,7,9, 10-tetrahydro-12H-pyrazino[2,1-c]pyrido[2,3-f][1,4] oxazepine-8(6H)-carboxylate (0.375 g, 61%) as a yellow gum. m/z: ES+ [M+H]+=544.

Tert-butyl (6aR)-4-chloro-3-(2-chloro-6-hydroxyphenyl)-2-[(trimethylsilyl)ethynyl]-6a,7,9,10-tetrahydro-12H-pyrazino[2,1-c]pyrido[2,3-f][1,4] oxazepine-8(6H)-carboxylate

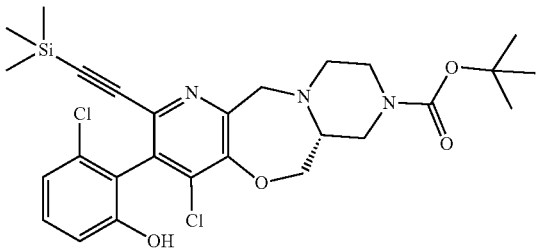 [SMILES: CC(C)(C)OC(=O)N1CCN2Cc3nc(C#C[Si](C)(C)C)c(-c4c(O)cccc4Cl)c(Cl)c3OC[C@H]2C1]

A solution of tert-butyl (6aR)-3-bromo-4-chloro-2-[(trimethylsilyl)ethynyl]-6a,7,9,10-tetrahydro-12H-pyrazino[2,1-c]pyrido[2,3-f][1,4]oxazepine-8(6H)-carboxylate (0.369 g, 0.72 mmol), (2-chloro-6-hydroxyphenyl)boronic acid (0.247 g, 1.43 mmol), 2M aqueous sodium carbonate (1.075 mL, 2.15 mmol) and 2-methyl-THF (10 mL) was de-gassed with nitrogen for 15 minutes. RuPhos-Pd-G3 (0.060 g, 0.07 mmol) and 2-dicyclohexylphosphino-2',6'-diisopropoxybiphenyl (0.033 g, 0.07 mmol) were added and reaction mixture then heated at 90° C. for 1.5 hours. The reaction mixture was cooled to room temperature on standing overnight, water added and extracted with EtOAc. The organic layer was washed with saturated brine and dried by passing through a phase separator cartridge. Evaporation afforded crude product as a yellow gum. The crude product was then purified by flash silica chromatography, elution gradient 0 to 100% EtOAc in heptane. Pure fractions were combined and evaporated to afford tert-butyl (6aR)-4-chloro-3-(2-chloro-6-hydroxyphenyl)-2-[(trimethylsilyl)ethynyl]-6a,7,9,10-tetrahydro-12H-pyrazino[2,1-c]pyrido[2,3-f][1,4]oxazepine-8(6H)-carboxylate (0.16 g, 39%) as a yellow foam. m/z: ES+ [M+H]+=562.

3-Chloro-2-{(6aR)-4-chloro-2-[(trimethylsilyl)ethynyl]-6,6a,7,8,9,10-hexahydro-12H-pyrazino[2,1-c]pyrido[2,3-f][1,4]oxazepin-3-yl}phenol

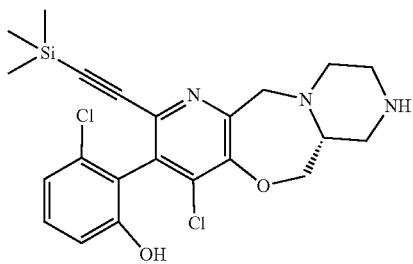 [SMILES: C[Si](C)(C)C#Cc1nc2c(c(Cl)c1-c1c(O)cccc1Cl)OC[C@H]1CNCCN1C2]

Tert-butyl (6aR)-4-chloro-3-(2-chloro-6-hydroxyphenyl)-2-[(trimethylsilyl)ethynyl]-6a,7,9,10-tetrahydro-12H-pyrazino[2,1-c]pyrido[2,3-f][1,4]oxazepine-8(6H)-carboxylate (0.156 g, 0.28 mmol) was dissolved in DCM (5 mL) and TFA (2.12 mL, 27.73 mmol) was added. The solution was stirred at room temperature for 1 hour then heated at 60° C. for 30 minutes. The reaction mixture was then stirred at room temperature overnight. The reaction mixture was purified by ion exchange chromatography, using an SCX column. The desired product was eluted from the column using 1M NH₃/MeOH and pure fractions were evaporated to dryness to afford 3-chloro-2-{(6aR)-4-chloro-2-[(trimethylsilyl)ethynyl]-6,6a,7,8,9,10-hexahydro-12H-pyrazino[2,1-c]pyrido[2,3-f][1,4]oxazepin-3-yl}phenol (0.153 g, >100%) as yellow foam. m/z: ES+ [M+H]+=462.

3-Chloro-2-[(6aR)-4-chloro-2-ethynyl-6,6a,7,8,9,10-hexahydro-12H-pyrazino[2,1-c]pyrido[2,3-f][1,4]oxazepin-3-yl]phenol

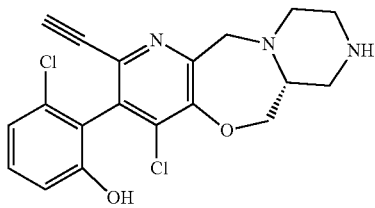 [SMILES: C#Cc1nc2c(c(Cl)c1-c1c(O)cccc1Cl)OC[C@H]1CNCCN1C2]

A suspension of 3-chloro-2-{(6aR)-4-chloro-2-[(trimethylsilyl)ethynyl]-6,6a,7,8,9,10-hexahydro-12H-pyrazino[2,1-c]pyrido[2,3-f][1,4]oxazepin-3-yl}phenol (0.155 g, 0.34 mmol) and potassium carbonate (0.139 g, 1.01 mmol) in MeOH (5 mL) was stirred at room temperature for 2 hours. Water was added to reaction mixture and the resulting solution was purified by ion exchange chromatography, using an SCX column. The desired product was eluted from the column using 1M NH₃/MeOH and pure fractions were evaporated to dryness to afford 3-chloro-2-[(6aR)-4-chloro-2-ethynyl-6,6a,7,8,9,10-hexahydro-12H-pyrazino[2,1-c]pyrido[2,3-f][1,4]oxazepin-3-yl]phenol (0.164 g, >100%) as a yellow foam. m/z: ES+ [M+H]+=390.

1-[(6aR)-4-Chloro-3-(2-chloro-6-hydroxyphenyl)-2-ethynyl-6a,7,9,10-tetrahydro-12H-pyrazino[2,1-c]pyrido[2,3-f][1,4]oxazepin-8(6H)-yl]prop-2-en-1-one Rotational Isomer 1, Example 87 and Rotational Isomer 2, Example 88

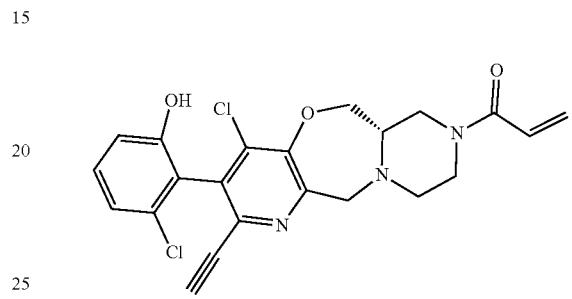

To a suspension of 3-chloro-2-[(6aR)-4-chloro-2-ethynyl-6,6a,7,8,9,10-hexahydro-12H-pyrazino[2,1-c]pyrido[2,3-f][1,4]oxazepin-3-yl]phenol (0.164 g, 0.42 mmol) and DIPEA (0.095 mL, 0.55 mmol) in DCM (2 mL) and DMF (0.5 mL) under nitrogen at 0° C. was added acryloyl chloride (0.037 mL, 0.46 mmol) dropwise. The reaction mixture was stirred at 0° C. for 30 minutes. The reaction mixture was evaporated (40° C. water bath) to afford a yellow oil. This oil was dissolved in cold 7N NH₃/MeOH (10 mL) and the resulting solution stirred to room temperature over 30 minutes. Evaporation at 40° C. afforded crude product in a yellow DMF solution. The crude product was purified by preparative HPLC (Waters CSH C18 OBD column, 30×100 mm id, 5 micron particle size), using decreasingly polar mixtures of water (containing 1% by volume of NH₄OH (28-30% in H₂O)) and MeCN as eluents. Shallow gradient: 10 to 30% MeCN. Detection UV @ 254 nm. Fractions containing the desired compound were evaporated to dryness to afford firstly rotational isomer 1 of 1-[(6aR)-4-chloro-3-(2-chloro-6-hydroxyphenyl)-2-ethynyl-6a,7,9,10-tetrahydro-12H-pyrazino[2,1-c]pyrido[2,3-f][1,4]oxazepin-8(6H)-yl]prop-2-en-1-one (0.018 g, 10%) as a white solid. 1H NMR (400 MHz, DMSO, 30° C.) 2.75 (1H, td), 2.91 (2H, dd), 3.02 (1H, s), 3.24 (1H, d), 3.58 (1H, s), 3.79-3.98 (3H, m), 4.17 (2H, d), 4.52 (1H, s), 5.74 (1H, d), 6.14 (1H, d), 6.71-6.92 (2H, m), 6.96 (1H, d), 7.24 (1H, t), 10.01 (1H, s). m/z: ES+ [M+H]+=444. This was followed by rotational isomer 2 of 1-[(6aR)-4-chloro-3-(2-chloro-6-hydroxyphenyl)-2-ethynyl-6a,7,9,10-tetrahydro-12H-pyrazino[2,1-c]pyrido[2,3-f][1,4]oxazepin-8(6H)-yl]prop-2-en-1-one (0.047 g, 25%) as a white solid. 1H NMR (400 MHz, DMSO, 30° C.) 2.76 (1H, s), 2.94 (2H, d), 3.16 (1H, s), 3.30 (1H, s), 3.75-4.05 (4H, m), 4.1-4.27 (2H, m), 4.55 (1H, s), 5.72 (1H, s), 6.14 (1H, d), 6.84 (1H, s), 6.92 (1H, d), 6.96-7.04 (1H, m), 7.27 (1H, t), 9.98 (1H, s). m/z: ES+ [M+H]+=444.

Tert-butyl (3R)-4-(4-bromo-2-fluoro-3-methylbenzoyl)-3-(hydroxymethyl)piperazine-1-carboxylate

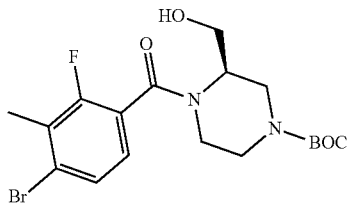 [SMILES: Cc1c(Br)ccc(C(=O)N2CCN(C(=O)OC(C)(C)C)C[C@@H]2CO)c1F]

DIPEA (33.7 mL, 193.10 mmol) was added to 4-bromo-2-fluoro-3-methylbenzoic acid (15 g, 64.37 mmol), tert-butyl (3R)-3-(hydroxymethyl)piperazine-1-carboxylate (13.92 g, 64.37 mmol) and HATU (36.70 g, 96.55 mmol) in DMF (200 mL) at 0° C. The resulting mixture was stirred at 25° C. for 2 hours. The reaction mixture was diluted with EtOAc (500 mL), washed sequentially with 0.5M citric acid (500 mL×3), water (500 mL×3) and saturated brine (500 mL). The organic layer was dried over anhydrous sodium sulphate, filtered and evaporated to afford crude product. The crude product was purified by crystallisation from EtOAc/MeCN (200 mL)(100:1 ratio) to afford tert-butyl (3R)-4-(4-bromo-2-fluoro-3-methylbenzoyl)-3-(hydroxymethyl)piperazine-1-carboxylate (26.7 g, 96%) as a yellow solid. 1H NMR (400 MHz, DMSO, 30° C.) 1.38 (9H, s), 2.28 (3H, d), 2.64-3.01 (3H, m), 3.04-3.24 (1H, m), 3.44-3.24 (1H, m), 3.82-3.88 (1H, m), 3.92-4.12 (1H, m), 4.18-4.56 (1H, m), 4.76-4.98 (1H, m), 7.13-7.19 (1H, m), 7.51-7.61 (1H, m). m/z: ES+ [M+Na]+=453.

Tert-butyl (12aR)-9-bromo-10-methyl-6-oxo-3,4,12,12a-tetrahydro-6H-pyrazino[2,1-c][1,4]benzoxazepine-2(1H)-carboxylate

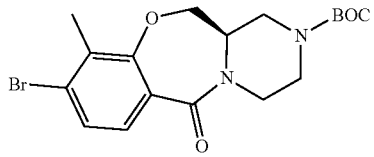 [SMILES: Cc1c(Br)ccc2c1OC[C@H]1CN(C(=O)OC(C)(C)C)CCN1C2=O]

Sodium hydride (5.56 g, 139.11 mmol) was added to tert-butyl (3R)-4-(4-bromo-2-fluoro-3-methylbenzoyl)-3-(hydroxymethyl)piperazine-1-carboxylate (20 g, 46.37 mmol) in DMF (200 mL) at 0° C. The resulting mixture was stirred at 25° C. for 2 hours. The reaction mixture was poured into ice water. The precipitate formed was collected by filtration, washed with water and dried under vacuum to afford tert-butyl (12aR)-9-bromo-10-methyl-6-oxo-3,4,12,12a-tetrahydro-6H-pyrazino[2,1-c][1,4]benzoxazepine-2(1H)-carboxylate (16 g, 84%) as a yellow solid. 1H NMR (400 MHz, DMSO, 30° C.) 1.40 (9H, s), 2.29 (3H, s), 3.38-3.50 (2H, m), 3.53 (2H, d), 3.62-3.77 (1H, m), 3.77-3.94 (2H, m), 4.23 (2H, d), 7.37 (1H, d), 7.46 (1H, d). m/z: ES+ [M-Boc]+=355.

(12aR)-9-Bromo-8-iodo-10-methyl-1,2,3,4,12,12a-hexahydro-6H-pyrazino[2,1-c][1,4]benzoxazepin-6-one

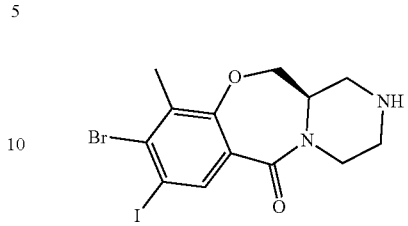

1-Iodopyrrolidine-2,5-dione (16.41 g, 72.94 mmol) was added to tert-butyl (12aR)-9-bromo-10-methyl-6-oxo-3,4,12,12a-tetrahydro-6H-pyrazino[2,1-c][1,4]benzoxazepine-2(1H)-carboxylate (10 g, 24.31 mmol) in concentrated sulphuric acid (50 mL) at 0° C. The resulting mixture was stirred at 25° C. for 2 hours. The reaction mixture was poured into ice water and made basic with 2M NaOH. The mixture was diluted with DCM (500 mL) and washed sequentially with 2M Na2S2O3 (500 mL×2), saturated brine (500 mL). The organic layer was dried over anhydrous sodium sulphate, filtered and evaporated to afford product (12aR)-9-bromo-8-iodo-10-methyl-1,2,3,4,12,12a-hexahydro-6H-pyrazino[2,1-c][1,4]benzoxazepin-6-one (6.7 g, 63%) as a red solid. 1H NMR (400 MHz, DMSO, 30° C.) 2.41 (3H, s), 2.64-2.83 (2H, m), 2.84-3.01 (2H, m), 3.43-3.68 (2H, m), 3.72-3.84 (2H, m), 4.13 (1H, dd), 4.59 (1H, t), 8.02 (1H, s). m/z: ES+ [M+H]+=437.

Tert-butyl (12aR)-9-bromo-8-iodo-10-methyl-6-oxo-3,4,12,12a-tetrahydro-6H-pyrazino[2,1-c][1,4]benzoxazepine-2(1H)-carboxylate

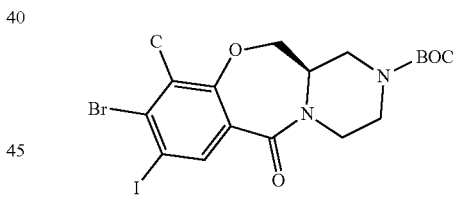

Di-tert-butyl dicarbonate (2.87 mL, 12.35 mmol) was added to (12aR)-9-bromo-8-iodo-10-methyl-1,2,3,4,12,12a-hexahydro-6H-pyrazino[2,1-c][1,4]benzoxazepin-6-one (4.5 g, 10.3 mmol) and triethylamine (4.31 mL, 30.89 mmol) in DCM (50 mL) cooled to 0° C. The resulting solution was stirred at room temperature for 2 hours. The reaction mixture was diluted with DCM (50 mL) and washed with water (100 mL×3). The organic layer was dried over anhydrous sodium sulphate, filtered and evaporated to afford crude product. The crude product was purified by flash silica chromatography, elution gradient 0 to 40% EtOAc in petroleum ether. Pure fractions were evaporated to dryness to afford tert-butyl (12aR)-9-bromo-8-iodo-10-methyl-6-oxo-3,4,12,12a-tetrahydro-6H-pyrazino[2,1-c][1,4]benzoxazepine-2(1H)-carboxylate (5.2 g, 94%) as a yellow solid. 1H NMR (400 MHz, DMSO, 30° C.) 1.41 (9H, s), 2.42 (3H, s), 3.41-3.60 (4H, m), 3.66-3.79 (1H, m), 3.80-3.97 (2H, m), 4.25 (2H, d), 7.96 (1H, s). m/z: ES+ [M-tBu]+=481.

203

Tert-butyl (12aR)-9-bromo-8-iodo-10-methyl-3,4,12,12a-tetrahydro-6H-pyrazino[2,1-c][1,4]benzoxazepine-2(1H)-carboxylate

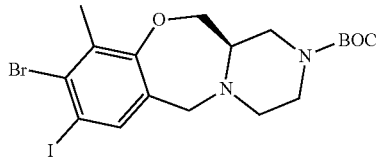 [SMILES: Cc1c(Br)c(I)cc2c1OC[C@H]1CN(C(=O)OC(C)(C)C)CCN1C2]

Tert-butyl (12aR)-9-bromo-8-iodo-10-methyl-6-oxo-3,4,12,12a-tetrahydro-6H-pyrazino[2,1-c][1,4]benzoxazepine-2(1H)-carboxylate (3 g, 5.58 mmol) was added to 1M Borane-THF complex solution in THF (30 mL, 30 mmol) under nitrogen at room temperature. The resulting solution was stirred at 60° C. for 2 hours. The reaction mixture was quenched with MeOH (30 mL). The solvent was removed under reduced pressure. The crude product obtained was purified by flash silica chromatography, elution gradient 0 to 50% EtOAc in petroleum ether. Pure fractions were evaporated to dryness to afford tert-butyl (12aR)-9-bromo-8-iodo-10-methyl-3,4,12,12a-tetrahydro-6H-pyrazino[2,1-c][1,4]benzoxazepine-2(1H)-carboxylate (2.9 g, 99%) as a pale yellow solid. 1H NMR (300 MHz, CDCl$_3$, 30° C.) 1.41 (9H, s), 2.40-2.43 (1H, m), 2.43 (3H, s), 2.69-2.96 (3H, m), 3.17-3.30 (1H, m), 3.43 (1H, d), 3.52-3.76 (3H, m), 3.84 (1H, d), 4.21 (1H, dd), 7.56 (1H, s). m/z: ES+ [M+H]+=523.

Tert-butyl (12aR)-9-bromo-10-methyl-8-[(trimethylsilyl)ethynyl]-3,4,12,12a-tetrahydro-6H-pyrazino[2,1-c][1,4]benzoxazepine-2(1H)-carboxylate

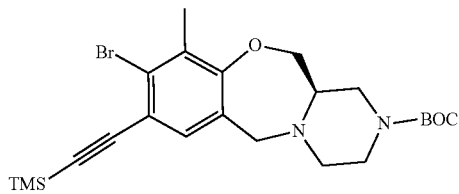 [SMILES: Cc1c(Br)c(C#C[Si](C)(C)C)cc2c1OC[C@H]1CN(C(=O)OC(C)(C)C)CCN1C2]

Triethylamine (1.598 mL, 11.47 mmol) was added to tert-butyl (12aR)-9-bromo-8-iodo-10-methyl-3,4,12,12a-tetrahydro-6H-pyrazino[2,1-c][1,4]benzoxazepine-2(1H)-carboxylate (1.5 g, 2.87 mmol), ethynyltrimethylsilane (1.126 g, 11.47 mmol), tetrakis(triphenylphosphine)palladium(0) (0.331 g, 0.29 mmol) and copper(I) iodide (0.546 g, 2.87 mmol) in toluene (20 mL) under nitrogen in a sealed tube. The resulting solution was stirred at 100° C. for 6 hours. The solvent was removed under reduced pressure. The crude product obtained was purified by flash silica chromatography, elution gradient 0 to 40% EtOAc in petroleum ether. Pure fractions were evaporated to dryness to afford tert-butyl (12aR)-9-bromo-10-methyl-8-[(trimethylsilyl)ethynyl]-3,4,12,12a-tetrahydro-6H-pyrazino[2,1-c][1,4]benzoxazepine-2(1H)-carboxylate (1.1 g, 78%) as a brown foam. 1H NMR (300 MHz, CDCl$_3$, 30° C.) 0.27 (9H, s), 1.46 (9H, s), 2.35 (3H, s), 2.38-2.47 (1H, m), 2.70-2.99 (3H, m), 3.21-3.36 (1H, m), 3.51 (1H, d), 3.57-3.76 (3H, m), 3.89 (1H, d), 4.24 (1H, d), 7.22 (1H, s). m/z: ES+ [M+H]+=493.

204

Tert-butyl (12aR)-9-(2-chloro-6-hydroxyphenyl)-10-methyl-8-[(trimethylsilyl)ethynyl]-3,4,12,12a-tetrahydro-6H-pyrazino[2,1-c][1,4]benzoxazepine-2(1H)-carboxylate

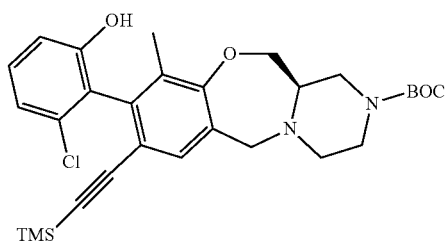 [SMILES: Cc1c2c(cc(C#C[Si](C)(C)C)c1-c1c(O)cccc1Cl)CN1CCN(C(=O)OC(C)(C)C)C[C@@H]1CO2]

A solution of potassium carbonate (252 mg, 1.82 mmol) in water (4 mL) was added to a stirred solution of tert-butyl (12aR)-9-bromo-10-methyl-8-[(trimethylsilyl)ethynyl]-3,4,12,12a-tetrahydro-6H-pyrazino[2,1-c][1,4]benzoxazepine-2(1H)-carboxylate (900 mg, 1.82 mmol), (2-chloro-6-hydroxyphenyl)boronic acid (943 mg, 5.47 mmol), RuPhos-Pd-G3 (139 mg, 0.18 mmol) and 2-dicyclohexylphosphino-2',6'-diisopropoxybiphenyl (85 mg, 0.18 mmol) in 1,4-dioxane (20 mL) under nitrogen. The resulting solution was stirred at 100° C. for 2 hours. The reaction mixture was purified directly by flash C18-flash chromatography, elution gradient 0 to 80% MeCN in water. Pure fractions were evaporated to dryness to afford tert-butyl (12aR)-9-(2-chloro-6-hydroxyphenyl)-10-methyl-8-[(trimethylsilyl)ethynyl]-3,4,12,12a-tetrahydro-6H-pyrazino[2,1-c][1,4]benzoxazepine-2(1H)-carboxylate (0.57 g, 58%) as a brown foam. 1H NMR (300 MHz, DMSO, 30° C.) −0.06 (9H, s), 1.40 (9H, s), 1.85 (3H, s), 2.22-2.41 (1H, m), 2.58-2.87 (4H, m), 2.97-3.12 (1H, m), 3.50-3.71 (3H, m), 3.71-3.84 (1H, m), 4.29 (1H, d), 6.81-6.92 (1H, m), 6.92-7.01 (1H, m), 7.18 (1H, t), 7.24 (1H, s), 9.60 (1H, d). m/z: ES+ [M+H]+=541.

Tert-butyl (12aR)-9-(2-chloro-6-hydroxyphenyl)-8-ethynyl-10-methyl-3,4,12,12a-tetrahydro-6H-pyrazino[2,1-c][1,4]benzoxazepine-2(1H)-carboxylate

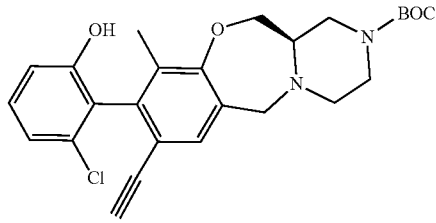 [SMILES: C#Cc1cc2c(c(C)c1-c1c(O)cccc1Cl)OC[C@H]1CN(C(=O)OC(C)(C)C)CCN1C2]

Cs$_2$CO$_3$ (2258 mg, 6.93 mmol) was added to tert-butyl (12aR)-9-(2-chloro-6-hydroxyphenyl)-10-methyl-8-[(trimethylsilyl)ethynyl]-3,4,12,12a-tetrahydro-6H-pyrazino[2,1-c][1,4]benzoxazepine-2(1H)-carboxylate (750 mg, 1.39 mmol) in MeOH (20 mL). The resulting solution was stirred at 25° C. for 1 hour. The reaction mixture was evaporated to dryness and dissolved in EtOAc (50 mL) and washed sequentially with water (50 mL×3) and saturated brine (50 mL). The organic layer was dried over anhydrous sodium sulphate, filtered and evaporated to afford tert-butyl (12aR)-9-(2-chloro-6-hydroxyphenyl)-8-ethynyl-10-methyl-3,4,12, 12a-tetrahydro-6H-pyrazino[2,1-c][1,4]benzoxazepine-2(1H)-carboxylate (0.6 g, 92%) as a yellow solid. 1H NMR (300 MHz, DMSO, 30° C.) 1.40 (9H, s), 1.81 (3H, s), 2.31 (1H, t), 2.56-2.88 (3H, m), 2.90-3.12 (1H, m), 3.45-3.59 (1H, m), 3.59-3.69 (3H, m), 3.72-3.81 (1H, m), 4.29 (1H, d), 5.76 (1H, s), 6.83-6.91 (1H, m), 6.93-7.00 (1H, m), 7.14-7.26 (1H, m), 7.26-7.35 (1H, m), 9.60-9.76 (1H, m). m/z: ES+ [M+H]+=469.

3-Chloro-2-[(12aR)-8-ethynyl-10-methyl-1,2,3,4,12,12a-hexahydro-6H-pyrazino[2,1-c][1,4]benzoxazepin-9-yl]phenol

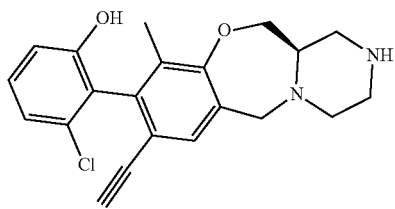 [SMILES: C#Cc1cc2c(c(C)c1-c1c(O)cccc1Cl)OC[C@H]1CNCCN1C2]

Tert-butyl (12aR)-9-(2-chloro-6-hydroxyphenyl)-8-ethynyl-10-methyl-3,4,12,12a-tetrahydro-6H-pyrazino[2,1-c][1,4]benzoxazepine-2(1H)-carboxylate (550 mg, 1.17 mmol) was added to TFA (1 mL, 12.98 mmol) in DCM (5 mL). The resulting solution was stirred at 25° C. for 1 hour. The solvent was removed under reduced pressure. The crude product obtained was purified by ion exchange chromatography, using an SCX column. The desired product was eluted from the column using 7M NH$_3$/MeOH and pure fractions were evaporated to dryness to afford 3-chloro-2-[(12aR)-8-ethynyl-10-methyl-1,2,3,4,12,12a-hexahydro-6H-pyrazino[2,1-c][1,4]benzoxazepin-9-yl]phenol (0.32 g, 74%) as a brown solid. 1H NMR (300 MHz, DMSO, 30° C.) 1.82 (3H, d), 2.20-2.33 (2H, m), 2.55-2.70 (1H, m), 2.70-2.89 (4H, m), 3.44-3.61 (2H, m), 3.62-3.73 (2H, m), 4.13-4.28 (1H, m), 6.81-6.92 (1H, m), 6.92-7.04 (1H, m), 7.14-7.30 (2H, m) two exchangeable protons not seen. m/z: ES+ [M+H]+=369.

1-[(12aR)-9-(2-Chloro-6-hydroxyphenyl)-8-ethynyl-10-methyl-3,4,12,12a-tetrahydro-6H-pyrazino[2,1-c][1,4]benzoxazepin-2(1H)-yl]prop-2-en-1-one Rotational Isomer 1, Example 89 and Rotational Isomer 2, Example 90

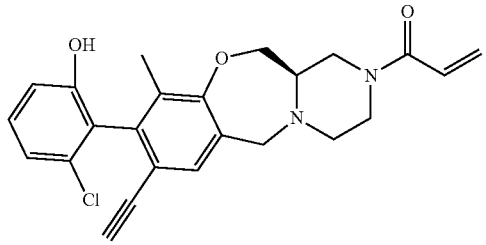 [SMILES: C#Cc1cc2c(c(C)c1-c1c(O)cccc1Cl)OC[C@H]1CN(C(=O)C=C)CCN1C2]

Acryloyl chloride (66.2 mg, 0.73 mmol) was added to DIPEA (142 μl, 0.81 mmol) and 3-chloro-2-[(12aR)-8-ethynyl-10-methyl-1,2,3,4,12,12a-hexahydro-6H-pyrazino[2,1-c][1,4]benzoxazepin-9-yl]phenol (300 mg, 0.81 mmol) in DMF (6 mL). The resulting solution was stirred at room temperature for 1 hour. The reaction mixture was quenched with water (50 mL) and extracted with EtOAc (3×50 mL). The organic layer was dried over anhydrous sodium sulphate, filtered and evaporated to afford crude product as a brown gum. The crude product was purified by preparative HPLC (XBridge Shield RP18 OBD column, 5μ silica, 19 mm diameter, 150 mm length), using decreasingly polar mixtures of water (containing 10 mmol/L NH$_4$HCO$_3$+0.1% NH$_3$·H$_2$O) and MeCN as eluents. Fractions containing the desired compounds were evaporated to dryness to afford firstly rotational isomer 1 of 1-[(12aR)-9-(2-chloro-6-hydroxyphenyl)-8-ethynyl-10-methyl-3,4,12,12a-tetrahydro-6H-pyrazino[2,1-c][1,4]benzoxazepin-2(1H)-yl]prop-2-en-1-one (0.055 g, 16%) as a white solid. 1H NMR (300 MHz, DMSO, 30° C.) 1.82 (3H, s), 2.23-2.44 (1H, m), 2.59-2.75 (1H, m), 2.75-2.92 (2H, m), 2.95-3.15 (1H, m), 3.47-3.60 (1H, m), 3.61-3.82 (3H, m), 3.82-3.96 (1H, m), 3.95-4.19 (1H, m), 4.34 (1H, t), 5.70 (1H, d), 6.13 (1H, d), 6.71-6.92 (2H, m), 6.96 (1H, d), 7.18 (1H, t), 7.28 (1H, s), 9.68 (1H, s). m/z: ES+ [M+H]+=423. This was followed by rotational isomer 2 of 1-[(12aR)-9-(2-chloro-6-hydroxyphenyl)-8-ethynyl-10-methyl-3,4,12,12a-tetrahydro-6H-pyrazino[2,1-c][1,4]benzoxazepin-2(1H)-yl]prop-2-en-1-one (0.058 g, 17%) as a white solid. 1H NMR (300 MHz, DMSO, 30° C.) 1.82 (3H, s), 2.25-2.44 (1H, m), 2.62-2.76 (1H, m), 2.76-2.93 (2H, m), 2.94-3.15 (1H, m), 3.50-3.70 (2H, m), 3.71 (1H, s), 3.75-3.95 (2H, m), 3.95-4.15 (1H, m), 4.34 (1H, t), 5.69 (1H, d), 6.13 (1H, d), 6.72-6.92 (2H, m), 6.95 (1H, d), 7.18 (1H, t), 7.29 (1H, s), 9.66 (1H, s). m/z: ES+ [M+H]+=423.

Tert-butyl (3aR)-1-oxotetrahydro-1H-1λ$^4$-[1,2,3]oxathiazolo[3,4-a]pyrazine-5(3H)-carboxylate

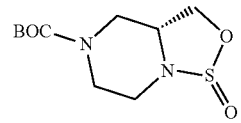

Thionyl chloride (14.17 mL, 194.19 mmol) was added dropwise to Imidazole (43.9 g, 644.99 mmol) in DCM (180 mL) at 0° C. The resulting mixture was stirred at room temperature for 1 hour. The reaction mixture was cooled to −78° C. A solution of tert-butyl (3R)-3-(hydroxymethyl)piperazine-1-carboxylate (15 g, 69.35 mmol) in DCM (180 mL) was added dropwise. The resulting mixture was warmed to room temperature and stirred overnight. The reaction mixture was quenched with saturated NH$_4$Cl (200 mL) and extracted with DCM (2×200 mL). The organic layer was dried over anhydrous sodium sulphate, filtered and evaporated to afford tert-butyl (3aR)-1-oxotetrahydro-1H-1λ$^4$-[1,2,3]oxathiazolo[3,4-a]pyrazine-5(3H)-carboxylate (11.4 g, 63%) as a yellow solid. (3R)-4-(4-bromo-5-chloro-2,3-difluorobenzoyl)-3-(hydroxymethyl)piperazine-1-carboxylate (2.3 g, 27%) as a yellow solid. 1H NMR (400 MHz, CDCl$_3$, 30° C.) 1.46 (9H, s), 2.67-2.70 (1H, m), 2.81-2.90 (1H, m), 2.95-3.01 (1H, m), 3.23-3.40 (1H, m), 3.59-3.62 (1H, m), 3.87-3.92 (1H, m), 4.19-4.23 (1H, m), 4.43-4.62 (1H, m), 4.76-4.90 (1H, m). m/z: [M-tBu]+=207.

Tert-butyl (3aR)-1,1-dioxotetrahydro-1H-1λ⁶-[1,2,3]oxathiazolo[3,4-a]pyrazine-5(3H)-carboxylate

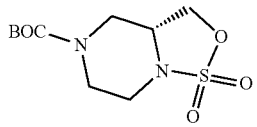

A solution of sodium periodate (12.08 g, 56.5 mmol) in water (100 mL) was added dropwise to a stirred solution of tert-butyl (3aR)-1-oxotetrahydro-1H-1λ⁴-[1,2,3]oxathiazolo[3,4-a]pyrazine-5(3H)-carboxylate (11.4 g, 43.46 mmol) in acetonitrile (300 mL) and ethyl acetate (50 mL) at 0° C., followed by Ruthenium(III) chloride (0.018 g, 0.09 mmol). The resulting mixture was stirred at room temperature for 16 hours. The reaction mixture was quenched with saturated aqueous NH₄Cl (200 mL) and extracted with DCM (2×200 mL). The organic layer was dried over anhydrous sodium sulphate, filtered and evaporated to afford tert-butyl tert-butyl (3aR)-1,1-dioxotetrahydro-1H-1λ⁶-[1,2,3]oxathiazolo[3,4-a]pyrazine-5(3H)-carboxylate (9.5 g, 79%) as a pale yellow solid. 1H NMR (400 MHz, CDCl₃, 30° C.) 1.48 (9H, s), 2.96-3.05 (2H, m), 3.13-3.20 (1H, m), 3.45-3.60 (1H, m), 3.64-3.72 (1H, m), 4.08-4.12 (1H, m), 4.24-4.31 (2H, m), 4.64-4.70 (1H, m).

3-Chloro-5,6-difluoro-2-methoxybenzoic acid

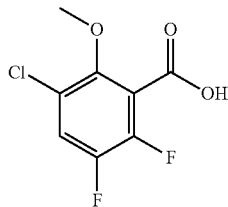

1-Chloropyrrolidine-2,5-dione (51.50 g, 385.37 mmol) was added to 2,3-difluoro-6-methoxybenzoic acid (29 g, 154.15 mmol) in DMF (300 mL) at room temperature. The resulting mixture was stirred at 60° C. overnight. The reaction mixture was diluted with EtOAc (500 mL) and washed sequentially with saturated brine (400 mL×6). The organic layer was dried over anhydrous sodium sulphate, filtered and evaporated to afford crude product. The crude product was purified by flash C18-flash chromatography, elution gradient 0 to 50% MeCN in water (0.1% formic acid). Pure fractions were evaporated to dryness to afford 3-chloro-5,6-difluoro-2-methoxybenzoic acid (20 g, 58%) as a white solid. 1H NMR (400 MHz, DMSO, 30° C.) 3.50-4.04 (3H, s), 7.13-8.24 (1H, d) one exchangeable proton not seen.

3-Chloro-5,6-difluoro-4-iodo-2-methoxybenzoic acid

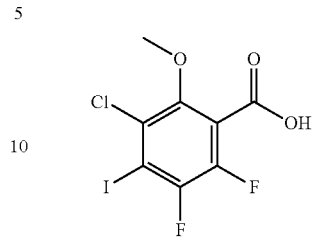

1M 2,2,6,6-Tetramethylpiperidinylmagnesium chloride lithium chloride complex solution in THF/toluene (162 mL, 161.75 mmol) was added to 3-chloro-5,6-difluoro-2-methoxybenzoic acid (9 g, 40.44 mmol) in THF (120 mL) at −40° C. under nitrogen. The resulting mixture was stirred at −50° C. for 30 minutes. Diiodine (41.1 g, 161.75 mmol) in THF (20 mL) was then added to the mixture at −40° C. under nitrogen. The resulting solution was stirred at −50° C. for 2 hours. The reaction mixture was quenched with saturated NH₄Cl (100 mL) and extracted with DCM (200 mL×5). The organic layer was dried over anhydrous sodium sulphate, filtered and evaporated to afford crude product as brown solid. The crude product was purified by flash C18-flash chromatography, elution gradient 5 to 60% MeCN in water (0.1% formic acid). Pure fractions were evaporated to dryness to 3-chloro-5,6-difluoro-4-iodo-2-methoxybenzoic acid (7 g, 50%) as a white solid. 1H NMR (400 MHz, DMSO, 30° C.) 3.82 (3H, s) one exchangeable proton not seen.

3-Chloro-5,6-difluoro-2-hydroxy-4-iodobenzoic acid

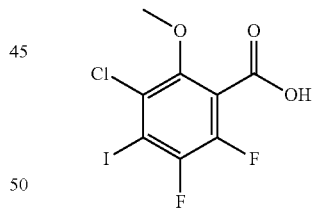

1M Boron tribromide solution in DCM (20.09 mL, 20.09 mmol) was added to 3-chloro-5,6-difluoro-4-iodo-2-methoxybenzoic acid (7 g, 20.09 mmol) in DCM (10 mL) at 0° C. The resulting mixture was stirred at room temperature for 16 hours. The reaction mixture was quenched with saturated aqueous NH₄Cl (20 mL) and extracted with DCM (200 mL×2). The organic layer was dried over anhydrous sodium sulphate, filtered and evaporated to afford 3-chloro-5,6-difluoro-2-hydroxy-4-iodobenzoic acid (5 g, 74%) as a brown solid that was used without further purification.

Methyl 3-chloro-5,6-difluoro-2-hydroxy-4-iodobenzoate

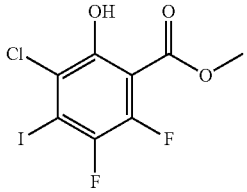

Concentrated sulphuric acid (0.797 mL, 14.95 mmol) was added to 3-chloro-5,6-difluoro-2-hydroxy-4-iodobenzoic acid (5 g, 14.95 mmol) in MeOH (150 mL). The resulting mixture was stirred at 100° C. for 16 hours. The solvent was removed under reduced pressure. The reaction mixture was poured into ice water and extracted with EtOAc (200 mL×3). The organic layer was dried over anhydrous sodium sulphate, filtered and evaporated to afford crude product as a brown solid. The crude product was purified by flash silica chromatography, elution gradient 0 to 10% EtOAc in petroleum ether. Pure fractions were evaporated to dryness to afford methyl 3-chloro-5,6-difluoro-2-hydroxy-4-iodobenzoate (3.6 g, 69%) as a white solid. 1H NMR (400 MHz, DMSO, 30° C.) 3.90 (3H, s), 11.06 (1H, s).

2-{[(2R)-4-(Tert-butoxycarbonyl)piperazin-2-yl]methoxy}-3-chloro-5,6-difluoro-4-iodobenzoic acid

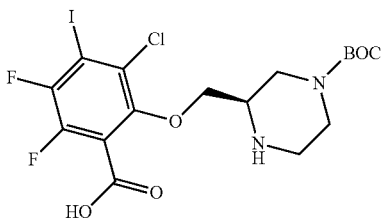 [SMILES: CC(C)(C)OC(=O)N1CCN[C@@H](COc2c(Cl)c(I)c(F)c(F)c2C(=O)O)C1]

Sodium hydride (0.826 g, 20.66 mmol) was added dropwise to methyl 3-chloro-5,6-difluoro-2-hydroxy-4-iodobenzoate (2.4 g, 6.89 mmol) and tert-butyl (3aR)-1,1-dioxotetrahydro-1H-1λ⁶-[1,2,3]oxathiazolo[3,4-a]pyrazine-5(3H)-carboxylate (5.75 g, 20.66 mmol) in DMF (30 mL) at 0° C. The resulting mixture was stirred at room temperature for 40 minutes. The reaction mixture was poured into ice water and extracted with EtOAc (150 mL×3). The organic layers were combined, washed with saturated brine (100 mL) then dried over anhydrous sodium sulphate, filtered and evaporated to afford crude product as a yellow solid. The crude product was purified by flash C18-flash chromatography, elution gradient 5 to 40% MeCN in water (0.1% TFA). Pure fractions were evaporated to dryness to afford 2-{[(2R)-4-(tert-butoxycarbonyl)piperazin-2-yl]methoxy}-3-chloro-5,6-difluoro-4-iodobenzoic acid (1.5 g, 41%) as a white solid. 1H NMR (400 MHz, DMSO, 30° C.) 1.37 (9H, s), 2.14 (1H, d), 2.73-2.76 (2H, m), 2.89-2.96 (2H, m), 3.08-3.20 (2H, m), 3.64-3.78 (1H, m), 3.85-4.26 (2H, m) one exchangeable proton not seen. m/z: ES+ [M-tBu]+=477.

Tert-butyl (12aR)-10-chloro-7,8-difluoro-9-iodo-6-oxo-3,4,12,12a-tetrahydro-6H-pyrazino[2,1-c][1,4]benzoxazepine-2(1H)-carboxylate

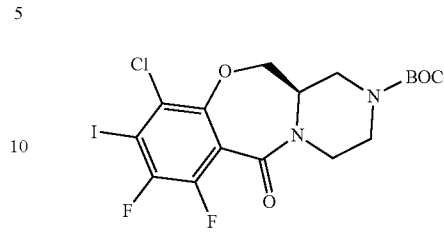

DIPEA (0.738 mL, 4.22 mmol) was added to (2-{[(2R)-4-(tert-butoxycarbonyl)piperazin-2-yl]methoxy}-3-chloro-5,6-difluoro-4-iodobenzoic acid (750 mg, 1.41 mmol) and HATU (1071 mg, 2.82 mmol) in DMF (4 mL) under nitrogen. The resulting mixture was stirred at room temperature for 2 hours. The reaction mixture was diluted with water and extracted with EtOAc (3×150 mL). The organic layers were combined and washed with saturated brine (5×100 mL), dried over anhydrous sodium sulphate, filtered and evaporated to afford crude product as a brown solid. The crude product was purified by flash silica chromatography, elution gradient 0 to 20% EtOAc in petroleum ether. Pure fractions were evaporated to dryness to afford tert-butyl (12aR)-10-chloro-7,8-difluoro-9-iodo-6-oxo-3,4,12,12a-tetrahydro-6H-pyrazino[2,1-c][1,4]benzoxazepine-2(1H)-carboxylate (660 mg, 91%) as a yellow solid. 1H NMR (400 MHz, DMSO, 30° C.) 1.41 (9H, s), 3.46-3.50 (1H, m), 3.60-3.74 (3H, m), 3.74-4.16 (3H, m), 4.22-4.30 (2H, m). m/z: ES+ [M-tBu]+=459.

Tert-butyl (12aR)-10-chloro-7,8-difluoro-9-iodo-3,4,12,12a-tetrahydro-6H-pyrazino[2,1-c][1,4]benzoxazepine-2(1H)-carboxylate

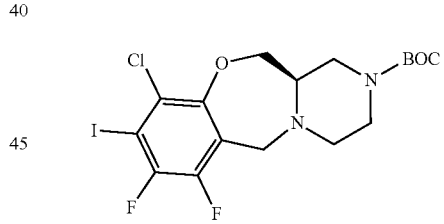

1M Borane-THF complex solution in THF (6 mL, 6 mmol) was added to tert-butyl (12aR)-10-chloro-7,8-difluoro-9-iodo-6-oxo-3,4,12,12a-tetrahydro-6H-pyrazino[2,1-c][1,4]benzoxazepine-2(1H)-carboxylate (650 mg, 1.26 mmol) in THF (6 mL) at room temperature. The resulting mixture was stirred at 60° C. for 1 hour. The reaction mixture was quenched with saturated NH₄Cl (10 mL). The reaction mixture was diluted with water (70 mL) and extracted with EtOAc (3×200 mL). The organic layer was dried over anhydrous sodium sulphate, filtered and evaporated to afford crude product as a white solid. The crude product was purified by flash C18-flash chromatography, elution gradient 5 to 80% MeCN in water (0.1% formic acid). Pure fractions were evaporated to dryness to afford tert-butyl (12aR)-10-chloro-7,8-difluoro-9-iodo-3,4,12,12a-tetrahydro-6H-pyrazino[2,1-c][1,4]benzoxazepine-2(1H)-carboxylate (500 mg, 79%) as a white solid. 1H NMR (400 MHz, DMSO, 30° C.) 1.38 (9H, s), 2.35-2.42 (1H, m), 2.78-2.88 (3H, m), 3.10-3.25 (1H, m), 3.56-3.60 (2H, m), 3.70-3.80 (2H, m), 3.93-3.96 (1H, m), 4.35-4.40 (1H, m). m/z: ES+ [M+H]+=501.

Tert-butyl (12aR)-10-chloro-9-(2-chloro-6-hydroxyphenyl)-7,8-difluoro-3,4,12,12a-tetrahydro-6H-pyrazino[2,1-c][1.4]benzoxazepine-2(1H)-carboxylate

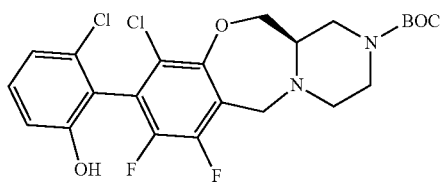 [SMILES: CC(C)(C)OC(=O)N1CCN2Cc3c(F)c(F)c(-c4c(O)cccc4Cl)c(Cl)c3OC[C@H]2C1]

Tert-butyl (12aR)-10-chloro-7,8-difluoro-9-iodo-3,4,12,12a-tetrahydro-6H-pyrazino[2,1-c][1,4]benzoxazepine-2(1H)-carboxylate (450 mg, 0.9 mmol), (2-chloro-6-hydroxyphenyl)boronic acid (465 mg, 2.7 mmol) RuPhos-Pd-G3 (75 mg, 0.09 mmol), Na$_2$CO$_3$ (191 mg, 1.80 mmol) and 2-dicyclohexylphosphino-2',6'-diisopropoxybiphenyl (84 mg, 0.18 mmol) were dissolved in 1,4-dioxane (16 mL) and H$_2$O (4 mL)(4:1 ratio) then sealed into a microwave tube. The reaction was heated to 120° C. for 30 minutes in the microwave reactor and cooled to room temperature. The solvent was removed under reduced pressure. The crude product obtained was purified by flash C18-flash chromatography, elution gradient 5 to 50% MeCN in water (0.1% TFA). Pure fractions were evaporated to dryness to afford tert-butyl (12aR)-10-chloro-9-(2-chloro-6-hydroxyphenyl)-7,8-difluoro-3,4,12,12a-tetrahydro-6H-pyrazino[2,1-c][1,4]benzoxazepine-2(1H)-carboxylate (374 mg, 83%) as a white solid. 1H NMR (400 MHz, DMSO, 30° C.) 1.42 (9H, s), 2.87-3.06 (2H, m), 3.14-3.20 (2H, m), 3.66-4.04 (4H, m), 4.28-4.31 (2H, m), 4.58-4.63 (1H, m), 6.94 (1H, d), 7.05 (1H, d), 7.32 (1H, t), 10.28 (1H, s). m/z: ES+ [M+H]+=501.

3-Chloro-2-[(12aR)-10-chloro-7,8-difluoro-1,2,3,4,12,12a-hexahydro-6H-pyrazino[2,1-c][1,4]benzoxazepin-9-yl]phenol

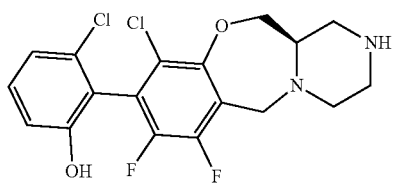 [SMILES: Oc1cccc(Cl)c1-c1c(F)c(F)c2c(c1Cl)OC[C@H]1CNCCN1C2]

TFA (1 mL, 12.98 mmol) was added to tert-butyl (12aR)-10-chloro-9-(2-chloro-6-hydroxyphenyl)-7,8-difluoro-3,4,12,12a-tetrahydro-6H-pyrazino[2,1-c][1,4]benzoxazepine-2(1H)-carboxylate (364 mg, 0.73 mmol) in DCM (5 mL) at 20° C. The resulting mixture was stirred at room temperature for 1 hour. The solvent was removed under reduced pressure. The crude product obtained was purified by ion exchange chromatography, using an SCX column. The desired product was eluted from the column using 7M NH$_3$/MeOH and pure fractions were evaporated to dryness to afford 3-chloro-2-[(12aR)-10-chloro-7,8-difluoro-1,2,3,4,12,12a-hexahydro-6H-pyrazino[2,1-c][1,4]benzoxazepin-9-yl]phenol (290 mg, 100%) as a yellow solid. 1H NMR (400 MHz, DMSO, 30° C.) 2.75-2.80 (1H, m), 2.86-2.90 (1H, m), 2.97-3.17 (3H, m), 3.27-3.41 (3H, m), 3.87-4.09 (3H, m), 4.47 (1H, d), 6.99 (2H, d), 7.31 (1H, d), 10.24 (1H, s). m/z: ES+ [M+H]+=401.

1-[(12aR)-10-chloro-9-(2-chloro-6-hydroxyphenyl)-7,8-difluoro-3,4,12,12a-tetrahydro-6H-pyrazino[2,1-c][1,4]benzoxazepin-2(1H)-yl]prop-2-en-1-one Rotational Isomer 1, Example 91 and Rotational Isomer 2, Example 92

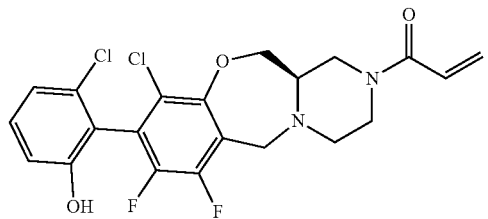 [SMILES: C=CC(=O)N1CCN2Cc3c(F)c(F)c(-c4c(O)cccc4Cl)c(Cl)c3OC[C@H]2C1]

DIPEA (609 μl, 3.49 mmol) and acryloyl chloride (63.2 mg, 0.70 mmol) were added to 3-chloro-2-[(12aR)-10-chloro-7,8-difluoro-1,2,3,4,12,12a-hexahydro-6H-pyrazino[2,1-c][1,4]benzoxazepin-9-yl]phenol (280 mg, 0.70 mmol) in DMF (5 mL) at −20° C. under nitrogen. The resulting mixture was stirred at −20° C. for 1 hour. The reaction mixture was quenched with water (1 mL) and purified directly by preparative HPLC (Column: Xselect CSH OBD Column 30*150 mm 5 um; Mobile Phase A:Water (0.1% formic acid), Mobile Phase B:MeCN; Flow rate:60 mL/min; Gradient:35 B to 45 B in 9 min; 254; 220 nm) and MeCN as eluents. Fractions containing the desired compounds were evaporated to dryness to afford firstly rotational isomer 1 of 1-[(12aR)-10-chloro-9-(2-chloro-6-hydroxyphenyl)-7,8-difluoro-3,4,12,12a-tetrahydro-6H-pyrazino[2,1-c][1,4]benzoxazepin-2(1H)-yl]prop-2-en-1-one (0.041 g, 12%) as a white solid. 1H NMR (400 MHz, DMSO, 30° C.) 2.80-2.82 (1H, m), 2.91-2.95 (2H, m), 3.23-3.28 (2H, m), 3.74-3.98 (3H, m), 4.02-4.05 (2H, m), 4.45-4.50 (1H, m), 5.70-5.72 (1H, m), 6.18-7.21 (1H, m), 6.65-6.93 (1H, m), 6.99 (2H, d), 7.30 (1H, t), 10.45 (1H, s). m/z: ES+ [M+H]+=455. This was followed by rotational isomer 2 of 1-[(12aR)-10-chloro-9-(2-chloro-6-hydroxyphenyl)-7,8-difluoro-3,4,12,12a-tetrahydro-6H-pyrazino[2,1-c][1,4]benzoxazepin-2(1H)-yl]prop-2-en-1-one (0.074 g, 23%) as a white solid. 1H NMR (400 MHz, DMSO, 30° C.) 2.80-2.82 (1H, m), 2.91-2.93 (2H, m), 3.23-3.26 (2H, m), 3.74-3.98 (3H, m), 4.02-4.23 (2H, m), 4.45-4.50 (1H, m), 5.70-5.73 (1H, m), 6.13-6.17 (1H, m), 6.65-6.93 (1H, m), 6.99 (2H, d), 7.30 (1H, t), 10.45 (1H, s). m/z: ES+ [M+H]+=455.

4-Bromo-2,3-difluoro-5-iodobenzoic acid

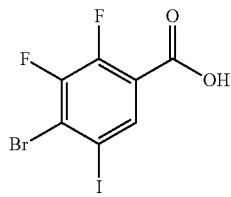

1-Iodopyrrolidine-2,5-dione (57.0 g, 253.16 mmol) was added to 4-bromo-2,3-difluorobenzoic acid (40 g, 168.78 mmol) and concentrated sulphuric acid (160 mL) at 0° C. The resulting mixture was stirred at room temperature for 3 hours. The reaction mixture was poured onto ice water (500 mL) and extracted with EtOAc (2×400 mL). The organic layer was dried over anhydrous sodium sulphate, filtered and evaporated to afford 4-bromo-2,3-difluoro-5-iodobenzoic acid (60 g, 98%) as a white solid. 1H NMR (400 MHz, DMSO, 30° C.) 8.04-8.19 (1H, m), 11.06 (1H, s). m/z: ES– [M–H]–=361.

Tert-butyl (3R)-4-(4-bromo-2,3-difluoro-5-iodobenzoyl)-3-(hydroxymethyl)piperazine-1-carboxylate

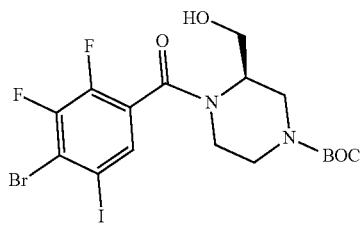 [SMILES: CC(C)(C)OC(=O)N1CCN(C(=O)c2cc(I)c(Br)c(F)c2F)[C@@H](CO)C1]

DIPEA (72.2 mL, 413.34 mmol) was added dropwise to 4-bromo-2,3-difluoro-5-iodobenzoic acid (50 g, 137.78 mmol), tert-butyl (3R)-3-(hydroxymethyl)piperazine-1-carboxylate (29.8 g, 137.78 mmol) and HATU (79.0 g, 206.67 mmol) in DMF (500 mL) at 0° C. The resulting mixture was stirred at room temperature for 2 hours. The reaction mixture was diluted with EtOAc (1000 mL), washed sequentially with water (1000 mL) and saturated brine (750 mL×3). The organic layer was dried over anhydrous sodium sulphate, filtered and evaporated to afford tert-butyl (3R)-4-(4-bromo-2,3-difluoro-5-iodobenzoyl)-3-(hydroxymethyl)piperazine-1-carboxylate (70 g, 91%) as a yellow solid. 1H NMR (300 MHz, DMSO, 30° C.) 1.38 (9H, s), 3.05-3.24 (2H, m), 3.40-3.68 (3H, m), 3.69-3.90 (1H, m), 4.17-4.55 (2H, m), 4.77-5.00 (1H, m), 8.11-8.28 (1H, m) one exchangeable proton not seen. m/z: ES+ [M+H]+=561.

Tert-butyl (12aR)-9-bromo-10-fluoro-8-iodo-6-oxo-3,4,12,12a-tetrahydro-6H-pyrazino[2,1-c][1,4]benzoxazepine-2(1H)-carboxylate

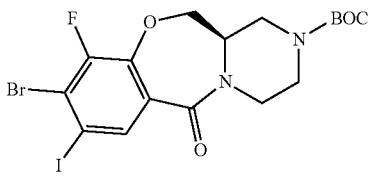 [SMILES: CC(C)(C)OC(=O)N1CCN2C(=O)c3cc(I)c(Br)c(F)c3OC[C@H]2C1]

Sodium hydride (8.55 g, 213.84 mmol) was added to tert-butyl (3R)-4-(4-bromo-2,3-difluoro-5-iodobenzoyl)-3-(hydroxymethyl)piperazine-1-carboxylate (60 g, 106.92 mmol) in DMF (600 mL) at 0° C. The resulting mixture was stirred at room temperature for 2 hours. The reaction mixture was quenched with ice water. The mixture was diluted with EtOAc (1000 mL), washed sequentially with water (1000 mL) and saturated brine (750 mL×2). The organic layer was dried over anhydrous sodium sulphate, filtered and evaporated to afford crude product. The crude product was purified by flash silica chromatography, elution gradient 0 to 25% EtOAc in petroleum ether. Pure fractions were evaporated to dryness to afford tert-butyl (12aR)-9-bromo-10-fluoro-8-iodo-6-oxo-3,4,12,12a-tetrahydro-6H-pyrazino[2,1-c][1,4]benzoxazepine-2(1H)-carboxylate (42 g, 73%) as a yellow solid. 1H NMR (400 MHz, DMSO, 30° C.) 1.41 (9H, s), 3.38-3.55 (3H, m), 3.61-3.81 (2H, m), 3.84-3.97 (1H, m), 3.98-4.09 (1H, m), 4.31-4.42 (2H, m), 8.00 (1H, d). m/z: ES+ [M+H]+=541.

Tert-butyl (12aR)-9-bromo-10-fluoro-8-methoxy-6-oxo-3,4,12,12a-tetrahydro-6H-pyrazino[2,1-c][1,4]benzoxazepine-2(1H)-carboxylate

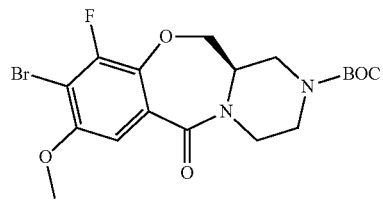 [SMILES: COc1cc2c(c(F)c1Br)OC[C@H]1CN(C(=O)OC(C)(C)C)CCN1C2=O]

Copper (I) iodide (0.352 g, 1.85 mmol) was added to tert-butyl (12aR)-9-bromo-10-fluoro-8-iodo-6-oxo-3,4,12,12a-tetrahydro-6H-pyrazino[2,1-c][1,4]benzoxazepine-2(1H)-carboxylate (10 g, 18.48 mmol), $N^1,N^2$-bis(4-hydroxy-2,6-dimethylphenyl)ethanediamide (0.607 g, 1.85 mmol) and $Cs_2CO_3$ (18.06 g, 55.44 mmol) in MeOH (160 mL). The resulting mixture was stirred at 80° C. for 2 hours. The reaction mixture was diluted with EtOAc (150 mL), washed sequentially with water (150 mL) and saturated brine (150 mL). The organic layer was dried over anhydrous sodium sulphate. The solvent was removed under reduced pressure. The crude product obtained was purified by flash silica chromatography, elution gradient 0 to 40% EtOAc in petroleum ether. Pure fractions were evaporated to dryness to afford tert-butyl (R)-9-bromo-10-fluoro-8-methoxy-6-oxo-3,4,12,12a-tetrahydro-6H-benzo[f]pyrazino[2,1-c][1,4]oxazepine-2(1H)-carboxylate (3.9 g, 47%) as a white solid. 1H NMR (400 MHz, DMSO, 30° C.) 1.41 (9H, s), 3.42-3.67 (5H, m), 3.83-3.86 (1H, m), 3.89 (3H, s), 3.92-4.01 (1H, m), 4.17-4.30 (2H, m), 7.11 (1H, s). m/z: ES+ [M+H]+=445.

(12aR)-9-Bromo-10-fluoro-8-hydroxy-1,2,3,4,12,12a-hexahydro-6H-pyrazino[2,1-c][1,4]benzoxazepin-6-one

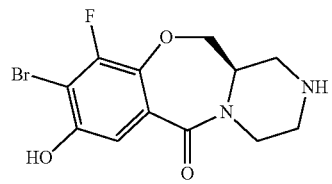 [SMILES: O=C1c2cc(O)c(Br)c(F)c2OC[C@H]2CNCCN12]

1M Boron tribromide solution in DCM (62.9 mL, 62.88 mmol) was added to tert-butyl (12aR)-9-bromo-10-fluoro-8-methoxy-6-oxo-3,4,12,12a-tetrahydro-6H-pyrazino[2,1-c][1,4]benzoxazepine-2(1H)-carboxylate (3.5 g, 7.86 mmol) in DCM (20 mL) at 0° C. The resulting mixture was stirred at 20° C. for 2 hours. The reaction mixture was quenched with MeOH (25 mL). The solvent was removed under reduced pressure to afford ((12aR)-9-bromo-10-fluoro-8-hydroxy-1,2,3,4,12,12a-hexahydro-6H-pyrazino[2,1-c][1,4]benzoxazepin-6-one (2.5 g, 96%) as a yellow solid. 1H NMR (400 MHz, DMSO, 30° C.) 3.21-3.25 (3H, m), 3.33-3.50 (1H, m), 3.73-3.84 (1H, m), 3.84-3.95 (1H, m), 4.01-4.12 (1H, m), 4.13-4.27 (2H, m), 7.28 (1H, s), 9.11-9.19 (1H, s), 9.19-9.30 (1H, s). m/z: ES+ [M+H]+=331.

Tert-butyl (12aR)-9-bromo-10-fluoro-8-hydroxy-6-oxo-3,4,12,12a-tetrahydro-6H-pyrazino[2,1-c][1,4]benzoxazepine-2(1H)-carboxylate

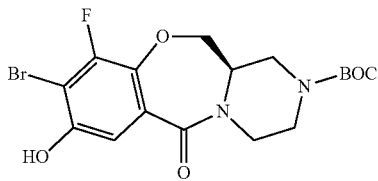 [SMILES: CC(C)(C)OC(=O)N1CCN2C(=O)c3cc(O)c(Br)c(F)c3OC[C@H]2C1]

Di-tert-butyl dicarbonate (1.648 g, 7.55 mmol) was added to (12aR)-9-bromo-10-fluoro-8-hydroxy-1,2,3,4,12,12a-hexahydro-6H-pyrazino[2,1-c][1,4]benzoxazepin-6-one (2.5 g, 7.55 mmol) and triethylamine (6.31 mL, 45.30 mmol) in DCM (75 mL) at 0° C. under nitrogen. The resulting mixture was stirred at 0° C. for 1 hour. The reaction mixture was diluted with DCM (100 mL), washed sequentially with 5% aqueous citric acid (200 mL×2) and saturated brine (200 mL×2). The organic layer was dried over anhydrous sodium sulphate and the solvent was removed under reduced pressure. The crude product obtained was purified by flash silica chromatography, elution gradient 0 to 30% THF in petroleum ether. Pure fractions were evaporated to dryness to afford tert-butyl (12aR)-9-bromo-10-fluoro-8-hydroxy-6-oxo-3,4,12,12a-tetrahydro-6H-pyrazino[2,1-c][1,4]benzoxazepine-2(1H)-carboxylate (1.7 g, 52%) as a brown solid. 1H NMR (400 MHz, DMSO, 30° C.) 1.41 (9H, s), 3.30-3.31 (2H, m), 3.43-3.52 (2H, m), 3.52-3.60 (1H, m), 3.68-3.90 (1H, m), 3.92-4.01 (1H, m), 4.12-4.25 (2H, m), 7.02 (1H, s), 10.76-10.81 (1H, m). m/z: ES+ [M+H]+=431.

Tert-butyl (12aR)-9-bromo-8-(difluoromethoxy)-10-fluoro-6-oxo-3,4,12,12a-tetrahydro-6H-pyrazino[2,1-c][1,4]benzoxazepine-2(1H)-carboxylate

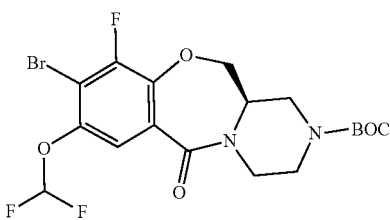 [SMILES: CC(C)(C)OC(=O)N1CCN2C(=O)c3cc(OC(F)F)c(Br)c(F)c3OC[C@H]2C1]

Difluoromethyl triflate (0.791 mL, 6.26 mmol) was added to tert-butyl (12aR)-9-bromo-10-fluoro-8-hydroxy-6-oxo-3,4,12,12a-tetrahydro-6H-pyrazino[2,1-c][1,4]benzoxazepine-2(1H)-carboxylate (900 mg, 2.09 mmol) and 6M KOH (8 mL, 48.00 mmol) in CH$_3$CN (8 mL) at 0° C. The resulting mixture was stirred at 0° C. for 1 hour. The reaction mixture was diluted with EtOAc (80 mL), washed sequentially with water (50 mL×3), and saturated brine (25 mL). The organic layer was dried over anhydrous sodium sulphate, filtered and evaporated to afford tert-butyl (12aR)-9-bromo-8-(difluoromethoxy)-10-fluoro-6-oxo-3,4,12,12a-tetrahydro-6H-pyrazino[2,1-c][1,4]benzoxazepine-2(1H)-carboxylate (950 mg, 95%) as a brown solid. 1H NMR (400 MHz, CDCl$_3$, 30° C.) 1.50 (9H, s), 3.53-3.70 (3H, m), 3.71-3.78 (1H, m), 3.80-3.88 (1H, m), 3.90-4.02 (1H, m), 4.10-4.15 (1H, m), 4.28-4.35 (1H, m), 4.35-4.49 (1H, m), 6.36-6.80 (1H, m), 7.57 (1H, s). m/z: ES+ [M-tBu]+=425.

Tert-butyl (12aR)-9-(2-chloro-6-hydroxyphenyl)-8-(difluoromethoxy)-10-fluoro-6-oxo-3,4,12,12a-tetrahydro-6H-pyrazino[2,1-c][1,4]benzoxazepine-2(1H)-carboxylate

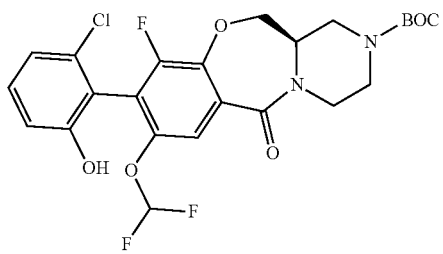 [SMILES: CC(C)(C)OC(=O)N1CCN2C(=O)c3cc(OC(F)F)c(-c4c(O)cccc4Cl)c(F)c3OC[C@H]2C1]

2-Dicyclohexylphosphino-2',6'-diisopropoxybiphenyl (87 mg, 0.19 mmol) and RuPhos-Pd-G3 (156 mg, 0.19 mmol) were added to tert-butyl (12aR)-9-bromo-8-(difluoromethoxy)-10-fluoro-6-oxo-3,4,12,12a-tetrahydro-6H-pyrazino[2,1-c][1,4]benzoxazepine-2(1H)-carboxylate (900 mg, 1.87 mmol), (2-chloro-6-hydroxyphenyl)boronic acid (645 mg, 3.74 mmol) and K$_2$CO$_3$ (517 mg, 3.74 mmol) in 1,4-dioxane (20 mL) and water (5 mL)(4:1 ratio) at 25° C. under nitrogen. The resulting mixture was stirred at 100° C. for 8 hours. The reaction mixture was purified directly by flash C18-flash chromatography, elution gradient 0 to 100% MeCN in water (0.1% formic acid). Pure fractions were evaporated to dryness to afford tert-butyl (12aR)-9-(2-chloro-6-hydroxyphenyl)-8-(difluoromethoxy)-10-fluoro-6-oxo-3,4,12,12a-tetrahydro-6H-pyrazino[2,1-c][1,4]benzoxazepine-2(1H)-carboxylate (380 mg, 38%) as a yellow solid. 1H NMR (400 MHz, DMSO, 30° C.) 1.42 (9H, s), 3.40-3.61 (3H, m), 3.69-3.83 (2H, m), 3.94-4.13 (2H, m), 4.32-4.44 (2H, m), 6.90-6.95 (1H, m), 7.00-7.05 (1H, m), 7.11-7.32 (2H, m), 7.42 (1H, s), 10.20 (1H, s). m/z: ES+ [M-tBu]+=473.

Tert-butyl (12aR)-9-(2-chloro-6-hydroxyphenyl)-8-(difluoromethoxy)-10-fluoro-3,4,12,12a-tetrahydro-6H-pyrazino[2,1-c][1,4]benzoxazepine-2(1H)-carboxylate

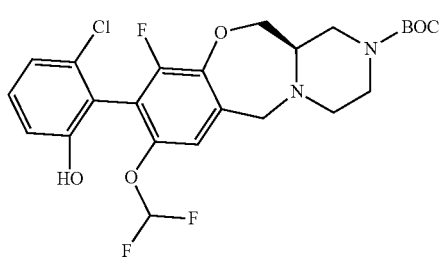 [SMILES: CC(C)(C)OC(=O)N1CCN2Cc3cc(OC(F)F)c(-c4c(O)cccc4Cl)c(F)c3OC[C@H]2C1]

1M Borane-THF complex solution in THF (4 mL, 4 mmol) was added to tert-butyl (12aR)-9-(2-chloro-6-hydroxyphenyl)-8-(difluoromethoxy)-10-fluoro-6-oxo-3,4,12,12a-tetrahydro-6H-pyrazino[2,1-c][1,4]benzoxazepine-2(1H)-carboxylate (350 mg, 0.66 mmol) in THF (4 mL) at 25° C. under nitrogen. The resulting mixture was stirred at 60° C. for 1 hour. The reaction mixture was quenched with saturated NH₄Cl (10 mL) and extracted with EtOAc (3×25 mL). The organic layer was dried over anhydrous sodium sulphate, filtered and evaporated to afford tert-butyl (12aR)-9-(2-chloro-6-hydroxyphenyl)-8-(difluoromethoxy)-10-fluoro-3,4,12,12a-tetrahydro-6H-pyrazino[2,1-c][1,4]benzoxazepine-2(1H)-carboxylate (320 mg, 94%) as a brown solid. 1H NMR (400 MHz, DMSO, 30° C.) 1.40 (9H, s), 2.29-2.41 (1H, m), 2.63-2.87 (4H, m), 2.99-3.09 (1H, m), 3.57-3.66 (2H, m), 3.70-3.78 (1H, m), 3.84-3.95 (1H, m), 4.29-4.34 (1H, m), 6.47-6.59 (1H, m), 6.87-6.94 (1H, m), 6.95-6.99 (1H, m), 7.01-7.04 (1H, m), 7.21-7.29 (1H, m), 10.06 (1H, s). m/z: ES+ [M+H]+=515.

3-Chloro-2-[(12aR)-8-(difluoromethoxy)-10-fluoro-1,2,3,4,12,12a-hexahydro-6H-pyrazino[2,1-c][1,4]benzoxazepin-9-yl]phenol

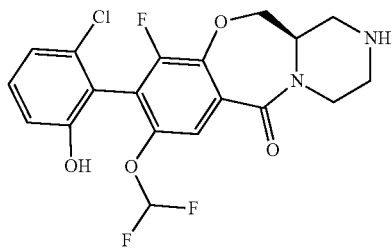 [SMILES: O=C1c2cc(OC(F)F)c(-c3c(O)cccc3Cl)c(F)c2OC[C@H]2CNCCN12]

TFA (0.8 mL, 10.38 mmol) was added to tert-butyl (12aR)-9-(2-chloro-6-hydroxyphenyl)-8-(difluoromethoxy)-10-fluoro-3,4,12,12a-tetrahydro-6H-pyrazino[2,1-c][1,4]benzoxazepine-2(1H)-carboxylate (350 mg, 0.68 mmol) in DCM (4 mL) at 25° C. The resulting mixture was stirred at room temperature for 1 hour. The solvent was removed under reduced pressure. The crude product obtained was purified by ion exchange chromatography, using an SCX column. The desired product was eluted from the column using 7M NH₃/MeOH and pure fractions were evaporated to dryness to afford 3-chloro-2-[(12aR)-8-(difluoromethoxy)-10-fluoro-1,2,3,4,12,12a-hexahydro-6H-pyrazino[2,1-c][1,4]benzoxazepin-9-yl]phenol (230 mg, 82%) as a yellow solid. 1H NMR (400 MHz, DMSO, 30° C.) 2.29-2.37 (2H, m), 2.59-2.71 (2H, m), 2.72-2.88 (3H, m), 3.60-3.69 (2H, m), 3.76-3.85 (1H, m), 4.19-4.32 (1H, m), 6.88-6.93 (1H, m), 6.95-6.99 (1H, m), 6.99-7.04 (2H, m), 7.22-7.29 (1H, m) two exchangeable protons not seen. m/z: ES+ [M+H]+=415.

1-[(12aR)-9-(2-chloro-6-hydroxyphenyl)-8-(difluoromethoxy)-10-fluoro-3,4,12,12a-tetrahydro-6H-pyrazino[2,1-c][1,4]benzoxazepin-2(1H)-yl]prop-2-en-1-one Rotational Isomer 1, Example 93 and Rotational Isomer 2, Example 94

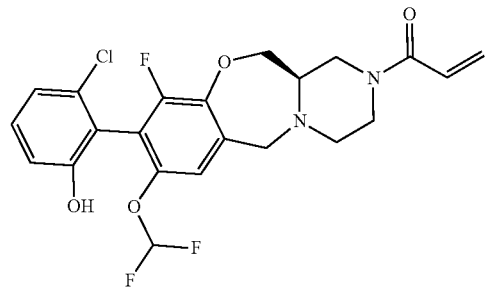 [SMILES: C=CC(=O)N1CCN2Cc3cc(OC(F)F)c(-c4c(O)cccc4Cl)c(F)c3OC[C@H]2C1]

DIPEA (185 µl, 1.06 mmol) and acryloyl chloride (48.0 mg, 0.53 mmol) were added to 3-chloro-2-[(12aR)-8-(difluoromethoxy)-10-fluoro-1,2,3,4,12,12a-hexahydro-6H-pyrazino[2,1-c][1,4]benzoxazepin-9-yl]phenol (220 mg, 0.53 mmol) in DMF (2.5 mL) at −20° C. under nitrogen. The resulting mixture was stirred at −20° C. for 1 hour. The reaction mixture was quenched with water and filtered through a microfiltration membrane. The filtrate was purified by preparative HPLC Column: Xselect CSH OBD Column 30*150 mm 5 um; Mobile Phase A:Water (0.1% formic acid), Mobile Phase B:MeCN; Flow rate:60 mL/min; Gradient:26 B to 36 B in 9 min; 254; 220 nm. Fractions containing the desired compound were evaporated to dryness to afford firstly rotational isomer 1 of 1-[(12aR)-9-(2-chloro-6-hydroxyphenyl)-8-(difluoromethoxy)-10-fluoro-3,4,12,12a-tetrahydro-6H-pyrazino[2,1-c][1,4]benzoxazepin-2(1H)-yl]prop-2-en-1-one (0.036 g, 14%) as a white solid. 1H NMR (400 MHz, DMSO, 30° C.) 2.34-2.45 (1H, m), 2.63-2.92 (1H, m), 2.97-3.12 (1H, m), 3.62-3.71 (1H, m), 3.73-3.82 (1H, m), 3.83-3.98 (2H, m), 3.98-4.16 (1H, m), 4.30-4.45 (1H, m), 5.62-5.76 (1H, m), 6.13 (1H, d), 6.77-7.18 (5H, m), 7.25 (1H, t), 10.09 (1H, s). m/z: ES+ [M+H]+= 469. This was followed by rotational isomer 2 of 1-[(12aR)-9-(2-chloro-6-hydroxyphenyl)-8-(difluoromethoxy)-10-fluoro-3,4,12,12a-tetrahydro-6H-pyrazino[2,1-c][1,4]benzoxazepin-2(1H)-yl]prop-2-en-1-one (0.048 g, 19%) as a white solid. 1H NMR (400 MHz, DMSO, 30° C.) 2.36-2.45 (1H, m), 2.69-2.78 (1H, m), 2.76-2.98 (2H, m), 2.94-3.13 (1H, m), 3.60-3.69 (1H, m), 3.69-3.83 (1H, m), 3.83-3.97 (2H, m), 3.96-4.10 (1H, m), 4.33-4.47 (1H, m), 5.62-5.75 (1H, m), 6.13 (1H, d), 6.74-7.16 (5H, m), 7.25 (1H, t), 10.07 (1H, s). m/z: ES+ [M+H]+=469.

Tert-butyl (3R)-4-[(4-bromo-2,3,6-trifluorophenyl)methyl]-3-(hydroxymethyl)piperazine-1-carboxylate

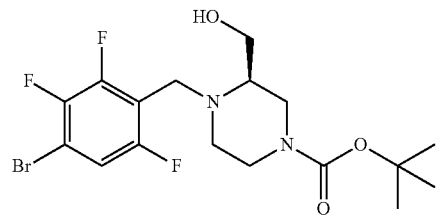 [SMILES: CC(C)(C)OC(=O)N1CCN(Cc2c(F)cc(Br)c(F)c2F)[C@@H](CO)C1]

A solution of 4-bromo-2,3,6-trifluorobenzaldehyde (5 g, 20.92 mmol), tert-butyl (R)-3-(hydroxymethyl)piperazine-1-carboxylate (5.43 g, 25.11 mmol) and acetic acid (0.12 mL, 2.09 mmol) in DCM (150 mL) was stirred at room temperature for 24 hours. Sodium triacetoxyhydroborate (8.87 g, 41.84 mmol) was added and the resulting mixture was stirred at room temperature for 7 hours, further sodium triacetoxyhydroborate (4.4 g, 20.92 mmol) was added and the mixture was stirred at room temperature for a further 17 hours. The reaction mixture was diluted with saturated aqueous $NaHCO_3$ (200 mL), and the mixture was stirred at room temperature until the effervescence subsided, then the organic layer was washed sequentially with water (125 mL), and saturated brine (125 mL). The organic layer was dried with a phase separating cartridge, filtered and evaporated to afford tert-butyl (3R)-4-[(4-bromo-2,3,6-trifluorophenyl)methyl]-3-(hydroxymethyl)piperazine-1-carboxylate (9.67 g, >100%) as a pale yellow gum, which was used without further purification. 1H NMR (400 MHz, $CDCl_3$, 30° C.) 1.45 (9H, s), 2.26-2.49 (2H, m), 2.56 (1H, s), 2.67-2.83 (1H, m), 3.03-3.18 (1H, m), 3.31 (1H, dd), 3.53-3.76 (4H, m), 3.92 (1H, dd), 4.03 (1H, d), 7.13 (1H, ddd), m/z: ES+ [M+H]+ 439.

Tert-butyl (12aR)-9-bromo-7,10-difluoro-3,4,12,12a-tetrahydro-6H-pyrazino[2,1-c][1,4]benzoxazepine-2(1H)-carboxylate

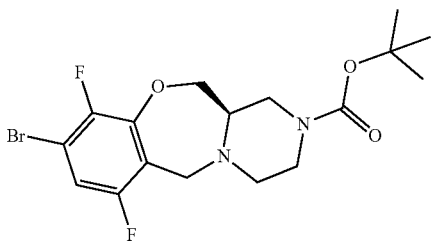 [SMILES: CC(C)(C)OC(=O)N1CCN2Cc3c(F)cc(Br)c(F)c3OC[C@H]2C1]

Sodium hydride (1.3 g, 33.02 mmol) was added to a stirred solution of tert-butyl (3R)-4-[(4-bromo-2,3,6-trifluorophenyl)methyl]-3-(hydroxymethyl)piperazine-1-carboxylate (9.67 g, 22.01 mmol) in THF (220 mL). The resulting solution was stirred at room temperature for 2 days. Additional Sodium hydride (1 g) was added then the mixture heated at 50° C. for 3 hours. The reaction mixture was quenched with water (150 mL), extracted with EtOAc (2×300 mL), the organic extracts were combined, washed with saturated brine (300 mL). The organic layer was dried with $MgSO_4$, filtered and evaporated to afford crude product. The crude product was purified by flash silica chromatography, elution gradient 0 to 60% EtOAc in heptane. Pure fractions were evaporated to dryness to afford tert-butyl (12aR)-9-bromo-7,10-difluoro-3,4,12,12a-tetrahydro-6H-pyrazino[2,1-c][1,4]benzoxazepine-2(1H)-carboxylate (8.7 g, 94%) as a yellow foam. 1H NMR (400 MHz, $CDCl_3$, 30° C.) 1.46 (9H, s), 2.47 (1H, ddd), 2.78-2.87 (2H, m), 2.95 (1H, s), 3.24 (1H, ddd), 3.6-3.78 (3H, m), 3.82 (1H, dd), 4.01 (1H, dd), 4.30 (1H, dd), 7.00 (1H, dd).

(12aR)-9-Bromo-7,10-difluoro-8-iodo-1,2,3,4,12,12a-hexahydro-6H-pyrazino[2,1-c][1,4]benzoxazepine

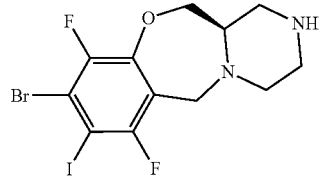 [SMILES: Fc1c(I)c(Br)c(F)c2c1CN1CCNC[C@@H]1CO2]

Concentrated $H_2SO_4$ (50 mL) was added slowly to tert-butyl (12aR)-9-bromo-7,10-difluoro-3,4,12,12a-tetrahydro-6H-pyrazino[2,1-c][1,4]benzoxazepine-2(1H)-carboxylate (8.7 g, 20.75 mmol), addition accompanied by an exotherm. The resulting solution was stirred at room temperature for 20 minutes. 1-iodopyrrolidine-2,5-dione (9.3 g, 41.5 mmol) was added portion wise over a period of 5 minutes. The resulting mixture was stirred at room temperature for 90 minutes. The reaction mixture was slowly poured onto ice (150 mL), then the mixture was placed in an ice water cooling bath and slowly adjusted to pH 10 with NaOH (25% solution, 300 mL). The mixture was extracted with EtOAc (4×400 mL), the organic extracts were combined washed sequentially with water (200 mL), and saturated brine (200 mL). The organic layer was dried with MgSO4, filtered and evaporated to afford (12aR)-9-bromo-7,10-difluoro-8-iodo-1,2,3,4,12,12a-hexahydro-6H-pyrazino[2,1-c][1,4]benzoxazepine (8.28 g, 90%) as a brown solid, which was used without further purification. 1H NMR (400 MHz, DMSO, 30° C.) 2.33-2.47 (2H, m), 2.65-2.93 (5H, m), 3.65-3.76 (1H, m), 3.82-3.96 (2H, m), 4.33 (1H, dd), NH not observed. m/z: ES+ [M+H]+ 445.

Tert-butyl (12aR)-9-bromo-7,10-difluoro-8-iodo-3,4,12,12a-tetrahydro-6H-pyrazino[2,1-c][1,4]benzoxazepine-2(1H)-carboxylate

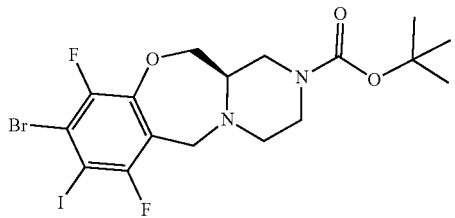 [SMILES: CC(C)(C)OC(=O)N1CCN2Cc3c(F)c(I)c(Br)c(F)c3OC[C@H]2C1]

Di-tert-Butyl dicarbonate (6.09 g, 27.91 mmol) was added to a stirred solution of (12aR)-9-bromo-7,10-difluoro-8-iodo-1,2,3,4,12,12a-hexahydro-6H-pyrazino[2,1-c][1,4]benzoxazepine (8.28 g, 18.6 mmol) and triethylamine (7.8 mL, 55.81 mmol) in DCM (300 mL) at room temperature. The resulting solution was stirred at room temperature for 17 hours. The reaction mixture was washed sequentially with water (400 mL), and saturated brine (400 mL), the organic layer separated, dried with a phase separating cartridge, filtered and evaporated to afford crude product. The crude product was purified by flash silica chromatography, elution gradient 0 to 30% EtOAc in heptane. Pure fractions were evaporated to dryness to afford tert-butyl (12aR)-9-bromo-7,10-difluoro-8-iodo-3,4,12,12a-tetrahydro-6H-pyrazino[2, 1-c][1,4]benzoxazepine-2(1H)-carboxylate (6.26 g, 62%) as a cream foam. 1H NMR (400 MHz, CDCl₃, 30° C.) 1.45 (9H, s), 2.49 (1H, ddd), 2.84 (2H, dddd), 2.99 (1H, s), 3.26 (1H, ddd), 3.71 (3H, ddd), 3.84 (1H, dd), 4.06 (1H, dd), 4.31 (1H, dd), m/z: ES+ [M+H]+ 545.

Tert-butyl (12aR)-9-(2-chloro-6-hydroxyphenyl)-7, 10-difluoro-8-[(trimethylsilyl)ethynyl]-3,4,12,12a-tetrahydro-6H-pyrazino[2,1-c][1,4]benzoxazepine-2 (1H)-carboxylate Rotational Isomers 1 and 2

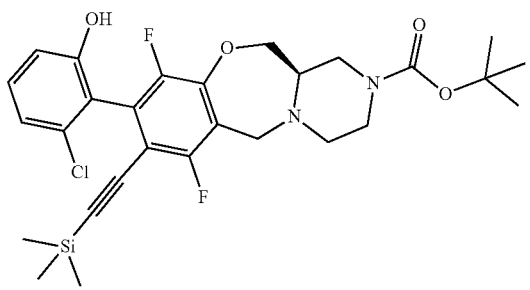 [SMILES: CC(C)(C)OC(=O)N1CCN2Cc3c(F)c(C#C[Si](C)(C)C)c(-c4c(O)cccc4Cl)c(F)c3OC[C@H]2C1]

Potassium carbonate (1.5 g, 11.17 mmol), RuPhos Pd G3 (0.312 g, 0.37 mmol), dicyclohexyl(2',6'-diisopropoxy-[1,1'-biphenyl]-2-yl)phosphane (0.174 g, 0.37 mmol), and (2-chloro-6-hydroxyphenyl)boronic acid (1.3 g, 7.45 mmol) were added to a stirred and degassed solution of tert-butyl (12aR)-9-bromo-7,10-difluoro-8-iodo-3,4,12,12a-tetrahydro-6H-pyrazino[2,1-c][1,4]benzoxazepine-2(1H)-carboxylate (1.92 g, 3.72 mmol) in dioxane (30 mL) and water (6 mL) under nitrogen. The resulting solution was stirred at 90° C. for 3 hours. The reaction mixture was diluted with water (75 mL), extracted with EtOAc (2×125 mL). The combined organic layers dried with MgSO₄, filtered and evaporated to afford crude product. The crude product was purified by flash silica chromatography, elution gradient 0 to 50% EtOAc in heptane. Pure fractions were evaporated to dryness to afford tert-butyl (12aR)-9-(2-chloro-6-hydroxyphenyl)-7,10-difluoro-8-[(trimethylsilyl)ethynyl]-3,4,12,12a-tetrahydro-6H-pyrazino[2,1-c][1,4]benzoxazepine-2 (1H)-carboxylate (1.150 g) as a red foam. Separation of stable atropisomers was carried out using the following SFC conditions: Column: Chiralpak IC 20×250 mm, 5 micron. Mobile phase: 15% MeOH+0.1% NH₃/85% scCO2. Flow rate: 60 mL/min. BPR: 120 bar. Column temperature: 40° C. to give firstly rotational isomer 1 (401 mg) which was further purified by flash silica chromatography, elution gradient 0 to 50% EtOAc in heptane. Pure fractions were evaporated to dryness to afford tert-butyl (12aR)-9-(2-chloro-6-hydroxyphenyl)-7,10-difluoro-8-[(trimethyl silyl) ethynyl]-3,4,12,12a-tetrahydro-6H-pyrazino[2,1-c][1,4] benzoxazepine-2(1H)-carboxylate (338 mg, 16%) as a yellow foam. 1H NMR (400 MHz, CDCl₃, 30° C.) 0.03 (9H, s), 1.47 (9H, s), 2.42-2.63 (1H, m), 2.86 (3H, ddd), 3.21 (1H, ddd), 3.63-3.84 (3H, m), 3.90 (1H, dd), 4.10 (1H, d), 4.35 (1H, dd), 5.30 (1H, brd), 6.89 (1H, dd), 7.07 (1H, dd), 7.23 (1H, t), m/z: ES+ [M+H]+ 563. This was followed by rotational isomer 2 of tert-butyl (12aR)-9-(2-chloro-6-hydroxyphenyl)-7,10-difluoro-8-[(trimethylsilyl)ethynyl]-3,4, 12,12a-tetrahydro-6H-pyrazino[2,1-c][1,4]benzoxazepine-2 (1H)-carboxylate (326 mg, 15%) as a yellow foam. 1H NMR (400 MHz, CDCl₃, 30° C.) 0.03 (9H, s), 1.47 (9H, s), 2.46-2.6 (1H, m), 2.75-3.1 (3H, m), 3.23 (1H, ddd), 3.76 (3H, dd), 3.91 (1H, dd), 4.11 (1H, d), 4.33 (1H, dd), 4.93 (1H, brs), 6.88 (1H, dd), 7.08 (1H, dd), 7.23 (1H, t), m/z: ES+ [M+H]+ 563.

3-Chloro-2-[(12aR)-8-ethynyl-7,10-difluoro-1,2,3,4, 12,12a-hexahydro-6H-pyrazino[2,1-c][1,4]benzoxazepin-9-yl]phenol Rotational Isomer 1

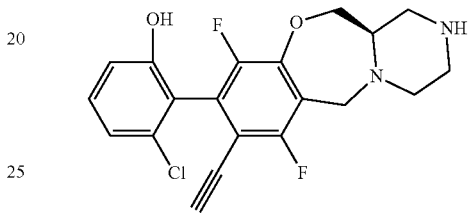

TFA (1.2 mL, 16.21 mmol) was added to a stirred solution of tert-butyl (12aR)-9-(2-chloro-6-hydroxyphenyl)-7,10-difluoro-8-[(trimethylsilyl)ethynyl]-3,4,12,12a-tetrahydro-6H-pyrazino[2,1-c][1,4]benzoxazepine-2(1H)-carboxylate (338 mg, 0.6 mmol) in DCM (2.5 mL). The resulting suspension was stirred at room temperature for 5 hours. The reaction mixture was evaporated to afford crude product. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents. Fractions containing the desired compound were purified ion exchange chromatography, using an SCX column. The desired product was eluted from the column using 1M NH3/MeOH and pure fractions were evaporated to dryness to afford 3-chloro-2-[(12aR)-8-ethynyl-7,10-difluoro-1,2,3,4,12,12a-hexahydro-6H-pyrazino[2,1-c][1,4] benzoxazepin-9-yl]phenol (146 mg, 62%) as a cream solid. 1H NMR (400 MHz, DMSO) 2.38-2.51 (2H, m), 2.57-2.93 (5H, m), 3.6-3.86 (3H, m), 3.97 (1H, s), 4.28 (1H, d), 6.75 (1H, d), 6.83 (1H, d), 7.10 (1H, t), 9.95 (1H, s), NH not observed, m/z: ES+ [M+H]+ 391.

3-Chloro-2-[(12aR)-8-ethynyl-7,10-difluoro-1,2,3,4, 12,12a-hexahydro-6H-pyrazino[2,1-c][1,4]benzoxazepin-9-yl]phenol Rotational Isomer 2

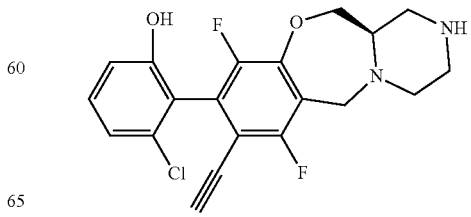

TFA (1.2 mL, 16.21 mmol) was added to a stirred solution of tert-butyl (12aR)-9-(2-chloro-6-hydroxyphenyl)-7,10-difluoro-8-[(trimethylsilyl)ethynyl]-3,4,12,12a-tetrahydro-6H-pyrazino[2,1-c][1,4]benzoxazepine-2(1H)-carboxylate (326 mg, 0.58 mmol) in DCM (2.5 mL). The resulting suspended was stirred at room temperature for 7 hours. The reaction mixture was evaporated to afford crude product. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents, 10 to 40% gradient. Fractions containing the desired compound were evaporated to dryness to afford 3-chloro-2-[(12aR)-8-ethynyl-7,10-difluoro-1,2,3,4,12,12a-hexahydro-6H-pyrazino[2,1-c][1,4]benzoxazepin-9-yl]phenol (190 mg, 84%) as a white solid. 1H NMR (400 MHz, DMSO) 2.58 (2H, d), 2.71-3.09 (5H, m), 3.86 (3H, dd), 4.20 (1H, s), 4.42 (1H, d), 6.91 (1H, d), 7.00 (1H, d), 7.25 (1H, t), 10.08 (1H, s), NH not observed. m/z: ES+ [M+H]+ 391.

1-[(12aR)-9-(2-Chloro-6-hydroxyphenyl)-8-ethynyl-7,10-difluoro-3,4,12,12a-tetrahydro-6H-pyrazino[2,1-c][1,4]benzoxazepin-2(1H)-yl]prop-2-en-1-one Rotational Isomer 1, Example 95

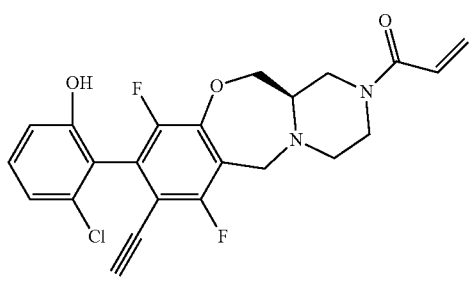 [SMILES: C#Cc1c(F)c2c(c(F)c1-c1c(O)cccc1Cl)OC[C@H]1CN(C(=O)C=C)CCN1C2]

Acryloyl chloride (33.4 μL, 0.41 mmol) was added to a stirred suspension of 3-chloro-2-[(12aR)-8-ethynyl-7,10-difluoro-1,2,3,4,12,12a-hexahydro-6H-pyrazino[2,1-c][1,4]benzoxazepin-9-yl]phenol (146 mg, 0.37 mmol) and DIPEA (85 μL, 0.49 mmol) in DCM (5 mL) at 0° C. The resulting suspension was stirred at 0° C. for 30 minutes. The reaction mixture was evaporated (keeping water bath below 40° C.), the residue was dissolved in cold 1M NH₃/MeOH (5 mL) and stirred at 0° C. for 40 minutes. The reaction mixture was evaporated to afford crude product. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents, 25-60% gradient. Fractions containing the desired compound were evaporated to dryness to afford 1-[(12aR)-9-(2-chloro-6-hydroxyphenyl)-8-ethynyl-7,10-difluoro-3,4,12,12a-tetrahydro-6H-pyrazino[2,1-c][1,4]benzoxazepin-2(1H)-yl]prop-2-en-1-one (74 mg, 45%) as a white solid. 1H NMR (400 MHz, DMSO) 2.44-2.54 (1H, m), 2.70 (1H, dd), 2.81-3.2 (3H, m), 3.79-4.06 (4H, m), 4.15 (1H, d), 4.23 (1H, s), 4.51 (1H, t), 5.71 (1H, t), 6.14 (1H, d), 6.78-6.9 (1H, m), 6.92 (1H, dd), 7.00 (1H, dd), 7.27 (1H, t), 10.07 (1H, s), m/z: ES+ [M+H]+ 445.

1-[(12aR)-9-(2-chloro-6-hydroxyphenyl)-8-ethynyl-7,10-difluoro-3,4,12,12a-tetrahydro-6H-pyrazino[2,1-c][1,4]benzoxazepin-2(1H)-yl]prop-2-en-1-one Rotational Isomer 2, Example 96

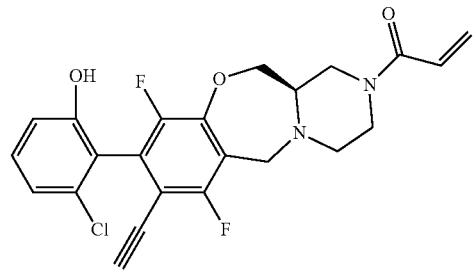 [SMILES: C#Cc1c(F)c2c(c(F)c1-c1c(O)cccc1Cl)OC[C@H]1CN(C(=O)C=C)CCN1C2]

Acryloyl chloride (43.4 μL, 0.53 mmol) was added to a stirred suspension of 3-chloro-2-[(12aR)-8-ethynyl-7,10-difluoro-1,2,3,4,12,12a-hexahydro-6H-pyrazino[2,1-c][1,4]benzoxazepin-9-yl]phenol (190 mg, 0.49 mmol) and DIPEA (110 μL, 0.63 mmol) in DCM (5 mL) at 0° C. The resulting suspension was stirred at 0° C. for 30 minutes. The reaction mixture was evaporated (keeping water bath below 40° C.), the residue was dissolved in cold 1M NH₃/MeOH (5 mL) and stirred at room temperature for 50 minutes. The reaction mixture was evaporated to afford crude product. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents, 30-60% gradient. Fractions containing the desired compound were evaporated to dryness to afford 1-[(12aR)-9-(2-chloro-6-hydroxyphenyl)-8-ethynyl-7,10-difluoro-3,4,12,12a-tetrahydro-6H-pyrazino[2,1-c][1,4]benzoxazepin-2(1H)-yl]prop-2-en-1-one (99 mg, 46%) as a white solid. 1H NMR (400 MHz, DMSO, 30° C.) 2.4-2.55 (1H, m), 2.69-2.78 (1H, m), 2.84-3.2 (3H, m), 3.82-4.04 (4H, m), 4.08-4.19 (1H, m), 4.19 (1H, s), 4.39-4.57 (1H, m), 5.71 (1H, d), 6.13 (1H, d), 6.76-6.89 (1H, m), 6.91 (1H, dd), 6.95-7.03 (1H, m), 7.26 (1H, t), 10.00 (1H, s), m/z: ES+ [M+H]+ 445.

(12aR)-9-Bromo-10-chloro-8-hydroxy-1,2,3,4,12,12a-hexahydro-6H-pyrazino[2,1-c][1,4]benzoxazepin-6-one

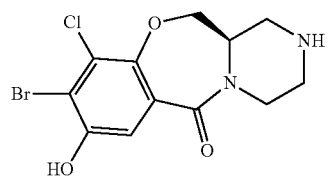

1M Boron tribromide solution in DCM (59.8 mL, 59.77 mmol) was added to tert-butyl (12aR)-9-bromo-10-chloro-8-methoxy-6-oxo-3,4,12,12a-tetrahydro-6H-pyrazino[2,1-c][1,4]benzoxazepine-2(1H)-carboxylate (4.6 g, 9.96 mmol) in DCM (20 mL). The resulting mixture was stirred at room temperature for 2 hours. The reaction mixture was quenched with MeOH. The solvent was removed under reduced pressure. The crude product obtained was purified by ion exchange chromatography, using an SCX column. The desired product was eluted from the column using 7M NH₃/MeOH and pure fractions were evaporated to dryness to afford (12aR)-9-bromo-10-chloro-8-hydroxy-1,2,3,4,12,12a-hexahydro-6H-pyrazino[2,1-c][1,4]benzoxazepin-6-one (3.4 g, 98%) as a yellow solid. 1H NMR (400 MHz, DMSO, 30° C.) 0.75-0.89 (1H, m), 3.15-3.22 (1H, m), 3.67-3.81 (1H, m), 3.81-3.93 (1H, m), 3.93-4.06 (1H, m), 4.09-4.19 (2H, m), 4.52-4.66 (2H, m), 7.28 (1H, s) two exchangeable protons not seen. m/z: ES+ [M+H]+=347.

Tert-butyl (12aR)-9-bromo-10-chloro-8-hydroxy-6-oxo-3,4,12,12a-tetrahydro-6H-pyrazino[2,1-c][1,4]benzoxazepine-2(1H)-carboxylate

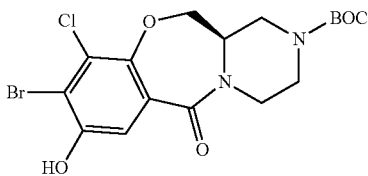 [SMILES: CC(C)(C)OC(=O)N1CCN2C(=O)c3cc(O)c(Br)c(Cl)c3OC[C@H]2C1]

Di-tert-butyl dicarbonate (1.842 mL, 7.93 mmol) was added to (12aR)-9-bromo-10-chloro-8-hydroxy-1,2,3,4,12,12a-hexahydro-6H-pyrazino[2,1-c][1,4]benzoxazepin-6-one (3.4 g, 7.93 mmol) and triethylamine (6.64 mL, 47.61 mmol) in DCM (50 mL) at 0° C. under nitrogen. The resulting mixture was stirred at 0° C. for 1 hour. The reaction mixture was diluted with DCM (100 mL), washed sequentially with 5% aqueous citric acid (200 mL×2) and saturated brine (200 mL). The organic layer was dried over anhydrous sodium sulphate and the solvent was removed under reduced pressure. The crude product obtained was purified by flash silica chromatography, elution gradient 0 to 30% THF in petroleum ether. Pure fractions were evaporated to dryness to afford tert-butyl (12aR)-9-bromo-10-chloro-8-hydroxy-6-oxo-3,4,12,12a-tetrahydro-6H-pyrazino[2,1-c][1,4]benzoxazepine-2(1H)-carboxylate (1.8 g, 51%) as a brown solid. 1H NMR (400 MHz, DMSO, 30° C.) 1.41 (9H, s), 1.99 (1H, s), 3.40-3.52 (2H, m), 3.52-3.60 (2H, m), 3.86-3.94 (1H, m), 3.97-4.09 (1H, m), 4.07-4.25 (2H, m), 7.14 (1H, s), 10.79 (1H, s). m/z: ES+ [M+H]+=447.

Tert-butyl (12aR)-9-bromo-10-chloro-8-(difluoromethoxy)-6-oxo-3,4,12,12a-tetrahydro-6H-pyrazino[2,1-c][1,4]benzoxazepine-2(1H)-carboxylate

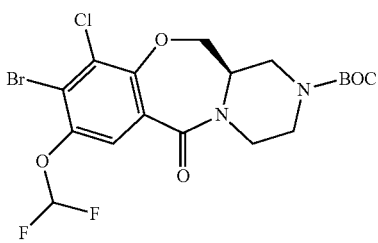 [SMILES: CC(C)(C)OC(=O)N1CCN2C(=O)c3cc(OC(F)F)c(Br)c(Cl)c3OC[C@H]2C1]

Difluoromethyl triflate (0.564 mL, 4.47 mmol) was added to tert-butyl (12aR)-9-bromo-10-chloro-8-hydroxy-6-oxo-3,4,12,12a-tetrahydro-6H-pyrazino[2,1-c][1,4]benzoxazepine-2(1H)-carboxylate (1 g, 2.23 mmol) and 6M KOH (2 mL, 12 mmol) in CH₃CN (8 mL) at 0° C. under nitrogen. The resulting mixture was stirred at 0° C. for 1 hour. The reaction mixture was diluted with EtOAc (30 mL) and washed sequentially with water (50 mL×3) and saturated brine (25 mL). The organic layer was dried over anhydrous sodium sulphate, filtered and evaporated to afford crude product. The crude product was purified by flash silica chromatography, elution gradient 25 to 50% THF in petroleum ether. Pure fractions were evaporated to dryness to afford tert-butyl (12aR)-9-bromo-10-chloro-8-(difluoromethoxy)-6-oxo-3,4,12,12a-tetrahydro-6H-pyrazino[2,1-c][1,4]benzoxazepine-2(1H)-carboxylate (1.1 g, 99%) as a brown oil. 1H NMR (400 MHz, DMSO, 30° C.) 1.09-1.24 (1H, m), 1.41 (9H, s), 3.42-3.54 (4H, m), 3.57-3.69 (1H, m), 3.69-3.84 (1H, m), 3.84-4.12 (1H, m), 4.24-4.44 (2H, m), 7.55 (1H, s). m/z: ES+ [M+H]+=497.

Tert-butyl (12aR)-9-bromo-10-chloro-8-(difluoromethoxy)-3,4,12,12a-tetrahydro-6H-pyrazino[2,1-c][1,4]benzoxazepine-2(1H)-carboxylate

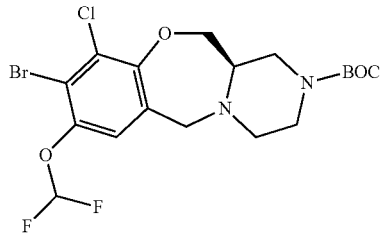 [SMILES: CC(C)(C)OC(=O)N1CCN2Cc3cc(OC(F)F)c(Br)c(Cl)c3OC[C@H]2C1]

1M Borane-THF complex solution in THF (10 mL, 10 mmol) was added to tert-butyl (12aR)-9-bromo-10-chloro-8-(difluoromethoxy)-6-oxo-3,4,12,12a-tetrahydro-6H-pyrazino[2,1-c][1,4]benzoxazepine-2(1H)-carboxylate (1 g, 2.01 mmol) in THF (10 mL) at 25° C. under nitrogen. The resulting mixture was stirred at 60° C. for 1 hour. The reaction mixture was quenched with saturated NH₄Cl (50 mL) and extracted with EtOAc (2×100 mL). The organic layer was dried over anhydrous sodium sulphate, filtered and evaporated to afford tert-butyl (12aR)-9-bromo-10-chloro-8-(difluoromethoxy)-3,4,12,12a-tetrahydro-6H-pyrazino[2,1-c][1,4]benzoxazepine-2(1H)-carboxylate (0.95 g, 98%) as a pale yellow solid. 1H NMR (400 MHz, CDCl₃, 30° C.) 1.47 (9H, s), 2.38-2.55 (1H, m), 2.72-2.85 (1H, m), 2.82-3.03 (2H, m), 3.22-3.39 (1H, m), 3.56 (1H, d), 3.61-3.78 (3H, m), 3.98 (1H, d), 4.28-4.38 (1H, m), 6.48 (1H, t), 7.03 (1H, s). m/z: ES+ [M+H]+=483.

Tert-butyl (12aR)-10-chloro-9-(2-chloro-6-hydroxyphenyl)-8-(difluoromethoxy)-3,4,12,12a-tetrahydro-6H-pyrazino[2,1-c][1,4]benzoxazepine-2(1H)-carboxylate

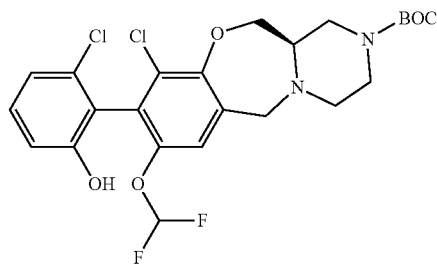 [SMILES: CC(C)(C)OC(=O)N1CCN2Cc3cc(OC(F)F)c(-c4c(O)cccc4Cl)c(Cl)c3OC[C@H]2C1]

RuPhos-Pd-G3 (225 mg, 0.27 mmol) and 2-dicyclohexylphosphino-2',6'-diisopropoxybiphenyl (125 mg, 0.27 mmol) were added to K₂CO₃ (557 mg, 4.03 mmol), (2-chloro-6-hydroxyphenyl)boronic acid (695 mg, 4.03 mmol) and tert-butyl (12aR)-9-bromo-10-chloro-8-(difluoromethoxy)-3,4,12,12a-tetrahydro-6H-pyrazino[2,1-c][1,4]benzoxazepine-2(1H)-carboxylate (650 mg, 1.34 mmol) in 1,4-dioxane (10 mL) and water (2.5 mL) (4:1 ratio) at 25° C. under nitrogen. The resulting mixture was stirred at 100° C. for 2 hours. The solvent was removed under reduced pressure. The crude product obtained was purified by flash C18-flash chromatography, elution gradient 0 to 100% MeCN in water (0.1% formic acid). Pure fractions were evaporated to dryness to afford tert-butyl (12aR)-10-chloro-9-(2-chloro-6-hydroxyphenyl)-8-(difluoromethoxy)-3,4,12,12a-tetrahydro-6H-pyrazino[2,1-c][1,4]benzoxazepine-2(1H)-carboxylate (120 mg, 17%) as a yellow solid. m/z: ES+ [M+H]+=531.

3-Chloro-2-[(12aR)-10-chloro-8-(difluoromethoxy)-1,2,3,4,12,12a-hexahydro-6H-pyrazino[2,1-c][1,4]benzoxazepin-9-yl]phenol

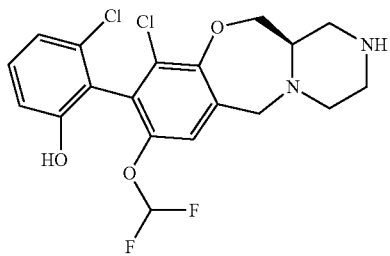 [SMILES: Oc1cccc(Cl)c1-c1c(OC(F)F)cc2c(c1Cl)OC[C@H]1CNCCN1C2]

TFA (0.5 mL, 6.49 mmol) was added to tert-butyl (12aR)-10-chloro-9-(2-chloro-6-hydroxyphenyl)-8-(difluoromethoxy)-3,4,12,12a-tetrahydro-6H-pyrazino[2,1-c][1,4]benzoxazepine-2(1H)-carboxylate (100 mg, 0.19 mmol) in DCM (2.5 mL) at 20° C. The resulting mixture was stirred at room temperature for 1 hour. The solvent was removed under reduced pressure. The residue obtained was purified by flash C18-flash chromatography, elution gradient 0 to 100% MeCN in water (0.1% formic acid). Pure fractions were evaporated to dryness to afford crude product as a yellow solid. The crude product was purified by ion exchange chromatography, using an SCX column. The desired product was eluted from the column using 7M NH₃/MeOH and pure fractions were evaporated to dryness to afford 3-chloro-2-[(12aR)-10-chloro-8-(difluoromethoxy)-1,2,3,4,12,12a-hexahydro-6H-pyrazino[2,1-c][1,4]benzoxazepin-9-yl]phenol (45 mg, 55%) as a yellow solid. m/z: ES+ [M+H]+=431.

1-[(12aR)-10-Chloro-9-(2-chloro-6-hydroxyphenyl)-8-(difluoromethoxy)-3,4,12,12a-tetrahydro-6H-pyrazino[2,1-c][1,4]benzoxazepin-2(1H)-yl]prop-2-en-1-one Rotational Isomer 1, Example 97 and Rotational Isomer 2, Example 98

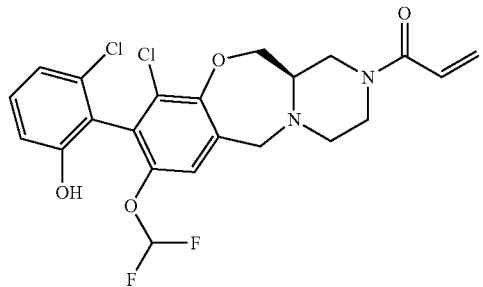 [SMILES: C=CC(=O)N1CCN2Cc3cc(OC(F)F)c(-c4c(O)cccc4Cl)c(Cl)c3OC[C@H]2C1]

DIPEA (0.032 mL, 0.19 mmol) and acryloyl chloride (8.39 mg, 0.09 mmol) were added to 3-chloro-2-[(12aR)-10-chloro-8-(difluoromethoxy)-1,2,3,4,12,12a-hexahydro-6H-pyrazino[2,1-c][1,4]benzoxazepin-9-yl]phenol (40 mg, 0.09 mmol) in DMF (2 mL) at −20° C. under nitrogen. The resulting mixture was stirred at −20° C. for 1 hour. The reaction mixture was quenched with water and purified directly by preparative HPLC Column: Xselect CSH OBD Column 30*150 mm 5 um; Mobile Phase A:Water (0.1% formic acid), Mobile Phase B:MeCN; Flow rate: 60 mL/min; Gradient:27 B to 37 B in 9 min; 254; 220 nm. Fractions containing the desired compound were evaporated to dryness to afford firstly rotational isomer 1 of 1-[(12aR)-10-chloro-9-(2-chloro-6-hydroxyphenyl)-8-(difluoromethoxy)-3,4,12,12a-tetrahydro-6H-pyrazino[2,1-c][1,4]benzoxazepin-2(1H)-yl]prop-2-en-1-one (7 mg, 15%) as a purple solid. 1H NMR (400 MHz, DMSO, 30° C.) 2.34-2.43 (1H, m), 2.69-2.90 (3H, m), 2.99-3.09 (1H, m), 3.54-3.64 (1H, m), 3.73-3.81 (1H, m), 3.83-3.94 (2H, m), 3.99-4.11 (1H, m), 4.34-4.46 (1H, m), 5.70 (1H, t), 6.13 (1H, d), 6.73-7.02 (4H, m), 7.17-7.30 (2H, m), 9.99 (1H, s). m/z: ES+ [M+H]+=485. This was followed by rotational isomer 2 of 1-[(12aR)-10-chloro-9-(2-chloro-6-hydroxyphenyl)-8-(difluoromethoxy)-3,4,12,12a-tetrahydro-6H-pyrazino[2,1-c][1,4]benzoxazepin-2(1H)-yl]prop-2-en-1-one (8 mg, 18%) as a white solid. 1H NMR (400 MHz, DMSO, 30° C.) 2.34-2.44 (1H, m), 2.65-2.91 (3H, m), 3.01-3.05 (1H, m), 3.55-3.65 (1H, m), 3.72-3.80 (1H, m), 3.83-3.97 (2H, m), 3.98-4.12 (1H, m), 4.38-4.46 (1H, m), 5.66-5.75 (1H, m), 6.08-6.17 (1H, m), 6.70-7.01 (4H, m), 7.06-7.27 (2H, m), 10.13 (1H, s). m/z: ES+ [M+H]+=485.

Tert-butyl (12aR)-9-bromo-10-fluoro-8-methoxy-3,4,12,12a-tetrahydro-6H-pyrazino[2,1-c][1,4]benzoxazepine-2(1H)-carboxylate

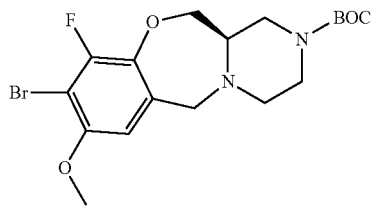 [SMILES: COc1cc2c(c(F)c1Br)OC[C@H]1CN(C(=O)OC(C)(C)C)CCN1C2]

1M Borane-THF complex solution in THF (30.3 mL, 30.32 mmol) was added to tert-butyl (12aR)-9-bromo-10-fluoro-8-methoxy-6-oxo-3,4,12,12a-tetrahydro-6H-pyrazino[2,1-c][1,4]benzoxazepine-2(1H)-carboxylate (2.7 g, 6.06 mmol) in THF (30 mL). The resulting solution was stirred at 60° C. for 1 hour. The reaction mixture was quenched with 2M HCl (10 mL) and poured into water (30 mL) then extracted with EtOAc (3×50 mL). The organic layer was dried over anhydrous sodium sulphate, filtered and evaporated to afford crude product as a white solid. The crude product was purified by flash silica chromatography, elution gradient 0 to 80% petroleum ether in EtOAc. Pure fractions were evaporated to dryness to afford tert-butyl (12aR)-9-bromo-10-fluoro-8-methoxy-3,4,12,12a-tetrahydro-6H-pyrazino[2,1-c][1,4]benzoxazepine-2(1H)-carboxylate (2.2 g, 84%) as a white solid. 1H NMR (400 MHz, DMSO, 30° C.) 1.39 (9H, s), 2.27-2.37 (1H, m), 2.65-2.94 (3H, m), 3.06-3.17 (1H, m), 3.49-3.58 (2H, m), 3.58-3.65 (1H, m), 3.67-3.74 (1H, m), 3.75-3.79 (1H, m), 3.80 (3H, s), 4.25 (1H, dd), 6.91 (1H, s). m/z: ES+ [M+H]+=431.

(12aR)-9-Bromo-10-fluoro-1,2,3,4,12,12a-hexahydro-6H-pyrazino[2,1-c][1,4]benzoxazepin-8-ol

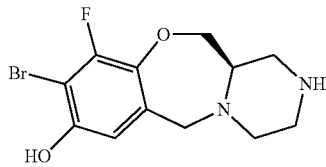

1M Boron tribromide solution in DCM (20.4 mL, 20.4 mmol) was added to tert-butyl (12aR)-9-bromo-10-fluoro-8-methoxy-3,4,12,12a-tetrahydro-6H-pyrazino[2,1-c][1,4]benzoxazepine-2(1H)-carboxylate (1.1 g, 2.55 mmol) in DCM (10 mL) at 0° C. The resulting mixture was stirred at 20° C. for 2 hours. The reaction mixture was quenched with MeOH (25 mL). The solvent was removed under reduced pressure to afford crude product as a yellow solid. The crude product was purified by ion exchange chromatography, using an SCX column. The desired product was eluted from the column using 7M NH3/MeOH and pure fractions were evaporated to dryness to afford (12aR)-9-bromo-10-fluoro-1,2,3,4,12,12a-hexahydro-6H-pyrazino[2,1-c][1,4]benzoxazepin-8-ol (0.75 g, 93%) as a yellow solid. 1H NMR (300 MHz, DMSO, 30° C.) 2.76-2.99 (2H, m), 3.01-3.19 (2H, m), 3.49-3.59 (1H, m), 3.64-3.82 (2H, m), 3.94-4.18 (2H, m), 4.32-4.47 (2H, m), 6.75 (1H, s), 9.06 (1H, s) one exchangeable proton not seen. m/z: ES+ [M+H]+=317.

Tert-butyl (12aR)-9-bromo-10-fluoro-8-hydroxy-3,4,12,12a-tetrahydro-6H-pyrazino[2,1-c][1,4]benzoxazepine-2(1H)-carboxylate

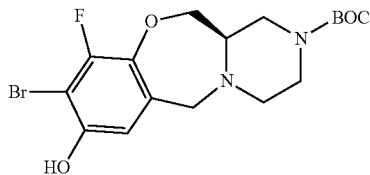 [SMILES: CC(C)(C)OC(=O)N1CCN2Cc3cc(O)c(Br)c(F)c3OC[C@H]2C1]

Di-tert-butyl dicarbonate (0.551 mg, 2.52 mmol) was added to (12aR)-9-bromo-10-fluoro-1,2,3,4,12,12a-hexahydro-6H-pyrazino[2,1-c][1,4]benzoxazepin-8-ol (800 mg, 2.52 mmol) and triethylamine (2.11 mL, 15.13 mmol) in DCM (15 mL) at 0° C. under nitrogen. The resulting mixture was stirred at 0° C. for 2 hours. The solvent was removed under reduced pressure and the crude product obtained was purified by flash silica chromatography, elution gradient 0 to 50% THF in petroleum ether. Pure fractions were evaporated to dryness to afford tert-butyl (12aR)-9-bromo-10-fluoro-8-hydroxy-3,4,12,12a-tetrahydro-6H-pyrazino[2,1-c][1,4]benzoxazepine-2(1H)-carboxylate (900 mg, 86%) as a brown solid. 1H NMR (400 MHz, DMSO, 30° C.) 1.38 (9H, s), 2.11-2.26 (4H, m), 3.12-3.18 (2H, m), 3.74-3.82 (2H, m), 4.22-4.28 (3H, m), 6.61-6.64 (1H, m) one exchangeable proton not seen. m/z: ES+ [M+H]+=417.

Tert-butyl (12aR)-9-bromo-8-(cyclopropyloxy)-10-fluoro-3,4,12,12a-tetrahydro-6H-pyrazino[2,1-c][1,4]benzoxazepine-2(1H)-carboxylate

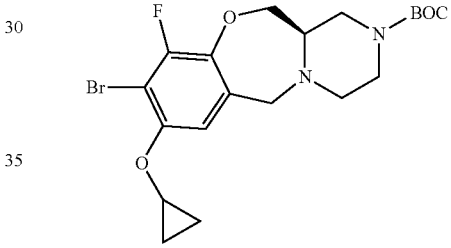

Bromocyclopropane (2.9 g, 23.96 mmol) was added to tert-butyl (12aR)-9-bromo-10-fluoro-8-hydroxy-3,4,12,12a-tetrahydro-6H-pyrazino[2,1-c][1,4]benzoxazepine-2(1H)-carboxylate (1 g, 2.4 mmol) and Cs2CO3 (1.562 g, 4.79 mmol) in DMF (30 mL) at 25° C. under nitrogen. The resulting mixture was stirred at 150° C. for 20 hours. The reaction mixture was diluted with EtOAc (200 mL), washed sequentially with water (150 mL×2) and saturated brine (150 mL×3). The organic layer was dried over anhydrous sodium sulphate, filtered and evaporated to afford crude product. The crude product was purified by flash silica chromatography, elution gradient 0 to 60% THF in petroleum ether. Pure fractions were evaporated to dryness to afford tert-butyl (12aR)-9-bromo-8-(cyclopropyloxy)-10-fluoro-3,4,12,12a-tetrahydro-6H-pyrazino[2,1-c][1,4]benzoxazepine-2(1H)-carboxylate (0.45 g, 41%) as a brown solid. 1H NMR (400 MHz, DMSO, 30° C.) 0.67-0.75 (2H, m), 0.80-0.86 (2H, m), 1.40 (9H, s), 2.24-2.37 (1H, m), 2.66-2.82 (3H, m), 3.02-3.21 (1H, m), 3.52-3.63 (3H, m), 3.73-3.85 (2H, m), 3.88-4.00 (1H, m), 4.28 (1H, d), 7.15 (1H, d). m/z: ES+ [M+H]+=457.

Tert-butyl (12aR)-9-(2-chloro-6-methoxyphenyl)-8-(cyclopropyloxy)-10-fluoro-3,4,12,12a-tetrahydro-6H-pyrazino[2,1-c][1,4]benzoxazepine-2(1H)-carboxylate

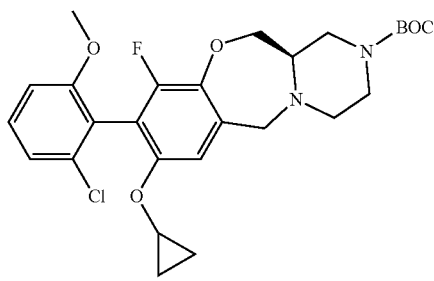 [SMILES: COc1cccc(Cl)c1-c1c(OC2CC2)cc2c(c1F)OC[C@H]1CN(C(=O)OC(C)(C)C)CCN1C2]

RuPhos-Pd-G3 (73.2 mg, 0.09 mmol) and 2-dicyclohexylphosphino-2',6'-diisopropoxybiphenyl (40.8 mg, 0.09 mmol) were added to tert-butyl (12aR)-9-bromo-8-(cyclopropyloxy)-10-fluoro-3,4,12,12a-tetrahydro-6H-pyrazino[2,1-c][1,4]benzoxazepine-2(1H)-carboxylate (400 mg, 0.87 mmol), (2-chloro-6-methoxyphenyl)boronic acid (326 mg, 1.75 mmol) and $K_2CO_3$ (363 mg, 2.62 mmol) in 1,4-dioxane (10 mL) and water (2.5 mL)(4:1 ratio) at 25° C. under nitrogen. The resulting mixture was stirred at 100° C. for 1 hour. The solvent was removed under reduced pressure. The crude product obtained was purified by flash silica chromatography, elution gradient 20 to 70% THF in petroleum ether. Pure fractions were evaporated to dryness to afford tert-butyl (12aR)-9-(2-chloro-6-methoxyphenyl)-8-(cyclopropyloxy)-10-fluoro-3,4,12,12a-tetrahydro-6H-pyrazino[2,1-c][1,4]benzoxazepine-2(1H)-carboxylate (330 mg, 73%) as a yellow solid. 1H NMR (300 MHz, DMSO, 30° C.) 0.68-0.73 (2H, m), 0.80-0.88 (2H, m), 1.41 (9H, s), 2.24-2.40 (1H, m), 2.60-2.87 (4H, m), 3.46-3.64 (5H, m), 3.62-3.72 (3H, m), 3.75-3.97 (1H, m), 4.20-4.35 (1H, m), 6.98-7.09 (2H, m), 7.07-7.18 (1H, m), 7.28-7.46 (1H, m). m/z: ES+ [M+H]+=519.

3-Chloro-2-[(12aR)-8-(cyclopropyloxy)-10-fluoro-1,2,3,4,12,12a-hexahydro-6H-pyrazino[2,1-][1,4]benzoxazepin-9-yl]phenol

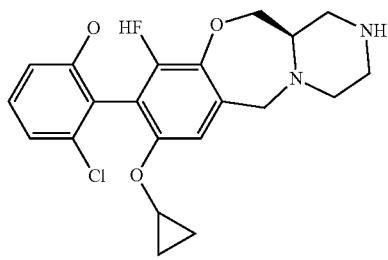 [SMILES: Oc1cccc(Cl)c1-c1c(OC2CC2)cc2c(c1F)OC[C@H]1CNCCN1C2]

1M Boron tribromide solution in DCM (4.62 mL, 4.62 mmol) was added to tert-butyl (12aR)-9-(2-chloro-6-methoxyphenyl)-8-(cyclopropyloxy)-10-fluoro-3,4,12,12a-tetrahydro-6H-pyrazino[2,1-c][1,4]benzoxazepine-2(1H)-carboxylate (300 mg, 0.58 mmol) in DCM (5 mL) at 0° C. The resulting mixture was stirred at 20° C. for 2 hours. The solvent was removed under reduced pressure. The crude product obtained was purified by flash C18-flash chromatography, elution gradient 0 to 100% MeOH in water (0.1% $NH_4HCO_3$). Pure fractions were evaporated to dryness to afford 3-chloro-2-[(12aR)-8-(cyclopropyloxy)-10-fluoro-1,2,3,4,12,12a-hexahydro-6H-pyrazino[2,1-c][1,4]benzoxazepin-9-yl]phenol (80 mg, 34%) as a white solid. 1H NMR (300 MHz, DMSO, 30° C.) 0.39-0.56 (2H, m), 0.61-0.74 (2H, m), 1.41 (1H, s), 2.20-2.41 (3H, m), 2.54-2.76 (1H, m), 2.77-2.96 (3H, m), 3.45-3.67 (2H, m), 3.68-3.87 (2H, m), 4.04-4.24 (1H, m), 6.76-6.89 (1H, m), 6.87-6.97 (1H, m), 6.96-7.07 (1H, m), 7.09-7.25 (1H, m), 9.78 (1H, s). m/z: ES+ [M+H]+=405.

1-[(12aR)-9-(2-chloro-6-hydroxyphenyl)-8-(cyclopropyloxy)-10-fluoro-3,4,12,12a-tetrahydro-6H-pyrazino[2,1-c][1,4]benzoxazepin-2(1H)-yl]prop-2-en-1-one Rotational Isomer 1, Example 99 and Rotational Isomer 2, Example 100

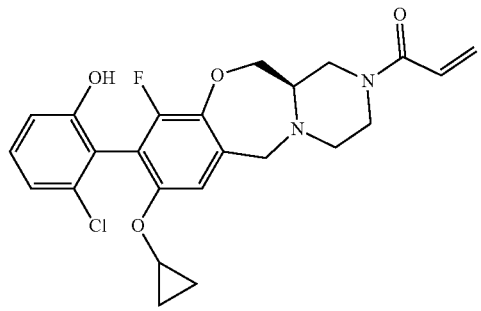 [SMILES: C=CC(=O)N1CCN2Cc3cc(OC4CC4)c(-c4c(O)cccc4Cl)c(F)c3OC[C@H]2C1]

Acryloyl chloride (0.06 mL, 0.74 mmol) was added to 3-chloro-2-[(12aR)-8-(cyclopropyloxy)-10-fluoro-1,2,3,4,12,12a-hexahydro-6H-pyrazino[2,1-c][1,4]benzoxazepin-9-yl]phenol (300 mg, 0.74 mmol) and DIPEA (0.518 mL, 2.96 mmol) in DMF (5 mL) at 0° C. The resulting mixture was stirred at 0° C. for 30 minutes. The reaction mixture was quenched with water and purified directly by preparative HPLC Column: Xselect CSH OBD Column 30*150 mm 5 um; Mobile Phase A:Water (0.1% formic acid), Mobile Phase B:MeCN; Flow rate:60 mL/min; Gradient:24 B to 34 B in 8 min; 254; 220 nm. Fractions containing the desired compounds were evaporated to dryness to afford firstly rotational isomer 1 of 1-[(12aR)-9-(2-chloro-6-hydroxyphenyl)-8-(cyclopropyloxy)-10-fluoro-3,4,12,12a-tetrahydro-6H-pyrazino[2,1-c][1,4]benzoxazepin-2(1H)-yl]prop-2-en-1-one (70 mg, 21%) as a white solid. 1H NMR (300 MHz, DMSO, 30° C.) 0.40-0.55 (2H, m), 0.56-0.77 (2H, m), 2.30-2.45 (1H, m), 2.57-3.18 (3H, m), 3.49-4.17 (7H, m), 4.21-4.39 (1H, m), 5.61-5.74 (1H, m), 6.03-6.19 (1H, m), 6.76-7.00 (3H, m), 7.01-7.08 (1H, m), 7.10-7.25 (1H, m), 9.78 (1H, s). m/z: ES+ [M+H]+=459. This was followed by rotational isomer 2 of 1-[(12aR)-9-(2-chloro-6-hydroxyphenyl)-8-(cyclopropyloxy)-10-fluoro-3,4,12,12a-tetrahydro-6H-pyrazino[2,1-c][1,4]benzoxazepin-2(1H)-yl]prop-2-en-1-one (71 mg, 21%) as a white solid. 1H NMR (300 MHz, DMSO, 30° C.) 0.37-0.53 (2H, m), 0.59-0.74 (2H, m), 2.24-2.42 (1H, m), 2.57-2.77 (2H, m), 2.76-2.94 (1H, m), 2.96-3.11 (1H, m), 3.47-3.62 (1H, m), 3.64-3.81 (1H, m), 3.82-3.99 (4H, m), 4.23-4.40 (1H, m), 5.62-5.77 (1H, m), 6.05-6.18 (1H, m), 6.71-7.00 (3H, m), 7.00-7.08 (1H, m), 7.10-7.21 (1H, m), 9.66-9.92 (1H, m). m/z: ES+ [M+H]+=459.

Tert-butyl (12aR)-9-bromo-8-[3-(dimethylamino) prop-1-yn-1-yl]-10-fluoro-3,4,12,12a-tetrahydro-6H-pyrazino[2,1-c][1,4]benzoxazepine-2(1H)-carboxylate

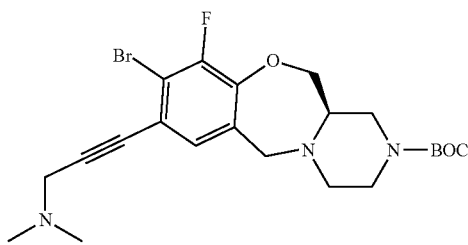 [SMILES: CN(C)CC#Cc1cc2c(c(F)c1Br)OC[C@H]1CN(C(=O)OC(C)(C)C)CCN1C2]

Tetrakis(triphenylphosphine)palladium(0) (175 mg, 0.15 mmol) was added to tert-butyl (12aR)-9-bromo-10-fluoro-8-iodo-3,4,12,12a-tetrahydro-6H-pyrazino[2,1-c][1,4]benzoxazepine-2(1H)-carboxylate (800 mg, 1.52 mmol), 3-dimethylamino-1-propyne (0.654 mL, 6.07 mmol), triethylamine (0.423 mL, 3.04 mmol) and copper(I) iodide (578 mg, 3.04 mmol) in toluene (20 mL) at 25° C. under nitrogen in a sealed tube. The resulting mixture was stirred at 100° C. for 16 hours. The solvent was removed under reduced pressure. The crude product obtained was purified by flash silica chromatography, elution gradient 0 to 100% THF in petroleum ether. Pure fractions were evaporated to dryness to afford tert-butyl (12aR)-9-bromo-8-[3-(dimethylamino)prop-1-yn-1-yl]-10-fluoro-3,4,12,12a-tetrahydro-6H-pyrazino[2,1-c][1,4]benzoxazepine-2(1H)-carboxylate (600 mg, 82%) as a brown solid. 1H NMR (400 MHz, DMSO, 30° C.) 1.39 (9H, s), 2.23-2.42 (4H, m), 2.69-2.77 (2H, m), 3.06-3.15 (1H, m), 3.30 (4H, s), 3.49-3.67 (4H, m), 3.68-3.83 (3H, m), 4.30-4.39 (1H, m), 7.32 (1H, d). m/z: ES+ [M-Boc]−=439.

Tert-butyl (12aR)-9-(2-chloro-6-methoxyphenyl)-8-[3-(dimethylamino)prop-1-yn-1-yl]-10-fluoro-3,4,12,12a-tetrahydro-6H-pyrazino[2,1-c][1,4]benzoxazepine-2(1H)-carboxylate

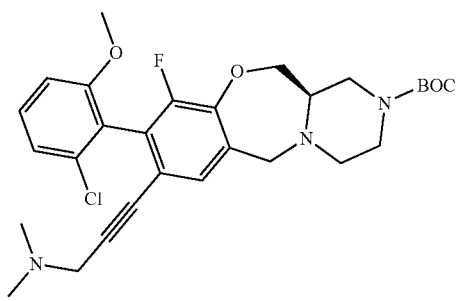 [SMILES: COc1cccc(Cl)c1-c1c(C#CCN(C)C)cc2c(c1F)OC[C@H]1CN(C(=O)OC(C)(C)C)CCN1C2]

2-Dicyclohexylphosphino-2',6'-dimethoxy-1,1'-biphenyl (51.1 mg, 0.12 mmol) and methanesulfonato(2-dicyclohexylphosphino-2,6-dimethoxy-1,1-biphenyl)(2-amino-1,1-biphenyl-2-yl)palladium(II) dichloromethane adduct (97 mg, 0.12 mmol) were added to tert-butyl (12aR)-9-bromo-8-[3-(dimethylamino)prop-1-yn-1-yl]-10-fluoro-3,4,12,12a-tetrahydro-6H-pyrazino[2,1-c][1,4]benzoxazepine-2(1H)-carboxylate (600 mg, 1.24 mmol), (2-chloro-6-methoxyphenyl)boronic acid (464 mg, 2.49 mmol) and potassium phosphate (528 mg, 2.49 mmol) in 1,4-dioxane (8 mL) and water (2 mL)(4:1 ratio) at 25° C. under nitrogen. The resulting mixture was stirred at 120° C. for 3 hours. The solvent was removed under reduced pressure. The crude product obtained was purified by flash silica chromatography, elution gradient 40 to 90% THF in petroleum ether. Pure fractions were evaporated to dryness to afford tert-butyl (12aR)-9-(2-chloro-6-methoxyphenyl)-8-[3-(dimethylamino)prop-1-yn-1-yl]-10-fluoro-3,4,12,12a-tetrahydro-6H-pyrazino[2,1-c][1,4]benzoxazepine-2(1H)-carboxylate (450 mg, 67%) as a brown solid. 1H NMR (400 MHz, DMSO, 30° C.) 1.40 (9H, d), 1.86 (6H, s), 2.31-2.42 (1H, m), 2.61-2.74 (1H, m), 2.75-2.83 (1H, m), 3.00-3.11 (1H, m), 3.23 (2H, s), 3.57-3.79 (8H, m), 3.85-3.95 (1H, m), 4.36 (1H, d), 7.07-7.18 (2H, m), 7.23 (1H, s), 7.40 (1H, t). m/z: ES+ [M+H]+=544.

3-Chloro-2-{(12aR)-8-[3-(dimethylamino)prop-1-yn-1-yl]-10-fluoro-1,2,3,4,12,12a-hexahydro-6H-pyrazino[2,1-c][1,4]benzoxazepin-9-yl}phenol

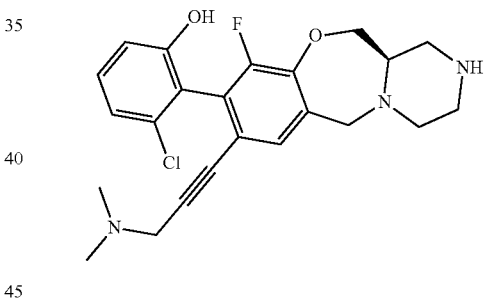

1M boron tribromide solution in DCM (4742 µl, 4.74 mmol) was added to tert-butyl (12aR)-9-(2-chloro-6-methoxyphenyl)-8-[3-(dimethylamino)prop-1-yn-1-yl]-10-fluoro-3,4,12,12a-tetrahydro-6H-pyrazino[2,1-c][1,4]benzoxazepine-2(1H)-carboxylate (430 mg, 0.79 mmol) in DCM (5 mL) at 0° C. under nitrogen. The resulting mixture was stirred at room temperature for 3 hours. The reaction mixture was quenched with MeOH (20 mL) and the solvent was removed under reduced pressure to afford crude product as a brown solid. The crude product was purified by flash C18-flash chromatography, elution gradient 0 to 100% MeCN in water (0.1% TFA). Pure fractions were evaporated to dryness to afford 3-chloro-2-{(12aR)-8-[3-(dimethylamino)prop-1-yn-1-yl]-10-fluoro-1,2,3,4,12,12a-hexahydro-6H-pyrazino[2,1-c][1,4]benzoxazepin-9-yl}phenol (0.32 g, 75%) as a brown solid. 1H NMR (400 MHz, DMSO, 30° C.) 2.52 (6H, s), 2.65-2.96 (4H, m), 2.99-3.12 (1H, m), 3.18-3.26 (1H, m), 3.28-3.42 (2H, m), 3.50-3.61 (1H, m), 3.90-4.04 (2H, m), 4.13-4.20 (2H, m), 6.85-7.08 (2H, m), 7.10-7.46 (2H, m), 8.90 (1H, s) one exchangeable proton not seen. m/z: ES+ [M+H]+=430.

1-((12aR)-9-(2-Chloro-6-hydroxyphenyl)-8-(3-(dimethylamino)prop-1-yn-1-yl)-10-fluoro-3,4,12,12a-tetrahydro-6H-benzo[f]pyrazino[2,1-c][1,4]oxazepin-2(1H)-yl)prop-2-en-1-one Rotational Isomer 1, Example 101 and Rotational Isomer 2, Example 102

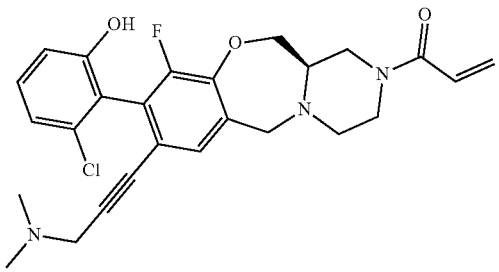 [SMILES: C=CC(=O)N1CCN2Cc3cc(C#CCN(C)C)c(-c4c(O)cccc4Cl)c(F)c3OC[C@H]2C1]

DIPEA (387 µl, 2.21 mmol) and acryloyl chloride (50.1 mg, 0.55 mmol) were added to 3-chloro-2-{(12aR)-8-[3-(dimethylamino)prop-1-yn-1-yl]-10-fluoro-1,2,3,4,12,12a-hexahydro-6H-pyrazino[2,1-c][1,4]benzoxazepin-9-yl}phenol (300 mg, 0.55 mmol) in DMF (2 mL) at −20° C. under nitrogen. The resulting mixture was stirred at −20° C. for 1 hour. The reaction mixture was quenched with water and purified directly by flash C18-flash chromatography, elution gradient 0 to 80% MeCN in water (0.1% formic acid) then further purified by preparative HPLC Column: XBridge Prep OBD C18 Column, 30×150 mm 5 um; Mobile Phase A:Water (10 mmol/L NH$_4$HCO$_3$), Mobile Phase B:MeCN; Flow rate:60 mL/min; Gradient:31 B to 41 B in 7 min; 254; 220 nm. Fractions containing the desired compound were evaporated to dryness to afford firstly rotational isomer 1 of 1-((12aR)-9-(2-chloro-6-hydroxyphenyl)-8-(3-(dimethylamino)prop-1-yn-1-yl)-10-fluoro-3,4,12,12a-tetrahydro-6H-benzo[f]pyrazino[2,1-c][1,4]oxazepin-2(1H)-yl)prop-2-en-1-one (0.013 g, 5%) as a white solid. 1H NMR (400 MHz, DMSO, 30° C.) 1.88 (6H, s), 2.28-2.46 (1H, m), 2.63-2.77 (1H, m), 2.80-2.92 (2H, m), 3.01-3.15 (1H, m), 3.23 (2H, s), 3.68-3.81 (2H, m), 3.82-3.97 (2H, m), 3.98-4.13 (1H, m), 4.39 (1H, t), 5.70 (1H, s), 6.13 (1H, d), 6.76-6.91 (2H, m), 6.97 (1H, dd), 7.17-7.26 (2H, m), 9.89 (1H, s). m/z: ES+ [M+H]+=484. This was followed by rotational isomer 2 of 1-((12aR)-9-(2-chloro-6-hydroxyphenyl)-8-(3-(dimethylamino)prop-1-yn-1-yl)-10-fluoro-3,4,12,12a-tetrahydro-6H-benzo[f]pyrazino[2,1-c][1,4]oxazepin-2(1H)-yl)prop-2-en-1-one (0.02 g, 7%) as a white solid. 1H NMR (400 MHz, DMSO, 30° C.) 1.88 (6H, s), 2.29-2.46 (1H, m), 2.63-2.78 (1H, m), 2.78-2.95 (2H, m), 3.00-3.15 (1H, m), 3.23 (2H, s), 3.68-3.80 (2H, m), 3.81-3.96 (2H, m), 3.96-4.15 (1H, m), 4.40 (1H, t), 5.70 (1H, s), 6.03-6.20 (1H, m), 6.76-6.93 (2H, m), 6.96 (1H, dd), 7.14-7.30 (2H, m), 9.87 (1H, s). m/z: ES+ [M+H]+=484.

Tert-butyl (12aR)-9-bromo-10-fluoro-8-[(pyridin-4-yl)methoxy]-3,4,12,12a-tetrahydro-6H-pyrazino[2,1-c][1,4]benzoxazepine-2(1H)-carboxylate

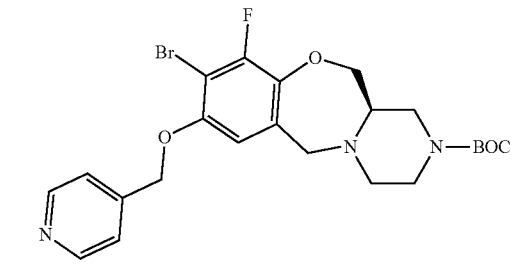 [SMILES: CC(C)(C)OC(=O)N1CCN2Cc3cc(OCc4ccncc4)c(Br)c(F)c3OC[C@H]2C1]

K$_2$CO$_3$ (1192 mg, 8.63 mmol) was added into 4-(chloromethyl)pyridine (550 mg, 4.31 mmol), (12aR)-9-bromo-10-fluoro-1,2,3,4,12,12a-hexahydro-6H-pyrazino[2,1-c][1,4]benzoxazepin-8-ol (900 mg, 2.16 mmol) in DMF (20 mL) at room temperature. The reaction mixture was stirred at 100° C. for 2 hours. The reaction mixture was diluted with EtOAc (100 mL), washed sequentially with water (50 mL×3) and saturated brine (50 mL). The organic layer was dried over anhydrous sodium sulphate, filtered and evaporated to afford crude product. The crude product was purified by flash silica chromatography, elution gradient 0 to 40% THF in petroleum ether. Pure fractions were evaporated to dryness to afford tert-butyl (12aR)-9-bromo-10-fluoro-8-[(pyridin-4-yl)methoxy]-3,4,12,12a-tetrahydro-6H-pyrazino[2,1-c][1,4]benzoxazepine-2(1H)-carboxylate (0.6 g, 55%) as a white solid. 1H NMR (300 MHz, DMSO, 30° C.) 1.36 (9H, s), 2.25-2.35 (1H, m), 2.63-2.86 (3H, m), 3.06-3.15 (1H, m), 3.48-3.70 (4H, m), 3.78-3.87 (1H, m), 4.22-4.31 (1H, m), 5.23 (2H, s), 6.96-7.02 (1H, m), 7.42-7.50 (2H, m), 8.56-8.63 (2H, m).

Tert-butyl (12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepine-2(1H)-carboxylate

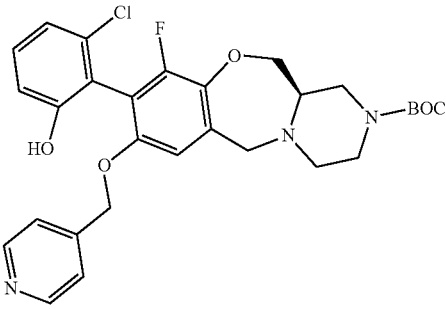 [SMILES: CC(C)(C)OC(=O)N1CCN2Cc3cc(OCc4ccncc4)c(-c4c(O)cccc4Cl)c(F)c3OC[C@H]2C1]

RuPhos-Pd-G3 (82 mg, 0.1 mmol) and 2-dicyclohexylphosphino-2',6'-diisopropoxybiphenyl (45.9 mg, 0.10 mmol) were added to tert-butyl (12aR)-9-bromo-10-fluoro-8-[(pyridin-4-yl)methoxy]-3,4,12,12a-tetrahydro-6H-pyrazino[2,1-c][1,4]benzoxazepine-2(1H)-carboxylate (500 mg, 0.98 mmol), K$_2$CO$_3$ (340 mg, 2.46 mmol) and (2-chloro-6-methoxyphenyl)boronic acid (509 mg, 2.95 mmol) in 1,4-dioxane (8 mL) and water (2 mL)(4:1 ratio) at room temperature under nitrogen. The reaction mixture was stirred at 100° C. for 2 hours. The reaction mixture was diluted with EtOAc (50 mL), washed sequentially with water (50 mL×2) and saturated brine (50 mL). The organic layer was dried over anhydrous sodium sulphate, filtered and evaporated to afford crude product. The crude product was purified by flash C-18 chromatography, elution gradient 0 to 40% CH₃CN in water (0.1% TFA). Pure fractions were evaporated to dryness to afford tert-butyl (12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepine-2(1H)-carboxylate (0.5 g, 91%) as a brown solid. 1H NMR (300 MHz, DMSO, 30° C.) 1.35 (9H, s), 2.83-3.03 (1H, m), 3.13-3.32 (2H, m), 3.40-3.55 (2H, m), 3.68-3.83 (3H, m), 3.95-4.11 (2H, m), 4.30-4.43 (1H, m), 4.54-4.70 (2H, m), 6.90-6.96 (1H, m), 6.99-7.07 (2H, m), 7.22-7.30 (1H, m), 7.47-7.55 (2H, m), 8.66-8.74 (2H, m) one exchangeable proton not seen. m/z: ES+ [M+H]+=556.

3-Chloro-2-{(12aR)-10-fluoro-8-[(pyridin-4-yl)methoxy]-1,2,3,4,12,12a-hexahydro-6H-pyrazino[2,1-c][1,4]benzoxazepin-9-yl}phenol

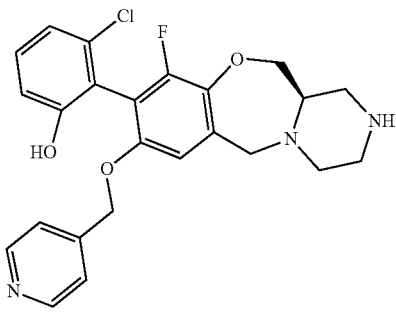 [SMILES: Oc1cccc(Cl)c1-c1c(OCc2ccncc2)cc2c(c1F)OC[C@H]1CNCCN1C2]

TFA (1386 µl, 17.98 mmol) was added into tert-butyl (12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepine-2(1H)-carboxylate (500 mg, 0.90 mmol) in DCM (10 mL) at room temperature. The reaction mixture was stirred at 25° C. for 3 hours. The reaction mixture was evaporated to afford crude product. The crude product was purified by ion exchange chromatography by using an ion exchange column. The desired product was eluted from the column using 7M NH₃/MeOH and pure fractions were evaporated to dryness to afford 3-chloro-2-{(12aR)-10-fluoro-8-[(pyridin-4-yl)methoxy]-1,2,3,4,12,12a-hexahydro-6H-pyrazino[2,1-c][1,4]benzoxazepin-9-yl}phenol (0.25 g, 61%) as a yellow solid. 1H NMR (300 MHz, DMSO, 30° C.) 2.61-2.84 (2H, m), 2.92-3.07 (3H, m), 3.19-3.35 (2H, m), 3.65-3.79 (4H, m), 3.88-4.03 (2H, m), 6.78-6.88 (1H, m), 6.88-6.94 (1H, m), 6.96-7.04 (1H, m), 7.20-7.28 (1H, m), 7.47-7.55 (2H, m), 8.64-8.75 (2H, m), 9.99 (1H, s) one exchangeable proton not seen. m/z: ES+ [M+H]+=456.

1-[(12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepin-2(1H)-yl]prop-2-en-1-one Rotational Isomer 1, Example 103 and Rotational Isomer 2, Example 104

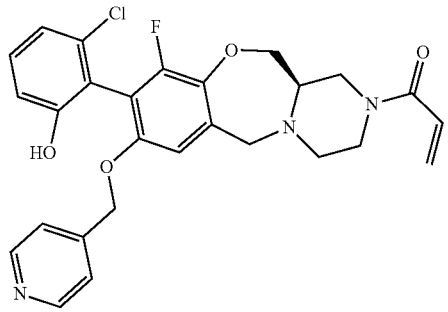 [SMILES: C=CC(=O)N1CCN2Cc3cc(OCc4ccncc4)c(-c4c(O)cccc4Cl)c(F)c3OC[C@H]2C1]

Acryloyl chloride (49.6 mg, 0.55 mmol) was added to 3-chloro-2-{(12aR)-10-fluoro-8-[(pyridin-4-yl)methoxy]-1,2,3,4,12,12a-hexahydro-6H-pyrazino[2,1-c][1,4]benzoxazepin-9-yl}phenol (250 mg, 0.55 mmol) and DIPEA (287 µl, 1.65 mmol) in DMF (5 mL) at 0° C. The reaction mixture was stirred at 0° C. for 2 hours. The reaction mixture was quenched with water (0.5 mL) and purified directly by preparative HPLC (Column: XBridge Prep OBD C18 Column, 30×150 mm 5 um; Mobile Phase A: Water (10 mmol/L NH₄HCO₃+0.1% NH₃·H₂O), Mobile Phase B:MeCN; Flow rate:60 mL/min; Gradient:25 B to 35 B in 10 min; 254/220 nm. Fractions containing the desired compounds were evaporated to dryness to afford firstly rotational isomer 1 of 1-[(12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepin-2(1H)-yl]prop-2-en-1-one (0.061 g, 22%) as a white solid. 1H NMR (400 MHz, DMSO, 30° C.) 2.31-2.44 (1H, m), 2.66-2.77 (1H, m), 2.80-2.88 (1H, m), 3.00-3.14 (1H, m), 3.35-3.37 (1H, m), 3.55-3.71 (2H, m), 3.81-3.92 (2H, m), 3.96-4.09 (1H, m), 4.26-4.39 (1H, m), 5.09 (2H, s), 5.65-5.75 (1H, m), 6.09-6.18 (1H, m), 6.75-6.83 (1H, m), 6.84-6.87 (1H, m), 6.90-6.94 (1H, m), 6.99-7.03 (1H, m), 7.18-7.21 (2H, m), 7.22-7.28 (1H, m), 8.46-8.52 (2H, m), 9.87 (1H, s). m/z: ES+ [M+H]+=510. This was followed by rotational isomer 2 of 1-[(12aR)-9-(2-chloro-6-hydroxyphenyl)-10-fluoro-8-[(pyridin-4-yl)methoxy]-3,4,12,12a-tetrahydro-6H-pyrazino[2,1-c][1,4]benzoxazepin-2(1H)-yl]prop-2-en-1-one (0.065 g, 23%) as a white solid. 1H NMR (400 MHz, DMSO, 30° C.) 2.27-2.45 (1H, m), 2.61-2.75 (1H, m), 2.78-2.89 (1H, m), 2.98-3.15 (1H, m), 3.34-3.35 (1H, m), 3.55-3.70 (2H, m), 3.80-3.92 (2H, m), 3.93-4.11 (1H, m), 4.26-4.39 (1H, m), 5.08 (2H, s), 5.65-5.74 (1H, m), 6.08-6.20 (1H, m), 6.75-6.84 (1H, m), 6.84-6.88 (1H, m), 6.90-6.95 (1H, m), 6.98-7.03 (1H, m), 7.18-7.21 (2H, m), 7.22-7.28 (1H, m), 8.45-8.51 (2H, m), 9.82 (1H, s). m/z: ES+ [M+H]+=510.

Tert-butyl (12aR)-9-bromo-10-chloro-8-(2-methoxyethoxy)-3,4,12,12a-tetrahydro-6H-pyrazino[2,1-c][1,4]benzoxazepine-2(1H)-carboxylate

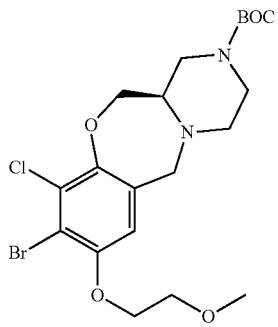 [SMILES: COCCOc1cc2c(c(Cl)c1Br)OC[C@H]1CN(C(=O)OC(C)(C)C)CCN1C2]

Caesium carbonate (3.38 g, 10.38 mmol) was added to tert-butyl (12aR)-9-bromo-10-chloro-8-hydroxy-6-oxo-3,4,12,12a-tetrahydro-6H-pyrazino[2,1-c][1,4]benzoxazepine-2(1H)-carboxylate (1.5 g, 3.46 mmol) to 1-chloro-2-methoxyethane (0.49 g, 5.19 mmol) in DMF (20 mL). The resulting solution was stirred at 100° C. for 2 hours. The reaction mixture was diluted with EtOAc (50 mL) and washed sequentially with water (50 mL×3). The organic layer was dried over anhydrous sodium sulphate, filtered and evaporated to afford crude product tert-butyl (12aR)-9-bromo-10-chloro-8-(2-methoxyethoxy)-3,4,12,12a-tetrahydro-6H-pyrazino[2,1-c][1,4]benzoxazepine-2(1H)-carboxylate (1 g, 59%) as a brown solid. 1H NMR (300 MHz, DMSO, 30° C.) 11.39 (9H, s), 2.01-2.44 (2H, m), 2.65-2.87 (3H, m), 3.01-3.19 (2H, m), 3.46-3.98 (8H, m), 4.03-4.38 (3H, m), 7.10 (1H, s). m/z: ES+ [M+H]+=491.

Tert-butyl (12aR)-10-chloro-9-(2-chloro-6-hydroxyphenyl)-8-(2-methoxyethoxy)-3,4,12,12a-tetrahydro-6H-pyrazino[2,1-c][1,4]benzoxazepine-2(1H)-carboxylate

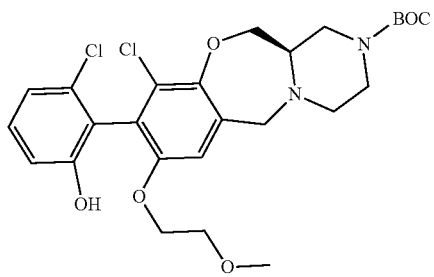 [SMILES: COCCOc1cc2c(c(Cl)c1-c1c(O)cccc1Cl)OC[C@H]1CN(C(=O)OC(C)(C)C)CCN1C2]

K$_2$CO$_3$ (0.984 g, 7.12 mmol) was added to RuPhos-Pd-G3 (0.155 g, 0.20 mmol), 2-dicyclohexylphosphino-2',6'-diisopropoxybiphenyl (0.095 g, 0.2 mmol), (2-chloro-6-hydroxyphenyl)boronic acid (0.876 g, 5.08 mmol) and tert-butyl (12aR)-9-bromo-10-chloro-8-(2-methoxyethoxy)-3,4,12,12a-tetrahydro-6H-pyrazino[2,1-c][1,4]benzoxazepine-2(1H)-carboxylate (1 g, 2.03 mmol) in 1,4-dioxane (16 mL) and water (4.00 mL)(4:1 ratio) under nitrogen. The resulting solution was stirred at 100° C. for 1 hour. The reaction mixture was diluted with EtOAc (100 mL) extracted, washed sequentially with water (100 mL×3) and saturated brine (50 mL×2). The organic layer was dried over anhydrous sodium sulphate, filtered and evaporated to afford crude product. The crude product was purified by flash silica chromatography, elution gradient 30 to 40% THF in petroleum ether. Pure fractions were evaporated to dryness to afford tert-butyl (12aR)-10-chloro-9-(2-chloro-6-hydroxyphenyl)-8-(2-methoxyethoxy)-3,4,12,12a-tetrahydro-6H-pyrazino[2,1-c][1,4]benzoxazepine-2(1H)-carboxylate (0.6 g, 55%) as a white foam. 1H NMR (300 MHz, DMSO, 30° C.) 1.41 (9H, s), 2.25-2.44 (1H, m), 2.61-2.90 (3H, m), 3.11 (3H, s), 3.34 (1H, d), 3.40-3.45 (2H, m), 3.48-3.56 (1H, m), 3.60-3.70 (3H, m), 3.78-3.92 (1H, m), 4.00 (2H, dd), 4.28 (1H, d), 6.80-6.87 (1H, m), 6.90-6.97 (1H, m), 7.00 (1H, s), 7.17 (1H, t), 9.66 (1H, d). m/z: ES+ [M+H]+=539.

3-Chloro-2-[(12aR)-10-chloro-8-(2-methoxyethoxy)-1,2,3,4,12,12a-hexahydro-6H-pyrazino[2,1-c][1,4]benzoxazepin-9-yl]phenol

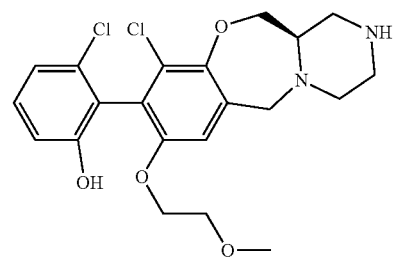 [SMILES: COCCOc1cc2c(c(Cl)c1-c1c(O)cccc1Cl)OC[C@H]1CNCCN1C2]

TFA (2 mL, 25.96 mmol) was added to tert-butyl (12aR)-10-chloro-9-(2-chloro-6-hydroxyphenyl)-8-(2-methoxyethoxy)-3,4,12,12a-tetrahydro-6H-pyrazino[2,1-c][1,4]benzoxazepine-2(1H)-carboxylate (550 mg, 1.02 mmol) in DCM (20 mL) at room temperature. The resulting solution was stirred at room temperature for 12 hours. The solvent was removed under reduced pressure. The crude product obtained was purified by ion exchange chromatography, using an SCX column. The desired product was eluted from the column using 7M NH$_3$/MeOH and pure fractions were evaporated to dryness to afford 3-chloro-2-[(12aR)-10-chloro-8-(2-methoxyethoxy)-1,2,3,4,12,12a-hexahydro-6H-pyrazino[2,1-c][1,4]benzoxazepin-9-yl]phenol (0.3 g, 67%) as a yellow foam. 1H NMR (300 MHz, DMSO, 30° C.) 2.28-2.34 (2H, m), 2.62-2.85 (5H, m), 3.10 (3H, s), 3.38-3.48 (2H, m), 3.48-3.64 (2H, m), 3.70-3.84 (1H, m), 3.92-4.09 (2H, m), 4.19 (1H, d), 6.79-6.89 (1H, m), 6.87-6.96 (1H, m), 6.98 (1H, s), 7.17 (1H, t), 9.66 (1H, s) one exchangeable proton not seen. m/z: ES+ [M+H]+=439.

1-[(12aR)-10-chloro-9-(2-chloro-6-hydroxyphenyl)-8-(2-methoxyethoxy)-3,4,12,12a-tetrahydro-6H-pyrazino[2,1-c][1,4]benzoxazepin-2(1H)-yl]prop-2-en-1-one Rotational Isomer 1, Example 105 and Rotational Isomer 2, Example 106

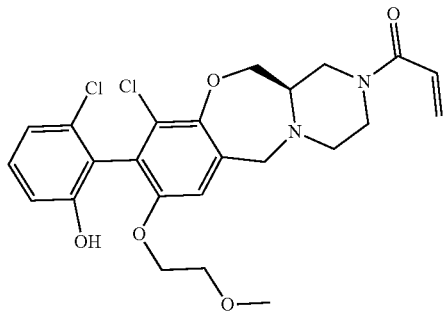 [SMILES: C=CC(=O)N1CCN2Cc3cc(OCCOC)c(-c4c(O)cccc4Cl)c(Cl)c3OC[C@H]2C1]

Acryloyl chloride (103 mg, 1.14 mmol) was added to 3-chloro-2-[(12aR)-10-chloro-8-(2-methoxyethoxy)-1,2,3,4,12,12a-hexahydro-6H-pyrazino[2,1-c][1,4]benzoxazepin-9-yl]phenol (250 mg, 0.57 mmol) in DMF (5 mL) cooled to 0° C. under nitrogen. The resulting solution was stirred at room temperature for 1 hour. The reaction mixture was quenched with water (50 mL), extracted with EtOAc (3×50 mL). The organic layer was dried over anhydrous sodium sulphate, filtered and evaporated to afford crude product as a brown gum. The crude product was purified by preparative HPLC (XBridge Shield RP18 OBD column, 5µ silica, 50 mm diameter, 100 mm length), using decreasingly polar mixtures of water (containing 0.05% NH₃) and MeCN as eluents. Fractions containing the desired compound were evaporated to dryness to afford firstly rotational isomer 1 of 1-[(12aR)-10-chloro-9-(2-chloro-6-hydroxyphenyl)-8-(2-methoxyethoxy)-3,4,12,12a-tetrahydro-6H-pyrazino[2,1-c][1,4]benzoxazepin-2(1H)-yl]prop-2-en-1-one (0.057 g, 20%) as a white solid. 1H NMR (300 MHz, DMSO, 30° C.) 2.29-2.45 (1H, m), 2.68-2.92 (3H, m), 2.98-3.19 (4H, m), 3.41-3.58 (3H, m), 3.69 (1H, d), 3.86 (2H, d), 3.93-4.14 (3H, m), 4.33 (1H, t), 5.71-5.75 (1H, m), 6.13 (1H, d), 6.76-7.05 (4H, m), 7.17 (1H, t), 9.66 (1H, s). m/z: ES+ [M+H]+=493. This was followed by rotational isomer 2 of 1-[(12aR)-10-chloro-9-(2-chloro-6-hydroxyphenyl)-8-(2-methoxyethoxy)-3,4,12,12a-tetrahydro-6H-pyrazino[2,1-c][1,4]benzoxazepin-2(1H)-yl]prop-2-en-1-one (0.07 g, 25%) as a white solid. 1H NMR (300 MHz, DMSO, 30° C.) 2.31-2.44 (1H, m), 2.66-2.96 (3H, m), 2.98-3.23 (4H, m), 3.41-3.48 (2H, m), 3.48-3.62 (1H, m), 3.68 (1H, d), 3.79-4.16 (5H, m), 4.32 (1H, t), 5.70-5.75 (1H, m), 6.14 (1H, d), 6.73-7.07 (4H, m), 7.17 (1H, t), 9.63 (1H, s). m/z: ES+ [M+H]+=493.

Tert-butyl (12aR)-9-bromo-10-fluoro-8-[2-(piperidin-1-yl)ethoxy]-3,4,12,12a-tetrahydro-6H-pyrazino[2,1-c][1,4]benzoxazepine-2(1H)-carboxylate

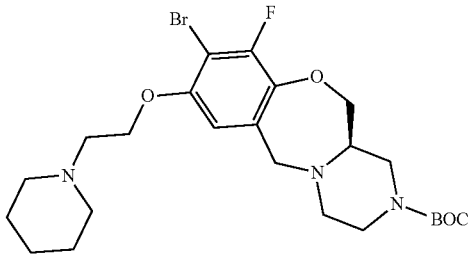 [SMILES: CC(C)(C)OC(=O)N1CCN2Cc3cc(OCCN4CCCCC4)c(Br)c(F)c3OC[C@H]2C1]

1-(2-Chloroethyl)-piperidine (177 mg, 1.2 mmol) was added to K₂CO₃ (497 mg, 3.59 mmol) and (12aR)-9-bromo-10-fluoro-1,2,3,4,12,12a-hexahydro-6H-pyrazino[2,1-c][1,4]benzoxazepin-8-ol (500 mg, 1.2 mmol) in DMF (10 mL). The resulting solution was stirred at 100° C. for 3 hours. The reaction mixture was diluted with EtOAc (50 mL), washed sequentially with water (50 mL×3) and saturated brine (50 mL). The organic layer was dried over anhydrous sodium sulphate, filtered and evaporated to afford crude product. The crude product was purified by flash silica chromatography, elution gradient 10 to 40% THF in petroleum ether. Pure fractions were evaporated to dryness to afford tert-butyl (12aR)-9-bromo-10-fluoro-8-[2-(piperidin-1-yl)ethoxy]-3,4,12,12a-tetrahydro-6H-pyrazino[2,1-c][1,4]benzoxazepine-2(1H)-carboxylate (0.6 g, 95%) as a white solid. 1H NMR (300 MHz, DMSO, 30° C.) 1.31 (9H, s), 1.35-1.41 (1H, m) 1.44-1.59 (5H, m), 2.21-2.38 (2H, m), 2.38-2.48 (3H, m), 2.64-2.91 (5H, m), 3.07-3.19 (1H, m), 3.47-3.73 (4H, m), 3.76-3.87 (1H, m), 4.06-4.16 (2H, m), 4.21-4.30 (1H, m), 6.94 (1H, d). m/z: ES+ [M+H]+=530.

Tert-butyl (12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepine-2(1H)-carboxylate

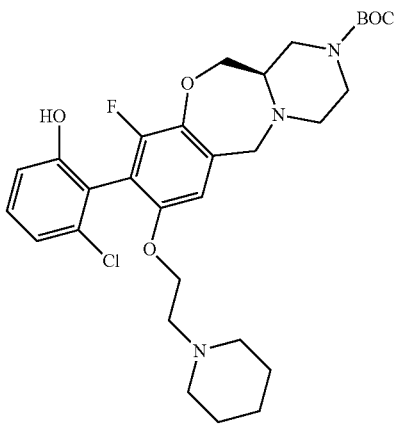 [SMILES: CC(C)(C)OC(=O)N1CCN2Cc3cc(OCCN4CCCCC4)c(-c4c(O)cccc4Cl)c(F)c3OC[C@H]2C1]

RuPhos-Pd-G3 (95 mg, 0.11 mmol) was added to tert-butyl (12aR)-9-bromo-10-fluoro-8-[2-(piperidin-1-yl)ethoxy]-3,4,12,12a-tetrahydro-6H-pyrazino[2,1-c][1,4]benzoxazepine-2(1H)-carboxylate (600 mg, 1.14 mmol), (2-chloro-6-methoxyphenyl)boronic acid (587 mg, 3.41 mmol), 2-dicyclohexylphosphino-2',6'-diisopropoxybiphenyl (53 mg, 0.11 mmol) and K$_2$CO$_3$ (392 mg, 2.84 mmol) in 1,4-dioxane (16 mL) and water (4 mL) (4:1 ratio) under nitrogen. The resulting solution was stirred at 100° C. for 1 hour. The reaction mixture was diluted with EtOAc (50 mL), washed sequentially with water (20 mL×2) and saturated brine (20 mL). The organic layer was dried over anhydrous sodium sulphate, filtered and evaporated to afford the crude product. The crude product was purified by flash C18-flash chromatography, elution gradient 5 to 60% MeCN in water (0.1% TFA). Pure fractions were evaporated to dryness to afford tert-butyl (12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepine-2(1H)-carboxylate (0.5 g, 76%). 1H NMR (300 MHz, DMSO, 30° C.) 1.17-1.30 (2H, m), 1.34 (9H, s), 1.41-1.50 (1H, m), 1.50-1.72 (7H, m), 2.62-2.78 (3H, m), 2.95-3.11 (2H, m), 3.44-3.53 (1H, m), 3.74-3.84 (2H, m), 3.98-4.09 (2H, m), 4.24-4.39 (3H, m), 4.54-4.69 (2H, m), 6.92-6.95 (1H, m), 6.98-7.03 (1H, m), 7.07-7.11 (1H, m), 7.22-7.27 (1H, m), 9.76 (1H, s). m/z: ES+ [M+H]+=576.

3-Chloro-2-{(12aR)-10-fluoro-8-[2-(piperidin-1-yl)ethoxy]-1,2,3,4,12,12a-hexahydro-6H-pyrazino[2,1-c][1,4]benzoxazepin-9-yl}phenol

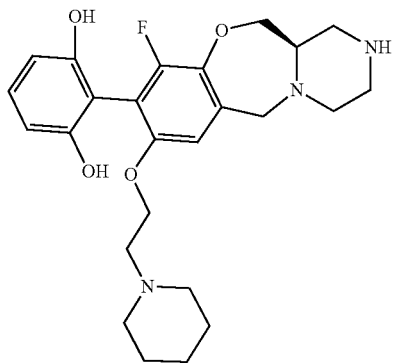 [SMILES: Oc1cccc(O)c1-c1c(OCCN2CCCCC2)cc2c(c1F)OC[C@H]1CNCCN1C2]

TFA (2 mL, 25.96 mmol) was added to tert-butyl (12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepine-2(1H)-carboxylate (400 mg, 0.69 mmol) in DCM (10 mL). The resulting solution was stirred at 25° C. for 1 hour. The solvent was removed under reduced pressure to afford the crude product. The crude product was purified by ion exchange chromatography, using an SCX column. The desired product was eluted from the column using 7M NH$_3$/MeOH and pure fractions were evaporated to dryness to afford 3-chloro-2-{(12aR)-10-fluoro-8-[2-(piperidin-1-yl)ethoxy]-1,2,3,4,12,12a-hexahydro-6H-pyrazino[2,1-c][1,4]benzoxazepin-9-yl}phenol (0.3 g, 91%) as a brown solid. 1H NMR (300 MHz, DMSO, 30° C.) 1.22-1.44 (7H, m), 2.16-2.37 (7H, m), 2.55-2.69 (2H, m), 2.72-2.88 (3H, m), 3.56-3.60 (1H, m), 3.92-4.01 (2H, m), 3.92-4.01 (2H, m), 4.11-4.21 (1H, m), 6.78-6.81 (1H, m), 6.82-6.88 (1H, m), 6.90-6.96 (1H, m), 7.17 (1H, t) two exchangeable protons not seen. m/z: ES+ [M+H]+=476.

1-[(12aR)-9-(2-Chloro-6-hydroxyphenyl)-10-fluoro-8-[2-(piperidin-1-yl)ethoxy]-3,4,12,12a-tetrahydro-6H-pyrazino[2,1-c][1,4]benzoxazepin-2(1H)-yl]prop-2-en-1-one Rotational Isomer 1, Example 107 and Rotational Isomer 2, Example 108

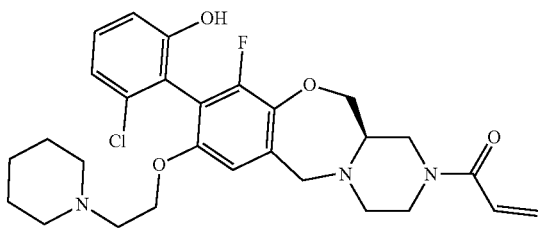 [SMILES: C=CC(=O)N1CCN2Cc3cc(OCCN4CCCCC4)c(-c4c(O)cccc4Cl)c(F)c3OC[C@H]2C1]

Acryloyl chloride (41.8 mg, 0.46 mmol) was added to 3-chloro-2-{(12aR)-10-fluoro-8-[2-(piperidin-1-yl)ethoxy]-1,2,3,4,12,12a-hexahydro-6H-pyrazino[2,1-c][1,4]benzoxazepin-9-yl}phenol (200 mg, 0.42 mmol) and DIPEA (220 µl, 1.26 mmol) in DMF (5 mL). The resulting solution was stirred at 0° C. for 1 hour. The reaction mixture was quenched with water (0.5 mL) and purified directly by preparative HPLC (XBridge Prep C18 OBD column, 5µ silica, 30 mm diameter, 100 mm length), using decreasingly polar mixtures of water (containing 10 mmol % NH$_4$HCO$_3$+ 0.1 mmol % NH$_3$·H$_2$O) and MeCN as eluents. Fractions containing the desired compound were evaporated to dryness to afford firstly rotational isomer 1 of 1-[(12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepin-2(1H)-yl]prop-2-en-1-one (0.06 g, 27%) as white solid. 1H NMR (400 MHz, DMSO, 30° C.) 1.20-1.48 (7H, m), 2.18-2.31 (4H, m), 2.67-2.73 (2H, m), 2.77-2.92 (2H, m), 3.03-3.11 (1H, m), 3.48-3.76 (3H, m), 3.79-4.12 (5H, m), 4.23-4.39 (1H, m), 5.70 (1H, d), 6.12 (1H, d), 6.12 (1H, d), 6.79-6.89 (2H, m), 6.94 (1H, d), 7.18 (1H, t) one exchangeable proton not seen. m/z: ES+ [M+H]+=530. This was followed by rotational isomer 2 of 1-[(12aR)-9-(2-chloro-6-hydroxyphenyl)-10-fluoro-8-[2-(piperidin-1-yl)ethoxy]-3,4,12,12a-tetrahydro-6H-pyrazino[2,1-c][1,4]benzoxazepin-2(1H)-yl]prop-2-en-1-one (0.07 g, 31%) as white solid. 1H NMR (400 MHz, DMSO, 30° C.) 1.20-1.44 (7H, m), 2.17-2.30 (4H, m), 2.61-2.77 (2H, m), 2.77-2.93 (2H, m), 2.96-3.18 (1H, m), 3.48-3.75 (3H, m), 3.79-4.08 (5H, m), 4.23-4.37 (1H, m), 5.70 (1H, d), 6.13 (1H, d), 6.67-6.88 (3H, m), 6.93 (1H, d), 7.18 (1H, t) one exchangeable proton not seen. m/z: ES+ [M+H]+=530.

Tert-butyl (12aR)-9-bromo-10-chloro-8-(prop-1-yn-1-yl)-3,4,12,12a-tetrahydro-6H-pyrazino[2,1-c][1,4]benzoxazepine-2(1H)-carboxylate

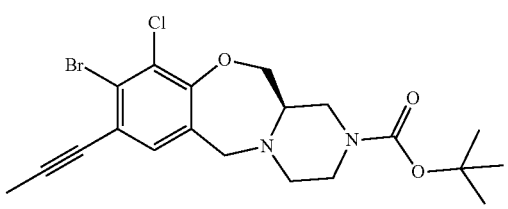 [SMILES: CC#Cc1cc2c(c(Cl)c1Br)OC[C@H]1CN(C(=O)OC(C)(C)C)CCN1C2]

Tert-butyl (12aR)-9-bromo-10-chloro-8-iodo-3,4,12,12a-tetrahydro-6H-pyrazino[2,1-c][1,4]benzoxazepine-2(1H)-carboxylate (1.60 g, 2.94 mmol), tetrakis(triphenylphosphine) palladium(0) (0.17 g, 0.15 mmol) and copper(I) iodide (0.17 g, 0.88 mmol) were suspended in toluene (24 mL) and triethylamine (1.35 mL, 9.71 mmol) was added. 1-(Trimethylsilyl)propyne (0.48 mL, 3.24 mmol) and tetrabutylammonium fluoride (3.24 mL of a 1.0 M solution in THF, 3.24 mmol) were added consecutively and the solution was stirred at room temperature overnight. Further portions of 1-(trimethylsilyl)propyne (0.48 mL, 3.24 mmol) and tetrabutylammonium fluoride (3.24 mL of a 1.0 M solution in THF, 3.24 mmol) were added and the mixture was continued stirring at room temperature overnight. The mixture was diluted with ethyl acetate (20 mL), passed through a short pad of celite and concentrated under reduced pressure to give a brown residue. The crude product was purified by flash silica chromatography, elution gradient 0 to 40% ethyl acetate in heptane. Pure fractions were evaporated to dryness to afford tert-butyl (12aR)-9-bromo-10-chloro-8-(prop-1-yn-1-yl)-3,4,12,12a-tetrahydro-6H-pyrazino[2,1-c][1,4]benzoxazepine-2(1H)-carboxylate (1.28 g, 95%) as a brown residue. 1H NMR (400 MHz, CDCl$_3$, 30° C.): 1.45 (9H, s), 2.09 (3H, s), 2.41 (1H, ddd), 2.68-2.8 (1H, m), 2.84-2.92 (1H, m), 2.92-3.04 (1H, m), 3.29 (1H, ddd), 3.52 (1H, d), 3.57-3.69 (2H, m), 3.72 (1H, dd), 3.92 (1H, d), 4.29 (1H, dd), 7.17 (1H, s). m/z: ES+ [M+H]+ 455.2.

Tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate Rotational Isomer 1 and 2

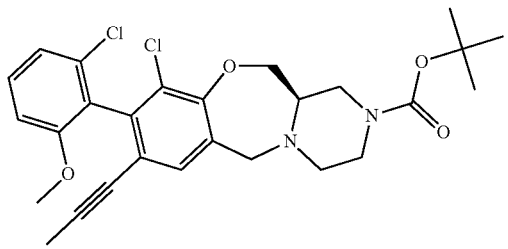 [SMILES: CC#Cc1cc2c(c(Cl)c1-c1c(Cl)cccc1OC)OC[C@H]1CN(C(=O)OC(C)(C)C)CCN1C2]

A solution of tert-butyl (12aR)-9-bromo-10-chloro-8-(prop-1-yn-1-yl)-3,4,12,12a-tetrahydro-6H-pyrazino[2,1-c][1,4]benzoxazepine-2(1H)-carboxylate (1.28 g, 2.81 mmol), (2-chloro-6-methoxyphenyl)boronic acid (0.79 g, 4.21 mmol) and aqueous 2 M sodium carbonate (4.21 mL, 8.43 mmol) in 1,4-dioxane (24 mL) was degassed with nitrogen for 5 minutes. RuPhos Pd G3 (0.235 g, 0.28 mmol) and dicyclohexyl(2',6'-diisopropoxy-[1,1'-biphenyl]-2-yl)phosphane (0.13 g, 0.28 mmol) were added and the mixture was heated at 90° C. After 3 hours, the mixture was cooled to room temperature and diluted with ethyl acetate (50 mL) and water (50 mL). The organic portion was collected and the aqueous was washed with ethyl acetate (50 mL). The combined organics were dried over magnesium sulphate, filtered and concentrated under reduced pressure to give a brown dry film. The crude product was purified by flash silica chromatography, elution gradient 0 to 40% ethyl acetate in heptane. Pure fractions were evaporated to dryness to afford tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate (683 mg) as a pale yellow dry film (as a mixture of atropisomers). The atropisomers were separated using supercritical fluid chromatography (SFC) (Column: Phenomenex C4, 30×250 mm, 5 micron Mobile phase A: 30% MeOH (+0.1% NH$_3$)/Mobile phase B: 70% scCO2; flow rate: 90 mL/min; BPR: 120 bar; Column temperature: 40° C.; UV max: 216 nm). Fractions containing the first eluting isomer were collected and concentrated to give atropisomer 1 of tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate (190 mg, 0.37 mmol, 13%) as a pale yellow solid. 1H NMR (400 MHz, CDCl$_3$, 30° C.): 1.45 (9H, s), 1.76 (3H, s), 2.37-2.56 (1H, m), 2.75-2.99 (2H, m), 3.15-3.34 (1H, m), 3.47 (1H, s), 3.52-3.64 (1H, m), 3.65-3.87 (6H, m), 3.91-4.07 (1H, m), 4.26-4.42 (1H, m), 6.88 (1H, d), 7.08 (1H, d), 7.2-7.24 (1H, m), 7.27-7.31 (1H, m). m/z: ES+ [M+H]+ 517.2. Fractions containing the second eluting isomer were collected and concentrated to give atropisomer 2 of tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate (265 mg, 18%) as a pale yellow solid. 1H NMR (400 MHz, CDCl$_3$, 30° C.): 1.49 (9H, s), 1.80 (3H, s), 2.43-2.57 (1H, m), 2.78-2.99 (2H, m), 3.19-3.38 (1H, m), 3.51 (1H, s), 3.55-3.66 (1H, m), 3.68-3.84 (6H, m), 3.94-4.08 (1H, m), 4.3-4.42 (1H, m), 6.91 (1H, d), 7.13 (1H, d), 7.25-7.27 (1H, m), 7.31-7.38 (1H, m). m/z: ES+ [M+H]+ 517.2.

3-Chloro-2-[(12aR)-10-chloro-8-(prop-1-yn-1-yl)-1,2,3,4,12,12a-hexahydro-6H-pyrazino[2,1-c][1,4]benzoxazepin-9-yl]phenol Rotational Isomer 1

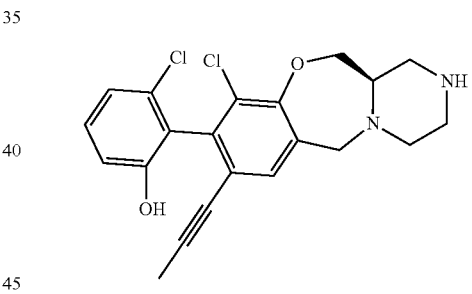

A solution of tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate rotational isomer 1 (190 mg, 0.37 mmol) in DCM (2 mL) was cooled to 0° C. and tribromoborane (3.67 mL of a 1.0 M solution in DCM, 3.67 mmol) was added dropwise with stirring. On addition the mixture was brought to room temperature and stirred overnight. The reaction mixture was diluted with DCM (20 mL) and was added dropwise to a vigorously stirred solution of aqueous saturated sodium hydrogen carbonate (50 mL). The organic portion was collected and the aqueous was washed with ethyl acetate (50 mL) and then 2-methyl-THF (50 mL). The combined organics were dried over magnesium sulphate, filtered and concentrated under reduced pressure to give a pale yellow solid (150 mg). The crude product was purified by ion exchange chromatography, using an SCX column. The desired product was eluted from the column using 1.0 M NH$_3$ in MeOH and pure fractions were evaporated to dryness to afford rotational isomer 1 of 3-chloro-2-[(12aR)-10-chloro-8-(prop-1-yn-1-yl)-1,2,3,4,12,12a-hexahydro-6H-pyrazino[2,1-c][1,4]

benzoxazepin-9-yl]phenol (118 mg, 80%) as a pale yellow dry film. 1H NMR (400 MHz, DMSO, 30° C.): 1.76 (3H, s), 2.38-2.45 (2H, m), 2.69-2.95 (5H, m), 3.6-3.75 (3H, m), 3.81 (1H, d), 4.29 (1H, dd), 6.88 (1H, dd), 6.96 (1H, dd), 7.21 (1H, t), 7.31 (1H, s), 9.70 (1H, s). m/z: ES+ [M+H]+ 403.2.

1-[(12aR)-10-Chloro-9-(2-chloro-6-hydroxyphenyl)-8-(prop-1-yn-1-yl)-3,4,12,12a-tetrahydro-6H-pyrazino[2,1-c][1,4]benzoxazepin-2(1H)-yl]prop-2-en-1-one Rotational Isomer 1, Example 109

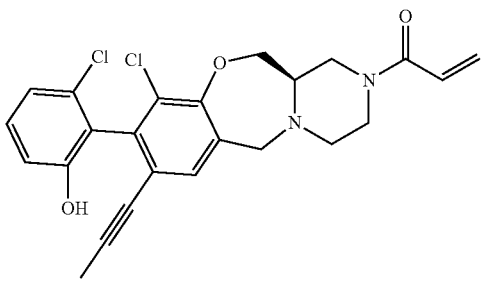 [SMILES: C=CC(=O)N1CCN2Cc3cc(C#CC)c(-c4c(O)cccc4Cl)c(Cl)c3OC[C@H]2C1]

Rotational isomer 1 of 3-chloro-2-[(12aR)-10-chloro-8-(prop-1-yn-1-yl)-1,2,3,4,12,12a-hexahydro-6H-pyrazino[2,1-c][1,4]benzoxazepin-9-yl]phenol (118 mg, 0.29 mmol) was suspended in DCM (1 mL) and triethylamine (0.08 mL, 0.59 mmol) was added. Acryloyl chloride (0.03 mL, 0.35 mmol) was added and the mixture was stirred at room temperature. After 5 minutes, the reaction mixture was quenched by addition of aqueous saturated sodium hydrogen carbonate solution (5 mL). The organic portion was collected and the aqueous was washed with DCM (10 mL). The combined organics were passed through a phase separator cartridge and concentrated under reduced pressure. The crude residue was dissolved in MeOH (1 mL) and 7 N ammonia in MeOH (1 mL) and stirred at room temperature. After 10 minutes the reaction mixture was concentrated under reduced pressure to give a pale yellow foam. The crude product was purified by preparative HPLC (Waters XSelect CSH C18 ODB column, 5μ silica, 30 mm diameter, 100 mm length), using decreasingly polar mixtures of water (containing 0.1% formic acid) and acetonitrile as eluents. Fractions containing the desired compound were evaporated to dryness to afford rotational isomer 1 of 1-[(12aR)-10-chloro-9-(2-chloro-6-hydroxyphenyl)-8-(prop-1-yn-1-yl)-3,4,12,12a-tetrahydro-6H-pyrazino[2,1-c][1,4]benzoxazepin-2(1H)-yl]prop-2-en-1-one (33 mg, 25%) as a pale yellow solid. 1H NMR (400 MHz, CDCl₃, 30° C.): 1.79 (3H, s), 2.47-2.6 (1H, m), 2.84-3.27 (3H, m), 3.35-3.55 (1H, m), 3.60 (1H, d), 3.68-3.9 (2H, m), 4.01-4.2 (2H, m), 4.24-4.47 (2H, m), 5.74 (1H, d), 6.31 (1H, dd), 6.54 (1H, dd), 6.91 (1H, d), 7.07 (1H, d), 7.22 (1H, t), 7.28 (1H, s). m/z: ES+ [M+H]+ 457.2.

3-Chloro-2-[(12aR)-10-chloro-8-(prop-1-yn-1-yl)-1,2,3,4,12,12a-hexahydro-6H-pyrazino[2,1-c][1,4]benzoxazepin-9-yl]phenol Rotational Isomer 2

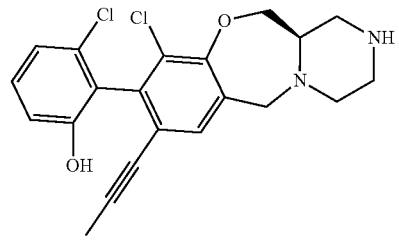 [SMILES: CC#Cc1cc2c(c(Cl)c1-c1c(O)cccc1Cl)OC[C@H]1CNCCN1C2]

A solution of rotational isomer 2 of tert-butyl (12aR)-10-chloro-9-(2-chloro-6-methoxyphenyl)-8-(prop-1-yn-1-yl)-3,4,12,12a-tetrahydro-6H-pyrazino[2,1-c][1,4]benzoxazepine-2(1H)-carboxylate (265 mg, 0.51 mmol) in DCM (2 mL) was cooled to 0° C. and tribromoborane (5.12 mL of a 1.0 M solution in DCM, 5.12 mmol) was added dropwise with stirring. On addition the mixture was brought to room temperature and stirred overnight. The reaction mixture was diluted with DCM (20 mL) and was added dropwise to a vigorously stirred solution of aqueous saturated sodium hydrogen carbonate (50 mL). The organic portion was collected and the aqueous was washed with ethyl acetate (50 mL) and then 2-methyl-THF (50 mL). The combined organics were dried over magnesium sulphate, filtered and concentrated under reduced pressure to give a pale yellow solid (500 mg). The crude product was purified by ion exchange chromatography, using an SCX column. The desired product was eluted from the column using 1.0 M NH3 in MeOH and pure fractions were evaporated to dryness to afford rotational isomer 2 of 3-chloro-2-[(12aR)-10-chloro-8-(prop-1-yn-1-yl)-1,2,3,4,12,12a-hexahydro-6H-pyrazino[2,1-c][1,4]benzoxazepin-9-yl]phenol (203 mg, 98%) as a pale yellow dry film. 1H NMR (400 MHz, DMSO, 30° C.): 1.76 (3H, s), 2.44-2.52 (1H, m), 2.77-2.93 (4H, m), 2.97-3.1 (2H, m), 3.64-3.78 (3H, m), 3.85 (1H, d), 4.33 (1H, d), 6.87 (1H, dd), 6.97 (1H, dd), 7.21 (1H, t), 7.32 (1H, s), 9.72 (1H, s). m/z: ES+ [M+H]+ 403.2.

1-[(12aR)-10-Chloro-9-(2-chloro-6-hydroxyphenyl)-8-(prop-1-yn-1-yl)-3,4,12,12a-tetrahydro-6H-pyrazino[2,1-c][1,4]benzoxazepin-2(1H)-yl]prop-2-en-1-one Rotational Isomer 2, Example 110

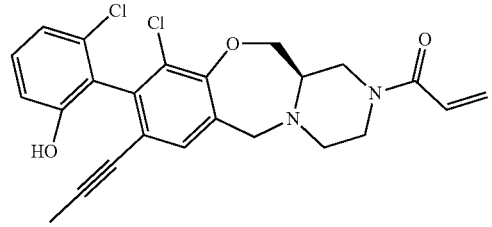 [SMILES: C=CC(=O)N1CCN2Cc3cc(C#CC)c(-c4c(O)cccc4Cl)c(Cl)c3OC[C@H]2C1]

Rotational isomer 2 of 3-chloro-2-[(12aR)-10-chloro-8-(prop-1-yn-1-yl)-1,2,3,4,12,12a-hexahydro-6H-pyrazino[2,1-c][1,4]benzoxazepin-9-yl]phenol (200 mg, 0.5 mmol) was suspended in DCM (4 mL) and triethylamine (0.14 mL, 0.99 mmol) was added. Acryloyl chloride (0.05 mL, 0.60 mmol)

was added and the mixture was stirred at room temperature. After 10 minutes the reaction mixture was quenched by addition of aqueous saturated sodium hydrogen carbonate solution (5 mL). The organic portion was collected and the aqueous was washed with DCM (10 mL). The combined organics were passed through a phase separator cartridge and concentrated under reduced pressure. The crude residue was dissolved in MeOH (2 mL) and 7 N ammonia in MeOH (2 mL) and stirred at room temperature. After 20 minutes the reaction mixture was concentrated under reduced pressure to give a pale yellow foam. The crude product was purified by preparative HPLC (Waters XSelect CSH C18 ODB column, 5μ silica, 30 mm diameter, 100 mm length), using decreasingly polar mixtures of water (containing 0.1% formic acid) and acetonitrile as eluents. Fractions containing the desired compound were evaporated to dryness to afford rotational isomer 2 of 1-[(12aR)-10-chloro-9-(2-chloro-6-hydroxyphenyl)-8-(prop-1-yn-1-yl)-3,4,12,12a-tetrahydro-6H-pyrazino[2,1-c][1,4]benzoxazepin-2(1H)-yl]prop-2-en-1-one (81 mg, 36%) as a pale yellow solid. 1H NMR (400 MHz, DMSO, 30° C.): 1.77 (3H, s), 2.37-2.45 (1H, m), 2.7-2.78 (1H, m), 2.8-2.93 (1H, m), 3.04-3.15 (1H, m), 3.26-3.29 (1H, m), 3.61-3.77 (2H, m), 3.82-3.93 (2H, m), 3.97-4.09 (1H, m), 4.35-4.47 (1H, m), 5.65-5.76 (1H, m), 6.13 (1H, d), 6.74-6.91 (2H, m), 6.97 (1H, dd), 7.21 (1H, t), 7.33 (1H, s), 9.71 (1H, s). m/z: ES+ [M+H]+ 457.2.

Ethyl 5-bromo-3-fluoro-6-[(²H₃)methyloxy]pyridine-2-carboxylate

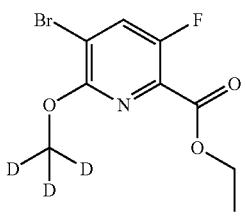

To a suspension of ethyl 5-bromo-3-fluoro-6-hydroxypyridine-2-carboxylate (10 g, 37.9 mmol) and silver carbonate (23.0 g, 83.3 mmol) in chloroform (100 mL) was added iodomethane-d3 (11.8 mL, 189 mmol) and the reaction mixture was stirred at 40° C. overnight. The reaction mixture was cooled to room temperature, diluted with DCM (100 mL) and filtered through a short pad of celite. The celite was washed with DCM (100 mL) and the filtrate was concentrated under reduced pressure to give a pale yellow oil (11.5 g). The crude product was purified by flash silica chromatography, elution gradient 0 to 30% ethyl acetate in heptane. Pure fractions were evaporated to dryness to afford ethyl 5-bromo-3-fluoro-6-[(²H₃)methyloxy]pyridine-2-carboxylate (9.02 g, 85%) as a colourless oil which solidified on standing. 1H NMR (400 MHz, DMSO): 1.32 (3H, t), 4.36 (2H, q), 8.39 (1H, d). 19F NMR (376 MHz, DMSO): -126.47. m/z: ES+ [M+H]+ 281.0.

5-Bromo-3-fluoro-6-[(²H₃)methyloxy]pyridine-2-carboxylic acid

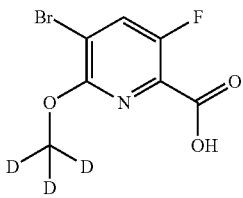

Ethyl 5-bromo-3-fluoro-6-[(²H₃)methyloxy]pyridine-2-carboxylate (9.02 g, 32.1 mmol) was dissolved in THF (90 mL) and water (18 mL) and lithium hydroxide hydrate (1.75 g, 41.7 mmol) were added sequentially. The resulting mixture was stirred at room temperature overnight. The volatiles were removed under reduced pressure and the aqueous was acidified to pH 4 with 1 M citric acid and extracted with 2-methyl-THF (2×100 mL). The combined organics were dried over magnesium sulphate, filtered and concentrated to give 5-bromo-3-fluoro-6-[(²H₃)methyloxy]pyridine-2-carboxylic acid (8.2 g, 100%) as a white solid. 1H NMR (400 MHz, DMSO, 30° C.): 8.32 (1H, dd), 12.68 (1H, s). 19F NMR (376 MHz, DMSO, 30° C.): -127.09. m/z: ES- [M-H]- 251.1.

Tert-butyl (3R)-4-{5-bromo-3-fluoro-6-[(²H₃)methyloxy]pyridine-2-carbonyl}-3-(hydroxymethyl)piperazine-1-carboxylate

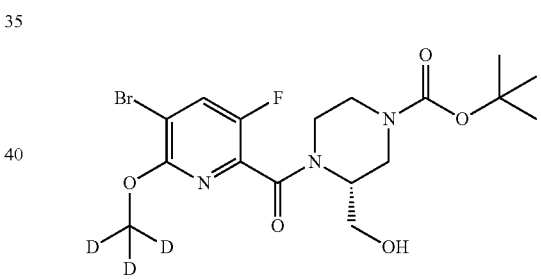

5-Bromo-3-fluoro-6-[(²H₃)methyloxy]pyridine-2-carboxylic acid (5.00 g, 19.8 mmol) and tert-butyl (3R)-3-(hydroxymethyl)piperazine-1-carboxylate (4.70 g, 21.74 mmol) were dissolved in THF (120 mL). N,N-Diisopropylethylamine (8.60 mL, 49.4 mmol) was added and then HATU (11.27 g, 29.64 mmol) was added in portions over 5 minutes. The mixture was stirred at room temperature for 4 hours. The reaction mixture was concentrated under reduced pressure and the resultant residue was dissolved in DCM (100 mL) and washed with water (100 mL). The aqueous portion was extracted with DCM (100 mL) and the combined organics were passed through a phase separator cartridge and concentrated to give a brown sticky oil. The crude product was purified by flash silica chromatography, elution gradient 0 to 70% ethyl acetate in heptane. Pure fractions were evaporated to dryness to afford tert-butyl (3R)-4-{5-bromo-3-fluoro-6-[(²H₃)methyloxy]pyridine-2-carbonyl}-3-(hydroxymethyl)piperazine-1-carboxylate (6.82 g, 76%) as a white foam. 1H NMR (400 MHz, DMSO, 30° C.): 1.41 (9H, s), 2.74-3.22 (3H, m), 3.35-3.83 (3H, m), 3.9-4.16 (2H, m), 4.22-4.54 (1H, m), 4.69-4.97 (1H, m), 8.28-8.35 (1H, m). 19F NMR (376 MHz, DMSO, 30° C.): −134.12, −132.96. m/z: ES+ [M+H]+ 451.2.

Tert-butyl (6aR)-3-bromo-2-[($^2$H$_3$)methyloxy]-12-oxo-6a,7,9,10-tetrahydro-12H-pyrazino[2,1-c]pyrido[2,3-f][1,4]oxazepine-8(6H)-carboxylate

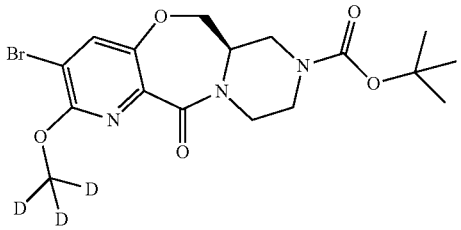 [SMILES: [2H]C([2H])([2H])Oc1nc2c(cc1Br)OC[C@H]1CN(C(=O)OC(C)(C)C)CCN1C2=O]

Caesium carbonate (14.8 g, 45.3 mmol) was added to a stirred solution of tert-butyl (3R)-4-{5-bromo-3-fluoro-6-[($^2$H$_3$)methyloxy]pyridine-2-carbonyl}-3-(hydroxymethyl)piperazine-1-carboxylate (6.82 g, 15.1 mmol) in acetonitrile (120 mL). The resulting suspension was stirred at 80° C. overnight. The mixture was left to stir for a further hour and then filtered whilst hot. The filtrate was concentrated under reduced pressure to give a brown residue and the resulting residue was dissolved in DCM (100 mL) and washed with water (50 mL) and then brine (50 mL). The organic portion was passed through a phase separator cartridge and concentrated under reduced pressure to give tert-butyl (6aR)-3-bromo-2-[($^2$H$_3$)methyloxy]-12-oxo-6a,7,9,10-tetrahydro-12H-pyrazino[2,1-c]pyrido[2,3-f][1,4]oxazepine-8(6H)-carboxylate (6.49 g, 99%) as a light brown foam. Material used without further purification. 1H NMR (400 MHz, DMSO, 30° C.): 1.42 (9H, s), 3.45 (1H, s), 3.51-3.65 (3H, m), 3.7-3.92 (2H, m), 3.95-4.09 (1H, m), 4.20 (2H, d), 7.94 (1H, s). m/z: ES+ [M+H]+ 431.2.

Tert-butyl (6aR)-3-bromo-2-[($^2$H$_3$)methyloxy]-6a,7,9,10-tetrahydro-12H-pyrazino[2,1-c]pyrido[2,3-f][1,4]oxazepine-8(6H)-carboxylate

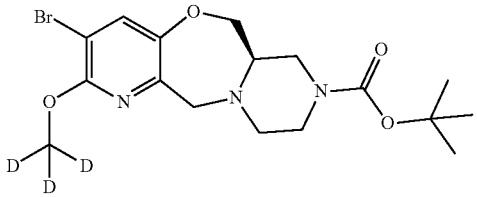 [SMILES: [2H]C([2H])([2H])Oc1nc2c(cc1Br)OC[C@H]1CN(C(=O)OC(C)(C)C)CCN1C2]

Borane-THF complex solution (60.2 mL of a 1.0 M solution in THF, 60.12 mmol) was added dropwise to a solution of tert-butyl (6aR)-3-bromo-2-[($^2$H$_3$)methyloxy]-12-oxo-6a,7,9,10-tetrahydro-12H-pyrazino[2,1-c]pyrido[2,3-f][1,4]oxazepine-8(6H)-carboxylate (6.49 g, 15.1 mmol) in THF (100 mL) at 0° C. The resultant solution was brought to room temperature and then heated at 80° C. After 1 hour the reaction mixture was slowly cooled to room temperature and then cooled in an ice-bath and quenched by dropwise addition of aqueous saturated ammonium chloride solution (80 mL). The mixture was diluted with water (80 mL) and washed with ethyl acetate (100 mL). The organic portion was collected and the aqueous was washed with a further portion of ethyl acetate (100 mL). The combined organics were washed with brine (100 mL), dried over magnesium sulphate, filtered and concentrated under reduced pressure to give a pale yellow oil. The crude product was purified by flash silica chromatography, elution gradient 0 to 40% ethyl acetate in heptane. Pure fractions were evaporated to dryness to afford tert-butyl (6aR)-3-bromo-2-[($^2$H$_3$)methyloxy]-6a,7,9,10-tetrahydro-12H-pyrazino[2,1-c]pyrido[2,3-f][1,4]oxazepine-8(6H)-carboxylate (4.98 g, 79%) as a white foam. 1H NMR (400 MHz, DMSO): 1.40 (9H, s), 2.27-2.4 (1H, m), 2.58-2.72 (1H, m), 2.72-2.85 (2H, m), 3.05 (1H, t), 3.58-3.7 (4H, m), 3.92 (1H, d), 4.22 (1H, dd), 7.72 (1H, s). m/z: ES+ [M+H]+ 417.2.

Tert-butyl (6aR)-3-bromo-4-chloro-2-[($^2$H$_3$)methyloxy]-6a,7,9,10-tetrahydro-12H-pyrazino[2,1-c]pyrido[2,3-f][1,4]oxazepine-8(6H)-carboxylate

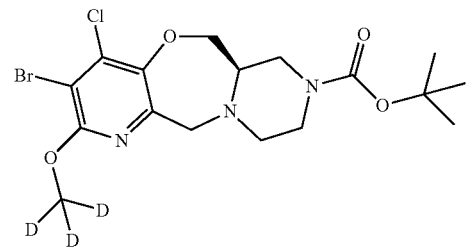 [SMILES: [2H]C([2H])([2H])Oc1nc2c(c(Cl)c1Br)OC[C@H]1CN(C(=O)OC(C)(C)C)CCN1C2]

A solution of tert-butyl (6aR)-3-bromo-2-[($^2$H$_3$)methyloxy]-6a,7,9,10-tetrahydro-12H-pyrazino[2,1-c]pyrido[2,3-f][1,4]oxazepine-8(6H)-carboxylate (4.98 g, 11.9 mmol) in THF (100 mL) was cooled to −40° C. and 2,2,6,6-tetramethylpiperidinylmagnesium chloride lithium chloride complex solution (14.3 mL of a 1.0 M solution in THF/toluene, 14.32 mmol) was added dropwise. The solution was allowed to stir at −40° C. After 30 minutes, a further portion of 2,2,6,6-tetramethylpiperidinylmagnesium chloride lithium chloride complex solution (14.3 mL of a 1.0 M solution in THF/toluene, 14.32 mmol) was added and the mixture was stirred for a further 30 minutes at −40° C. Perchloroethane (3.11 g, 13.1 mmol) was added in one portion and the mixture was allowed to warm to room temperature and stirred overnight. The mixture was cooled in an ice-bath and quenched by dropwise addition of aqueous saturated ammonium chloride solution (100 mL). The aqueous was extracted with ethyl acetate (2×100 mL) and the combined organics were dried over magnesium sulphate, filtered and concentrated under reduced pressure to give a brown residue. The crude product was purified by flash silica chromatography, elution gradient 0 to 30% ethyl acetate in heptane. Pure fractions were evaporated to dryness to afford tert-butyl (6aR)-3-bromo-4-chloro-2-[($^2$H$_3$)methyloxy]-6a,7,9,10-tetrahydro-12H-pyrazino[2,1-c]pyrido[2,3-f][1,4]oxazepine-8(6H)-carboxylate (4.75 g, 88%) as a pale brown foam. 1H NMR (400 MHz, DMSO, 30° C.): 1.40 (9H, s), 2.3-2.42 (1H, m), 2.55-2.66 (1H, m), 2.72-2.89 (3H, m), 3.04-3.14 (1H, m), 3.55-3.71 (3H, m), 4.00 (1H, d), 4.28-4.38 (1H, m). m/z: ES+ [M+H]+ 451.2.

Tert-butyl (6aR)-4-chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepine-8(6H)-carboxylate

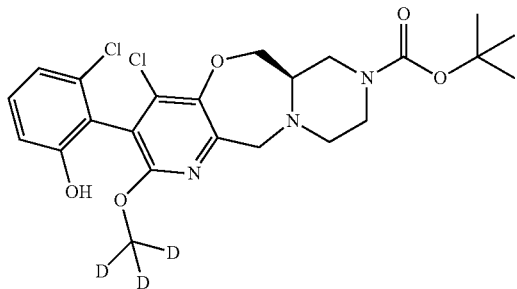 [SMILES: [2H]C([2H])([2H])Oc1nc2c(c(Cl)c1-c1c(O)cccc1Cl)OC[C@H]1CN(C(=O)OC(C)(C)C)CCN1C2]

A solution of tert-butyl (6aR)-3-bromo-4-chloro-2-[($^2$H$_3$)methyloxy]-6a,7,9,10-tetrahydro-12H-pyrazino[2,1-c]pyrido[2,3-f][1,4]oxazepine-8(6H)-carboxylate (4.75 g, 10.5 mmol) and (2-chloro-6-hydroxyphenyl)boronic acid (2.72 g, 15.8 mmol) in 2-methyl-THF (90 mL) and 2 M aqueous sodium carbonate solution (15.8 mL, 31.5 mmol) was degassed with nitrogen for 10 minutes. RuPhos Pd G3 (0.879 g, 1.05 mmol) and dicyclohexyl(2',6'-diisopropoxy-[1,1'-biphenyl]-2-yl)phosphane (0.491 g, 1.05 mmol) were added and the solution was stirred at 80° C. After 4 hours the reaction mixture was cooled to room temperature and diluted with water (50 mL). The organic portion was collected and the aqueous was washed with ethyl acetate (50 mL). The combined organics were washed with brine (50 mL), dried over magnesium sulphate, filtered and concentrated under reduced pressure to give a brown residue. The crude product was purified by flash silica chromatography, elution gradient 0 to 60% ethyl acetate in heptane. Fractions containing product were evaporated to dryness to afford tert-butyl (6aR)-4-chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepine-8(6H)-carboxylate (3.64 g, 69%) as a pale yellow solid (as a mixture of atropisomers). m/z: ES+ [M+H]+ 499.2.

3-Chloro-2-{(6aR)-4-chloro-2-[($^2$H$_3$)methyloxy]-6,6a,7,8,9,10-hexahydro-12H-pyrazino[2,1-c]pyrido[2,3-f][1,4]oxazepin-3-yl}phenol Rotational Isomer 1 and 2

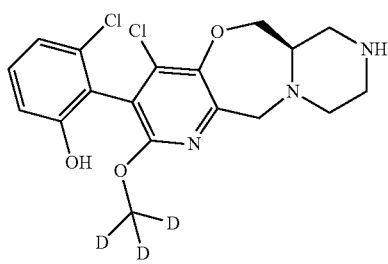 [SMILES: [2H]C([2H])([2H])Oc1nc2c(c(Cl)c1-c1c(O)cccc1Cl)OC[C@H]1CNCCN1C2]

Tert-butyl (6aR)-4-chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepine-8(6H)-carboxylate (3.64 g, 7.29 mmol) was suspended in DCM (50 mL) and trifluoroacetic acid (5.58 mL, 72.9 mmol) was added. The solution was stirred at room temperature for 3 hours. The solution was concentrated under reduced pressure to give a red foam which was dissolved in DCM (100 mL) and washed with aqueous saturated sodium hydrogen carbonate solution (100 mL). The organic portion was collected and the aqueous was washed with ethyl acetate (100 mL). The combined organics were dried over magnesium sulphate, filtered and concentrated under reduced pressure to give an orange solid. The crude product was purified by reverse phase chromatography (Waters XSelect CSH C18 ODB, 450 g), using decreasingly polar mixtures of water (containing 1% NH$_3$) and acetonitrile as eluents. Fractions containing the first eluting isomer were collected and concentrated to give atropisomer 1 of 3-chloro-2-{(6aR)-4-chloro-2-[($^2$H$_3$)methyloxy]-6,6a,7,8,9,10-hexahydro-12H-pyrazino[2,1-c]pyrido[2,3-f][1,4]oxazepin-3-yl}phenol (334 mg, 11%) as a white solid. 1H NMR (500 MHz, DMSO, 27° C.): 2.29-2.39 (2H, m), 2.6-2.68 (2H, m), 2.72-2.83 (3H, m), 3.57-3.68 (3H, m), 3.96 (1H, d), 4.25 (1H, dd), 6.86-6.89 (1H, m), 6.98 (1H, dd), 7.23 (1H, t), 9.85 (1H, s). m/z: ES+ [M+H]+ 399.2. Fractions containing the second eluting isomer were collected and concentrated to give atropisomer 2 of 3-chloro-2-{(6aR)-4-chloro-2-[($^2$H$_3$)methyloxy]-6,6a,7,8,9,10-hexahydro-12H-pyrazino[2,1-c]pyrido[2,3-f][1,4]oxazepin-3-yl}phenol (641 mg, 22%) as a white solid. 1H NMR (500 MHz, DMSO, 27° C.): 2.11 (1H, s), 2.29-2.38 (2H, m), 2.59-2.67 (2H, m), 2.72-2.84 (3H, m), 3.56-3.69 (2H, m), 3.97 (1H, d), 4.26 (1H, dd), 6.88 (1H, dd), 6.94-6.99 (1H, m), 7.23 (1H, t), 9.84 (1H, s). m/z: ES+ [M+H]+ 399.2.

1-[(6aR)-4-Chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepin-8(6H)-yl]prop-2-en-1-one Rotational Isomer 1, Example 111

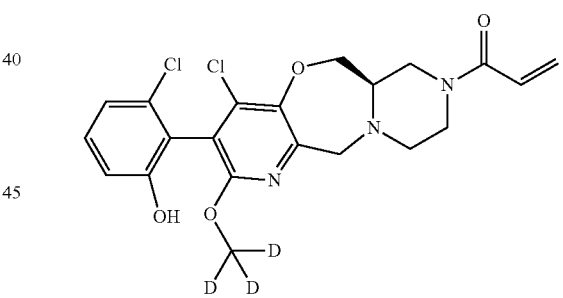

Rotational isomer 1 of 3-chloro-2-{(6aR)-4-chloro-2-[($^2$H$_3$)methyloxy]-6,6a,7,8,9,10-hexahydro-12H-pyrazino[2,1-c]pyrido[2,3-f][1,4]oxazepin-3-yl}phenol (330 mg, 0.83 mmol) was suspended in DCM (5 mL) and triethylamine (225 μL, 1.65 mmol) was added. Acryloyl chloride (80 μL, 0.99 mmol) was added and the mixture was stirred at room temperature. After 30 minutes the reaction mixture was concentrated under reduced pressure to give a cream solid. The crude solid was dissolved in MeOH (5 mL) and 7 N ammonia in MeOH (5 mL) and stirred at room temperature. After 10 minutes the reaction mixture was concentrated under reduced pressure to give a pale yellow foam. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN (25-50% gradient) as eluents. Fractions containing the desired compound were evaporated to dryness to afford rotational isomer 1 of 1-[(6aR)-4-chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepin-8(6H)-yl]prop-2-en-1-one (146 mg, 39%) as a white solid. 1H NMR (400 MHz, DMSO, 30° C.): 2.37-2.47 (1H, m), 2.7-2.78 (1H, m), 2.79-2.98 (2H, m), 3-3.16 (1H, m), 3.63-3.76 (2H, m), 3.85-3.98 (1H, m), 4.01-4.16 (2H, m), 4.31-4.5 (1H, m), 5.66-5.75 (1H, m), 6.14 (1H, d), 6.78-6.91 (2H, m), 6.98 (1H, dd), 7.23 (1H, t), 9.84 (1H, s). m/z: ES+ [M+H]+ 453.2.

1-[(6aR)-4-Chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepin-8(6H)-yl]prop-2-en-1-one Rotational Isomer 2, Example 112

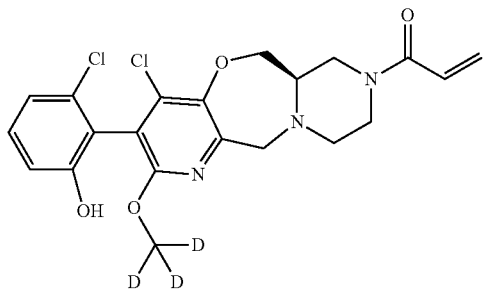 [SMILES: [2H]C([2H])([2H])Oc1nc2c(c(Cl)c1-c1c(O)cccc1Cl)OC[C@H]1CN(C(=O)C=C)CCN1C2]

Rotational isomer 2 of 3-chloro-2-{(6aR)-4-chloro-2-[($^2$H$_3$)methyloxy]-6,6a,7,8,9,10-hexahydro-12H-pyrazino[2,1-c]pyrido[2,3-f][1,4]oxazepin-3-yl}phenol (640 mg, 1.60 mmol) was suspended in DCM (10 mL) and triethylamine (437 µL, 3.21 mmol) was added. Acryloyl chloride (155 µL, 1.92 mmol) was added and the mixture was stirred at room temperature. After 10 minutes the reaction mixture was concentrated under reduced pressure to give a cream solid. The solid was suspended in acetonitrile (2 mL)/MeOH (2 mL)/dimethylsulfoxide (1 mL), filtered and washed with acetonitrile (2 mL) and dried in a vacuum oven at 45° C. to give rotational isomer 2 of 1-[(6aR)-4-chloro-3-(2-chloro-6-hydroxyphenyl)-2-[($^2$H$_3$)methyloxy]-6a,7,9,10-tetrahydro-12H-pyrazino[2,1-c]pyrido[2,3-f][1,4]oxazepin-8(6H)-yl]prop-2-en-1-one (290 mg, 40%) as a white solid. 1H NMR (400 MHz, DMSO, 30° C.): 2.38-2.46 (1H, m), 2.7-2.79 (1H, m), 2.81-2.99 (2H, m), 3.01-3.13 (1H, m), 3.71 (2H, dd), 3.85-4.01 (1H, m), 4.01-4.16 (2H, m), 4.33-4.47 (1H, m), 5.65-5.78 (1H, m), 6.14 (1H, d), 6.74-6.92 (2H, m), 6.97 (1H, dd), 7.23 (1H, t), 9.81 (1H, s). m/z: ES+ [M+H]+ 453.2.

Tert-butyl (12aR)-9-bromo-10-chloro-8-(hydroxymethyl)-3,4,12,12a-tetrahydro-6H-pyrazino[2,1-c][1,4]benzoxazepine-2(1H)-carboxylate

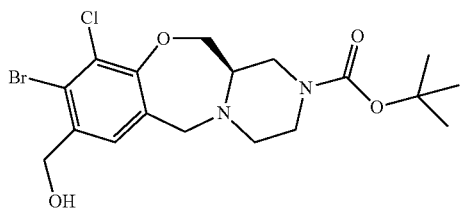 [SMILES: CC(C)(C)OC(=O)N1CCN2Cc3cc(CO)c(Br)c(Cl)c3OC[C@H]2C1]

Tert-butyl (12aR)-9-bromo-10-chloro-8-iodo-3,4,12,12a-tetrahydro-6H-pyrazino[2,1-c][1,4]benzoxazepine-2(1H)-carboxylate (1 g, 1.84 mmol) was dissolved in THF (15 mL) and cooled to 0° C. Isopropyl magnesium chloride lithium chloride complex (1.56 mL of a 1.3 M solution in THF, 2.02 mmol) was added dropwise and the solution was stirred at 0° C. for 30 minutes. DMF (0.17 mL, 2.21 mmol) was added and the mixture was stirred at 0° C. for 5 minutes and then brought to room temperature and stirred. After 45 minutes the reaction mixture was cooled in an ice-bath and quenched by dropwise addition of aqueous saturated ammonium chloride solution (5 mL) and water (5 mL). The solution was extracted with ethyl acetate (2×20 mL). The combined organics were dried over magnesium sulphate, filtered and concentrated to give tert-butyl (12aR)-9-bromo-10-chloro-8-formyl-3,4,12,12a-tetrahydro-6H-pyrazino[2,1-c][1,4]benzoxazepine-2(1H)-carboxylate as a pale brown residue (850 mg). This crude material (820 mg) was dissolved in THF (10 mL) and cooled in an ice-bath. Sodium tetrahydroborate (139 mg, 3.68 mmol) was added in one portion and the mixture was allowed to warm to room temperature and stirred. After 2 hours the mixture quenched by addition of aqueous ammonium chloride solution (5 mL) and water (5 mL). The mixture was extracted with ethyl acetate (2×20 mL) and the combined organics portions were washed with brine (10 mL). The organics were dried over magnesium sulphate, filtered and concentrated to give a brown foam. The crude product was purified by flash silica chromatography, elution gradient 0 to 100% ethyl acetate in heptane. Pure fractions were evaporated to dryness to afford tert-butyl (12aR)-9-bromo-10-chloro-8-(hydroxymethyl)-3,4,12,12a-tetrahydro-6H-pyrazino[2,1-c][1,4]benzoxazepine-2(1H)-carboxylate (300 mg, 36%) as a pale yellow foam. 1H NMR (400 MHz, DMSO, 30° C.): 1.40 (9H, s), 2.3-2.38 (1H, m), 2.44-2.48 (1H, m), 2.69-2.87 (2H, m), 3.04-3.14 (1H, m), 3.48-3.67 (3H, m), 3.72 (1H, d), 3.83 (1H, d), 4.33 (1H, dd), 4.47 (2H, d), 5.46 (1H, t), 7.38 (1H, s). m/z: ES+ [M+H]+ 447.2.

Tert-butyl (12aR)-9-bromo-10-chloro-8-(methoxymethyl)-3,4,12,12a-tetrahydro-6H-pyrazino[2,1-c][1,4]benzoxazepine-2(1H)-carboxylate

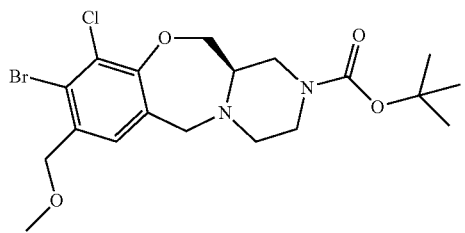 [SMILES: COCc1cc2c(c(Cl)c1Br)OC[C@H]1CN(C(=O)OC(C)(C)C)CCN1C2]

Sodium hydride (40 mg, 60% by weight in mineral oil, 1.01 mmol) was added in one portion to a solution of tert-butyl (12aR)-9-bromo-10-chloro-8-(hydroxymethyl)-3,4,12,12a-tetrahydro-6H-pyrazino[2,1-c][1,4]benzoxazepine-2(1H)-carboxylate (300 mg, 0.67 mmol) and iodomethane (213 µL, 3.35 mmol) in DMF (2 mL) cooled to 0° C. The resulting solution was brought to room temperature and stirred. After 10 minutes the mixture was quenched by addition of aqueous saturated ammonium chloride solution (2 mL) and water (2 mL). The mixture was extracted with ethyl acetate (2×10 mL) and the combined organics were washed with brine (10 mL). The organics were passed through a phase separator cartridge and concentrated under reduced pressure. The crude product was purified by flash silica chromatography, elution gradient 0 to 40% ethyl acetate in heptane. Pure fractions were evaporated to dryness to afford tert-butyl (12aR)-9-bromo-10-chloro-8-(methoxymethyl)-3,4,12,12a-tetrahydro-6H-pyrazino[2,1-c][1,4]benzoxazepine-2(1H)-carboxylate (0.125 g, 40%) as a white foam. 1H NMR (400 MHz, DMSO, 30° C.): 1.40 (9H, s), 2.32-2.37 (1H, m), 2.69-2.8 (3H, m), 3.05-3.15 (1H, m), 3.36 (3H, s), 3.53-3.68 (3H, m), 3.72 (1H, d), 3.82 (1H, d), 4.34 (1H, dd), 4.42 (2H, s), 7.33 (1H, s). m/z: ES+ [M+H]+ 461.2.

Tert-butyl (12aR)-10-chloro-9-(2-chloro-6-hydroxyphenyl)-8-(methoxymethyl)-3,4,12,12a-tetrahydro-6H-pyrazino[2,1-c][1,4]benzoxazepine-2(1H)-carboxylate

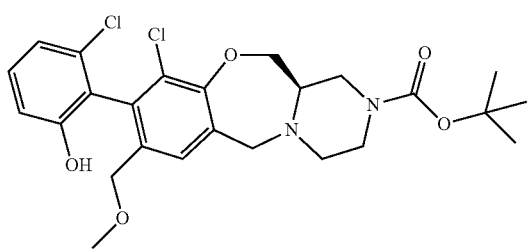 [SMILES: COCc1cc2c(c(Cl)c1-c1c(O)cccc1Cl)OC[C@H]1CN(C(=O)OC(C)(C)C)CCN1C2]

A solution of tert-butyl (12aR)-9-bromo-10-chloro-8-(methoxymethyl)-3,4,12,12a-tetrahydro-6H-pyrazino[2,1-c][1,4]benzoxazepine-2(1H)-carboxylate (120 mg, 0.26 mmol) and (2-chloro-6-hydroxyphenyl)boronic acid (134 mg, 0.78 mmol) in 2-methyl-THF (2 mL) and 2 M aqueous sodium carbonate solution (390 µL, 0.78 mmol) was degassed with nitrogen for 10 minutes. RuPhos Pd G3 (22 mg, 0.03 mmol) and dicyclohexyl(2',6'-diisopropoxy-[1,1'-biphenyl]-2-yl)phosphane (12 mg, 0.03 mmol) were added and the solution was stirred at 85° C. After 1 hour the reaction mixture was cooled to room temperature and diluted with water (5 mL). The organic portion was collected and the aqueous was washed with ethyl acetate (10 mL). The combined organics were washed with brine (5 mL), dried over magnesium sulphate, filtered and concentrated under reduced pressure to give a brown residue. The crude product was purified by flash silica chromatography, elution gradient 0 to 60% ethyl acetate in heptane. Fractions containing product were evaporated to dryness to afford tert-butyl (12aR)-10-chloro-9-(2-chloro-6-hydroxyphenyl)-8-(methoxymethyl)-3,4,12,12a-tetrahydro-6H-pyrazino[2,1-c][1,4]benzoxazepine-2(1H)-carboxylate (80 mg, 60%) as a pale yellow solid (as a mixture of atropisomers). m/z: ES+ [M+H]+ 509.2.

1-[(12aR)-10-Chloro-9-(2-chloro-6-hydroxyphenyl)-8-(methoxymethyl)-3,4,12,12a-tetrahydro-6H-pyrazino[2,1-c][1,4]benzoxazepin-2(1H)-yl]prop-2-en-1-one Rotational Isomer 1, Example 113 and Rotational Isomer 2, Example 114

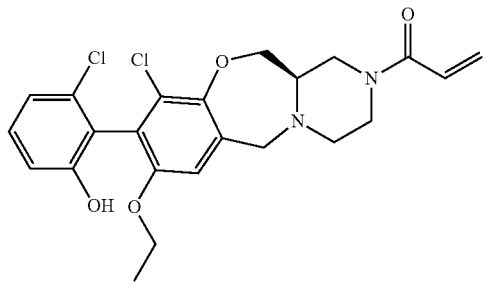 [SMILES: C=CC(=O)N1CCN2Cc3cc(OCC)c(-c4c(O)cccc4Cl)c(Cl)c3OC[C@H]2C1]

Tert-butyl (12aR)-10-chloro-9-(2-chloro-6-hydroxyphenyl)-8-(methoxymethyl)-3,4,12,12a-tetrahydro-6H-pyrazino[2,1-c][1,4]benzoxazepine-2(1H)-carboxylate (80 mg, 0.16 mmol) was suspended in DCM (1 mL) and trifluoroacetic acid (120 µL, 1.57 mmol) was added. After 1 hour the reaction mixture was concentrated under reduced pressure and the crude product was purified by ion exchange chromatography, using an SCX column. The product was eluted using 1.0 M NH₃ in MeOH and fractions containing product were evaporated to dryness to afford a pale yellow dry film that was suspended in DCM (1 mL) and triethylamine (40 µL, 0.29 mmol) was added. Acryloyl chloride (14.21 µl, 0.18 mmol) was added and the mixture was stirred at room temperature. After 10 minutes the reaction mixture was concentrated under reduced pressure to give a yellow residue. The crude residue was dissolved in MeOH (1 mL) and 7 N ammonia in MeOH (1 mL) and stirred at room temperature. After 10 minutes the reaction mixture was concentrated under reduced pressure to give a pale yellow residue. The crude product was purified by preparative HPLC (Waters XSelect CSH C18 ODB column, 5µ silica, 30 mm diameter, 100 mm length), using decreasingly polar mixtures of water (containing 0.1% formic acid) and acetonitrile as eluents. Fractions containing the first eluting isomer were collected and concentrated to give atropisomer 1 of 1-[(12aR)-10-chloro-9-(2-chloro-6-hydroxyphenyl)-8-(methoxymethyl)-3,4,12,12a-tetrahydro-6H-pyrazino[2,1-c][1,4]benzoxazepin-2(1H)-yl]prop-2-en-1-one (1 mg, 2%) as an off-white solid. 1H NMR (400 MHz, CDCl₃, 30° C.): 2.53-2.66 (1H, m), 2.83-3.14 (3H, m), 3.25 (3H, s), 3.37-3.57 (1H, m), 3.63-3.9 (3H, m), 3.98-4.11 (2H, m), 4.12-4.24 (2H, m), 4.3-4.48 (1H, m), 5.74 (1H, d), 6.32 (1H, dd), 6.54 (1H, dd), 6.94-7.01 (1H, m), 7.11 (1H, dd), 7.27-7.3 (2H, m). m/z: ES+ [M+H]+ 463.2. Fractions containing the second eluting isomer were collected and concentrated to give atropisomer 2 of 1-[(12aR)-10-chloro-9-(2-chloro-6-hydroxyphenyl)-8-(methoxymethyl)-3,4,12,12a-tetrahydro-6H-pyrazino[2,1-c][1,4]benzoxazepin-2(1H)-yl]prop-2-en-1-one (3 mg, 5%) as an off white solid. 1H NMR (400 MHz, CDCl₃, 30° C.): 2.47-2.66 (1H, m), 2.86-3.11 (3H, m), 3.26 (3H, s), 3.32-3.59 (1H, m), 3.69 (1H, d), 3.74-3.91 (2H, m), 3.96-4.25 (4H, m), 4.29-4.45 (1H, m), 5.74 (1H, d), 6.31 (1H, dd), 6.55 (1H, dd), 6.98 (1H, dd), 7.10 (1H, dd), 7.27-7.32 (2H, m). m/z: ES+ [M+H]+ 463.2.

4-Bromo-2,3,6-trifluorobenzoic acid

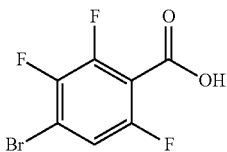

2,2,6,6-Tetramethylpiperidine (48 mL, 284.39 mmol) was added dropwise to 2.5M n-Butyllithium solution in hexanes (114 mL, 284.39 mmol) in THF (500 mL) at −78° C. under nitrogen. The resulting mixture was stirred at −78° C. for 30 minutes. 1-bromo-2,3,5-trifluorobenzene (17.06 mL, 142.19 mmol) was added dropwise to the mixture at −78° C. under nitrogen. The resulting solution was stirred at −78° C. for 1 hour. Solid carbon dioxide (18.77 g, 426.58 mmol) was then added portion wise at −78° C. The resulting solution was stirred at −78° C. for 4 hours. The reaction mixture was quenched with 2M HCl (100 mL), diluted with water (500 mL) and extracted with EtOAc (3×300 mL). The organic layer was dried over anhydrous sodium sulphate, filtered and evaporated to afford crude product as a brown oil. The crude product was purified by flash silica chromatography, elution gradient 0 to 20% MeOH in DCM. Pure fractions were evaporated to dryness to afford 4-bromo-2,3,6-trifluorobenzoic acid (30 g, 83%) as a brown solid. 1H NMR (400 MHz, CDCl$_3$, 30° C.) 7.16-7.23 (1H, m) one exchangeable proton not seen.

Tert-butyl (3R)-4-(4-bromo-2,3,6-trifluorobenzoyl)-3-(hydroxymethyl)piperazine-1-carboxylate

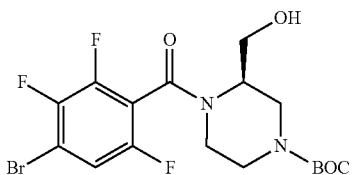 [SMILES: CC(C)(C)OC(=O)N1CCN(C(=O)c2c(F)cc(Br)c(F)c2F)[C@@H](CO)C1]

DIPEA (61.6 mL, 352.95 mmol) was added dropwise to 4-bromo-2,3,6-trifluorobenzoic acid (30 g, 117.65 mmol), tert-butyl (3R)-3-(hydroxymethyl)piperazine-1-carboxylate (38.2 g, 176.48 mmol) and HATU (89 g, 235.3 mmol) in DMF (400 mL) at 0° C. The resulting mixture was stirred at room temperature for 1 hour. The reaction mixture was quenched with saturated NH$_4$Cl (200 mL). Diluted with EtOAc (1000 mL), washed sequentially with water (300 mL) and saturated brine (3×600 mL). The organic layer was dried over anhydrous sodium sulphate, filtered and evaporated to afford crude product as a brown oil. The crude product was purified by flash silica chromatography, elution gradient 0 to 50% EtOAc in petroleum ether. Pure fractions were evaporated to dryness to afford tert-butyl (3R)-4-(4-bromo-2,3,6-trifluorobenzoyl)-3-(hydroxymethyl)piperazine-1-carboxylate (12 g, 23%) as a brown solid. 1H NMR (400 MHz, CDCl$_3$, 30° C.) 1.46 (9H, s), 2.78-2.87 (2H, m), 2.87-3.17 (2H, m), 3.18-3.42 (1H, m), 3.51-3.67 (1H, m), 3.67-3.81 (1H, m), 3.82-4.36 (2H, m), 4.47-4.89 (1H, m), 7.14-7.23 (1H, m). m/z: ES+ [M-tBu]+=397.

Tert-butyl (12aR)-9-bromo-7,10-difluoro-6-oxo-3,4,12,12a-tetrahydro-6H-pyrazino[2,1-c][1,4]benzoxazepine-2(1H)-carboxylate

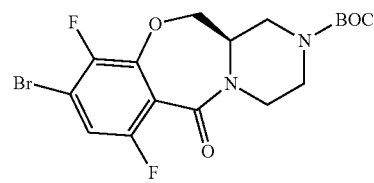 [SMILES: CC(C)(C)OC(=O)N1CCN2C(=O)c3c(F)cc(Br)c(F)c3OC[C@H]2C1]

Sodium hydride (1.456 g, 36.4 mmol) was added to tert-butyl (3R)-4-(4-bromo-2,3,6-trifluorobenzoyl)-3-(hydroxymethyl)piperazine-1-carboxylate late (11 g, 24.27 mmol) in DMF (60 mL) at 0° C. under nitrogen. The resulting mixture was stirred at room temperature for 1 hour. The reaction mixture was quenched with saturated NH$_4$Cl (50 mL), diluted with water (200 mL) and extracted with EtOAc (2×300 mL). The organic layer was washed with saturated brine (2×400 mL), dried over anhydrous sodium sulphate, filtered and evaporated to afford crude product as a yellow oil. The crude product was purified by flash silica chromatography, elution gradient 10 to 50% EtOAc in petroleum ether. Pure fractions were evaporated to dryness to afford tert-butyl (12aR)-9-bromo-7,10-difluoro-6-oxo-3,4,12,12a-tetrahydro-6H-pyrazino[2,1-c][1,4]benzoxazepine-2(1H)-carboxylate (6 g, 57%) as a yellow solid. 1H NMR (400 MHz, DMSO, 30° C.) 1.42 (9H, s), 3.43-3.55 (1H, m), 3.56-3.73 (4H, m), 3.83-3.97 (1H, m), 4.10-4.19 (1H, m), 4.21-4.40 (2H, m), 7.57-7.70 (1H, m). m/z: ES+ [M-tBu]+=377.

Tert-butyl (12aR)-9-bromo-7-[2-(dimethylamino)ethoxy]-10-fluoro-6-oxo-3,4,12,12a-tetrahydro-6H-pyrazino[2,1-c][1,4]benzoxazepine-2(1H)-carboxylate

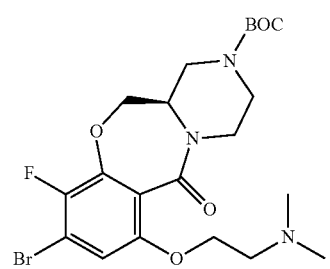 [SMILES: CN(C)CCOc1cc(Br)c(F)c2c1C(=O)N1CCN(C(=O)OC(C)(C)C)C[C@@H]1CO2]

Sodium hydride (0.208 g, 5.19 mmol) was added to 2-dimethylaminoethanol (0.383 mL, 3.81 mmol) in DMF (30 m) at 0° C. under nitrogen. The resulting mixture was stirred at 0° C. for 20 minutes. Tert-butyl (12aR)-9-bromo-7,10-difluoro-6-oxo-3,4,12,12a-tetrahydro-6H-pyrazino[2,1-c][1,4]benzoxazepine-2(1H)-carboxylate (1.5 g, 3.46 mmol) in DMF (30 mL) was added to the mixture at 0° C. under nitrogen. The resulting solution was stirred at room temperature for 1 hour. The reaction mixture was quenched with saturated NH$_4$Cl (50 mL), extracted with EtOAc (3×75 mL). The organic layers were combined and washed with saturated brine (2×150 mL), dried over anhydrous sodium sulphate, filtered and evaporated to afford crude product as a yellow oil. The crude product was purified by flash silica chromatography, elution gradient 10 to 30% MeOH in DCM. Pure fractions were evaporated to dryness to afford tert-butyl (12aR)-9-bromo-7-[2-(dimethylamino)ethoxy]-10-fluoro-6-oxo-3,4,12,12a-tetrahydro-6H-pyrazino[2,1-c][1,4]benzoxazepine-2(1H)-carboxylate (1.1 g, 63%) as a yellow solid. 1H NMR (400 MHz, DMSO, 30° C.) 1.42 (9H, s), 2.21 (6H, s), 2.54-2.64 (2H, m), 3.22-3.30 (1H, m), 3.30-3.39 (2H, m), 3.61-3.82 (2H, m), 3.90-4.16 (5H, m), 4.15-4.29 (1H, m), 7.29 (1H, s). m/z: ES+ [M+H]+=502.

Tert-butyl (12aR)-9-bromo-7-[2-(dimethylamino)ethoxy]-10-fluoro-3,4,12,12a-tetrahydro-6H-pyrazino[2,1-c][1,4]benzoxazepine-2(1H)-carboxylate

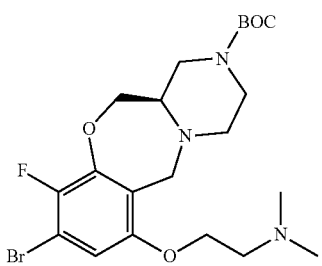 [SMILES: CN(C)CCOc1cc(Br)c(F)c2c1CN1CCN(C(=O)OC(C)(C)C)C[C@@H]1CO2]

(Acetylacetonato)(1,5-cyclooctadiene)-rhodium(I) (136 mg, 0.44 mmol) was added to phenylsilane (1896 mg, 17.52 mmol) and tert-butyl (12aR)-9-bromo-7-[2-(dimethylamino)ethoxy]-10-fluoro-6-oxo-3,4,12,12a-tetrahydro-6H-pyrazino[2,1-c][1,4]benzoxazepine-2(1H)-carboxylate (1100 mg, 2.19 mmol) in THF (50 mL) at 25° C. under nitrogen. The resulting mixture was stirred at 70° C. for 2 hours. The reaction mixture was quenched with saturated NH$_4$F (50 mL), extracted with EtOAc (3×50 mL). The organic layer was dried over anhydrous sodium sulphate, filtered and evaporated to afford crude product as a yellow oil. The crude product was purified by flash C18-flash chromatography, elution gradient 0 to 80% MeCN in water (0.1% formic acid). Pure fractions were evaporated to dryness to afford tert-butyl (12aR)-9-bromo-7-[2-(dimethylamino)ethoxy]-10-fluoro-3,4,12,12a-tetrahydro-6H-pyrazino[2,1-c][1,4]benzoxazepine-2(1H)-carboxylate (0.8 g, 75%) as a yellow solid. 1H NMR (400 MHz, DMSO, 30° C.) 1.40 (9H, s), 2.29-2.43 (1H, m), 2.53 (6H, s), 2.62-2.67 (1H, m), 2.69-2.81 (1H, m), 2.97-3.03 (1H, m), 3.40-3.54 (2H, m), 3.57-3.68 (2H, m), 3.68-3.81 (2H, m), 3.98-4.10 (1H, m), 4.09-4.23 (2H, m), 4.29-4.39 (1H, m), 7.05 (1H, s). m/z: ES+ [M+H]+=488.

Tert-butyl (12aR)-9-(2-chloro-6-hydroxyphenyl)-7-[2-(dimethylamino)ethoxy]-10-fluoro-3,4,12,12a-tetrahydro-6H-pyrazino[2,1-c][1,4]benzoxazepine-2(1H)-carboxylate

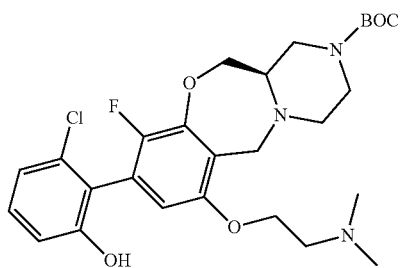 [SMILES: CN(C)CCOc1cc(-c2c(O)cccc2Cl)c(F)c2c1CN1CCN(C(=O)OC(C)(C)C)C[C@@H]1CO2]

(2-Chloro-6-methoxyphenyl)boronic acid (371 mg, 2.15 mmol) was added to K$_2$CO$_3$ (396 mg, 2.87 mmol), tetrakis(triphenylphosphine)palladium(0) (166 mg, 0.14 mmol) and tert-butyl (12aR)-9-bromo-7-[2-(dimethylamino)ethoxy]-10-fluoro-3,4,12,12a-tetrahydro-6H-pyrazino[2,1-c][1,4]benzoxazepine-2(1H)-carboxylate (700 mg, 1.43 mmol) in 1,4-dioxane (16 mL) and H$_2$O (4 mL)(4:1 ratio) at 25° C. under nitrogen. The resulting mixture was stirred at 80° C. for 1 hour. The solvent was removed under reduced pressure. The crude product obtained was purified by flash C18-flash chromatography, elution gradient 20 to 40% MeCN in water (0.1% formic acid). Pure fractions were evaporated to dryness to afford tert-butyl (12aR)-9-(2-chloro-6-hydroxyphenyl)-7-[2-(dimethylamino)ethoxy]-10-fluoro-3,4,12,12a-tetrahydro-6H-pyrazino[2,1-c][1,4]benzoxazepine-2(1H)-carboxylate (0.5 g, 65%) as a colourless solid. 1H NMR (400 MHz, DMSO, 30° C.) 1.44 (9H, s), 2.90 (6H, s), 3.07-3.21 (2H, m), 3.50-3.61 (2H, m), 3.75-3.92 (2H, m), 4.19-4.97 (9H, m), 6.67-6.83 (1H, m), 6.93 (1H, d), 7.02 (1H, d), 7.24 (1H, t), 9.97 (1H, s). m/z: ES+ [M+H]+=536.

3-Chloro-2-{(12aR)-7-[2-(dimethylamino)ethoxy]-10-fluoro-1,2,3,4,12,12a-hexahydro-6H-pyrazino[2,1-c][1,4]benzoxazepin-9-yl}phenol

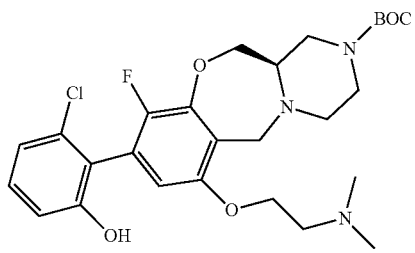 [SMILES: CN(C)CCOc1cc(-c2c(O)cccc2Cl)c(F)c2c1CN1CCN(C(=O)OC(C)(C)C)C[C@@H]1CO2]

TFA (1 mL, 12.98 mmol) was added to tert-butyl (12aR)-9-(2-chloro-6-hydroxyphenyl)-7-[2-(dimethylamino)ethoxy]-10-fluoro-3,4,12,12a-tetrahydro-6H-pyrazino[2,1-c][1,4]benzoxazepine-2(1H)-carboxylate (500 mg, 0.93 mmol) in DCM at 25° C. The resulting mixture was stirred at 25° C. for 30 minutes. The solvent was removed under reduced pressure. The crude product obtained was purified by ion exchange chromatography, using an SCX column. The desired product was eluted from the column using 7M NH$_3$/MeOH and pure fractions were evaporated to dryness to afford 3-chloro-2-{(12aR)-7-[2-(dimethylamino)ethoxy]-

10-fluoro-1,2,3,4,12,12a-hexahydro-6H-pyrazino[2,1-c][1,4]benzoxazepin-9-yl}phenol (0.4 g, 98%) as a yellow solid. 1H NMR (400 MHz, DMSO, 30° C.) 2.82-2.90 (2H, m), 2.89 (6H, s), 2.94-3.19 (4H, m), 3.39-3.60 (2H, m), 3.70-4.01 (3H, m), 4.13-4.32 (3H, m), 4.36-4.47 (1H, m), 6.58-6.69 (1H, m), 6.86-6.96 (1H, m), 7.01 (1H, d), 7.24 (1H, d), 9.01 (1H, t), 9.96 (1H, s). m/z: ES+ [M+H]+=436.

1-[(12aR)-9-(2-Chloro-6-hydroxyphenyl)-7-[2-(dimethylamino)ethoxy]-10-fluoro-3,4,12,12a-tetrahydro-6H-pyrazino[2,1-c][1,4]benzoxazepin-2(1H)-yl]prop-2-en-1-one Rotational Isomer 1, Example 115 and Rotational Isomer 2, Example 116

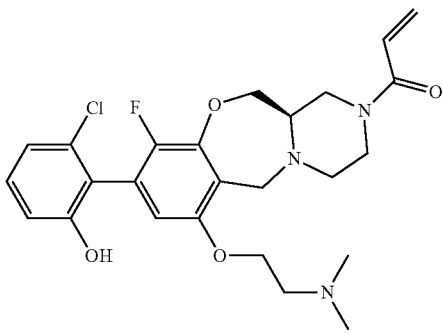 [SMILES: C=CC(=O)N1CCN2Cc3c(OCCN(C)C)cc(-c4c(O)cccc4Cl)c(F)c3OC[C@H]2C1]

Acryloyl chloride (83 mg, 0.92 mmol) was added to DIPEA (481 µl, 2.75 mmol) and 3-chloro-2-{(12aR)-7-[2-(dimethylamino)ethoxy]-10-fluoro-1,2,3,4,12,12a-hexahydro-6H-pyrazino[2,1-c][1,4]benzoxazepin-9-yl}phenol (400 mg, 0.92 mmol) in DMF (10 mL) at 0° C. under nitrogen. The resulting mixture was stirred at 0° C. for 1 hour. The reaction mixture was quenched with water (1 mL) and purified directly by preparative HPLC (Column: XBridge Shield RP18 OBD Column, 30*150 mm, 5 um; Mobile Phase A:Water (0.1% formic acid), Mobile Phase B:MeCN; Flow rate:60 mL/min; Gradient:8 B to 18 B in 10 min; 254; 220 nm. Fractions containing the desired compound were evaporated to dryness to afford firstly rotational isomer 1 of 1-[(12aR)-9-(2-chloro-6-hydroxyphenyl)-7-[2-(dimethylamino)ethoxy]-10-fluoro-3,4,12,12a-tetrahydro-6H-pyrazino[2,1-c][1,4]benzoxazepin-2(1H)-yl]prop-2-en-1-one (0.059 g, 11%) as a white solid. 1H NMR (400 MHz, DMSO, 30° C.) 2.26 (6H, s), 2.40-2.43 (1H, m), 2.56-2.73 (3H, m), 2.73-3.41 (3H, m), 3.56-3.60 (1H, m), 3.67-3.90 (1H, m), 3.82-4.29 (5H, m), 4.38-4.31 (1H, m), 5.70 (1H, d), 6.13 (1H, d), 6.53 (1H, d), 6.81-6.90 (1H, m), 6.84-7.05 (2H, m), 7.22-7.30 (1H, m) one exchangeable proton not seen. m/z: ES+ [M+H]+=490. This was followed by rotational isomer 2 of 1-[(12aR)-9-(2-chloro-6-hydroxyphenyl)-7-[2-(dimethylamino)ethoxy]-10-fluoro-3,4,12,12a-tetrahydro-6H-pyrazino[2,1-c][1,4]benzoxazepin-2(1H)-yl]prop-2-en-1-one (0.055 g, 11) as a white solid. 1H NMR (400 MHz, CD3OD, 30° C.) 2.58 (1H, d), 2.94-3.01 (7H, m), 3.00-3.32 (3H, m), 3.60 (2H, d), 3.61-4.04 (3H, m), 4.22-4.67 (5H, m), 5.79 (1H, d), 6.14-6.38 (1H, m), 6.67 (1H, d), 6.75-6.96 (2H, m), 6.99 (1H, d), 7.21-7.25 (1H, m) one exchangeable proton not seen. m/z: ES+ [M+H]+=490.

Methyl 2,5-dichloro-4-fluoronicotinate

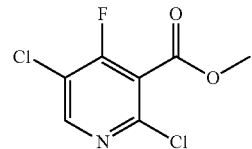

A solution of methyl 2-chloro-4-fluoropyridine-3-carboxylate (20 g, 105.5 mmol) in THF (300 mL) was cooled to −45° C. under nitrogen and 1M lithium magnesium 2,2,6,6-tetramethylpiperidin-1-ide dichloride in THF (127 mL, 126.6 mmol) was added dropwise. The reaction mixture was stirred for 20 minutes at −45° C. then a solution of perchloroethane (31.2 g, 131.88 mmol) in THF (50 mL) was added dropwise and the mixture stirred at room temperature for 1.5 hours. The reaction was quenched by addition of saturated ammonium chloride then partitioned between EtOAc and water. The organic layer was washed with brine and evaporated. The crude product obtained was purified by flash silica chromatography, elution gradient 0 to 50% EtOAc in heptane. Pure fractions were evaporated to dryness to afford methyl 2,5-dichloro-4-fluoronicotinate (14 g, 59%) as a colourless oil. 1H NMR (400 MHz, CDCl$_3$, 30° C.) 4.02 (3H, s), 8.47 (1H, d). m/z: ES+ [M+H]+=224.

2,5-Dichloro-4-fluoropyridine-3-carbaldehyde

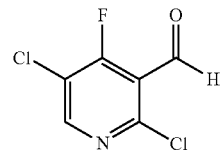 [SMILES: O=Cc1c(Cl)ncc(Cl)c1F]

A solution of methyl 2,5-dichloro-4-fluoronicotinate (14 g, 50 mmol) in DCM (200 mL) was cooled to −78° C. under nitrogen. 1M Di-isobutylaluminium hydride solution in hexanes (52.5 mL, 52.5 mmol) was added dropwise keeping the internal reaction temperature below −70° C. The resulting mixture was stirred at −78° C. for 1 hour. The reaction mixture was quenched with 2M HCl (100 mL) and extracted with DCM (2×200 mL). The organic layer was dried over anhydrous sodium sulphate, filtered and evaporated to afford 2,5-dichloro-4-fluoropyridine-3-carbaldehyde (8 g, 82%) as a colourless oil. 1H NMR (400 MHz, CDCl$_3$, 30° C.) 8.60 (1H, d), 10.39 (1H, d). No mass ion observed.

Tert-butyl (3R)-4-[(2,5-dichloro-4-fluoropyridin-3-yl)methyl]-3-(hydroxymethyl)piperazine-1-carboxylate

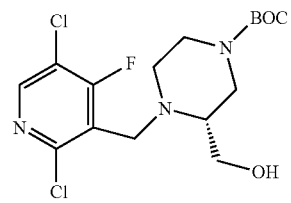 [SMILES: CC(C)(C)OC(=O)N1CCN(Cc2c(Cl)ncc(Cl)c2F)[C@@H](CO)C1]

Glacial acetic acid (0.212 mL, 3.71 mmol) was added to 2,5-dichloro-4-fluoropyridine-3-carbaldehyde (8 g, 37.12 mmol) and tert-butyl (3R)-3-(hydroxymethyl)piperazine-1-carboxylate (9.63 g, 44.54 mmol) in DCM (150 mL) at 20° C. The resulting mixture was stirred at 20° C. for 1 hour. Sodium triacetoxyborohydride (11.8 g, 55.67 mmol) was then added to the mixture at 20° C. The resulting mixture was stirred at 20° C. for 16 hours. Additional sodium triacetoxyborohydride (3.93 g, 18.56 mmol) was added and the resulting mixture was stirred at 20° C. for a further 4 hours. The reaction mixture was quenched by careful addition of aqueous saturated sodium hydrogen carbonate solution and the aqueous layer extracted with DCM. The organic layer was washed with saturated brine and dried over anhydrous sodium sulphate, filtered and evaporated. The residue obtained was purified by flash silica chromatography, elution gradient 0 to 30% THF in petroleum ether. Pure fractions were evaporated to dryness to afford tert-butyl (3R)-4-[(2,5-dichloro-4-fluoropyridin-3-yl)methyl]-3-(hydroxymethyl)piperazine-1-carboxylate (9 g, 62%) as a colourless oil. 1H NMR (400 MHz, CDCl$_3$, 30° C.) 1.41 (9H, s), 2.33-2.45 (1H, m), 2.63-2.84 (2H, m), 3.24-3.34 (1H, m), 3.41-3.55 (2H, m), 3.57-3.64 (1H, m), 3.65-3.73 (2H, m), 3.74-3.79 (1H, m), 3.82-3.94 (1H, m), 4.09-4.19 (1H, m), 8.38 (1H, d). m/z: ES+ [M+H]+=394.

Tert-butyl (6aR)-1,4-dichloro-6a,7,9,10-tetrahydro-12H-pyrazino[2,1-c]pyrido[3,4-f][1,4]oxazepine-8(6H)-carboxylate

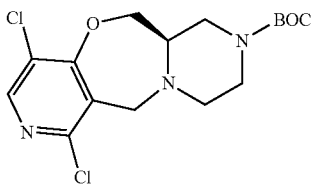 [SMILES: CC(C)(C)OC(=O)N1CCN2Cc3c(Cl)ncc(Cl)c3OC[C@H]2C1]

A solution of tert-butyl (3R)-4-[(2,5-dichloro-4-fluoropyridin-3-yl)methyl]-3-(hydroxymethyl) piperazine-1-carboxylate (9 g, 22.83 mmol) in DMF (100 mL) under nitrogen was cooled to 0° C. Sodium hydride (2.74 g, 68.48 mmol) was added in one portion and the reaction mixture was stirred at 20° C. for 1 hour. The reaction mixture was quenched with water (15 mL) and diluted with EtOAc (200 mL). The organic layer was washed with water (3×250 mL), saturated brine and dried over anhydrous sodium sulphate, filtered then evaporated to afford crude product as brown oil. The crude product was purified by flash silica chromatography, elution gradient 0 to 25% THF in petroleum ether. Pure fractions were evaporated to dryness to afford tert-butyl (6aR)-1,4-dichloro-6a,7,9,10-tetrahydro-12H-pyrazino[2,1-c]pyrido[3,4-f][1,4]oxazepine-8(6H)-carboxylate (8 g, 94%) as a white solid. 1H NMR (400 MHz, DMSO, 30° C.) 1.41 (9H, s), 2.60-2.66 (1H, m), 2.80-2.97 (4H, m), 3.70-3.77 (1H, m), 3.78-3.85 (1H, m), 3.88-3.97 (1H, m), 3.98-4.07 (1H, m), 4.14-4.23 (1H, m), 4.50-4.59 (1H, m), 8.30 (1H, s). m/z: ES+ [M+H]+=374.

Tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate

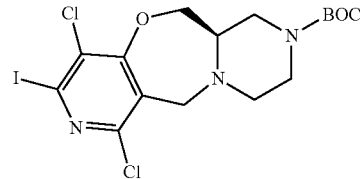 [SMILES: CC(C)(C)OC(=O)N1CCN2Cc3c(Cl)nc(I)c(Cl)c3OC[C@H]2C1]

Tert-butyl (6aR)-1,4-dichloro-6a,7,9,10-tetrahydro-12H-pyrazino[2,1-c]pyrido[3,4-f][1,4]oxazepine-8(6H)-carboxylate (8 g, 21.38 mmol) was dissolved in THF (100 mL) and cooled to −45° C. under nitrogen. 1M 2,2,6,6-Tetramethylpiperidinylmagnesium chloride lithium chloride complex solution in THF/toluene (64.1 mL, 64.13 mmol) was added dropwise and the resulting mixture stirred for 30 minutes at −45° C. A solution of diiodine (8.14 g, 32.06 mmol) in THF (50 mL) was then added. The reaction mixture was stirred at −45° C. for 15 minutes then allowed to warm to 0° C. and quenched at 0° C. with saturated ammonium chloride (10 mL), diluted with water (200 mL) then extracted with EtOAc (3×200 mL). The organic layer was washed with saturated sodium thiosulfate, brine then dried over anhydrous sodium sulphate, filtered and evaporated to afford a crude brown oil. The crude product was purified by flash silica chromatography, elution gradient 0 to 40% THF in petroleum ether. Pure fractions were evaporated to dryness to afford tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate (9.7 g, 91%) as a yellow oil. 1H NMR (400 MHz, DMSO, 30° C.) 1.40 (9H, s), 2.60-2.69 (1H, m), 2.73-3.06 (3H, m), 3.33-3.42 (1H, m), 3.66-3.85 (2H, m), 3.87-4.04 (2H, m), 4.16-4.24 (1H, m), 4.45-4.60 (1H, m). m/z: ES+ [M+H]+=500.

Tert-butyl (6aR)-1,4-dichloro-3-(2-chloro-6-methoxyphenyl)-6a,7,9,10-tetrahydro-12H-pyrazino[2,1-c]pyrido[3,4-f][1,4]oxazepine-8(6H)-carboxylate

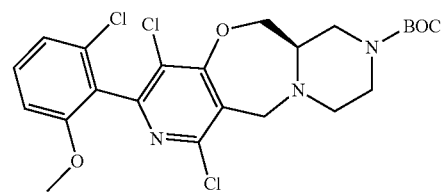 [SMILES: COc1cccc(Cl)c1-c1nc(Cl)c2c(c1Cl)OC[C@H]1CN(C(=O)OC(C)(C)C)CCN1C2]

RuPhos-Pd-G3 (0.936 g, 1.12 mmol) and 2-Dicyclohexylphosphino-2',6'-diisopropoxybiphenyl (0.522 g, 1.12 mmol) were added to a de-oxygenated suspension of tert-butyl (6aR)-1,4-dichloro-3-iodo-6a,7,9,10-tetrahydro-12H-pyrazino[2,1-c]pyrido[3,4-f][1,4]oxazepine-8(6H)-carboxylate (5.60 g, 11.20 mmol), (2-chloro-6-methoxyphenyl) boronic acid (2.71 g, 14.56 mmol) and sodium carbonate (2.37 g, 22.39 mmol) in 1,4-dioxane (32 mL) and water (8 mL) (4:1 ratio). The resulting mixture was stirred at 50° C. for 3 hours under a nitrogen atmosphere. The solvent was removed under reduced pressure. The crude product obtained was purified by flash silica chromatography, elution gradient 0 to 40% THF in petroleum ether. Pure fractions were evaporated to dryness to afford tert-butyl (6aR)-1,4-dichloro-3-(2-chloro-6-methoxyphenyl)-6a,7,9,10-tetrahydro-12H-pyrazino[2,1-c]pyrido[3,4-f][1,4]oxazepine-8(6H)-carboxylate (2.2 g, 38%) as a brown solid. 1H NMR (400 MHz, DMSO, 30° C.) 1.40 (9H, s), 2.55-2.64 (1H, m), 2.77-3.01 (3H, m), 3.54-3.63 (1H, m), 3.74-3.98 (3H, m), 4.03-4.31 (2H, m), 4.58-4.69 (1H, m), 6.84-6.92 (1H, m), 7.07-7.17 (2H, m), 7.24 (1H, t), 7.46 (1H, t), 8.18 (1H, s). m/z: ES+ [M+H]+=514.

Tert-butyl (6aR)-4-chloro-3-(2-chloro-6-methoxyphenyl)-1-(prop-1-yn-1-yl)-6a,7,9,10-tetrahydro-12H-pyrazino[2,1-c]pyrido[3,4-f][1,4]oxazepine-8(6H)-carboxylate

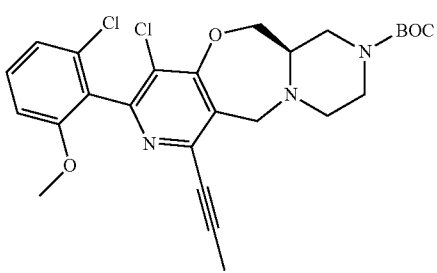 [SMILES: CC#Cc1nc(-c2c(Cl)cccc2OC)c(Cl)c2c1CN1CCN(C(=O)OC(C)(C)C)C[C@@H]1CO2]

N-Ethyl-N-isopropylpropan-2-amine (3.39 mL, 19.42 mmol) and 1M prop-1-yne in THF (19.42 mL, 19.42 mmol) were added to tert-butyl (6aR)-1,4-dichloro-3-(2-chloro-6-methoxyphenyl)-6a,7,9,10-tetrahydro-12H-pyrazino[2,1-c]pyrido[3,4-f][1,4]oxazepine-8(6H)-carboxylate (1.00 g, 1.94 mmol), 1,1'-ferrocenediyl-bis(diphenylphosphine) (0.108 g, 0.19 mmol) and methanesulfonato 1,1-ferrocenediyl-bis(diphenylphosphino) (2'-amino-1,1'-biphenyl-2-yl) palladium(II) (0.179 g, 0.19 mmol) in DMF (15 mL) at 20° C. under an nitrogen atmosphere. The resulting mixture was stirred at 120° C. for 16 hours in a microwave. The solvent was removed under reduced pressure. The crude product obtained was purified by flash silica chromatography, elution gradient 0 to 40% THF in petroleum ether. Pure fractions were evaporated to dryness to afford tert-butyl (6aR)-4-chloro-3-(2-chloro-6-methoxyphenyl)-1-(prop-1-yn-1-yl)-6a,7,9,10-tetrahydro-12H-pyrazino[2,1-c]pyrido[3,4-f][1,4]oxazepine-8(6H)-carboxylate (0.39 g, 39%) as a brown solid. 1H NMR (400 MHz, DMSO, 30° C.) 1.40 (9H, s), 2.09 (3H, s), 2.55-2.73 (2H, m), 2.79-2.89 (2H, m), 2.90-3.02 (1H, m), 3.69 (3H, d), 3.71-3.86 (2H, m), 4.00-4.13 (3H, m), 4.49-4.59 (1H, m), 7.11 (2H, t), 7.43 (1H, t). m/z: ES+ [M+H]+=518.

3-Chloro-2-[(6aR)-4-chloro-1-(prop-1-yn-1-yl)-6,6a,7,8,9,10-hexahydro-12H-pyrazino[2,1-c]pyrido[3,4-f][1,4]oxazepin-3-yl]phenol

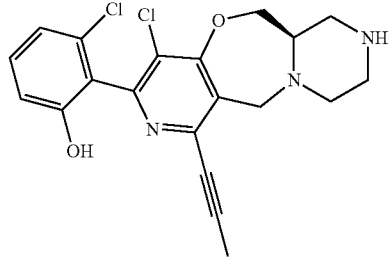 [SMILES: CC#Cc1nc(-c2c(O)cccc2Cl)c(Cl)c2c1CN1CCNC[C@@H]1CO2]

1M Boron tribromide in DCM (3.47 mL, 3.47 mmol) was added to tert-butyl (6aR)-4-chloro-3-(2-chloro-6-methoxyphenyl)-1-(prop-1-yn-1-yl)-6a,7,9,10-tetrahydro-12H-pyrazino[2,1-c]pyrido[3,4-f][1,4]oxazepine-8(6H)-carboxylate (0.3 g, 0.58 mmol) in DCM (5 mL) at 0° C. under nitrogen. The resulting mixture was stirred at 20° C. for 2 hours. The reaction mixture was quenched with MeOH (20 mL). The solvent was removed under reduced pressure. The residue obtained was purified by flash C18-flash chromatography, elution gradient 0 to 80% MeCN in water (0.1% TFA). Fractions containing product were evaporated to dryness to afford crude product. The crude product was purified by ion exchange chromatography, using an SCX column. The desired product was eluted from the column using 7M NH$_3$/MeOH and pure fractions were evaporated to dryness to afford 3-chloro-2-[(6aR)-4-chloro-1-(prop-1-yn-1-yl)-6,6a,7,8,9,10-hexahydro-12H-pyrazino[2,1-c]pyrido[3,4-f][1,4]oxazepin-3-yl]phenol (0.14 g, 60%) as a yellow solid. 1H NMR (400 MHz, DMSO, 30° C.) 2.09 (3H, d), 2.75-2.92 (1H, m), 2.93-3.01 (2H, m), 3.01-3.14 (2H, m), 3.24-3.35 (2H, m), 4.00-4.12 (1H, m), 4.16-4.26 (2H, m), 4.55-4.68 (1H, m), 6.86-7.01 (2H, m), 7.17-7.33 (1H, m), 9.98 (1H, s). one exchangeable proton not seen. m/z: ES+ [M+H]+=404.

1-[(6aR)-4-Chloro-3-(2-chloro-6-hydroxyphenyl)-1-(prop-1-yn-1-yl)-6a,7,9,10-tetrahydro-12H-pyrazino[2,1-c]pyrido[3,4-f][1,4]oxazepin-8(6H)-yl]prop-2-en-1-one Rotational Isomer 1, Example 117 and Rotational Isomer 2, Example 118

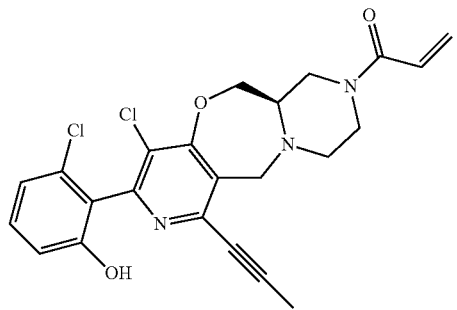 [SMILES: C=CC(=O)N1CCN2Cc3c(C#CC)nc(-c4c(O)cccc4Cl)c(Cl)c3OC[C@H]2C1]

Acryloyl chloride (19.5 mg, 0.22 mmol) and N-ethyl-N-isopropylpropan-2-amine (168 µl, 0.96 mmol) were added to 3-chloro-2-[(6aR)-4-chloro-1-(prop-1-yn-1-yl)-6,6a,7,8,9, 10-hexahydro-12H-pyrazino[2,1-c]pyrido[3,4-f][1,4]oxazepin-3-yl]phenol (0.13 g, 0.32 mmol) in DMF (3 mL) at −20° C. under nitrogen. The resulting mixture was stirred at −20° C. for 1 hour. The reaction mixture was quenched with water and filtered. The filtrate was directly purified and each atropisomer separated by preparative HPLC Column: SunFire C18 OBD Prep Column, 100 Å, 5 μm, 19 mm×250 mm; Mobile Phase A: Water (0.1% FA), Mobile Phase B: MeCN; Flow rate: 20 mL/min; Gradient: 35 B to 45 B in 10 min; 254; 220 nm. Fractions containing the desired compounds were evaporated to dryness. To give firstly 1-[(6aR)-4-Chloro-3-(2-chloro-6-hydroxyphenyl)-1-(prop-1-yn-1-yl)-6a,7,9,10-tetrahydro-12H-pyrazino[2,1-c]pyrido[3,4-f][1,4]oxazepin-8(6H)-yl]prop-2-en-1-one rotational isomer 1 (0.013 g, 9%) as a white solid. 1H NMR (400 MHz, DMSO, 30° C.) 2.11 (3H, s), 2.53-2.58 (1H, m), 2.61-2.75 (1H, m), 2.76-3.01 (2H, m), 3.04-3.21 (1H, m), 3.88-4.16 (4H, m), 4.16-4.31 (1H, m), 4.48-4.64 (1H, m), 5.72 (1H, d), 6.14 (1H, d), 6.74-6.93 (2H, m), 6.97 (1H, d), 7.25 (1H, t), 9.95 (1H, s). m/z: ES+ [M+H]+=458. This was followed by 1-[(6aR)-4-Chloro-3-(2-chloro-6-hydroxyphenyl)-1-(prop-1-yn-1-yl)-6a,7,9,10-tetrahydro-12H-pyrazino[2,1-c]pyrido[3,4-f][1,4]oxazepin-8(6H)-yl]prop-2-en-1-one rotational isomer 2 (9.1 mg, 6%) as a white solid. 1H NMR (400 MHz, DMSO, 30° C.) 2.11 (3H, s), 2.53-2.58 (1H, m), 2.61-2.75 (1H, m), 2.76-3.01 (2H, m), 3.04-3.21 (1H, m), 3.88-4.16 (4H, m), 4.16-4.31 (1H, m), 4.48-4.64 (1H, m), 5.72 (1H, d), 6.14 (1H, d), 6.74-6.93 (2H, m), 6.97 (1H, d), 7.25 (1H, t), 9.95 (1H, s). m/z: ES+ [M+H]+=458.

Tert-butyl (6aR)-4-chloro-3-(2-chloro-6-methoxyphenyl)-1-[(trimethylsilyl)ethynyl]-6a,7,9,10-tetrahydro-12H-pyrazino[2,1-c]pyrido[3,4-f][1,4]oxazepine-8(6H)-carboxylate

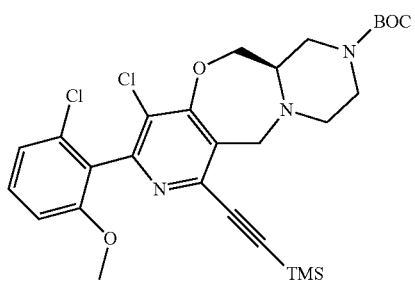 [SMILES: COc1cccc(Cl)c1-c1nc(C#C[Si](C)(C)C)c2c(c1Cl)OC[C@H]1CN(C(=O)OC(C)(C)C)CCN1C2]

N-Ethyl-N-isopropylpropan-2-amine (2 mL, 11.65 mmol) and ethynyltrimethylsilane (1.5 mL, 11.65 mmol) were added to tert-butyl (6aR)-1,4-dichloro-3-(2-chloro-6-methoxyphenyl)-6a,7,9,10-tetrahydro-12H-pyrazino[2,1-c]pyrido[3,4-f][1,4]oxazepine-8(6H)-carboxylate (0.6 g, 1.17 mmol), 1,1'-ferrocenediyl-bis(diphenylphosphine) (64.6 mg, 0.12 mmol) and methanesulfonato 1,1-ferrocenediyl-bis(diphenylphosphino) (2'-amino-1,1'-biphenyl-2-yl) palladium (II) (108 mg, 0.12 mmol) in DMF (10 mL) at 20° C. under an nitrogen atmosphere. The resulting mixture was stirred at 120° C. for 16 hours in a microwave. The reaction mixture was purified by flash C18-flash chromatography, elution gradient 0 to 100% MeCN in water (0.1% TFA). Pure fractions were evaporated to dryness to afford tert-butyl (6aR)-4-chloro-3-(2-chloro-6-methoxyphenyl)-1-[(trimethylsilyl)ethynyl]-6a,7,9,10-tetrahydro-12H-pyrazino[2,1-c]pyrido[3,4-f][1,4]oxazepine-8(6H)-carboxylate (0.3 g, 45%) as a black solid. 1H NMR (400 MHz, DMSO, 30° C.) 0.25 (9H, s), 1.40 (9H, s), 2.77-3.03 (3H, m), 3.11-3.18 (1H, m), 3.70 (3H, d), 3.78-3.93 (3H, m), 4.25-4.40 (3H, m), 4.61-4.67 (1H, m), 7.13 (2H, t), 7.45 (1H, t). m/z: ES+ [M+H]+=576.

3-Chloro-2-[(6aR)-4-chloro-1-ethynyl-6,6a,7,8,9,10-hexahydro-12H-pyrazino[2,1-c]pyrido[3,4-f][1,4]oxazepin-3-yl]phenol

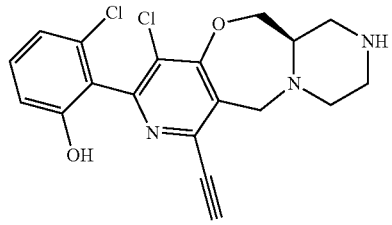 [SMILES: C#Cc1nc(-c2c(O)cccc2Cl)c(Cl)c2c1CN1CCNC[C@@H]1CO2]

1M Boron tribromide in DCM (1977 μl, 1.98 mmol) was added to tert-butyl (6aR)-4-chloro-3-(2-chloro-6-methoxyphenyl)-1-[(trimethylsilyl)ethynyl]-6a,7,9,10-tetrahydro-12H-pyrazino[2,1-c]pyrido[3,4-f][1,4]oxazepine-8(6H)-carboxylate (190 mg, 0.33 mmol) in DCM (2 mL) at 0° C. under nitrogen. The resulting mixture was stirred at 20° C. for 2 hours. The reaction mixture was quenched with MeOH (20 mL). The solvent was removed under reduced pressure. The residue obtained was purified by flash C18-flash chromatography, elution gradient 0 to 100% MeCN in water (0.1% TFA). Fractions containing product were evaporated to dryness to afford crude product. The crude product was purified by ion exchange chromatography, using an SCX column. The desired product was eluted from the column using 7M NH3/MeOH and pure fractions were evaporated to dryness to afford 3-chloro-2-[(6aR)-4-chloro-1-ethynyl-6,6a,7,8,9,10-hexahydro-12H-pyrazino[2,1-c]pyrido[3,4-f][1,4]oxazepin-3-yl]phenol (0.085 g, 66%) as a yellow solid. 1H NMR (400 MHz, DMSO, 30° C.) 2.54-2.68 (2H, m), 2.69-2.88 (3H, m), 2.90-3.07 (2H, m), 3.68-3.77 (1H, m), 4.02-4.12 (2H, m), 4.45-4.67 (2H, m), 6.87-7.01 (2H, m), 7.23-7.32 (1H, m). Two exchangeable protons not seen. m/z: ES+ [M+H]+=390.

1-((6aR)-4-Chloro-3-(2-chloro-6-hydroxyphenyl)-1-ethynyl-6a,7,9,10-tetrahydro-12H-pyrazino[2,1-c]pyrido[3,4-f][1,4]oxazepin-8(6H)-yl)prop-2-en-1-one Rotational Isomer 1, Example 119 and Rotational Isomer 2, Example 120

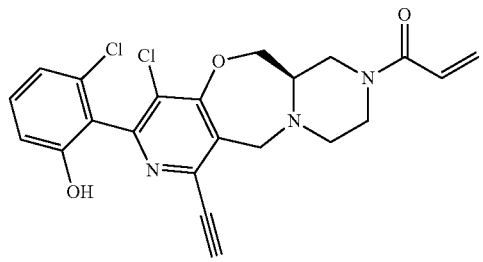 [SMILES: C#Cc1nc(-c2c(O)cccc2Cl)c(Cl)c2c1CN1CCN(C(=O)C=C)C[C@@H]1CO2]

Acryloyl chloride (19.71 mg, 0.22 mmol) and N-ethyl-N-isopropylpropan-2-amine (114 μl, 0.65 mmol) were added to 3-chloro-2-[(6aR)-4-chloro-1-ethynyl-6,6a,7,8,9,10- hexahydro-12H-pyrazino[2,1-c]pyrido[3,4-f][1,4]oxazepin-3-yl]phenol (85.00 mg, 0.22 mmol) in DMF (2 mL) at −20° C. under nitrogen. The resulting mixture was stirred at −20° C. for 1 hour. The reaction mixture was quenched with water and filtered. The filtrate was directly purified and each atropisomer separated by preparative HPLC Column: SunFire C18 OBD Prep Column, 100 Å, 5 μm, 19 mm×250 mm; Mobile Phase A: Water (0.1% FA), Mobile Phase B: MeCN; Flow rate: 20 mL/min; Gradient: 35 B to 45 B in 10 min; 254; 220 nm. Fractions containing the desired compounds were evaporated to dryness to afford firstly 1-((6aR)-4-chloro-3-(2-chloro-6-hydroxyphenyl)-1-ethynyl-6a,7,9,10-tetrahydro-12H-pyrazino[2,1-c]pyrido[3,4-f][1,4]oxazepin-8(6H)-yl)prop-2-en-1-one rotational isomer 1 (0.011 g, 12%) as a white solid. 1H NMR (400 MHz, DMSO, 30° C.) 2.52-2.61 (1H, m), 2.64-2.73 (1H, m), 2.82-3.00 (2H, m), 3.09-3.22 (1H, m), 3.89-4.17 (4H, m), 4.18-4.36 (1H, m), 4.51-4.62 (1H, m), 4.67 (1H, s), 5.63-5.75 (1H, m), 6.14 (1H, d), 6.77-6.89 (1H, m), 6.94 (2H, dd), 7.27 (1H, t), 10.01 (1H, s). m/z: ES+ [M+H]+=444. This was followed by 1-((6aR)-4-chloro-3-(2-chloro-6-hydroxyphenyl)-1-ethynyl-6a,7,9,10-tetrahydro-12H-pyrazino[2,1-c]pyrido[3,4-f][1,4]oxazepin-8(6H)-yl)prop-2-en-1-one rotational isomer 2 (6.6 mg, 7%) as a white solid. 1H NMR (400 MHz, DMSO, 30° C.) 2.52-2.61 (1H, m), 2.64-2.73 (1H, m), 2.82-3.00 (2H, m), 3.09-3.22 (1H, m), 3.89-4.17 (4H, m), 4.18-4.36 (1H, m), 4.51-4.62 (1H, m), 4.67 (1H, s), 5.63-5.75 (1H, m), 6.14 (1H, d), 6.77-6.89 (1H, m), 6.94 (2H, dd), 7.27 (1H, t), 10.01 (1H, s). m/z: ES+ [M+H]+=444.

The invention claimed is:

1. A compound, or a pharmaceutically acceptable salt thereof, that is 1-[(12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepin-2 (1H)-yl]prop-2-en-1-one,

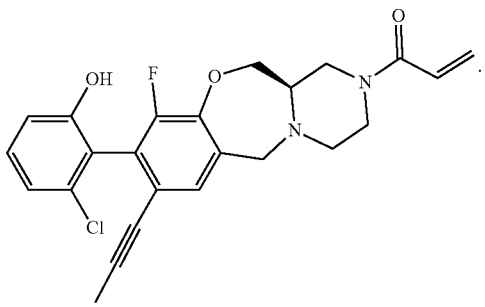 [SMILES: C=CC(=O)N1CCN2Cc3cc(C#CC)c(-c4c(O)cccc4Cl)c(F)c3OC[C@H]2C1]

2. A compound that is 1-[(12aR)-9-(2-chloro-6-hydroxyphenyl)-10-fluoro-8-(prop-1-yn-1-yl)-3,4,12,12a-tetrahydro-6H-pyrazino[2,1-c][1,4]benzoxazepin-2 (1H)-yl]prop-2-en-1-one,

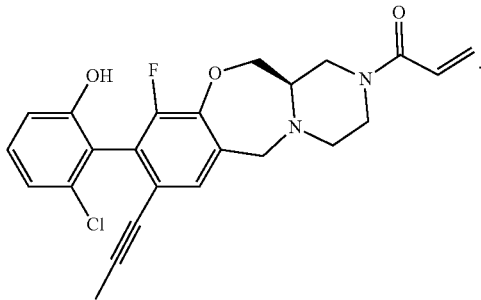 [SMILES: C=CC(=O)N1CCN2Cc3cc(C#CC)c(-c4c(O)cccc4Cl)c(F)c3OC[C@H]2C1]

3. A pharmaceutical composition comprising a compound, or a pharmaceutically acceptable salt thereof, according to claim 1 and a pharmaceutically acceptable excipient.

4. The compound, or a pharmaceutically acceptable salt thereof, according to claim 1, wherein the compound is the rotational isomer 1

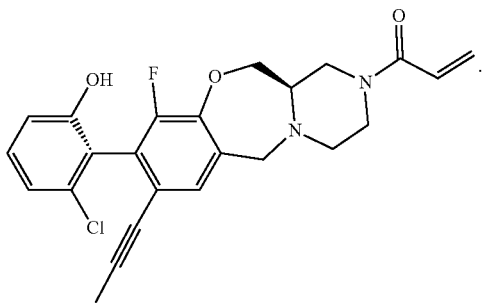

5. The compound, or a pharmaceutically acceptable salt thereof, according to claim 1, wherein the compound is the rotational isomer 2

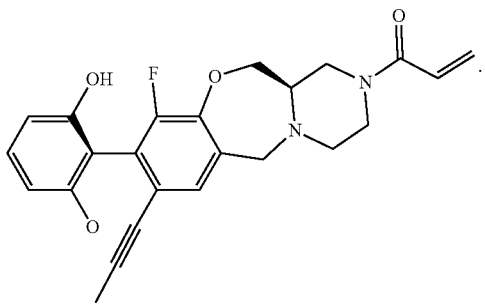

* * * * *